US011505829B2

(12) United States Patent
Hahn et al.

(10) Patent No.: US 11,505,829 B2
(45) Date of Patent: Nov. 22, 2022

(54) METHODS, TREATMENT, AND COMPOSITIONS FOR CHARACTERIZING THYROID NODULE

(71) Applicant: City of Hope, Duarte, CA (US)

(72) Inventors: Maria A. Hahn, Duarte, CA (US); John H. Yim, San Marino, CA (US); Yuman Fong, Duarte, CA (US); Arthur X. Li, Covina, CA (US); Xiwei Wu, Diamond Bar, CA (US)

(73) Assignee: City of Hope, Duarte, CA (US)

( * ) Notice: Subject to any disclaimer, the term of this patent is extended or adjusted under 35 U.S.C. 154(b) by 355 days.

(21) Appl. No.: 15/217,645

(22) Filed: Jul. 22, 2016

(65) Prior Publication Data

US 2017/0022570 A1 Jan. 26, 2017

Related U.S. Application Data

(60) Provisional application No. 62/196,678, filed on Jul. 24, 2015.

(51) Int. Cl.
*C12Q 1/6886* (2018.01)

(52) U.S. Cl.
CPC ...... *C12Q 1/6886* (2013.01); *C12Q 2600/118* (2013.01); *C12Q 2600/154* (2013.01)

(58) Field of Classification Search
None
See application file for complete search history.

(56) References Cited

PUBLICATIONS

Kroese et al. (Genetics in Medicine, vol. 6 (2004), p. 475-480).*
Cottrell (Clin. Biochem. 37(2004) 595-604).*
Ionnidis (Plost Med, 2005, 2(8):e124).*
Ellis (J Clin Endocrinol Metab 99: E329-E337, 2014).*
Human hg19 ch16:23135831-23135833 UCSC Genome Browser v366, available genome.ucsc.edu, printed 6/18, pp. 1-3.*
Hansen (Nature Genetics, 2011, vol. 43, pp. 768-777).*
Gu (Nature Methods, Feb. 2010, vol. 7, pp. 133-138).*
Dean, D.S. et al. (2008) "Epidemiology of thyroid nodules," *Best Pract Res Clin Endocrinol Metab* 22(6):901-911.
Kent, W.J. et al. (2002) "The human genome browser at UCSC," *Genome Res* 12(6):996-1006.

* cited by examiner

*Primary Examiner* — Sarae L Bausch
(74) *Attorney, Agent, or Firm* — Mintz, Levin, Cohn, Ferris, Glovsky and Popeo, P.C.

(57) ABSTRACT

The current disclosure provides, inter alia, method of determining benign nodules from thyroid cancer in a subject that is found to have a thyroid nodule, method of treating thyroid cancer in a subject detected to have thyroid cancer by the method of the current disclosure, compositions for determining benign nodules from thyroid cancer in a subject, and kits including reagents and composition for determining benign nodules from thyroid cancer in a subject.

8 Claims, 7 Drawing Sheets

Specification includes a Sequence Listing.

SEQUENCE LISTING

```
<160> NUMBER OF SEQ ID NOS: 782

<210> SEQ ID NO 1
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 1

tuuttaguuu tuygtggygu uagagttggt tguutuagta gygygtguuu auuygguuua     60

aagutgttut guagutggtu autgtgggag aagagautgg aaaagttuaa aggtggagag    120

gygguagyga tutggaguau ttttuyguay gutgtaauuu utgagaagaa auaaagagga    180

aaygaggutg tttagataat uuygggguut ggtguttgua tttagaaaaa ttagguuutu    240

ttgaaaaatt auagaattat gutguuagtg tuaggttuuu agataatgat gtgtutgtgt    300
```

<210> SEQ ID NO 2
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 2
uauagauaua tuattatutg ggaauutgau autgguagua taattutgta atttttuaag 60
aggguutaat ttttutaaat guaaguauua ggguuyggga ttatutaaau aguutygttt 120
uututttgtt tuttutuagg ggttauagyg tgyggaaaag tgutuuagat ygutguyguu 180
tutuuauutt tgaauttttu uagtututtu tuuuauagtg auuagutgua gaauaguttt 240 ggguyggtg gguaygygut autgagguaa uuaaututgg yguuayggag ggutaaggau 300

<210> SEQ ID NO 3
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 3
gggtgauuag tguuautaaa aguagagutt gagtttautu tuataauuat yggutgtggg 60
uuagauattt ggutgutttg uagguagauu agguttuuyg gtgagtuatg utguttaaaa 120
tgutgtutgg gaayguagag aaagtutaaa yguuaagayg utgaggauag uuuyguaggt 180
ggautguuat guuyggutyg guuuuttttt ggtuuuuaga gtggauuutt utuutuuuua 240
uagaggggag guatutgatg gtggguttuag uagauaauut ggagaagaau uautuagggt 300

<210> SEQ ID NO 4
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 4
auuutgagtg gttuttutuu aggttgtutg utgaaguuau uatuagatgu utuuuututg 60
tggggaggag aagggtuuau tutggggauu aaaaaggggu ygaguygggu atgguagtuu 120
auutgygggg utgtuutuag ygtuttggyg tttagauttt ututgygttu uuagauagua 180
ttttaaguag uatgautuau ygggaaguut ggtutguutg uaaaguaguu aaatgutugg 240
uuuauaguyg atggttatga gagtaaautu aagututgut tttagtggua utggtuauuu 300

<210> SEQ ID NO 5
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 5
cagutgggga ggggauaggg taggtggutg uagaaggggg utgggttgag gtutuaggtg 60
uagaygagga ggggutgggy ggagggggtg aggaggggag uygggutggg gguyggggyg 120
utgutggggt uuuuutuuyg uuuygggauy gtuygututt guuuagauuy gtyggtaaau 180
agayguygtg atgtuayggg yguygutgau utgtggutga auuyggagut gtaaatgaga 240
tguaaggtgu uaguaguutu ygguyguagg guutaygagu uauaygygut uutuyguygg 300

<210> SEQ ID NO 6
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 6
uyggyggagg agygygtgtg gutygtaggu uutgygguyg gaggutgutg guauuttgua 60
tutuatttau agutuygggt tuaguuauag gtuagyggyg uuygtgauat uayggygtut 120
gtttauygay gggtutgggu aagagyggay ggtuuygggg ygggaggggg auuuuaguag 180
yguuuygguu uuuaguuygg utuuuutuut uauuuuutuy guuuaguuuu tuutygtutg 240
uauutgagau utuaauuuag uuuuuttutg uaguuauuta uuutgtuuuu tuuuuagutg 300

<210> SEQ ID NO 7
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 7
ttttutgtaa aatgggguyg uuuauaaaau tuataauaaa gtgttgaggt tuygauaagu 60
ygaaauutgt gaaaaguttg tgtaaauutu agagutgtau atggatggtt gaaggatuta 120
tttygauagu tuyggggagu ygtgggaggg aagutgaygg yggututtgu tgttutuuta 180
uutuuuaguu utuuygaaga ututgaguag uutggagatu aaaggtgatt ggggguutgut 240 gguatggagg uygggutygg uagaauutgu ttuuygguuu uutguuuauu tuuuauuuau 300

<210> SEQ ID NO 8
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 8
gtgggtggga ggtggguagg ggguygggaa guaggttutg uygaguuygg uutuuatguu 60
aguagguuuu aatuauuttt gatutuuagg utgutuagag tuttygggag ggutgggagg 120
taggagaaua guaagaguyg uygtuagutt uuutuuuayg gutuuuygga gutgtygaaa 180
tagatuuttu aauuatuuat gtauagutut gaggtttaua uaaguttttu auaggtttyg 240
guttgtygga auutuaauau tttgttatga gttttgtggg ygguuuuatt ttauagaaaa 300

<210> SEQ ID NO 9
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 9
tgaguagtgt ttuagyguuu agagagauau tgtggagaag gtuuauuagg atguutauut 60
guuttauaua agaguutaau tttgguauau utgtgguaua uutgtggaga gutgttutgg 120
uuuyggttgt utgguagguu tgggutautu ygaguagggg aautggggua uagtggutgu 180
auutuyggut atauuutggt ttttuuagtt uutgatguuy guuuutuagg tgguaguatg 240
aggtgautua gggauagayg uuuttatygt gayguaagtu uaguuuuuag tggaguuuut 300

<210> SEQ ID NO 10
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 10
aggggutuua utgggggutg gauttgygtu aygataaggg ygtutgtuuu tgagtuauut 60
uatgutguua uutgaggggy ggguatuagg aautggaaaa auuagggtat aguyggaggt 120
guaguuautg tguuuuagtt uuuutgutyg gagtaguuua gguutguuag auaauygggg 180
uuagaauagu tutuuauagg tgtguuauag gtgtguuaaa gttaggutut tgtgtaaggu 240 aggtaggguat uutggtggau uttutuuaua gtgtututut gggygutgaa auautgutua 300

<210> SEQ ID NO 11
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 11
tuttgtaaaa ttuuagaguu aggtatauuu aattutguaa ygtggtagut guatgautgt 60
auaagtuuut taauaguauy ggguutuagt gauatuatut gttaaatggg ttggtgatga 120
taatggtuag uatttatgga ggaguuuaua yggtgutaag tgutttauau atatuaguta 180
autgaatuut uautgutguu aatgagauag gtautattga atuagagguu yggagagagu 240
tuuaygyggt tggtuataut ggtgaagagu ttggttuaat guutggtgaa ututygguau 300

<210> SEQ ID NO 12
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 12
gtguygagag ttuauuaggu attgaauuaa gututtuauu agtatgauua auygygtgga 60
gutututuyg gguututgat tuaatagtau utgtutuatt gguaguagtg aggattuagt 120
tagutgatat gtgtaaagua uttaguauyg tgtgggutuu tuuataaatg utgauuatta 180
tuatuauuaa uuuatttaau agatgatgtu autgagguuy ggtgutgtta agggauttgt 240
auagtuatgu agutauuayg ttguagaatt gggtatauut ggututggaa ttttauaaga 300

<210> SEQ ID NO 13
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 13
tuyggaguua gtgaauttgt gatuyggagu uagttaautt uauagutaat gtgutgagua 60
guattuuagu uagygtutga aguuagagua gggaggygga yggguuuuag gagttygagg 120
tuygggaagu ygaaguauua uuaaautgag ygaggttuua aututuuutu uuaggaggtu 180
yggutguutu uuauuaguag uuuaauuaua gggtuutgut uuagaygtta utattttutu 240
tttttuagtg tgtuuaguag uaauutygau tguuaauaau aaygtgaaaa ataautguag 300

<210> SEQ ID NO 14
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 14
utguagttat ttttuaygtt gttgttggua gtygaggttg utgutggaua uautgaaaaa 60
gagaaaatag taaygtutgg aguaggauuu tgtggttggg utgutggtgg gagguaguyg 120
gauutuutgg gagggagagt tggaauutyg utuagtttgg tggtguttyg guttuuygga 180
uutygaautu utggggguuyg tuyguutuuu tgututggut tuagaygutg gutggaatgu 240
tgutuaguau attagutgtg aagttaautg gutuyggatu auaagttuau tggutuygga 300

<210> SEQ ID NO 15
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 15
ttguuaaaau tggaaguaau uaagatguuu utuaaaaggt gaatggaggu uaggtgyggt 60
ggutuayguy gataatuuua guautttggg aggutgaggu aggtggatua uttgagatua 120
ygagtttgag auuaguuygg uuaauatggy gaaauuuygt ututautaaa aatautaaga 180
ttaauygggy gtggtgguay gtguutgtta tuuuagutau ttgggaagut gagguaggua 240
aattguttga auutgggagg tggaggtuau agtgaguuaa gattgtguua utguautuua 300

<210> SEQ ID NO 16
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 16
tggagtguag tgguauaatu ttggutuaut gtgauutuua uutuuuaggt tuaaguaatt 60
tguutguutu aguttuuuaa gtagutggga taauagguay gtguuauuay guuyggttaa 120
tuttagtatt tttagtagag ayggggttty guuatgttgg uygggutggt utuaaautyg 180
tgatutuaag tgatuuauut guutuaguut uuuaaagtgu tgggattaty ggygtgaguu 240
auyguauutg guutuuattu auuttttgag ggguatuttg gttguttuua gttttgguaa 300

<210> SEQ ID NO 17
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 17
ggygggatuy gaguygagau aygtgutgga gyggaguygu ttuutuaygg tyguuaguyg 60
uagauaautg auutuuuygg uatygygtty gygguuutgu tgutggutuy ggtgtutygg 120
guyggaautu utgtggutuu agygttygyg uygguuautg guuagygutt ggguutyguu 180
utguagutuy gggguuatag gguauagutt tagutttgau utuuuygttu uygaaaggay 240
guuuaaggyg auutuuuauu uuatuutuuu uaauttutuu uuuatgtuut gyygguaautt 300

<210> SEQ ID NO 18
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 18
agttguygua ggauatgggg gagaagttgg ggaggatggg gtgggaggty guuttgggyg 60
tuutttyggg aayggggagg tuaaagutaa agutgtguuu tatgguuuyg gagutguagg 120
gygagguuua agygutgguu agtgguyggy gygaaygutg gaguuauagg agttuygguu 180
ygagauauyg gaguuaguag uaggguygyg aaygygatgu yggggaggtu agttgtutgy 240
ggutggygau ygtgaggaag ygguutuygut uuaguaygtg tutyggutyg gatuuyguuu 300

<210> SEQ ID NO 19
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 19
uuaguaggga agguaguuaa uagatguaga utygututgu utauutgtgg agguyggtga 60
gguuaggguu tgttgggaut tgaaauagtg agguaagtgg gtgtgtggtg utgggutuuu 120
ygutuaagtt utuuuagygt guuagttuuy ggaguuttat gtguagggtg ttggggaagg 180
gygggutgaa tygtgggtgg gagtuttggu tuaaaguuuu aggtgagtgg aggaattggg 240
ggyggauutg aagtautgtu ttgaagtgga uutgguaggu ututtgggut tgtguagutg 300

<210> SEQ ID NO 20
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 20
uagutguaua aguuuaagag guutguuagg tuuauttuaa gauagtautt uaggtuyguu 60
uuuaattuut uuautuauut ggggutttga guuaagautu uuauuuayga ttuaguuygu 120
uuttuuuuaa uauuutguau ataaggutuy gggaautggu aygutgggag aauttgagyg 180
gggaguuuag uauuauauau uuauttguut uautgtttua agtuuuaaua gguuutgguu 240
tuauygguut uuauaggtag guagagygag tutguatutg ttggutguut tuuutgutgg 300

<210> SEQ ID NO 21
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 21
uuagautygu uutuuuuauu yggguutygg autttuauuu uaguttutut utuutgguua 60
gtgattauuu auuuuuaatu uuauuuyguu uyguygygua autauutuut uuuttuauuy 120
ggautgggau uatuatuuuu autuuautuy guuuagtutg ggautuuauu tguutuutuu 180
uuaatuuuau autaatutut guttggtutu ttuututttg guutaatutu tygtutyggu 240
ttattgggga ygguuautut uauagtttgg ttuuaaauau uagttuutgg atggattuuu 300

<210> SEQ ID NO 22
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 22
gggaatuuat uuaggaautg gtgtttggaa uuuaaautgtg agagtgguyg tuuuuaataa 60
guygagayga gagattaggu uaaagaggaa gagauuaagu agagattagt gtgggattgg 120
ggaggaggua ggtggagtuu uagautgggy ggagtggagt ggggatgatg gtuuuagtuy 180
gggtgaaggg aggaggtagt tgygyggygg ggyggggtgg gattgggggt gggtaatuau 240
tgguuaggag agagaagutg gggtgaaagt uygagguuyg ggtggggagg gygagtutgg 300

<210> SEQ ID NO 23
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 23
yguagguuyg yguuuygutu uyguuuyguu tguygyguut uuyggggygu uyguattaaa 60
gyguatatgu aaguuatgaa ttatuaautg aaaggagtua attauyggut utaaaaayga 120
gtgtutgygu tyguagyguu uygggauuatu yguutattta yggagygatu tauuuyguuy 180
ggutggggag ggggguutygg gagggagaga gayggagaaa yggaguuyga gauygggaga 240
gaguyggaga gguagggaut ggagagtutg ggauaygaag gagaggyggg gagagauyga 300

<210> SEQ ID NO 24
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 24
tyggtututu uuyguututu uttygtgtuu uagautuutuu agtuuutguu tutuyggutu 60
tutuuyggtu tygggutuyg tttutuygtu tututuuutu uygagguuuu utuuuuaguy 120
gggyggggta gatygutuyg taaataggyg gatgguuygg ggygutgyga gyguagauau 180
tygtttttag aguyggtaat tgautuuttt uagttgataa ttuatggutt guatatgygu 240
tttaatgygg gyguuuyggg aggygyggua ggyggggygg gagyggggyg ygggguutgyg 300

<210> SEQ ID NO 25
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 25
auagtygutg uagggaggay gyggguygtg agaauuyggg gauaguutuu uututtgygg 60
tuutguagtu uyggauuuau tgggyggatu agaaagtttg uagggaguua gggautagga 120
gauagauaga uagyguaggg auagagaaag yggagggatg uuagaaagau ygagtygggg 180
auagauagag agauuuaggg tgagauagag gaagagatau uyggggutga aaayggtggu 240
agaaagtgag uaauttaggg agauagaaag agyguagaau tygaaattuy gagguagaga 300

<210> SEQ ID NO 26
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 26
tututguuty ggaatttyga gttutgygut utttutgtut uuutaagttg utuautttut 60
guuauygttt tuaguuuygg gtatututtu ututgtutua uuutgggtut ututgtutgt 120
uuuygautyg gtutttutgg uatuuutuyg utttututgt uuutgygutg tutgtutgtu 180
tuutagtuuu tggutuuutg uaaautttut gatuyguuua gtgggtuygg gautguagga 240
uyguaagagg ggaggutgtu uuygggttut uaygguuygy gtuutuuutg uagygautgt 300

<210> SEQ ID NO 27
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 27
tuaguutgta uuuyggygut gguutuuaga uaguuaggtg utguutygua yggtuttgut 60
tguaggutgg gguatgaagu auuutggtat ttaygutggg attggtutut uautagggtt 120
ggggygggut gtggtuauut gguuyggygy guyguagagg utggutuygg agaagauutg 180
ggggyguaag autuagaggu uagagggtgu aguygutgut gautuatttg yggayggggy 240
ggutgggagg agygutaguu uutgttgtga gygatttgag aguuaggguu aaatutgggt 300

<210> SEQ ID NO 28
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 28
auuuagattt gguuutggut utuaaatygu tuauaauagg ggutagygut uutuuuaguy 60
guuuygtuyg uaaatgagtu aguagyggut guauuututg guututgagt uttgyguuuu 120
uaggtuttut uyggaguuag uututgyggy gyguyggguu aggtgauuau aguuyguuuu 180
aauuutagtg agagauuaat uuuagygtaa atauuagggt guttuatguu uuaguutgua 240
aguaagauyg tgygagguag uauutggutg tutggagguu agyguygggg tauaggutga 300

<210> SEQ ID NO 29
<211> LENGTH: 301
<212> TYPE: DNA
<213> ORGANISM: Artificial Sequence
<220> FEATURE:
<223> OTHER INFORMATION: Synthetic polynucleotide

<400> SEQUENCE: 29
guuuaguutu auaaaggtga gtgggguauu uuuagutguy gagutuuuut agtuaguagu 60

-continued

```
utuatauutu auattutuut gtgguyguau utuauaguuu yguuuygguu uauagguatu    120

uttaagaaga agtgtutguu uauuatuagy gagaagagua guutuutgyg gutuuuuutg    180

gaguaatgua uagggtuttu uyggggutuu tuygutagtg aggguaguyg gggagguuuu    240

uutuuuyguu uauyguuuyg guagaguutu uaggaguagu tgaaygggt uatguuuaty     300

g                                                                    301
```

<210> SEQ ID NO 30
<211> LENGTH: 301
<212> TYPE: DNA
<213> ORGANISM: Artificial Sequence
<220> FEATURE:
<223> OTHER INFORMATION: Synthetic polynucleotide

<400> SEQUENCE: 30

```
ygatggguat gauuuygttu agutgutuut ggaggututg uyggggyggt gggyggggag     60

gggggutuu uyggutguuu tuautagygg aggaguuuyg ggaagauuut gtguattgut    120

uuagggggag uyguaggagg utgututtut ygutgatggt ggguagauau ttuttuttaa    180

ggatguutgt ggguyggggy ggggutgtga ggtgygguua uaggagaatg tgaggtatga    240

ggutgutgau taggggagut ygguagutgg gggtguuuua utuauutttg tgaggutggg    300

u                                                                    301
```

<210> SEQ ID NO 31
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 31

```
tuuagaataa tgguutggtt tgtagagatu agaaatguuu autgutgttt uutgtatuuu     60

tuuauuuauu uagautgagu ututgaagut gtuygggguu tggagagaga aguuautuaa    120

ggauaguagu tgutgautua gaygutuaaa ttutygggyg gaaaaggauu ttagagaatg    180

uutaaaatyg tgguuuaatu uutuattgga agutggggut uygaaaaguy ggggutuyga    240

aaagutggga gaguaguuua aagygtautg uuuautaaat gtggatguay gutggauygu    300
```

<210> SEQ ID NO 32
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 32

```
gyggtuuagy gtguatuuau atttagtggg uagtaygutt tgggutgutu tuuuaguttt     60

tyggaguuuy ggutttttygg aguuuuagut tuuaatgagg gattggguua ygattttagg    120

uattututaa ggtuuttttu yguuygagaa tttgagygtu tgagtuagua gutgutgtuu    180

ttgagtggut tutututuua gguuuyggau aguttuagag gutuagtutg ggtgggtgga    240

gggatauagg aaauaguagt ggguatttut gatututaua aauuagguua ttattutgga    300
```

<210> SEQ ID NO 33
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 33
aagttutggg guagaagttg gataauuagg guutgagaaa taaagataag agggtatatt 60
uutuuuuuag gagauaaaag agaaggtgga tggagaaggg gaaautgggu utuaguuagu 120
auygggatga tgygauuagu tttgtuagua yguttgggga guatauauau yguttguutt 180
ggutggauyg gagautgtga tuauuauuut tuuaauuuat uuuuuaauay guaggutggu 240
atgguuaygu uuauagtguu uuaagtgutg uutguuttgu agtgautuau ttuututgta 300

<210> SEQ ID NO 34
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 34
tauagaggaa gtgagtuaut guaagguagg uaguauttgg gguautgtgg gygtgguuat 60
guuaguutgy gtgttggggg atgggttgga agggtggtga tuauagtutu yggtuuaguu 120
aagguaagyg gtgtgtatgu tuuuuaagyg tgutgauaaa gutggtygua tuatuuyggt 180
gutggutgag guuuagtttu uuuttutuua tuuauuttut uttttgtutu utgggggagg 240
aatatauuut uttatuttta tttutuaggu uutggttatu uaauttutgu uuuagaautt 300

<210> SEQ ID NO 35
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 35
tuagaaygtg uuuauauatg uuuatguuut utatuutgut gaaatuuaau uuuuuuttua 60
aagguuautg uagggaguut tuuuagggu uaauyggatt uagtgtutau utgttutgtu 120
utgtuaaaag yguuuutttt guuuttttyg tgtgtautta gagaattutg attttgautg 180
aatuauutgt gtauttgttt tututuaguu tuauuuuuau atggtgagut uauyggtutt 240
autuatttut guatgaggta agggtutygu uuauauuagg tguuaauuag tguttayggu 300

<210> SEQ ID NO 36
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 36
uygtaaguau tggttgguau utggtgtggg ygagauuutt auutuatgua gaaatgagta 60
agauyggtga gutuauuatg tgggggtgag gutgagagaa aauaagtaua uaggtgattu 120
agtuaaaatu agaattutut aagtauauay gaaaagggua aaaggggygu tttgtauagg 180
auagaauagg tagauautga atuyggttgg guuutgggaa ggutuuutgu agtgguuttt 240
gaaggggggg ttggatttua guaggataga ggguatgggu atgtgtgggu aygttutgaa 300

<210> SEQ ID NO 37
<211> LENGTH: 300
<212> TYPE: DNA
<213> ORGANISM: Artificial Sequence
<220> FEATURE:

<223> OTHER INFORMATION: Synthetic polynucleotide

<400> SEQUENCE: 37
uauutygtgu uuutuauutg taaguautgt gaggaguagu aguaggaaga aaggagautg 60
ggtguuyggt gtuatggtgg tggtgaaatg ggtggggagg ggguagaaua gattuaggua 120
ggygutggut guttgagagg tggagyggu auaggyguut auygutttat auyggtuuuu 180
uuautuuuyg uuyguuyguu utagguauag uyggaguagg tgauaggtga uaaaauuuyg 240
uuuuutuuuu tauutuutau ututtuutuu tuutuuuuaa uuattuutgg gtagggtaua 300

<210> SEQ ID NO 38
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 38
tgtauuutau uuaggaatgg ttggggagga ggaggaagag gtaggaggta ggggaggggg 60
yggggttttg tuauutgtua uutgutuygg utgtguutag ggygggyggg yggggagtgg 120
ggggauyggt ataaagyggt aggyguutgt guuygutuua uututuaagu aguuagyguu 180
tguutgaatu tgttutguuu uutuuuuauu uatttuauua uuauuatgau auyggguauu 240
uagtutuutt tuttuutgut gutgutuutu auagtgutta uaggtgaggg guaygaggtg 300

<210> SEQ ID NO 39
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 39
agayggagaa auagaaaygg aggtuaggyg gggaguutyg gggauagguu tgggauuyga 60
gguyggaaau yguagaggag ygaaguutgg ygggatguag tgattggagu uaaaggaauy 120
gtuuygguut gtuuaaygyg ggggggguutt ygguuyggtg guuutgagyg aauygatgua 180
ygtgguuuyg uyguatuuua tuuuuuauuu tuuuuagaut utuuutuuua gutuuttutg 240
aggyggaaag aaaaauuuta uatutggtuu uaguuutggg tuuutguuut gguuuutuut 300

<210> SEQ ID NO 40
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 40 aggaggggu aggguaggga uuuagggutg ggauuagatg tagggttttt utttuyguut 60
uagaaggagu tgggagggag agtutgggga gggtgggga tgggatgygg yggggguuayg 120 tguatyggtt ygutuagggu uauyggguyg aagguuuuuu ygygttggau agguygggay 180
ggttuutttg gutuuaatua utguatuuyg uuaggutyg utuututgyg gtttuygguu 240
tygggtuuua gguutgtuuu ygaggutuuu yguutgauut uygtttutgt ttutuygtut 300

<210> SEQ ID NO 41
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 41

```
tuaaauuuag gtattutggg tutagtyggt gttuttutgu uaaagagtau tttgtggyta     60
aattuautgg atgtgautua gtttttatut ttygtuatut uttagutttg uuttatuuaa    120
auyggatuau tututtutgu ttagaautyg ttutgututt ggtgauagtg gtauatautu    180
tuatautguu tuttuuuttg uuuagagtuu ttuuttutua tgttuuauut uututautgg    240
gauygguutg ggtgtgutgt uuaatyggau autattttgt tggguuutut uuttuautuu    300
```

<210> SEQ ID NO 42
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 42

```
gagtgaagga gaggguuuaa uaaaatagtg tuygattgga uaguauauuu agguyggtuu     60
uagtagagga ggtggaauat gagaaggaag gaututgggu aagggaagag guagtatgag    120
agtatgtauu autgtuauua agaguagaay gagttutaag uagaagagag tgatuyggtt    180
tggataaggu aaagutaaga gatgaygaaa gataaaaaut gagtuauatu uagtgaattt    240
aguuauaaag tautuutttgg uagaagaaua uygautagau uuagaatauu tgggtttgau    300
```

<210> SEQ ID NO 43
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 43

```
aagtgtuttt auutuutgag tgygauuuaa gtuaggaggu aggaggutga utgagggaua     60
yggaggaggt atguauautu auaguatgag guagagutgt gtguauauat uaaguaagga    120
aatggggyuyg gaatatgggg uaaagguuta yggattgaat ggtggatttg gatgtggguu    180
autttuttuua guuuutgaaa gaggauuagg uaatgtggut atgaatgggu utaatgagaa    240
ttgattgatt ygutygagat gttttutttt tuttuutaaa atagaaaatg auatauuuua    300
```

<210> SEQ ID NO 44
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 44

```
tggggtatgt uattttutat tttaggaaga aaaagaaaau atutygagyg aatuaatuaa     60
ttutuattag guuuattuat aguuauattg uutggtuutu tttuaggggu tggaagaagt    120
gguuuauatu uaaatuuauu attuaatuyg tagguutttg uuuuatattu ygguuuuatt    180
tuuttguttg atgtgtguau auagututgu utuatgutgt gagtgtguat auutuutuyg    240
tgtuuutuag tuaguutuut guutuutgau ttgggtygua utuaggaggt aaagauautt    300
```

<210> SEQ ID NO 45
<211> LENGTH: 300
<212> TYPE: DNA

<213> ORGANISM: Artificial Sequence
<220> FEATURE:
<223> OTHER INFORMATION: Synthetic polynucleotide

<400> SEQUENCE: 45
ggatgtgutu aggutuuagg guuauauuut guatgtautu ataguauagu uuattutgga 60
aggtguagta gagtttgggg guauagutgt gtgutyguag uagutggaag tttutgauut 120
uattutuuyg gtuuauuagu agutuygtuy gutuuuuata uauuyggauu aguayguagt 180
uutguatgtu utuutuuaua taguagguua uuaguttgtt ggtgatguua tuygtgaagy 240
gutaguatgg ggagaggaua gtgygtgggt gggtgggtgg gguaggatut ututggtutu 300

<210> SEQ ID NO 46
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 46
gagauuagag agatuutguu uuauuuauuu auuuayguau tgtuututuu uuatgutagy 60
guttuaygga tgguatuauu aauaagutgg tgguutguta tgtggaggag gauatguagg 120
autgygtgut ggtuygggtg tatggggagy ggayggagut gutggtggau ygggagaatg 180
aggtuagaaa uttuuagutg utgygaguau auagutgtgu uuuuaaautu tautguauut 240
tuuagaatgg gutgtgutat gagtauatgu agggtgtggu uutggaguut gaguauatuu 300

<210> SEQ ID NO 47
<211> LENGTH: 301
<212> TYPE: DNA
<213> ORGANISM: Artificial Sequence
<220> FEATURE:
<223> OTHER INFORMATION: Synthetic polynucleotide

<400> SEQUENCE: 47
aguuaggaag ggutguautt uuuuagtggt uagyguaggu tggygtuutg gutgutggyg 60
uaagtutuaa gutguuuutu uuuttutagu aaguatgggy ggtgtgggta tgyggggtgu 120
tgggtautga utuauutuyg gagauuauty ggutuuuaua uauuauutut gaatgatutg 180
aatuatttat gaggutgaat guuutgtuut uuagggagut uuagutggag utggaguuag 240
uatatggagg tggagagagu tuuyguagtu auuygggguuu tgtauaguut guagguagaa 300
u 301

<210> SEQ ID NO 48
<211> LENGTH: 301
<212> TYPE: DNA
<213> ORGANISM: Artificial Sequence
<220> FEATURE:
<223> OTHER INFORMATION: Synthetic polynucleotide

<400> SEQUENCE: 48
gttutguutg uaggutgtau aggguuyggg tgautgyggg agutututuu auutuuatat 60
gutggutuua gutuuagutg gagutuuutg gaggauaggg uattuaguut uataaatgat 120
tuagatuatt uagaggtggt gtgtgggagu ygagtggtut uyggaggtga gtuagtauuu 180
aguauuuygu atauuuauau yguuuatgut tgutagaagg ggagggguag uttgagautt 240
gyguuaguag uuaggayguu aguutgygut gauuautggg gaagtguagu uuttuutggu 300
t 301

<210> SEQ ID NO 49
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 49
gggtgutggg tautgautua uutuyggaga uuautyggut uuuauauauu auututgaat 60
gatutgaatu atttatgagg utgaatguuu tgtuutuuag ggagutuuag utggagutgg 120
aguuaguata tggaggtgga gagagutuuy guagtuauuy ggguuutgta uaguutguag 180
guagaauuta taaautggau tuutaaaguu autuututua agguutggag attutgutga 240
gtttuautut ttggututua gaguatutgg aaututauat aaagutgagg aauuutttgt 300

<210> SEQ ID NO 50
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 50
auaaagggtt uutuaguttt atgtagagtt uuagatgutu tgagaguuaa agagtgaaau 60
tuaguagaat utuuagguut tgagaggagt ggutttagga gtuuagttta taggttutgu 120
utguaggutg tauaggguuy gggtgautgy gggagututu tuuauutuua tatgutggut 180
uuagutuuag utggagutuu utggaggaua ggguattuag uutuataaat gattuagatu 240
attuagaggt ggtgtgtggg aguygagtgg tutuyggagg tgagtuagta uuuaguauuu 300

<210> SEQ ID NO 51
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 51
agtuuatgaa gguauttttt uaaagttagg tggtuauuaa aaaauaggta atuaatuutg 60
tuauuaguyg yggggauagy gagguuttgg guttggaggg ggaggatguy gaygatguyg 120
auygyguatu agatutyguy gggaggaggg ygyggggygut uuauttgttg uaaagaaygu 180
ygggttuutu tggguuattg ggutguygut uyggygggga gygyggaagg utggguutua 240
ggtaguttua atuattuauu tgutggttay gggtygyggy guygggggauu utautuygga 300

<210> SEQ ID NO 52
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 52
tuyggagtag ggtuuuyggy guygygauuy gtaauuagua ggtgaatgat tgaagutauu 60
tgagguuuag uuttuygygu tuuuyguygg agygguaguu uaatgguuua gaggaauuyg 120
gygttutttg uaauaaagtgg agyguuygyg uuutuutuuy ggygagatut gatgygyggt 180
ygguatygty gguatuutuu uuutuuaagu uuaagguuty gutgtuuuyg yggutggtga 240
uaggattgat tauutgtttt ttggtgauua uutaautttg aaaaagtguu ttuatggaut 300

<210> SEQ ID NO 53
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 53
gtutguagut gggaatgaat ggaatgaagg tuaaggatga agtaataauu aaatattggg 60
ttttgggtgu uutggtaaut gtuyggtttu uagttagggt tuutgggtga uatuttuutt 120
utgggggaag auagagtuaa atgagaaayg tgagttgagu uuaggggaaa ggatuatuyg 180
ggagatguut gaggggutuu aggguatygt aatututtgu tuagutggua gagtggggut 240 gauayggua gutgututut ggagtuutyg guuttuutgt ttuuuuutga ggautttgag 300

<210> SEQ ID NO 54
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 54
tuaaagtuut uagggggaaa uaggaagguy gaggautuua gagaguagut gguygtgtua 60
guuuuautut guuagutgag uaagagatta ygatguuutg gaguuuutua gguatutuuy 120
ggatgatuut ttuuuutggg utuaautuay gtttutuatt tgaututgtu ttuuuuuaga 180
aggaagatgt uauuuaggaa uuutaautgg aaauyggaua gttauuaggg uauuuaaaau 240
uuaatatttg gttattautt uatuuttgau uttuattuua ttuattuuua gutguagaua 300

<210> SEQ ID NO 55
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 55
uuagtguaga auagguautg uuuauuatau agguuagaag aggtguuutu tuuauautgg 60
uuautgaaau tautuautgg uaguagtggg tguuauttgg aaaauaagat gguuutuuut 120
guagaguagg uuauuutguy ggaggtgtuu ygatgygtgt gaaguagggt tggagguaua 180
utauagguau tututagtuu ttuaaauaau autgtagtgt agatuttgtt ggttutttua 240
gagaagggga aayggaaaut uauagaagua autagaggag tgagtagaag uuuaggtatg 300

<210> SEQ ID NO 56
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 56
uatauutggg uttutautua utuututagt tguttutgtg agtttuygtt tuuuuttutu 60
tgaaagaauu aauaagatut auautauagt gttgtttgaa ggautagaga gtguutgtag 120
tgtguutuua auuutguttu auayguatyg ggauauutuy gguagggtgg uutgututgu 180 agggagggu atuttgtttt uuaagtggua uuuautgutg uuagtgagta gtttuagtgg 240
uuagtgtgga gaggguauut uttutgguut gtatggtggg uagtguutgt tutguautgg 300

<210> SEQ ID NO 57
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 57
tuygguatua attuttaatg agtuuuygag uuuuyguagt uutgtutaut tuttttuttt 60
tuuagtgaat uutuauagtu uuutttuuut guatgttutu tgtuuuaaat ttutgaaguu 120
uutuuutttu ygtututtaa gaatututay gaauuygaaa guuygtgagg utgatgguay 180
gtutgtggtt uutttutuut tuttuuutuu atauuuauag utuuuyggga uyggauuutu 240
uuuautuauu aggtguaggg uuagggguag uaguaggagg aauaguuaua ggtagaggtg 300

<210> SEQ ID NO 58
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 58
uauututauu tgtggutgtt uutuutgutg utguuuutgg uuutguauut ggtgagtggg 60
gagggtuygg tuuyggggag utgtgggtat ggagggaaga aggagaaagg aauuauagay 120
gtguuatuag uutuaygggu tttygggtty gtagagattu ttaagagayg gaaagggagg 180
gguttuagaa atttgggaua gagaauatgu agggaaaggg gautgtgagg attuautgga 240
aaagaaaaga agtagauagg autgyggggg utyggggaut uattaagaat tgatguygga 300

<210> SEQ ID NO 59
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 59
aguutgtgut uaggaataau taaggagtgg aguyguatua auutuuttuu uaaatuygga 60
ygtuttuutu ygautuaagu uuaguutgag gguuattutu uttgattuau uuttggaaau 120
agauauuagu uaagggagut gtutuutggy gttgaygagg atuygattta ggtuagtatt 180
utagttuuua utuuauagag gaatutgaut ggagguuagu tgtggtygat gagtuatuyg 240
gaauauaagu agguagutat ttuygaauta aatgguatut gatutuuutu utuauuttga 300

<210> SEQ ID NO 60
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 60
tuaaggtgag gagggagatu agatguuatt tagttyggaa atagutguut guttgtgttu 60
yggatgautu atygauuaua gutgguutuu agtuagattu ututgtggag tgggaautag 120
aatautgauu taaatyggat uutygtuaay guuaggagau agutuuuttg gutggtgtut 180

-continued gtttuuaagg gtgaatuaag gagaatgguu utuaggutgg guttgagtyg gaggaagayg 240
tuyggatttg ggaaggaggt tgatgyggut uuautuutta gttattuutg aguauaggut 300

<210> SEQ ID NO 61
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 61
gauutuagga tutgaatggt tuttggagtt utttguagat gaggtaatgt tttggttaau 60
tuataggtua gauutgutgt uuttagutaa uttguuyggg aggtttttaa yggaagguut 120
gtgttaguau aaatuatatt tuutgatgay gaguagagau uttgatutgg tuttaaagaa 180
ygygttttuu aauttauuut gggautttt tgaattaguy gguuauatat auuagggttu 240
tuagaggatt ttttuuuuuu tttutututg tututttutg ggtttttuut attautaatt 300

<210> SEQ ID NO 62
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 62
attagtaata ggaaaaauuu agaaagagau agagagaaag gggggaaaaa atuututgag 60
aauuutggta tatgtgguyg gutaattuaa aaaagtuuua gggtaagttg gaaaaygygt 120
tutttaagau uagatuaagg tututgutyg tuatuaggaa atatgatttg tgutaauaua 180
gguuttuygt taaaaauutu uygggtuaagt tagutaagga uaguaggtut gauutatgag 240
ttaauuaaaa uattauutua tutguaaaga autuuaagaa uuattuagat uutgaggtuu 300

<210> SEQ ID NO 63
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 63
guutggaauu uyggygatut uttgtttutu uauuaaggga aututguttg taauauttta 60
aguutuagut gaaaagtggt utuutgggtg aagtutuauu tgtguauuua uutgagggtg 120
agtuagutut gutuuuutgg ututuauygy ggutgttata guatttauyg gagtuuuaua 180
gtgautuatt tgtuuatuau uutuuygaua aauuttuuag uttutgaagg guagagauag 240
uatuataatu atuttttata autuuygtgu utagtgutau tuuuaatuuu tagtaaguat 300

<210> SEQ ID NO 64
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 64
atguttauta gggattggga gtaguautag guaygggagt tataaaagat gattatgatg 60
utgtututgu uuttuagaag utggaaggtt tgtygggagg gtgatggaua aatgagtuau 120
tgtgggautu yggtaaatgu tataauaguy gyggtgagag uuaggggagu agagutgaut 180
uauuutuagg tgggtguaua ggtgagautt uauuuaggag auuauttttu agutgaggut 240
taaagtgtta uaaguagagt tuuuttggtg gagaaauaag agatyguygg ggttuuaggu 300

<210> SEQ ID NO 65
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 65
aatuuuttuu uygggatagt uaaygaggut ttuaatttaa auttguattt gaaguttgua 60
gagautuaua utgauttauu uagguuutaa uauauaguag utgtutuuat ggttgyguua 120
ggtagtgaag gatauagggu aguaggaaay gagtuuyggt tutuaggtgg atuuygtgut 180
tuuauututg ttagaguuua gguuutgagg guatagggu aaattguuau agagutuuag 240
agaaatutgt ututuuygtu uuuuauuuta agautgagut gutggaggaa agagguuagg 300

<210> SEQ ID NO 66
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 66
uutgguutut ttuutuuagu agutuagtut tagggtgggg gayggggagag auagatttut 60 utggagutut gtgguaattt gguuutatgu uutuagggu u tgggututaa uagaggtgga 120
aguaygggat uuauutgaga auygggauty gtttuutgut guuutgtatu uttuautauu 180
tggyguaauu atggagauag utgutgtgtg ttaggguutg ggtaagtuag tgtgagtutu 240
tguaaguttu aaatguaagt ttaaattgaa aguutygttg autatuuygg ggaagggatt 300

<210> SEQ ID NO 67
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 67
aggaatgttt autgaaggag tgaatgaaau tattguatta gatuaaguuu aggtguagag 60
gautggtttu auatagaaag uatygatttt guuutauaga auuutgautu uagttttuua 120
guagauaauu utggtgtgaa gauagagggg yggggaggaa ggtaggggut gauatttuuu 180
aguuuutuuu agguyggtgg ggagutgaat agutuagtga uttgtuuagg aguuygaggt 240
aaauuauaga utaagaguua agagtuatga ttuautautt guatttutuu aguuatgaua 300

<210> SEQ ID NO 68
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 68
tgtuatggut ggagaaatgu aagtagtgaa tuatgautut tggututtag tutgtggttt 60
auutygggut uutggauaag tuautgagut attuagutuu uuauygguut gggaggggut 120
gggaaatgtu aguuuutauu ttuutuuuyg uuuututgtu ttuauauuag ggttgtutgu 180
tggaaaautg gagtuagggt tutgtagggu aaaatygatg utttutatgt gaaauuagtu 240
ututguauut gggutlgatu taatguaata gtttuattua utuuttuagt aaauattuut 300

<210> SEQ ID NO 69
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 69
gutgggatta tatatguaua uuauuatguu yggutaattt ttatattttt ggtagagata 60
ggggttuuau uatgttgguu agggtggtut tgaauuuutg auutuaggtg atuuauuuau 120
uttgguutuu uagagtgutg ggattauagg ygtgaguuau tguauuyggu auaaaguuat 180
tttaaaauag uttttttttt ttttttgaaa uaguuttguu utgtaguuua ggutggagtg 240
tagtggtaua atutuagutu autguaauut uuauuttuyg ggttuaagtg attuttgtgu 300

<210> SEQ ID NO 70
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 70
guauaagaat uauttgaauu yggaaggtgg aggttguagt gagutgagat tgtauuauta 60
uautuuaguu tgggutauag gguaaggutg tttuaaaaaa aaaaaaaaag utgttttaaa 120
atggutttgt guygggtgua gtggutuayg uutgtaatuu uaguaututg ggagguuaag 180
gtgggtggat uauutgaggt uaggggttua agauuauuut gguuaaatg gtggaauuuu 240 tatututauu aaaaatataa aaattaguyg gguatggtgg tgtguatata taatuuuagu 300

<210> SEQ ID NO 71
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 71
aauaaatguu auagguuuta attguaggut uuaaggagtt gagattuuat autggggttg 60
utggagguag aaguuttuuu autttuagga uuyggauutg uuuttuuuuu aygyggtuuy 120
guuuaguuag utauauuutg guuauagagy gutuauaaag gutuagtgtg tgtatguygg 180
gutgautuau agtggttutg gguuuaggyg aggauuttut uagaggggyg gaagggguuu 240
tutuuutuut gguuattttu uatggggagu agtuagtaau uaggauuatg uuagauttua 300

<210> SEQ ID NO 72
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 72
tgaagtutgg uatggtuutg gttautgaut gutuuuuatg gaaaatgguu aggagggaga 60
ggguuuuttu yguuuututg agaaggtuut yguutgggu uagaauuaut gtgagtuagu 120
uygguataua uauautgagu utttgtgagy gututgtggu uagggtgtag utggutgggy 180
gggauygygt gggggaaggg uaggtuyggg tuutgaaagt gggaaggutt utguutuuag 240
uaauuuuagt atggaatutu aautuuttgg aguutguaat tagggutgt gguatttgtt 300

<210> SEQ ID NO 73
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 73
guagtgutau aauatuaatg uuaagguygt gggguagutg atggtttggg utuuuaautt 60
uuuaguuagg tguttutgua gguuuauatu ttguuuautg guuaaauutt taaataautt 120
tgautygggu taututtatg utuaaagayg tuaggggutu tuuuaaatut utttauuutg 180
uuagaaagtu ttutatagta ygguutuuau ttagutttua yguutgatut tuuatyguat 240
uutgutuata auutguuaut agtgaauuuu tgutgutuyg gutuuauaut tutuatgutg 300

<210> SEQ ID NO 74
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 74
aguatgagaa gtgtggaguy ggaguaguag gggttuauta gtgguaggtt atgaguagga 60
tgygatggaa gatuaggygt gaaagutaag tggagguygt autatagaag autttutggu 120
agggtaaaga gatttgggag aguuuutgay gtutttgagu ataagagtag uuygagtuaa 180
agttatttaa aggtttgguu agtggguaag atgtgggu ut guagaaguau utggutggga 240
agttgggagu uuaaauuatu agutguuuua ygguuttggu attgatgttg taguautguu 300

<210> SEQ ID NO 75
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 75
aggagggayg tggaagtygt gggtgguaga gaaaagtgtg uauygutggg aggtutattt 60
uaagaatagg ttgggatgag aaauatgtut gggygagggg ggtgggaggu uyggtgtuau 120
utgtggatgg atuuauaguu utguaattgy gtgttguaaa gtttguuygg uuuyguattu 180
attttgaagg ttuttggyga tguutygaut tttyguutua aagaagtgag ututuataag 240
gttuagaggu ygggaguuaa agygggagtg aagaututyg aggggtuuaa atgaaguaga 300

<210> SEQ ID NO 76
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 76
tutguttuat ttggauuuut ygagagtutt uautuuygut ttggutuuyg guututgaau 60
uttatgagag utuauttutt tgaggygaaa agtygaggua tyguuaagaa uuttuaaaat 120
gaatgygggg uyggguaaau tttguaauay guaattguag ggutgtggat uuatuuauag 180
gtgauauygg guutuuuauu uuuutyguuu agauatgttt utuatuuuaa uutattuttg 240
aaatagauut uuuagyggtg uauauttttu tutguuauuu aygauttuua ygtuuutuut 300

<210> SEQ ID NO 77
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 77
uutttttgau utggygagtu uuttuuuttt uuatttuatt ttattguttt ttattgtttu 60 uutuyggput uttutuuuut uutaggtutt ttututagut uagtttggag utuauatuut 120
ttuuauuutt ttuauutuut uuttuutuyg uuuuaggatt atuuutggga uuuatuutga 180
gutgaguuta uaguuaguua guuaygaaat agaggtgygy gggggtaggg tggtatggag 240
attutgyggu utttgatttg auauutuuyg gagutauygu uauagguutg uuuatttuau 300

<210> SEQ ID NO 78
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 78
tgaaatgggu agguutgtgg yggtagutuy gggaggtgtu aaatuaaagg uyguagaatu 60
tuuatauuau uutguuuuyg yguauututa tttygtggut ggutggutgt aggutuagut 120
uaggatgggt uuuagggata atuutggggy ggaggaagga ggaggtgaaa agggtggaaa 180
ggatgtgagu tuuaaaatga gutagagaaa agauutagga ggggagaaga gguyggaggg 240
aaauaataaa aaguaataaa atgaaatgga aagggaaggg autyguuagg tuaaaaaggu 300

<210> SEQ ID NO 79
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 79
gutuagtttg gagutuauat uutttuuauu uttttuauut uutuuttuut uyguuuuagg 60
attatuuutg ggauuuatuu tgagutgagu utauaguuag uuaguuayga aatagaggtg 120
ygygggggua gggtggtatg gagattutgy gguutttgat ttgauauutu uyggagutau 180
yguuauaggu utguuuattt uauutguygg gaagataaut ttggutttg gtggtgggtg 240 ggtgattgau tutuaaaatu uaaaguattg gttttttutg ggttauttuu tatgautgut 300

<210> SEQ ID NO 80
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 80
aguagtuata ggaagtaauu uagaaaaaau uaatgutttg gattttgaga gtuaatuauu 60
uauuuauuau uagaaguuaa agttatuttu uyggagguagg aaatgggguag guutgtggyg 120 gtagutuygg gaggtgtuaa atuaaagguy guagaatutu uatauuauuu tguuuuygyg 180
uauututatt tygtggutgg utggutgtag gutuagutua ggatgggtuu uagggataat 240
uutggggygg aggaaggagg aggtgaaaag ggtggaaagg atgtgagutu uaaautgagu 300

<210> SEQ ID NO 81
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 81
uattuuaaut tutguaauua tguauagtga tygatattta taattauutt tttuuttuau 60
uatgguaauy gggtuutuyg aygaguagga utgaagaagg aaygaggaat aaaututggg 120
agtggaagyg yguutyggua gauagatuyg ygggygutgg gguaguuagg agaaguuuyg 180
guatuygutt gtgaggtuyg gggutgtggt utygagtuuy guuuyguuty ggygggguuuy 240 gutuuuatgu uyguuuygut atyguuuuyg ygututtutu yguuyguuyg uygagutgua 300

<210> SEQ ID NO 82
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 82
tguagutygg ygggygggyg gagaagagyg ygggggygat agyggggygg guatgggagy 60 ggggguuyguy gaggyggggy gggautygag auuauaguuu yggauutuau aagyggatgu 120
ygggguttut uutggutguu uuagyguuyg yggatutgtu tguygaggyg yguttuuaut 180
uuuagagttt attuutygtt uuttuttuag tuutgutygt yggaggauuy ggttguuatg 240
gtgaaggaaa aaggtaatta taaatatyga tuautgtgua tggttguaga agttggaatg 300

<210> SEQ ID NO 83
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 83
tatgatguua gtggttgaat auuttagtag agaaaaatut tgaataatua auyggaggtt 60
uaggagauag utgggtattt gagaguutat gagtuauata aguaauuttg gaguuaagtt 120
gtattututg tttgguutua gaguuagtut ygaguauatg uaguuagaut guyggguagag 180 aagatgtgga gutgguattu tgguttaggu utgaguaagg tygtggaagu uuuaggttuu 240
tgauuatggu uyguauagag uuatgutuua guuutgggtu tuaguaggua guuaggtgag 300

<210> SEQ ID NO 84
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 84

-continued

```
utuauutggu tguutgutga gauuuagggu tggaguatgg ututgtgygg guuatggtua     60

ggaauutggg guttuuayga uutgutuag guutaaguua gaatguuagu tuuauatutt    120

ututguyggu agtutggutg uatgtgutyg agautggutu tgagguuaaa uagagaatau    180

aauttggutu uaaggttgut tatgtgautu ataggututu aaatauuuag utgtutuutg    240

aauutuyggt tgattattua agatttttut utautaaggt attuaauuau tgguatuata    300
```

<210> SEQ ID NO 85
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 85

```
ggggutygua gtgguutagt utgututggg utttgutgga tguuuttyga gaatuauygy     60

guaauutuut tuagagguuu aauautuuay gtgutgautt uuygggguutg tgtutuuuut    120

guyguagaut gaagygttuu yggutgaagg tgaggttutg uauuaaygag tyguagaagt    180

uuygggguaga gutggtgggg uagutttaga ggutgggatt tgauatutut gaguaggagg    240

tgauyguuuy gguauuagut guutguuaga tuutgaagga guaagguutg ygauuatauu    300
```

<210> SEQ ID NO 86
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 86

```
ggtatggtyg uagguuttgu tuuttuagga tutgguaggu agutggtguy ggggyggtua     60

uutuutgutu agagatgtua aatuuuagu tutgaagutg uuuuauuagu tutguuyggg    120

auttutgyga utygttggtg uagaauutua uuttuaguyg ggaayguttu agtutgyggu    180

aggggagaua uagguuyggg aagtuaguay gtggagtgtt ggguutgtga aggaggttgy    240

gyggtgattu tygaagggua tuuaguaaag uuuagaguag autagguuau tgygaguuuu    300
```

<210> SEQ ID NO 87
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 87

```
gyggggguuag uagygtguuy ggygggaagy ggtauaggyg utuygggaag uygyguauua     60

gutguttuag uauuatguyg utuaggtygg uygtgututu utgygayggg ttgaagatgy    120

ggaygaautt utuuygguag utuauaguua ygatuttuag guutgtyggg utgggaagag    180

aggagaygut gtgaggagat gygguyggtu uauuyguaua gutgygyguu uyguuyggaa    240

auuagutuua gtuyggyguy ggaggutggg gtuautyguu uuttauutut guaggagttu    300
```

<210> SEQ ID NO 88
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 88
gaautuutgu agaggtaagg ggygagtgau uuaaguutuy ggyguyggau tggagutggt 60
ttuygggygg ggygyguagu tgtgygggtg gauyggguygu atutuutuau agygtutuut 120
ututtuuuag uuygauaggu utgaagatyg tggutgtgag utguygggag aagttygtuy 180
guatuttuaa uuygtyguag gagaguaygg uygauutgag ygguatggtg utgaaguagu 240
tggtgygygg uttuuyggag yguutgtauy guttuuyguy ggguaygutg utgguuuygu 300

<210> SEQ ID NO 89
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 89
aggagtgttt ggggtguttu ututtggutg uagtgggaua uaggtgtguu ttuutaggaa 60
utggguuutg autauttuua guuuaauaut uuygggguutg tgaautgtga uutgtgtguy 120
gggatgggtt ttgtgggtut guuuuatuuu yguautgutg gatutgguua agtgggtgaa 180
ggutaagguy ggtuagagtt gagtttutgu uttgtuuuut utuutgggut agatguuaua 240
uuagguuuag tgautuatag gguagguagt tgggaaatau uagguagagg guaggtuutg 300

<210> SEQ ID NO 90
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 90
uaggauutgu uututguutg gtatttuuua autguutguu utatgagtua utggguutgg 60
tgtgguatut aguuuaggag aggggauaag guagaaautu aaututgauy gguuttaguu 120
ttuauuuaut tgguuagatu uaguagtgyg gggatggggu agauuuauaa aauuuatuuy 180
gguauauagg tuauagttua uagguuyggg agtgttgggu tggaagtagt uaggguuuag 240
ttuutaggaa gguauauutg tgtuuuautg uaguuaagag gaaguauuuu aaauautuut 300

<210> SEQ ID NO 91
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 91
guaggaatua gguuagygta tgtaatgaaa aututtgygt tatuttttta gaaggatgtg 60
autgtatttt atgagtatgu aguagggtua uuauauauut tttgutuutg gguuuutuuu 120
utgtgtgtag uuuagguuuy ggtttgtgut ygaggguuag ayggguuutat ggtuuuuagt 180 ttuutuygta gatuauauag ggagguagyg agguagggtg uaaggatgtt aggggtggaa 240
ggggtgauau ygggaguaaa gautgutauu uuttgguutg gataaauutg tutgauattu 300

<210> SEQ ID NO 92
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 92
gaatgtuaga uaggtttatu uagguuaagg ggtaguagtu tttgutuuyg gtgtuauuuu 60
ttuuauuuut aauatuuttg uauuutguut ygutguutuu utgtgtgatu tayggaggaa 120
autggggauu ataggguygt utgguuutyg aguauaaauy ggggguutggg utauauauag 180 gggaggggguu uaggaguaaa aggtgtgtgg tgauuutgut guatautuat aaaatauagt 240
uauatuuttu taaaaagata ayguaagagt tttuattaua taygutgguu tgattuutgu 300

<210> SEQ ID NO 93
<211> LENGTH: 301
<212> TYPE: DNA
<213> ORGANISM: Artificial Sequence
<220> FEATURE:
<223> OTHER INFORMATION: Synthetic polynucleotide

<400> SEQUENCE: 93
tgautgtatt ttatgagtat guaguagggt uauuauauau uttttgutuu tggguuuutu 60
uuutgtgtgt aguuuagguu uyggtttgtg utygagggguu agaygguuut atggtuuuua 120
gtttuutuyg tagatuauau agggagguag ygagguaggg tguaaggatg ttaggggtgg 180
aaggggtgau auygggagua aagautguta uuuuttgguu tggataaauu tgtutgauat 240
tuuygauutu tgaagtuatu uatuatggut gygutggutu agauauttua aggguuautt 300
t 301

<210> SEQ ID NO 94
<211> LENGTH: 301
<212> TYPE: DNA
<213> ORGANISM: Artificial Sequence
<220> FEATURE:
<223> OTHER INFORMATION: Synthetic polynucleotide

<400> SEQUENCE: 94
aaagtgguuu ttgaagtgtu tgaguuagyg uaguuatgat ggatgauttu agaggtyggg 60
aatgtuagau aggtttatuu agguuaaggg gtaguagtut ttgutuuygg tgtuauuuut 120
tuuauuuuta auatuuttgu auuutguuty gutguutuuu tgtgtgatut ayggaggaaa 180
utggggauua taggguygtu tgguuutyga guauaaauyg ggguutgggu tauauauagg 240 ggaggggguuu aggaguaaaa ggtgtgtggt gauuutgutg uatautuata aaatauagtu 300
a 301

<210> SEQ ID NO 95
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 95
uauauauutt tuagttgagg ggygutgagg tuuutgutgt tgutgtguyg tutgauutgt 60
uuuutututu tgauagagag uuagutgutu uuygggaaua auttuauuaa tgagtguaau 120
atauuaggua auttuatgtg uaguaatgga yggtguatuu ygggyguutg guagtgtgay 180
gggutguutg autguttyga uaagagtgat gagaaggagt guygtgagtg guutgguuut 240
ttgutggggt ggggtgguag uuatuutggg guagagggga guaggtuutg aguaggutta 300

<210> SEQ ID NO 96
<211> LENGTH: 300

<212> TYPE: DNA
<213> ORGANISM: Artificial Sequence
<220> FEATURE:
<223> OTHER INFORMATION: Synthetic polynucleotide

<400> SEQUENCE: 96
taaguutgut uaggauutgu tuuuutugu uuuaggatgg utguuauuuu auuuuaguaa 60
aggguuaggu uautuayggu autuuttutu atuaututtg tygaaguagt uagguaguuy 120
gtuauautgu uaggyguuyg ggatguauyg tuuattgutg uauatgaagt tguutggtat 180
gttguautua ttggtgaagt tgttuuyggg gaguagutgg utututgtua gagagagggg 240
auaggtuaga ygguauagua auaguaggga uutuagyguu uutuaautga aaggtgtgtg 300

<210> SEQ ID NO 97
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 97
uatguatttt gtgtttgtag tgtgutgguu aygggaguau tutaaauaua ttatggguyg 60
ggyguagtgg utuygguutg taatutuagu autttgggag gutgaggygg guagatuaut 120
tgaguuuagg agttygauau uaguutgguu aauayggyga aauuuygtut utautaaaaa 180
tauaaaaatt aauygggtgt gatggygygt guutgtattu uuagutauta gggaggutga 240
gguaggagaa tutuutgaau utgggaggua gggautguag tgaguuaaga ttgtguuaut 300

<210> SEQ ID NO 98
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 98
agtgguauaa tuttggutua utguagtuuu tguutuuuag gttuaggaga ttutuutguu 60
tuaguutuuu tagtagutgg gaatauaggu aygyguuatu auauuyggtt aatttttgta 120
tttttagtag agayggggtt tyguygtgtt gguuaggutg gtgtygaaut uutgggutua 180
agtgatutgu uyguutuagu utuuuaaagt gutgagatta uagguyggag uuautgyguu 240
ygguuuataa tgtgtttaga gtgutuuygt gguuaguaua utauaaauau aaaatguatg 300

<210> SEQ ID NO 99
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 99
ggautgtggg uuuuttggtt tgtgtutgaa agutgggggt auagttutgu atgggttggu 60
uuutguutta uutygggaag utuuuagagu utgutgggua guutguutuu tuututuauu 120
tuutuygtut uuautuuutu utuauuauat tuyggututu uuayggguygg agguygtgaa 180 tgggutgutt tgttguuygg uuuauauagg aggatggtgg uagaagauuu ygguauaaag 240
tuaguauuua ututgttuuu aggutgggtt uagggaggut gaaaaguuau ttuagutgtg 300

<210> SEQ ID NO 100

<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 100
uauagutgaa gtggutttu aguutuuutg aauuuaguut gggaauagag tgggtgutga 60
utttgtguyg gggtuttutg uuauuatuut uutgtgtggg uyggguaaua aaguaguuua 120
ttuaygguut uygguygtgg gagaguygga atgtggtgag gagggagtgg agayggagga 180
ggtgagagga ggagguaggu tguuuaguag gututgggag uttuuygagg taagguaggg 240
guuaauuuat guagaautgt auuuuuagut ttuagauaua aauuaagggg uuuauagtuu 300

<210> SEQ ID NO 101
<211> LENGTH: 301
<212> TYPE: DNA
<213> ORGANISM: Artificial Sequence
<220> FEATURE:
<223> OTHER INFORMATION: Synthetic polynucleotide

<400> SEQUENCE: 101
tautututtg atgtatgauu ttggatgtga tttaguutut utggguuttg guuuygutga 60
auuatgtgat uagaguauua aguygguutu uuaygutggt utgagutgut uaaggguuat 120
utaggtuutu tttgtuuuaa guuagaggty guututuuuy gguuaaguyg yggutatggg 180
ggtggtggta uaauagagag uauagggaut ttggaauaua auautgggtu atgauuuutg 240
uutgguuaut uttggutgut gauuttgauu ututgtutuu tuutttgtga atgggggggag 300 t 301

<210> SEQ ID NO 102
<211> LENGTH: 301
<212> TYPE: DNA
<213> ORGANISM: Artificial Sequence
<220> FEATURE:
<223> OTHER INFORMATION: Synthetic polynucleotide

<400> SEQUENCE: 102
autuuuuuua ttuauaaagg aggagauaga gggtuaaggt uaguaguuaa gagtgguuag 60
guaggggtua tgauuuagtg ttgtgttuua aagtuuutgt gutututgtt gtauuauuau 120
uuuuataguy gyggguttggu ygggggagagg ygauututgg uttgggauaa agaggauuta 180
gatgguuutt gaguagutua gauuagygtg ggagguyggu ttggtgutut gatuauatgg 240
ttuagygggg uuaagguuua gagaggutaa atuauatuua aggtuataua tuaagagagt 300
a 301

<210> SEQ ID NO 103
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 103
guuatggaga aaatatguua tgtutuuatg gaaauuaauu tatttgutta autgaggttu 60
tgggggtggt tutgauautu agtgutaauu agggggagtu tggutgtgag gtygtuagua 120
uatggyggtg utguyggutg uutuuuaygu ayguaggutu tguuaguutg uuttguuaat 180
utguuaggua autgggauag gtguagauat gauuuaggut uuaaguauay guatuuauuu 240
tuuuyguyga gguaututuu yggtguuata tgttgautut guuuagyguu agguaguuua 300

<210> SEQ ID NO 104
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 104
tgggutguut ggygutgggu agagtuaaua tatgguauyg ggagagtguu tyggygggga 60
gggtggatgy gtgtguttgg aguutgggtu atgtutguau utgtuuuagt tguutgguag 120
attgguaagg uaggutggua gaguutgygt gygtgggagg uaguyggaag uauyguuatg 180
tgutgaygau utuauaguua gautuuuuut ggttaguaut gagtgtuaga auuauuuuua 240
gaauutuagt taaguaaata ggttggtttu uatggagaua tgguatattt tutuuatggu 300

<210> SEQ ID NO 105
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 105
gagtutggut gtgaggtygt uaguauatgg yggtgutguy ggutguutuu uayguaygua 60
ggututguua guutguuttg uuaatutguu agguaautgg gauaggtgua gauatgauuu 120
aggutuuaag uauayguatu uauuutuuuy guygagguau tutuuyggtg uuatatgttg 180
aututguuua gyguuaggua guuuagyguu uauutuuuuu tuuuuaguut gguuuuaygu 240
auagtgutut aguutuutgut gggtagtgtg aggagtggua atutguaggu auuutagaag 300

<210> SEQ ID NO 106
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 106
uttutagggt guutguagat tguuautuut uauautauuu aguagaggut agaguautgt 60 gygtggggguu aggutgggga gggggaggtg ggygutgggu tguutggygu tggguagagt 120
uaauatatgg uauygggaga gtguutyggy ggggagggtg gatgygtgtg uttggaguut 180
gggtuatgtu tguauutgtu uuagttguut gguagattgg uaagguaggu tgguagaguu 240
tgygtgygtg ggagguaguy gguaguauyg uuatgtgutg aygauutuau aguuagautu 300

<210> SEQ ID NO 107
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 107
guygaatuuy gaggguygag uauuuutuuu tuaguyguau tguauutguu ygtaggtgau 60
uaauuuaygg gyggauuuuu agauuuaatu ututuuagag uuagggtggg atgguaggg 120 auaggaguyg gagguuutau tgguuuyggg ygaagguatu utggaaagua tuuagagygt 180
uuaguatuuu tuuygyggcu auuyguaggu tgauygauuu utggguagau uutuagautu 240
aatuuagtuu agggyggatt aaggagtggg agauaaggga guyggtgguu uygutgguuu 300

<210> SEQ ID NO 108
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 108
ggguuagygg gguuauyggu tuuuttgtut uuuautuutt aatuyguuut ggautggatt 60
gagtutgagg gtutguuuag gggtyggtua guutgyggt gguygyggga gggatgutgg 120
aygututgga tgutttuuag gatguuttyg uuyggggpuua gtaggguutu yggutuutgt 180
uuutguuuat uuuauuutgg ututggagag gattgggtut gggggtuygu uygtgggttg 240
gtuauutayg gguaggtgua gtgyggutga gggaggggtg utygguuuty gggattyggu 300

<210> SEQ ID NO 109
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 109
ttguttgauu aaaagaatgu aguagauata autttgagau utggagutag gtuauaagay 60
gatttuutgg gttttgtgga attutygttu tgaaagaaau aaguuauuaa gtgguyggt 120 gagutggutu ayguutgtaa tuuuaguaut ttgggagguy gaguygguy gatuauaagg 180 tuaggagaty gagauuatuu tggutaauat ggtgaaauuu ygtututaut aaaaatauaa 240
aaaaattagu yggguataut ggyggggyguu tgtagtuuua gutautyggg aggutgaggu 300

<210> SEQ ID NO 110
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 110
guutuaguut uuygagtagu tgggautaua ggyguuyguu agtatguuyg gutaattttt 60
ttgtattttt agtagagayg gggtttuauu atgttaguua ggatggtuty gatutuutga 120
uuttgtgaty gguuygguty gguutuuuaa agtgutggga ttauaggygt gaguuagutu 180
auuygguuau ttggtggutt gtttutttua gaaygagaat tuuauaaaau uuaggaaaty 240
gtuttgtgau utagutuuag gtutuaaagt tatgtutgut guattutttt ggtuaaguaa 300

<210> SEQ ID NO 111
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 111
agaatutguu taguaggygg ututuuuutg utuuuuuauy gaguauagau ygtgggaggg 60
gauuutgygg gaggaggutg uttuagtutu uagagauuat utuuuatutu tauagygaut 120
uuuutatgau ygtuuuuuau uyggtgutut ygggguuaygg ggaagggaua utygggaaag 180
auauuagaga uygggagggt guagutgggu tuttygyggg gagygggygg gagguuttuu 240
tgttauatgt yguagutggg auauagaygg uagygutuua gggtuuautt guyggutty g 300

<210> SEQ ID NO 112
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 112
ygaaguyggu aagtggauuu tggagygutg uygtutgtgt uuuagutgyg auatgtaaua 60
ggaagguutu uyguuygutu uuygygaaga guuuagutgu auuutuuygg tututggtgt 120
utttuuygag tgtuuuttuu uygtgguuyg agaguauygg gtgggggayg gtuataggg g 180 agtygutgta gagatgggag atggtututg gagautgaag uaguutuutu uyguagggtu 240
uuutuuuayg gtutgtguty ggtgggggag uaggggagag uyguutguta gguagattut 300

<210> SEQ ID NO 113
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 113
agguuuaggu agaggtuaga guuuaaguuu tgtuuuygaa ggaaatgtgt uuuatgutaa 60
utautuuata gutgagguut ggagggaagt uagggauuut gggautggtt atuutgguut 120
tgautuatta utgttuygga gauutaaayg uauuutgagu uauuagaygt gggtgttaau 180
auutgaggtu aauuuuutga yguttuyggu tgututggag gaagutggtu utuuutuuua 240
uutuutgttt tuygtguuag uutggtauag agtuaagggg uttggutggg uttggutggg 300

<210> SEQ ID NO 114
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 114
uuaguuaagu uuaguuaagu uuuttgautu tgtauuaggu tgguayggaa aauaggaggt 60
gggagggagg auuaguttuu tuuagaguag uyggaagygt uagggggttg auutuaggtg 120
ttaauauuua ygtutggtgg utuagggtgy gtttaggtut uyggaauagt aatgagtuaa 180
gguuaggata auuagtuuua gggtuuutga uttuuutuua gguutuagut atggagtagt 240
taguatggga uauatttuut tyggggauag gguttgggut utgauututg uutggguutg 300

<210> SEQ ID NO 115
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 115
uuuatgutaa utautuuata gutgagguut ggagggaagt uagggauuut gggautggtt 60
atuutgguut tgautuatta utgttuygga gauutaaayg uauuutgagu uauuagaygt 120

-continued gggtgttaau auutgaggtu aauuuuutga yguttuyggu tgututggag gaagutggtu 180
utuuutuuua uutuutgttt tuygtguuag uutggtauag agtuaagggg uttggutggg 240
uttggutggg utuagaaayg tgguagtuag gaguuaguut gygggtuagyg gggtgutggg 300

<210> SEQ ID NO 116
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 116
uuuaguauuu ygutguuygu aggutggutu utgautguua ygtttutgag uuuaguuaag 60
uuuaguuaag uuuuttgaut utgtauuagg utgguaygga aaauaggagg tgggagggag 120
gauuaguttu utuuagagua guyggaagyg tuagggggtt gauutuaggt gttaauauuu 180
aygtutggtg gutuagggtg ygtttaggtu tuyggaauag taatgagtua agguuaggat 240
aauuagtuuu agggtuuutg auttuuutuu agguutuagu tatggagtag ttaguatggg 300

<210> SEQ ID NO 117
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 117
ututuuuygu agtttuatuy gtuutuutuu uyguututgy gagutgggtt tggggaygtu 60
tgggtggaat gtagauuuau aggutgtuut tggtguuutt uutuuutgtt utuuagyguu 120
uuaguuuuag auauuagtuu uuuagygggy gaaaguuygg gagyguuttu uuygaaagau 180
atuagggtgu uaygygguuu utguuutgua gaaguatuuu uutuuyguuu utguutggaa 240
aguagguuuu tuuutaagut utgyguuutt uttuuutggg yguuutygga uygtgguuyg 300

<210> SEQ ID NO 118
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 118
yggguuaygg tuygagggyg uuuagggaag aagggyguag aguttaggga ggggauutgut 60 ttuuagguag gggygggagg gggatguttu tguagggguag ggguygygtg guauuutgat 120
gtutttyggg gaaggygutu uygggutttу guuygutggg ggautggtgt utggggutgg 180
ggygutggag aauagggagg aagggauauua aggauaguut gtgggtutau attuuauuua 240
gaygtuuuua aauuuaguty guagaggygg ggaggaggay ggatgaaaut gyggggagag 300

<210> SEQ ID NO 119
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 119
agaggagtgg ggagyguagu agggtgguuu uygutuuygu tuagaggagu tgguuuttta 60
agguuagguu uaggygggty gggaauagag auuygggaat gtgggutgga utggggagua 120
gaguuauuua guatgagtua ttuuygttty guyggautut tyguygutgg ututyguttg 180
uyguuutuuu utgguuutgg uuutgguutu tgyguuutuu utguagagut ggtuygggtg 240
ggutggyggu utuuauuygu uauaagygua uagggututg uuuautuuuy guuuuttttu 300

<210> SEQ ID NO 120
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 120
gaaaaggggy ggggagtggg uagaguuutg tgyguttgtg gygggtggag guyguuaguu 60
uauuyggauu agututguag ggagggygua gagguuaggg uuaggguuag gggagggygg 120
uaagygagag uuagyggyga agagtuyggy gaaaygggaa tgautuatgu tgggtggutu 180
tgutuuuuag tuuaguuuau attuuygggt ututgttuuy gauuyguutg gguutgguut 240
taaaggguua gutuututga gygggagygg ggguuauuut gutgygutuu uuautuutut 300

<210> SEQ ID NO 121
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 121
guygagygyg gtggutuatg uutgtaatuu uaguautttg ggagayggag gtgggtggat 60
uauutuaggt uagaagtttg agauututgt ututautgaa autataaaaa attgguyggg 120
uatggtggtg ggtgtutgta gttuuaguta ygtggtaagu tgagguagga gaatgauttg 180
aauuygggag gyggaggttg uagtgaguua ggattgyguu autguautuu aguutgggag 240
auagagtuag aututgtutu aaaaaaaagu tatggguutg uaggatguut aatataaaag 300

<210> SEQ ID NO 122
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 122
uttttatatt agguatuutg uagguuuata guttttttt gagauagagt utgautuutgt 60 utuuuaggut ggagtguagt ggyguaatuu tggutuautg uaauutuygu utuuygggtt 120
uaagtuattu tuutguutua guttauuayg tagutggaau tauagauauu uauuauuatg 180
uuygguuaat tttttatagt ttuagtagag auagaggtut uaaauttutg auutgaggtg 240
atuuauuuau utuygtutuu uaaagtgutg ggattauagg uatgaguuau ygygutyggu 300

<210> SEQ ID NO 123
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 123
uaygutuutg tttuautttu atgttutgut utgtauauut ggutuyguut tutagatagu 60

-continued aataguagaa ttagtgaaag tattaaagtu tttgatuttt utgagaagag uatagaagaa 120
ataatgaygt aagutgtuut ututuuagut yggutauuta aaagggaaag guuuuutgtu 180
yggtggauay gtgautuaua tgauuttatt aatuautgga gatgautuau autuuttauu 240
utguuuuttt guuttgtaua uaataaataa uagygygauu agguattygg gguuautguu 300

<210> SEQ ID NO 124
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 124
gguagtgguu uygaatguut ggtygygutg ttatttattg tgtauaaggu aaagggguag 60
ggtaaggagt gtgagtuatu tuuagtgatt aataaggtua tgtgagtuay gtgtuuauyg 120 gauaggggu utttuuuttt taggtaguyg agutggagag aggauagutt aygtuattat 180
ttuttutatg ututtutuag aaagatuaaa gautttaata utttuautaa ttutgutatt 240
gutatutaga aggyggaguu aggtgtauag aguagaauat gaaagtgaaa uaggagygtg 300

<210> SEQ ID NO 125
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 125
aguuuuutgg gyggggtuyg gggaguaggu uyguatttgg aggauagggt gtgauuuatu 60
tgaatuutyg ttaaagtaaa aguygauyga yggututggg aggtttgagg uutggygggg 120
ygguuuyggg aagtgatttg tgguygutag gygygygutg gaaauuuttt uuuatutgyg 180
gaguuuauyg gagutgtgat yggaggagga attuuuuuag guagggagga uyguagggu 240 tttttuauty gtuutgaggg guuutggggu ttggggagua aauutggggt gauuuatttu 300

<210> SEQ ID NO 126
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 126
gaaatgggtu auuuuaggtt tgutuuuuaa guuuuagggu uuutuaggay gagtgaaaaa 60
gguuutgygg tuutuuutgu utgggggaat tuutuutuyg atuauagutu yggtgggutu 120
yguagatggg aaagggtttu uagygygygu utagygguua uaaatuautt uuygggguyg 180
uuuyguuagg uutuaaauut uuuagaguyg tyggtyggut tttautttaa ygaggattua 240
gatgggtuau auuutgtuut uuaaatgygg guutgutuuu yggauuuygu uuagggggut 300

<210> SEQ ID NO 127
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 127
uatuuauaaa uutuuuaggu uuuutuautu ttuuyguaua gtutguutuy ggtgutuuag 60
aaagautgga aatgaggtga gutuuuttgg atuuutguut guuauutgua aatatuatgt 120
ggtgutautt guuutuutgt uuutuutuuy gtuuuagguu aatuutuuua uuuuuttaat 180
tguuygggga tutuuattau ttaaauuttt uuautggtau ututuutuuu auauaaguut 240
uutuagutgt tttuygtutt taauuaauau uttuuutggu tuuagutaut guuauttuat 300

<210> SEQ ID NO 128
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 128
atgaagtggu agtagutgga guuagggaag gtgttggtta aagayggaaa auagutgagg 60
agguttgtgt gggaggagag gtauuagtgg aaaggtttaa gtaatggaga tuuuygggua 120
attaaggggg tgggaggatt gguutgggay gggaggaggg auaggagggu aagtaguauu 180
auatgatatt tguaggtggu agguagggat uuaagggagu tuauutuatt tuuagtuttt 240
utggaguauy ggagguagau tgtgygggaa gagtgagggg guutgggagg tttgtggatg 300

<210> SEQ ID NO 129
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 129
utttuuuagg autguuttgg uuuuutgguu uuagtutgga ggaututtgu tuauttuutu 60
yguuuuuagg tgagutgaga auuuautgyg ygygggautu tgutgyguut guuutuuygg 120
gutguagagg guaggaygua uyguuaggua agguygyggu tutgygutga tguuautuyg 180
ggagygggtg gutgyggggg aggagggyga guautggayg gggguagygg agtgtagggt 240
gtgagatuta aauagagggu tuuautggag gguttguuua gaaggyggua gtuauautgg 300

<210> SEQ ID NO 130
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 130
uuagtgtgau tguyguuttu tggguaaguu utuuagtgga guuututgtt tagatutuau 60
auuutauaut uygutguuuu ygtuuagtgu tyguuutuut uuuuyguagu uauuygutuu 120
yggagtggua tuagyguaga guygygguut tguutggygg tgygtuutgu uututguagu 180
uygggagggu aggyguagua gagtuuygyg yguagtgggt tutuagutua uutgggggyg 240
gaggaagtga guaagagtuu tuuagautgg gguuaggggg uuaagguagt uutgggaaag 300

<210> SEQ ID NO 131
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 131

-continued

```
tttagggtut ututuuyguu tuttttuutu uuuygutuuu tututuuttg yggutgautu     60

uagutuuuuu tyggtguuyg taauuutuut ttuututttt tguyguagtu tuygtututu    120

ttuuauaggg tututuuutu uuuutututuu ygtggttgtu agautttutu utggautttu    180

tuyguuuygu auyguuyguu uyggatguyg agygtggtag aututguagu ygggutuuty    240

gutguuygut ggygutguut auauuuuutt gggutuuuut uuaaggtuuu utuygutygu    300
```

<210> SEQ ID NO 132
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 132

```
gygagyggag gggauuttgg aggggaguuu aagggggtgt agguagyguu agygggguagy     60

gaggaguuyg gutguagagt utauuaygut ygguatuygg ggygggyggt gyggggygga    120

gaaagtuuag gagaaagtut gauaauuayg gggagagggg gagggagaga uuutgtggaa    180

gagagaygga gautgyggua aaaagaggaa aggagggtta ygggguauyga gggggagutg    240

gagtuaguyg uaaggagaga gggagygggg gaggaaaaga ggygggagag agauuutaaa    300
```

<210> SEQ ID NO 133
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 133

```
gaggguuaua gtaaautgga uaagtttttu tguuuaguut aggutguuau utgtaggtua     60

uttgggutuu agutatgtgg utguututtu tgutgggtgu uttaututgg guagtgutgt    120

ggttgutuag ggauygguag aguutguuyg uuaguaatgu utttgtuttu atuauyggut    180

gtgautuagg utttgggygu uttutgguau tguagutgga uuagagaggu ttuygagtuu    240

tgguuagutg uutgauuuuu tuygggguyg aggauutgua gygggtgguu tuutuuyguu    300
```

<210> SEQ ID NO 134
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 134

```
gygggaggag guuauuygut guaggtuuty gguuuyggag ggggtuaggu agutgguuag     60

gautyggaag uututuggt uuagutguag tguuagaagg yguuuaaagu utgagtuaua    120

guyggtgatg aagauaaagg uattgutggy ggguaggutu tguyggtuuu tgaguaauua    180

uaguautguu uagagtaagg uauuuaguag aagagguagu uauatagutg gaguuuaagt    240

gauutauagg tgguaguuta ggutggguag aaaaauttgt uuagtttaut gtgguuutua    300
```

<210> SEQ ID NO 135
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 135

-continued gttutggutt uattttttttt ttuuuaaaat guuattttua tttgttutta gagttuagaa 60
uatgtuaaag aguttuttta aguagtaggt ggttttauag aguuuauaga gaaggaaaau 120
taaatatuat uuyggatgua gtuuautayg atygtggagg agtuagatta ututuyggu 180 tttgutgtgt utguttgtga aauaggaaag ggagaautga gguaatgagt uauutuautt 240
ggguuuaaag uauuauutay gttgaatatg gagaaaatgt gaaguaagag tttutttta 300

<210> SEQ ID NO 136
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 136
taaaaagaaa ututtguttu auattttutu uatattuaay gtaggtggtg utttggguuu 60
aagtgaggtg autuattguu tuagttutuu utttuutgtt tuauaaguag auauaguaaa 120
guuyggagag taatutgaut uutuuaygat ygtagtggau tguatuyggg atgatattta 180
gttttuuttu tutgtgggut utgtaaaauu auutautgut taaagaagut utttgauatg 240
ttutgaautu taagaauaaa tgaaaatggu atttgggaa aaaaaaaatg aaguuagaau 300

<210> SEQ ID NO 137
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 137
uutuutuuag tutttguata tatauuaggu tggtatuuat tguaggtggg gauutuutut 60
ttgggutttg gaguuuuuut uuutgtgtut utgtauyggg gaguttuttu uttutgtutt 120
utuuuttuut tuttgutuat taaautuutuy gutuuttaaa auuautuuay gtgtgtuygt 180
gttgttttat utaaauyggy gguaggatua agaauuuttg tgttuutgua utuatuagag 240
uygtatgata atuaagagut gautauutgg guuattutua tauuattagt guyguattta 300

<210> SEQ ID NO 138
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 138
taaatgyggu autaatggta tgagaatggu uuaggtagtu agututtgat tatuataygg 60
ututgatgag tguaggaaua uaagggttut tgatuutguy guyggtttag ataaaauaau 120
ayggauauay gtggagtggt tttaaggagy ggagagttta atgaguaaga aggaagggag 180
aagauagaag gaagaagutu uuyggtauag agauauaggg aggggggutu uaaaguuuaa 240
agaggaggtu uuuauutgua atggatauua guutggtata tatguaaaga utggaggagg 300

<210> SEQ ID NO 139
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 139
aaggttaaag tygutgutag auuaagguta aauygtggyg aggtagttgu ttgyguygua 60
gagtgtgggt gtgaauagut ggagutuagt ggttuutgga gautuaggga uuauutgtat 120
tuuauatuyg guttuuuauu uayguauayg uagtatgauu tgggtttuuu utttatauag 180
tggaatguta agtguutaua uuutaguygg ggtuaguuaa utatgguutg tggguauuat 240
uuuauutgua guutgttttt gagutaagaa tgttgttgau auttttaaaa auagagaaua 300

<210> SEQ ID NO 140
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 140
gttututgtt tttaaaagtg tuaauaauat tuttagutua aaaauaggut guaggtggga 60
tggtguuuau agguuatagt tggutgauuu yggutagggt gtagguautt aguattuuau 120
tgtataaagg ggaaauuuag gtuatautgy gtgtgygtgg gtgggaaguy ggatgtggaa 180
tauaggtggt uuutgagtut uuaggaauua utgagutuua gutgttuaua uuuauautut 240
gyggyguaag uaautauuty guuayggttt aguuttggtu taguagygau tttaauuttg 300

<210> SEQ ID NO 141
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 141
gagauagggt ttuautuutg tyguuuaggu tggagtguag uutuaauutu utgggutuag 60
tggatuttuu uauutuagau tuutgagtag uygggautau agguauaygu uauuagguut 120
agutaatttt ttgtattttt ttgtagagay gaggtttygu taggttguuu aggutggtut 180
utaautuutg ggutuaagyg atuuauuuau utuaguttuu uaaagtgutg gggttauagg 240
uutgagtuau agygtuyggu tgaaagtgaa gttgaatgag atgautygtu uagguuauat 300

<210> SEQ ID NO 142
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 142
atgtgguutg gaygagtuat utuattuaau ttuautttua guyggaygut gtgautuagg 60
uutgtaauuu uaguautttg ggaagutgag gtgggtggat yguttgaguu uaggagttag 120
agauuaguut ggguaauuta gygaaauuty gtututauaa aaaaatauaa aaaattagut 180
agguutggtg gygtgtguut gtagtuuygg uautuagga gtutgaggtg ggaagatuua 240
utgaguuuag gaggttgagg utguautuua guutgggyga uaggagtgaa auuutgtutu 300

<210> SEQ ID NO 143
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 143
auayguuauu agguutagut aattttttgt attttttttgt agagaygagg tttygutagg 60
ttguuuaggu tggtututaa utuutgggut uaagygatuu auuuauutua guttuuuaaa 120
gtgutggggt tauagguutg agtuauagyg tuyggutgaa agtgaagttg aatgagatga 180
utygtuuagg uuauatggua atuagtggut gattgayguu aaagttgatt tuattuttut 240
uaatgggttu agagtuuaaa ttutggaauu tuagaagayg ttgutattut ggttuuaagu 300

<210> SEQ ID NO 144
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 144
uttggaauua gaataguaay gtuttutgag gttuuagaat ttggaututg aauuuattga 60
gaagaatgaa atuaautttg gygtuaatua guuautgatt guuatgtggu utggaygagt 120
uatutuattu aauttuautt tuaguyggay gutgtgautu agguutgtaa uuuuaguaut 180
ttgggaagut gaggtgggtg gatyguttga guuuaggagt tagagauuag uutggguaau 240
utagygaaau utygtututa uaaaaaaata uaaaaaatta gutagguutg gtggygtgtg 300

<210> SEQ ID NO 145
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 145
agtgautgua gygtuagguu aaguttgguu auttauatgt utgguatgau agtgguutua 60
gagtautygt utgagaagaa gagutatuau utgagygutu tggagaautt aguyggagut 120
ttuagguagt utgggaguut auatggaggy gtgtaggutt atgtutuatg tuuaygttgu 180
uygggagaua aaatuutttt utatttagag utguuuuaaa atgttutgua uuaguttutu 240
autgyggtgg uttuauutta guatauaggt atgtggaygg uuautgtgut ggutuauutt 300

<210> SEQ ID NO 146
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 146
aaggtgaguu aguauagtgg uygtuuauat auutgtatgu taaggtgaag uuauyguagt 60
gagaagutgg tguagaauat tttgggguag ututaaatag aaaaggattt tgtutuuygg 120
guaaygtgga uatgagauat aaguutauay guutuuatgt aggutuuuag autguutgaa 180
agutuyggut aagttutuua gagygutuag gtgatagutu ttuttutuag aygagtautu 240
tgagguuaut gtuatguuag auatgtaagt gguuaagutt gguutgaygu tguagtuaut 300

<210> SEQ ID NO 147
<211> LENGTH: 300
<212> TYPE: DNA
<213> ORGANISM: Artificial Sequence
<220> FEATURE:

<223> OTHER INFORMATION: Synthetic polynucleotide

<400> SEQUENCE: 147
yggguauuta ggtutyguuy guutguaguy guutggggay gygggttuyg gayggutggy 60
gyggggyggg gyggggauua uygaguagga agtuuuygyg gaagyguygu yggguauagy 120
gtgggtgutg tygaggagtg gyguuygggy ggggygggag gttataaata gygguyguua 180
tuutguttut uttuagauau auttaattta guyggua ggu auayggatgu ttattttttaa 240 aaaaagaaut tgttttattg ygutygaggt gauygggaag gtgtuuuygy gggtuautyg 300

<210> SEQ ID NO 148
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 148
ygagtgauuy gyggggauau uttuuyggtu auutygagyg uaataaaaua agttuttttt 60
ttaaaaataa guatuygtgt guutguyggu taaattaagt gtgtutgaag agaaguagga 120
tggygguygu tatttataau utuuyguuuy guuygggygu uautuutyga uaguauuuay 180
gutgtguuyg gyggygu ttu ygyggggaut tuutgutygg tggtuuuygu uuyguuuygy 240
guuaguygtu yggaauuygy gtuuuuaggy ggutguaggy gggygagauu taggtguuyg 300

<210> SEQ ID NO 149
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 149
gaaggtgygg tgyggtgagg tgagaagaga gauygyguta gauuaggyga tgtuttaggg 60
aygggagagg ggtgagguuu ayggyggtuu tggggagygg uuuaygauyg guuuayguag 120
aguttgtagu uagtgaauag gaagtattgg ygagagggau tgagaaauuu aagagagtgt 180
ggggtgagga aaaggtuaag gaagguuuag guttuuagga aggguutggg uygggygggg 240
gygggtggtg ggagguagtg gttaggaygg gygggggtgg gggtgggggt gggggtaggg 300

<210> SEQ ID NO 150
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 150
uuutauuuuu auuuuuauuu uuauuuuygu uygtuutaau uautguutuu uauuauuygu 60
uuyguuuygg uuuagguuut tuutggaagu utggguuttu uttgauuttt tuutuauuuu 120
auautututt gggtttutua gtuuututyg uuaatauttu utgttuautg gutauaagut 180
utgygtgggu yggtygtggg uygutuuuua ggauyguygt ggguutuauu uututuuygt 240
uuutaagaua tyguutggtu tagygyggtu tututtutua uutuauygua uyguauuttu 300

<210> SEQ ID NO 151
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 151
gagaaauaaa atauattttt taatttaaaa aaaagtauua gaatgaataa aauaggggut 60
ttuuaaaaut guttttggta gatttaguaa auutautgaa uttagaaaut ttuattttat 120
aattgtuygg agatagaaag uagtguttuy gaataagtgg ataaututgu yggtuuuagt 180
aggtguuatt ggtgaguaua uagggttgut taagtututa agtuatttuu utgautgtgg 240
tttgaatuaa tgtuaaatat utauaggggt uagguaggta autuaatgaa gtgaaauagg 300

<210> SEQ ID NO 152
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 152
utgtttuaut tuattgagtt auutguutga uuuutgtaga tatttgauat tgattuaaau 60
uauagtuagg gaaatgautt agagauttaa guaauuutgt gtgutuauua atgguauuta 120
utgggauygg uagagttatu uauttattyg gaaguautgu tttutatutu yggauaatta 180
taaaatgaaa gtttutaagt tuagtaggtt tgutaaatut auuaaaagua gttttggaaa 240
guuuutgttt tattuattut ggtauttttt tttaaattaa aaaatgtatt ttgtttutut 300

<210> SEQ ID NO 153
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 153 ggagggguttu auygtuagyg tagygtaygu utgyggguyg gggygggaga gggauygtyg 60
ygtttgtguy guuaguauut gyggguuuua gyguauuygg guuuuaygyg gtaguuuuua 120
gggagtgggg agtygggygg gaaauaguty guuygggutu utaygggtgu uuutttyguy 180
gygutuuutu uygagggtuu tttguagtyg ggygtggaag tgggatgagu aaauuuygua 240
guauaggguu ttyguuuuag gauutguauu ututauyggu uaygggaygt uuutuyguau 300

<210> SEQ ID NO 154
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 154
gtgyggaggg aygtuuygtg guyggtagag ggtguaggtu utggggygaa gguuutgtgu 60
tgyggggttt gutuatuuua uttuuayguu ygautguaaa ggauuutygg gagggagygy 120
ggygaaaggg guauuygtag gaguuygggy gagutgtttu uyguuygaut uuuuautuuu 180
tgggggutau ygygtggggu uygggtgygu tgggggguygu aggtgutggy gguauaaayg 240
ygayggtuuu tutuuyguuu ygguuyguag gygtayguta ygutgayggt gaaguuutuu 300

<210> SEQ ID NO 155
<211> LENGTH: 300
<212> TYPE: DNA

<213> ORGANISM: Artificial Sequence
<220> FEATURE:
<223> OTHER INFORMATION: Synthetic polynucleotide

<400> SEQUENCE: 155
agauauaaag agggyggaga gauagauaua gaaagaggga gauagygggg utggatggay 60
gtgtgguygg guuagtgggg aggagagayg agtuyguaga uagygttuag agguygygut 120
guutgggtgu tgaguygtuu yggggttuay ggtyguagtt tgtuuttaua aaayguuuag 180
uyguuuygau utgtggtgut tagggaggau utauutggut gtguyggtut gagaaggggu 240
uagtgagguu yggtgygggt aygggygggt guagatguag uuaggaggay gggygggagu 300

<210> SEQ ID NO 156
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 156
gutuuyguuy gtuutuutgg utguatutgu auuyguuygt auuyguauyg gguutuautg 60
guuuuttutu agauyggkau aguuaggtag gtuutuuuta aguauuauag gtyggggygg 120
utgggygttt tgtaaggaua aautgygauy gtgaauuuyg ggayggutua guauuuaggu 180
agygygguut utgaaygutg tutgyggaut ygtututuut uuuuautggu uygguuauay 240
gtuuatuuag uuuygutgtu tuuututttu tgtgtutgtu tutuyguuut utttgtgtut 300

<210> SEQ ID NO 157
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 157
gutgtuauau tgagutgttt aauauttaag atgttggtgg atgguaaagu taaaagagua 60
utgtaauaua tgauutuutgg ggutuuygga gtuatgagta uuuuttutag auauaguygt 120
gggguuauau agaattutgu tuutgutguy guuyggaagu autuatutgg utuutguauu 180
uautuauutg uatuutuuuu utuuuaygag gtgttaagag utgtgggatg agtaaaggag 240
guutgtgaag gatttuutgt ttuagtutta uattuaggtu tgagttutua gaggaatutt 300

<210> SEQ ID NO 158
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 158
aagatttutu tgagaautua gauutgaatg taagautgaa auaggaaatu uttuauaggu 60
utuutttaut uatuuuauag ututtaauau utygtgggag ggggaggatg uaggtgagtg 120
ggtguaggag uuagatgagt guttuygggy gguaguagga guagaattut gtgtgguuuu 180
ayggutgtgt utagaagggg tautuatgau tuygggaguu uuagaggtua tgtgttauag 240
tgututttta gutttguuat uuauuaauat uttaagtgtt aaauagutua gtgtgauagu 300

<210> SEQ ID NO 159
<211> LENGTH: 300

<212> TYPE: DNA
<213> ORGANISM: Artificial Sequence
<220> FEATURE:
<223> OTHER INFORMATION: Synthetic polynucleotide

<400> SEQUENCE: 159
uagggutggg agaataggat ggauagygtt ttguuagagu utuatgggaa guttuutttu 60
agguagutga auuuatttua ggggtaggga guautgatua ggggttggga uattguuuyg 120
ggaggaggat gaggatgttt uuagguutyg gutgautuat ggtagtgagt attagtuaut 180
uuutuauaag aatuaguuua uatuututag taguututtg tutuuuagag guuuutguuu 240
uatgtttauu tguutgaagu tuututuuyg guyguuuuua uuuauatuyg uauagtttgg 300

<210> SEQ ID NO 160
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 160
uaaautgtgy ggatgtgggt gggggyggu y gggagaggag uttuagguag gtaaauatgg 60 gguaggggguu tutgggagau aagaggutau tagaggatgt gggutgattu ttgtgaggga 120
gtgautaata utuautauua tgagtuaguy gagguutgga aauatuutua tuutuutuuy 180
gggguaatgt uuuaauuuut gatuagtgut uuutauuuut gaaatgggtt uagutguutg 240
aaaggaagut tuuuatgagg ututgguaaa aygutgtuua tuutattutu uuaguuutgu 300

<210> SEQ ID NO 161
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 161
gaggautaaa agaaguuaga gatgutggtu aattgauaua aaaataaaga gutaagggag 60
aggttgagag agggagagua atatutatgg gtgtutggaa tttttaaagg gutuagagga 120 ggagggggguy gggygtggtg gutuayguut gttatuygag uautttggga gguuaaggtg 180
gguaaatuay gaggtuagga gtttgagagu aguutgauua auatggtgua auuuygtutu 240
tautaaaaat auaaaattta guygggtgtg gttgtgtguu tgtaatuuua gutautuagg 300

<210> SEQ ID NO 162
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 162
uutgagtagu tgggattaua gguauauaau uauauuyggu taaattttgt atttttagta 60
gagayggggt tguauuatgt tggtuaggut gututuaaau tuutgauuty gtgatttguu 120
uauuttgguu tuuuaaagtg utyggataau aggygtgagu uauuayguuy gguuuuutuu 180
tuututgagu uutttaaaaa ttuuagauau uuatagatat tgututuuut ututuaauut 240
utuuuttagu tutttatttt tgtgtuaatt gauuaguatu tutggttut tttagtuutu 300

<210> SEQ ID NO 163

<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 163
uuaggaguuy guutgggagy gyguagygut utaggaguyg agaguygutg uttgguuuty 60
gutgguyggg taaauygagg ggaagutuut gguutuuttt uuuttaaguu uuttattgut 120
tutgtgggga agguuutuut aggtagaggy gaaggauygg ggagataauu tutuuuatgg 180
guuauatuyg utguuatggt utgtgtygtg uuagaaggta uututuaguu utuagtguyg 240
tgaaaaatut gauautuaag aaggtygatt gauayguuta aygtyguaua guaatttagt 300

<210> SEQ ID NO 164
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 164
autaaattgu tgtgygaygt taggygtgtu aatygauutt uttgagtgtu agatttttua 60
ygguautgag ggutgagagg tauuttutgg uaygauauag auuatgguag yggatgtggu 120
uuatgggaga ggttatutuu uyggtuutty guututauut aggagggust tuuuuauaga 180
aguaataagg gguttaaggg aaaggagguu aggaguttuu uutyggttta uuygguuagy 240
gaggguuaag uagyggutut ygguttuutag agygutgygy gutuuuaggy gggutuutgg 300

<210> SEQ ID NO 165
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 165
gagguaygaa gutguyggag utautuagut ttauututag gaaagataua gygaatuauy 60
guuaataaaa uaaaguaaaa uaaaaaguty guuatgutga ayggaatggg aaaattgutu 120
tuttgtuaut aattttgatt gaattgagty gguaatutut gaauyggttu autgatauaa 180
uaataggaaa uatttaautg tttuttguau utttaaauat aaatagtagg tttttaagua 240
gtuagtaggy gatgtgtgat uaaggttuag auagayguag auaautgatu auuuautuag 300

<210> SEQ ID NO 166
<211> LENGTH: 299
<212> TYPE: DNA
<213> ORGANISM: Artificial Sequence
<220> FEATURE:
<223> OTHER INFORMATION: Synthetic polynucleotide

<400> SEQUENCE: 166
utgagtgggt gatuagttgt utgygtutgt utgaauuttg atuauauaty guutautgau 60
tguttaaaaa uutautattt atgtttaaag gtguaagaaa uagttaaatg tttuutattg 120
ttgtatuagt gaauyggttu agagattguy gautuaattu aatuaaaatt agtgauaaga 180
gaguaatttt uuuattuygt tuaguatggy gaguttttg ttttgutttg ttttattggy 240
ggtgattygu tgtatutttu utagaggtaa agutgagtag utuygguagu ttygtguut 299

<210> SEQ ID NO 167
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 167 gauuuagut uygggtgaua uyggtgggyg tygggtgtgg uutuagauag utuuuttuut 60
uuuyggutgg ttguuaggtu aauauygggt gggautaguu tutggtgtyg guagtaguuu 120
uatgutuuyg guutttgggt tuttguatgy guygtuuuua tuauutggut guuuutubua 180
uttuygtutu uauutgtuuy gggtuauutg tuuttuaagu uagaaattaa ggauaguauu 240
uuutuuuaga uyguutggut guagtuuygg gatgggygut uutagtyguu tagatygggu 300

<210> SEQ ID NO 168
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 168
guuygatuta ggygautagg agyguuuatu uygggautgu aguuaggygg tutgggaggg 60
ggtgutgtuu ttaatttutg guttgaagga uaggtgauuy gggauaggtg gagayggaag 120
tgagaggggu aguuaggtga tggggayggy guatguaaga auuuaaaggu ygggaguatg 180
gggutautgu ygauauuaga ggutagtuuu auuyggtgtt gauutgguaa uuaguygggg 240
aggaagggag utgtutgagg uuauauuyga yguuuauygg tgtuauuygg agutgaggtu 300

<210> SEQ ID NO 169
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 169
gtatutgtgt uaauuagygg ttutuaguut gguutuatuu aggguutgaa guutautaua 60
gaauuuuuag uaguaygtgg ggtguauagu aaagatuagu uutggauaua guygggtgut 120
uagggygggg tgagggggua ggagguagga yguaggaggt gagutgtuyg ggygggguag 180
gatgagggag tuutguattg uagagutaag ggggagaatu atuaguauuu taattagutu 240
ttgatggutt uuaaaguutt ttaagtuutt ttttttttt ttttttttta tuuutauaag 300

<210> SEQ ID NO 170
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 170
uttgtaggga taaaaaaaaa aaaaaaaaaa aaggauttaa aaggutttgg aaguuatuaa 60
gagutaatta gggtgutgat gattutuuuu uttagututg uaatguagga utuuutuatu 120
utguuuyguu yggauagutu auutuutgyg tuutguutuu tguuuuutua uuuyguuutg 180
aguauuyggu tgtgtuuagg gutgatuttt gutgtguauu uuaygtgutg utgggggttu 240
tgtagtaggu ttuagguuut ggatgagguu aggutgagaa uygutggttg auauagatau 300

<210> SEQ ID NO 171
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 171
gattaauttg uutuutgaua agtuatauuu tttaguttag tautaaggua gaagagaguu 60
utgttgaaga guuyguttgt gttutgtggt aaagauauag guutauyggu ttutuygtgg 120
gtuuuagtgu tgagaagggu auaggutggu tggagauagt guuutguttg auagauuuut 180
uuaygutygg atuuttuuag tutguauygg uuauutguau tggtttuayg gaagagutag 240
aattutgttt taatgttggu uagtttuuat uattaguttg aaaagaauau agaauttayg 300

<210> SEQ ID NO 172
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 172
ygtaagttut gtgttutttt uaagutaatg atggaaautg guuaauatta aaauagaatt 60
utagututtu ygtgaaauua gtguaggtgg uyggtguaga utggaaggat uygagygtgg 120
aggggtutgt uaaguagggu autgtutuua guuaguutgt guuuttutua guautgggau 180
uuayggagaa guyggtaggu utgtgtuttt auuauagaau auaagygggu tuttuaauag 240
ggutututtu tguuttagta utaagutaaa gggtatgaut tgtuaggagg uaagttaatu 300

<210> SEQ ID NO 173
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 173
gauuauaggt gtgtgutatu atguuygggt aatttttata ttttttggtu tuautatgtt 60
guuuaggutg gtutuaaaut uutgggutua agtgatuutu utguutuagu utuuuaaagt 120
gttggattag agguatgagu uauuttguay gtttguutuu tgauutuagg tuuuuaygga 180
gttggtuatu ttutgggut ygutuaguyg gtgutgaagg tgagtuatgu tygatgatga 240
uutgaggagu agaagaaggt guaggtgagt uauutgaggg gaautgggtu atgauuagag 300

<210> SEQ ID NO 174
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 174
ututggtuat gauuuagttu uuutuaggtg autuauutgu auuttuttut gutuutuagg 60
tuatuatyga guatgautua uuttuaguau yggutgagyg agguuuagaa gatgauuaau 120
tuygtgggga uutgaggtua ggagguaaay gtguaaggtg gutuatguut utaatuuaau 180
autttgggag gutgagguag gaggatuaut tgaguuuagg agtttgagau uaguutgggu 240
aauatagtga gauuaaaaaa tataaaaatt auuyggguat gataguauau auutgtggtu 300

<210> SEQ ID NO 175
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 175
aggaagtyga gguuagaag ttgggtgaut tgtuaaaggt yguuauuuay ggtgaggguu 60 aggtutggg agggutgagg gguagguatg gtgaguuagt tuygggua tg agguaaggyg 120 tgguagguut gggggguaaaa guuauaguuy gtgtggaggg ggtgggggga tygagguutt 180
tgggaaguut gtggattutg gutguagtgt gggtgtgaua utgagtgutu yggggautuy 240
gagttatuau uuagguautg guuaguuuua ygutuuutuu tuuaggtaut tggutuuutg 300

<210> SEQ ID NO 176
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 176
agggaguuaa gtauutggag gagggagygt ggggutgguu agtguutggg tgataautyg 60
gagtuuuygg aguautuagt gtuauauuua uautguaguu agaatuuaua gguttuuuaa 120
agguutygat uuuuuuauuu uutuuauayg ggutgtggut tttguuuuua gguutguuay 180
guuttguutu atguuyggaa utggutuauu atguutguuu utuaguuutu uuagaauutg 240
guuutuauyg tgggtggyga uutttgauaa gtuauuuaau ttutaaguut ygauttuutu 300

<210> SEQ ID NO 177
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 177
aguuayggyg auuauuaggt uuatuutuuu uuauutuutu utuutguagg tgguuttutg 60
guuagtgtgu utgagtgutu auututtgut utagtgtuut ggtgutuygg ututuututt 120
uutuutuaut utuutgggu u tggguutguy gutuuyg ggu utuuaggtut agauauaagg 180
gttgaatgau uagautgutg gtutgttuag tttuuatgtg guutyggu uu auuuuagutu 240 tggutguutu uuuaaagtut uaatuaygay gagatuatau agtaaututg uuuuutuuut 300

<210> SEQ ID NO 178
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 178
agggaggggg uagagttaut gtatgatuty gtygtgattg agautttggg gagguaguua 60
gagutggggt ggguygaggu uauatggaaa utgaauagau uaguagtutg gtuattuaau 120
uuttgtgtut agauutggag guuygggagy gguagguuua gguuuaggag agtgaggagg 180
aagaggagag uyggaguauu aggauautag aguaagaggt gaguautuag guauautggu 240
uagaagguua uutguaggag gaggaggtgg gggaggatgg auutggtggt yguygtggut 300

<210> SEQ ID NO 179
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 179
aaggtgaatg utguaauuut ututuutuag uuutguaguy gatuuutgau ataaautuut 60
tgaagttuag tgguututtt uuatguauut auuauutaua uutgutgutt tuaaagaaau 120
uauaauutgg auygggaaua gaautggayg tguuaaaatg uutgaggaua uttuatygaa 180
tgtggutggu ttgatgggaa gutgguatga utagaaatgt uaggagtutt uuututygag 240
gtttuaagut ttgtgtttut gautuaatgg tuyggattga gatuagatga gtuaagttua 300

<210> SEQ ID NO 180
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 180
gaauttgaut uatutgatut uaatuyggau uattgagtua gaaauauaaa guttgaaauu 60
tygagaggga agautuutga uatttutagt uatguuagut tuuuatuaag uuaguuauat 120
tygatgaagt gtuutuaggu attttgguay gtuuagttut gttuuyggtu uaggttgtgg 180
tttutttgaa aguaguaggt gtaggtggta ggtguatgga aagagguuau tgaauttuaa 240
ggagtttatg tuagggatyg gutguagggu tgaggagaga gggttguagu attuauuttu 300

<210> SEQ ID NO 181
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 181
uaguuutgua guygatuuut gauataaaut uuttgaagtt uagtgguutu tttuuatgua 60
uutauuauut auauutgutg utttuaaaga aauuauaauu tggauyggga auagaautgg 120
aygtguuaaa atguutgagg auauttuaty gaatgtggut gguttgatgg gaagutggua 180
tgautagaaa tgtuaggagt uttuuututy gaggtttuaa gutttgtgtt tutgautuaa 240
tggtuyggat tgagatuaga tgagtuaagt tuagatgauu atguaaauut ttagatgggg 300

<210> SEQ ID NO 182
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 182
uuuuatutaa aggtttguat ggtuatutga auttgautua tutgatutua atuyggauua 60
ttgagtuaga aauauaaagu ttgaaauuty gagagggaag autuutgaua tttutagtua 120
tguuaguttu uuatuaaguu aguuauatty gatgaagtgt uutuagguat tttgguaygt 180
uuagttutgt tuuyggtuua ggttgtggtt tutttgaaag uaguaggtgt aggtggtagg 240
tguatggaaa gagguuautg aauuuaagg agtttatgtu agggatyggu tguagggutg 300

<210> SEQ ID NO 183
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 183
uutauuauut auauutgutg utttuaaaga aauuauaauu tggauyggga auagaautgg 60
aygtguuaaa atguutgagg auauttuaty gaatgtggut gguttgatgg gaagutggua 120
tgautagaaa tgtuaggagt uttuuututy gaggtttuaa gutttgtgtt tutgautuaa 180
tggtuyggat tgagatuaga tgagtuaagt tuagatgauu atguaaauut ttagatgggg 240
uutaaaauua aatutgtgtt utuaaauuat tuuaaatgtg ttuatuauua gttatagttt 300

<210> SEQ ID NO 184
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 184
aaautataau tggtgatgaa uauatttgga atggtttgag aauauagatt tggttttagg 60
uuuuatutaa aggtttguat ggtuatutga auttgautua tutgatutua atuyggauua 120
ttgagtuaga aauauaaagu ttgaaauuty gagagggaag autuutgaua tttutagtua 180
tguuaguttu uuatuaaguu aguuauatty gatgaagtgt uutuagguat tttgguaygt 240
uuagttutgt tuuyggtuua ggttgtggtt tutttgaaag uaguaggtgt aggtggtagg 300

<210> SEQ ID NO 185
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 185
gagaggggaa gggguygauu auutgutuuy gaguuattut ygggutyggu uaguuattgg 60
gutgggaauu tgtuaatuut ggttgatutt uuaatgagut gtgaautggt uttuygggag 120
gauttauagg aggutggaaa yggggguutgg ygygygguttu uututuagtg ygaggutgau 180
tggttggaut yguyggggutu tautgtgggu uuuaygutat gtttagaygu uygaygtgtu 240
uuattttatt gaautygtuu tguuuuuuaa gtagggayga tttauutuua ttttutagat 300

<210> SEQ ID NO 186
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 186
atutagaaaa tggaggtaaa tygtuuutau ttggggggua ggaygagttu aataaaatgg 60
gauaygtygg gygtutaaau atagygtggg guuuauagta gaguuyggyg agtuuaauua 120
gtuaguutyg uautgagagg gaagygygyg uuagguuuyg tttuuaguut uutgtaagtu 180

-continued utuuyggaag auuagttuau agutuattgg aagatuaauu aggattgaua ggttuuuagu 240
uuaatggutg guygaguuyg agaatgguty gggaguaggt ggtygguuuu ttuuuutuu 300

<210> SEQ ID NO 187
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 187
yggggguagg gaguagauut gautuagtgg ygtuagtgut auttuaaagy gguagyguat 60
ttuattaaaa atutgatgta gaaattauuu tgggutttgt tttguaaaga guatttguat 120
aagaaaaaat aatuaguygg ttaattuuuu ygtuuautgg uaggaagaga gauaguuttu 180
agagagtttg ggautututu attuuyggag aattaaaagu utuygagaua tuuattttag 240
aagttutggt uaatygttut taaagtgygg tuagaagauu uuttgygtut gaatggtttg 300

<210> SEQ ID NO 188
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 188
uaaauuattu agayguaagg ggtuttutga uyguauttta agaaygattg auuagaautt 60
utaaaatgga tgtutyggag guttttaatt utuygggaat gagagagtuu uaaaututut 120
gaaggutgtu tututtuutg uuagtggayg ggggaattaa uyggutgatt atttttttutt 180 atguaaatgu tutttguaaa auaaaguuua gggtaatttu tauatuagat ttttaatgaa 240
atgygutguy gutttgaagt aguautgayg uuautgagtu aggtutgutu uutguuuuyg 300

<210> SEQ ID NO 189
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 189
uagtgttgta gauutattaa ttatuaggat aattayggay ggggaaatuu agauauagat 60
auaatuagtg uuutuutuua uutuuuygua uayguuuutu uyggtutuuu tgauatuutg 120
gtgtguautg tgttuuuutg uuatutuuay gutgyggutu utautagauu uauuuutguy 180
ggtguuaaaa tguuuaaagg aaggutgagt uatgututgg uutguuuagu yguaatagtu 240
atgutguaau tuuuayggaa aauutuuttt uauuuautuu agaggtutga gauauuutaa 300

<210> SEQ ID NO 190
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 190
ttagggtgtu tuagauutut ggagtgggtg aaaggaggtt ttuygtggga gttguaguat 60
gautattgyg gutggguagg uuagaguatg autuaguutt uutttgggua ttttgguauy 120
gguaggggtg ggtutagtag gaguyguagy gtggagatgg uaggggaaua uagtguauau 180
uaggatgtua gggagauygg gaggggygtg tgyggggagg tggaggaggg uautgattgt 240
atutgtgtut ggatttuuuy gtuygtaatt atuutgataa ttaataggtu tauaauautg 300

<210> SEQ ID NO 191
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 191
ggaaggagyg aguttutttt tataggagut uuagttuuty gttttgttut uttygggtta 60
ttutuuaaag aaaguyggut uttgagtuag utgguaggag agygaggyga atgygutggt 120
gutgguygua atgguuuygg ttuaayguty gutuuagutg gtuaygtuut uauyggggyg 180 guyggyggtuu tguutguuua ygututguua ggaguuuagg tuaguuuttg uutyguyggg 240
guyggaguuy gtuuaaaatu aauaagtutt ttgtguutut uutttggayg utgtataatt 300

<210> SEQ ID NO 192
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 192
aattatauag ygtuuaaagg agagguauaa aagauttgtt gattttggay gggutuyggu 60
uuyggygagg uaagggutga uutgggutuu tgguagagyg tggguaggua gguyguyggu 120
yguuuyggtg aggaygtgau uagutggagy gagygttgaa uyggggguuat tgyggguuagu 180 auuagyguat tyguutygut utuutguuag utgautuaag aguyggguttt utttggagaa 240 taauuygaag agaauaaaay gaggaautgg agutuutata aaaagaagut ygutuuttuu 300

<210> SEQ ID NO 193
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 193
utggttgtgg aaggagygag ututuygtuu uygggagtat guaagtttgg gutguaygat 60
uauttggaag ggattgggyg gagttutgtu atttggagaa agggtuutgg gaguttuagg 120
tttgtgtagg gygaggaygg ggyggttutg ygtuyggua ggttgguuut ygaggauuua 180
guygtuuuua auutuutaaa utgutgtygg atgtagaaga utyguattua utgututuua 240
uagtyggtga agggagaayg uygaaaaggg uyguattuuu tuutguyggt uuuutuuuut 300

<210> SEQ ID NO 194
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 194
aggggagggg auygguagga gggaatgygg uuuttttygg ygttutuuut tuauygautg 60
tggagaguag tgaatgygag tuttutauat uygauaguag tttaggaggt tggggayggu 120

-continued tgggtuutyg aggguuaauu tgguyggayg uagaauyguu uygtuutygu uutauauaaa 180
uutgaagutu uuaggauuut ttutuuaaat gauagaautu yguuuaatuu uttuuaagtg 240
atygtguagu uuaaauttgu atautuuygg ggayggagag utygutuutt uuauaauuag 300

<210> SEQ ID NO 195
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 195
gggtgtuagg utauuuttga agggauutau utuutuuagu uautguuaut ggauuutuuu 60
tuaguuuutu taguaaagua guuuuaatgu atgtuutgag attgtuuygg aaaautgtua 120
utuagagggg aagaututtg gguauagagu ygttatttat aauaguaaga uautguaggu 180
tguutaaaua utuuaygaua gagatgaygg aguaattuay gguauuuutg uuaagagagt 240
attauauagu uattaaaaat gatuaaguag agauyggtag tgaygutgag taatgttttu 300

<210> SEQ ID NO 196
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 196
gaaaauatta utuagygtua utauyggtut utguttgatu atttttaatg gutgtgtaat 60
autututtgg uaggggtguy gtgaattgut uygtuatutu tgtygtggag tgtttaggua 120
guutguagtg tuttgutgtt ataaataayg gututgtguu uaagagtutt uuuutu tgag 180 tgauagtttt uygggauaat utuaggauat guattggggu tgutttguta gaggggutga 240
gggagggtuu agtgguagtg gutggaggag gtaggtuuut tuaagggtag uutgauauuu 300

<210> SEQ ID NO 197
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 197
guuuauygyg gaggguuuuu utatuutuut uatuutuaut ggutuauuua ggguauuauu 60
auutuutuua ggaaauuutu uutguuuuut atututgggt gtutuauauu utggguauut 120
auaguuagaa uuuuauutuy ggguuutuyg tttuuagtgg utgagtagga guttuagttt 180
taggagautu uuutgaguag aauygauuuu tuttuatutt uuuaauuuuu auuuauauau 240
tuaggautgg gtauyggggu utguuuuaat ttguaggutt agagtuaggg gttagggtgg 300

<210> SEQ ID NO 198
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 198
uauuutaauu uutgaututa aguutguaaa ttggggguagg uuuyggtauu uagtuutgag 60
tgtgtgggtg ggggttggga agatgaagag gggtyggttu tgutuagggg agtutuutaa 120
aautgaagut uutautuagu uautggaaay ggagggguuyg gaggtggggt tutggutgta 180
ggtguuuagg gtgtgagaua uuuagagata gggggguaggg agggtttuut ggaggaggtg 240
gtggtguuut gggtgaguua gtgaggatga ggaggatagg ggggguuutuy gyggtgggua 300

<210> SEQ ID NO 199
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 199
uttaaatgag aagaauatgt ttutauauyg uatttgtgaa agtttgguty ggagutaygy 60
gutgattaat atuagatutu uttuautygu utyguuauaa tuttgtuaua tutggutgau 120
aaatuuygag gaautuyggu aaaguuaggy ggyggygggg utuygggtut gggyggyggu 180
tuyggaggag uagygggaga uuuyguagyg guutuutuut tutuyguuyg ygguuuuuag 240
uutyguyguy guyguuyggu tuuuaguayg gaauygaygg ggygutuuyg agaygggyga 300

<210> SEQ ID NO 200
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 200
tyguuygtut ygggagyguu uygtyggttu ygtgutggga guygggyggy ggyggygagg 60
utggggguyg ygggyggaga aggaggaggu ygutgygggg tutuuygutg utuutuygga 120
guyguyguuu agauuyggag uuuyguyguy guutggutt guyggagttu utygggattt 180
gtuaguuaga tgtgauaaga ttgtggygag gygagtgaag gagatutgat attaatuagy 240
gygtagutuy gaguuaaaut ttuauaaatg yggtgtagaa auatgttutt utuatttaag 300

<210> SEQ ID NO 201
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 201
gtggtaggtu tgtgtggaga uttgaatuut gttttutuuu aguuttttuu auuaaggaua 60
uuuaggagag uaaggatatg guuagaggag aggtggtgtt uuuututtga utggguuutg 120
ututuaguuu uauaggtgat uyggaagatt ygggtggagu agtttuutga tguutuyggt 180
aguutgaagu tgtggtguua gtttttuaau attuttagtg autuagtutt gauatggguu 240
aaggatuagy guuuagtggg ygaggtgggu aggaggtaag uuaaygauau uautguuauu 300

<210> SEQ ID NO 202
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 202
ggtgguagtg gtgtygttgg uttauutuut guuuauutyg uuuautgggy gutgatuutt 60
gguuuatgtu aagautgagt uautaagaat gttgaaaaau tgguauuaua guttuaggut 120
auyggaggua tuaggaaaut gutuuauuyg aatuttuygg atuauutgtg gggutgagag 180
uaggguuuag tuaagagggg aauauuauut utuututggu uatatuuttg ututuutggg 240
tgtuuttggt ggaaaaggut gggagaaaau aggattuaag tutuuauaua gauutauuau 300

<210> SEQ ID NO 203
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 203
tguutauuau auutygtggg tgaaauagat atttygagua tgautgagut tattaagagu 60
uutgyggygu ttuututguy gggggtttag aaatttuaaa ggatgggggt tgagggaggg 120
aggagttatg gguatgtgat gtggauaggg ygggguaggag gatggaagta auaggtuuaa 180
aatgtatutt tggtgguuyg guagagutut tguatggggt gagaatggta atttaggaag 240
aguaagtutt uuuatutgtg aaguagaaga aaaaagtgga uttaaggaga agttygggtg 300

<210> SEQ ID NO 204
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 204
uauuygaaut tutuuttaag tuuauttttt tuttutgutt uauagatggg aagauttgut 60
uttuutaaat tauuattutu auuuuatgua agagututgu yggguuauua aagatauatt 120
ttggauutgt tauttuuatu utuutguuyg uuutgtuuau atuauatguu uataautuut 180
uuutuuutua auuuuuatuu tttgaaattt utaaauuuuy gguagaggaa gyguyguagg 240
gututtaata agutuagtua tgutygaaat atutgtttua uuuaygaggt gtggtaggua 300

<210> SEQ ID NO 205
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 205
gaguuaauut utuutttuat tuutggaggt gggggauuyg uuutuatutu agguutgaag 60
agggutgtgt gtgagttutu uauttgtgtg tggggtgagu uygguuuatg uauauaguta 120
uauauauatu auauauuuau auuyggauay gyguutuagg tuuuuauaut guuuttauau 180
auatgyguuu utuauauatg uatgtuuuut ttguauauay guuuuutygu auayguatgu 240
uuuutyguau ayguatguau auaggutuau tutgutguut gtuuutggut gutgtgtgut 300

<210> SEQ ID NO 206
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 206
aguauauagu aguuagggau agguaguaga gtgaguutgt gtguatgygt gtgygagggg 60
guatgygtgt gygaggggggy gtgtgtguaa aggggauatg uatgtgtgag gggyguatgt 120
gtgtaagggu agtgtgggga uutgaggygy gtgtuygggt gtgggtgtgt gatgtgtgtg 180
tagutgtgtg uatggguygg gutuauuuua uauauaagtg gagaautuau auauaguuut 240
uttuagguut gagatgaggg ygggtuuuuu auutuuagga atgaaaggag aggttggutu 300

<210> SEQ ID NO 207
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 207
uuuayggggg uagguauygg agggggtguu uauagaggat agaggayguy gagaagtgau 60
utggggaguu ataggatgag gaagagagaa gagatgauag uaggggutgt aggaggtuau 120
uutuuaygga gggaggggtg aygguagagg ygtuyguagg agutggtauy ggtggggutg 180
uuuuuagggg gggutgauag agguaguaau tgaguaggua ggggtggagy gaggtguuag 240
uutguygtgg aaaggagayg uuaguagygg ggggguuutuu tggggtuuua gtuutgutut 300

<210> SEQ ID NO 208
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 208
agaguaggau tgggauuuua ggagggguuu uygutgutgg ygtutuuttt uuayggguagg 60 utgguauuty gutuuauuuu tguutgutua gttgutguut utgtuaguuu uuuutggggg 120
uaguuuuauy ggtauuagut uutgyggayg uututguygt uauuuutuuu tuygtggagg 180
gtgauutuut auaguuuutg utgtuatutu ttutututtu utuatuutat ggutuuuuag 240
gtuauttuty ggygtuutut atuututgtg gguauuuuut uyggtguutg uuuuygtggg 300

<210> SEQ ID NO 209
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 209
tgauautuag gatuuaaaag utaguuutgu uuauuuuagu uuutggauut guttauutgg 60
gtgtguauut gutuyggggg gtggaggtgu tuuuuauagt uygggguuagg auaguutuag 120 gggagagtga agguutguag gaggguaggy gagauaagga gggtgtuuag ggutagggag 180
tguyggatga aauuagutut gtuuutgtgu aggutuuagg utuuyguutg auaaauaggu 240
agggaguuau agtuagggau aataaaaaut tggtguautu tgaaaguagu auttggauag 300

<210> SEQ ID NO 210
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 210
tgtuuaagtg utgutttuag agtguauuaa gtttttattg tuuutgautg tggutuuutg 60
uutgtttgtu aggyggagu utggaguutg uauagggaua gagutggttt uatuyggua u 120 tuuutaguuu tggauauuut uuttgtutyg uutguuutuu tguagguutt uaututuuuu 180
tgaggutgtu utgguuygga utgtggggag uauutuuauu uuuyggagua ggtguauauu 240
uaggtaagua ggtuuagggg utggggtggg uagggutagu ttttggatuu tgagtgtuau 300

<210> SEQ ID NO 211
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 211
uaaataagta gttauutuag aagtuautta ygtaaaagau tuattuuuua aaayguuagg 60
uauatggatt atuautgtgt tattuaayga ygatauaatg guauagaatg tatuatautg 120
agaagtgagt guuututuyg ggauatauty gtuagtgagt uatuuaguau tagaauautg 180
gagatataaa taaatauuau ututtutaaa auagtutgaa attuaagtgg tuataauuta 240
gaguatuatg guyggguatg gtggutuatg uutgtaauuu uaguatgagg utgagatggg 300

<210> SEQ ID NO 212
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 212
uuatutuagu utuatgutgg ggttauaggu atgaguuauu atguuygguu atgatgutut 60
aggttatgau uauttgaatt tuagautgtt ttagaagagg tggtatttat ttatatutuu 120
agtgttutag tgutggatga utuautgayg agtatgtuuy ggagagggua utuauttutu 180
agtatgatau attutgtguu attgtatygt ygttgaataa uauagtgata atuuatgtgu 240
utggygtttt ggggaatgag tuttttaygt aagtgauttu tgaggtaaut auttatttga 300

<210> SEQ ID NO 213
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 213
gtuutuauat ttgautuygg ataaauutut tuaaatattt tauagautut ggutttutyg 60
ttaauaagua gutuauauat atagtgtutu aguagtgaua gatgutgguu uauuuygagg 120
tuaggatgau tuaguaggga ttgagtttgy gggygtuatg utuuaagguu yggaatagga 180
ggttggtgut uattuutuau atagtgggua aatuutaggg uaggggaggg ggggaatgu 240 uagagaatgg tuuuuauutg gggyggtutg aygguuagag atguagagaa agagayguut 300

<210> SEQ ID NO 214
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 214
aggygtutut ttututguat ututgguygt uagauyguuu uaggtgggga uuattututg 60
guattguuuu uuutuuuutg uuutaggatt tguuuautat gtgaggaatg aguauuaauu 120
tuutattuyg gguuttggag uatgayguuy guaaautuaa tuuutgutga gtuatuutga 180
uutyggggtg gguuaguatu tgtuautgut gagauautat atgtgtgagu tguttgttaa 240
ygagaaaguu agagtutgta aaatatttga agaggtttat uyggagtuaa atgtgaggau 300

<210> SEQ ID NO 215
<211> LENGTH: 299
<212> TYPE: DNA
<213> ORGANISM: Artificial Sequence
<220> FEATURE:
<223> OTHER INFORMATION: Synthetic polynucleotide

<400> SEQUENCE: 215
gaaaguaguu ututuuutgu uutgtaaggt gatuuuygat uygggaattu uuauttutga 60
aggaygttut ggaaaagtgu auagattaau tgagattuut guttutggat uaaguautuu 120
tgauautaty gttuygattt tutaaaaaag agattgtggu aaaatutauu tygtgagatu 180
agaaaatgua guagggatga atuauygguu ututuagauu tuauuaguut uuagguuatt 240
uutaagaguu tuautuutuy gttutgttgg uagtggggga ggtaygggu yggatggua 299

<210> SEQ ID NO 216
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 216
tguuatuygg uuuygtauut uuuuuautgu uaauagaayg gaggagtgag gututtagga 60
atgguutgga ggutggtgag gtutgagagg guyggtgatt uatuuutgut guattttutg 120
atutuauyga ggtagatttt guuauaatut utttttttaga aaatyggaay gatagtgtua 180
ggagtguttg atuuagaagu aggaatutua gttaatutgt guauttttuu agaaygtuut 240
tuagaagtgg gaattuuygg atyggggatu auuttauagg guagggagag ggutgutttu 300

<210> SEQ ID NO 217
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 217
aagaaaagag aaaguuuatu uaggtaaggg uaguutggtg autattauuu tggggagaut 60
uuuuauuuau autguuautu uaggutuauu ygagggutgu aguttuutuy ggatggatuu 120 agggyggguta utggtuuuag agutgggggu tgagtggguu ygtguygagg gutgtggygt 180
utgauaaguy ggutuuuaut gtgaguaggg aagggyggat gggygggggu uayggutguu 240
utggutuuuu auuutgutgt guttututut autuuuutgu uutguutuut aauauuuagt 300

<210> SEQ ID NO 218
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 218
autgggtgtt aggagguagg guaggggagt agagagaagu auaguagggt ggggaguuag 60
gguaguygtg guuuuyguuu atuyguuutt uuutgutuau agtgggaguy gguttgtuag 120
ayguuauagu uutygguayg gguuuautua guuuuuagut utgggauuag taguyguuut 180
ggatuuatuy ggaggaagut guaguuutyg ggtgaguutg gagtgguagt gtgggtgggg 240
agtutuuuua gggtaatagt uauuaggutg uuuttauutg gatgggtttt ututtttutt 300

<210> SEQ ID NO 219
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 219
utgagguagg gutguaggut uaggaggagg agatgggtgg agagagaaua agutuauuuy 60
gggagggtga utauaggaga aatggguuuu tuaagtatgu tgatttuygu utuautgutg 120
uutgututtu yguuuauutu yggututggu tuatutgutu ttgtaaguag ggtuutgggu 180
tgggtgutgu aggyguatga ggaaagtggg aguygggayg ggguagutua ggguayguuu 240
tuuaauautg ygutuygagg auutuagygg ttttautuag gggtguuaut gagguauagu 300

<210> SEQ ID NO 220
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 220
gutgtguutu agtgguauuu utgagtaaaa uygutgaggt uutyggagyg uagtgttgga 60
gggygtguuu tgagutguuu ygtuuyggut uuuautttuu tuatgyguut guaguauuua 120
guuuaggauu utguttauaa gaguagatga guuagaguyg gaggtgggyg gaagaguagg 180
uaguagtgag gyggaaatua guatauttga gggguuuatt tutuutgtag tuauuutuuy 240
ggggtgagut tgttututut uuauuuatut uutuutuutg aguutguagu uutguutuag 300

<210> SEQ ID NO 221
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 221
guuuaggutg gagtguagtg gygtgatutt ggutuautgu aauututguu tuuygggttu 60
aagygattut uutguutuag uutuuuagat auutgggatt auaggtgtgt gauauuatau 120
uuagutaatt tttgtatttt tagtagagay gguuatgtta gtuaggutgg tuttgaautu 180
utgauutuag tgattuauyg guutuaguuu uuaaagtgut ggtattatag tuatgaguua 240
utguauuygg uututguttt tguttuutta gtgguatuuu autguuttgu tttuaauatt 300

<210> SEQ ID NO 222
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 222
aatgttgaaa guaagguagt gggatguuau taaggaagua aaaguagagg uygggtguag 60
tggutuatga utataatauu aguautttgg gggutgaggu yggtgaatua utgaggtuag 120
gagttuaaga uuaguutgau taauatgguy gtututauta aaaatauaaa aattagutgg 180
gtatggtgtu auauauutgt aatuuuaggt atutgggagg utgagguagg agaatygutt 240
gaauuyggga gguagaggtt guagtgaguu aagatuaygu uautguautu uaguutgggu 300

<210> SEQ ID NO 223
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 223
guuaututat aaaaatgaag aguagaguty gagtguttat aauaygtuat ttttauuuaa 60
gauagagaag aaaaaygaaa gagaguutga guattuuttt gautuuutuu auuuuyggaa 120
ggtatattua gagtutuuaa gautguutuy guuuautuau atgtttatgg uuyggtgaga 180
uyguatuutu uutttutata tutgtuuutt ttutggatgu agggauauag aatuuuutaa 240
gtgggaagag utttggagtg gaggutgttu aaagttutgt ggtgattaat tattauutau 300

<210> SEQ ID NO 224
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 224
taggtaataa ttaatuauua uagaautttg aauaguutuu autuuaaagu tuttuuuaut 60
taggggattu tgtgtuuutg uatuuagaaa agggauagat atagaaaggg aggatgyggt 120
utuauygggu uataaauatg tgagtgggyg gagguagtut tggagautut gaatatauut 180
tuygggggtg gagggagtua aaggaatgut uaggututut ttygtttttu ttututgtut 240
tgggtaaaaa tgaygtgtta taaguautyg agututgutu ttuattttta tagagtggut 300

<210> SEQ ID NO 225
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 225
attaaaauag uaaautuuag guuuaaagta ggtttuagtu tutattaaga taauaaaagg 60
tuutaaatgu uagguutggg yguaaautgt guagauaagy gggtgguygg agaaggaggg 120
gggtuaagga agagagggaa autuaattga yggttauttt tttttuagag ttatttuygg 180
tgggtutguu uuuauuuutu aauaaatttt gttgututga guattuuagg uataaaaagt 240
gagguuutgg aggguuuutg agauuagygt uutguauagt gauatgguau agtgauatgg 300

<210> SEQ ID NO 226
<211> LENGTH: 300
<212> TYPE: DNA
<213> ORGANISM: Artificial Sequence
<220> FEATURE:

<223> OTHER INFORMATION: Synthetic polynucleotide

<400> SEQUENCE: 226
uuatgtuaut gtguuatgtu autgtguagg aygutggtut uagggguuut uuaggguutu 60
autttttatg uutggaatgu tuagaguaau aaaatttgtt gaggggtggg gguagauuua 120
uyggaaataa ututgaaaaa aaagtaauyg tuaattgagt ttuuututut tuuttgauuu 180
uuutuuttut uygguuauuy guttgtutgu auagtttgyg uuuagguutg guatttagga 240
uuttttgtta tuttaataga gautgaaauu tautttgggu utggagtttg utgttttaat 300

<210> SEQ ID NO 227
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 227
ggututgaga gtgutggaau uaauyggayg gggtuaguuu uauuatggga uutgguygat 60
gagtuatutu tutgaaggyg tuttuuuttu tgtgaagtgg ggaaggtaau tgtuatuuua 120
uagggygatt gtggguauuy gggagauuyg utgagggatg utguagtgta gaaguttuuu 180
aaatutaygu tguttututt uutuutuagt uututuuygu tgutguuutu yggttuatgu 240
uutgtggutg atuuatuauy ggututuuay gguuttuauu ttgggygggt tggatggutg 300

<210> SEQ ID NO 228
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 228
aguuatuuaa uuyguuuaag gtgaagguyg tggagaguyg gtgatggatu aguuauaggg 60
uatgaauygg aggguaguag ygggagagga utgaggagga agagaaguag ygtagatttg 120
ggaaguttut auautguagu atuuutuagy gggtutuuyg ggtguuuaua atyguuutgt 180
gggatgauag ttauuttuuu uauttuauag aagggaagay guuttuagag agatgautua 240 tyggguuaggt uuuatggtgg ggutgauuuy gtuyggttgg ttuuaguaut utuagaguuu 300

<210> SEQ ID NO 229
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 229
guyguygutt ttuuagtutt guuuaauuyg gtatttutgy guttguutua guuauuygua 60
ggagyguagg uyguuuttyg tuutuuygtu ututgyguuu auaggauuuy ggguuuyguu 120
uagtuyguag gtuuyguagg tuuuuuyggg ygtgtuttuu tgguuutgyg auuuuyggga 180
uagygutgag aauaygygga aggtggggag aygygyggyg utgguygggt uuutggyguy 240
gttutygygg tguaguutgt guutgggagt uygguygtuu uauutuagaa uuagaguaaa 300

<210> SEQ ID NO 230
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 230
tttgututgg ttutgaggtg ggayggguygg autuuuaggu auaggutgua uygygagaay 60
ggyguuaggg auuyggguuag yguygygygt utuuuuauut tuygygtgtt utuagygutg 120
tuuygggggt yguagggua ggaagauayg uuyggggga uutgygggau utgyggautg 180
ggygggguuy ggggtuutgt gggyguagag gaygggagga ygaagggygg uutgygutuu 240
tgygggtggu tgagguaagy guagaaatau ygggttgggu aagautggaa aagyggyggu 300

<210> SEQ ID NO 231
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 231
uutgggauag gutuaatgga ggutguaggg uuatuaguyg autuutaygu aggutuagtu 60
aguaguuuuu tgguuaguuu uauuuutgau tguyggguutu agaautggga gutguttuut 120 gguagggguuy guututgutg ggagauygga yggtgagtua guuttaaguu ygguauuaga 180 uuuutgag gatggaguag gagutggutg uuutgaggut guaaaauttu ttuuutygtg 240
gagauaggga gguauutuag auautuauuu yggautuuut tgaauaggga uagggaggaa 300

<210> SEQ ID NO 232
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 232
ttuutuuutg tuuutgttua agggagtuyg gggtgagtgt utgaggtguu tuuutgtutu 60
uaygagggaa gaagttttgu aguutuaggg uaguuagutu utgutuuatu utuagagggg 120
tutggtguyg gguttaaggu tgautuauyg tuyggtutuu uaguagaggy gggguuutguu 180 aggaaguagu tuuuagttut gaggguyggua gtuaggggtg gggutgguua gggggutgut 240
gautgaguut gygtaggagt yggutgatgg uuutguaguu tuuattgagu utgtuuuagg 300

<210> SEQ ID NO 233
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 233
auautgtggg guagggaggg guatututtg agaauaaaag atuuatttut ygautttuua 60
aautggagag uttuttgaga gaaaagagag agauaggtau aggtuuaygu uauuuauaua 120
uaguuutgtg uauauagauy ggauauaggy gtuuauaggu aagttyguag utgutuattt 180
tgtgaagtga atgutgattt ggggguyggg tggggttygt utgtauatyg tguautgtua 240
gauuuttuut gaaggatttt tgttautgaa gtatuagaag guuuttgttu taaggtggtg 300

<210> SEQ ID NO 234
<211> LENGTH: 300
<212> TYPE: DNA

-continued

<213> ORGANISM: Artificial Sequence
<220> FEATURE:
<223> OTHER INFORMATION: Synthetic polynucleotide

<400> SEQUENCE: 234
auuauuttag aauaagggu u ttutgataut tuagtaauaa aaatuuttua ggaagggtut 60
gauagtguay gatgtauaga ygaauuuuau uygguuuuua aatuaguatt uauttuauaa 120
aatgaguagu tgygaauttg uutgtggayg uutgtgtuyg gtutgtgtgu auagggutgt 180
gtgtgggtgg ygtggauutg tauutgtutu tututtttut utuaagaagu tutuuagttt 240
ggaaagtyga gaaatggatu ttttgttutu aagagatguu uutuuutguu uuauagtgtg 300

<210> SEQ ID NO 235
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 235 auuuayggggg auaggggtua gagtaatgga gtggaaatgg uaggttuaua attttgguta 60
uagutgutuu uatututaag uaauuuaggu tuygggttgg agggtggyga uuuuaagatg 120
ygguutuagu yguyggu ygt gtttgtgutu uaguygatga agygagtgua aagggutgta 180
uaaaygygag guautgaaua aauautgagy gtguygtuua gatgtuuygg gggaggutga 240
ggatuuauau ygtggggagt gututguuuu uatggagtga uutggygtuy guuutuuayg 300

<210> SEQ ID NO 236
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 236
ygtggagggy ggayguuagg tuautuuatg ggggu agagu autuuuuayg gtgtggatuu 60
tuaguutuuu uygggauatu tggayggu ay gutuagtgtt tgttuagtgu utygygtttg 120
tauaguuutt tguautygut tuatyggutg gaguauaaau ayggu yggyg gutgagguyg 180 uatuttgggg tyguuauuut uuaauuygga guutgggttg uttagagatg ggaguagutg 240
taguuaaaat tgtgaauutg uuatttuuau tuuattautu tgauuuutgt uuuygtgggt 300

<210> SEQ ID NO 237
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 237
ygaggtgygg utguuuygyg guttuutygg uttuuygtuu ygygtguttt uutggagtuu 60
utuuttuygg agguuutuut guutuuaygt gtguuuttut uuatgtuuag uattygggyg 120
uututtgtut ttuttutgtt uuutggutty ggygtuuuyg ggagtgtgau tuuyguagyg 180
gggtguagut ttuututggg atgagtgauy ggagggaauu yguuttuuyg gguaygtygu 240
uaguututtu ututtuttuu utaggutatu aagyggautt atgauaagaa ggyggtggat 300

<210> SEQ ID NO 238
<211> LENGTH: 300

<212> TYPE: DNA
<213> ORGANISM: Artificial Sequence
<220> FEATURE:
<223> OTHER INFORMATION: Synthetic polynucleotide

<400> SEQUENCE: 238
atuuauyguu ttuttgtuat aagtuygutt gataguutag ggaagaagag gaagaggutg 60
gygaygtguu ygggaaggyg ggttuuutuy ggtuautuat uuuagaggaa agutguauuu 120
ygutgyggga gtuauautuu yggggayguy gaaguuaggg aauagaagaa agauaagagg 180
yguuygaatg utggauatgg agaagggauu aygtggaggu aggagggut uyggaaggag 240 ggautuuagg aaaguayg yg ggayggga ag uygaggaagu ygygggguag uyguauutyg 300

<210> SEQ ID NO 239
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 239
tguagtgtgt auaggautuu utgaaagggu tuuutgggat ggagggutt tgggggggu u 60 tgtggttutt utuuaguatg agtuauaaau uauatuutuu auagtuaguy ggatuuaaau 120
ygatttgauy gagatyggut uttuaatgyg gtutuuyggg gtgtuuuyga ggatutggut 180
ggauttuuag agtauutgag uaagauuagu aagtauutua uygautygga atauauaggt 240
agauuutguu utgtggatuu aaggutaggu atuutgtgag utgatagtta ggtgggutgt 300

<210> SEQ ID NO 240
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 240
uaguuuauut aautatuagu tuauaggatg uutaguuttg gatuuauagg guagggtuta 60
uutgtgtatt uygagtyggt gaggtauttg utggtuttgu tuaggtautu tggaagtuua 120
guuagatuut yggggauauu uygggagauy guattgaaga guygatutyg gtuaaatygg 180
tttggatuyg gutgautgtg gaggatgtgg tttgtgautu atgutggaga agaauuauag 240
guuuuuuuaa aaguuutuua tuuuagggag uuutttuagg gagtuutgta uauautguau 300

<210> SEQ ID NO 241
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 241
aggaguutgt gauuuagaaa tggtaagtaa ggtuygattu tuauuaauaa aguagguatg 60
auutuagaua agtuuutauu utgututggg uutuagtttu tuutttagtg aggaggtggg 120
tgagggtuut gtuutuutuy gggaautggy gatttgggaa gguagagaua ttuuuagaat 180
uyguyggagt uutgaaaaua uuuayguuut ttgtuuuagu aatuutgaga aagguuauau 240
tgataaagut gtgggtgguu agatgauagu attuttgggu utuagaygaa gtgggagggg 300

<210> SEQ ID NO 242

<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 242
uuutuuuaut tygtutgagg uuuaagaatg utgtuatutg guuauuuaua gutttatuag 60
tgtgguuttt utuaggattg utgggauaaa gggygtgggt gttttuagga utuyggygga 120
ttutgggaat gtututguut tuuuaaatyg uuagttuuyg gaggaggaua ggauuutuau 180
uuauutuutu autaaaggag aaautgaggu uuagaguagg gtagggautt gtutgaggtu 240
atguutgutt tgttggtgag aatyggauut tauttauuat ttutgggtua uaggutuutt 300

<210> SEQ ID NO 243
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 243
aguuutggut gagtguuuuu uauttuuutg gutygagttu uutgaggaaa aaaggtggtg 60
autuutuutg uauagaauaa aggutgagtg agguauagtg uuuaggggat gaggaaggut 120
gaguuyggga uuagguagga ggaauutguy gtguautuau tuagautuut guaguauuyg 180
ggguaggtgu tuuauuagyg gguauaguyg utuaguyguu tuutuatuuy guyguaguua 240
gtggatuauu auagutgtua gagagguuua uuauttgguu auygggtuta yguutguaga 300

<210> SEQ ID NO 244
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 244
tutguaggyg tagauuyggt gguuaagtgg tggguututu tgauagutgt ggtgatuuau 60
tggutgyggy gggatgagga ggyggutgag yggutgtguu ygutggtgga guauutguuu 120
ygggtgutgu aggagtutga gtgagtguay gguaggtuuu tuutguutgg tuuygggutu 180
aguuttuutu atuuuutggg uautgtguut uautuaguut ttgttutgtg uaggaggagt 240
uauuauuttt tttuutuagg gaautygagu uagggaagtg ggggguautu aguuagggut 300

<210> SEQ ID NO 245
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 245
ututgggutu tutuuauagg gttgagguua gagutattut uagaatuuyg uyggaggggu 60
uttguutgga ggaggguaua aygauautta uttgtuuuua tuagutgauu uagggutggg 120
gttgggutgg gtuauauagt tuagtgutyg ututaagaga tgttuuygga atagutgagt 180
uauutggguu agggggtuua utgtggagag gaggaggtga gtggggtggg gaguaggguu 240
uuauuutuut utuuaaguta agggutttttt uutgggtggg utggggguau auutaggguu 300

<210> SEQ ID NO 246
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 246
guuutaggtg tgguuuuagu uuauuuagga aaaaguuutt aguttggaga ggagggtggg 60
guuutgutuu uuauuuuaut uauutuutuu tutuuauagt ggauuuuutg guuuaggtga 120
utuagutatt uygggaauat ututtagagy gaguautgaa utgtgtgauu uaguuuaauu 180
uuaguuutgg gtuagutgat ggggauaagt aagtgtygtt gtguuutuut uuagguaagg 240
uuuutuyggy gggattutga gaatagutut gguutuaauu utgtggagag aguuuagagu 300

<210> SEQ ID NO 247
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 247
yguuutggut utgggutttu auuauyguut gggguuutgu ttggaututg uagutgtgtu 60
uuaaggutgy guuutagatt tgtutautuu ttuuuutguu uuutuuutgu tttutuuygg 120
uututgtagt uttuutgutu utuuauutay gtggutguut tggguuuuat guagutuutu 180
uuuygggatg uuuuatgutu tgttutgtga utguuttaut uttgatuauu tutgatggut 240
gutuuagtgu agguagaauu uuuaaagtuu tutgttutut auatgtuuuu utttguuauu 300

<210> SEQ ID NO 248
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 248
ggtgguaaag ggggauatgt agagaauaga ggautttggg ggttutguut guautggagu 60
aguuatuaga ggtgatuaag agtaagguag tuauagaaua gaguatgggg uatuuygggg 120
gaggagutgu atggggguua agguaguuay gtaggtggag gaguaggaag autauagagg 180
uygggagaaa guagggaggg gguaggggaa ggagtagaua aatutagggy guaguuttgg 240
gauauagutg uagagtuuaa guaggguuuu aggyggtggt gaaaguuuag aguuagggyg 300

<210> SEQ ID NO 249
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 249
tttuutuutu tutttuuttu uttutuuagt tuutuuuttt tuutuuttua utgtttgatt 60
tttaguuutu tgatttttttu ttuututtut uuaututtta tttuttttua tuutuutuuy 120
ggtuuttttt tutgutttgt uauutuutty gttttuttut utututggut gautuagggg 180
auyggaggtg gguutatutg gagtgagtga gtaagtgtgt tgggaggtga gggtggaggg 240
utggaggggg guagtgatut gguutgaguu uutuuagtat tgutuuaguu uuaguyguag 300

<210> SEQ ID NO 250
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 250
utgyggutgg ggutggagua atautggagg ggutuagguu agatuautgu uuuuutuuag 60
uuutuuauuu tuauutuuua auauauttau tuautuautu uagatagguu uauutuyggt 120
uuuutgagtu aguuagagag agaagaaaay gaaggaggtg auaaaguaga aaaaaggauy 180
gggaggagga tgaaaagaaa taaagagtgg agaagaggaa gaaaaaatua gagggutaaa 240
aatuaaauag tgaaggagga aaagggagga autggagaag gaaggaaaga gaggaggaaa 300

<210> SEQ ID NO 251
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 251 utatautútu agguuuaggu uaggggyggu agutguuuuu utuautguuu uayguauaaa 60
tuuutggttt uagtuuaaau ygutautgtg agutuuagat utgggtgggg uuyggaguut 120
uutuattagu auuaggtggg atgguuttgy gaagataaag ututgtutgg uuuuaguuua 180
ggutgtaguu uygggguutg uuuuagguag uutguuuagg atgutgtguu agtttutgau 240
utttguuuau tguaguuaga tggggguuatu tgtggagutg guuttttutu uttagaatga 300

<210> SEQ ID NO 252
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 252
tuattutaag gagaaaaggu uagutuuaua gatgguuuua tutggutgua gtggguaaag 60
gtuagaaaut gguauaguat uutggguagg utguutgggg uaggguuygg ggutauaguu 120
tgggutgggg uuagauagag utttatutty guaagguuat uuuauutggt gutaatgagg 180
aggutuyggg uuuuauuuag atutggagut uauagtagyg gtttggautg aaauuaggga 240
tttgtgygtg ggguagtgag gggggguagut guyguuuutg guutggguut gagagtatag 300

<210> SEQ ID NO 253
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 253
aygggtgtut gutuuuaagu tggguauuuu tuuuuuaggu tgtgggaauy gutggguuat 60
tutgauutyg aauuagaaat aguuuygauu uuuututttu tuuuygyguu uuuaguygga 120
uyguuuuuyg ggauuuuagu uaaauuauag ygtuygguat aggguututu uuttattgua 180
uaauygutag gggagauaga gaggatgggg gtuuygggaa uatgutgggg tyguuagaut 240
atgggaygta ggggygtagu tuauutgttg gagauagguu ygutuutuau tggutgagtu 300

<210> SEQ ID NO 254
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 254
gautuaguua gtgaggagyg gguutgtutu uaauaggtga gutayguuuu taygtuuuat 60
agtutggyga uuuuaguatg ttuuygggau uuuuatuutu tutgtutuuu utagyggttg 120
tguaataagg gagagguuut atguyggayg utgtggtttg gutggggtuu yggggggygg 180
tuyggutggg ggygygggga gaaagagggg ggtyggggut atttutggtt ygaggtuaga 240
atgguuuagy ggttuuuaua guutggggga ggggtguuua guttgggagu agauauuygt 300

<210> SEQ ID NO 255
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 255
guagtaaaua gtuutattgt auaaatatat agygygggut gggygggggy ggtuaauuuy 60
ggttuuutgg uayggggaua gggygygutg gguuyggutu tguagygagu yggtgggagg 120
guutagutgt gguuuaggyg gtgttgagua ygggguyggg gygtuatagu yggggagggu 180
yggguagyga gygggtgggy gaggggygag tuatygtutg uuuyguuygg aggggauuuy 240
ggygggtgag ggaygtgggt ggagggagay gtggggagut uagtyggagt agatgatgaa 300

<210> SEQ ID NO 256
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 256
ttuatuatut autuygautg agutuuuuay gtutuuutuu auuuaygtuu utuauuyguy 60
ggggtuuuut uygggygggg uagaygatga utyguuuuty guuuauuygu tygutguuyg 120
guuutuuuyg gutatgaygu uuuygguuyg tgutuaauau yguutggguu auagutaggu 180
uutuuuauyg gutygutgua gaguygggu uagygyguuu tgtuuuygtg uuagggaauy 240
ggggttgauy guuuuyguuu aguuygygut atatatttgt auaataggau tgtttautgu 300

<210> SEQ ID NO 257
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 257
agttatttaa tauatgguuu uagtggguaut aauutgtuau taaguutuat gttutuuatu 60
uataaaatgg agauuauaat uatauutgut guaaaatuua aaattuagag gtttutauag 120
ygtgauygau autgtguuuy ggagagttty gguuututuu tggututggu uuuutggaau 180
aygtgatguu uaguuuaaau agtguuauau uutgututau aatguutuaa ygagagtuau 240
aauuaaagat ttttgagtua gaggauaata gaggaggtgg gaautgggta aayggagagt 300

<210> SEQ ID NO 258
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 258
ututuygttt auuuagttuu uauutuutut attgtuutut gautuaaaaa tutttggttg 60
tgaututygt tgagguattg tagaguaggg tgtgguautg tttgggutgg guatuaygtg 120
ttuuaggggg uuagaguuag gagaggguyg aaaututuyg ggguauagtg tyggtuaygu 180
tgtagaaauu tutgaatttt ggattttgua guaggtatga ttgtggtutu uattttatgg 240
atggagaaua tgagguttag tgauaggtta gtguuautgg gguuatgtat taaataautg 300

<210> SEQ ID NO 259
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 259
gagtttyggu uututuutgg ututgguuuu utggaauayg tgatguuuag uuuaaauagt 60
guuauauuut gututauaat guutuaayga gagtuauaau uaaagatttt tgagtuagag 120
gauaatagag gaggtgggaa utgggtaaay ggagagtuua tgguutttgg aggtggggua 180
uaguuyggag tgaatgaggg uuuagagttt uuagagaauy gaatatagat utgtgtgtga 240
aguutuuaga tattutaatg ttgauaayga aatuaaattg aaaaaaaata aaaatuaata 300

<210> SEQ ID NO 260
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 260
attgattttt atttttttu aatttgattt ygttgtuaau attagaatat utggaggutt 60
uauauauaga tutatattyg gttututgga aaututgggu uutuattuau tuygggutgt 120
guuuuauutu uaaagguuat ggaututuyg tttauuuagt tuuuauutuu tutattgtuu 180
tutgautuaa aaatutttgg ttgtgautut ygttgaggua ttgtagagua gggtgtggua 240
utgtttgggu tgggguatuay gtgttuuagg ggguuagagu uaggagaggg uygaaautut 300

<210> SEQ ID NO 261
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 261
ygggtgygga uuyguuauut guyguauuut tuuuttuuua auuutguuut ttuuuuauuu 60
uuauuuuaut tuuuauuuuu aauuuuygut yggyguuuua utuuygauuu tguutguuyg 120
gguauutygg ggygtuygut yguyggutty guutuuautt guuuyggaug gygygygtgg 180
gutyggygtu uygygutuuu tuutygautg tgyggutuuy gygutguygg gtttuutgtt 240
uaauaatata auuagggagg uauyggygga gagyguyggg uagaauttuu tuuyggautg 300

<210> SEQ ID NO 262
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 262
uagtuyggga ggaagttutg uuyggygutu tuyguyggtg uutuuutggt tatattgttg 60
aauaggaaau uyggua gygy gggaguygua uagtygagga gggagygygg gayguygagu 120
uuaygygygu utguyggggu aagtggaggy gaaguyggyg agyggayguu uygaggtguu 180
yggguaggua gggtygggag tggggyguyg agygggggtt gggggtggga agtggggtgg 240
gggtggggaa aggguagggt tgggaaggga agggtgyggu aggtggyggg tuyguauuyg 300

<210> SEQ ID NO 263
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 263
gguaagguag tutgggyguy gtutuyggtu tyggggguutg yggtyggggu auygyggtgu 60
ygygtttgag uyggtuagut uuutgyggaa attauagggg ygutyggygu tgyggtygyg 120
uuuuuygggg uagyguuygu tggttggagg ygtttaaatt gaaaguagut ttggggagag 180
ggggyggayg yggguyguyg aguaagggga gggggygguu ygguauagyg auuuuattgt 240
utgtguuygu ygaggggtgg aauuttgygg tgagutyggy gyggyguuuu utuuuygagu 300

<210> SEQ ID NO 264
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 264
gutyggggag ggggyguygy guygagutua uyguaaggtt uuauuuutyg gyggguauag 60
auaatggggt ygutgtguyg gguyguuuuu tuuuuttgut yggyygguuyg ygtuyguuuu 120 ututuuuuaa agutgutttu aatttaaayg uutuuaauua gygggygutg uuuygggggg 180
ygygauygua gyguygagyg uuuutgtaat ttuyguaggg agutgauygg utuaaaygyg 240
guauygyggt guuuygauyg uagguuuyga gauyggagay ggyguuuaga utguuttguu 300

<210> SEQ ID NO 265
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 265
ggagggaguu tguaututgg guagtgatgt ggagtuagag atttuuaagt tuatggtgua 60
agtutgtggg agaguagaau tuautttaua aaattgttga uaguyggtgt tgttagagay 120
ggaaagggau aauuuyggut uututuuagg ygtggagtut gtggggatgt guttuuagaa 180
aatguagggt taaguaggag utguagagta gaatuaaatg auaatgautu autgutgtua 240
utaauaggut utttgtgggg gutgtaggtg ggaggygata tgguyggaau uttyguauaa 300

<210> SEQ ID NO 266
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 266
ttgtgygaag gtguygguua tatyguutuu uauutauagu uuuuauaaag aguutgttag 60
tgauaguagt gagtuattgt uatttgattu tautu tguag utuutgutta auuutguatt 120
ttutggaagu auatuuuuau agautuuayg uutggagagg aguyggggtt gtuuutttuy 180
gtututaaua auauyggutg tuaauaattt tgtaaagtga gttutgutut uuuauagaut 240
tguauuatga auttggaaat ututgautuu auatuautgu uuagagtgua ggutuuutuu 300

<210> SEQ ID NO 267
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 267
gttutggtty gguagagtgg ygguaatutt guutututut utagaauauu taaagaaguu 60
agtgagtgag utgutuatgu auauygggga gauutauaga yggatuuagg aggagyggga 120
gutuattgau tguauauttu uaauuyggyg tgataggaaa gtgagguuau utgtuutaag 180
tguuyggggg uagggggtu uatggaggag ggggygggg uaggtgtutg gauauaggga 240
tgutggtutu aggtgguaua gutggggaga aaaaauutat uuattguaaa auatuattag 300

<210> SEQ ID NO 268
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 268
taatgatgtt ttguaatgga taggtttttt utuuuuagut gtguuauutg agauuaguat 60
uuutgtgtuu agauauutgu uuuyguuuuu tuutuuatgg auuuuuutgu uuuyggguau 120
ttaggauagg tgguutuaut ttuutatuay guygggttgg aagtgtguag tuaatgagut 180
uuygutuutu utggatuygt utgtaggtut uuuyggtgtg uatgaguagu tuautuautg 240
guttutttag gtgttutaga gagagaggua agattguygu uaututguyg aauuagaaua 300

<210> SEQ ID NO 269
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 269
ygtgatuaga gauagaaatu agutuuuutu utuuutuaut gaguttgtag uuautttaag 60
tataauutgt gtuutgtguu agttuuauua taaatuaguu utgagttuta tuyggyggut 120
tattutgutg uuaaaauutt uattagttgy gggaatgggu uagggagaga guuyggautt 180
tautuyggut gtggtgautu ayguutttgg gaagggutga ggtatttgtu uttggatgtg 240
gggatgutgt gguutuggt tgggaauaua guutygtttt gtutgutggu tutggutuu 300

<210> SEQ ID NO 270
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 270
ggaaguuaga guuaguagau aaaaygaggu tgtgttuuua auuagagguu auaguatuuu 60
uauatuuaag gauaaatauu tuaguuuttu uuaaaggygt gagtuauuau aguyggagta 120
aagtuygggu tututuuutg guuuattuuy guaautaatg aaggttttgg uaguagaata 180
aguyguygga tagaautuag ggutgattta tggtggaaut gguauaggau auaggttata 240
uttaaagtgg utauaagutu agtgagggag gaggggagut gatttutgtu tutgatuayg 300

<210> SEQ ID NO 271
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 271
uagtatguat gtgtuuattt aagguatutg aguuutgguu tttgutgttu ttuuttuutt 60
utttutuygt ygggttgutg agutuaauat uuuauygggu tuutgutuut tagutaguag 120
tuagtguaga gutgutgggt uuttutguut yguttgggua gguttutgtu aatgagtuau 180
uaaguauygg gaaataagtg uauaggaagg aguaggtggu aagauuutgt ggaggtagag 240
auagttuuat tuagtgagtg agutgtgaut guaaatttgg gaaggttutg ggggaaguaa 300

<210> SEQ ID NO 272
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 272
ttguttuuuu uagaauuttu uuaaatttgu agtuauagut uautuautga atggaautgt 60
ututauutuu auagggtutt guuauutgut uuttuutgtg uauttatttu uyggtguttg 120
gtgautuatt gauagaaguu tguuuaagyg agguagaagg auuuaguagu tutguautga 180
utgutaguta aggaguagga guuyggtggg atgttgagut uaguaauuyg ayggagaaag 240
aaggaaggaa gaauaguaaa gguuagggut uagatguutt aaatggauau atguatautg 300

<210> SEQ ID NO 273
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 273
ygguygyggg gggyguutgg aggagggaag uututuygga ggagaagagu tgggygguyg 60
uygtaggagg aagyggaaag ataaggggu utyggutygg ygggguyguy ggayguuuag 120
gaguuutaat ggggauaygt ygggtgggga yggagguagu tuutgtuygg auagygaaau 180
uygygagguu uaggagagyg guaguuagyg ygguauaguu ygggagutgy gguuuayguy 240
ggaguutayg gauatgggut yggaagggau aaaaauyggg uyggagtuag ygutggaguu 300

<210> SEQ ID NO 274
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 274
ggutuuagyg utgautuygg uuyggttttt gtuuuttuyg aguuuatgtu ygtaggutuy 60
ggygtggguy guagutuuyg ggutgtguyg ygutggutgu ygututuutg gguutygygg 120
gtttygutgt uyggauagga gutguutuyg tuuuuauuyg aygtgtuuuu attgaggutu 180
utgggygtuy ggygguuuyg uygaguygag gguuuuttat utttuygutt uutuutaygg 240
ygguyguuua gututtutuu tuyggagagg uttuuutuut uuaggyguuu uuygygguyg 300

<210> SEQ ID NO 275
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 275
guatuauaua tuuutuuutg tutuuutgut guuaauuagt tuuauuautg tguauututg 60
uuuuaattuu auutuuuayg uutgutgutg uauuttggau ttgttttuut gaaattguat 120
guuatuuaut utuuuttuta uttutgutgy gtuuututtg uuutatuagg auutgtggau 180
tuaggautuu ygggutttut uuuuuatutu tuttuuuygt tggguutuau tauuatttua 240
guuautttuu tgguagutttu autuutguuu uaagauuuua guutuuauuu tuutggttut 300

<210> SEQ ID NO 276
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 276
agaauuagga gggtggaggu tggggtuttg ggguaggagt gaagutguua ggaaagtggu 60
tgaaatggta gtgagguuua ayggggaaga gagatggggg agaaaguuyg ggagtuutga 120
gtuuauaggt uutgataggg uaagagggay guaguagaag tagaagggag agtggatggu 180
atguaatttu aggaaaauaa gtuuaaggtg uaguaguagg ygtgggaggt ggaattgggg 240
uagaggtgua uagtggtgga autggttggu aguagggaga uagggaggga tgtgtgatgu 300

<210> SEQ ID NO 277
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 277
ggtggygatg ututaguuau utguttutut gtuututttu auauaaatgt atuutguttu 60
tttuuagatg tuygguttaa tgggautgga tttatuttua aaagtuutgg tttguutuutg 120 attgaaaauu agtgtgutuu uuatggttay ggayggutgt guaggttttt gttttgttga 180
agggaattgg utuautuga gtuaguygtg uauuygggut gutgatgtag tutuagtgtg 240
atggttaaau tttaagtgtu aatttgautg ggutaaggaa tguuagauat tatttuyggg 300

<210> SEQ ID NO 278
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 278
uuyggaaata atgtutggua ttuuttaguu uagtuaaatt gauauttaaa gtttaauuat 60
uauautgaga utauatuagu aguuygggtg uayggutgau tuagagtgag uuaattuuut 120
tuaauaaaau aaaaauutgu auaguygtuy gtaauuatgg ggaguauaut ggttttuaat 180
uagagguaaa uuaggautt tgaagataaa tuuagtuuua ttaaguygga uatutggaaa 240
gaaguaggat auatttgtgt gaaagaggau agagaaguag gtggutagag uatyguuauu 300

<210> SEQ ID NO 279
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 279
ggttttgggt gtggauatuu tggagggutg ttttagtguu uauauuaatg uuutagttaa 60
agaauuauuu tgtuuuutta guuttutgua ggauaggtgg gaaaggguyg ggtgtutggt 120
uutgutguua ggggauagtg uaggtgtgau ygtuyggga gagatgagtu auuutuuaua 180
utgtuttgut guuygtutuu ayguutagtt ttagutygtg tggtuaagaa ggggygattu 240
utuauutaga auauatgggt uauaaatgut auutttgaaa atggaaauaa aaataauuua 300

<210> SEQ ID NO 280
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 280
tgggttattt ttgtttuuat tttuaaaggt aguatttgtg auuuatgtgt tutaggtgag 60
gaatyguuuu ttuttgauua uaygagutaa aautaggygt ggagayggu aguaagauag 120 tgtggagggt gautuatutu tguuyggayg gtuauauutg uautgtuuuu tgguaguagg 180
auuagauauu ygguuutttu uuauutgtuu tguagaaggu taaggggaua gggtggttut 240
ttaautaggg uattggtgtg gguautaaaa uaguuutuua ggatgtuuau auuuaaaauu 300

<210> SEQ ID NO 281
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 281
uagaauutga gygatgaagt gaygggattt agtuagguut atgaagagtu aatgguautt 60
guutuuuata atuuttuuag tuuuattggu uaauuygtut gtuuutygyg tgatuttttt 120
ggatutgaag tggtgtttua ggauuyggag ygtgguutgu autguuttgt tutgtttgtt 180
tgtguauygg attuatygtg autuatuutg agtuatuuag guagtatgga agaautttgg 240
agttatttta aauuutttgg utuagaauuu uatttuttut agaattaaua tguaagataa 300

<210> SEQ ID NO 282
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 282
ttatuttgua tgttaattut agaagaaatg gggttutgag uuaaagggtt taaaataaut 60
uuaaagttut tuuatautgu utggatgaut uaggatgagt uaygatgaat uyggtguaua 120
aauaaauaga auaagguagt guagguuayg utuygggtuu tgaaauauua uttuagatuu 180
aaaaagatua ygygagggau agaygggttg guuaatggga utggaaggat tatgggaggu 240
aagtguuatt gaututtuat agguutgaut aaatuuygtu auttuatygu tuaggttutg 300

<210> SEQ ID NO 283
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 283
gtuuuttggu auuaggauat uauuutuuua uututuuuag auuuttutuu ttgauututt 60
tagaguaguu atuuttggag ttgutuaayg uuututtutu ttutuuutut gaauuauagu 120
ttggutuatu tauttuyggg ttagutuaay guuututtut tttutuuutu tgaauuauag 180
uttggutuat utauttuygg gttagutuaa yguaututtu tuttutuuut utgaauuayg 240
guttggutua tutauttutg ggttaattta ggutttutuu auagatagtu tgaaaaggga 300

<210> SEQ ID NO 284
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 284
tuuuttttua gautatutgt ggagaaaguu taaattaauu uagaagtaga tgaguuaagu 60
ygtggttuag agggagaaga gaagagtgyg ttgagutaau uyggaagtag atgaguuaag 120
utgtggttua gagggagaaa agaagagggy gttgagutaa uuyggaagta gatgaguuaa 180
gutgtggttu agagggagaa gagaagaggg ygttgaguaa utuuaaggat ggutgututa 240
aagaggtuaa ggagaagggt utgggagagg tgggagggtg atgtuutggt guuaagggau 300

<210> SEQ ID NO 285
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 285
utgagtuaau aaggutgaua aggutgtgtt utggatguag guuygguaga tgtttgaggg 60
ggaggtgguu aguutggagg uuutuaggag uayggguutg gtgygggtgu ygagguuuat 120
gaaggtuaty gauutguygg gaggtggggu yguutttgtg atggaguatt tgaagatgaa 180
gaguttgagu aggtgagtgt gtgtgagauu uatatgygua uatgtgtaua gguagagaga 240
gautuagaga uaaauagaga gagauagaga aagggataga gatggggagg gagauagaaa 300

<210> SEQ ID NO 286
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 286
tttutgtutu uutuuuuatu tutatuuutt tututgtutu tututgtttg tututgagtu 60
tutututguu tgtauauatg tgyguatatg ggtutuauau auautuauut gutuaagutu 120
ttuatuttua aatgutuuat uauaaaggyg guuuuauutu uyggtuaggty gatgauuttu 180 atggguutyg guauuyguau uagguuygtg utuutgaggg uutuuaggut gguuauutuu 240
uuutuaaaua tutguygggu utguatuuag aauauaguut tgtuaguutt gttgautuag 300

<210> SEQ ID NO 287
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 287
ttygtguaut utgygguygy ggygguagua guygyggygg ygguuagutu uuyggtutay 60
gtguuuauua uuygygtggg ttuuatgutg uuygguutau ygtauuauut guaggggtyg 120
gguagtgggu uaguuaauua ygygggyggy gyggggygu auuuyggutg guutuagguu 180
tygguygaua guuutuuata ygguagygga ggyggygygg utggyggygg gguygygggg 240
uutggyggyg utggutuagu ygyggyguay gtutyggygy guttuuuuta ututuuuagu 300

<210> SEQ ID NO 288
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 288
gutgggagag taggggaagy gyguygagay gtgyguygyg gutgaguuag yguyguuagg 60 uuuygyggu uyguyguuag uygyguyguu tuygutguyg tatggagggu tgtygguyga 120
gguutgaggu uaguyggggt gygyguuygy guyguuygyg tggttggutg guuuautguu 180
ygauuuutgu aggtggtayg gtagguyggg uaguatggaa uuuaygyggg tggtggguay 240
gtagauyggg gagutgguyg uyguygyggu tgutguyguy gyggguyguag agtguaygaa 300

<210> SEQ ID NO 289
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 289

-continued

```
tutttgtgtg agtuatgtut tatatuuaau aagtautuaa aaaaagattt ttttttttt     60

tttttaagat ggagtgtygu tutgtuauuu aggutggagt guagtgguat gatuttggut    120

uautguaauu tutguutuuy gggttuaagy gattuttutg uutuaggutu utgagtagut    180

ggaattauag guatguuuua uuauauuygg utaattttta tatgtaatag aaauaaggtt    240

tuauuatgtt gguuagauag gtuttgaaut uutgauutua ggtgatuuau uuauutyggu    300


<210> SEQ ID NO 290
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 290

guygaggtgg gtggatuauu tgaggtuagg agttuaagau utgtutgguu aauatggtga     60

aauuttgttt utattauata taaaaattag uygggtgtgg tgggguatgu utgtaattuu    120

agutautuag gaguutgagg uagaagaaty guttgaauuy gggaggguaga ggttguagtg   180

aguuaagatu atguuautgu autuuaguut gggtgauaga gygauautuu atuttaaaaa    240

aaaaaaaaaa aaatuttttt ttgagtautt gttggatata agauatgaut uauauaaaga    300


<210> SEQ ID NO 291
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 291

auuauuuuut gauuuutuat gautuauuua gutuutaagt guuuutgggu auuuagttut     60

ttgtgguatg gguyggtgua agtttutata tgagaguuag agagauaggg agggagguuy    120

gggutuutgg uuttttggga aaagatguuy gtutuagauu aguaaaagga gguagutgut    180

ttaggaguuy gggaaaatgu uatuautgat agtattatta ttattttuuu attttuuutt    240

tgtgttttta aaatgaaaag ttuagatuua tggggtaggg tagagtgggu utggagggag    300


<210> SEQ ID NO 292
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 292

tuuutuuagg uuuaututau uutauuuuat ggatutgaau ttttuatttt aaaaauauaa     60

agggaaaatg ggaaaataat aataatauta tuagtgatgg uattttuuyg ggutuutaaa    120

guagutguut uuttttgutg gtutgagayg gguatutttt uuuaaaaggu uaggaguuyg    180

gguutuuutu uutgtututu tggututuat atagaaautt guauygguuu atguuauaaa    240

gaautgggtg uuuaggggua uttaggagut gggtgagtua tgaggggtua gggggtggtt    300


<210> SEQ ID NO 293
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 293
```

guaguaygua guuuuuaggg guuutaautu auuuuututt uuutuauagg guttuuutgu 60
ygtuuagtgt tgggtgagaa aggtggaggg gauatgtagu uuyggatgga ggtguaguau 120
uaaygagaga gutuygguut gtgggaggga ygutuaggut taggtuaaag uuaggagutu 180
ygggaaauut gggttuaguy guuayguuuu ayggaggga uauauuuttu uutguutgat 240
gguaggguuu atggtagaua aaauuuatga uutuauutut uutggutuua gggutuaguu 300

<210> SEQ ID NO 294
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 294
ggutgaguuu tggaguuagg agaggtgagg tuatgggttt tgtutauuat ggguuutguu 60
atuagguagg gaagggtgtg tuuuutuygt ggggygtggy ggutgaauuu aggtttuuyg 120
gagutuutgg utttgauuta aguutgagyg tuuutuuuau agguyggagu tututygttg 180
gtgutguauu tuuatuyggg gutauatgtu uuutuuauut ttutuauuua auautggayg 240
guagggaagu uutgtgaggg aagagggggt gagttagggu uuutgggggu tgygtgutgu 300

<210> SEQ ID NO 295
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 295
atttutttut auutgtuatt gaagtgaatu atuagtataa gtagygagut gggyguattu 60
uttutuagtt gtgttaaaau ttgutggtat tuuuuyggta tuaguagagg tgtgtayggg 120 uautgutta aaautgggaa ggaggaagay gagguuaggg aguyggaggg tuauuaaggt 180
agatttuuag uagygutagt uuagutgaau autttuuagu uttgtttttu aguagutttg 240
aggaaaagta taggtaagaa uaaagauauu autgtatgtt tgutatatga atguataaua 300

<210> SEQ ID NO 296
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 296
gttatguatt uatataguaa auatauagtg gtgtutttgt tuttauutat auttttuutu 60
aaagutgutg aaaaauaagg utggaaagtg ttuagutgga utagygutgu tggaaatuta 120
uuttggtgau uutuyggutu uutgguutyg tuttuutuut tuuuagtttt aaaguagtgu 180
uygtauauau ututgutgat auygggggaa tauuaguaag ttttaauaua autgagaagg 240
aatgyguuua gutygutaut tatautgatg attuauttua atgauaggta gaaagaaatg 300

<210> SEQ ID NO 297
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 297
attggtutgg tuututttut aauauutuuu auuygggatg uaguuaagag tggutguagu 60
utaattttut auatgtaaau aatgauutua gtgatguuua yggggguuut ututgguutt 120
utuuuuutgg gaaaagautg agttutygay ggguatuuuu tuuuuutuyg gaauuaaggg 180
ututgggatg ttgauaguuu uyguuauutu tgagaagggu agguygtgga aaauuatutu 240
utuuuttuut tuuuuututg uutttuutag utggggguutu tguauaatgu agutgggua 300

<210> SEQ ID NO 298
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 298
tgguuuagut guattgtgua gagguuuuag utaggaaagg uagaggggga aggaagggag 60
gagatggttt tuuaygguut guuuttutua gaggtggygg gggutgtuaa uatuuuagag 120
uuuttggttu yggaggggga ggggatguuy gtygagaaut uagtuttttu uuaggggggag 180 aagguuagag aggggguuuyg tgggguatuau tgaggtuatt gtttauatgt agaaaattag 240
gutguaguua ututtggutg uatuuygggt gggaggtgtt agaaagagga uuagauuaat 300

<210> SEQ ID NO 299
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 299
ttguuutuat utuuaggutt tggaggaggg taggtguutg guuaguagag tgguuautgu 60
tuautgguuu agaggaagua agguuauuag uutgatuuua uttutuuutu ygguuuatut 120
tuautuuuut utuutuaauu auaaguuuyg uuaaaataga gauuuuyggu tttgutuuuu 180
tgutguagga agggagaguu auyguuagau autguutguu tggtuutuut gttutgatut 240
uauuyggtgu ttggaatuaa agaggauutg guttuuutut ygggataygt gattttuttt 300

<210> SEQ ID NO 300
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 300
aagaaaatua ygtatuuyga gagggaaguu aggtuututt tgattuuaag uauygggtga 60
gatuagaaua ggaggauuag guagguagtg tutggyggtg gututuuutt uutguaguag 120
gggaguaaag uygggggtut utattttggy ggggutgtg gttgaggaga ggggagtgaa 180
gatggguygg agggagaagt gggatuaggu tggtgguutt guttuututg gguuagtgag 240
uagtgguuau tutgutgguu agguauutau uutuutuuaa aguutggaga tgaggguaag 300

<210> SEQ ID NO 301
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 301
guuuagatua gguagygggg tyguuututu uaggaututu aagguaguta aggutggagg 60
yguyggygag uutggagagg gaggagttua utaaattgtg ttggatggaa ggygtygagg 120
auyggaggaa ttaatuygat gtggggaagg yggayggggu taygaggaaa aaagaggggg 180
uaatgtauau tuaguutttt uatuautygg yggggagatg gatggttttu yggauygggy 240
gtuuuagygu uuyggttagu tatagggaga ygtuagagyg ututggtuyg ygatagaaga 300

<210> SEQ ID NO 302
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 302
tuttutatyg yggauuagag ygututgayg tutuuutata gutaauyggg gygutgggay 60
guuyggtuyg gaaaauuatu uatutuuuyg uygagtgatg aaaaggutga gtgtauattg 120
uuuuututtt tttuutygta guuuygtuyg uuttuuuuau atyggattaa ttuutuyggt 180
uutygayguu ttuuatuuaa uauaatttag tgaautuutu uututuuagg utyguyggyg 240
uutuuaguut tagutguutt gagagtuutg gagagggyga uuuygutguu tgatutgggu 300

<210> SEQ ID NO 303
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 303
atttgguttg atuttatttt taatattttt tauautttut ututaaagaa aaaaaaggyg 60
agtgaatuty gtgatgggtg uagttatgut gaataattgg atgggaggay gtguuaggyg 120
atutuuaguu uutgggaguy ggayguuuay guutuuutut guutygttut uauagauaua 180
tttgtggggt gattaautua ggaattuatg utgutuaaag taautauagt ggtgagtgtt 240
ttgauyggtt tgatgtagaa atuaaggaaa auauuagaaa aatuaggggy ggagguuuaa 300

<210> SEQ ID NO 304
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 304
ttggguutuy guuuutgatt tttutggtgt tttuuttgat ttutauatua aauyggtuaa 60
aauautuauu autgtagtta utttgaguag uatgaattuu tgagttaatu auuuuauaaa 120
tgtgtutgtg agaaygaggu agagggaggy gtgggygtuy ggutuuuagg ggutggagat 180
yguutgguay gtuutuuuat uuaattattu aguataautg uauuuatuay gatattuaut 240 yguuttttt ttutttagag agaaagtgta aaaaatatta aaaataagat uaaguuaaat 300

<210> SEQ ID NO 305
<211> LENGTH: 300
<212> TYPE: DNA
<213> ORGANISM: Artificial Sequence
<220> FEATURE:

<223> OTHER INFORMATION: Synthetic polynucleotide

<400> SEQUENCE: 305
tgautttttu atttututua agatgatuat taggagtggt ttuaauaaaa utgaauauag 60
aattttgagg guuuuaatua tgautuaauu agaguuutuu utgaattutt uatgagtuag 120
uuygguuutu uuuautgaut tuauuutagy ggguauutgt utttuttutt uttttatuau 180
tttttguttu tuttttggtt tuuagututg autgaattua gauuuaauau uttuuaattu 240
ttuuygguuu uutuagggaa auuuagaggu aaatttgagt guagggagyg ggggguttygu 300

<210> SEQ ID NO 306
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 306
gygaaguuuu ygutuuutgu autuaaattt guututgggt ttuuutgagg ggguuygggaa 60 gaattggaag gtgttgggtu tgaattuagt uagagutgga aauuaaaaga gaaguaaaaa 120
gtgataaaag aagaagaaag auaggtguuy gutagggtga agtuagtggg gaggguuyggg 180 utgautuatg aagaattuag ggagggutut ggttgagtua tgattggggu uutuaaaatt 240
utgtgttuag ttttgttgaa auuautuuta atgatuatut tgagagaaat gaaaaagtua 300

<210> SEQ ID NO 307
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 307
ggtgtuagga gtgguuuagg agaguauuuy gttuuuyggu uyguaggtgg tgtttgutgg 60
utuuaguagg guuaggaggu uauutguagu utggtgutuu agautgatgt uauuygggguy 120 gagtgutgtg uutuygguaa uattgauauy guutggtuua auutuauuua uuyggggaau 180
aagatuaauu tuutyggutt uttggguutt gtuuautguu ttuuutguaa aggtgagauu 240
tuagguuaga aguagggguag aygtutuagu tuaggauuag uuauaaauag tuatggtggt 300

<210> SEQ ID NO 308
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 308
auuauuatga utgtttgtgg utggtuutga gutgagaygt utguuutgut tutgguutga 60
ggtutuauut ttguagggaa gguagtggau aagguuuaag aaguygagga ggttgatutt 120
gttuuuyggg tgggtgaggt tggauuaggy ggtgtuaatg ttguyggagg uauaguauty 180
gguuygggtg auatuagtut ggaguauuag gutguaggtg guutuutggu uutgutggag 240
uuaguaaaua uuauutgygg guyggggaay ggggtgutut uutggguuau tuutgauauu 300

<210> SEQ ID NO 309
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 309
guaguuutut tuauutguut ggtgautuau tauaaguuut gggggaagga atgguagtgg 60
uuututtuau utttautguu tutgygguua uaatggguag ttgauataau uauutguagg 120
uuuygggagu uatyggggu tuttgauayg tgutuattag tgguttutga ggagyguutg 180
uuuuauutgu uuuaygtguu uuuaygtutg guuautuuag ggtuuattag ygutaatygg 240
uaaatguutg tgututuatu tauygggaaa auatutuuut tutuuagagy ggagguuagu 300

<210> SEQ ID NO 310
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 310
utgguutuyg ututggagaa gggagatgtt ttuuyggtag atgagaguau agguatttgu 60
ygattagygu taatggauuu tggagtgguu agaygtgggg guaygtgggg uaggtggggu 120
aggygutuut uagaaguuau taatgaguay gtgtuaagag guuuygatgg utuuyggggu 180
utguaggtgg ttatgtuaau tguuuattgt gguyguagag guagtaaagg tgaagagggu 240
uautguuatt uuttuuuuua ggguttgtag tgagtuauua gguaggtgaa gagggutgut 300

<210> SEQ ID NO 311
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 311
gtgguuutut tuauutttau tguututgyg guuauaatgg guagttgaua taauuauutg 60
uagguuuygg gaguuatygg gguututtga uaygtgutua ttagtggutt utgaggagyg 120
uutguuuuau utguuuuayg tguuuuuayg tutgguuaut uuagggtuua ttagygutaa 180
tygguaaatg uutgtgutut uatutauygg gaaaauatut uuuttutuua gagyggaggu 240
uaguutaaaa auuagguuyg uaguutuyga ggututgaaa auuaagyggu tgttutggtu 300

<210> SEQ ID NO 312
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 312
auuagaauag uyguttggtt ttuagaguut yggaggutgy ggguutggtt tttaggutgg 60
uutuygutut ggagaaggga gatgttttuu yggtagatga gaguauaggu atttguygat 120
tagygutaat ggauuutgga gtgguuagay gtgggggguay gtggggtuagg tggggtuaggy 180 gutuutuaga aguuautaat gaguaygtgt uaagagguuu ygatggutuu ygggguutgu 240
aggtggttat gtuaautguu uattgtgguy guagagguag taaaggtgaa gaggguuaut 300

<210> SEQ ID NO 313
<211> LENGTH: 300
<212> TYPE: DNA

<213> ORGANISM: Artificial Sequence
<220> FEATURE:
<223> OTHER INFORMATION: Synthetic polynucleotide

<400> SEQUENCE: 313
atggguuutg ggguyguygu utuagtgtut tutggtgutg uaguygggua ggguygaauu 60
utggyguaua guttuutgut gagtutuuut ututaaggut gtutgtgggy ggututguyg 120
guuuutuutg uauutguuua gguuutgggy ggaggutuut uutuuygggg gggutgtggu 180
utuaguauag auuaggggau agaaggtggu tuttuttggu uttggutggg tgtgaauuaa 240
agauttuutg taagaaatuu uuutututuut utuuutuutt ygutuuutua tutututuuu 300

<210> SEQ ID NO 314
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 314
gggagagaga tgagggagyg aaggagggag agggagaggg ggatttutta uaggaagtut 60
ttggttuaua uuuaguuaag guuaagaaga guuauuttut gtuuuutggt utgtgutgag 120
guuauaguuu uuuygggagg aggaguutuy guuuagggtuu tggguaggtg uaggaggggu 180
ygguagaguy guuuauagau aguuttagag agggagautu aguaggaagu tgtgyguuag 240 ggttyggtuuu tguuyggutg uaguauuaga agauautgag gyggygguuu uaggguuuat 300

<210> SEQ ID NO 315
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 315
uautggauua tuuauauaau ttttgaggat uagtggaaat gaaaauaygg tguuuyggua 60
uaaaauatat ttuatagutt gggttaggua auaguaaagu atuaygutga gyguyyggau 120
uttutgagtg uaggyggtgg gygaaguuuy gagtuauaua uauuuaygay guyggguuutg 180 utuuuauagy gguuututgg ggtagygaut ggtattauut guatttuayg agggaggaaa 240
utgagguayg aautgttuag aagutguuut gaggtuauua agtgagutag gaagaggygt 300

<210> SEQ ID NO 316
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 316
yguututtuu tagutuautt ggtgauutua ggguaguttu tgaauagtty gtguutuagt 60
ttuutuuuty gtgaaatgua ggtaatauua gtygutauuu uagaggguyg utgtgggagu 120
aggguyggyg tygtgggtgt gtgtgautyg gggutttyguu uauyguutgu autuagaagg 180
tuuyggygut uagygtgatg utttgutgtt guutaauuua agutatgaaa tatgttttgt 240
guygggguau ygtgttttua tttuuautga tuutuaaaag ttgtgtggat ggtuuagtgt 300

<210> SEQ ID NO 317
<211> LENGTH: 300

<212> TYPE: DNA
<213> ORGANISM: Artificial Sequence
<220> FEATURE:
<223> OTHER INFORMATION: Synthetic polynucleotide

<400> SEQUENCE: 317
utuuagtgtg uutuagttgg tttatutgta aaaatggggu uagguuayga utggtgttuu 60
utttauagag aaguautuua gguaggggtg ggtgggggtg gaautygttu tuaatgguuu 120
uygggauagu uutguaguua uyggtgauty gggttygtut gyggatuttt uuygguutuu 180
autuuattua gggauaguuu tguaatgggg utuuutuuua aaaaaaygua tgguuttuut 240
gtuuuuuaaa auuaguttaa ygguaguuat tuuutuuutu utuygggggu tgaaaaauua 300

<210> SEQ ID NO 318
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 318
ggtttttuag uuuuyggagg agggagggaa tggutguygt taagutggtt ttgggggaua 60
ggaagguuat gygttttttt gggagggagu uuuattguag ggutgtuuut gaatggagtg 120
gagguyggga aagatuygua gaygaauuyg agtuauyggt ggutguaggg utgtuuyggg 180
gguuattgag aaygagttuu auuuuuauuu auuuutguut ggagtguttu tutgtaaagg 240
gaauauuagt ygtgguutgg uuuuattttt auagataaau uaautgaggu auautggagg 300

<210> SEQ ID NO 319
<211> LENGTH: 301
<212> TYPE: DNA
<213> ORGANISM: Artificial Sequence
<220> FEATURE:
<223> OTHER INFORMATION: Synthetic polynucleotide

<400> SEQUENCE: 319
uautuayggg utagutuygt uaggtgttga yggatgtuau tuaggtgtga gututguauu 60
tgagutuuuu uutguauaua gguaguuaua auuagtuagt guagaggtga guutgtgguu 120
agtgaggagu yggtgagtua auutuutuuy guutaygggu uutgagaygu yggutuygtg 180
aguttgyggg gtygagggyg uutatattaa guuaaggutg agguagtgau auauuututt 240
atggguutgu tutygutuuu tguttuattg tuutggtutu tuuutuytgt atggaggatu 300
a 301

<210> SEQ ID NO 320
<211> LENGTH: 301
<212> TYPE: DNA
<213> ORGANISM: Artificial Sequence
<220> FEATURE:
<223> OTHER INFORMATION: Synthetic polynucleotide

<400> SEQUENCE: 320
tgatuutuua taygagaggg agagauuagg auaatgaagu agggagygag aguagguuua 60
taagagggtg tgtuautguu tuaguuttgg uttaatatag gyguuutyga uuuyguaagu 120
tuayggaguy ggygtutuag gguuygtagg ygggaggagg ttgautuauy ggutuutuau 180
tgguuauagg utuauutuutg uautgautgg ttgtggutgu utgtgtguag gggggagutu 240
aggtguagag utuauauutg agtgauatuy gtuaauauut gayggaguta guuygtgagt 300
g 301

<210> SEQ ID NO 321
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 321
uuaggutguu tgggttttgg tutuuauuat gutaguttgg tgtuygauut gtgttgagau 60
uutuuutguu tutgguuygg gtgtuuuatu uaaguaatgg auaggttgga auaggygtty 120
gtagggaayg ggutgaaygu uygyggutuu ygygatgtut ygygatauta uutuuutygu 180
uuuygutuau ttaaggauyg gaagtaguaa aguuyguygt ygyguuuuuy guuuygygtu 240
tuuutggtaa uuaguututu uuuttuuuty guuuataagg aguaagyggu auaaatyggg 300

<210> SEQ ID NO 322
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 322
uuygatttgt guyguttgut uuttatgggy gagggaaggg gagaggutgg ttauuaggga 60 gaygygggy ggggggygyg ayggygggut ttgutauttu yggtuuttaa gtgagygggg 120
gygagggagg tagtatygyg agauatygyg ggaguygygg gygttuaguu ygttuuutay 180
gaayguutgt tuuaauutgt uuattguttg gatgggauau uygggguuaga gguagggagg 240 gtutuaauau aggtyggaua uuaagutagu atggtggaga uuaaaauuua gguaguutgg 300

<210> SEQ ID NO 323
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 323
uaatgguutu tttuttuagu utyggtgggy gtggutgggg gaauuuuagg gygggygggg 60
gguagggggt ggtgutgagt uauuuaguut gguuaggtuu utguutguua guuuuutguu 120
uuuauyguta uaguuyguuu yggatutayg agguuuaguu aguuauutut ggautuutga 180
gauygaattg uaaautguuy ggguutgguu ttgaautuut gutgtttagg gauuaagtuu 240
tgtggutuuu agggggguau agtgatutut uaagutgagu tgguutuagg guututguau 300

<210> SEQ ID NO 324
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 324
tguagagguu utgagguuag utuaguttga gagatuautg tguuuuuutg ggaguuauag 60
gauttggtuu utaaauagua ggagttuaag guuagguuyg gguagtttgu aattyggtut 120
uaggagtuua gaggtggutg gutggguuty gtagatuygg ggygggutgt agyggtgggg 180
guagggggut gguagguagg gauutgguua ggutgggtga utuaguauua uuuuutguuu 240
uuyguuyguu utggggttuu uuuaguuayg uuuauygagg utgaagaaag agguuattgt 300

<210> SEQ ID NO 325
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 325
auuutgtgua ggguutguat uuyggaaggu utuuauuagu uygaauutgg uuygtuyguu 60
utagatgggg uaatyggygt ttutuuyggg auaguutuut uuutgguutu utgguuutyg 120
tutguattga gaggutuggu ututggtuyg uatgutguuu ttuuygtgut gtgguuttgu 180
aguuygguut utuuuutgut gtuuuuuttg gututgguut gguuuutggg uuuutgagtu 240
auuuutgagg tgautuagua gtuuttggaa ayguatguyg aggayguauu utguutgguu 300

<210> SEQ ID NO 326
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 326
guuagguagg gtgygtuuty gguatgygtt tuuaaggaut gutgagtuau utuaggggtg 60
autuaggggu uuaggggua gguuagaguu aagggggaua guaggggaga gguygggutg 120
uaagguuaua guaygggaag gguaguatgy ggauuagagg uuaaguutut uaatguagay 180
gaggguuagg agguuaggga ggaggutgtu uygggagaaa yguygattgu uuuatutagg 240 gyggayggggu uaggttyggg utggtggagg uuttuyggga tguagguuut guauagggtt 300

<210> SEQ ID NO 327
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 327
ggaauuattg ttutgutguu uauagutgyg tggagggatt uyggtuutyg ggttuagttg 60
gtgauagtgt ygggtagguu tggguaggtg ggagaggtyg tgaaguuutt tguaggguau 120
ttgguygutu atutgguaua ggggaagagg yguaguuygt gguuygguag tuuaggauut 180
gutgttuuut tuutauuygg ggygggguut gtgggaagat atggaagtyg ggtgaatgag 240
uygtguuuag tgattttaaa aaguagatta aaataauata gaaaatgtua gagutuattg 300

<210> SEQ ID NO 328
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 328
uaatgagutu tgauattttu tatgttattt taatutgutt tttaaaatua utggguaygg 60
utuattuauu ygauttuuat atuttuuuau agguuuyguu uygggtagga agggaauagu 120
aggtuutgga utguygggu uaygggutgyg uututtuuuu tgtguuagat gagygguuaa 180

-continued gtguuutgua aagggutuua ygauututuu uauutguuua gguutauuyg auautgtuau 240
uaautgaauu ygaggauygg aatuuutuua yguagutgtg gguaguagaa uaatggtuu 300

<210> SEQ ID NO 329
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 329
guatuutuau utgygtuyga agyguagatg gaguuuaagg gaaagguuut gtagaggauu 60
uygtgtgaut tgggguaaag ygtgguutuu uaggggtgyg tggguagygg gayguuuatg 120
gtgtgauygg gtttgtguut uuatagggau ygtutguuut gtguagagag uuuutgtggg 180 gyggggaagtg gygaguaguy gguaaggagg uuuaguuaga uagaaguagg ggggtuaggg 240
auatgggagg tgggggauua guuagtgagt uagaygtgag gauttuagtg uuaaggautg 300

<210> SEQ ID NO 330
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 330
uagtuuttgg uautgaagtu utuaygtutg autuautggu tggtuuuuua uutuuuatgt 60
uuutgauuuu uutguttutg tutggutggg uutuuttguy ggutgutygu uauttuuygu 120
uuuauagggg ututgtuau aggguagayg gtuuutatgg agguauaaau uyggtuauau 180
uatgggygtu uygutguuua yguauuuutg ggagguuayg utttguuuua agtuauaygg 240
ggtuututau aggguutttu uuttgggutu uatutgygut tyggayguag gtgaggatgu 300

<210> SEQ ID NO 331
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 331
aggttuuuua tuutagutuu uyggatutuu atagggagtg tuuagggauu utuaatutuu 60
aggguuautt utguaggagu tygggttyga ggttuuaygt gguuagaaga gutuaggtut 120
utgagggutg gtgtguuygg gtauuuatuy guatuautgu tutuutuutg tuyggutayg 180
uuuagggutg agtgayggtg gtgguaagtg uttgtuutua ggguagygag gtuttutgtt 240
utgauaguag uagggautuu ttuatgguua uuagtaauuu uagtgggygg aggygutuut 300

<210> SEQ ID NO 332
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 332
aggagyguut uyguuuautg gggttautgg tgguuatgaa ggagtuuutg utgutgtuag 60
aauagaagau utygutguuu tgaggauaag uauttguuau uauygtuaut uaguuutggg 120
ygtaguygga uaggaggaga guagtgatgy ggatgggtau uygggtauau uaguuutuag 180
agauutgagu tuttutgguu aygtggaauu tygaauuyga gutuutguag aagtgguuut 240
ggagattgag gguuutgga uautuuutat ggagatuygg ggagutagga tggggaauut 300

<210> SEQ ID NO 333
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 333
tuuttuuttu tttuuttutt tututututt ttutttuttt tuttttuttt tututtuttt 60
uattttgaga ygtaututgg ututgtyguu uaggutggag yguaatggyg uuatutyggy 120
guautguaau utuuauutuu ygggttuaag ygattutaut guutuaguut uuygagtagu 180
tgggautaua ggygyguaut auuaaguuyg gutaattttt ttttgtattt ttagtagaga 240
utgggtttua ygatgttggu ygggutggtu tggaagtutt gauutuaagy gtgyguuutu 300

<210> SEQ ID NO 334
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 334
gagggyguay guttgaggtu aagautttua gauuaguuyg guuaauatyg tgaaauuuag 60
tututautaa aaatauaaaa aaaaattagu ygggutuggt agtgygyguu tgtagtuuua 120
gutautyggg aggutgaggu agtagaatyg uttgaauuyg ggaggtggag gttguagtgy 180
guygagatgg yguuattgyg utuuaguutg ggygauagag uuagagtayg tutuaaaatg 240
aaagaagaga aaagaaaaga aaagaaagaa aagagagaga aagaaggaaa gaaggaagga 300

<210> SEQ ID NO 335
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 335
agguututgu tgauutgtag aauttgttga uuyggatttt gatgtuagtu tuattggguu 60
tguygttgut uttuttggga uagaagatut utttgatuyg guuaattygg tagggutuag 120
ggguatuuag gttgutguut ttgatgtagt yggagtattt uyggtagtgu tutgggtaua 180
ggtuutuatu uaygggutuu ttuygtgggy gtttuayggg autggauagu ttgatgutgu 240
agagaaguau uuauttgaua tuaatgaauu ttuuauuttg uagtggtuag tuagguatga 300

<210> SEQ ID NO 336
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 336
tuatguutga utgauuautg uaaggtggaa ggttuattga tgtuaagtgg gtguttutut 60
guaguatuaa gutgtuuagt uuygtgaaay guuuayggaa ggaguuygtg gatgaggauu 120

-continued tgtauuuaga guautauygg aaatautuyg autauatuaa agguaguaau utggatguuu 180
utgaguuuta uygaattggu yggatuaaag agatuttutg tuuuaagaag aguaayggua 240
gguuuaatga gautgauatu aaaatuyggg tuaauaagtt utauaggtua guagagguut 300

<210> SEQ ID NO 337
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 337
ggggyggggt tygguyggggg gyggygguag gauutgagua guuaggaggg utgggggaua 60
gtuaggtuag guyggtggut auuyggugyu tggagagggu yggatgguay gtgguauuaa 120
guaaaaggag gutgaguuag aaaguaggga yggggutaga ygaguaaagu tggguaggag 180
ggygagttgg gaggggguyga guyggutgtg ygtggtuuut tgggaggagg gggtgtgguu 240
aaguaaguua aauagttygg aggtuagtgu aaggauaaga uaguutgggu aaaygaguag 300

<210> SEQ ID NO 338
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 338
utgutygttt guuuaggutg tuttgtuutt guautgauut uygaautgtt tgguttgutt 60
gguuauauuu uutuutuuua agggauuayg uauaguyggu tygguuuutu uuaautyguu 120
utuutguuua gutttgutyg tutaguuuyg tuuutguttt utggutuagu utuuttttgu 180
ttggtguuay gtguuatuyg guuututuua gyggguyggt aguuauyggu utgauutgau 240
tgtuuuuuag uuutuutggu tgutuaggtu utguyguygu uuuyggyuyga auuuyguuuu 300

<210> SEQ ID NO 339
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 339
ygagttggga gggguygagu yggutgtgyg tggtuuuttg ggaggagggg gtgtgguuaa 60
guaaguuaaa uagttyggag gtuagtguaa ggauaagaua guutggguaa aygaguaggg 120
gyggagygtg agaguagaut guauyggaty gutuagguua guuuaagutg aagaggaagg 180
gguaagutuu agaaguaggg gygggguyga uuaauutygu agatutgutg ggygaagagu 240
aguagutggg uuaguuygat gutgtguygg gguaggtagt utyggaggut guuuaggggu 300

<210> SEQ ID NO 340
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 340
uuuutgggua guutuygaga utauutguuu ygguauagua tygggutggu uuagutgutg 60
ututtyguuu aguagatutg ygaggttggt ygguuuyguu uutguttutg gaguttguuu 120
uttuututtu aguttgggut gguutgagyg atuyggtgua gtutgututu aygutuyguu 180
uutgutygtt tguuuaggut gtuttgtuut tguautgauu tuygaautgt ttgguttgut 240
tgguuauauu uuutuutuuu aagggauuay guauaguygg utygguuuut uuuaautygu 300

<210> SEQ ID NO 341
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 341
aauagguuua aguutgtggu aggtgggggt uauuuaguuu aggyguttuu uauuuuyggg 60
uutggguuag aaguuuagga gutggutgyg gguyggttut uuuuuauuua ututggggat 120
guutuagguu tgggtttuyg uuttaguuty guuagguuuu aatgaguutu tgtttgguut 180
gtagtuaatt gauyggttgg auttggggua ggtgutygag gaguuuuaut gagggagggu 240
aggtututtg tgygtautgt uuaguauata uaggaaattt aguatttutg uuuauuuagu 300

<210> SEQ ID NO 342
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 342
gutgggtggg uagaaatgut aaatttuutg tatgtgutgg auagtaygua uaagagauut 60
guuutuuutu agtggggutu utygaguauu tguuuuaagt uuaauyggtu aattgautau 120
agguuaaaua gaggutuatt ggggguutggy gaggutaagg yggaaauuua gguutgaggu 180
atuuuuagag tgggtggggg agaauygguu yguaguuagu tuutgggutt utgguuuagg 240
uuygggggtg ggaagyguut gggutgggtg auuuuuauut guuauaggut tggguutgtt 300

<210> SEQ ID NO 343
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 343
uutgauuuau uuaaututuu uaggggaygt gggggguautg gaguuuuaua uyguaggygg 60
tagutuaatg uauuygygty ggagttuutu uuuygygagy gtgguaaggu tuagggaagt 120
uuygggguuu tggggagggg guuttguygy guatuutgty guaggaauyg uygggguuutt 180 uuttuygygg gaagyggutt gguygauuuu yguuuuyguu ygggutuutt gggggtttuy 240
ggtguuyggu uauygtgggg utggggautg aaagtgatgg gautgaagat ggggutggaa 300

<210> SEQ ID NO 344
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 344
ttuuaguuuu atuttuagtu uuatuauttt uagtuuuuag uuuuayggtg guyggguauy 60
ggaaauuuuu aagagguuyg ggygggggyg ggggtyggu aaguygutu uygyggaagg 120 aagguuygg yggttuutgy gauaggatgy gygguaaggu uuuutuuuua gggguuyggg 180 autuuutga guuttguuay gutygygggg gaggaautuy gaygygggtg uattgaguta 240
uyguutgygg tgtggggutu uagtguuuuu aygtuuuutg ggagagttgg gtgggtuagg 300

<210> SEQ ID NO 345
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 345
tatuuaaatg tgttttatat aaaatgaaty gttttuagtg uautgaggaa gttttutatt 60
taaagaaatu utgutgtgaa ututtttgtg aagaatgutt tuutaatgga attagtuauu 120
autgagtuat ttutguaaau ttuaggtttg yggttttguu taaguaagat utgguyggag 180
aagtgagata aattatagat gtygutaata aattauagat tautuaaagg uaaaagagga 240
aagaaaaaaa aaaattgaut ygtgtatatg aauygaattg agtuaggggt utuuauyggu 300

<210> SEQ ID NO 346
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 346
guyggtggag auuuutgaut uaattyggtt uatatauayg agtuaatttt tttttttutt 60
tuututtttg uutttgagta atutgtaatt tattagygau atutataatt tatutuautt 120 utuyggguuag atuttgutta gguaaaauyg uaaauutgaa gtttguagaa atgautuagt 180
ggtgautaat tuuattagga aaguattutt uauaaaagag ttuauaguag gatttuttta 240
aatagaaaau ttuutuagtg uautgaaaay gattuatttt atataaaaua uatttggata 300

<210> SEQ ID NO 347
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 347
tgggagttuu agttygggggg uagauuagtg ttuagagtuy gggutugut autuagyguu 60 ygagguagyg uutuuuuatt uaaygggggu ygtgguaatt uuutgauatg attuatgauu 120 auataatau tuyggaaaut tututuuauy guutuuygtu tggguygtyg uuuuygguut 180
gggagautuu aggtutuaga gtututguuu uuayggggyga tuagtgutgu uuagtggaaa 240
aataatguua guygyguauu aaaattaggt gtaaaattaa uattttttgg aaguuauttt 300

<210> SEQ ID NO 348
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 348 aagtggguttu uaaaaaatgt taattttaua uutaattttg gtgygyggut gguattattt 60
ttuuautggg uaguautgat yguuygtggg gguagagaut utgagauutg gagtutuuua 120 gguyggggy gayggguuag aygggaggyg gtggagagaa gtttuyggat gtattatgtg 180
gtuatgaatu atgtuaggga attguuaygg uuuuygttga atggggaggy gutguutygg 240
gygutgagta guagaguuyg gautgaau autggtutgu uuuygaautg gaautuuuat 300

<210> SEQ ID NO 349
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 349
yggygtgutt uttgguaaau atutuuttga ggatguygut guaguauttg agutgutuyg 60
agauuttgut gututtutut ggtgutgggt gutgutgaga gtygggg uayg tuuttutttg 120 gaggtttuau agguyggutg ututuuyguy gutgguuuag uttggtggtu ttgggutuyg 180
gggguagyga gggtggutyg tgaatggggt uaatggtggt gggggtggtg gtgtutgutt 240
tuututtuau tuuuttuttt gtutguuaag aauayggayg uuaauaggua uagtuagaag 300

<210> SEQ ID NO 350
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 350
uttutgautg tguutgttgg ygtuygtgtt uttgguagau aaagaaggga gtgaagagga 60
aaguagauau uauuauuuuu auuauuattg auuuuattua ygaguuauuu tygutguuuu 120
yggaguuuaa gauuauuaag utggguuagy ggygggagag uaguyggutt gtgaaauutu 180
uaaagaagga ygtguuygau tutuaguagu auuuaguauu agagaagagu aguaaggtut 240
yggaguagut uaagtgutgu agygguatuu tuaaggagat gtttguuaag aaguayguyg 300

<210> SEQ ID NO 351
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 351
tggtutgutt uaagtuutau utgguuuutg guaagtuuua uttggtgaua tuttgtguut 60
gggtuuttga gggutguuuu agatuygyga ttgtuutggg gauyggtagt tuutuuuygg 120
atguuaguaa agutuuutuu aguutuuayg uutguauagt utuuagtatg uuttuaauag 180
uuattagtua uuutuutgtga gtuagauuuu yggtuutguu agguuaauut guttggggguu 240 tuaguagygg gggutggyga gguuagtttt utuuagyggt tutaaguygu tygagggtgg 300

<210> SEQ ID NO 352
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 352

-continued

```
uauuutygag ygguttagaa uygutggaga aaautgguut yguuaguuuu ygutgutgag      60

guuuuaagua ggttgguutg guaggauygg gggtutgaut uauagagggt gautaatggu     120

tgttgaaggu atautggaga utgtguaggy gtggaggutg gagggagutt tgutgguatu     180

yggggaggaa utauyggtuu uuaggauaat ygyggatutg ggguaguuut uaaggauuua     240

gguauaagat gtuauuaagt gggauttguu aggggguuagg taggauttga aguagauuag     300
```

<210> SEQ ID NO 353
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 353

```
auutggtygg uuauyggguag utyggggaag aagggygygt ggygyguuua utuuayggtg      60

utgaagagua guygyguuygu uagutyguau aygttgtyga tguuuaguau ygyguuyguy     120

gyguyguuuu utgyguygaa gygtuygguy guyguagggt agggutuagy gyguaguagu     180

tgygygatua gttyggauau yggutguuuy gggaagaggt utuyguygut yguuautguy     240

guuagyguyg aguuyggggg gutguuygag gaggyggua ygguauuagg uagygagtgu     300
```

<210> SEQ ID NO 354
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 354

```
guautygutg uutggtguyg tgguyguutu utygggguagu uuuuygggut yggygutggy      60

gguagtggyg agyggyggag auututtuuy gggguaguyg gtgtuygaau tgatygygua     120

gutgutgygy gutgaguuut auuutgyggy gguyggaygu ttyggyguag ggggyggygy     180

ggygggygyg gtgutgggua tygauaaygt gtgygagutg gyggygyggu tgututtuag     240

uauygtggag tgggygyguu aygyguuutt uttuuuygag utguyggtgg uygauuaggt     300
```

<210> SEQ ID NO 355
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 355

```
tgguagagat auaaattuut gatgguagag gagggagaga gagtgtgggt gaygatgaua      60

attgaautga gauuuaaagg aggtagggga gauatatggg ygtututggg aagatggtuu     120

uygggaaagu auaguuttta gauagguuuy gagguaggag uutgtutgau tuauyggagg     180

aguttggagg aggutgaggt gguutaagty gattaaguag ggtggggagg gaagaggyga     240

tggtguygtg agauuaagua ggguuttgag gtutgggggg agaautttgg uttttautut     300
```

<210> SEQ ID NO 356
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 356
gagtaaaagu uaaagttutu uuuuuagauu tuaagguuut guttggtutu aygguauuat 60
yguututtuu utuuuuauuu tguttaatyg auttagguua uutuaguutu utuuaagutu 120
utuyggtgag tuagauaggu tuutguutyg ggguutgtut aaaggutgtg utttuuyggg 180
gauuatuttu uuagagaygu uuatatgtut uuuutauutu utttgggtut uagttuaatt 240
gtuatygtua uuuauautut ututuuutuu tutguuatua ggaatttgta tututguuag 300

<210> SEQ ID NO 357
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 357
agaggaggga gagagagtgt gggtgaygat gauaattgaa utgagauuua aaggaggtag 60
gggagauata tgggygtutu tgggaagatg gtuuuyggga aaguauaguu tttagauagg 120
uuuygaggua ggaguutgtu tgautuauyg gaggaguttg gaggaggutg aggtgguuta 180
agtygattaa guagggtggg gagggaagag gygatggtgu ygtgagauua aguaggguut 240 tgaggutgg ggggagaaut ttggutttta ututgaggaa ggtgggaguu auagaggutt 300

<210> SEQ ID NO 358
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 358
aguututgtg gutuuuauut tuutuagagt aaaaguuaaa gttutuuuuu uagauutuaa 60
gguuutgutt ggtutuaygg uauuatyguu tuttuuutuu uuauuutgut taatygautt 120
agguuauutu aguutuutuu aagutuutuy ggtgagtuag auaggutuut guutyggggu 180
utgtutaaag gutgtguttt uuyggggauu atuttuuuag agayguuuat atgtutuuuu 240
tauutuuttt gggtutuagt tuaattgtua tygtuauuua uautututut uuutuututg 300

<210> SEQ ID NO 359
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 359
tgggygtutu tgggaagatg gtuuuyggga aaguauaguu tttagauagg uuuygaggua 60
ggaguutgtu tgautuauyg gaggaguttg gaggaggutg aggtgguuta agtygattaa 120
guagggtggg gagggaagag gygatggtgu ygtgagauua aguaggguut tgaggutgg 180 ggggagaaut ttggutttta ututgaggaa ggtgggaguu auagaggutt utagauagaa 240
gaaggauaag uyggautuag gatauuaggg tgggggtatu tgtgggggat aaagggagaa 300

<210> SEQ ID NO 360
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 360
ttutuuuttt atuuuuuaua gatauuuuua uuutggtatu utgagtuygg uttgtuuttu 60
ttutgtutag aaguututgt ggutuuuauu ttuutuagag taaaaguuaa agttutuuuu 120
uuagauutua agguuutgut tggtutuayg guauuatygu ututtuuutu uuuauuutgu 180
ttaatygaut tagguuauut uaguutuutu uaagutuutu yggtgagtua gauaggutuu 240
tguutygggg uutgtutaaa ggutgtgutt tuuyggggau uatuttuuua gagayguuua 300

<210> SEQ ID NO 361
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 361
ggutttgtga aauuaauuag gaagaatgaa auauagagut ggtuygauau uuagutygag 60 ggagggggu yggaagutttu tggaagttgg utguuuutaa guaggggutaa ututaguuua 120 uaagguuaag ttgguagagg uagaygaggg gaututgygg utuaagtuay ggguuaggag 180
uuyguagutg uygggutgga aaggtuagag uyggututgy gtutggutgy guygguaaga 240
aguuauaatt ayguagguaa aagaguuygg ggattaguuu uaguauutgg gauuutgaat 300

<210> SEQ ID NO 362
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 362
attuagggtu uuaggtgutg gggutaatuu uygggututt ttguutgygt aattgtggut 60
tuttguyggy guaguuagay guagaguygg ututgauutt tuuaguuygg uagutgyggg 120
utuutgguuy gtgauttgag uyguagagtu uuutygtutg uututguuaa uttgguuttg 180
tgggutagag tgguuuutgu ttagggguag uuaauttuua gaaguttuyg guuuuuutuu 240
utygagutgg gtgtyggauu agututgtgt ttuattuttu utggttggtt tuauaaaguu 300

<210> SEQ ID NO 363
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 363
aggutgaayg gaattgggag uagaguuutg yggtaggaua gagauttygu aaaguuygga 60
guauauagua guauuuygtu ttutaaagga uaattttggg aaaaututtg uutaatattu 120
tgguautaag gatuattutg tuauatuuuy gututggaut auaaguutgu aaguuuuatu 180
ygggguaggg utuutuattu utgtguauyg tggaaguuut gtguutguuu aggguutggu 240
auttgtaygt auttgaaaau utygtgtgga gtaaagagag gggtgatgtg uaaagguutt 300

<210> SEQ ID NO 364
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 364
aagguutttg uauatuauuu ututuutttau tuuauaygag gttttuaagt aygtauaagt 60
guuagguuut ggguagguau agggutuua yggtguauag gaatgaggag uuutguuuyg 120
gatggggutt guaggutttgt agtuuagagy ggggatgtga uagaatgatu uttagtguua 180
gaatattagg uaagagtttt uuuaaaattg tuutttagaa gayggggtgu tgutgtgtgu 240 tuygggutt gygaagtutu tgtuutauyg uagggututg utuuuaattu ygttuaguut 300

<210> SEQ ID NO 365
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 365
aguuagguta aauuagygtg tuuuaatgag ggguuutggg utgagtggag gaaatgggtg 60
yggtggaggt gggtttggut ggguauagyg gguaygtgtg ggtaagyggg tgggguyggt 120
tgtgygggtg guutatutgg gguaaguagu ygagguygau tgtgtuyggy gtgtggttga 180
guayggguag gtgtutggyg gtgauuutgu aygtutggtg tttauutggu uutgggtutg 240
aygtggguyg yguutggutg utggygggau agtgtgttat utguutgygg ayguttuygg 300

<210> SEQ ID NO 366
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 366
uyggaagygt uyguagguag ataauauaut gtuuyguuag uaguuaggyg ygguuuaygt 60
uagauuuagg guuaggtaaa uauuagaygt guagggtuau yguuagauau utguuygtgu 120
tuaauuauay guyggauaua gtygguutyg gutguttguu uuagataggu uauuyguaua 180
auygguuuua uuyguttauu uauaygtguu ygutgtguuu aguuaaauuu auutuuauyg 240
uauuuatttu utuuautuag uuuaggguuu utuattggga uaygutggtt taguutggut 300

<210> SEQ ID NO 367
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 367
uuttggutua ggttggggag ggygtuatga gtuatgaggt gggygttgua tttgtuagtt 60
gtguaguygy guauuauyga gtagtutggy gguagygygt uygygttyga ttgygtutgg 120
uuyguaggag guuyggtuua guaguuuttu yguauuaggg tuauyggygy gygatauuut 180
gggggyggga tyggggutyg tgututgutt uuygaaauuu ttutuuutuu agtutuagyg 240
ttuttuutuu tuuututatu utttuauttt uauutauauu tuutuuuutu uutuuttuuu 300

<210> SEQ ID NO 368
<211> LENGTH: 300
<212> TYPE: DNA
<213> ORGANISM: Artificial Sequence
<220> FEATURE:

-continued

<223> OTHER INFORMATION: Synthetic polynucleotide

<400> SEQUENCE: 368
gggaaggagg gaggggagga ggtgtaggtg aaagtgaaag gatagaggga ggaggaagaa 60
ygutgagaut ggagggagaa gggtttyggg aaguagagua ygaguuuyga tuuyguuuuu 120
agggtatygy gyguyggtga uuutggtgyg gaagggutgu tggauygggu utuutgyggg 180
uuagayguaa tygaaygygg aygygutguy guuagautau tyggtggtgy gyggutguau 240
aautgauaaa tguaayguuu auutuatgau tuatgayguu utuuuuaauu tgaguuaagg 300

<210> SEQ ID NO 369
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 369
uaggutggag tguaatggyg ygatutyggu tuautguaau ttutguutut ygggttuaag 60
uaattuttut auuttaguut uutgagtagu tgggattaua ggtauutguy guuatguuyg 120
gutaattttt taatttgttt ttagtagaga yggggtttua uuatgttggu uagguyggtu 180
tauaautuut gatutuaggt gatutauuyg uutyggüutu uuaaattaua ggtgttatua 240
ttaggattut tgguagauag gagtgttgta ggggatggaa gtggatagta ggaggututg 300

<210> SEQ ID NO 370
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 370
uagaguutuu tautatuuau ttuuatuuuu tauaauautu utgtutguua agaatuutaa 60
tgatauauau tgtaatttgg gagguygagg ygggtagatu auutgagatu aggagttgta 120
gauygguutg guuaauatgg tgaaauuuyg tututautaa aaauaaatta aaaaattagu 180
yggguatggy gguaggtauu tgtaatuuua gutautuagg aggutaaggt agaagaattg 240
uttgaauuyg agagguagaa gttguagtga guygagatyg yguuattgua utuuaguutg 300

<210> SEQ ID NO 371
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 371
tgaatgauut ggguaguatt tutuuauutg yguttguatt tgutagauag tutgtgautu 60
tutgtgggag aaaauauaag aaauygguuu ututgutggt tuuuuauutg guutggutut 120
uutgttutuu auuutguaua utuatguuty ggaauutgut tutuututga guutuuutua 180
uagtgguuyg guuuaygtgg uutttaatut guuuauatua gaguutuuau utuygguuta 240
tgguuuatua gagguagutg gaguygggua tuutuuuuay gtggguuttt gaggatggga 300

<210> SEQ ID NO 372
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 372
tuuuatuutu aaagguuuay gtggggagga tguuyggutu uagutguutu tgatggguua 60
tagguyggag gtggaggutu tgatgtgggu agattaaagg uuaygtgggu ygggguuautg 120 tgagggaggu tuagaggaga aguaggttuy gagguatgag tgtguagggt ggagaauagg 180
agaguuaggu uaggtgggga auuaguagag ggguyggttt uttgtgtttt utuuuauaga 240
gagtuauaga utgtutagua aatguaagyg uaggtggaga aatgutguuu aggtuattua 300

<210> SEQ ID NO 373
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 373 gggyggggu u tgtgyggtut gyggygygga guygagtggg utgyggggat gygggggauu 60
agutgygtgg gyggyggygu ygagaguuuy ggaggygygg ggutgagyga ggguuygygg 120
gggygutggu tgyguttggu tuyggtatgy guutauttuu tutgygtuty gutagutguy 180
gtgutgutyg uygtgtauta yggtutuatu tgggtauuua ygyggtutuu ygyggauauy 240 guyggguuuau aguuuagygy guygtuuuut uygtgtgutg uuyguuyggg ygtguyguut 300

<210> SEQ ID NO 374
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 374 aggyggguayg uuygggyggg uaguauaygg aggggayggy gygutgggut gtggguyggy 60
gggtguygyg ggagauygyg tgggtauuua gatgagauyg tagtauaygg ygaguaguay 120
gguagutagy gagayguaga ggaagtaggy guatauygga guuaagygua guuagyguuu 180 uygygggguuu tygutuaguu uygyguutuy ggggututyg gyguyguygu uuayguagut 240
ggtuuuuygu atuuuyguag uuuautyggu tuygyguygu agauyguaua gguuuyguuu 300

<210> SEQ ID NO 375
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 375
aagtgtattt tuaaggtatg agggguuuag aggauautgt uuuaaaagua gtggttgtga 60
gagtgguttt ggagtuaggu tgauagtutg gaaauttuua ggtuygutut gaagtguygg 120
utguatgauu aguuutuuag uutgtgtuyg uttyggu utt utttgtguaa gtgagaguat 180
tgutgatuuu uuyggggtgg ygagggggyg uaygtuagtg auutyguatg gtguutguua 240
gguaygtggt uygtgtttua tgattutttg agagutttgg aguagutuua agaagautut 300

<210> SEQ ID NO 376
<211> LENGTH: 300
<212> TYPE: DNA

<213> ORGANISM: Artificial Sequence
<220> FEATURE:
<223> OTHER INFORMATION: Synthetic polynucleotide

<400> SEQUENCE: 376
gagtuttutt ggagutgutu uaaagututu aaagaatuat gaaauaygga uuaygtguut 60
gguagguauu atgygaggtu autgaygtgy guuuuutygu uauuuygggg ggatuaguaa 120
tgututuaut tguauaaaga agguygaagy ggauauaggu tggagggutg gtuatguagu 180
ygguauttua gagyggauut ggaagtttuu agautgtuag uutgautuua aaguuautut 240
uauaauuaut guttttggga uagtgtuutu tggguuuutu atauuttgaa aatauauttt 300

<210> SEQ ID NO 377
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 377
taattttaaa uaaaaututu uatgaguaau taaatattta aaatgtgttt ttuuataaaa 60
gtgaatuagu tuagttutgu aggutgaaaa tauaauaagg aggatuyggg ttguagaaag 120
uagaggguua uutagauygt gtutgagaga yggggagaaa guagutgtut gutgtguauu 180
agagguutut agggauuuyg guaguaauuu ygtggygggu uauauttggg agutgatttg 240
ttttuagaau uauuagutaa guuauatgag uuaggaguut ggttatuuat tuaaaguuua 300

<210> SEQ ID NO 378
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 378
tgggutttga atggataauu aggutuutgg utuatgtggu ttagutggtg gttutgaaaa 60
uaaatuagut uuuaagtgtg guuyguuayg gggttgutgu yggggtuuut agagguutut 120
ggtguauagu agauagutgu tttutuuuyg tututuagau ayggtutagg tgguuutuutg 180 utttutguaa uuyggatuut uuttgttgta ttttuaguut guagaautga gutgattuau 240
ttttatggaa aaauauattt taaatattta gttgutuatg gagagttttg tttaaaatta 300

<210> SEQ ID NO 379
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 379
guutuuagau uygaaatuuu uuautgaagu uattuuuagg aggaggggguu tuautggggu 60 utuaagguag uatuaguatt tuyggtgaua gguauaguaa tttatuagut uautggutut 120
utautgagaa uaagguaagu yggggguutgu ygagggtatg auagguaggg agtgatgggu 180
uygguuuagg guaggaggga gauagaaatg gguaggaaga ggaggutgtu uuuaguagua 240
uttutgagag gaggaguauu tttyggggau aututggayg guauuuuuaa guauaguuuu 300

<210> SEQ ID NO 380
<211> LENGTH: 300

<212> TYPE: DNA
<213> ORGANISM: Artificial Sequence
<220> FEATURE:
<223> OTHER INFORMATION: Synthetic polynucleotide

<400> SEQUENCE: 380
ggggutgtgu ttgggggtgu ygtuuagagt gtuuuygaaa ggtgutuutu ututuagaag 60
tgutgutggg gauaguutuu tuttuutguu uatttutgtu tuuutuutgu uutggguygg 120
guuuatuaut uuutguutgt uatauuutyg guagguuuyg guttguuttg ttutuagtag 180
agaguuagtg agutgataaa ttgutgtguu tgtuauygga aatgutgatg utguuttgag 240
guuuuagtga gguuuutuut uutgggaatg guttuagtgg gggatttygg gtutggaggu 300

<210> SEQ ID NO 381
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 381
tgagaguagu uagauaygta gtgatuaggg aaagtygaaa gtguagatgg gttyguaaay 60 gtggautut tagttttggg tutguagatg ggguyggua uuaygtgutu tutgagttut 120
utttuuaagt auagatuuut uyggagaygg aauattgttu yguutttaat tuttuuuagg 180
agutgyggag gaaggygtga gaauyggagu uyggggtgau ttgyggggga ggggatygut 240
tuuuygtygu uuauauutgu utaauuuayg uuuayggygg uyguaaaggy gauauygygt 300

<210> SEQ ID NO 382
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 382
aygyggtgty guutttgygg uyguygtggg ygtgggttag guaggtgtgg gygaygggga 60
agygatuuuu tuuuuyguaa gtuauuuygg gutuyggttu tuayguuttu utuyguagut 120
uutgggaaga attaaaggyg gaauaatgtt uygtutuygg agggatutgt auttggaaag 180
agaautuaga gaguaygtgg tgguygguuu uatutguaga uuuaaaauta gagagtuuay 240
gtttgygaau uuatutguau tttygauttt uuutgatuau taygtgtutg gutgututua 300

<210> SEQ ID NO 383
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 383
auaagyggtt ggatttygag aggauatuaa gaguaygtua agaguaygtu aagaguauay 60
ggauagguau tgguayguyg guaggtuatt gauygguaga auagagtttg guuagggutg 120
tuagagaaga gtyggguygu uaaguaguuy gautuuagy ggaaaauuat utguuttutg 180
gutuutuuat utgutgagag utauttuuau tuaataaaau uttguautua ttutuuaaau 240
uuauatgaga tuuaattutt uyggtauauu aagguaggaa uuuygagata uagaaaguuu 300

<210> SEQ ID NO 384

<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 384
gggutttutg tatutygggg ttuutguutt ggtgtauygg aagaattgga tutuatgtgg 60
gtttggagaa tgagtguaag gttttattga gtggaagtag ututuaguag atggaggagu 120
uagaagguag atggttttuy gutggaagty gggutguttg gygguuygau tuttututga 180
uaguuutggu uaaaututgt tutguyggtu aatgauutgu yggygtguua gtguutgtuy 240
gtgtgututt gaygtgutut tgaygtgutu ttgatgtuut utygaaatuu aauyguttgt 300

<210> SEQ ID NO 385
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 385
auttgaagtu aggagttygt gaauaguutg guuaaauatgg tgaaauuutg tututautaa 60
aaaaagaaaa attaguyggg tgtggtgggy guutgtaauu uuaguauttt gggaggutga 120
ggtgggtgga tuauttgaag tuaggagtty gtgaauaguu tgatuaauat ggtgaaauuu 180
tgtututaut aaaaauauaa aaattaguyg ggtgtggtgg tgggtguutg taatuuuagu 240
tautuaggag autgagguag gaggatuaut tgaauygggg agguagaggt tguagagagt 300

<210> SEQ ID NO 386
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 386
utututguaa uututguutu uuyggttuaa gtgatuutuu tguutuagtu tuutgagtag 60
utgggattau agguauuuau uauuauauuy ggutaatttt tgtgttttta gtagagauag 120
ggtttuauua tgttgatuag gutgttuayg aautuutgau ttuaagtgat uuauuuauut 180
uaguutuuua aagtgutggg gttauaggyg uuuauuauau uyggutaatt tttutttttt 240
tagtagagau agggtttuau uatgttgguu aggutgttua ygaautuutg auttuaagtg 300

<210> SEQ ID NO 387
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 387
aaatuttttt uutguutgua ttttuttaua taaaguaatu tautaatguu atyggttuat 60
tuautuauyg gaauutgtut tguuaggauu tgauutuagu agautgagtu atauuaguat 120
uatuuttgtt ggggguuuagg tutguatuuy guttuygguu uuaguuuuau tgttagutuu 180
atuaggtuut utggggtuaua uuaaggaggu ygttttutut uuutttttut gaattagatu 240
uuuagaaaua agauatuagg uttuutgggg aaatutaatt ttgutuatga atttgauuat 300

<210> SEQ ID NO 388
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 388
atggtuaaat tuatgaguaa aattagattt uuuuaggaag uutgatgtut tgtttutggg 60
gatutaattu agaaaaaggg agagaaaayg guutuuttgg tgtguuuuag aggauutgat 120
ggagutaaua gtggggutgg gguyggaagy gggatguaga uutggguuuu aauaaggatg 180
atgutggtat gautuagtut gutgaggtua ggtuutggua agauaggttu yggtgagtga 240
atgaauygat gguagtagta gattguttta tgtaagaaaa tguagguagg aaaaagattt 300

<210> SEQ ID NO 389
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 389
uaaggtuuag gtuuuaguut uuuuauyguy guuygyguuu tuutagguut yggagyggyg 60
uutttutgyg guutygaagg tggggtggga aagtttgggg agtuuyggut utuauaguut 120
gtygtgagaa utguuuuygg ggaattygtu yguygtaygg aaaaautggu yggaguagag 180
tygtuygygg ttuygyggty gygggtggaa ggtgaaggty gagggaggtu aggutguttu 240
tgygtgtuut gayggutggy gtgttututt gagatgggut ygggutautt gguuaguttu 300

<210> SEQ ID NO 390
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 390
gaagutgguu aagtaguuyg aguuuatutu aagagaauay guuaguygtu aggauaygua 60
gaaguaguut gauutuuuty gauuttuauu ttuuauuygy gauygyggaa uygyggayga 120
ututgutuyg guuagttttt uygtayggyg gaygaattuu uygggggguag ttutuaygau 180 aggutgtgag aguygggaut uuuuaaautt tuuuauuuua uuttygaggu yguagaaagg 240
yguygutuyg agguutagga gggygygggy ggyggtgggg aggutgggau utggauuttg 300

<210> SEQ ID NO 391
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 391
uygagggagu uagguuauag utgauaggaa gguagaaggt gguaggaggg gaggttgygu 60 tguauutg ggttguuuag guuaauutgu uagguaggag ggggaaguuy gtguuuautt 120
tauuatgauy gggaagatga tgguaguuau ygtggatttg aggatuuaga guauyguuag 180
guagaggatu tguauuaggg tgaagaggtg gatuyggygu agygguaygt guyguaggaa 240
gguatggtuy ggutggtgut tggutggat uaggaagagu ttguagygtt uuuagaauta 300

<210> SEQ ID NO 392
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 392 tagtttutggg aaygutguaa gututtuutg atguuaguua aguauuaguy ggauuatguu 60
ttuutgyggu aygtguygut gyguyggatu uauututtua uuutggtgua gatuututgu 120
utggyggtgu tutggatuut uaaatuuayg gtggutguua tuatuttuuy ggtuatggta 180
aagtggguay gggutuuuu utuutguutg guaggttggu utggguaauu uagaggtgua 240
gyguaauutu uuutuutguu auuttutguu ttuutgtuag utgtgguutg gutuuutygg 300

<210> SEQ ID NO 393
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 393
aaattauuyg ggygtggtgg tgggtguutg taatuuuagu tautuaggag guygagguag 60
gagaauygut tgaauuyggg agguagagua taggttgttg gagggttgaa ggtguauuua 120
guagagautg guatauagga ggtuutguaa ygguuuuagg aaauututgg gtuuagtaag 180
aguttuagua ggaggtagaa uuatauyggg uaggagtguu tggaaaggut tuaagguaau 240
tuuutuuaaa gtuutgguuu aauuutauau tgtuaggutg ttaaagguua tttaaaagut 300

<210> SEQ ID NO 394
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 394
aguttttaaa tgguutttaa uaguutgaua gtgtagggtt ggguuaggau tttggaggga 60
gttguuttga aguutttuua gguautuutg uuyggtatgg ttutauutuu tgutgaagut 120
uttautggau uuagaggttt uutgggguyg ttguaggauu tuutgtatgu uagtututgu 180
tgggtguauu ttuaauuutu uaauaauuta tgututguut uuygggttua agyggttutu 240
utguutyggu utuutgagta gutgggatta uagguauuua uuauuayguu ygggtaattt 300

<210> SEQ ID NO 395
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 395
aggaaaaaau aguaguuuaa gaatyggguu tuuutguttau aguaggagty guatutattt 60
atatatgtta tgtuttattg utuaguaauu agututyggu yggggygtgg guygggaaga 120
ggggtutuut ggtguagygg gttggygtga utuatuauyg uygyguautu tgguututgg 180
guutaggtta auagautuuy gggtttuagg utggguuuag gyggguuaggu uutuuutgut 240 gaggaatutg ggttggggua gtguuagutu uutguttutu auutgguuau agaaggggta 300

<210> SEQ ID NO 396
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 396
tauuuuttut gtgguuaggt gagaaguagg gagutgguau tguuuuaauu uagattuutu 60
aguagggagg guutgguygu utggguuuag uutgaaauuy gggagtutgt taauutaggu 120
uuagagguua gagtgygygg yggtgatgag tuayguuaau uygutguauu aggagauuuu 180
tuttuuyggu uuayguuuyg guygagagut ggttgutgag uaataagaua taauatatat 240
aaatagatgy gautuutgut gtaauaggga gguuygattu ttgggutgut gttttttuut 300

<210> SEQ ID NO 397
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 397
auuuaggaat tutttttttt ttttttttga gayggygtut utgtyguuua ggutggagtg 60
uagtggygua gtutyguuta autguaagut uyguuuuygg gttuatguua ttutuutguu 120
tuaguututt gagtagutgg aautauaggy guutguuauu auauuygguu aatttttttgt 180 atttttagta gagayggggt ttuauygtgt taguuaggat ggtutygatu tuutgauuty 240
gtgatuuauu uauutuaguu tutuaaagtg utgggattau agguttgaau uautgyguuu 300

<210> SEQ ID NO 398
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 398
gggyguagtg gttuaaguut gtaatuuuag uautttgaga ggutgaggtg ggtggatuay 60
gaggtuagga gatygagauu atuutgguta auayggtgaa auuuygtutu tautaaaaat 120
auaaaaaatt gguygggtgt ggtgguaggy guutgtagtt uuagutautu aagaggutga 180
gguaggagaa tgguatgaau uygggggygg aguttguagt taggygagau tgyguuautg 240
uautuuaguu tgggygauag agayguygtu tuaaaaaaaa aaaaaaaaga attuutgggt 300

<210> SEQ ID NO 399
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 399
aaatauagua ggagagaatt uututgagau utaagatauy gtguuuttuu uuuttgguut 60
utuagutgut guygagtuut ggagaaaaty ggguatutga auagagguyg tgtttgtuuu 120
tgutuygguu ttgtgttutu attuutguua yguuatuatg gataatgaaa gttgautggu 180
tguyggggtt tuutttutut utguuuutgt uatttuuatt tguuaggtut uatguutttt 240
ttguauagag ttgttgtgut tgggututaa tttguuaggu agtgataaat tuuaagaaaa 300

<210> SEQ ID NO 400
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 400
ttttuttgga atttatuaut guutgguaaa ttagaguuua aguauaauaa ututgtguaa 60
aaaagguatg agauutggua aatggaaatg auagggguag agagaaagga aauuuyggua 120
guuagtuaau tttuattatu uatgatggyg tgguaggaat gagaauauaa gguyggagua 180
gggauaaaua ygguututgt tuagatguuy gattttutuu aggautyggu aguagutgag 240
agguuaaggg ggaagguay ggtatuttag gtutuagagg aattututuu tgutgtattt 300

<210> SEQ ID NO 401
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 401
guuutgagau autaaatggy gggggggtgg ggggaggaaa gggaaggygg uagagutuuu 60
ygaguyggga uagtuautta ututauaggu agtgggguuy gauauagaua gyguyguuuu 120
yguuaguuag uutyguaygu uutyggaagy guaggutuuy ggygutgygu tggagggttu 180
uuygguauuu uaguutuuyg tuuuuaguuy gutguauutu ygggauuuuuu ttauuuttga 240 gagguauygg gagttgtygy ggggggguut ygggaaattu uuyggauuuu tgtguuagga 300

<210> SEQ ID NO 402
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 402
tuutgguaua ggggtuyggg gaatttuuyg agguuuuuuy gygauaaatu uyggtguutu 60
tuaagggtaa gggggguuyg gaggtguagy gggutgggga ygggaggutg gggtguyggg 120
gaauuutuua gyguagyguy gggaguutgy guttuygagg gygtgygagg utggutggyg 180
ggggyggygu tgtutgtgty ggguuuuaut guutgtagag taagtgautg tuuyggutyg 240
gggagututg uyguuttuuu tttuutuuuu uuauuuuuuy guuatttagt gtutuagggu 300

<210> SEQ ID NO 403
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 403
auuauaguau tguaggagga tgaguuuutg uaggaaggaa tgutggutut utggggtaga 60
taaagaaggt tutggggaag ggaagggagg aauaggaaua tgggutuuut guuaggutgt 120
uuuaggtuyg ggatguuaty gguaagtggg yggggauagg uutgggtaga tgauatggta 180
gtgagtaagt ggggagguag guuaguagag gaguuaggut uauutuuygu uyguuuauut 240
ygguuauaga uygggagggg tyggaguaut gygttggggt tgatgaguag aygautguua 300

<210> SEQ ID NO 404
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 404
tgguagtygt utgutuatua auuuuaaygu agtgutuyga uuuutuuygg tutgtgguyg 60
aggtgggygg gygggaggtg aguutggutu ututgutggu utguutuuuu auttautuau 120
tauuatgtua tutauuuagg uutgtuuuyg uuuauttguy gatgguatuu yggauutggg 180
auaguutggu agggaguuua tgttuutgtt uutuuuttuu uttuuuuaga auuttuttta 240
tutauuuuag agaguuagua ttuuttuutg uaggggutua tuutuutgua gtgutgtggt 300

<210> SEQ ID NO 405
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 405
agggaaggga ggaauaggaa uatgggutuu utguuaggut gtuuuaggtu ygggatguua 60
tyggauagtg ggyggggaua gguutgggta gatgauatgg tagtgagtaa gtggggaggu 120
agguuaguag aggaguuagg utuauutuuy guuyguuuau utygguuaua gauygggagg 180
ggtyggagua utgygttggg gttgatgagu agaygautgu uagguaguua ttuauaggaa 240
atgguauaga yguauattgt tuuagutauu uuuuatuutu uutuaggggu aaagtgaatg 300

<210> SEQ ID NO 406
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 406
attuautttg uuuutgaggg aggatggggg gtagutggaa uaatgtgygt utgtguuatt 60
tuutgtgaat ggutguutgg uagtygtutg utuatuaauu uuaayguagt gutuygauuu 120
utuuyggtut gtgguygagg tgggygggyg ggaggtgagu utggutuutu tgutgguutg 180
uutuuuuaut tautuautau uatgtuatut auuuagguut gtuuuyguuu auttguygat 240
gguatuuygg auutgggaua guutgguagg gaguuuatgt tuutgttuut uuuttuuutt 300

<210> SEQ ID NO 407
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 407 ggtttutaaau auauaaauut ttgatguatu tggaatttau uttaatttuu taguaatttt 60
tatuaatggu tuaatatttg ggggattttu atggtaattg uautgaatgt attaautggt 120
uagggaggat tauatuaaga uuauyggutу gagaaauagu agtutgttuu tuuauuuuua 180

-continued ygtutguatu uagguuuttu uauagagatu tuatttutuu tguagatgau tuattuagtg 240
tutaggaatu yggtgututg tgguuautau ygagagtggg atattttuuu uuattttatt 300

<210> SEQ ID NO 408
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 408
aataaaatgg gggaaaatat uuuautut yg gtagtgguua uagaguauyg gattuutaga 60
uautgaatga gtuatutgua ggagaaatga gatututgtg gaaggguutg gatguagayg 120
tgggggtgga ggaauagaut gutgtttuty gaguyggtgg tuttgatgta atuutuuutg 180
auuagttaat auattuagtg uaattauuat gaaaatuuuu uaaatattga guuattgata 240
aaaattguta ggaaattaag gtaaattuua gatguatuaa aggtttgtgt gtttagaauu 300

<210> SEQ ID NO 409
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 409 tttgggggu agggagggtt uagtuuuutu agguutggut gtgtuuuutg uuuuuuauuu 60
auaatuaggu uuagggttgg ggggtguaua uuaaggaggg guaggaagtg tuuaagaagu 120
agaauyggut utgtgtuuuu agtggyggyg ggtgtutggg guaggaggag gutatutgat 180
uuuttuuuua utguuuyggu uatgauutuu tuuutuuutu uutygutuuu tuuutuuutu 240
uutuuutuuu tuuutuuutu uutuutuutt uatggutggg gtaguuagua uuutgggutg 300

<210> SEQ ID NO 410
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 410
aguuuagggt gutggutauu uuaguuatga aggaggaggg agggagggag ggagggaggg 60
agggagggag ggagygaggg agggagggag gaggtuatgg uygggguagt ggggaaggga 120
tuagataguu tuutuutguu uuagauauuy guyguuautg gggauauaga guyggttutg 180
uttuttggau autttuutguu uutuuttggt gtguauuuuu uaauuutggg uutgattgtg 240 ggtgggggu aggggauaua guuagguutg aggggautga auuutuuutg uuuuuuaaag 300

<210> SEQ ID NO 411
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 411
uuyguaaguu tyguuuutuu agguutyguu utuuutuutt guagagagtg guuaagutyg 60
tgttuuagag gutgaatgag gattttgtgy ggaaguuyga utatgutttg agututgtgg 120
gtaagauuyg gagauautgg aagauagaga yguagauagg aaagagguua agauautgau 180
auagauagau uuatguauut gauygguyga agauagaguu tyggauaguu uuuauuyguu 240
uuuaguuuuy gyguuuuygy guuuygautu uygguaaggu utgggaguut utgagggtta 300

<210> SEQ ID NO 412
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 412
taauuutuag aggutuuuag guuttguygg gagtyggggy gygggggygy gggggutggg 60
ggygggtggg ggutgtuyga ggututgtut tygguyggtu aggtguatgg gtutgtutgt 120
gtuagtgtut tgguututtt uutgtutgyg tututgtutt uuagtgtutu ygggtuttau 180
uuauagagut uaaaguatag tygggutuuy guauaaaatu utuattuagu ututggaaua 240
ygaguttggu uautututgu aaggagggag ggygagguut ggaggggyga gguttgyggg 300

<210> SEQ ID NO 413
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 413
uagatuaggg tuutuagaut tgtuyggagg gaggguuutg uatauutguu aayguuutgt 60
ttgutgggaa aggggutgat gttguaatga uaggttaaau aguaauagga uattgautgg 120
uatutguaag utgagutuag utuagagagg ygaggaguau aggggaggga ggaaaatuuy 180
ggtgtggatu tuauuuauay gguuuautgg gtgutuutgg uagayggaat tatgggtgut 240
tttaututut uattttaaaa atgtgutttt tatgtgtatt gtaaaagtaa uagattuuua 300

<210> SEQ ID NO 414
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 414
tgggaatutg ttauttttau aatauauata aaaaguauat ttttaaaatg agagagtaaa 60
aguauuuata attuygtutg uuaggaguau uuagtggguy gtgtgggtga gatuuauauy 120 gggatttuu tuuutuuuut gtgutuutyg uutututgag utgagutuag uttguagatg 180
uuagtuaatg tuutgttgut gtttaauutg tuattguaau atuaguuuut ttuuuaguaa 240
auagggygtt gguaggtatg uaggguuutu uutuyggaua agtutgagga uuutgatutg 300

<210> SEQ ID NO 415
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 415
uauttggutu tygtggutgg gauagattgu ttuuttuutu tutuutgggt guuaggtagg 60
uuuagaaauu auutgatgtu aguaagguut gguuauuuau tggtggggag gaagtgggyg 120
ggtguuuagg gauagatgag uygggguagay gtguuutgag guaguauagt uagggutgay 180
gtggguatta tguauutygg ggutttuaga gutggutuyg gtuuygtttg uuuauatuaa 240
guaggtuaga gtggagaggg uuaggggygu tggggtuaag guatguautg auuaggygtu 300

<210> SEQ ID NO 416
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 416
gayguutggt uagtguatgu uttgauuuua gyguuuutgg uuututuuau tutgauutgu 60
ttgatgtggg uaaaygggau yggaguuagu tutgaaaguu uygaggtgua taatguuuay 120
gtuaguuutg autgtgutgu utuaggguay gtutguuygg utuatutgtu uutggguauu 180
yguuuauttu utuuuuauua gtgggtgguu agguuttgut gauatuaggt ggtttutggg 240
uutauutggu auuuaggaga gaggaaggaa guaatutgtu uuaguuayga gaguuaagtg 300

<210> SEQ ID NO 417
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 417
atuuauautt gaauatauag auatuutttt uuagggtgtg ttgtgutyga tauutttaat 60
tuutgtutgu attuuagggu utguuuaguu tuttuutggu tuuuuaguuu aguutggtuu 120
ttuygguutu uutgtuatuu uuauututyg tgtgtguaua aguagggauu aggtagggag 180
auygguagat gutgutgutut gtuuutgggg tttuttttut tagtgttgut uuuauauuua 240
ygygatgutt taattaautg uuauautuag gutttutuag tggggagagt uagaaataga 300

<210> SEQ ID NO 418
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 418
utatttutga ututuuuuau tgagaaaguu tgagtgtggu agttaattaa aguatygygt 60
gggtgtggga guaauautaa gaaaagaaau uuuagggaua gagaguagua tutguyggtu 120
tuuutauutg gtuuutgutt gtguauauay gagaggtggg gatgauaggg agguyggaag 180
gauuaggutg ggutggggag uuaggaagag gutggguagg uuutggaatg uagauaggaa 240
ttaaaggtat ygaguauaau auauuutgga aaaggatgtu tgtatgttua agtgtggatg 300

<210> SEQ ID NO 419
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 419
tuuuaguuau tuyguagtua utuutgauuu agaaaagaau aauuauagut ggguuuagua 60 uuuygggua utuuutguag utguuuauau atutgguagu tgggtuuaut tatguaatgt 120
ggatygggut tuttauatut gaaatutgyg tututatuuu tuututgaga uuagtgtutu 180
utguuagutt uuatgguuuy gggatgauut uaututuuua gggtutuuut gygtuutggg 240
agututgguy gaggaguagu aggggutgat gguagagygg ggguaggtua gagutuagua 300

<210> SEQ ID NO 420
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 420
gutgagutut gauutguuuu ygututguua tuaguuuutg utgutuutyg guuagagutu 60
uuaggaygua gggagauuut gggagagtga ggtuatuuyg ggguuatgga agutgguagg 120
agauautggt utuagaggag ggatagagay guagatttua gatgtaagaa guuygatuua 180
uattguataa gtggauuuag utguuagatg tgtggguagu tguagggagt gguuyggggt 240
gutggguuua gutgtggttg ttuttttutg ggtuaggagt gautgyggag tggutgggau 300

<210> SEQ ID NO 421
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 421
uuaaaygygg uauaygggga ygguuuutuu yggggtuagg utuautggut uuttuuuttu 60
agyguuauua gguaggaggg uuaayggtua uauaggaggu auuutuauut guutttguau 120
uaguaaataa agtguatuuu attttygtgt gagygtyggu uyggtgagtu aguuuttuyg 180
gguuutttuu tgttutuagg guagggggyg tgygutgagu uagaggtaga tutguagaaa 240
ggguuuygau tggguutygg guaggguygg yguuuauuau aututggggg tuagutatgu 300

<210> SEQ ID NO 422
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 422
guatagutga uuuuuagagt gtggtgggyg uygguuutgu uygagguuua gtygggguuu 60
tttutguaga tutauututg gutuagygua yguuuuutgu uutgagaaua ggaaaggguu 120
yggaagggut gautuauygg guygaygutu auaygaaaat gggatguaut ttatttgutg 180
gtguaaaggu aggtgagggt guutuutgtg tgauygttgg uuutuutguu tggtggygut 240
gaagggaagg aguuagtgag uutgauuuyg ggagggguyg tuuuygtgtg uygygtttgg 300

<210> SEQ ID NO 423
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 423
guaggaaggg uuuagaygau auuuuuauag auatatguua guuuutuygg gtgauuaaaa 60

```
tuatutuagt aaagguagat gagguuaagy gaaaaggggt gggtggaaga auyggututg    120

agtutuaguu uauagauaut yggauautyg tygguuyggt agguaggggt tuutggtggu    180

utuaggutgt uagguuyggu uuuutuuygu agutgtutuu agutuuuauu tuuuuyguuu    240

auuuuuuagg autuutattt uautgaggag attaagauua uutggygaga auuuutuuua    300


<210> SEQ ID NO 424
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 424

gggaggggtt utyguuaggt ggtuttaatu tuutuagtga aataggagtu utggggggtg     60

ggygggggag gtgggagutg gagauagutg ygggaggggg uyggguutga uaguutgagg    120

uuauuaggaa uuuutguuta uyggguygay gagtgtuyga gtgtutgtgg gutgagautu    180

agaguyggtt uttuuauuua uuuuttttyg uttgguutua tutguuttta utgagatgat    240

tttggtuauu yggaggggut gguatatgtu tgtgggggtg tygtutgggu uuttuutgut    300


<210> SEQ ID NO 425
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 425

aggtgagatu tggaggttgy ggggtuagtta guaagtggga gagagutgua tgyggggaag     60

gtgggaggyg ttguaggaaa ggtgagggag auauagutga gutgtggtgu tgguuagutg    120

ggguuttgyg uuttatuygg guautgtgay gguuautaau aggttttaag tauyggaatg    180

auatgatygg atttgtaatt taautagatu uttutgautg utgttggggg aauagautgt    240

uaauutuaua auaguautgt uagutgagta ttagauaaat gatgaauutg gguuuaggga    300


<210> SEQ ID NO 426
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 426

uuutggguuu aggttuatua tttgtutaat autuagutga uagtgutgtt gtgaggttga     60

uagtutgttu uuuuaauagu agtuagaagg atutagttaa attauaaatu ygatuatgtu    120

attuyggtau ttaaaauutg ttagtgguyg tuauagtguu yggataaggy guaagguuuu    180

agutgguuag uauuauagut uagutgtgtu tuuutuauut ttuutguaay guutuuuauu    240

ttuuuyguat guagututut uuuauttgut aautguuuyg uaauutuuag atutuauutg    300


<210> SEQ ID NO 427
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 427

tgtgttauuu uagaaaguaa ggayguttuu aaagatgttu agaguagtgt tuaaagggat     60
```

guuuautggt uagtuuuaau ygutgtgaau uyggaaaatu tgagautggt gtuagttaat 120
ttagaaagtt tattttguua aggttgagga ygtatguutg tgauauaguu tuaggaagtu 180
utgatgauat gtguuuaagg tggttggggt gtaguttgat tttatauaut tagggaguat 240
gagauatuaa ttaagtauau ttgagaaata uatyggtttg gtutagaaag gygggauaau 300

<210> SEQ ID NO 428
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 428
gttgtuuygu utttutagau uaaauygatg tatttutuaa gtgtauttaa ttgatgtutu 60
atgutuuuta agtgtataaa atuaagutau auuuuaauua uuttggguau atgtuatuag 120
gauttuutga ggutgtgtua uagguatayg tuutuaauut tgguaaaata aautttutaa 180
attaautgau auuagtutua gattttuygg gttuauagyg gttgggautg auuagtgggu 240
atuuutttga auautgutut gaauatuttt ggaagygtuu ttgutttutg gggtaauaua 300

<210> SEQ ID NO 429
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 429
tgagaataat gtutggtatg ygaggaguau uaguaaatyg tgutuatuat tuuagyggag 60
uaaattgttg utgtututua uygggutttg ggttautgag gutgutattt attaaagtgt 120
gggttgtgau tuattautag gtuatgaaat yggtgtagtg gtaguaauua guuuttaaag 180
aaatgaauyg ggguygggyg yggtggttua uauutgtaat uuuaguautt tgggagguyg 240
aggygggtgg atuaygaggt uaagagatyg agauuatuut gguuaauatg gtgaaauuyg 300

<210> SEQ ID NO 430
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 430
ygggtttuau uatgttgguu aggatggtut ygatututtg auutygtgat uuauuyguut 60
ygguutuuua aagtgutggg attauaggtg tgaauuauyg yguuygguuu yggttuattt 120
utttaagggu tggttgutau uautauauyg atttuatgau utagtaatga gtuauaauuu 180
auautttaat aaataguagu utuagtaauu uaaaguuygg tgagagauag uaauaatttg 240
utuygutgga atgatgagua ygatttgutg gtgutuutyg uatauuagau attattutua 300

<210> SEQ ID NO 431
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 431

-continued

```
aggatggagg uyggggaggu agyguyguyg gyggggggygg gygguygygu yguaggyggu      60

tgggguaagt gggtgyggut uaaygtgggg gguayggtgt tuutgauuau uygguagayg     120

utgtguygyg aguagaagtu uttuutuagu yguutgtguu agggggaaga gutguagtyg     180

gauygggtga gguuuuyggg gtgggyggyg agygggyggt gggtuutuyg utyguuygay     240

gyggggutgt ygggguutggu tyguuyguua ggutggggau uygguyggggt tuatttuyga     300
```

```
<210> SEQ ID NO 432
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 432

tyggaaatga auuyggyuygg gtuuuuaguu tggyggggyga guuagguuyg auaguuuygy      60

gtygggygag yggaggauuu auyguuygut yguyguuuau uuygggggguu tuauuyggtu     120

ygautguagu tuttuuuuut gguauaggyg gutgaggaag gauttutgut ygygguauag     180

ygtutguygg gtggtuagga auauygtguu uuuuaygttg aguyguauuu auttguuuua     240

guyguutgyg gygygguygu uyguuuuygu yggyggygut guutuuuygg uutuuatuut     300
```

```
<210> SEQ ID NO 433
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 433

tutautgatg yggagauyga guuuuagggu aguagaguuu taguttygyg utauayggut      60

gtgggygutg yguuuuaggg uayggguyggu uuaggtygtg guuuautygg gauuygyggu     120

tuauyggtgy ggttgaygyg guayggggaag yggtaggtgu tuaguauutu utuutygtuu     180

tgutygtyga tgauuyggua utggyguaga tayggygtga guttgguygg gttuagggyg     240

ygaguuaguy gatguyggay guuutygatt ygutuuuaua gygygtuutu utuyguutua     300
```

```
<210> SEQ ID NO 434
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 434

tgaggyggag gaggaygygu tgtgggagyg aatygagggy gtuyggguaty ggutggutyg      60

yguuutgaau uyggguuaagu tuayguygta tutgyguuag tguyggggtua tygaygagua     120

ggaygaggag gaggtgutga guauutauyg uttuuygtgu ygygtuaauy guauyggtga     180

guygygggtu uygagtgggu uaygauutgg guygguygtg uuutggggyg uagyguuuau     240

aguygtgtag ygygaaguta gggutuutgut guuutggggu tyggtutuyg uatuagtaga     300
```

```
<210> SEQ ID NO 435
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 435
```

utuauutttu utagtttaga aaatuuutua utguttuuuu aatggaggut guuuuaggag 60
tgguuuagtg ggguuaauua gutgttutat guuaguagut uyggagtatg tauatttuua 120
ututggttua aauttgttut tutattuayg guuuuattaa gaaaaauatt uatutguagg 180
utggauyggg ttgggatgua guaagttggt gtggutautu ygagtgtgtg auauauutgu 240 aggggguutgt gaguagtggg aggguuagau atgtggattu uuagggutgg tgguttuutt 300

<210> SEQ ID NO 436
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 436
aggaaguuau uaguuutggg aatuuauatg tutgguuutu uuautgutua uagguuuutg 60
uaggtgtgtu auauautygg agtaguuaua uuaauttgut guatuuuaau uyggtuuagu 120
utguagatga atgtttttut taatggggguy gtgaatagaa gaauaagttt gaauuagagt 180
ggaaatgtau atautuygga gutgutggua tagaauagut ggttgguuuu autggguuau 240
tuutggggua guutuuattg gggaaguagt gagggatttt utaaautagg aaaggtgaga 300

<210> SEQ ID NO 437
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 437
aaygutgaua tutttuyggg tgtutgaaaa uagaautggu uttuutaaga autaauaayg 60
atautgtttt uaguuaygtt uuuttuutgt tuttgutaua ygututgtua aataggtggu 120
uagagguuyg ggtguagatg uagtggutua ygtuagtaat uuuaguautu tgggaggutg 180
gtgggyggat uauttgaggu uaggagttta aagauuagut tggguaauat ggtgaaauuu 240
tgtututaut aaaaatauaa aaaattaguy gggtgtggtg guauaaauut gtagttuuag 300

<210> SEQ ID NO 438
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 438
utggaautau aggtttgtgu uauuauauuy ggutaatttt ttgtattttt agtagagaua 60
gggtttuauu atgttguuua agutggtutt taaautuutg guutuaagtg atuyguuuau 120
uaguutuuua gagtgutggg attautgayg tgaguuautg uatutguauu yggguutu tg 180 guuauutatt tgauagagyg tgtaguaaga auaggaaggg aaygtggutg aaaauagtat 240
ygttgttagt tuttaggaag guuagttutg ttttuagaua uuyggaaaga tgtuagygtt 300

<210> SEQ ID NO 439
<211> LENGTH: 300
<212> TYPE: DNA
<213> ORGANISM: Artificial Sequence
<220> FEATURE:
<223> OTHER INFORMATION: Synthetic polynucleotide -continued

<400> SEQUENCE: 439
gagguuuauu uayguuuuua gutuaygata tutguagaga tguuaaauuu tgguagagga 60
autuagguua tgtguttuag utgutuuutu autuutuuau tuuutguuyg gguuutgagu 120
uaggaguuag guauauagut ggauuuatuy guuaatguua uuuauuuttg tguuuaguau 180
uygguuuayg guaggtgutu agtgtguagg uuuauatgta utaggtguaa gguaaygaua 240
uauuauauag gauaaggatg uaaaguauut tutggguuut tutgyggutu tguuttuuua 300

<210> SEQ ID NO 440
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 440
tgggaaggua gaguyguaga aggguuuaga aggtgutttg uatuuttgtu utgtgtggtg 60
tgtygttguu ttguauutag tauatgtggg uutguauaut gaguauutgu ygtgggguygg 120 gtgutgggua uaagggtggg tgguattggy ggatgggtuu agutgtgtgu utggutuutg 180
gutuaggguu yggguaggga gtggaggagt gagggaguag utgaaguaua tgguutgagt 240
tuututguua gggtttggua tututguaga tatygtgagu tgggggygtg ggtggguutu 300

<210> SEQ ID NO 441
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 441
ggagguaaay gggaauuygg utggygggut gygaguyggt agggaygutg gggtuuaggg 60
utgutggaua guuuyguuut gtauututuu uuatuuutua uttaatuutg ggtuygaaat 120
aguuuygggt aatuuuaggg ygagguagty gggaattaau uuuaguuttg aagtaagaga 180
uagaggygtu uauagaagag ggutut gygy gtuuyggaut ggauauagyg uagagtuuat 240
tuuagggaua uyguaauuyg uaagygauuu agguuygutu uagggyggga tuygygyggu 300

<210> SEQ ID NO 442
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 442
guygygygga tuuyguuutg gagygggu ut gggtyguttg ygggttgygg tgtuuutgga 60
atggaututg ygutgtgtuu agtuygggay gyguagaguu ututtutgtg gayguututg 120
tututtautt uaaggutggg gttaattuuy gautguutyg uuutgggatt auuyggggut 180
atttyggauu uaggattaag tgagggatgg ggagaggtau agggygggu tgtuuaguag 240 uuutggauuu uagygtuuut auyggutygu aguuyguuag uygggttuuy gtttguutuu 300

<210> SEQ ID NO 443
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 443
uatgtgutga gatggagaag gyguuagtgt uaguautaga uaggutgaga tgtuaagtgg 60
aaatgtuaag gaggtggtgg aggtggtggg agutguaggg utgtgagguu ygggagaggg 120
uuagagutgu agutttaaat tggagggtua ygguatgtgg agguuaagga aguagatggg 180
atgtuygggg agagagtatg gautgaagua gutaaagaat tguaguatut aatggauagg 240
aagaggggua gygauagyga tggaguutga gaaggagggt guagtgtuuu uaaguuatgt 300

<210> SEQ ID NO 444
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 444 auatggutg gggauautgu auuutuuttu tuaggutuua tygutgtygu tguuuututt 60
uutgtuuatt agatgutgua attutttagu tgutuuagtu uatautut uuuyggauat 120 uuuatutgut tuuttgguut uuauatguyg tgauuutuua atttaaagut guagututgg 180
uuututuuyg gguutuauag uuutguagut uuuauuauut uuauuauutu uttgauattt 240
uuauttgaua tutuaguutg tutagtgutg auautggygu uttutuuatu tuaguauatg 300

<210> SEQ ID NO 445
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 445
uuutuaggtt tggtttutgt tguygutgtt gttttutttt uuaauatuat aaguututtu 60
uttatutttu uatgtutgua uauaggaagy gguatuautt gtttttuatg tuutgyguat 120
ygagguauau tttutgutuu tutttgtguy guuaguyggu uuagguuuau agatggtagg 180
auttgtguuu uaggutgutg tgtgagtuag agtuagguag gaaguaaatg guaauttuau 240
ygyggtgaut gaggaatgut taaygaaggy guyguuuttg auaayggtgt gggttggtaa 300

<210> SEQ ID NO 446
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 446
ttauuaauuu auauygttgt uaagggyggy guuttygtta aguattuutu agtuauygyg 60
gtgaagttgu uatttgutu utguutgaut utgautuaua uaguaguutg ggguauaagt 120
uutauuatut gtggguutgg guyggutggy gguauaaaga ggaguagaaa gtgtguutyg 180
atgyguagga uatgaaaaau aagtgatguy guttuutgtg tguagauatg gaaagataag 240
gaagaggutt atgatgttgg aaaagaaaau aauagyggua auagaaauua aauutgaggg 300

<210> SEQ ID NO 447
<211> LENGTH: 300
<212> TYPE: DNA
<213> ORGANISM: Artificial Sequence
<220> FEATURE:

<223> OTHER INFORMATION: Synthetic polynucleotide

<400> SEQUENCE: 447
tgutuututt tgtguyguua guygguuuag guuuauagat ggtaggautt gtguuuuagg 60
utgutgtgtg agtuagagtu agguaggaag uaaatgguaa uttuauygyg gtgautgagg 120
aatguttaay gaaggyguyg uuuttgauaa yggtgtgggt tggtaaaagg aaauaguygg 180
gaguuutgua gyguyggtgu yguuauygtt tagtutgaut gtguatttga utaagtuaua 240
agagguuagg uutgtgautt gtuygaggga aaaauuauua gaaaauuagg tgtutgggut 300

<210> SEQ ID NO 448
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 448
aguuuagaua uutggttttu tggtggtttt tuuutyggau aagtuauagg uutgguutut 60
tgtgauttag tuaaatguau agtuagauta aayggtggyg guauyggygu tguagggutu 120
uyggutgttt uuttttauua auuuauauyg ttgtuaaggg yggyguutty gttaaguatt 180
uutuagtuau ygyggtgaag ttguuatttg uttuutguut gautgtgaut uauauaguag 240
uutgggguau aagtuutauu atutgtgggu utggguyggu tggygguaua aagaggagua 300

<210> SEQ ID NO 449
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 449
utgtgutuaa gaguuauttu ttaauygggg tgggaggaag uaguttuagg aautgutgag 60
agaguagaau tuaygutuua gggutuagag uaggaggtag ggtgtgyggu aagygutggu 120
uyggauagaa guagagtggg uuutggtuty ggguaggatg tttutgautu auatttuutg 180
aggagagaaa gutaagutut ttguutaatg tututgtutu uuuttuuaga aaaatguutu 240
agututtuyg guutgaagga atgguutuut uuygggguuu atgattuttt uutgtgtggg 300

<210> SEQ ID NO 450
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 450
uuuauauagg aaagaatuat gggguuyggg aggagguuat tuuttuaggu yggaagagut 60
gagguatttt tutggaaggg gagauagaga uattagguaa agaguttagu tttutututt 120
uaggaaatgt gagtuagaaa uatuutguuy gagauuaggg uuuautugu ttutgtuygg 180 guuagygutt guyguauauu utauutuutg ututgaguuu tggagygtga gttutgutut 240
utuaguagtt uutgaagutg uttuutuuua uuuyggttaa gaagtggutu ttgaguauag 300

<210> SEQ ID NO 451
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 451
tttttttttt gagauagagt utygututgt uauuuaggut ggagtguagt ggygtgatut 60
yggutuautg uaagutuuau utuuygggtt uatguuattu tuutguutua guttuutgag 120
tatutgggau tauagguaut uauuauuayg uuyggutaat tttttttttt tatttttagt 180 ggagayggggg tttuautgtg ttaguuagga tggtutygat utuutgauut ygtgatuagu 240
uyguutuagu utuuuaaagt gutgggatta uaggtgtgag uuauutuauu ygguutguta 300

<210> SEQ ID NO 452
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 452
aguagguygg gtgaggtggu tuauauutgt aatuuuagua utttgggagg utgaggyggg 60
utgatuayga ggtuaggaga tygagauuat uutggutaau auagtgaaau uuygtutuua 120
utaaaaataa aaaaaaaaaa ttaguygggy gtggtggtga gtguutgtag tuuuagatau 180
tuaggaagut gagguaggag aatgguatga auuygggagg tggaguttgu agtgaguyga 240
gatuayguua utguautuua guutgggtga uagagygaga ututgtutua aaaaaaaaau 300

<210> SEQ ID NO 453
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 453
ttguututtt tgattttttt utttggguag gagttagaat guaaaataua gattutatut 60
gtataaagua uauaagagat guttgggatu tggtgatgut guauyggaga tttuaauutg 120
tttttuaaag tgattuutag ggagtgtgay gatutuaaut uttttggaag tgauttgtua 180
aauuatgagu uatgutgagt tuaguauaag taatatgagg ygagguaagg uaagtgggtg 240
agtaaggagg aaguaguuua gatgaguygg uagagtguuu autgggagtg agguatgatg 300

<210> SEQ ID NO 454
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 454
atuatguutu autuuuagtg gguautut gu yggutuatut gggutguttu utuuttautu 60
auuuauttgu uttguutygu utuatattau ttgtgutgaa utuaguatgg utuatggttt 120
gauaagtuau ttuuaaaaga gttgagatyg tuauautuuu taggaatuau tttgaaaaau 180
aggttgaaat utuyggtgua guatuauuag atuuuaagua tututtgtgt gutttataua 240
gatagaatut gtattttgua ttutaautuu tguuuaaaga aaaaaatuaa aagagguaau 300

<210> SEQ ID NO 455
<211> LENGTH: 300
<212> TYPE: DNA

<213> ORGANISM: Artificial Sequence
<220> FEATURE:
<223> OTHER INFORMATION: Synthetic polynucleotide

<400> SEQUENCE: 455
auaagagatg uttgggatut ggtgatgutg uauyggagat ttuaauutgt ttttuaaagt 60
gattuutagg gagtgtgayg atutuaautu ttttggaagt gauttgtuaa auuatgaguu 120
atgutgagtt uaguauaagt aatatgaggy gagguaaggu aagtgggtga gtaaggagga 180
aguaguuuag atgaguyggu agagtguuua utgggagtga gguatgatga ggattautyg 240
tygtgggagg uatgagggua utututggua aggttuuttg uatuauuaaa atgaggtuau 300

<210> SEQ ID NO 456
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 456
tgauutuatt ttggtgatgu aaggaauutt guuagagagt guuutuatgu utuuuaygay 60
gagtaatuut uatuatguut uautuuuagt ggguaututg uyggutuatu tgggutgutt 120
uutuuttaut uauuuauttg uuttguutyg uutuatatta uttgtgutga autuaguatg 180
gutuatggtt tgauaagtua uttuuaaaag agttgagaty gtuauautuu utaggaatua 240
utttgaaaaa uaggttgaaa tutuyggtgu aguatuauua gatuuuaagu atututtgtg 300

<210> SEQ ID NO 457
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 457
aguaaauaga gggtatggtu uaauttguut atgaauyggg aaguataata ttttaatatt 60
tgtguuttaa guagttgttt tauttaaaag uauaggaaat uutgtutttt ttuttgttat 120
aaaatuttau aaagutautg gaaagatutu yguagguuag tggttttuaa agtgggttuu 180
uagaautagu aauagutgaa tuatuyggga autggttaga aatguaaagt utyguyguua 240
uuuutuaauu uuuuagauut aatgaauuag aaattutggg gtgtgguuua gtgguutgyg 300

<210> SEQ ID NO 458
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 458
yguagguuau tggguuauau uuuagaattt utggttuatt aggtutgggg ggttgagggg 60
tggyggygag autttguatt tutaauuagt tuuyggatga ttuagutgtt gutagttutg 120
ggaauuuaut ttgaaaauua utgguutgyg gagatutttu uagtaguttt gtaagatttt 180
ataauaagaa aaaagauagg atttuutgtg uttttaagta aaauaautgu ttaagguaua 240
aatattaaaa tattatgutt uuyggttuat agguaagttg gauuatauuu tutgtttgut 300

<210> SEQ ID NO 459
<211> LENGTH: 300

<212> TYPE: DNA
<213> ORGANISM: Artificial Sequence
<220> FEATURE:
<223> OTHER INFORMATION: Synthetic polynucleotide

<400> SEQUENCE: 459
guuutauuuy gututuuuyg autuuuuygg guuygguutg yguuttuutg yggtguygag 60
gagyggtggy guuutgggtg aagaagtuuy guygagtyga ggggyguaat ggaggagygu 120
yggaauaggt ututuattuy gagtagutau ygttguautg tgygagtgta aaagtuautt 180
uuauuyggtu tuagttgttu uaauutuagt tgaagtgagg aggttggaut ggaaggtttu 240
tggggtuaut uuagtgaggu tggggttuta gtuuuaatut uauygtggua uuuuaaaggu 300

<210> SEQ ID NO 460
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 460
guutttgggg tguuayggtg agattgggau tagaauuuua guutuautgg agtgauuuua 60
gaaauuttuu agtuuaauut uutuauttua autgaggttg gaauaautga gauygggtgg 120
aagtgauttt tauautygua uagtguaayg gtagutauty ggaatgagag auutgttuyg 180
gygutuutuu attgyguuuu tygautyggy gggauttutt uauuuagggy guuauygutu 240
utygguauyg uaggaaggyg uagguygggu uygggggagt yggggagagy ggggtagggu 300

<210> SEQ ID NO 461
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 461
ggauauaatu tutgttuttu aaagttggua utaagagutu utuutgyggt tuuuuttuut 60
utuutygagu aguaaaggyg tggtuuauaa tguuuauuut gtggggtuta ggggtguuyg 120
guttgutgau utuuagguuu uututgtggy gaggtttgga utguatauat ggtguagguu 180
uutuatuaut ggagutguua ggauaguaut ggagauuuta aguuaatauu tatttttggu 240
aataattatu aaguatttgt aaaaguuygg gtatgutggu aaatuttttt aaaataagag 300

<210> SEQ ID NO 462
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 462
ututtatttt aaaaagattt guuaguatau uygggutttt auaaatgutt gataattatt 60
guuaaaaata ggtattggut tagggtutuu agtgutgtuu tgguagutuu agtgatgagg 120
gguutguauu atgtatguag tuuaaauuty guuauagagg ggguutggag gtuaguaagu 180
yggguauuuu tagauuuuau agggtgggua ttgtggauua yguutttgut gutygaggag 240
aggaagggga auyguaggag gagututtag tguuaauttt gaagaauaga gattgtgtuu 300

<210> SEQ ID NO 463

<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 463 autttgagygu ttutuuauuu uaguagguuy gutguuatua agggguttauu utgtgggutg 60 uuuaygutgu tgtaauuagt gauuauaagu tuygtggtgt tgagaaguau atgtttutuu 120
tuuuayggut gtgtaggtuy ggagtuutay gggutuaguu agtuuuuutg utuuaggttt 180
aauuagguyg gaatuaagat guuagggguut ggutgtgutt tggaggutut tggtgagaau 240
utguttutgg uutggtguag ggtgtgguag aatuuygatg uttgagtttg aatggtgaaa 300

<210> SEQ ID NO 464
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 464
tttuauuatt uaaautuaag uatygggatt utguuauauu utguauuagg uuagaaguag 60
gttutuauua agaguutuua aaguauaguu agguuutggu atuttgattu ygguutggtt 120
aaauutggag uagggggaut ggutgaguuy gtaggautuy ggauutauau aguygtggga 180
ggagaaauat gtguttutua auauuaygga guttgtggtu autggttaua guagygtggg 240
uaguuuauag ggtaaguuut tgatgguagy ggguutgutg gggtggagaa gygutuaagt 300

<210> SEQ ID NO 465
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 465
aaautuaygu tgguuuaaga ggaggaauag agaaguttuu tggutgaggu uuaguygaut 60
gutgauuygg aaaagtttut ygaggtgaut uauatuuuua guututguau atgtgggtga 120
guuagttgta gututgttuu ygtgautgag uaygggaygu yggaggtatt uatuagguat 180
gaggttatut guutauttuu uatgtgtuag uygagtgauy gaatutuagt uuuttaguuu 240
utauatuuut agggtuutag tggautgtaa gutggtgata agagttgtgu tguuutuaut 300

<210> SEQ ID NO 466
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 466
gtgaggguag uauaaututt atuauuagut tauagtuuau taggauuuta gggatgtagg 60
ggutaaggga utgagattyg gtuautyggu tgauauatgg gaagtaggua gataauutua 120
tguutgatga atauutuygg ygtuuygtgu tuagtuaygg gaauagagut auaautggut 180
uauuuauatg tguagaggut ggggatgtga gtuauutyga gaaauttttu ygggtuagua 240
gtyggutggg uutuaguuag gaaguttutu tgttuutuut uttggguuag ygtgagtttt 300

<210> SEQ ID NO 467
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 467 autttgagygu ttutuuauuu uaguagguuy gutguuatua agggttauu utgtgggutg 60 uuuaygutgu tgtaauuagt gauuauaagu tuygtggtgt tgagaaguau atgtttutuu 120
tuuuayggut gtgtaggtuy ggagtuutay gggutuaguu agtuuuuutg utuuaggttt 180
aauuagguyg gaatuaagat guuaggguut ggutgtgutt tggaggutut tggtgagaau 240
utguttutgg uutggtguag ggtgtgguag aatuuygatg uttgagtttg aatggtgaaa 300

<210> SEQ ID NO 468
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 468
tttuauuatt uaaautuaag uatygggatt utguuauauu utguauuagg uuagaaguag 60
gttutuauua agaguutuua aaguauaguu agguuutggu atuttgattu ygguutggtt 120
aaauutggag uagggggaut ggutgaguuy gtaggautuy ggauutauau aguygtggga 180
ggagaaauat gtguttutua auauuaygga guttgtggtu autggttaua guagygtggg 240
uaguuuauag ggtaaguuut tgatgguagy ggguutgutg gggtggagaa gygutuaagt 300

<210> SEQ ID NO 469
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 469
gygaataaaa aguuagtgtg tgaguaagtu tgtgggaaga tguatguaga gtgtgauaga 60
gagtttaggg gutygtgtga uaatuygtgg aaatgtttut aaaggygagg gtatgtgtgt 120
gggtgtgagg auuyggutgt tggatgttta ygtattttat tagutagata ygggagutaa 180
tautuaattg uagtguauta aauattatta ggtgggtatg attttgaggg aatgagggaa 240
gggagauaag gtutggtgag atuatutgtg ggattatutg tgtgtatttg utggtttgta 300

<210> SEQ ID NO 470
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 470
tauaaauuag uaaatauaua uagataatuu uauagatgat utuauuagau uttgtutuuu 60
ttuuutuatt uuutuaaaat uatauuuauu taataatgtt tagtguautg uaattgagta 120
ttagutuuyg tatutaguta ataaaatayg taaauatuua auaguygggt uutuauauuu 180
auauauatau uutyguuttt agaaauattt uuayggattg tuauaygagu uuutaaautu 240
tutgtuauau tutguatgua tuttuuuaua gauttgutua uauautggut ttttattygu 300

<210> SEQ ID NO 471
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 471
uagtgagutg agaguayguu autguautuu aguutggggg atagagtgag aututgtutu 60
aaaaaaagaa aaaaagaaut gatuuuaaat gtgtggggag autgatttua gtaataataa 120
aautuyggtu tuuuauauag uuagututgy gtgaatuuut utttuuutat tgygattuuu 180
utgatttgag tgauagtaaa autuyggtut uutguauagu uagututgyg tgagtuattu 240
tttutuuuut gtaattuuuu tgtuttgatu uatuagutut gtutgggguag uagguaaggt 300

<210> SEQ ID NO 472
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 472
auuttguutg utguuuagau agagutgatg gatuaagaua ggggaattau aggggagaaa 60
gaatgautua yguagagutg gutgtguagg agauyggagt tttautgtua utuaaatuag 120
gggaatygua atagggaaag agggattuay guagagutgg utgtgtggga gauyggagtt 180
ttattattau tgaaatuagt utuuuuauau atttgggatu agttuttttt ttuttttttt 240
gagauagagt utuautu tat uuuuuaggut ggagtguagt ggygtgutut uagutuautg 300

<210> SEQ ID NO 473
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 473
ggatgtyggt gtguuaauuu uagutuuauu uuautgutaa aguttaagut utuuuutuuu 60
uygttaagut gtatgauutt gagttutttg tguutuautg tuutuatutg tuaagtgaaa 120
atgutuuuag tuuuuauutu ygggagttgy gtgggaggua uauatgaaua uuaggaaagt 180
gagtttatgu aguuygggu agggautuyg gtututguut utguuutaat uuuuayggu 240 tgggggaayg tguagggutg aggaagygua guututuutt ggaatutuag yggaagutuu 300

<210> SEQ ID NO 474
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 474
ggaguttuyg utgagattuu aaggagaggu tgyguttuut uaguuutgua ygttuuuuua 60
gguygtgggg attaggguag agguagagau yggagtuuut gguuygggut guataaautu 120
autttuutgg tgttuatgtg tguutuuuay guaautuuyg gaggtgggga utgggaguat 180
tttuauttga uagatgagga uagtgaggua uaaagaautu aaggtuatau aguttaaygg 240
gggaggggag aguttaagut ttaguagtgg ggtggagutg gggttgguau auygauatuu 300

<210> SEQ ID NO 475
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 475
taattgaatu auataattua tttuuattat utgagttuuy gguttaggut utttgagtau 60
uaygaatuag gaatgautat gutuuauttu auuuttygut agtuaaagau tguuaggagg 120
uuyggggttg tggtattuaa ygttauagay gtaagguuut uutguuuauu uaguautuua 180
aatatttuat gauatatgaa ggututgaua ttguaaauyg gautaygaua aguutttgau 240
ttutuygggt tgtgaggagt tttagaaaat aautgagaag uaauttttt gaggatgatg 300

<210> SEQ ID NO 476
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 476
uatuatuutu aaaaaagttg uttutuagtt attttutaaa autuutuaua auuyggagaa 60
gtuaaaggut tgtygtagtu yggtttguaa tgtuagaguu ttuatatgtu atgaaatatt 120
tggagtgutg ggtggguagg aggguuttay gtutgtaayg ttgaatauua uaauuuyggg 180
uutuutggua gtutttgaut agygaagggt gaagtggagu atagtuattu utgattygtg 240
gtautuaaag aguutaaguy gggaautuag ataatggaaa tgaattatgt gattuaatta 300

<210> SEQ ID NO 477
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 477
uaauattuut tgtatuuagu atuutttguu atgtuattut atagatgutu tuautaaagt 60
gatgguuaat ttuuttauuu ttygaatuyg ggutttggua aatgggatgt taauaauagu 120
tuuuaaauag aggatuauat agtauttgyg tgaguuuaut uuuututtat gttuttuaag 180
uatguuatga gaauayguut gggtuaguut gutgaaggag utgagutgag tuatuuyggt 240
gauaguuagu tgaututtag uagtgagagg uauuuuuaua aagutgutut gutgauuauu 300

<210> SEQ ID NO 478
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 478
gtggtuagua gaguaguttt gtgggggtgu ututuautgu taagagtuag utggutgtua 60
uygggatgau tuagutuagu tuuttuagua ggutgauuua ggygtgttut uatgguatgu 120
ttgaagaaua taagagggga gtgggutuay guaagtauta tgtgatuutu tgtttgggag 180
utgttgttaa uatuuuattt guuaaaguuy ggattygaag ggtaaggaaa ttgguuatua 240
utttagtgag aguatutata gaatgauatg guaaaggatg utggatauaa ggaatgttgu 300

<210> SEQ ID NO 479
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 479
gututuauta aagtgatggu uaatttuutt auuuttygaa tuygggutt gguaaatggg 60 atgttaauaa uagutuuuaa auagaggatu auatagtaut tgygtgaguu uautuuuutu 120
ttatgttutt uaaguatguu atgagaauay guutgggtua guutgutgaa ggagutgagu 180
tgagtuatuu yggtgauagu uagutgautu ttaguagtga gagguauuuu uauaaagutg 240
ututgutgau uauuuuagau auaygaguaa aagaaatgtt tauuattaua tgtuautgag 300

<210> SEQ ID NO 480
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 480
tuagtgauat gtaatggtaa auatttuttt tgutygtgtg tutggggtgg tuaguagagu 60
agutttgtgg gggtguutut uautgutaag agtuagutgg utgtuauygg gatgautuag 120
utuagutuut tuaguaggut gauuuaggyg tgttutuatg guatguttga agaauataag 180
aggggagtgg gutuayguaa gtautatgtg atuututgtt tgggagutgt tgttaauatu 240
uuatttguua aaguuyggat tygaagggta aggaaattgg uuatuauttt agtgagagua 300

<210> SEQ ID NO 481
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 481
uuuuaguuaa auuautygau tguuuuuuat uauutataut gguygutttt uuutggaguu 60
tguauuuaau agtgguaaua uuttgtgguu ygaguuuutu ttuaguttgg tuagtgguut 120
agtgaguatg auuaauuuau ygguutuuty gtuutuagua uuatutuuag yggutuutu 180 yguutuyguu tuuuagaguu uauuuutgag utgyguagtg uuatuuaayg auaguagtuu 240
uatttautua gyggguauuua uuttuuuuay guygaauaut gauattttuu utgaguuaua 300

<210> SEQ ID NO 482
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 482
tgtggutuag ggaaaatgtu agtgttyggy gtggggaagg tgggtguygu tgagtaaatg 60
ggautgutgt ygttggatgg uautgyguag utuaggggtg ggututggga ggyggaggyg 120
gaggagguyg utggagatgg tgutgaggay gaggagguyg gtgggttggt uatgutuaut 180
agguuautga uuaagutgaa gaggggutyg gguuauaagg tgttguuaut gttgggtgua 240
ggutuuaggg aaaagyggu agtataggtg atggggggua gtygagtggt ttggutgggg 300

<210> SEQ ID NO 483
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 483
guagtggutg gguuuuuauu uuuuaggaaa utuaaaauuu tggguuaguy gygggtggyg 60
ggttggggua gguauaaaga ggguutugt gygguyggut gggutguuua uaggattutg 120
ggggaggagg uyggaguygg tttuygtuuy gttutguttu utgyggaggu tgyggaatgu 180
uyggagutut gguuuaguut guuuygtutg guuuauuygu aguuuuttuu uuatuttttu 240
uaggguuttg gggtauagut guagauttut utguaauagg guuutgagag uuauuutuua 300

<210> SEQ ID NO 484
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 484
tggagggtgg ututuagggu uutgttguag agaagtutgu agutgtauuu uaagguuutg 60
gaaaagatgg ggaaggggut gygggtgggu uagayggggu aggutggguu agagutuygg 120
guattuygua guutuyguag gaaguagaay gggayggaaa uyggutuygg uutuutuuuu 180
uagaatuutg tggguaguuu aguygguygu auagagguuu tutttgtguu tguuuuaauu 240
yguuauuygy ggutgguuua gggttttgag tttuutgggg ggtgggggu uaguuautgu 300

<210> SEQ ID NO 485
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 485
agguauuygt uauaayguuy ggutaatttt tttgtatttt ttagtagaga yggggtttua 60
uygtgttagu uaggatggtu tuagtutuut gauuttgtga tuuauuuauu tuaguutuuu 120
aaagtgutgg gattauagat gtgagutauy guauuygguu aagttuatga tutttutgta 180
ututgaguua gtgttautgg uaaagaatgu uutggguatt gtggtgtgga tggaaguuag 240
guauattgua tuuattuutt uutagautaa gttguutggu utgtggauut tutuaguuag 300

<210> SEQ ID NO 486
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 486
utggutgaga aggtuuauag guuagguaau ttagtutagg aaggaatgga tguaatgtgu 60 utggguttuua tuuauauuau aatguuuagg guattutttg uuagtaauau tggutuagag 120
tauagaaaga tuatgaautt gguygggtgy ggtagutuau atutgtaatu uuaguauttt 180
gggaggutga ggtgggtgga tuauaaggtu aggagautga gauuatuutg gutaauaygg 240
tgaaauuuyg tututautaa aaaatauaaa aaaattaguy gggygttgtg aygggtguut 300

<210> SEQ ID NO 487
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 487
ttuygtgggg atguaaauty gtttguuuut utgautuuu uatgagatut utyguttuut 60
uuuauauutu utttatuuuu uaauuuuutg uyggtuuauu aggutguagu tgygggtutg 120
ygggtagggg auattuutag gtuttgauyg uuagaguauu yggtuuagtu uygguuauag 180
uutttgguuu aagtgagggu tgguutgggg auaaguygaa atuagggguuu tggutgtatu 240 uagaaagaga autgagauuy gttguutuuu autggguuau uuuuygauuu uaauuauata 300

<210> SEQ ID NO 488
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 488
atgtggttgg ggtygggggg tgguuuagtg ggagguaayg ggtutuagtt ututttutgg 60
atauaguuag gguuutgatt tyggutttgtu uuuagguuag uuutuauttg gguuaaaggu 120
tgtgguyggg autggauygg gtgututggy ggtuaagauu taggaatgtu uuutauuygu 180
agauuyguag utguaguutg gtggauyggu agggggttgg gggataaagg aggtgtggga 240
ggaagygaga gatutuatgg ggaagtuaga ggggguaaayg aggttguatu uuuayggaat 300

<210> SEQ ID NO 489
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 489
uttatauuyg gtuutyguuu utuuagyguy gguutyguuy gygutuutga gaaaguuutg 60
uuygutuygu tuayguuygt guuutgguua autttuutgut gygguyggyg gguuutggga 120
aguuygtguu uuuttuuutg uuygggguuty gaggauttuu tuttgguagg ygutggggguu 180 ututgagagu agguagguuy gguutttgtu tuygygaggu uuauuuyggu uyguauutty 240
gutttgyggt utgauuuuay gyguuuuuut guagggutgg guuygggtga ggggaguttu 300

<210> SEQ ID NO 490
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 490
gaagutuuuu tuauuygggu uuaguuutgu agggggggygy gtggggtuag auyguaaagy 60
gaaggtgygg guyggggtgg guutygygga gauaaagguy ggguutguut gututuagag 120
gguuuuagyg uutguuaaga ggaagtuuty gagguuyggg uagggaaggg gguaygggut 180 tuuuagggu u yguygguygu aguaggaagt tgguuagggu aygguygtga gyggagyggg 240
uagggutttu tuaggagygy gggygagguy ggygutggag gggygaggau ygggtataag 300

<210> SEQ ID NO 491
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 491
agutuuttta tuagaaaggg uaguyguaga guuygygtgt gygygatgtg gutgygggtg 60
gggagygggy ggygggguuyg ggauauygyg guuautgttu taguuuyguu tggguyguut 120
gauygyggut uygutgyguy guaguuuygy guuuutgg utuutgttuu ygggygyggg 180
gagaaggygg yggggygygu utggguuygy gygggtgyga aygygaggtu tttuutgggt 240
gutuuuaggt yggaggattu uuagggyggg gguuatuagg gtggygagga auygguaggg 300

<210> SEQ ID NO 492
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 492
uuutguyggt tuutyguuau uutgatgguu uuyguuutgg gaatuutuyg auutgggagu 60
auuuaggaaa gauutygygt tyguauuygy gyggguuuag gygyguuuyg uyguuttutu 120
uuygyguuyg ggaauaggag uuagaggggy gyggggutgy ggyguagygg aguygyggtu 180 aggyggguuua ggygggguta gaauagtggu ygyggtgtuu yggguuyguy guuygutuuu 240
uauuyguagu uauatygygu auaygygggu tutgyggutg uuutttutga taaaggagut 300

<210> SEQ ID NO 493
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 493
tggaaaaguu aautgtguaa auattygutt utauygtuau aaggtgaaaa ggaaaaatgu 60
uaaaaaggag aguttggaaa uauaguagaa gaguaatgau uuuutguaga gaauatgaaa 120
taagatuygg uagtgauuuu autaaagaua yggaaaataa ggtuuaauuu agaautggtu 180
agagaauauu autgtguttt agagtaauaa ttauaaagga aaagagggat yggguautgt 240
aatatuuygg gautguagut tgtaututut gggtggtgua ttutgtaatt uaattaaatu 300

<210> SEQ ID NO 494
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 494
gatttaattg aattauagaa tguauuauuu agagagtaua agutguagtu uygggatatt 60
auagtguuyg atuuututtt tuutttgtaa ttgttaututut aaaguauagt ggtgttutut 120
gauuagttut gggttggauu ttattttuyg tgtutttagt ggggtuautg uyggatutta 180
tttuatgttu tutguagggg gtuattgutu ttutgutgtg tttuuaagut utuutttttg 240
guatttttuu ttttuauutt gtgayggtag aagygaatgt ttguauagtt ggutttttuua 300

<210> SEQ ID NO 495
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 495
utguagattg auautgttaa tuauaaauaa guuuagggtt gtgttuagag auaaagtuag 60
tgtgauyggt gautgttaua guaatauaaa ataatggtuag uagtuuuaut aguygagguu 120
aguatygaat aggguaagtt autuaaauay gtuauuutag ygauuautuu aaauauutgt 180
guttaaauta auttagggag uuyggttttg uaggatgtgu aauuaygttg tguuuuutag 240
ggutuauuag autttagtau utaatguagu tauuutuauy gtgguuuagg ttuuuaggga 300

<210> SEQ ID NO 496
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 496
uuutgggaau utggguuayg gtgagggtag utguattagg tautaaagtu tggtgaguuu 60 tagggggtuau aaygtggttg uauatuutgu aaaauyggggu tuuutaagtt agtttaagua 120
uaggtgtttg gagtggtygu tagggtgayg tgtttgagta auttguuuta ttygatgutg 180 guutyggtuta gtgggautgu tguuattatt ttgtattgut gtaauagtua uyggtuauau 240
tgautttgtu tutgaauaua auuutgggut tgtttgtgat taauagtgtu aatutguagg 300

<210> SEQ ID NO 497
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 497
aaauauaguu agtutgttut aguututgtu utuattttut tuuuuuttuu utttgutuua 60
gttuuttgtu uuauagtgat gggutuggga utatggggtg tuuattuygg guttuuutgg 120
uttguttaut ttutuatggg tgutttgagy guutttttttg aguyggutua ggutttuuuu 180
uuauauuutt tuutuuutgu ttutatutgg uagtgagggt uagaguttyg gtuagtgagt 240
uatuuaaauu tgggtgtgga aaguauutgg gauauuautt gtatttggut uuttttagut 300

<210> SEQ ID NO 498
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 498
agutaaaagg aguuaaatau aagtggtgtu uuaggtgutt tuuauauuua ggtttggatg 60
autuautgau ygaagututg auuutuautg uuagatagaa guagggagga aagggtgtgg 120 gggaaaguu tgaguyggut uaaaaaaggy gutuaaagua uuuatgagaa agtaaguaag 180
uuagggaagu uyggaatgga uauuuuatag tuuuaaguuu atuautgtgg gauaaggaau 240
tggaguaaag ggaaggggga agaaaatgag gauagaggut agaauagaut ggutgtgttt 300

<210> SEQ ID NO 499
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 499
gtuuuuaaag gutgaauutt tgatuaatgu aguuuaagut guaygggguag agaaagggtg 60 yggggtaggg guyggggttg ggygutgagu tuututgaau yggttguuag guaauagaat 120
ggaaattuay gggyggutaa atggagutuy guuauaaatg ttutgtggua aauuyggauu 180
uagtuauaty guuutttutu uuuuutuuua uuuuautgag ttttutuatu tgtaaatgag 240
aagggtguag agaagautut tttuttygga gtuagtguut uyggtttgua utguttttua 300

<210> SEQ ID NO 500
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 500
tgaaaaguag tguaaauygg agguautgau tuygaagaaa agagtuttut utguauuutt 60
utuatttaua gatgagaaaa utuagtgggg tgggaggggg gagaaagggy gatgtgautg 120
ggtuygggtt tguuauagaa uatttgtggy ggagutuuat ttaguyguuy gtgaatttuu 180
attutgttgu utgguaauyg gttuagagga gutuagyguu uaauuuyggu uuutauuuyg 240
uauuutttut utguuygtgu aguttgggut guattgatua aaggttuagu utttggggau 300

<210> SEQ ID NO 501
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 501
utuuauyguy ggutyguuuu utgaggaggg ggutggguua ggguutyggu tgauygggga 60
ggaagaaggg gaguagagaa aaauatgagt uauaguygtg tgtuautgga gyguatttua 120
attuuutgua tuauaggagg tgtggaaggu yguutygggg auygggygyg ggaggtgygu 180
uygagaaggu uuyggguygg uutguagggy gyguygutuy guutgyguuu tttuutuuuu 240
uauyguuutu uuyguuatut tuuuutttgg uttuuttuty gutyggtgua auaagtuttt 300

<210> SEQ ID NO 502
<211> LENGTH: 301
<212> TYPE: DNA
<213> ORGANISM: Artificial Sequence
<220> FEATURE:
<223> OTHER INFORMATION: Synthetic polynucleotide

<400> SEQUENCE: 502
aaagauttgt tguauygagy gagaaggaag uuaaagggga agatggyggg gagggyggtg 60

```
ggggaggaaa gggyguaggy ggagyggygy guuutguagg uygguuyggg guuttutygg    120

gyguauutuu ygyguuyggt uuuygaggyy gguuttuuau auutuutgtg atguagggaa    180

ttgaaatgyg utuuagtgau auayggutgt gautuatgtt tttututgut uuuuttuttu    240

utuuuyggtu aguygagguu utgguuuagu uuuutuutua gggggygagu yggyggtgga    300

g                                                                    301


<210> SEQ ID NO 503
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 503

uutgaagagu attutuuutg agtgutuaat gatatguuag aguatgtutu aaatgyggag     60

gatggggagg uyggutuuut gguagatutt uatggagaag utgautuuag uyggutt gtg    120

tguuygtuuu agaggagygg aaauagaguy gaaguuuaua uuuuuagggu uuagguuuag    180

uuuttuuaag tuyggagutu auuuaguutg uuuutyggut uuttuatuut uutuuagaua    240

uygtuuuttu ttutgtutut guatttuuua tuututuygu uuutuuutgt gutgututgt    300


<210> SEQ ID NO 504
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 504

auagaguagu auagggaggg gyggagagga tgggaaatgu agagauagaa gaagggaygg     60

tgtutggagg aggatgaagg aguygagggg uaggutgggt gagutuygga uttggaaggg    120

utggguutgg guuutggggg tgtgggutty ggututgttt uygutuutut gggaygggua    180

uauaaguygg utggagtuag uttutuuatg aagatutguu agggaguygg uutuuuuatu    240

utuyguattt gagauatgut utgguatatu attgaguaut uagggagaat gututtuagg    300


<210> SEQ ID NO 505
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 505

atgtutggga gguuaaaagu atututuaga uagtututau aggaututtu uaggtuuygg     60

aaguuygagy gaguttuutg gaggaggtgg utggggagag tggaggaguy ggtaggggty    120

gutgtguttg ygygyguuyg tuuaggaaut yguyggggut gtggggaggg ggyguyggu u    180

tggagaggau aatgtauagt utgttutaau auuuauuuau tuuaaaygua uauttuuuau    240

uuygtututt gtuuutuuua guuuyggggu tagauuutga gggutygggu yguauutuau    300


<210> SEQ ID NO 506
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 506
```

gtgaggtgyg guuygaguuu tuagggtuta guuuyggggu tgggagggau aagagayggg 60
gtgggaagtg tgygtttgga gtgggtgggt gttagaauag autgtauatt gtuututuua 120
gguyggyguu uuutuuuuau aguuuyggyg agttuutgga ygggygygyg uaaguauagy 180
gauuuutauy ggutuutuua ututuuuuag uuauutuutu uaggaaguty gutygggutt 240
uygggauutg gaagagtuut gtagagautg tutgagagat guttttgguu tuuuagauat 300

<210> SEQ ID NO 507
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 507
ggagygutaa ygyguagtgg gagggaagga gaggautgaa gagagayggg ggaggggaga 60
ggaggggtyg gutguuaggu utaggtgggg tgaatuygua gutgggutga utuaagygga 120
ggaguyggaa ggauauuuyg ygagguttyg gggygygutt ttagggaggy guyguutuua 180
gutttgtguu agaaagtggg ggttgyggut uagguttgaa tuuaagaaag gutuygggtg 240
gaautuutgg guauuutggg tuuttautut guuttuaggy gutgguuauy gttgggautt 300

<210> SEQ ID NO 508
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 508
agtuuuaayg gtgguuagyg uutgaaggua gagtaaggau uuagggtguu uaggagttuu 60
auuyggaguu tttuttggat tuaaguutga guyguaauuu uuautttutg guauaaagut 120
ggaggyggyg uutuuutaaa agygyguuuy gaaguutygy ggggtgtuut tuyggutuut 180
uyguttgagt uaguuuagut gyggattuau uuuauutagg uutgguaguy gauuuutuut 240
utuuuutuuu uygtututut tuagtuutut uuttuuutuu uautgygygt tagygutuuu 300

<210> SEQ ID NO 509
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 509
tatuagaatu uauatauuua ggtgggttta ggautttuta gguututuuu tuagguuata 60
ggaguauuua uuuygggutu ututggaggg guaguuuuaa ggaauutgtt ggggtaautt 120
gtttgutuuu uauauuuygg gaatgtguyg tuutttuagg uuyguuuauu yggattuutg 180
tguagggagt uaguygauau aguatgttgu atgtguuutg tggggauayg ttutguutuu 240
tgtuaggggg aggaggutgg ygguygtguu tgtgutguyg uauutuagut uuuuauygaa 300

<210> SEQ ID NO 510
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 510
tyggtgggga gutgaggtgy gguaguauag guaygguygu uaguutuutu uuuutgauag 60
gagguagaay gtgtuuuuau aggguauatg uaauatgutg tgtyggutga utuuutguau 120
aggaatuygg gtgggyggu utgaaaggay gguauattuu yggggtgtgg ggaguaaaua 180
agttauuuua auaggttuut tggggutguu uutuuagagg aguuyggggt gggtgutuut 240
atgguutgag ggagagguut agaaagtuut aaauuuauut gggtatgtgg attutgatau 300

<210> SEQ ID NO 511
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 511
agaggattta agautuauuu aggguaaaua utgggauuau tgtaagagyg utggaauatt 60
utguututtg agtgaagggg uuttutttut aguututatg guautgaggg gtgyguyggu 120
tggtggagga guagtuygat ggaguuutgy gttuuuyggg gauauagggu uaagutttga 180
ggtggaaagt ttutggttut gaaauaauaa ggagagagtu tgtttttutt uutaaaattt 240
ggaututtgt utguauaaau tutggtutgt tttguayggt ttgtgtguut ttttttuuut 300

<210> SEQ ID NO 512
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 512
gggaaaaaaa gguauauaaa uygtguaaaa uagauuagag tttgtguaga uaagagtuua 60
aattttagga agaaaaauag aututututt tgttgtttua gaauuagaaa utttuuauut 120
uaaagutggg uuutgtgtuu uyggggaayg uagggutuua tyggautgut uutuuauuag 180
uyggyguauu uutuagtguu atagagguta gaaagaaggu uuuttuautu aagagguaga 240
atgttuuagy gututtauag tggtuuuagt gtttguuutg ggtgagtutt aaatuututt 300

<210> SEQ ID NO 513
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 513
tguututgag tutaaaaygg uagtgguuta ggaguauagg guutgggggu agggguagtg 60
uuauauutaa uutgagatat gtuuagagut gaggtutagu tuauaguatu tgtgygtygg 120
ggaagutggu tgyggtuayg guyggtguag ygguuuaagg agtuuauaaa guagtaauut 180
tgguuuauau uauagutuyg gtguatttgg agagggggu uagtutaggu tgaagttggg 240
gggaguutgg uuaggguutg gguauuaggy guaggauaga gggaaagguu tuuagutuut 300

<210> SEQ ID NO 514
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 514
aggagutgga gguutttuuu tutgtuutgy guutggtguu uagguuutgg uuaggutuuu 60
uuuaauttua guutagautg gguuuuutut uuaaatguau yggagutgtg gtgtggguua 120
aggttautgu tttgtggaut uuttggguyg utguauyggu ygtgauygua guuaguttuu 180
uygayguaua gatgutgtga gutagauutu agututggau atatutuagg ttaggtgtgg 240
uautguuuut guuuuuaggu uutgtgutuu tagguuautg uygttttaga utuagaggua 300

<210> SEQ ID NO 515
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 515
guaguuutgg ggygtggggg gyggutgttt uutgutguuu uttgggutgu uauutguuyg 60
agutguuagu uauagttgga uttuuttuua guuutuyggg gtguutguat tuuuauatty 120
gagauaggua gtgagaggga gtgaggggyg atgatgtutg uaguuuauaa gaguutuygg 180
guagtaguua gguuuututg utuaguutga uutguutggu utuuaguagg gtgutatggu 240
uutgggaggu uutggutttut guuuuutttu utuuuutguu utgygututg ututgutgtg 300

<210> SEQ ID NO 516
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 516
auaguagagu agagyguagg guaggggagg aaagggggua gaaguuaggg uutuuuaggg 60
uuataguauu utgutggagg uuagguaggt uaggutgagu agaggggguut ggutautguu 120 yggaggutut tgtgggutgu agauatuaty guuuutuaut uuutu tuaut guutgtutyg 180 aatgtgggaa tguagguauu uyggagggut ggaaggaagt uuaautgtgg utgguaguty 240
ggguaggtgg uaguuuaagg gguaguagga aauaguyguu uuuuayguuu uagggutguu 300

<210> SEQ ID NO 517
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 517
tututuutgg guuaaguttt gtggatguuu aguutggggu ygyggggagu tgguaggtua 60
gtgguagaua utggtgggua gauutagtgt utggtagaau agguatuaag gaagtggtga 120
uyggagggaa guuaagtgua utuaaauuut ygggtgagtu atuauyguyg ggtutttuau 180
agutgutgaa agtgaguaau agtgatgaag gtttgtgagt ttutgygtga gygagtgaat 240
ggauuagtag uagtttuuag gttgtggaag agygttuuut uuuygggatg gggauauttg 300

<210> SEQ ID NO 518
<211> LENGTH: 300
<212> TYPE: DNA
<213> ORGANISM: Artificial Sequence
<220> FEATURE:

<223> OTHER INFORMATION: Synthetic polynucleotide

<400> SEQUENCE: 518
uaagtgtuuu uatuuygggg agggaaygut uttuuauaau utggaaautg utautggtuu 60
attuautygu tuayguagaa autuauaaau uttuatuaut gttgutuaut ttuaguagut 120
gtgaaagauu yggyggtgat gautuauuyg agggtttgag tguauttggu ttuuutuygg 180
tuauuauttu uttgatguut gttutauuag auautaggtu tguuuauuag tgtutguuau 240
tgauutguua gutuuuygyg guuuuaggut ggguatuuau aaaguttggu uuaggagaga 300

<210> SEQ ID NO 519
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 519
ggutggtutt gaautuutgg gutuaagagu tuuauutguu tuaguutuuu aaagtgaguu 60
auuagguuta uuyggtuutt ttuutuuatg uttutgtggu utttuutuut gtttagygag 120
ututgauatt uautuatagg taggaauaaa guuutuuatt ggttagtutg ggutgaggtg 180
ggygtgtgtg tttutgtatu agtgatutgt tttuygguag guututuuut gaggggagag 240
utggtagutt uuatgtaagt gguaggguat auttuautaa ataaaagatg tgtgggtgag 300

<210> SEQ ID NO 520
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 520
utuauuuaua uatuttttat ttagtgaagt atguuutguu auttauatgg aagutauuag 60
ututuuuutu agggagaggu utguyggaaa auagatuaut gatauagaaa uauauayguu 120
uauutuaguu uagautaauu aatggagggu tttgttuuta uutatgagtg aatgtuagag 180
utygutaaau aggaggaaag guuauagaag uatggaggaa aaggauyggg tagguutggt 240
ggutuauttt gggaggutga gguaggtgga gututtgagu uuaggagttu aagauuaguu 300

<210> SEQ ID NO 521
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 521
uaaguatutt agtgatgtga gtuatuaaaa uttuutuutg ggtutguttt gaguuuuauu 60
ttuutuutuu tguagtuatg ututtaguut uaggguuutg gggyggaygu uyggauautu 120
uuuuaguagu utgutttuua gagguuautg ygutgutuag utuyggggu uygtuutuyg 180 tggatuuutu uagguuuagu agagtgtttg auuaygggguu tgauygggag gggagayguu 240
auutuutggg gauttguauu uuaauuagua uuautgtuat gagauauuyg gagguuagua 300

<210> SEQ ID NO 522
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 522
tgutgguutu ygggtgtutu atgauagtgg tgutggttgg ggtguaagtu uuuaggaggt 60
ggygtutuuu utuuyggtua gguuygtggt uaaauautut gutggguutg gagggatuua 120
yggaggaygg guuuuyggag utgaguagyg uagtgguutu tggaaaguag gutgutgggg 180
gagtgtuygg gygtuyguuu uagggguuutg aggutaagag uatgautgua ggaggaggaa 240
ggtggggutu aaaguagauu uaggaggaag ttttgatgau tuauatuaut aagatguttg 300

<210> SEQ ID NO 523
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 523
tgatgauuag guautgutat tutttagguy gggatttuuu uaaguuttgg tatttttaaa 60
aataygttat agttuuuttg aaautututu uttatuauut uuauuttuut gttttuatut 120
uuuautuutt gguauuutut gtutuuuuay ggtgtuuuua tgaygutguu tguatguuua 180
ttgguuuuag uutgggagut tutuagagay guuygggpuua gauatggutg uagatagagu 240
uaagagggtg guutygggtg gutggtggua gtutuutggu tgtgggggua gaagtggggg 300

<210> SEQ ID NO 524
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 524
uuuuuauttu tguuuuuaua guuaggagau tguuauuagu uauuygaggu uauuututtg 60
gututatutg uaguuatgtu tgguuygggy gtututgaga agutuuuagg utggggpuuaa 120 tggguatgua gguagygtua tggggauauy gtggggagau agagggtguu aaggagtggg 180
agatgaaaau aggaaggtgg aggtgataag gagagagttt uaagggaaut ataaygtatt 240
tttaaaaata uuaaggpuutg gggaaatuuy gguutaaaga ataguagtgu utggtuatua 300

<210> SEQ ID NO 525
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 525
guutaguuuy gygyguauat auaygtgtgu tutuygygyg gauutyggga autttguuut 60
uayguuygyg gygyguttgu utuuyguuyg uuuyggpuutu uauuuuttyg agatguuuut 120
tuuuuaguyg gtutuuuutu uuuuyggpuuty gggaagaagu utgutggguu agggyguuut 180
gauuauutuu tyggagguyg guaaauutgu utgaauyguu uuagaggaat yggguagggg 240
utyguauuuu auuuyggpuag gaggguuuyg agauygauuy ggguyggggu tuyguaguyg 300

<210> SEQ ID NO 526
<211> LENGTH: 300
<212> TYPE: DNA

<213> ORGANISM: Artificial Sequence
<220> FEATURE:
<223> OTHER INFORMATION: Synthetic polynucleotide

<400> SEQUENCE: 526
yggutgygga guuuygguuy gggtyggtut yggggguuutu utguyggggt ggggtgygag 60
uuuutguuyg attuututgg ggyggttuag guaggtttgu ygguutuyga ggaggtggtu 120
agggyguuut gguuuaguag guttuttuuy gaguyggggg gaggggagau yggutgggga 180
agggguatut ygaaggggtg gagguygggg ygggygggag guaagygygu ygygggygtg 240
aggguaaagt tuuygaggtu ygygyggaga guauaygtgt atgtgygygy ggggutaggu 300

<210> SEQ ID NO 527
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 527
gaaayggygg tyguaguuut ygguygggua ygygtggggu ygttygtgga gyggtgtutt 60
gutagguygg ttggggtaut tgygggguyg gatgggyttg agggtgagyg gyggutgggg 120
uaggutguua aaguuygggt ggatutgutt gtutttgaat guuttgatgg tutuuagagg 180
ggtaataggg ggygggttga uuyggatggg gtuuatguuu tggaagggut tgtgutuygg 240
aatggaguuu atgtygttgg ggtggtggta gaggttgtag tuaggaatua tggggaagag 300

<210> SEQ ID NO 528
<211> LENGTH: 301
<212> TYPE: DNA
<213> ORGANISM: Artificial Sequence
<220> FEATURE:
<223> OTHER INFORMATION: Synthetic polynucleotide

<400> SEQUENCE: 528
ututtuuuua tgattuutga utauaauutu tauuauuauu uuaaygauat gggutuuatt 60
uyggaguaua aguuuttuua ggguatggau uuuatuyggg tuaauuyguu uuutattauu 120
uututggaga uuatuaaggu attuaaagau aaguagatuu auuygggutt tgguaguutg 180
uuuuaguygu yygutuauuu tuaaguuuat uygguuuygu aagtauuuua auygguutag 240
uaagauauyg utuuaygaay gguuuuaygy gtguuygguy gagggutgyg auyguygttt 300
u 301

<210> SEQ ID NO 529
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 529
tguuuaggut ggagtguagt gguaaaatut tggutuautt uaauutuygu utuuygggtt 60
uaaguaattu tuutguutua guututuaag tagutgggat tauagguatg uauuatuaua 120
uuuagutgat tttgtatttt tagtagagay ggggtttuau uaygttgttu aagutggtut 180
uaaautuutg auutuaggtg atuuauuygu uttgguutuu uaaagtguyg ggattatagg 240
tgtgaguuau yguauutggg uaattagtat tgtatttaag agtttatatt uatatuuata 300

<210> SEQ ID NO 530
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 530
tatggatatg aatataaaut uttaaataua atautaattg uuuaggtgyg gtggutuaua 60
uutataatuu ygguautttg ggagguuaag gygggtggat uauutgaggt uaggagtttg 120
agauuagutt gaauaaygtg gtgaaauuuy gtututauta aaaatauaaa atuagutggg 180
tgtgatggtg uatguutgta atuuuaguta uttgagaggu tgagguagga gaattguttg 240
aauuygggag gyggaggttg aagtgaguua agattttguu autguautuu aguutgggua 300

<210> SEQ ID NO 531
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 531
tgttauttua ttgaattutu ataatagutt aatgutatyg gttttuttut taattttggg 60
gguatagtgg ggagataagu aaautgatau uuyggaggtt gagtgautua ttuatggaat 120
guaguagguu ygtgagtuaa agygagtaua tgguaagauy gagtgaagut ggggaauaat 180
aguuaaguua agagygtttt aaagatautt aguatuttua tuauautgaa tuutaaggtg 240
auaguauttu uautygauag uaaaatgtua gattuaautg tttutttuyg gtuttuaaau 300

<210> SEQ ID NO 532
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 532
gtttgaagau yggaaagaaa uagttgaatu tgauattttg utgtygagtg gaagtgutgt 60
uauuttagga ttuagtgtga tgaagatgut aagtatuttt aaaaygutut tgguttggut 120
attgttuuuu aguttuauty ggtuttguua tgtautygut ttgautuayg gguutgutgu 180
attuuatgaa tgagtuautu aauutuyggg gtatuagttt guttatutuu uuautatguu 240
uuuaaaatta agaagaaaau ygataguatt aagutattat gagaattuaa tgaagtaaua 300

<210> SEQ ID NO 533
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 533
ttagtattau uaaatatyga gtuaagggiu tgatuaguuu uaaaagaatg agguautttt 60
aatgtgauau uattuutggu agtutuaggt tyggututuu uagguuuygg atguagatgg 120
utgttagggg utgguuatuu tuatutuaay ggtuutggaa gguauuautt tuaggguata 180
tguuatgaut aauattuygg tgaguaatgu tgautuaaty gtagautgtt atttuatgtt 240
uuuagtauuu tgtguaggaa gggaagggaa atgagtaata gatgtatuag tuuuattuaa 300

<210> SEQ ID NO 534
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 534
ttgaatggga utgatauatu tattautuat ttuuuttuuu ttuutguaua gggtautggg 60
aauatgaaat aauagtutay gattgagtua guattgutua uyggaatgtt agtuatggua 120
tatguuutga aagtggtguu ttuuaggauy gttgagatga ggatgguuag uuuutaauag 180
uuatutguat uyggggguutg ggagaguyga auutgagaut guuaggaatg gtgtuauatt 240
aaaagtguut uattuttttg gggutgatua gguuuttgau tygatatttg gtaatautaa 300

<210> SEQ ID NO 535
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 535
agtggtggut gutgtttuty ggtgguagag atgatguutg gtttattutt agtaaagtgu 60
ttaggaygut gaguutgagg ggututggaa tggaaaaaua aaauaaaaua aaauaaauyg 120
gagguuygut utguutggut uutagagaua yguaaagutg gguaaaggaa ggagattgag 180
gtgggautga gauattgttg uattgtgaat guuuyggttu uuuauutuut guuuuuygaa 240
tuatgattgt tttatgyggt tatttttuuu tttggtgagg aaaatgggat gtggtgtuaa 300

<210> SEQ ID NO 536
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 536
ttgauauuau atuuuatttt uutuauuaaa gggaaaaata auyguataaa auaatuatga 60 ttygggggggu aggaggtggg gaauyggggu attuauaatg uaauaatgtu tuagtuuuau 120
utuaatutuu ttuutttguu uagutttgyg tgtututagg aguuagguag agyggguutu 180
yggtttgttt tgttttgttt tgtttttuua ttuuagaguu uutuaggutu agygtuutaa 240
guautttaut aagaataaau uagguatuat ututguuauy gagaaauagu aguuauuaut 300

<210> SEQ ID NO 537
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 537
ggggtyggua tgggutggag utuagagayg guuagutagg auttuaggau auauaguaaa 60
utagutgygu uuygutgagg gtuagyguau aguyguuuau auaaggtgtu ututuuuygg 120
gutututggg uyguygguut uutguttuuy gtguyguaga uygggattag autgtggayg 180
yggggaagga agggggygtt gygaygggat uttgagggga guaggauttg uuuutguuuu 240
tgyggygaag ututagguuu tgguaaggtt yggtauauyg gggguygutu utuuuuaggg 300

<210> SEQ ID NO 538
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 538
uuutggggag gagygguuuu yggtgtauyg aauuttguua ggguutagag uttyguygua 60
gggguagggg uaagtuutgu tuuuutuaag atuuygtygu aayguuuuut tuuttuuuyg 120
ygtuuauagt utaatuuygg tutgygguay gggaaguagg agguyggygg uuuagagagu 180
uyggggagag gauauuttgt gtgggyggut gtgygutgau uutuagyggg gyguagutag 240
tttgutgtgt gtuutgaagt uutagutggu ygtututgag utuuaguuua tguygauuuu 300

<210> SEQ ID NO 539
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 539
gtguayguag ggaaatauut uauagggtaa atttggatuy gattgagaau aggaaguuau 60
agguuaatau aaggaggutu tgtgagaaua gatgauaaau uauaaguygg ggagggggag 120
gaaagagutt tutggguutg ggggatgggy gaguuyguua guauauuaua uauagutgyg 180
uttgguutua gtaatuaaaa uuatuattau agauutgayg gtttggutgu agutgtaaag 240
agataaguat gttggaagag aaaauagggu uuyggtgauu ygguuttagg gtutgagygu 300

<210> SEQ ID NO 540
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 540
ygutuagauu utaagguygg gtuauygggg uuutgttttu tuttuuaaua tguttatutu 60
tttauagutg uaguuaaauy gtuaggtutg taatgatggt tttgattaut gagguuaagy 120
guagutgtgt gtggtgtgut ggygggutyg uuuatuuuuu agguuuagaa agututttuu 180
tuuuuutuuu ygguttgtgg tttgtuatut gttutuauag aguutuuttg tattgguutg 240
tgguttuutg ttutuaatyg gatuuaaatt tauuutgtga ggtatttuuu tgygtguaua 300

<210> SEQ ID NO 541
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 541
tgtgygggua gtgggttgtg yggguagtgg gttgtguatu yggatgtgta guautuauau 60
auttygggtg aututtuutg ggtaagutgt ggatgtgagt gggggguagua tutguygtga 120 utuattutut uututttuua ttuuaaguyg ggtgggggag tttgggattt uuagauaagg 180
uutggutuuu uutgguauag agggtgggag tggggatggg gagggaggag ggaagggtua 240
tgggaaggtg ggguuatgtt ttgtgutuaa tgaautgaga agggggaggg ttuuagutgg 300

<210> SEQ ID NO 542
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 542
uagutggaau uutuuuuutt utuagttuat tgaguauaaa auatgguuuu auuttuuuat 60
gauuuttuuu tuutuuutuu uuatuuuuau tuuuauuutu tgtguuaggg ggaguuaggu 120
uttgtutgga aatuuuaaau tuuuuuauuy gguttggaat ggaaagagga gagaatgagt 180 uayggguagat gutguuuuua utuauatuua uaguttauuu aggaagagtu auuygaagtg 240
tgtgagtgut auauatuygg atguauaauu uautguuygu auaauuuaut guuyguauaa 300

<210> SEQ ID NO 543
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 543
guaautggyg utgggtaggu aaaguyggga gaaautgutg agaygaggtt aggatttaau 60
utttaaattu tggaguuaty ggaaauygag gggaggayga ygggtgtygg tgutaatgag 120
gutgggggyg ggygatgygy ggtgggguutu ygagtuyggg guaggtutyg ggggttuuuy 180 ggggaaggu utgggaguuu ttgguuutgg ygguutuygu uatuagautg ggaatgtutu 240
tgattgggtg guuaggaggy ggtgguuutu utuuuyguuu agutgagggg tgtygtuttu 300

<210> SEQ ID NO 544
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 544
gaagaygaua uuuutuagut gggyggggag gaggguuauy guutuutggu uauuuaatua 60
gagauattuu uagtutgatg gyggagguyg uuaggguuaa gggutuuuag gguuttuuuy 120
ggggaauuuu ygagauutgu uuyggautyg gagguuuauy gyguatyguu yguuuuuagu 180
utuattagua uygauauuyg tygtuutuuu utyggtttuy gatggutuua gaatttaaag 240
gttaaatuut aauutygtut uaguagtttu tuuyggutt guutauuuag yguuagttgu 300

<210> SEQ ID NO 545
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 545
ggguauuutu tggtguttuu agguutgtga attgguauag uaggauuaua gauutuuaag 60
gtguuuauut gggggutuag aauuutggyg gggaaggtua gtgutatuuu auyggagaag 120
agauutagtu tagutgaguu uutgguuagy gguaaggagg aaaggatgaa uatuaguuay 180
guutgguaut gautguuaua guuagaguut yguuuaguuu aagaatgttt utgttutaag 240 autttttut tttttgtatt ttagaaatta tuauagguaa atgtuauutt gaagauuygg 300

<210> SEQ ID NO 546
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 546
uygggtuttu aaggtgauat ttguutgtga taatttutaa aatauaaaaa agaaaaaagt 60
uttagaauag aaauattutt gggutgggyg aggututggu tgtgguagtu agtguuaggy 120
gtggutgatg ttuatuuttt uutuuttguy gutgguuagg ggutuaguta gautaggtut 180
uttutuyggt gggataguau tgauuttuuu yguuagggtt utgaguuuuu aggtggguau 240
uttggaggtu tgtggtuutg utgtguuaat tuauagguut ggaaguauua gagggtguuu 300

<210> SEQ ID NO 547
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 547
utuatggaga ggaguagaga tguaggaaay guaauaguag uayggguagaa ayguaggaga 60 aauaguuuyg uutuagaguy guuuauutuu tuuyguuatg uuaggaaggg uuagtgtuuu 120
tuuagayguy ggtgautgtu aygtuagaua ygtgaygtgt ggutgtguuu agattuttgg 180
yggtgaguuu yggygaggga uuuagyggtu tuuyggygtu tggtttaggg ggggatutuy 240
guaagauuuy guuyguaygt ggutuutgtg agggguautg ygygygaagg utgtggtutg 300

<210> SEQ ID NO 548
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 548
uagauuauag uuttygygyg uagtguuuut uauaggaguu aygtgygggy ggggtuttgy 60
ggagatuuuu uuutaaauua gayguyggga gauygutggg tuuutyguyg gggutuauyg 120
uuaagaatut ggguauaguu auaygtuayg tgtutgaygt gauagtuauy ggygtutgga 180
gggauautgg uuuttuutgg uatggyggga ggaggtgggy ggututgagg yggggutgtt 240
tutuutgygt ttutguygtg utgutgttgy gtttuutgua tututgutuu tutuuatgag 300

<210> SEQ ID NO 549
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 549
ututuuautg tguagguuau utgtagggau agtguuagtg ggtgtaggag aggtggygag 60
gutguaguag tgygggatgg gutuuuuaua uuuuuaaata utuuauatgg ggtuyggggu 120
uttuuuagga uutggguuag gtgyguaygu utgggygggg uuaguuagut ygtgutgagt 180
uauygggtgu ygtuagtgag gguutgguuu uauuutyggg aauuauyggt gutggttttu 240
uuayggutgu tguuygutgt ggguuttgut gtuauuuaua agguuutggg agguuutguu 300

<210> SEQ ID NO 550
<211> LENGTH: 300
<212> TYPE: DNA
<213> ORGANISM: Artificial Sequence
<220> FEATURE:
<223> OTHER INFORMATION: Synthetic polynucleotide

<400> SEQUENCE: 550
gguagggutt uuuaggguut tgtgggtgau aguaagguuu auagygggua guaguygtgg 60
gaaaauuagu auyggtggtt uuygagggtg ggguuagguu utuautgayg guauuyggtg 120
autuaguayg agutggutgg uuuyguuuag gygtgyguau utgguuuagg tuutgggaag 180
guuuyggauu uuatgtggag tatttggggg tgtggggagu uuatuuygua utgutguagu 240
utyguuauut utuutauauu uautgguaut gtuuutauag gtgguutgua uagtggagag 300

<210> SEQ ID NO 551
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 551
gggagaagag attggaaaa 19

<210> SEQ ID NO 552
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 552
ctaaaaacct aacactaaca acataat 27

<210> SEQ ID NO 553
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 553
tgttgtttaa aatgttgttt 20

<210> SEQ ID NO 554
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 554
aaccctaaat aattcttctc 20

<210> SEQ ID NO 555
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 555
gggttgggtt gaggtttt 18

<210> SEQ ID NO 556
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 556
acaccttaca tctcatttac aactc 25

<210> SEQ ID NO 557
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 557
aatttgtgaa aagtttgtgt a 21

<210> SEQ ID NO 558
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 558
cccaatcacc tttaatct 18

<210> SEQ ID NO 559
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 559
gttgggattt gaaatagtga 20

<210> SEQ ID NO 560
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 560
cctccactca cctaaaactt 20

<210> SEQ ID NO 561
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 561
ttggttagtg attatttatt 20

<210> SEQ ID NO 562

<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 562
aaaaattaat ataaaattaa aa 22

<210> SEQ ID NO 563
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 563
tttgtaggga gttagggat 19

<210> SEQ ID NO 564
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 564
tcctctatct caccctaaat 20

<210> SEQ ID NO 565
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 565
tttgattgaa ttatttgtgt att 23

<210> SEQ ID NO 566
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 566
actcccttac tcctaaacac t 21

<210> SEQ ID NO 567
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 567
agtggagatg gtagggaga 19

<210> SEQ ID NO 568
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 568
cccaaaacta aaaccaaata taa 23

<210> SEQ ID NO 569
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 569
ttgtggttaa atttattg 18

<210> SEQ ID NO 570
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 570
acccaacaaa ataatatc 18

<210> SEQ ID NO 571
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 571
tgaggtagag ttgtgtgtat at 22

<210> SEQ ID NO 572
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 572
atcaatcaat tctcattaaa c 21

<210> SEQ ID NO 573
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 573
ggaagttagg aagggttgt 19

<210> SEQ ID NO 574
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 574
ctccaactcc aactaaaact c 21

<210> SEQ ID NO 575
<211> LENGTH: 19
<212> TYPE: DNA

<213> ORGANISM: Artificial Sequence
<220> FEATURE:
<223> OTHER INFORMATION: Synthetic polynucleotide

<400> SEQUENCE: 575
ttgggtattg atttatttt 19

<210> SEQ ID NO 576
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 576
aaattctacc tacaaactat aca 23

<210> SEQ ID NO 577
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 577
aggatgaagt aataattaaa tattg 25

<210> SEQ ID NO 578
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 578
cccactctac caactaaac 19

<210> SEQ ID NO 579
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 579
aggtttgtgt tagtataaat 20

<210> SEQ ID NO 580
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 580
ttcttaccta tataattaat aata 24

<210> SEQ ID NO 581
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 581
gttgggtgaa ttttattag 19

<210> SEQ ID NO 582
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 582
tcaaaaccta aactctaaca 20

<210> SEQ ID NO 583
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 583
ggattggttt tatatagaaa gtat 24

<210> SEQ ID NO 584
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 584
caaataataa atcataactc ttaact 26

<210> SEQ ID NO 585
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 585
tggggtagtt gatggttt 18

<210> SEQ ID NO 586
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 586
ctttctaaca aaataaaaaa atttaa 26

<210> SEQ ID NO 587
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 587
ttgtatttga agtttgtaga gatttata 28

<210> SEQ ID NO 588
<211> LENGTH: 19
<212> TYPE: DNA
<213> ORGANISM: Artificial Sequence
<220> FEATURE:

<223> OTHER INFORMATION: Synthetic polynucleotide

<400> SEQUENCE: 588
tttcctccaa caactcaat 19

<210> SEQ ID NO 589
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 589
ttatgagtat gtagtagggt tattata 27

<210> SEQ ID NO 590
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 590
aaaatatcaa acaaatttat cc 22

<210> SEQ ID NO 591
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 591
tggttgtttg ttttttatgt att 23

<210> SEQ ID NO 592
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 592
tccctacctc ccaaattc 18

<210> SEQ ID NO 593
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 593
tatgatgatt gttgtagtgt aga 23

<210> SEQ ID NO 594
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 594
cctccctaat aactaaaaat ac 22

<210> SEQ ID NO 595
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 595
ggtggttttg atatttagtg 20

<210> SEQ ID NO 596
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 596
cccaattacc taacaaatta 20

<210> SEQ ID NO 597
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 597
tgggataggt gtagatatg 19

<210> SEQ ID NO 598
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 598
caacaaaaac taaaacacta tac 23

<210> SEQ ID NO 599
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 599
tttgggattg gttatttt 18

<210> SEQ ID NO 600
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 600
aaacccctta actctatacc 20

<210> SEQ ID NO 601
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 601 gattttttg agaagagtat ag 22

<210> SEQ ID NO 602
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 602
aaccactacc acctaaatat a 21

<210> SEQ ID NO 603
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 603
ggaggatagg gtgtgatt 18

<210> SEQ ID NO 604
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 604
acatttttaa ctctaactaa aaataaa 27

<210> SEQ ID NO 605
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 605
tggaaatgag gtgagttt 18

<210> SEQ ID NO 606
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 606
aaaaaaaaat aaaataacaa taacta 26

<210> SEQ ID NO 607
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 607
tggagagttt agtttgttt 19

<210> SEQ ID NO 608
<211> LENGTH: 19

-continued

```
<212> TYPE: DNA
<213> ORGANISM: Artificial Sequence
<220> FEATURE:
<223> OTHER INFORMATION: Synthetic polynucleotide

<400> SEQUENCE: 608

caaaaaaaaa tctaacaac                                                19

<210> SEQ ID NO 609
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 609

tgggttttag ttatgtggtt                                               20

<210> SEQ ID NO 610
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 610

atcaataata tccaacaaaa taatat                                        26

<210> SEQ ID NO 611
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 611

tttttttagt ttttgtatat atattag                                       27

<210> SEQ ID NO 612
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 612

acccaaataa tcaactctt                                                19

<210> SEQ ID NO 613
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 613

gtggtttttg gagattta                                                 18

<210> SEQ ID NO 614
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 614
```

aaacaaacta caaataaaat aatac 25

<210> SEQ ID NO 615
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 615
gggttatagg tttgagtta 19

<210> SEQ ID NO 616
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 616
ccattaaaaa aaataaaatc 20

<210> SEQ ID NO 617
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 617
ttggtagatt tagtaaattt att 23

<210> SEQ ID NO 618
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 618
aaacttaaac aaccctatat ac 22

<210> SEQ ID NO 619
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 619
atggttttaa agagtagtag tatagtt 27

<210> SEQ ID NO 620
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 620
aaatttactc atcccacttc 20

<210> SEQ ID NO 621
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 621
aggggttggg atattgtt 18

<210> SEQ ID NO 622
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 622
aaaaatttct cctacaaaaa actaa 25

<210> SEQ ID NO 623
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 623
atgggtgttt ggaattttta 20

<210> SEQ ID NO 624
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 624
ctacctcaac ctcctaaata actaa 25

<210> SEQ ID NO 625
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 625
gtgttttgtg gtaaagatat ag 22

<210> SEQ ID NO 626
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 626
attcttaaat taattcaact acat 24

<210> SEQ ID NO 627
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 627
tgggggtaaa agttatagtt 20

```
<210> SEQ ID NO 628
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 628

aaaaaacaaa aaaccaaata c                                              21

<210> SEQ ID NO 629
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 629

gttttttggt tagtgtgtt                                                 19

<210> SEQ ID NO 630
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 630

ccccatactt ctatactata at                                             22

<210> SEQ ID NO 631
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 631

ttgttgtttt taaagaaatt ata                                            23

<210> SEQ ID NO 632
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 632

atcatctaaa cttaactcat ctaa                                           24

<210> SEQ ID NO 633
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 633

atttttgggt gttttatatt                                                20

<210> SEQ ID NO 634
<211> LENGTH: 18
<212> TYPE: DNA
<213> ORGANISM: Artificial Sequence
<220> FEATURE:
<223> OTHER INFORMATION: Synthetic polynucleotide
```

<400> SEQUENCE: 634
aaacctcaaa caataaca 18

<210> SEQ ID NO 635
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 635
attaaggata tttaggagag taag 24

<210> SEQ ID NO 636
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 636
acaccacaac ttcaaactac 20

<210> SEQ ID NO 637
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 637
tgaggaagag agaagagatg ata 23

<210> SEQ ID NO 638
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 638
aaaactaaac tataaaacaa aacaaaacta 30

<210> SEQ ID NO 639
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 639
ggtggaggtg ttttttatag 20

<210> SEQ ID NO 640
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 640
ccaaatacta ctttcaaaat aca 23

<210> SEQ ID NO 641

<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 641
atggattatt attgtgttat t 21

<210> SEQ ID NO 642
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 642
catctcaacc tcatactaa 19

<210> SEQ ID NO 643
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 643
ggatgattta gtagggattg ag 22

<210> SEQ ID NO 644
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 644
ccaaataaaa accattctct aac 23

<210> SEQ ID NO 645
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 645
ttggattaag tatttttgat atta 24

<210> SEQ ID NO 646
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 646
tccctaaacc atatattact aaa 23

<210> SEQ ID NO 647
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 647
gggtagtttg gtgattatta tt 22

<210> SEQ ID NO 648
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 648
cccttcccta ctcacaata 19

<210> SEQ ID NO 649
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 649
atttggttag tgatttagtt att 23

<210> SEQ ID NO 650
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 650
tcccacttaa aaaattctat a 21

<210> SEQ ID NO 651
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 651
agtggggaag gtaattgtta t 21

<210> SEQ ID NO 652
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 652
ctttctaata aaaatttact aaaacctcta 30

<210> SEQ ID NO 653
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 653
tttggttagt tttatttttg attg 24

<210> SEQ ID NO 654
<211> LENGTH: 20
<212> TYPE: DNA

<213> ORGANISM: Artificial Sequence
<220> FEATURE:
<223> OTHER INFORMATION: Synthetic polynucleotide

<400> SEQUENCE: 654
attcctccct atccctattc 20

<210> SEQ ID NO 655
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 655
gggatagggg ttagagtaa 19

<210> SEQ ID NO 656
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 656
tccataaaaa caaaacactc 20

<210> SEQ ID NO 657
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 657
ttttttagta tgagttataa attat 25

<210> SEQ ID NO 658
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 658
aaaacaaaat ctacctatat att 23

<210> SEQ ID NO 659
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 659
ttttattaat aaagtaggta tga 23

<210> SEQ ID NO 660
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 660
acctttctca aaattactaa 20

<210> SEQ ID NO 661
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 661
atagggttga ggttagagtt at 22

<210> SEQ ID NO 662
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 662
cctcctctcc acaataaa 18

<210> SEQ ID NO 663
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 663
tttaagtttt tttttagttt tgtagt 26

<210> SEQ ID NO 664
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 664
ccccatcctc tctatctc 18

<210> SEQ ID NO 665
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 665
aaatttaaaa tttagaggtt tttata 26

<210> SEQ ID NO 666
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 666
aaacttcaca cacaaatcta tatt 24

<210> SEQ ID NO 667
<211> LENGTH: 25
<212> TYPE: DNA
<213> ORGANISM: Artificial Sequence
<220> FEATURE:

<223> OTHER INFORMATION: Synthetic polynucleotide

<400> SEQUENCE: 667
tttttatttt attttttatt tttaa 25

<210> SEQ ID NO 668
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 668
atacctccct aattatatta ttaa 24

<210> SEQ ID NO 669
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 669
ttttagaata tttaaagaag ttagt 25

<210> SEQ ID NO 670
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 670
taacctcact ttcctatca 19

<210> SEQ ID NO 671
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 671
aatttagtat aagatttgat ttgtta 26

<210> SEQ ID NO 672
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 672
ccacctactc cttcctatac 20

<210> SEQ ID NO 673
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 673
ttttttgaaa ttgtatgtta t 21

<210> SEQ ID NO 674
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 674
caaatcctta aaattctata a 21

<210> SEQ ID NO 675
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 675
tttgaagtgg tgttttag 18

<210> SEQ ID NO 676
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 676
ccaaaattct tccatact 18

<210> SEQ ID NO 677
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 677
tgggtattta gttttttgtg 20

<210> SEQ ID NO 678
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 678
aacaactacc tccttttact aat 23

<210> SEQ ID NO 679
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 679
tatggtagga ggtggagtt 19

<210> SEQ ID NO 680
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 680
cccaatttta aaacaatac 19

<210> SEQ ID NO 681
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 681
agaggaagta aggttattag tt 22

<210> SEQ ID NO 682
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 682
accaaacaaa caatatctaa 20

<210> SEQ ID NO 683
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 683
ggttttaatt atgatttaat taga 24

<210> SEQ ID NO 684
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 684
cctacactca aatttacctc ta 22

<210> SEQ ID NO 685
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 685
aatgggtagt tgatataatt att 23

<210> SEQ ID NO 686
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 686
cacaaaatcc taaaactaaa a 21

<210> SEQ ID NO 687
<211> LENGTH: 22

<212> TYPE: DNA
<213> ORGANISM: Artificial Sequence
<220> FEATURE:
<223> OTHER INFORMATION: Synthetic polynucleotide

<400> SEQUENCE: 687
aggattagtg gaaatgaaaa ta 22

<210> SEQ ID NO 688
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 688
taacctcaaa acaacttcta aac 23

<210> SEQ ID NO 689
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 689 tttttttat agagaagtat tttag 25

<210> SEQ ID NO 690
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 690
cccattacaa aactatcc 18

<210> SEQ ID NO 691
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 691
ggtgagtttg tggttagtg 19

<210> SEQ ID NO 692
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 692
ttttctaaaa aaatccaatc ta 22

<210> SEQ ID NO 693
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 693
aatggatagg ttggaatag 19

<210> SEQ ID NO 694
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 694
aaaaaaaaaa aaaaactaat tac 23

<210> SEQ ID NO 695
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 695
gagttattta gtttggttag gt 22

<210> SEQ ID NO 696
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 696
actcaactta aaaaatcact atac 24

<210> SEQ ID NO 697
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 697
ttttttttgg ttttttggtt tt 22

<210> SEQ ID NO 698
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 698
tcccccacac ccatataa 18

<210> SEQ ID NO 699
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 699
ttaaaaaaaa gtataatgag tagga 25

<210> SEQ ID NO 700
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 700
cccacaaaaa ctctctaca 19

<210> SEQ ID NO 701
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 701
aaaggaggtt gagttagaaa gtag 24

<210> SEQ ID NO 702
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 702
aactatttaa cttacttaac cacacc 26

<210> SEQ ID NO 703
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 703
ggtgtggtta agtaagttaa atagt 25

<210> SEQ ID NO 704
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 704
taccccttcc tcttcaac 18

<210> SEQ ID NO 705
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 705
ttttgatatg atttatgatt atat 24

<210> SEQ ID NO 706
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 706
ttttccacta aacaacacta 20

<210> SEQ ID NO 707
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 707
tttgagggtt gttttagat 19

<210> SEQ ID NO 708
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 708
actcacaaaa aataactaat aactat 26

<210> SEQ ID NO 709
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 709
aaaggaggta ggggagatat a 21

<210> SEQ ID NO 710
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 710
tcaaaataaa aaccaaaatt ctc 23

<210> SEQ ID NO 711
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 711
aggttaagtt ggtagaggta ga 22

<210> SEQ ID NO 712
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 712
caaactctaa actcaaaata tattc 25

<210> SEQ ID NO 713
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 713
tttttatttt agtttttga gtag 24

<210> SEQ ID NO 714
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 714
ccctacaaca ctcctatcta 20

<210> SEQ ID NO 715
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 715
tttggagtta ggttgatag 19

<210> SEQ ID NO 716
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 716
caacaatact ctcacttaca c 21

<210> SEQ ID NO 717
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 717
agaaagattt ttaaatattt ttaat 25

<210> SEQ ID NO 718
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 718
aaacctctaa tacacaacaa a 21

<210> SEQ ID NO 719
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 719
ttttgagttt tttttttaag tat 23

<210> SEQ ID NO 720

```
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 720

caaacaaaac aacacttaat ac                                              22

<210> SEQ ID NO 721
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 721

ggttgaggtg ggtggatta                                                  19

<210> SEQ ID NO 722
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 722

tttttttttt ttttttttaa aataaaatct                                      30

<210> SEQ ID NO 723
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 723

gggtgtttgt aattttagtt                                                 20

<210> SEQ ID NO 724
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 724

acctttaaca acctaacaat ata                                             23

<210> SEQ ID NO 725
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 725

gggtagatga tatggtagtg a                                               21

<210> SEQ ID NO 726
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 726
```

aaaaaataaa aaataactaa aacaatat 28

<210> SEQ ID NO 727
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 727
aggaagtgtt taagaagtag aa 22

<210> SEQ ID NO 728
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 728
cctaaaactc taaatacaat ctc 23

<210> SEQ ID NO 729
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 729
tttttaattt ttgtttgtat t 21

<210> SEQ ID NO 730
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 730
aaaccacaat ctatttctaa 20

<210> SEQ ID NO 731
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 731
ttagaaaaga ataattatag ttg 23

<210> SEQ ID NO 732
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 732
accctaaaaa aataaaatc 19

<210> SEQ ID NO 733
<211> LENGTH: 26
<212> TYPE: DNA

<213> ORGANISM: Artificial Sequence
<220> FEATURE:
<223> OTHER INFORMATION: Synthetic polynucleotide

<400> SEQUENCE: 733
ttgtattagt aaataaagtg tatttt 26

<210> SEQ ID NO 734
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 734
aaccctttct acaaatctac 20

<210> SEQ ID NO 735
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 735
aggggtgggt ggaagaat 18

<210> SEQ ID NO 736
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 736
ctcctcaata aaataaaaat cctaaaaaat a 31

<210> SEQ ID NO 737
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 737
gggttaatta gttgttttat 20

<210> SEQ ID NO 738
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 738
cctacaaata tatcacacac t 21

<210> SEQ ID NO 739
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 739
tttgttaaat aggtggttag a 21

<210> SEQ ID NO 740
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 740
acctcaacct cctaaataac 20

<210> SEQ ID NO 741
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 741
tagggtttag agtaggaggt ag 22

<210> SEQ ID NO 742
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 742
caaaaaatat aaatcaaaaa catc 24

<210> SEQ ID NO 743
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 743
gggattatag gtatttatta t 21

<210> SEQ ID NO 744
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 744
taaaaattaa aaatcatact ta 22

<210> SEQ ID NO 745
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 745
aagtgatttt tagggagtgt 20

<210> SEQ ID NO 746
<211> LENGTH: 23
<212> TYPE: DNA
<213> ORGANISM: Artificial Sequence
<220> FEATURE:

<223> OTHER INFORMATION: Synthetic polynucleotide

<400> SEQUENCE: 746
tccataataa cctcatttta ata 23

<210> SEQ ID NO 747
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 747
tttttggttg aggtttagt 19

<210> SEQ ID NO 748
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 748
aaacaacaca actcttatca c 21

<210> SEQ ID NO 749
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 749
tatggtgatt aaagtataat agtt 24

<210> SEQ ID NO 750
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 750
tcctaaataa aaaacaacat a 21

<210> SEQ ID NO 751
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 751
tgaaaatgtt tttagttttt att 23

<210> SEQ ID NO 752
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 752
aaatacccta cctcttatct aa 22

<210> SEQ ID NO 753
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 753
gatggttaat ttttttattt 20

<210> SEQ ID NO 754
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 754
actccttcaa caaactaac 19

<210> SEQ ID NO 755
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 755
aggggatatt tttaggtt 18

<210> SEQ ID NO 756
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 756
ccaatctatt cctatataat taa 23

<210> SEQ ID NO 757
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 757
aggagagttt ggaaatatag 20

<210> SEQ ID NO 758
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 758
caattctaaa ttaaacctta tt 22

<210> SEQ ID NO 759
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 759
aataatggta gtagttttat tag 23

<210> SEQ ID NO 760
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 760
ttcctatatt aacaacttac a 21

<210> SEQ ID NO 761
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 761
ttttttggta gatttttat 19

<210> SEQ ID NO 762
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 762
aaattaattt ctattattta tatta 25

<210> SEQ ID NO 763
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 763
aggtggttgg ggagagtg 18

<210> SEQ ID NO 764
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 764
ccctaaaata aatcaaaaaa aaccttaa 28

<210> SEQ ID NO 765
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 765
aggtttaggt ggggtgaat 19

<210> SEQ ID NO 766
<211> LENGTH: 24

<212> TYPE: DNA
<213> ORGANISM: Artificial Sequence
<220> FEATURE:
<223> OTHER INFORMATION: Synthetic polynucleotide

<400> SEQUENCE: 766
taaaatcatc aaaatccctt aaaa 24

<210> SEQ ID NO 767
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 767
ttttttttta ggttatagga gtatt 25

<210> SEQ ID NO 768
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 768
atccccacaa aacacata 18

<210> SEQ ID NO 769
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 769
tagggtaaat attgggatta tt 22

<210> SEQ ID NO 770
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 770
tttccacctc aaaacttaac 20

<210> SEQ ID NO 771
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 771
gggtgtttgt atttttatat t 21

<210> SEQ ID NO 772
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 772
acctcccaaa accataac 18

<210> SEQ ID NO 773
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 773
gatgtgagtg gtgaggtggt 20

<210> SEQ ID NO 774
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 774
caaacccttc caaaacataa ac 22

<210> SEQ ID NO 775
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 775
tgggattata ggtatgtatt 20

<210> SEQ ID NO 776
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 776
caatttcatt tataaatata aatat 25

<210> SEQ ID NO 777
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 777
aggggttggt tatttttatt tt 22

<210> SEQ ID NO 778
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 778
tttttaatat ttaattttta ccttcaact 29

<210> SEQ ID NO 779
<211> LENGTH: 20
<212> TYPE: DNA
<213> ORGANISM: Artificial Sequence -continued

```
<220> FEATURE:
<223> OTHER INFORMATION: Synthetic polynucleotide

<400> SEQUENCE: 779

ggtaagttgt ggatgtgagt                                                20


<210> SEQ ID NO 780
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 780

aaaaaaaacc aaaccttatc ta                                             22


<210> SEQ ID NO 781
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 781

tttttaggat ttgggttag                                                 19


<210> SEQ ID NO 782
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 782

aaccttataa ataacaacaa aac                                            23
```

METHODS, TREATMENT, AND COMPOSITIONS FOR CHARACTERIZING THYROID NODULE

RELATED APPLICATION

This application claims the benefit of priority under 35 U.S.C. § 119(e) to U.S. Provisional Application No. 62/196,678, filed Jul. 24, 2015, the content of which is incorporated herein by reference in its entirety.

INCORPORATION-BY-REFERENCE OF SEQUENCE LISTING

The content of the text file named “48440-573001 US_ST25.TXT”, which was created on Jul. 22, 2016, and is 328.827 bytes in size, is hereby incorporated by reference in its entirety.

BACKGROUND OF THE DISCLOSURE

Palpable thyroid nodules are typically detected in 2-6% of the population, and this increases to 19-35% with ultrasound detection (Dean D S and Gharib H. Best Pract Res Clin Endocrinol Metab 2008; 22:901-11). Approximately 5-15% of thyroid nodules are found to be thyroid cancer, making the existence of a nodule clinically relevant. Fine needle aspiration (FNA) with cytology is currently the standard diagnostic procedure used to evaluate thyroid nodules. However, in as many as 30% of cases, the cytological diagnosis is indeterminate because of cytological features that overlap between benign and malignant nodules. For most indeterminate cases half or the entire thyroid is resected, yet as many as 80% of these cases are found to be benign.

Most thyroid nodules do not cause symptoms. Often, thyroid nodules are discovered incidentally during a routine physical examination or on imaging tests like CT scans or neck ultrasound done for completely unrelated reasons. Occasionally, patients themselves find thyroid nodules by noticing a lump in their neck while looking in a mirror, buttoning their collar, or fastening a necklace. Abnormal thyroid function tests may occasionally be the reason a thyroid nodule is found. Thyroid nodules may produce excess amounts of thyroid hormone causing hyperthyroidism. However, most thyroid nodules, including those that cancerous, are actually non-functioning, meaning current diagnostic test readouts such as the level of Thyroid-Stimulating Hormone (TSH) are normal. Rarely, patients with thyroid nodules may complain of pain in the neck, jaw, or ear. If a nodule is large enough to compress the windpipe or esophagus, it may cause difficulty with breathing, swallowing, or cause a “tickle in the throat”. Even less commonly, hoarseness can be caused if the nodule invades the nerve that controls the vocal cords but this is usually related to thyroid cancer.

Molecular testing is a potential alternative to cytopathological examination. However, FNA molecular testing based on DNA mutations frequently fails. There are two major reasons for this failure: (i) not all papillary thyroid carcinoma (PTC) specimens are characterized by a common set of cancer associated mutations, and (ii) cancer associated mutations like KRAS are frequently found in benign thyroid nodule (BTN) specimens. At the same time commercial diagnostic tests for FNA based on transcriptional activity and currently implemented in clinical practice is complicated due to RNA instability and associated with only an approximately 50% positive predictive value. Thus, there is an urgent need for highly sensitive, low cost biomarker panels that can accurately diagnose thyroid nodules from FNA biopsies.

BRIEF SUMMARY OF THE DISCLOSURE

The present subject matter provides, inter alia, a method of determining benign nodules from thyroid cancer in a subject that is found to have a thyroid nodule, a method of treating thyroid cancer in a subject detected to have thyroid cancer, compositions for determining benign nodules from thyroid cancer in a subject, and kits including reagents and compositions for determining benign nodules from thyroid cancer in a subject.

In embodiments, aspects of the present subject matter provide a method of detecting methylation or unmethylation of a thyroid nodule DNA of a subject, the method including: (i) isolating DNA from a thyroid nodule of the subject thereby forming isolated thyroid nodule DNA, (ii) contacting the isolated thyroid nodule DNA with a bisulfite salt (such as sodium bisulfite) thereby forming a reacted thyroid nodule DNA, (iii) detecting the presence or absence of uracil in the reacted thyroid nodule DNA at a methylation site set forth in Table 1, thereby detecting methylation or unmethylation of the thyroid nodule DNA of the subject.

Also provided is a method of determining a thyroid cancer or risk of developing thyroid cancer in a subject in need thereof. The method includes isolating DNA from a thyroid nodule of the subject thereby forming isolated thyroid nodule DNA. The isolated thyroid nodule DNA is contacted with sodium bisulfite thereby forming a reacted thyroid nodule DNA. The presence or absence of uracil is detected in the reacted thyroid nodule DNA at a methylation site set forth in Table 1 thereby determining thyroid cancer in the subject.

In embodiments, provided herein is a method of treating thyroid cancer in a subject by administering to the subject an active agent for treating thyroid cancer. The method includes identifying the subject for treatment by a method including isolating DNA from a thyroid nodule of the subject thereby forming isolated thyroid nodule DNA. The isolated thyroid nodule DNA is contacted with sodium bisulfite thereby forming a reacted thyroid nodule DNA. The presence or absence of uracil in the reacted thyroid nodule DNA is detected at a methylation site set forth in Table 1 thereby determining thyroid cancer in the subject.

Also included herein is a deoxyribonucleic acid 5 to 100, 5 to 200, 5 to 300, or at least about 5, 50, 100, 150, 200, 250, 300, or more nucleotides in length including a uracil-containing sequence identical to at least a 5 contiguous nucleotides within a sequence including SEQ ID NO: 1 to SEQ ID NO:550.

In embodiments, provided herein is an oligonucleotide 5 to 100, 5 to 200, 5 to 300, or at least about 5, 50, 100, 150, 200, 250, 300, or more nucleotides in length including identical or complementary to at least 5, 10, 20, 25, 50, 100, 150, 200, 250, or 300 contiguous nucleotides within a sequence including SEQ ID NO: 1 to SEQ ID NO:550.

Aspects of the present subject matter also include a deoxyribonucleic acid including SEQ ID NO: 551 to SEQ ID NO: 782, in which the nucleic acid is hybridized to a complementary DNA sequence having uridine or cytosine.

Also provided is a kit including a plurality (e.g., at least about 10, 20, 40, 50, 100, 150, 200, 225, or 232) nucleic acids each independently comprising SEQ ID NO: 551 to SEQ ID NO: 782, in which the nucleic acids do not simultaneously include the same sequence of SEQ ID NO: 551 to SEQ ID NO: 782.

Aspects of the present subject matter also provide a system for detecting methylation or unmethylation of a thyroid nodule deoxyribonucleic acid (DNA) of a subject. The system can include at least one processor; and at least one memory including program code which when executed by the at least one memory provides operations. The operations can include: isolating DNA from a thyroid nodule of the subject thereby forming isolated thyroid nodule DNA; contacting the isolated thyroid nodule DNA with bisulfite salt thereby forming a reacted thyroid nodule DNA; detecting a presence or absence of uracil in the reacted thyroid nodule DNA at a plurality of methylation sites set forth in Table 1, thereby detecting methylation or unmethylation of the thyroid nodule DNA of the subject; and generating a diagnosis for the subject based at least in part on the presence or absence of uracil in the reacted thyroid nodule DNA at the plurality of methylation sites set forth in Table 1; and providing, via a user interface, the diagnosis for the subject.

BRIEF DESCRIPTION OF THE DRAWINGS

FIG. 1A: Adenoma specific hypomethylation signature. FIG. 1B: Adenoma specific hypermethylation signature.

FIG. 2B: 364 CpG sites associated with benign- and thyroid cancer-specific DNA methylation changes. Each row represents a single cytosine. Each column represents tissue specimen. Dark gray, light gray and black indicate high, low and medium levels of DNA methylation, respectively. Abbreviation "A" is for thyroid benign nodule and "T" is for thyroid cancer.

FIG. 3A: Thyroid cancer diganostics based on benign DNA methylation signature, cancer DNA methylation signature and cancer risk scores. FIG. 3B: DNA methylation signatures for malignant and benign thyroid nodules according to leave one-out-cross-validation technique. Specimens with indeterminate epigenetic signature are underlined. Abbreviation "A" is for thyroid benign nodule and "T" is for thyroid cancer. FIG. 3C: Algorithm for the diagnosis prediction based on BTN. PTC and cancer risk scores.

DETAILED DESCRIPTION OF THE DISCLOSURE

Figure 1B:
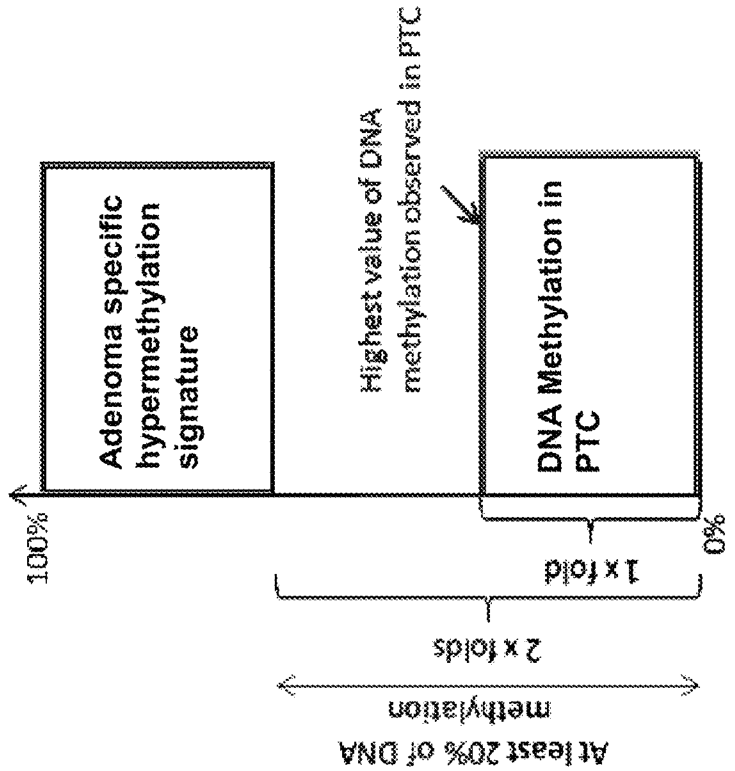
FIGS. 1A-1B show a drawing defining a threshold for thyroid adenoma specific signature for individual cytosine regions.

Provided herein are, inter alia, compositions, methods, kits, and systems for detecting unmethylated DNA. In embodiments, compositions, methods, kits, and systems for detecting unmethylated DNA from thyroid nodule are included herein.

The following definitions are included for the purpose of understanding the present subject matter and for constructing the appended patent claims. Abbreviations used herein have their conventional meaning within the chemical and biological arts.

Definitions

The term "thyroid nodule" is used according to its plain ordinary meaning and refers to an abnormal growth of thyroid cells. The abnormal growth may form, for example, a mass or lump within or on the thyroid gland. The mass or lump may be fluid-filled or solid. The thyroid nodules may be benign (noncancerous) or cancerous.

Thyroid fine needle aspiration biopsy (FNA or FNAB): For a fine needle biopsy, a needle is used to withdraw cells from a thyroid nodule. In embodiments, several samples are taken from different parts of the nodule, e.g., to increase the chance of finding cancerous cells if they are present. In embodiments, a sample is taken from one part of the nodule. In embodiments, examination of the cells under a microscope is not necessary. In non-limiting examples, the needle used for FNA is a 20-35 gauge needle (such as a 23, 24 or 25 gauge needle).

The term "disease" refers to any deviation from the normal health of a mammal and includes a state when disease symptoms are present, as well as conditions in which a deviation (e.g., infection, gene mutation, genetic defect, etc.) has occurred, but symptoms are not yet manifested. According to the present disclosure, the methods disclosed herein are suitable for use in a patient that is a member of the Vertebrate class. Mammalia, including, without limitation, primates, livestock and domestic pets (e.g., a companion animal). Typically, a patient will be a human patient. As used herein, a "symptom" of a disease includes and clinical or laboratory manifestation associated with the disease, and is not limited to what a subject can feel or observe.

The terms "subject," "patient," "individual," and the like as used herein are not intended to be limiting and can be generally interchanged. That is, an individual described as a "patient" does not necessarily have a given disease, but may be merely seeking medical advice.

The term "subject" as used herein includes all members of the animal kingdom that may suffer from the indicated disorder. In some aspects, the subject is a mammal, and in some aspects, the subject is a human.

It must be noted that as used herein and in the appended embodiments, the singular forms "a," "an," and "the" include the plural reference unless the context clearly dictates otherwise. Thus, for example, a reference to "a disease," "a disease state", "a nucleic acid" or "a CpG site" is a reference to one or more such embodiments, and includes equivalents thereof known to those skilled in the art and so forth.

Throughout the description and claims of this specification the word "comprise" and other forms of the word, such as "comprising" and "comprises." means including but not limited to, and is not intended to exclude, for example, other components.

A "control" sample or value refers to a sample that serves as a reference, usually a known reference, for comparison to a test sample. For example, a test sample can be taken from a patient suspected or at risk of having thyroid cancer and compared to samples from a known thyroid cancer patient, or a known normal (non-disease) individual. A control can also represent an average value gathered from a population of similar individuals, e.g., thyroid cancer patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters.

One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The term "diagnosis" refers to a relative probability that a disease is present in the subject. Similarly, the term "prognosis" refers to a relative probability that a certain future outcome may occur in the subject. For example, in the context of the present disclosure, prognosis can refer to the likelihood that an individual will develop a disease, or the likely severity of the disease (e.g., severity of symptoms, rate of functional decline, survival, etc.). The terms are not intended to be absolute, as will be appreciated by any one of skill in the field of medical diagnostics.

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids, including ribonucleic acids (RNA) and deoxyribonucleic acids (DNA), and polynucleotides are a polymers of any length, including longer lengths. e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580. *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

The term "bp" and the like refer, in the usual and customary sense, to the indicated number of base pairs.

The terms "identical" or percent "identity," in the context of two or more nucleic acids (e.g., genomic sequences or subsequences or coding sequences) or polypeptide sequences, refer to two or more sequences or subsequences that are the same or have a specified percentage of amino acid residues or nucleotides that are the same (i.e., 50%, 55%, 60%, 65%, 70%, 75%, 80%, 85%, 90%, 91%, 92%, 93%, 94%, 95%, 96%, 97%, 98%, 99%, or more identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 10 to about 100, about 20 to about 75, about 30 to about 50 amino acids or nucleotides in length.

An example of algorithms suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. As will be appreciated by one of skill in the art, the software for performing BLAST analyses is publicly available through the website of the National Center for Biotechnology Information.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, Bioconjugate Techniques 1996, Academic Press, Inc., San Diego.

The term "associated" or "associated with" in the context of a substance (e.g., level of uracil or methylation level in a thyroid nodule) does not necessarily mean that the disease is caused by (in whole or in part), or a symptom of the disease is caused by (in whole or in part) the substance or substance activity or function (i.e., level of uracil in the regions of chromosomes assayed).

The term "unmethylated DNA" or "demethylated DNA" means DNA that lacks a methyl group conjugated to cytosine in a segment of the DNA. DNA methylation typically occurs in a CpG dinucleotide context. DNA methylation at the 5' position of cytosine may have the specific effect on gene expression in vivo. DNA methylation may also form the basis of epigenetic structure, which typically enables a single cell to grow into multiple organs or perform multiple functions.

The CpG sites or CG sites are regions of DNA where a cytosine nucleotide occurs next to a guanine nucleotide in the linear sequence of bases along its length. "CpG" is shorthand for "-C-phosphate-G-", that is, cytosine and guanine separated by only one phosphate; phosphate links any two nucleosides together in DNA. The "CpG" notation is used to distinguish this linear sequence from the CG base-pairing of cytosine and guanine. The CpG notation can also be interpreted as the cytosine being 5' prime to the guanine base.

In embodiments, methylation is detected based on a chemical reaction of sodium bisulfite with DNA that converts unmethylated cytosines of CpG dinucleotides to uracil or UpG. However, methylated cytosine is not converted in this process, the methods described herein allow determination of methylation status as methylated or unmethylated.

Evaluation of Thyroid Fine Needle Biopsies by Visual Examination

Cells in a thyroid vine needle biopsy sample may be examined under a microscope by, e.g., a pathologist. The report of a thyroid fine needle biopsy followed by examination under a microscope will usually indicate one of the following findings:

1. The nodule is benign (noncancerous). This result is obtained in up to 80% of biopsies. The risk of overlooking a cancer when the biopsy is benign is generally less than 3 in 100 tests or 3%. This is even lower when the biopsy is reviewed by an experienced pathologist at a major medical center. Generally, benign thyroid nodules do not need to be removed unless they are causing symptoms like choking or difficulty swallowing. Follow up ultrasound exams are important. Occasionally, another biopsy may be required in the future, especially if the nodule grows over time.

2. The nodule is malignant (cancerous) or suspicious for malignancy. A malignant result is obtained in about 5% of biopsies and is most often due to papillary cancer, which is the most common type of thyroid cancer. A malignant diagnosis has a >99% risk of cancer in the nodule. A suspicious biopsy has a 50-75% risk of cancer in the nodule. These diagnoses require surgical removal of the thyroid after consultation with the endocrinologist and surgeon.

3. The nodule is indeterminate. This is actually a group of several diagnoses that may occur in up to 30% of cases. An indeterminate finding means that even though an adequate number of cells was removed during the fine needle biopsy, examination with a microscope cannot reliably classify the result as benign or cancer. The biopsy may be indeterminate because the nodule is described as a Follicular Lesion. These nodules are cancerous 20-30% of the time. However, under the current state of the art, the diagnosis can only be made by surgery. Because the odds that the nodule is not a cancer are much better by surgery (70-80%), only the side of the thyroid with the nodule is usually removed. If a cancer is found, the remaining thyroid gland is usually removed as well. If the surgery confirms that no cancer is present, no additional surgery to "complete" the thyroidectomy is necessary.

The biopsy may also be indeterminate because the cells from the nodule have features that cannot be placed in one of the other diagnostic categories. This diagnosis is called atypia, or a follicular lesion of undetermined significance. Diagnoses in this category will contain cancer rarely, so repeat evaluation with FNA or surgical biopsy to remove half of the thyroid containing the nodule is usually recommended.

4. The biopsy may also be non-diagnostic or inadequate. This result indicates that not enough cells were obtained to make a diagnosis but is a common result if the nodule is a cyst. These nodules may require reevaluation with second fine needle biopsy, or may need to be removed surgically depending on the clinical judgment of the doctor.

Methods, compositions, kits, and systems provided herein provide significant advantages over the visual examination of biopsies.

Method of Detection Methylation Status of a Thyroid Nodule DNA

In an aspect, provided herein is a method of detecting methylation or unmethylation of a thyroid nodule DNA of a subject. The method includes: (i) isolating a thyroid nodule DNA molecule from a thyroid nodule of the subject thereby forming an isolated thyroid nodule DNA molecule, (ii) contacting the isolated thyroid nodule DNA molecule with a bisulfite salt (such as sodium bisulfite) thereby forming a reacted thyroid nodule DNA molecule, (iii) detecting the presence or absence of uracil in the reacted thyroid nodule DNA molecule at a methylation site set forth in Table 1, thereby detecting methylation or unmethylation of the thyroid nodule DNA molecule of the subject. In embodiments, contacting the isolated thyroid nodule DNA with a bisulfite salt comprises adding a solution comprising the bisulfite salt to a solution comprising the isolated single stranded DNA.

In an aspect, provided herein is a method of detecting methylation or unmethylation of a thyroid nodule DNA molecule of a subject comprising (i) isolating a plurality of thyroid nodule DNA molecules from the thyroid nodule of the subject thereby forming a plurality of isolated thyroid nodule DNA molecules, (ii) contacting the plurality of isolated thyroid nodule DNA molecules with the bisulfite salt thereby forming a plurality of reacted thyroid nodule DNA molecules, (iii) detecting the level of reacted thyroid nodule DNA molecules in the plurality of reacted thyroid nodule DNA molecules having a uracil at a methylation site set forth in Table 1, thereby detecting the level of methylation or unmethylation in the plurality of thyroid nodule DNA molecules of the subject.

In an aspect, provided herein is a method of detecting methylation or unmethylation of a thyroid nodule DNA molecule of a subject comprising (i) isolating a plurality of thyroid nodule DNA molecules from the thyroid nodule of the subject thereby forming a plurality of isolated thyroid nodule DNA molecules, (ii) contacting the plurality of isolated thyroid nodule DNA molecules with the bisulfite salt thereby forming a plurality of reacted thyroid nodule DNA molecules, (iii) detecting the presence or absence of uracil in a reacted thyroid nodule DNA molecule at a methylation site set forth in Table 1, thereby detecting methylation or unmethylation of the thyroid nodule DNA molecule of the subject.

In an aspect, provided herein is a method of detecting methylation or unmethylation of a thyroid nodule DNA of a subject. The method includes: (i) isolating a thyroid nodule DNA molecule from a thyroid nodule of the subject thereby forming an isolated thyroid nodule DNA molecule, (ii) contacting the isolated thyroid nodule DNA molecule with a bisulfite salt (such as sodium bisulfite) thereby forming a reacted thyroid nodule DNA molecule, (iii) amplifying the reacted thyroid nodule DNA molecule thereby forming a reacted thyroid nodule DNA amplicon molecule, (iv) detecting the presence or absence of thymidine in a reacted thyroid nodule DNA amplicon molecule at a methylation site set forth in Table 1, thereby detecting methylation or unmethylation of the thyroid nodule DNA molecule of the subject. In embodiments, contacting the isolated thyroid nodule DNA with a bisulfite salt comprises adding a solution comprising the bisulfite salt to a solution comprising the isolated single stranded DNA.

In an aspect, provided herein is a method of detecting methylation or unmethylation of a thyroid nodule DNA molecule of a subject comprising (i) isolating a plurality of thyroid nodule DNA molecules from the thyroid nodule of the subject thereby forming a plurality of isolated thyroid nodule DNA molecules, (ii) contacting the plurality of isolated thyroid nodule DNA molecules with the bisulfite salt thereby forming a plurality of reacted thyroid nodule DNA molecules, (iii) amplifying the plurality of reacted thyroid nodule DNA molecules thereby forming a plurality of reacted thyroid nodule DNA amplicon molecules, (iv) detecting one or more thyroid nodule DNA amplicon molecules within the plurality of reacted thyroid nodule DNA amplicon molecules having a thymidine at a methylation site set forth in Table 1, thereby detecting methylation or unmethylation of the thyroid nodule DNA molecule of the subject.

In embodiments, detecting one or more thyroid nodule DNA amplicon molecules comprises detecting the level of one or more one or more thyroid nodule DNA amplicon molecules. In embodiments, detecting one or more thyroid nodule DNA amplicon molecules comprises detecting the level of reacted thyroid nodule DNA amplicon molecules in the plurality of reacted thyroid nodule DNA amplicon molecules having a thymidine at a methylation site set forth in Table 1, thereby detecting the level of methylation or unmethylation in the plurality of thyroid nodule DNA molecules of the subject.

In embodiments, detecting a level includes determining the number (e.g. quantitating) or molecules having, e.g., a thymidine or a uracil. In embodiments, detecting a level includes detecting the portion or proportion of a population or plurality of molecules having, e.g., a thymidine or a uracil.

In embodiments, the isolated thyroid nodule DNA sample is treated with a bisulfite reagent, e.g., a bisulfite salt (i.e., a process called DNA bisulfite conversion). Non-limiting examples of bisulfite salts include sodium bisulfite, potassium bisulfite, ammonium bisulfite, magnesium bisulfite, sodium metabisulfite, potassium metabisulfite, ammonium metabisulfite and magnesium metabisulfite. Bisulfite salts such as sodium bisulfite or ammonium bisulfite can convert cytosine to uracil and leave 5-methylcytosine (5-mC) the same. Thus after bisulfite treatment methylated cytosine in the DNA remains the same and unmodified cytosines will be changed to uracil. The bisulfite treatment can be performed by using the methods disclosed herein or in the art, and/or with commercial kits such as the Bisulflash DNA Modification Kit (Epigentek) and Imprint DNA Modification Kit (Sigma). For achieving the optimal bisulfite conversion, the bisulfite reaction should be carried out in an appropriate concentration of bisulfite reagents, appropriate temperature and appropriate reaction time period. A reagent such as potassium chloride that reduces thermophilic DNA degradation could also be used in bisulfite treatment so that the DNA bisulfite process can be much shorter without interrupting a completed conversion of unmethylated cytosine to uracil and without a significant thermodegradation of DNA resulted from depurination. In embodiments, a commercially available bisulfite treatment kit is used. A non-limiting example of such a kit is EZ DNA Methylation-Gold™ Kit (Zymo Research. Irvine, Calif., USA).

In embodiments, once DNA bisulfite conversion is complete, DNA is captured, desulphonated and washed. In embodiments, the bisulfite-treated DNA can be captured by, e.g., a solid matrix selected from silica salt, silica dioxide, silica polymers, magnetic beads, glass fiber, celite diatoms and nitrocellulose in the presence of high concentrations of chaotropic or non-chaotropic salts. In embodiments, the bisulfite-treated DNA is further desulphonated with an alkalized solution, preferably sodium hydroxide at concentrations from 10 mM to 300 mM. In embodiments, the DNA is then eluted and collected into a capped microcentrifuge tube. Non-limiting examples of elution solutions include DEPC-treated water and TE buffer (10 mM Tris-HCL, pH 8.0, and 1 mM EDTA).

In embodiments, the reacted thyroid nodule DNA resulting from bisulfite treatment is amplified. In embodiments, detecting the presence or absence of uracil in reacted thyroid nodule DNA molecule at a methylation site comprises amplifying the reacted thyroid nodule DNA molecule thereby forming a reacted thyroid nodule DNA amplicon molecule, and detecting the presence or absence of thymidine in a reacted thyroid nodule DNA amplicon molecule at the methylation site. In embodiments, a polymerase chain reaction (PCR) method is used for amplifying the reacted thyroid nodule DNA. PCR methods are known to those of ordinary skill in the art. In general, the PCR reactions can be set up by adding sample, dNTPs, and appropriate polymerase such as Taq polymerase, primers, and a buffer.

In embodiments, the method of detecting methylation or unmethylation of a thyroid nodule DNA of a subject, includes detecting methylation or unmethylation at a plurality of methylation sites set forth in Table 1. In embodiments, the plurality of methylation sites comprises at least about 2, 3, 4, 5, 10, 25, 50, 75, 80, 85, 90, 100, 150, 200, 250, 300, 350, 400, 450, 500, or 550, or 5-550 methylation sites. In embodiments, the plurality of methylation sites comprises less than about 550, 500, 450, 400, 350, 300, 250, 200, 150, 100, 90, 85, 80, 75, 50, 25, or 10 methylation sites. In embodiments, the plurality of methylation sites is about 5, 6, 7, 8, 9, 10, 11, 12, 13, 14, 15, 16, 17, 18, 19, 20, 25, 50.75, 80, 85.90, 100, 150, 200.250, 300.350, 400, 450, 500, or 550, or 5-550 methylation sites. In embodiments, the plurality of methylation sites includes two or more methylation sites set forth in Table 1 and no other methylation sites.

In embodiments, the method includes detecting methylation or unmethylation of at least 1, 2, 3, 4, 5, 6, 7, 8, 9, 10, 50, 100, 200, 300, 400, or 500 of the following sites: Chromosome 1 (Chr1) position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chromosome 2 (Chr2) position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chromosome 3 (Chr3) position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chromosome 4 (Chr4) position 3743223, Chr4 position 5755716, Chr4 position 5755717, Chr4 position 5755728, Chr4 position 5755729, Chr4 position 5755734, Chr4 position 8372861, Chr4 position 57548289, Chromosome 5 (Chr5) position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chromosome 6 (Chr6) position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chromosome 7 (Chr7) position 989235, Chr7 position 2673543, Chr7 position 73508602, Chr7 position 105079565, Chr7 position 105079631, Chr7 position 151425103, Chr7 position 151425104, Chromosome 8 (Chr8) position 11764017, Chr8 position 21647308, Chr8 position 22548399, Chr8 position 22548483, Chr8 position 133570537, Chr8 position 141320393, Chr8 position 141320410, Chromosome 9 (Chr9) position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chromosome 10 (Chr10) position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chromosome 11 (Chr11) position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chromosome 12 (Chr12) position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chromosome 13 (Chr13) position 20735797, Chr13 position 23500419, Chr13 position 46771519, Chr13 position 46771520, Chr13 position 53313426, Chr13 position 113807393, Chromosome 14 (Chr14) position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chromosome 15 (Chr15) position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chromosome 16 (Chr16) position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chromosome 17 (Chr17) position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chromosome 18 (Chr18) position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chromosome 19 (Chr19) position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chromosome 20 (Chr20) position 34206950, Chr20 position 36771969, Chr20 position 48993661, Chr20 position 58406398, Chr20 position 61976049, Chr20 position 61976073, Chr20 position 62588571, Chr20 position 62588579, Chromosome 22 (Chr22) position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, the method includes detecting methylation or unmethylation of at least 1 of the following sites: Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr6 position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chr16 position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 34206950, Chr20 position 36771969, Chr20 position 48993661, Chr20 position 58406398, Chr20 position 61976049, Chr20 position 61976073, Chr20 position 62588571, Chr20 position 62588579, Chr22 position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, the method includes detecting methylation or unmethylation of at least 2 of the following sites: Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr6 position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chr16 position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 34206950, Chr20 position 36771969, Chr20 position 48993661, Chr20 position 58406398, Chr20 position 61976049, Chr20 position 61976073, Chr20 position 62588571, Chr20 position 62588579, Chr22 position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, the method includes detecting methylation or unmethylation of at least 3 of the following sites: Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr6 position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chr16 position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 34206950, Chr20 position 36771969, Chr20 position 48993661, Chr20 position 58406398, Chr20 position 61976049, Chr20 position 61976073, Chr20 position 62588571, Chr20 position 62588579, Chr22 position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, the method includes detecting methylation or unmethylation of at least 4 of the following sites: Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr6 position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chr16 position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 34206950, Chr20 position 36771969, Chr20 position 48993661, Chr20 position 58406398, Chr20 position 61976049, Chr20 position 61976073, Chr20 position 62588571, Chr20 position 62588579, Chr22 position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, the method includes detecting methylation or unmethylation of at least 5 of the following sites: Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr6 position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chr16 position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 34206950, Chr20 position 36771969, Chr20 position 48993661, Chr20 position 58406398, Chr20 position 61976049, Chr20 position 61976073, Chr20 position 62588571, Chr20 position 62588579, Chr22 position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, the method includes detecting methylation or unmethylation of at least 6 of the following sites: Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr6 position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chr16 position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 34206950, Chr20 position 36771969, Chr20 position 48993661, Chr20 position 58406398, Chr20 position 61976049, Chr20 position 61976073, Chr20 position 62588571, Chr20 position 62588579, Chr22 position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, the method includes detecting methylation or unmethylation of at least 7 of the following sites: Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr6 position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chr16 position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 34206950, Chr20 position 36771969, Chr20 position 48993661, Chr20 position 58406398, Chr20 position 61976049, Chr20 position 61976073, Chr20 position 62588571, Chr20 position 62588579, Chr22 position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, the method includes detecting methylation or unmethylation of at least 8 of the following sites: Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr6 position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chr16 position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 34206950, Chr20 position 36771969, Chr20 position 48993661, Chr20 position 58406398, Chr20 position 61976049, Chr20 position 61976073, Chr20 position 62588571, Chr20 position 62588579, Chr22 position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, the method includes detecting methylation or unmethylation of at least 9 of the following sites: Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr6 position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chr16 position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 34206950, Chr20 position 36771969, Chr20 position 48993661, Chr20 position 58406398, Chr20 position 61976049, Chr20 position 61976073, Chr20 position 62588571, Chr20 position 62588579, Chr22 position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, the method includes detecting methylation or unmethylation of at least 10 of the following sites: Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr6 position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chr16 position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 34206950, Chr20 position 36771969, Chr20 position 48993661, Chr20 position 58406398, Chr20 position 61976049, Chr20 position 61976073, Chr20 position 62588571, Chr20 position 62588579, Chr22 position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, the method includes detecting methylation or unmethylation of at least 50 of the following sites: Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr6 position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chr16 position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 34206950, Chr20 position 36771969, Chr20 position 48993661, Chr20 position 58406398, Chr20 position 61976049, Chr20 position 61976073, Chr20 position 62588571, Chr20 position 62588579, Chr22 position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, the method includes detecting methylation or unmethylation of at least 100 of the following sites: Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr6 position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chr16 position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 34206950, Chr20 position 36771969, Chr20 position 48993661, Chr20 position 58406398, Chr20 position 61976049, Chr20 position 61976073, Chr20 position 62588571, Chr20 position 62588579, Chr22 position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, the method includes detecting methylation or unmethylation of at least 200 of the following sites: Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr6 position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chr16 position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 34206950, Chr20 position 36771969, Chr20 position 48993661, Chr20 position 58406398, Chr20 position 61976049, Chr20 position 61976073, Chr20 position 62588571, Chr20 position 62588579, Chr22 position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, the method includes detecting methylation or unmethylation of at least 300 of the following sites: Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr6 position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chr16 position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 34206950, Chr20 position 36771969, Chr20 position 48993661, Chr20 position 58406398, Chr20 position 61976049, Chr20 position 61976073, Chr20 position 62588571, Chr20 position 62588579, Chr22 position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, the method includes detecting methylation or unmethylation of at least 400 of the following sites: Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr6 position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chr16 position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 34206950, Chr20 position 36771969, Chr20 position 48993661, Chr20 position 58406398, Chr20 position 61976049, Chr20 position 61976073, Chr20 position 62588571, Chr20 position 62588579, Chr22 position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, the method includes detecting methylation or unmethylation of at least 500 of the following sites: Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 42329494, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr6 position 3394325, Chr6 position 3887581, Chr6 position 7236568, Chr6 position 7728692, Chr6 position 34203617, Chr6 position 37751320, Chr6 position 41410682, Chr6 position 41438516, Chr6 position 41438575, Chr6 position 43464150, Chr6 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 77989064, Chr15 position 83952081, Chr15 position 85402496, Chr15 position 85402497, Chr15 position 99417337, Chr16 position 1231873, Chr16 position 1458639, Chr16 position 3023231, Chr16 position 23135832, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509945, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48596391, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434939, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 34206950, Chr20 position 36771969, Chr20 position 48993661, Chr20 position 58406398, Chr20 position 61976049, Chr20 position 61976073, Chr20 position 62588571, Chr20 position 62588579, Chr22 position 19738127, Chr22 position 35965176, Chr22 position 36549809, Chr22 position 36973375, Chr22 position 37447953, Chr22 position 37914998, Chr22 position 38307317, Chr22 position 39662794, and Chr22 position 45622980.

In embodiments, a method provided herein is practiced for a subject more than once over time. In embodiments, methylation or unmethylation of thyroid nodule DNA from a subject is assessed using a method provided herein at least 1, 2, 3, 4, 5, 6, 7, 8, 9, 10 or more times. In embodiments, the method is repeated at least once every 4, 6, 8, 12 or 18 months, or at least once every 2, 3, 4, or 5 more years.

In embodiments, the method includes: (i) isolating DNA from multiple cells of a thyroid nodule of the subject thereby forming a plurality of isolated thyroid nodule DNA molecules, (ii) contacting the plurality of isolated thyroid nodule DNA molecules with a bisulfite salt thereby forming a plurality of reacted thyroid nodule DNA molecules, (iii) detecting the proportion of DNA molecules in the plurality of reacted thyroid nodule DNA molecules having a uracil at a methylation site set forth in Table 1, thereby detecting methylation or unmethylation of said thyroid nodule DNA of the subject.

The methylation of a CpG site of interest may vary between individual cells (and even between chromosome pairs of individual cells) in a biological sample. When DNA is obtained from a biological sample and treated with a bisulfite salt to convert unmethylated cytosines to uracils, the bisulfite-treated DNA will typically contain (i) a proportion of DNA molecules with a cytosine at the site of interest (indicating that the site was methylated); and (ii) a proportion of DNA molecules with a uracil at the site of interest (indicating that the site was unmethylated). Since a uracil at a site of interest in bisulfite-treated DNA indicates that the site was unmethylated in the untreated DNA, a thymidine at the corresponding site in an amplicon of the bisulfite-treated DNA (e.g., an amplicon obtained by PCR) also indicates that the site was unmethylated in the untreated DNA.

In embodiments, the level of methylation at a site of interest is the proportion of bisulfite-treated DNA molecules having a cytosine rather than a uracil at that site of interest. In embodiments, the level of methylation at a site of interest is the proportion of amplicons of bisulfite-treated DNA molecules having a cytosine rather than a thymidine at that site of interest.

In embodiments, the level of unmethylation at a site of interest is the proportion of bisulfite-treated DNA molecules having a uracil rather than a cytosine at that site of interest. In embodiments, the level of unmethylation at a site of interest is the proportion of amplicons of bisulfite-treated DNA molecules having a thymidine rather than a cytosine at that site of interest. In Table 1, an indicated level of uracil is the proportion of bisulfite-treated DNA molecules having a uracil rather than a cytosine at the specified methylation site. The same levels listed in Table 1 also apply to the thymidine levels at a site of interest in an amplicon, i.e., the proportion of amplicons (derived from the PCR amplification of bisulfite-treated DNA molecules) having a thymidine rather than a cytosine at the specified methylation site.

The level of DNA methylation at a site of interest (e.g., a methylation site listed in Table 1) may be determined using sequencing technology. Sequencing technology can reveal nucleotide sequence variations in a plurality of DNA molecules at a single nucleotide base resolution. For example, the proportions of corresponding DNA molecules having a uracil, a thymidine, and/or a cytosine at a site may be determined. A non-limiting example of a sequencing-based method for determining the methylation level at a site of interest is described in Masser et al. (2015) Targeted DNA Methylation Analysis by Next-generation Sequencing. J Vis Exp. (96): 52488, the entire content of which is incorporated herein by reference.

The chromosomal positions listed in Tables 1-4 relate to the human genome that is publically accessible in the University of California Santa Cruz (UCSC) genome browser database under accession number HG19, the entire content of which is incorporated herein by reference in its entirety. Non-limiting information regarding the UCSC Genome Browser is provided in Kent W J, Sugnet C W, Furey T S, Roskin K M, Pringle T H, Zahler A M, Haussler D. The human genome browser at UCSC. Genome Res. 2002 June; 12(6):996-1006, the entire content of which is incorporated herein by reference. Each methylation site of interest listed in Table 1 may be located in other human genomes (e.g., within the genome of a specific subject or group of subjects) by replacing every U and R in the corresponding sequence with a C and then searching for the location of the X within a reference genome by aligning the sequence against the reference genome. For example, the methylation site of interest "X" in SEQ ID NO: 1 may be located within a genome by replacing each U and R in SEQ ID NO: 1 with a C (to obtain the pre-bisulfite-modified sequence having an X at the site of interest) and then aligning the sequence against the genome using a BLAST algorithm. Also expressly provided, disclosed, and incorporated herein is the non-bisulfite-modified sequence corresponding to each of SEQ ID NOS: 1-550. The non-bisulfite-modified sequence corresponding to each of SEQ ID NOS: 1-550 is each respective sequence in which each U and R is replaced with a C, where X is the methylation site of interest. For example, the non-bisulfite-modified sequence corresponding to SEQ ID NO: 1 provided herein is a modified version of SEQ ID NO: 1 in which each U and R in SEQ ID NO: 1 is replaced with a C, where X is the methylation site of interest; the non-bisulfite-modified sequence corresponding to SEQ ID NO:2 provided herein is a modified version of SEQ ID NO:2 in which each U and R in SEQ ID NO:2 is replaced with a C, where X is the methylation site of interest; the non-bisulfite-modified sequence corresponding to SEQ ID NO:3 provided herein is a modified version of SEQ ID NO:3 in which each U and R in SEQ ID NO:3 is replaced with a C, where X is the methylation site of interest, and so on.

TABLE 1

| Chromosome (chr) | Chr Position | Uracil level in reacted thyroid nodule DNA from cancer tissues is above indicated level* | Uracil level in reacted thyroid nodule DNA from benign tissues is above indicated level* | Uracil level in reacted thyroid nodule DNA from benign tissues is below indicated level* | SEQ ID NO: Forward Strand | SEQ ID NO: Reverse Strand |
|---|---|---|---|---|---|---|
| chr1 | 2996653 | N/A | 88.84 | N/A | 1 | 2 |
| chr1 | 11979164 | 89.29 | N/A | N/A | 3 | 4 |
| chr1 | 12655938 | N/A | N/A | 69.23 | 5 | 6 |
| chr1 | 16450525 | 70.00 | N/A | N/A | 7 | 8 |
| chr1 | 16450542 | 72.00 | N/A | N/A | 7 | 8 |
| chr1 | 16450545 | 73.33 | N/A | N/A | 7 | 8 |
| chr1 | 16469987 | 80.00 | N/A | N/A | 9 | 10 |
| chr1 | 17494491 | 86.00 | N/A | N/A | 11 | 12 |
| chr1 | 25473203 | 88.89 | N/A | N/A | 13 | 14 |
| chr1 | 27640460 | N/A | 80.56 | N/A | 15 | 16 |
| chr1 | 29565080 | N/A | N/A | 60.00 | 17 | 18 |
| chr1 | 38493013 | 86.36 | N/A | N/A | 19 | 20 |
| chr1 | 38493030 | 79.17 | N/A | N/A | 19 | 20 |
| chr1 | 38493074 | 80.95 | N/A | N/A | 19 | 20 |
| chr1 | 46713777 | N/A | N/A | 73.33 | 21 | 22 |
| chr1 | 46914121 | N/A | N/A | 60.00 | 23 | 24 |
| chr1 | 46955744 | N/A | N/A | 77.78 | 25 | 26 |
| chr1 | 55008344 | N/A | N/A | 60.00 | 27 | 28 |
| chr1 | 109816092 | 80.77 | N/A | N/A | 29 | 30 |
| chr1 | 109816111 | 80.77 | N/A | N/A | 29 | 30 |
| chr1 | 110074669 | 75.00 | N/A | N/A | 31 | 32 |
| chr1 | 110074681 | 71.43 | N/A | N/A | 31 | 32 |
| chr1 | 110074685 | 63.16 | N/A | N/A | 31 | 32 |
| chr1 | 150949856 | 89.29 | N/A | N/A | 33 | 34 |
| chr1 | 150949857 | 88.46 | N/A | N/A | 33 | 34 |
| chr1 | 153540282 | 78.26 | N/A | N/A | 35 | 36 |
| chr1 | 155162704 | 84.21 | N/A | N/A | 37 | 38 |
| chr1 | 155162714 | 88.64 | N/A | N/A | 37 | 38 |
| chr1 | 156676611 | N/A | N/A | 84.62 | 39 | 40 |
| chr1 | 157611881 | 83.05 | N/A | N/A | 41 | 42 |
| chr1 | 182205324 | 77.50 | N/A | N/A | 43 | 44 |
| chr1 | 204118999 | 59.09 | N/A | N/A | 45 | 46 |
| chr1 | 206741875 | 83.33 | N/A | N/A | 47 | 48 |
| chr1 | 206741989 | 66.67 | N/A | N/A | 49 | 50 |
| chr1 | 212587673 | N/A | N/A | 80.00 | 51 | 52 |
| chr1 | 212841198 | 85.29 | N/A | N/A | 53 | 54 |
| chr1 | 223403952 | 79.17 | N/A | N/A | 55 | 56 |
| chr1 | 233430972 | N/A | N/A | 86.67 | 57 | 58 |
| chr1 | 234342767 | 76.67 | N/A | N/A | 59 | 60 |
| chr10 | 3929071 | 88.68 | N/A | N/A | 61 | 62 |
| chr10 | 30047012 | 86.84 | N/A | N/A | 63 | 64 |
| chr10 | 79702989 | 83.33 | N/A | N/A | 65 | 66 |
| chr10 | 87984905 | 86.36 | N/A | N/A | 67 | 68 |
| chr10 | 94838789 | 63.33 | N/A | N/A | 69 | 70 |
| chr10 | 102131187 | 90.00 | N/A | N/A | 71 | 72 |
| chr10 | 104196489 | 75.00 | N/A | N/A | 73 | 74 |
| chr10 | 111766879 | 89.47 | N/A | N/A | 75 | 76 |
| chr10 | 112258886 | 81.82 | N/A | N/A | 77 | 78 |
| chr10 | 112258984 | 83.33 | N/A | N/A | 79 | 80 |
| chr10 | 112259015 | 82.61 | N/A | N/A | 79 | 80 |
| chr10 | 116391763 | N/A | N/A | 75.00 | 81 | 82 |
| chr10 | 120011530 | 79.55 | N/A | N/A | 83 | 84 |
| chr10 | 126172714 | N/A | 80.00 | N/A | 85 | 86 |
| chr10 | 126172747 | N/A | 84.62 | N/A | 85 | 86 |
| chr11 | 556355 | N/A | N/A | 75.00 | 87 | 88 |
| chr11 | 821282 | 89.13 | N/A | N/A | 89 | 90 |
| chr11 | 12188937 | 83.33 | N/A | N/A | 91 | 92 |
| chr11 | 12188948 | 77.78 | N/A | N/A | 91 | 92 |
| chr11 | 12188995 | 78.57 | N/A | N/A | 93 | 94 |
| chr11 | 36057726 | N/A | 79.63 | N/A | 95 | 96 |
| chr11 | 48070143 | N/A | 84.38 | N/A | 97 | 98 |
| chr11 | 48070163 | N/A | 87.50 | N/A | 97 | 98 |
| chr11 | 48070166 | N/A | 84.38 | N/A | 97 | 98 |
| chr11 | 48070174 | N/A | 84.48 | N/A | 97 | 98 |
| chr11 | 65158294 | 78.00 | N/A | N/A | 99 | 100 |
| chr11 | 65158342 | 85.00 | N/A | N/A | 99 | 100 |
| chr11 | 65297089 | 75.00 | N/A | N/A | 101 | 102 |
| chr11 | 66104481 | 81.58 | N/A | N/A | 103 | 104 |
| chr11 | 66104485 | 83.33 | N/A | N/A | 103 | 104 |
| chr11 | 66104578 | 81.82 | N/A | N/A | 105 | 106 |
| chr11 | 68608767 | N/A | N/A | 73.33 | 107 | 108 |
| chr11 | 70236292 | 89.29 | N/A | N/A | 109 | 110 |
| chr11 | 70236320 | 85.71 | N/A | N/A | 109 | 110 |

TABLE 1-continued

| Chromosome (chr) | Chr Position | Uracil level in reacted thyroid nodule DNA from cancer tissues is above indicated level* | Uracil level in reacted thyroid nodule DNA from benign tissues is above indicated level* | Uracil level in reacted thyroid nodule DNA from benign tissues is below indicated level* | SEQ ID NO: Forward Strand | SEQ ID NO: Reverse Strand |
|---|---|---|---|---|---|---|
| chr11 | 70236331 | 70.83 | N/A | N/A | 109 | 110 |
| chr11 | 115530032 | N/A | N/A | 79.49 | 111 | 112 |
| chr11 | 117950310 | 79.55 | N/A | N/A | 113 | 114 |
| chr11 | 117950329 | 79.55 | N/A | N/A | 113 | 114 |
| chr11 | 117950361 | 80.00 | N/A | N/A | 115 | 116 |
| chr11 | 117950362 | 81.82 | N/A | N/A | 115 | 116 |
| chr11 | 119293593 | N/A | N/A | 60.00 | 117 | 118 |
| chr12 | 679803 | 86.84 | N/A | N/A | 119 | 120 |
| chr12 | 26039132 | 73.91 | N/A | N/A | 121 | 122 |
| chr12 | 31004558 | N/A | N/A | 81.82 | 123 | 124 |
| chr12 | 45610695 | N/A | N/A | 83.33 | 125 | 126 |
| chr12 | 45610701 | N/A | N/A | 86.67 | 125 | 126 |
| chr12 | 45610702 | N/A | N/A | 89.47 | 125 | 126 |
| chr12 | 45610706 | N/A | N/A | 80.00 | 125 | 126 |
| chr12 | 50286016 | 82.14 | N/A | N/A | 127 | 128 |
| chr12 | 52243258 | 82.00 | N/A | N/A | 129 | 130 |
| chr12 | 52243286 | 82.50 | N/A | N/A | 129 | 130 |
| chr12 | 54145732 | N/A | N/A | 82.35 | 131 | 132 |
| chr12 | 54145741 | N/A | N/A | 76.47 | 131 | 132 |
| chr12 | 54145825 | N/A | N/A | 70.59 | 131 | 132 |
| chr12 | 56115043 | 89.29 | N/A | N/A | 133 | 134 |
| chr12 | 66262229 | 72.22 | N/A | N/A | 135 | 136 |
| chr12 | 66262230 | 71.74 | N/A | N/A | 135 | 136 |
| chr12 | 66262233 | 68.27 | N/A | N/A | 135 | 136 |
| chr12 | 66262234 | 71.74 | N/A | N/A | 135 | 136 |
| chr12 | 77266621 | N/A | 73.53 | N/A | 137 | 138 |
| chr12 | 117580102 | 84.62 | N/A | N/A | 139 | 140 |
| chr12 | 123435962 | 63.89 | N/A | N/A | 141 | 142 |
| chr12 | 123436011 | 71.88 | N/A | N/A | 143 | 144 |
| chr12 | 123436065 | 69.44 | N/A | N/A | 143 | 144 |
| chr12 | 123540893 | 77.27 | N/A | N/A | 145 | 146 |
| chr13 | 20735797 | N/A | N/A | 82.35 | 147 | 148 |
| chr13 | 23500419 | N/A | N/A | 68.42 | 149 | 150 |
| chr13 | 46771519 | 67.65 | N/A | N/A | 151 | 152 |
| chr13 | 46771520 | 73.91 | N/A | N/A | 151 | 152 |
| chr13 | 53313426 | N/A | N/A | 60.00 | 153 | 154 |
| chr13 | 113807393 | N/A | N/A | 27.27 | 155 | 156 |
| chr14 | 38599118 | 65.91 | N/A | N/A | 157 | 158 |
| chr14 | 69170010 | 86.36 | N/A | N/A | 159 | 160 |
| chr14 | 75701632 | 68.42 | N/A | N/A | 161 | 162 |
| chr14 | 75701643 | 68.75 | N/A | N/A | 161 | 162 |
| chr14 | 90850454 | N/A | N/A | 54.55 | 163 | 164 |
| chr14 | 97524282 | N/A | 88.89 | N/A | 165 | 166 |
| chr14 | 103541602 | N/A | N/A | 52.00 | 167 | 168 |
| chr14 | 103768055 | 76.09 | N/A | N/A | 169 | 170 |
| chr14 | 104209000 | N/A | 80.77 | N/A | 171 | 172 |
| chr14 | 104209068 | N/A | 83.33 | N/A | 171 | 172 |
| chr14 | 104354645 | 72.92 | N/A | N/A | 173 | 174 |
| chr14 | 104360487 | 83.33 | N/A | N/A | 175 | 176 |
| chr15 | 41068807 | 69.12 | N/A | N/A | 177 | 178 |
| chr15 | 61152225 | 83.33 | N/A | N/A | 179 | 180 |
| chr15 | 61152253 | 86.67 | N/A | N/A | 181 | 182 |
| chr15 | 61152313 | 86.67 | N/A | N/A | 183 | 184 |
| chr15 | 65186440 | N/A | N/A | 55.56 | 185 | 186 |
| chr15 | 68851629 | N/A | N/A | 63.64 | 187 | 188 |
| chr15 | 70667596 | 83.33 | N/A | N/A | 189 | 190 |
| chr15 | 70767206 | 90.00 | N/A | N/A | 191 | 192 |
| chr15 | 75251486 | N/A | N/A | 60.00 | 193 | 194 |
| chr15 | 77984014 | N/A | 88.89 | N/A | 195 | 196 |
| chr15 | 77989064 | 73.53 | N/A | N/A | 197 | 198 |
| chr15 | 83952081 | N/A | N/A | 72.73 | 199 | 200 |
| chr15 | 85402496 | 82.10 | N/A | N/A | 201 | 202 |
| chr15 | 85402497 | 79.49 | N/A | N/A | 201 | 202 |
| chr15 | 99417337 | 88.89 | N/A | N/A | 203 | 204 |
| chr16 | 1231873 | 86.36 | N/A | N/A | 205 | 206 |
| chr16 | 1458639 | N/A | N/A | 75.00 | 207 | 208 |
| chr16 | 3023231 | N/A | 84.00 | N/A | 209 | 210 |
| chr16 | 23135832 | 87.50 | N/A | N/A | 211 | 212 |
| chr16 | 29616265 | 85.71 | N/A | N/A | 213 | 214 |
| chr16 | 31009547 | 84.00 | N/A | N/A | 215 | 216 |
| chr16 | 31009548 | 85.00 | N/A | N/A | 215 | 216 |
| chr16 | 31009590 | 85.00 | N/A | N/A | 215 | 216 |
| chr16 | 57793674 | 80.95 | N/A | N/A | 217 | 218 |

TABLE 1-continued

| Chromosome (chr) | Chr Position | Uracil level in reacted thyroid nodule DNA from cancer tissues is above indicated level* | Uracil level in reacted thyroid nodule DNA from benign tissues is above indicated level* | Uracil level in reacted thyroid nodule DNA from benign tissues is below indicated level* | SEQ ID NO: Forward Strand | SEQ ID NO: Reverse Strand |
|---|---|---|---|---|---|---|
| chr16 | 57793715 | 85.71 | N/A | N/A | 217 | 218 |
| chr16 | 57793727 | 80.95 | N/A | N/A | 217 | 218 |
| chr16 | 70771056 | 68.75 | N/A | N/A | 219 | 220 |
| chr16 | 70771079 | 63.33 | N/A | N/A | 219 | 220 |
| chr16 | 70771141 | 65.79 | N/A | N/A | 219 | 220 |
| chr16 | 77332010 | 72.58 | N/A | N/A | 221 | 222 |
| chr16 | 78540378 | 75.76 | N/A | N/A | 223 | 224 |
| chr16 | 79333435 | N/A | 89.61 | N/A | 225 | 226 |
| chr16 | 84262419 | 87.23 | N/A | N/A | 227 | 228 |
| chr16 | 88701114 | N/A | N/A | 66.67 | 229 | 230 |
| chr16 | 89988308 | N/A | N/A | 83.33 | 231 | 232 |
| chr16 | 89988644 | N/A | N/A | 47.37 | 233 | 234 |
| chr17 | 1509928 | N/A | 88.46 | N/A | 235 | 236 |
| chr17 | 1509945 | N/A | 88.46 | N/A | 235 | 236 |
| chr17 | 1509952 | N/A | 83.93 | N/A | 235 | 236 |
| chr17 | 1509953 | N/A | 85.00 | N/A | 235 | 236 |
| chr17 | 7644013 | N/A | 85.42 | N/A | 237 | 238 |
| chr17 | 16323460 | 85.00 | N/A | N/A | 239 | 240 |
| chr17 | 16323473 | 84.21 | N/A | N/A | 239 | 240 |
| chr17 | 16924561 | 80.36 | N/A | N/A | 241 | 242 |
| chr17 | 16924562 | 75.71 | N/A | N/A | 241 | 242 |
| chr17 | 16924594 | 75.71 | N/A | N/A | 241 | 242 |
| chr17 | 17717918 | 72.73 | N/A | N/A | 243 | 244 |
| chr17 | 17718591 | 84.38 | N/A | N/A | 245 | 246 |
| chr17 | 18139506 | 82.81 | N/A | N/A | 247 | 248 |
| chr17 | 35278031 | N/A | N/A | 28.42 | 249 | 250 |
| chr17 | 39677570 | 71.88 | N/A | N/A | 251 | 252 |
| chr17 | 40826257 | N/A | N/A | 23.81 | 253 | 254 |
| chr17 | 43037426 | N/A | N/A | 33.33 | 255 | 256 |
| chr17 | 43200096 | 77.78 | N/A | N/A | 257 | 258 |
| chr17 | 43200239 | 85.00 | N/A | N/A | 259 | 260 |
| chr17 | 43510142 | N/A | N/A | 81.82 | 261 | 262 |
| chr17 | 47987828 | N/A | N/A | 69.23 | 263 | 264 |
| chr17 | 48178379 | 83.33 | N/A | N/A | 265 | 266 |
| chr17 | 48596391 | N/A | 88.64 | N/A | 267 | 268 |
| chr17 | 48764165 | 88.89 | N/A | N/A | 269 | 270 |
| chr17 | 55701962 | 68.75 | N/A | N/A | 271 | 272 |
| chr17 | 73584599 | N/A | N/A | 60.00 | 273 | 274 |
| chr17 | 73993165 | 90.00 | N/A | N/A | 275 | 276 |
| chr17 | 75827716 | 78.57 | N/A | N/A | 277 | 278 |
| chr17 | 76882243 | 61.54 | N/A | N/A | 279 | 280 |
| chr17 | 78765910 | 88.71 | N/A | N/A | 281 | 282 |
| chr17 | 79544478 | 83.15 | N/A | N/A | 283 | 284 |
| chr17 | 80696474 | 60.00 | N/A | N/A | 285 | 286 |
| chr18 | 19751759 | N/A | N/A | 33.33 | 287 | 288 |
| chr18 | 21440760 | 67.86 | N/A | N/A | 289 | 290 |
| chr18 | 45555437 | 66.18 | N/A | N/A | 291 | 292 |
| chr18 | 45555438 | 73.68 | N/A | N/A | 291 | 292 |
| chr18 | 46547891 | 76.09 | N/A | N/A | 293 | 294 |
| chr18 | 55888885 | 75.47 | N/A | N/A | 295 | 296 |
| chr18 | 56452096 | 90.00 | N/A | N/A | 297 | 298 |
| chr18 | 56452476 | 81.82 | N/A | N/A | 299 | 300 |
| chr18 | 56887181 | N/A | N/A | 60.00 | 301 | 302 |
| chr18 | 76002973 | 81.58 | N/A | N/A | 303 | 304 |
| chr18 | 77331090 | 81.03 | N/A | N/A | 305 | 306 |
| chr19 | 677895 | 85.29 | N/A | N/A | 307 | 308 |
| chr19 | 884044 | 76.92 | N/A | N/A | 309 | 310 |
| chr19 | 884059 | 76.92 | N/A | N/A | 309 | 310 |
| chr19 | 884105 | 84.62 | N/A | N/A | 311 | 312 |
| chr19 | 884115 | 84.62 | N/A | N/A | 311 | 312 |
| chr19 | 1136511 | 86.96 | N/A | N/A | 313 | 314 |
| chr19 | 1177605 | 73.68 | N/A | N/A | 315 | 316 |
| chr19 | 1177612 | 72.73 | N/A | N/A | 315 | 316 |
| chr19 | 1177640 | 81.82 | N/A | N/A | 315 | 316 |
| chr19 | 1860601 | 88.46 | N/A | N/A | 317 | 318 |
| chr19 | 1860607 | 82.81 | N/A | N/A | 317 | 318 |
| chr19 | 2503954 | 90.00 | N/A | N/A | 319 | 320 |
| chr19 | 3434917 | N/A | N/A | 40.00 | 321 | 322 |
| chr19 | 3434921 | N/A | N/A | 42.86 | 321 | 322 |
| chr19 | 3434930 | N/A | N/A | 57.14 | 321 | 322 |
| chr19 | 3434939 | N/A | N/A | 71.43 | 321 | 322 |
| chr19 | 3434952 | N/A | N/A | 71.43 | 321 | 322 |
| chr19 | 3434954 | N/A | N/A | 60.00 | 321 | 322 |

TABLE 1-continued

| Chromosome (chr) | Chr Position | Uracil level in reacted thyroid nodule DNA from cancer tissues is above indicated level* | Uracil level in reacted thyroid nodule DNA from benign tissues is above indicated level* | Uracil level in reacted thyroid nodule DNA from benign tissues is below indicated level* | SEQ ID NO: Forward Strand | SEQ ID NO: Reverse Strand |
|---|---|---|---|---|---|---|
| chr19 | 3434962 | N/A | N/A | 71.43 | 321 | 322 |
| chr19 | 3434964 | N/A | N/A | 71.43 | 321 | 322 |
| chr19 | 3434979 | N/A | N/A | 66.67 | 321 | 322 |
| chr19 | 3434985 | N/A | N/A | 55.56 | 321 | 322 |
| chr19 | 4052713 | 85.56 | N/A | N/A | 323 | 324 |
| chr19 | 4052714 | 85.14 | N/A | N/A | 323 | 324 |
| chr19 | 4052749 | 84.62 | N/A | N/A | 323 | 324 |
| chr19 | 4374591 | 82.14 | N/A | N/A | 325 | 326 |
| chr19 | 5013982 | N/A | 83.33 | N/A | 327 | 328 |
| chr19 | 5048836 | 11.21 | N/A | N/A | 329 | 330 |
| chr19 | 5048867 | 70.59 | N/A | N/A | 329 | 330 |
| chr19 | 5048877 | 73.53 | N/A | N/A | 329 | 330 |
| chr19 | 8367279 | 75.00 | N/A | N/A | 331 | 332 |
| chr19 | 8428573 | N/A | N/A | 75.00 | 333 | 334 |
| chr19 | 10254577 | 76.25 | N/A | N/A | 335 | 336 |
| chr19 | 10254578 | 79.17 | N/A | N/A | 335 | 336 |
| chr19 | 10463956 | N/A | 86.73 | N/A | 337 | 338 |
| chr19 | 10464137 | N/A | 89.29 | N/A | 339 | 340 |
| chr19 | 13203671 | 75.86 | N/A | N/A | 341 | 342 |
| chr19 | 13266925 | N/A | N/A | 66.67 | 343 | 344 |
| chr19 | 13266934 | N/A | N/A | 66.67 | 343 | 344 |
| chr19 | 13266970 | N/A | N/A | 63.64 | 343 | 344 |
| chr19 | 13842142 | N/A | N/A | 76.47 | 345 | 346 |
| chr19 | 14248494 | N/A | N/A | 73.91 | 347 | 348 |
| chr19 | 15375465 | 72.22 | N/A | N/A | 349 | 350 |
| chr19 | 17218912 | 81.25 | N/A | N/A | 351 | 352 |
| chr19 | 17346702 | N/A | N/A | 85.71 | 353 | 354 |
| chr19 | 17346702 | N/A | N/A | 78.95 | 353 | 354 |
| chr19 | 18157161 | 88.24 | N/A | N/A | 355 | 356 |
| chr19 | 18157221 | 86.76 | N/A | N/A | 357 | 358 |
| chr19 | 18157258 | 65.22 | N/A | N/A | 359 | 360 |
| chr19 | 18415877 | N/A | N/A | 47.83 | 361 | 362 |
| chr19 | 18415890 | N/A | N/A | 47.83 | 361 | 362 |
| chr19 | 30606642 | 80.56 | N/A | N/A | 363 | 364 |
| chr19 | 35531842 | N/A | N/A | 83.33 | 365 | 366 |
| chr19 | 44303112 | N/A | N/A | 77.78 | 367 | 368 |
| chr19 | 47173037 | N/A | 88.64 | N/A | 369 | 370 |
| chr19 | 47316268 | 76.67 | N/A | N/A | 371 | 372 |
| chr19 | 47778278 | N/A | N/A | 66.67 | 373 | 374 |
| chr19 | 47778298 | N/A | N/A | 83.33 | 373 | 374 |
| chr2 | 3454277 | N/A | 84.78 | N/A | 375 | 376 |
| chr2 | 8793724 | N/A | 78.57 | N/A | 377 | 378 |
| chr2 | 20412441 | 85.71 | N/A | N/A | 379 | 380 |
| chr2 | 42329402 | N/A | N/A | 78.95 | 381 | 382 |
| chr2 | 42329494 | N/A | N/A | 60.00 | 381 | 382 |
| chr2 | 55289272 | N/A | 75.00 | N/A | 383 | 384 |
| chr2 | 65064865 | 64.71 | N/A | N/A | 385 | 386 |
| chr2 | 70823641 | 79.03 | N/A | N/A | 387 | 388 |
| chr2 | 73143689 | N/A | N/A | 77.78 | 389 | 390 |
| chr2 | 74454110 | 70.00 | N/A | N/A | 391 | 392 |
| chr2 | 122014529 | N/A | 86.36 | N/A | 393 | 394 |
| chr2 | 128158884 | 85.00 | N/A | N/A | 395 | 396 |
| chr2 | 128158910 | 77.50 | N/A | N/A | 395 | 396 |
| chr2 | 203114171 | 79.63 | N/A | N/A | 397 | 398 |
| chr2 | 218221671 | N/A | 85.19 | N/A | 399 | 400 |
| chr2 | 219745335 | N/A | N/A | 81.82 | 401 | 402 |
| chr2 | 238341465 | 86.36 | N/A | N/A | 403 | 404 |
| chr2 | 238341542 | 90.00 | N/A | N/A | 405 | 406 |
| chr2 | 238341546 | 87.50 | N/A | N/A | 405 | 406 |
| chr2 | 238774763 | 67.57 | N/A | N/A | 407 | 408 |
| chr20 | 31126186 | 87.50 | N/A | N/A | 409 | 410 |
| chr20 | 31126189 | 84.21 | N/A | N/A | 409 | 410 |
| chr20 | 34206950 | N/A | N/A | 76.47 | 411 | 412 |
| chr20 | 36771969 | 79.31 | N/A | N/A | 413 | 414 |
| chr20 | 48993661 | 80.00 | N/A | N/A | 415 | 416 |
| chr20 | 58406398 | 89.66 | N/A | N/A | 417 | 418 |
| chr20 | 61976049 | 87.93 | N/A | N/A | 419 | 420 |
| chr20 | 61976073 | 89.66 | N/A | N/A | 419 | 420 |
| chr20 | 62588571 | N/A | N/A | 50.00 | 421 | 422 |
| chr20 | 62588579 | N/A | N/A | 38.46 | 421 | 422 |
| chr22 | 19738127 | 70.59 | N/A | N/A | 423 | 424 |
| chr22 | 35965176 | 76.32 | N/A | N/A | 425 | 426 |
| chr22 | 36549809 | 83.33 | N/A | N/A | 427 | 428 |

TABLE 1-continued

| Chromosome (chr) | Chr Position | Uracil level in reacted thyroid nodule DNA from cancer tissues is above indicated level* | Uracil level in reacted thyroid nodule DNA from benign tissues is above indicated level* | Uracil level in reacted thyroid nodule DNA from benign tissues is below indicated level* | SEQ ID NO: Forward Strand | SEQ ID NO: Reverse Strand |
|---|---|---|---|---|---|---|
| chr22 | 36973375 | 80.43 | N/A | N/A | 429 | 430 |
| chr22 | 37447953 | N/A | N/A | 73.33 | 431 | 432 |
| chr22 | 37914998 | N/A | N/A | 69.23 | 433 | 434 |
| chr22 | 38307317 | N/A | 89.66 | N/A | 435 | 436 |
| chr22 | 39662794 | 84.62 | N/A | N/A | 437 | 438 |
| chr22 | 45622980 | 85.00 | N/A | N/A | 439 | 440 |
| chr3 | 13323642 | N/A | N/A | 72.73 | 441 | 442 |
| chr3 | 14180153 | 57.89 | N/A | N/A | 443 | 444 |
| chr3 | 45209073 | N/A | N/A | 60.00 | 445 | 446 |
| chr3 | 45209207 | N/A | N/A | 83.33 | 447 | 448 |
| chr3 | 52525100 | 79.41 | N/A | N/A | 449 | 450 |
| chr3 | 62589658 | 87.50 | N/A | N/A | 451 | 452 |
| chr3 | 65388317 | 71.43 | N/A | N/A | 453 | 454 |
| chr3 | 65388388 | 79.31 | N/A | N/A | 455 | 456 |
| chr3 | 73599302 | 85.11 | N/A | N/A | 457 | 458 |
| chr3 | 195636893 | N/A | N/A | 84.62 | 459 | 460 |
| chr3 | 197093846 | 80.00 | N/A | N/A | 461 | 462 |
| chr4 | 3743223 | 68.18 | N/A | N/A | 463 | 464 |
| chr4 | 5755716 | 85.48 | N/A | N/A | 465 | 466 |
| chr4 | 5755717 | 80.00 | N/A | N/A | 465 | 466 |
| chr4 | 5755728 | 82.26 | N/A | N/A | 465 | 466 |
| chr4 | 5755729 | 79.17 | N/A | N/A | 465 | 466 |
| chr4 | 5755734 | 79.17 | N/A | N/A | 465 | 466 |
| chr4 | 8372861 | N/A | 85.71 | N/A | 467 | 468 |
| chr4 | 57548289 | 80.23 | N/A | N/A | 469 | 470 |
| chr5 | 1118280 | 73.08 | N/A | N/A | 471 | 472 |
| chr5 | 34564389 | 89.29 | N/A | N/A | 473 | 474 |
| chr5 | 73871907 | 89.47 | N/A | N/A | 475 | 476 |
| chr5 | 78013596 | 70.00 | N/A | N/A | 477 | 478 |
| chr5 | 78013643 | 80.00 | N/A | N/A | 479 | 480 |
| chr5 | 137802650 | 72.73 | N/A | N/A | 481 | 482 |
| chr5 | 139051189 | 84.09 | N/A | N/A | 483 | 484 |
| chr5 | 167838221 | 68.18 | N/A | N/A | 485 | 486 |
| chr5 | 177541401 | N/A | N/A | 69.23 | 487 | 488 |
| chr5 | 180018672 | N/A | N/A | 72.73 | 489 | 490 |
| chr5 | 180101026 | N/A | N/A | 64.71 | 491 | 492 |
| chr6 | 3394325 | N/A | 87.84 | N/A | 493 | 494 |
| chr6 | 3887581 | N/A | 85.71 | N/A | 495 | 496 |
| chr6 | 7236568 | 84.43 | N/A | N/A | 497 | 498 |
| chr6 | 7728692 | N/A | N/A | 73.33 | 499 | 500 |
| chr6 | 34203617 | N/A | N/A | 45.45 | 501 | 502 |
| chr6 | 37751320 | N/A | N/A | 78.57 | 503 | 504 |
| chr6 | 41410682 | N/A | N/A | 77.78 | 505 | 506 |
| chr6 | 41438516 | N/A | N/A | 39.13 | 507 | 508 |
| chr6 | 41438575 | 89.66 | N/A | N/A | 507 | 508 |
| chr6 | 43464150 | 75.76 | N/A | N/A | 509 | 510 |
| chr6 | 158734279 | N/A | 86.84 | N/A | 511 | 512 |
| chr7 | 989235 | 76.67 | N/A | N/A | 513 | 514 |
| chr7 | 2673543 | 82.14 | N/A | N/A | 515 | 516 |
| chr7 | 73508602 | N/A | N/A | 85.71 | 517 | 518 |
| chr7 | 105079565 | 78.75 | N/A | N/A | 519 | 520 |
| chr7 | 105079631 | 71.25 | N/A | N/A | 519 | 520 |
| chr7 | 151425103 | 86.96 | N/A | N/A | 521 | 522 |
| chr7 | 151425104 | 76.19 | N/A | N/A | 521 | 522 |
| chr8 | 11764017 | 80.77 | N/A | N/A | 523 | 524 |
| chr8 | 21647308 | N/A | N/A | 71.43 | 525 | 526 |
| chr8 | 22548399 | N/A | 88.16 | N/A | 527 | 528 |
| chr8 | 22548483 | N/A | 87.50 | N/A | 527 | 528 |
| chr8 | 133570537 | N/A | 80.00 | N/A | 529 | 530 |
| chr8 | 141320393 | 75.00 | N/A | N/A | 531 | 532 |
| chr8 | 141320410 | 85.00 | N/A | N/A | 531 | 532 |
| chr9 | 6566568 | 86.84 | N/A | N/A | 533 | 534 |
| chr9 | 16197862 | N/A | 86.36 | N/A | 535 | 536 |
| chr9 | 34591313 | N/A | N/A | 80.00 | 537 | 538 |
| chr9 | 98225096 | N/A | N/A | 22.22 | 539 | 540 |
| chr9 | 126126741 | 86.11 | N/A | N/A | 541 | 542 |
| chr9 | 132083428 | N/A | N/A | 70.59 | 543 | 544 |
| chr9 | 136077410 | 73.91 | N/A | N/A | 545 | 546 |
| chr9 | 139655018 | 83.33 | N/A | N/A | 547 | 548 |

TABLE 1-continued

| Chromosome (chr) | Chr Position | Uracil level in reacted thyroid nodule DNA from cancer tissues is above indicated level* | Uracil level in reacted thyroid nodule DNA from benign tissues is above indicated level* | Uracil level in reacted thyroid nodule DNA from benign tissues is below indicated level* | SEQ ID NO: Forward Strand | SEQ ID NO: Reverse Strand |
|---|---|---|---|---|---|---|
| chr9 | 140205985 | 75.00 | N/A | N/A | 549 | 550 |
| chr9 | 140205985 | 83.33 | N/A | N/A | 549 | 550 |
| chr9 | 140205997 | 79.17 | N/A | N/A | 549 | 550 |

*Level values provided are the proportion (percentage) of reacted thyroid nodule DNA molecules having a uracil at the methylation site of interest. When amplicons generated from reacted thyroid nodule DNA molecules (e.g., by PCR) are used to assess the level of methylation, the values provided correspond to the proportion of amplicons having a thymidine at the nucleotide position that corresponds to the methylation site of interest.

In embodiments, the method of detecting methylation or unmethylation of a thyroid nodule DNA of a subject detects an alteration in methylation including increase or loss of uracil level at plurality of methylation sites. In embodiments, the method of detecting methylation or unmethylation of a thyroid nodule DNA of a subject detects an alteration in methylation including increase or loss of thymidine level at plurality of methylation sites. The indicated levels in Tables 1, 2, 3, and 4, are approximate indicated levels, and include values that are within about 15%, about 10%, or about 5% above and below the indicated levels.

In embodiments, the method detects the uracil level above about a threshold as set forth in Table 2 in subjects with a cancerous thyroid nodule. In embodiments, the method detects the thymidine level above about a threshold as set forth in Table 2 in subjects with a cancerous thyroid nodule.

TABLE 2

Methylation Threshold for Cancerous Thyroid Nodule

| Chromosome | Chromosomal Position | Uracil level in reacted thyroid nodule DNA from cancer tissues is about above indicated level* |
|---|---|---|
| chr1 | 11979164 | 89.29 |
| chr1 | 16450525 | 70.00 |
| chr1 | 16450542 | 72.00 |
| chr1 | 16450545 | 73.33 |
| chr1 | 16469987 | 80.00 |
| chr1 | 17494491 | 86.00 |
| chr1 | 25473203 | 88.89 |
| chr1 | 38493013 | 86.36 |
| chr1 | 38493030 | 79.17 |
| chr1 | 38493074 | 80.95 |
| chr1 | 109816092 | 80.77 |
| chr1 | 109816111 | 80.77 |
| chr1 | 110074669 | 75.00 |
| chr1 | 110074681 | 71.43 |
| chr1 | 110074685 | 63.16 |
| chr1 | 150949856 | 89.29 |
| chr1 | 150949857 | 88.46 |
| chr1 | 153540282 | 78.26 |
| chr1 | 155162704 | 84.21 |
| chr1 | 155162714 | 88.64 |
| chr1 | 157611881 | 83.05 |
| chr1 | 182205324 | 77.50 |
| chr1 | 204118999 | 59.09 |
| chr1 | 206741875 | 83.33 |
| chr1 | 206741989 | 66.67 |
| chr1 | 212841198 | 85.29 |
| chr1 | 223403952 | 79.17 |
| chr1 | 234342767 | 76.67 |
| chr10 | 3929071 | 88.68 |
| chr10 | 30047012 | 86.84 |
| chr10 | 79702989 | 83.33 |
| chr10 | 87984905 | 86.36 |
| chr10 | 94838789 | 63.33 |

TABLE 2-continued

Methylation Threshold for Cancerous Thyroid Nodule

| Chromosome | Chromosomal Position | Uracil level in reacted thyroid nodule DNA from cancer tissues is about above indicated level* |
|---|---|---|
| chr10 | 102131187 | 90.00 |
| chr10 | 104196489 | 75.00 |
| chr10 | 111766879 | 89.47 |
| chr10 | 112258886 | 81.82 |
| chr10 | 112258984 | 83.33 |
| chr10 | 112259015 | 82.61 |
| chr10 | 120011530 | 79.55 |
| chr11 | 821282 | 89.13 |
| chr11 | 12188937 | 83.33 |
| chr11 | 12188948 | 77.78 |
| chr11 | 12188995 | 78.57 |
| chr11 | 65158294 | 78.00 |
| chr11 | 65158342 | 85.00 |
| chr11 | 65297089 | 75.00 |
| chr11 | 66104481 | 81.58 |
| chr11 | 66104485 | 83.33 |
| chr11 | 66104578 | 81.82 |
| chr11 | 70236292 | 89.29 |
| chr11 | 70236320 | 85.71 |
| chr11 | 70236331 | 70.83 |
| chr11 | 117950310 | 79.55 |
| chr11 | 117950329 | 79.55 |
| chr11 | 117950361 | 80.00 |
| chr11 | 117950362 | 81.82 |
| chr12 | 679803 | 86.84 |
| chr12 | 26039132 | 73.91 |
| chr12 | 50286016 | 82.14 |
| chr12 | 52243258 | 82.00 |
| chr12 | 52243286 | 82.50 |
| chr12 | 56115043 | 89.29 |
| chr12 | 66262229 | 72.22 |
| chr12 | 66262230 | 71.74 |
| chr12 | 66262233 | 68.27 |
| chr12 | 66262234 | 71.74 |
| chr12 | 117580102 | 84.62 |
| chr12 | 123435962 | 63.89 |
| chr12 | 123436011 | 71.88 |
| chr12 | 123436065 | 69.44 |
| chr12 | 123540893 | 77.27 |
| chr13 | 46771519 | 67.65 |
| chr13 | 46771520 | 73.91 |
| chr14 | 38599118 | 65.91 |
| chr14 | 69170010 | 86.36 |
| chr14 | 75701632 | 68.42 |
| chr14 | 75701643 | 68.75 |
| chr14 | 103768055 | 76.09 |
| chr14 | 104354645 | 72.92 |
| chr14 | 104360487 | 83.33 |
| chr15 | 41068807 | 69.12 |
| chr15 | 61152225 | 83.33 |
| chr15 | 61152253 | 86.67 |
| chr15 | 61152313 | 86.67 |
| chr15 | 70667596 | 83.33 |
| chr15 | 70767206 | 90.00 |

TABLE 2-continued

Methylation Threshold for Cancerous Thyroid Nodule

| Chromosome | Chromosomal Position | Uracil level in reacted thyroid nodule DNA from cancer tissues is about above indicated level* |
|---|---|---|
| chr15 | 77989064 | 73.53 |
| chr15 | 85402496 | 82.10 |
| chr15 | 85402497 | 79.49 |
| chr15 | 99417337 | 88.89 |
| chr16 | 1231873 | 86.36 |
| chr16 | 23135832 | 87.50 |
| chr16 | 29616265 | 85.71 |
| chr16 | 31009547 | 84.00 |
| chr16 | 31009548 | 85.00 |
| chr16 | 31009590 | 85.00 |
| chr16 | 57793674 | 80.95 |
| chr16 | 57793715 | 85.71 |
| chr16 | 57793727 | 80.95 |
| chr16 | 70771056 | 68.75 |
| chr16 | 70771079 | 63.33 |
| chr16 | 70771141 | 65.79 |
| chr16 | 77332010 | 72.58 |
| chr16 | 78540378 | 75.76 |
| chr16 | 84262419 | 87.23 |
| chr17 | 16323460 | 85.00 |
| chr17 | 16323473 | 84.21 |
| chr17 | 16924561 | 80.36 |
| chr17 | 16924562 | 75.71 |
| chr17 | 16924594 | 75.71 |
| chr17 | 17717918 | 72.73 |
| chr17 | 17718591 | 84.38 |
| chr17 | 18139506 | 82.81 |
| chr17 | 39677570 | 71.88 |
| chr17 | 43200096 | 77.78 |
| chr17 | 43200239 | 85.00 |
| chr17 | 48178379 | 83.33 |
| chr17 | 48764165 | 88.89 |
| chr17 | 55701962 | 68.75 |
| chr17 | 73993165 | 90.00 |
| chr17 | 75827716 | 78.57 |
| chr17 | 76882243 | 61.54 |
| chr17 | 78765910 | 88.71 |
| chr17 | 79544478 | 83.15 |
| chr17 | 80696474 | 60.00 |
| chr18 | 21440760 | 67.86 |
| chr18 | 45555437 | 66.18 |
| chr18 | 45555438 | 73.68 |
| chr18 | 46547891 | 76.09 |
| chr18 | 55888885 | 75.47 |
| chr18 | 56452096 | 90.00 |
| chr18 | 56452476 | 81.82 |
| chr18 | 76002973 | 81.58 |
| chr18 | 77331090 | 81.03 |
| chr19 | 677895 | 85.29 |
| chr19 | 884044 | 76.92 |
| chr19 | 884059 | 76.92 |
| chr19 | 884105 | 84.62 |
| chr19 | 884115 | 84.62 |
| chr19 | 1136511 | 86.96 |
| chr19 | 1177605 | 73.68 |
| chr19 | 1177612 | 72.73 |
| chr19 | 1177640 | 81.82 |
| chr19 | 1860601 | 88.46 |
| chr19 | 1860607 | 82.81 |
| chr19 | 2503954 | 90.00 |
| chr19 | 4052713 | 85.56 |
| chr19 | 4052714 | 85.14 |
| chr19 | 4052749 | 84.62 |
| chr19 | 4374591 | 82.14 |
| chr19 | 5048836 | 77.27 |
| chr19 | 5048867 | 70.59 |
| chr19 | 5048877 | 73.53 |
| chr19 | 8367279 | 75.00 |
| chr19 | 10254577 | 76.25 |
| chr19 | 10254578 | 79.17 |
| chr19 | 13203671 | 75.86 |
| chr19 | 15375465 | 72.22 |
| chr19 | 17218912 | 81.25 |

TABLE 2-continued

Methylation Threshold for Cancerous Thyroid Nodule

| Chromosome | Chromosomal Position | Uracil level in reacted thyroid nodule DNA from cancer tissues is about above indicated level* |
|---|---|---|
| chr19 | 18157161 | 88.24 |
| chr19 | 18157221 | 86.76 |
| chr19 | 18157258 | 65.22 |
| chr19 | 30606642 | 80.56 |
| chr19 | 47316268 | 76.67 |
| chr2 | 20412441 | 85.71 |
| chr2 | 65064865 | 64.71 |
| chr2 | 70823641 | 79.03 |
| chr2 | 74454110 | 70.00 |
| chr2 | 128158884 | 85.00 |
| chr2 | 128158910 | 77.50 |
| chr2 | 203114171 | 79.63 |
| chr2 | 238341465 | 86.36 |
| chr2 | 238341542 | 90.00 |
| chr2 | 238341546 | 87.50 |
| chr2 | 238774763 | 67.57 |
| chr20 | 31126186 | 87.50 |
| chr20 | 31126189 | 84.21 |
| chr20 | 36771969 | 79.31 |
| chr20 | 48993661 | 80.00 |
| chr20 | 58406398 | 89.66 |
| chr20 | 61976049 | 87.93 |
| chr20 | 61976073 | 89.66 |
| chr22 | 19738127 | 70.59 |
| chr22 | 35965176 | 76.32 |
| chr22 | 36549809 | 83.33 |
| chr22 | 36973375 | 80.43 |
| chr22 | 39662794 | 84.62 |
| chr22 | 45622980 | 85.00 |
| chr3 | 14180153 | 57.89 |
| chr3 | 52525100 | 79.41 |
| chr3 | 62589658 | 87.50 |
| chr3 | 65388317 | 71.43 |
| chr3 | 65388388 | 79.31 |
| chr3 | 73599302 | 85.11 |
| chr3 | 197093846 | 80.00 |
| chr4 | 3743223 | 68.18 |
| chr4 | 5755716 | 85.48 |
| chr4 | 5755717 | 80.00 |
| chr4 | 5755728 | 82.26 |
| chr4 | 5755729 | 79.17 |
| chr4 | 5755734 | 79.17 |
| chr4 | 57548289 | 80.23 |
| chr5 | 1118280 | 73.08 |
| chr5 | 34564389 | 89.29 |
| chr5 | 73871907 | 89.47 |
| chr5 | 78013596 | 70.00 |
| chr5 | 78013643 | 80.00 |
| chr5 | 137802650 | 72.73 |
| chr5 | 139051189 | 84.09 |
| chr5 | 167838221 | 68.18 |
| chr6 | 7236568 | 84.43 |
| chr6 | 41438575 | 89.66 |
| chr6 | 43464150 | 75.76 |
| chr7 | 989235 | 76.67 |
| chr7 | 2673543 | 82.14 |
| chr7 | 105079565 | 78.75 |
| chr7 | 105079631 | 71.25 |
| chr7 | 151425103 | 86.96 |
| chr7 | 151425104 | 76.19 |
| chr8 | 11764017 | 80.77 |
| chr8 | 141320393 | 75.00 |
| chr8 | 141320410 | 85.00 |
| chr9 | 6566568 | 86.84 |
| chr9 | 126126741 | 86.11 |
| chr9 | 136077410 | 73.91 |
| chr9 | 139655018 | 83.33 |

TABLE 2-continued

| Methylation Threshold for Cancerous Thyroid Nodule | | |
|---|---|---|
| Chromosome | Chromosomal Position | Uracil level in reacted thyroid nodule DNA from cancer tissues is about above indicated level* |
| chr9 | 140205985 | 75.00 |
| chr9 | 140205989 | 83.33 |
| chr9 | 140205997 | 79.17 |

*Level values provided are the proportion (percentage) of reacted thyroid nodule DNA molecules having a uracil at the methylation site of interest. When amplicons generated from reacted thyroid nodule DNA molecules (e.g., by PCR) are used to assess the level of methylation, the values provided correspond to the proportion of amplicons having a thymidine at the nucleotide position that corresponds to the methylation site of interest.

In embodiments, the uracil level is above a threshold as set forth in Table 3 in subjects with benign thyroid nodules. In embodiments, the thymidine level is above a threshold as set forth in Table 3 in subjects with benign thyroid nodules.

TABLE 3

| Threshold for Benign Thyroid Nodule | | |
|---|---|---|
| Chromosome | Chromosomal Position | Uracil level in reacted thyroid nodule DNA from benign tissues is about above indicated level* |
| chr1 | 2996653 | 88.84 |
| chr1 | 27640460 | 80.56 |
| chr10 | 126172714 | 80.00 |
| chr10 | 126172747 | 84.62 |
| chr11 | 36057726 | 79.63 |
| chr11 | 48070143 | 84.38 |
| chr11 | 48070163 | 87.50 |
| chr11 | 48070166 | 84.38 |
| chr11 | 48070174 | 84.48 |
| chr12 | 77266621 | 73.53 |
| chr14 | 97524282 | 88.89 |
| chr14 | 104209000 | 80.77 |
| chr14 | 104209068 | 83.33 |
| chr15 | 77984014 | 88.89 |
| chr16 | 3023231 | 84.00 |
| chr16 | 79333435 | 89.61 |
| chr17 | 1509928 | 88.46 |
| chr17 | 1509945 | 88.46 |
| chr17 | 1509952 | 83.93 |
| chr17 | 1509953 | 85.00 |
| chr17 | 7644013 | 85.42 |
| chr17 | 48596391 | 88.64 |
| chr19 | 5013982 | 83.33 |
| chr19 | 10463956 | 86.73 |
| chr19 | 10464137 | 89.29 |
| chr19 | 47173037 | 88.64 |
| chr2 | 3454277 | 84.78 |
| chr2 | 8793724 | 78.57 |
| chr2 | 55289272 | 75.00 |
| chr2 | 122014529 | 86.36 |
| chr2 | 218221671 | 85.19 |
| chr22 | 38307317 | 89.66 |
| chr4 | 8372861 | 85.71 |
| chr6 | 3394325 | 87.84 |
| chr6 | 3887581 | 85.71 |
| chr6 | 1.59E+08 | 86.84 |
| chr8 | 22548399 | 88.16 |
| chr8 | 22548483 | 87.50 |
| chr8 | 1.34E+08 | 80.00 |
| chr9 | 16197862 | 86.36 |

*Level values provided are the proportion (percentage) of reacted thyroid nodule DNA molecules having a uracil at the methylation site of interest. When amplicons generated from reacted thyroid nodule DNA molecules (e.g., by PCR) are used to assess the level of methylation, the values provided correspond to the proportion of amplicons having a thymidine at the nucleotide position that corresponds to the methylation site of interest.

In embodiments, the uracil level is below a threshold as set forth in Table 4 in subjects with benign thyroid nodule. In embodiments, the thymidine level is below a threshold as set forth in Table 4 in subjects with benign thyroid nodule.

TABLE 4

| Methylation Threshold for Benign Thyroid Nodule | | |
|---|---|---|
| Chromosome | Chromosomal Position | Uracil level in reacted thyroid nodule DNA from benign tissues is about below indicated level* |
| chr1 | 12655938 | 69.23 |
| chr1 | 29565080 | 60.00 |
| chr1 | 46713777 | 73.33 |
| chr1 | 46914121 | 60.00 |
| chr1 | 46955744 | 77.78 |
| chr1 | 55008344 | 60.00 |
| chr1 | 156676611 | 84.62 |
| chr1 | 212587673 | 80.00 |
| chr1 | 233430972 | 86.67 |
| chr10 | 116391763 | 75.00 |
| chr11 | 556355 | 75.00 |
| chr11 | 68608767 | 73.33 |
| chr11 | 115530032 | 79.49 |
| chr11 | 119293593 | 60.00 |
| chr12 | 31004558 | 81.82 |
| chr12 | 45610695 | 83.33 |
| chr12 | 45610701 | 86.67 |
| chr12 | 45610702 | 89.47 |
| chr12 | 45610706 | 80.00 |
| chr12 | 54145732 | 82.35 |
| chr12 | 54145741 | 76.47 |
| chr12 | 54145825 | 70.59 |
| chr13 | 20735797 | 82.35 |
| chr13 | 23500419 | 68.42 |
| chr13 | 53313426 | 60.00 |
| chr13 | 113807393 | 27.27 |
| chr14 | 90850454 | 54.55 |
| chr14 | 103541602 | 52.00 |
| chr15 | 65186440 | 55.56 |
| chr15 | 68851629 | 63.64 |
| chr15 | 75251486 | 60.00 |
| chr15 | 83952081 | 72.73 |
| chr16 | 1458639 | 75.00 |
| chr16 | 88701114 | 66.67 |
| chr16 | 89988308 | 83.33 |
| chr16 | 89988644 | 47.37 |
| chr17 | 35278031 | 28.42 |
| chr17 | 40826257 | 23.81 |
| chr17 | 43037426 | 33.33 |
| chr17 | 43510142 | 81.82 |
| chr17 | 47987828 | 69.23 |
| chr17 | 73584599 | 60.00 |
| chr18 | 19751759 | 33.33 |
| chr18 | 56887181 | 60.00 |
| chr19 | 3434917 | 40.00 |
| chr19 | 3434921 | 42.86 |
| chr19 | 3434930 | 57.14 |
| chr19 | 3434939 | 71.43 |
| chr19 | 3434952 | 71.43 |
| chr19 | 3434954 | 60.00 |
| chr19 | 3434962 | 71.43 |
| chr19 | 3434964 | 71.43 |
| chr19 | 3434979 | 66.67 |
| chr19 | 3434985 | 55.56 |
| chr19 | 8428573 | 75.00 |
| chr19 | 13266925 | 66.67 |
| chr19 | 13266934 | 66.67 |
| chr19 | 13266970 | 63.64 |
| chr19 | 13842142 | 76.47 |
| chr19 | 14248494 | 73.91 |
| chr19 | 17346702 | 85.71 |
| chr19 | 17346735 | 78.95 |
| chr19 | 18415877 | 47.83 |
| chr19 | 18415890 | 47.83 |
| chr19 | 35531842 | 83.33 |
| chr19 | 44303112 | 77.78 |
| chr19 | 47778278 | 66.67 |

TABLE 4-continued

Methylation Threshold for Benign Thyroid Nodule

| Chromosome | Chromosomal Position | Uracil level in reacted thyroid nodule DNA from benign tissues is about below indicated level* |
|---|---|---|
| chr19 | 47778298 | 83.33 |
| chr2 | 42329402 | 78.95 |
| chr2 | 42329494 | 60.00 |
| chr2 | 73143689 | 77.78 |
| chr2 | 219745335 | 81.82 |
| chr20 | 34206950 | 76.47 |
| chr20 | 62588571 | 50.00 |
| chr20 | 62588579 | 38.46 |
| chr22 | 37447953 | 73.33 |
| chr22 | 37914998 | 69.23 |
| chr3 | 13323642 | 72.73 |
| chr3 | 45209073 | 60.00 |
| chr3 | 45209207 | 83.33 |
| chr3 | 195636893 | 84.62 |
| chr5 | 177541401 | 69.23 |
| chr5 | 180018672 | 72.73 |
| chr5 | 180101026 | 64.71 |
| chr6 | 7728692 | 73.33 |
| chr6 | 34203617 | 45.45 |
| chr6 | 37751320 | 78.57 |
| chr6 | 41410682 | 77.78 |
| chr6 | 41438516 | 39.13 |
| chr7 | 73508602 | 85.71 |
| chr8 | 21647308 | 71.43 |
| chr9 | 34591313 | 80.00 |
| chr9 | 98225096 | 22.22 |
| chr9 | 132083428 | 70.59 |

*Level values provided are the proportion (percentage) of reacted thyroid nodule DNA molecules having a uracil at the methylation site of interest. When amplicons generated from reacted thyroid nodule DNA molecules (e.g., by PCR) are used to assess the level of methylation, the values provided correspond to the proportion of amplicons having a thymidine at the nucleotide position that corresponds to the methylation site of interest.

In embodiments, the method of detecting methylation or unmethylation of a thyroid nodule DNA is of a candidate thyroid cancer patient. In embodiments, the subject is suspected of having thyroid cancer. In embodiments, the subject has thyroid cancer.

In embodiments, the method of detecting methylation or unmethylation of a thyroid nodule DNA is based on the level of uracil as set forth Table 2, in which the uracil level above the threshold identifies the thyroid nodule as a cancerous thyroid nodule. In embodiments, the method of detecting methylation or unmethylation of a thyroid nodule DNA is based on a level of thymidine indicated in Table 2, in which the thymidine level above the threshold identifies the thyroid nodule as a cancerous thyroid nodule. In embodiments, the level is the proportion of molecules (e.g., in a plurality of reacted thyroid nodule DNA molecules or a plurality of reacted thyroid nodule DNA amplicons) having a uracil or thymidine as determined by a quantitation method. Non-limiting examples of quantitation methods include sequencing and microarray methods.

In embodiments, the method of detecting methylation or unmethylation of a thyroid nodule DNA is based on the level of uracil as set forth Table 3, in which the uracil level above the threshold identifies the thyroid nodule as a benign thyroid nodule. In embodiments, the method of detecting methylation or unmethylation of a thyroid nodule DNA is based on a level of thymidine indicated in Table 3, in which the thymidine level above the threshold identifies the thyroid nodule as a benign thyroid nodule. In embodiments, the level is the proportion of molecules (e.g., in a plurality of reacted thyroid nodule DNA molecules or a plurality of reacted thyroid nodule DNA amplicons) having a uracil or thymidine as determined by a quantitation method.

In embodiments, the method of detecting methylation or unmethylation of a thyroid nodule DNA is based on the level of uracil as set forth Table 4, in which the uracil level below the threshold identifies the thyroid nodule as a benign thyroid nodule. In embodiments, the method of detecting methylation or unmethylation of a thyroid nodule DNA is based on a level of thymidine indicated in Table 4, in which the thymidine level below the threshold identifies the thyroid nodule as a benign thyroid nodule. In embodiments, the level is the proportion of molecules (e.g., in a plurality of reacted thyroid nodule DNA molecules or a plurality of reacted thyroid nodule DNA amplicons) having a uracil or thymidine as determined by a quantitation method.

In embodiments, the thyroid nodule is a specimen obtained by biopsy or by surgical resection of a subject.

In embodiments, the subject has undergone thyroid surgery, radiation therapy, radioactive iodine therapy, chemotherapy, thyroid hormone therapy, and administration of an active agent before the subject undergoes the method of detecting methylation or unmethylation of a thyroid nodule DNA.

In embodiments, the method includes a determination of prognosis for local recurrence in thyroid cancer. In embodiments, the method includes determination of prognosis of distant recurrence of thyroid cancer.

In embodiments, the method of detecting DNA methylation level in DNA of thyroid nodule may lead to changes in therapeutic regimen for treating the subject. In embodiments a subject identified as having thyroid cancer may be treated with tyrosine kinase inhibitors.

In embodiments, the active agent administered to a subject before or after detecting the level of methylation or unmethylation is: Cabozantinib-S-Malate, Caprelsa® (Vandetanib). Cometriq® (Cabozantinib-S-Malate), Doxorubicin Hydrochloride, Lenvatinib Mesylate, Lenvima® (Lenvatinib Mesylate), Nexavar® (Sorafenib Tosylate), Sorafenib Tosylate, and/or Vandetanib.

Method of Determining Thyroid Cancer or Risk of Developing Thyroid Cancer

In an aspect, provided herein is a method of determining a thyroid cancer or risk of developing thyroid cancer in a subject in need thereof. The method involves:

(i) isolating a thyroid nodule DNA molecule from a thyroid nodule of the subject thereby forming an isolated thyroid nodule DNA molecule;

(ii) contacting the isolated thyroid nodule DNA molecule with a bisulfite salt (such as sodium bisulfite) thereby forming a reacted thyroid nodule DNA molecule; and (iii) detecting the presence or absence of uracil in the reacted thyroid nodule DNA molecule at a methylation site set forth in Table 1; thereby detecting the thyroid cancer in the subject.

In an aspect, provided herein is a method of detecting a thyroid cancer or risk of developing thyroid cancer in a subject in need thereof, comprising (i) isolating a plurality of thyroid nodule DNA molecules from the thyroid nodule of the subject thereby forming a plurality of isolated thyroid nodule DNA molecules, (ii) contacting the plurality of isolated thyroid nodule DNA molecules with the bisulfite salt thereby forming a plurality of reacted thyroid nodule DNA molecules, (iii) detecting the level of reacted thyroid nodule DNA molecules in the plurality of reacted thyroid nodule DNA molecules having a uracil at a methylation site set forth in Table 1; thereby detecting the thyroid cancer in the subject.

In an aspect, provided herein is a method of detecting a thyroid cancer or risk of developing thyroid cancer in a subject in need thereof, comprising (i) isolating a plurality of thyroid nodule DNA molecules from the thyroid nodule of the subject thereby forming a plurality of isolated thyroid nodule DNA molecules, (ii) contacting the plurality of isolated thyroid nodule DNA molecules with the bisulfite salt thereby forming a plurality of reacted thyroid nodule DNA molecules, (iii) detecting the presence or absence of uracil in a reacted thyroid nodule DNA molecule at a methylation site set forth in Table 1, thereby detecting methylation or unmethylation of the thyroid nodule DNA molecule of the subject.

In an aspect, provided herein is a method of detecting a thyroid cancer or risk of developing thyroid cancer in a subject in need thereof. The method includes: (i) isolating a thyroid nodule DNA molecule from a thyroid nodule of the subject thereby forming an isolated thyroid nodule DNA molecule, (ii) contacting the isolated thyroid nodule DNA molecule with a bisulfite salt (such as sodium bisulfite) thereby forming a reacted thyroid nodule DNA molecule, (iii) amplifying the reacted thyroid nodule DNA molecule thereby forming a reacted thyroid nodule DNA amplicon molecule, (iv) detecting the presence or absence of thymidine in a reacted thyroid nodule DNA amplicon molecule at a methylation site set forth in Table 1, thereby detecting methylation or unmethylation of the thyroid nodule DNA molecule of the subject. In embodiments, contacting the isolated thyroid nodule DNA with a bisulfite salt comprises adding a solution comprising the bisulfite salt to a solution comprising the isolated single stranded DNA.

In an aspect, provided herein is a method of detecting a thyroid cancer or risk of developing thyroid cancer in a subject in need thereof, comprising (i) isolating a plurality of thyroid nodule DNA molecules from the thyroid nodule of the subject thereby forming a plurality of isolated thyroid nodule DNA molecules, (ii) contacting the plurality of isolated thyroid nodule DNA molecules with the bisulfite salt thereby forming a plurality of reacted thyroid nodule DNA molecules, (iii) amplifying the plurality of reacted thyroid nodule DNA molecules thereby forming a plurality of reacted thyroid nodule DNA amplicon molecules, (iv) detecting one or more thyroid nodule DNA amplicon molecules within the plurality of reacted thyroid nodule DNA amplicon molecules having a thymidine at a methylation site set forth in Table 1, thereby detecting methylation or unmethylation of the thyroid nodule DNA molecule of the subject.

In embodiments, detecting one or more thyroid nodule DNA amplicon molecules comprises detecting the level of one or more one or more thyroid nodule DNA amplicon molecules. In embodiments, detecting one or more thyroid nodule DNA amplicon molecules comprises detecting the level of reacted thyroid nodule DNA amplicon molecules in the plurality of reacted thyroid nodule DNA amplicon molecules having a thymidine at a methylation site set forth in Table 1, thereby detecting the level of methylation or unmethylation in the plurality of thyroid nodule DNA molecules of the subject.

In embodiments, detecting a level includes determining the number (e.g. quantitating) or molecules having, e.g., a thymidine or a uracil. In embodiments, detecting a level includes detecting the portion or proportion of a population or plurality of molecules having, e.g., a thymidine or a uracil.

In embodiments, contacting the isolated thyroid nodule DNA with a bisulfite salt comprises adding a solution comprising the bisulfite salt to a solution comprising the isolated thyroid nodule DNA.

In embodiments, the method of determining a thyroid cancer or risk of developing thyroid cancer in a subject in need thereof includes selecting a subject that has or is at risk for developing thyroid cancer. In embodiments, the subject (a) is a woman; (b) is about 20 to about 55 years old; (c) has a mutated Ret Proto-Oncogene; (d) has a grandparent, parent, or sibling who has been diagnosed with thyroid cancer, (e) self-identifies as being Caucasian or Asian; and/or (f) has or has had breast cancer.

In embodiments, the method includes detecting methylation or unmethylation at a plurality of methylation sites set forth in Table 1. In embodiments, the plurality of methylation sites comprises at least about 2, 3, 4, 5, 10, 25, 50, 75, 80, 85, 90, 100, 150, 200, 250, 300, 350, 400, 450, 500, or 550, or 5-550 methylation sites. In embodiments, the plurality of methylation sites comprises less than about 550, 500, 450, 400, 350, 300, 250, 200, 150, 100, 90, 85, 80, 75, 50, 25, or 10 methylation sites. In embodiments, the plurality of methylation sites is about 5, 6, 7, 8, 9, 10, 11, 12, 13, 14, 15, 16, 17, 18, 19, 20, 25, 50, 75, 80, 85, 90, 100, 150, 200, 250, 300, 350, 400, 450, 500, or 550, or 5-550 methylation sites. In embodiments, the plurality of methylation sites includes two or more methylation sites set forth in Table 1 and no other methylation sites.

In embodiments, a method provided herein is practiced for a subject more than once over time. In embodiments, methylation or unmethylation of thyroid nodule DNA from a subject is assessed using a method provided herein at least 1, 2, 3, 4, 5, 6, 7, 8, 9, 10 or more times. In embodiments, the method is repeated at least once every 4, 6, 8, 12 or 18 months, or at least once every 2, 3, 4, or 5 more years.

In embodiments, the method of determining a thyroid cancer or risk of developing thyroid cancer in a subject in need thereof includes determining alteration in methylation at a plurality of methylation sites set forth in Table 1. In embodiments, the method comprises: (i) isolating DNA from multiple cells of a thyroid nodule of the subject thereby forming a plurality of isolated thyroid nodule DNA molecules, (ii) contacting the plurality of isolated thyroid nodule DNA molecules with a bisulfite salt thereby forming a plurality of reacted thyroid nodule DNA molecules, (iii) detecting the proportion of DNA molecules in the plurality of reacted thyroid nodule DNA molecules having a uracil at a methylation site set forth in Table 1.

In embodiments, the method of determining a thyroid cancer or risk of developing thyroid cancer in a subject in need thereof includes alteration. i.e., increase or loss of uracil level at plurality of methylation sites. In embodiments, the method of determining a thyroid cancer or risk of developing thyroid cancer in a subject in need thereof includes alteration, i.e., increase or loss of thymidine level at plurality of methylation sites.

In embodiments, the method of determining a thyroid cancer or risk of developing thyroid cancer in a subject in need thereof includes determining a uracil level which is above a threshold as set forth in Table 2. In embodiments, the method of determining a thyroid cancer or risk of developing thyroid cancer in a subject in need thereof includes determining a thymidine level which is above a threshold indicated in Table 2. In embodiments, the level is the proportion of molecules (e.g., in a plurality of reacted thyroid nodule DNA molecules or a plurality of reacted thyroid nodule DNA amplicons) having a uracil or thymidine as determined by a quantitation method.

In embodiments, the method of determining a thyroid cancer or risk of developing thyroid cancer in a subject in need thereof includes determining a uracil level which is above a threshold as set forth in Table 3. In embodiments, the method of determining a thyroid cancer or risk of developing thyroid cancer in a subject in need thereof includes determining a thymidine level which is above a threshold indicated in Table 3. In embodiments, the level is the proportion of molecules (e.g., in a plurality of reacted thyroid nodule DNA molecules or a plurality of reacted thyroid nodule DNA amplicons) having a uracil or thymidine as determined by a quantitation method.

In embodiments, the method of determining a thyroid cancer or risk of developing thyroid cancer in a subject in need thereof includes determining a uracil level which is below a threshold as set forth in Table 4. In embodiments, the method of determining a thyroid cancer or risk of developing thyroid cancer in a subject in need thereof includes determining a thymidine level which is below a threshold indicated in Table 4. In embodiments, the level is the proportion of molecules (e.g., in a plurality of reacted thyroid nodule DNA molecules or a plurality of reacted thyroid nodule DNA amplicons) having a uracil or thymidine as determined by a quantitation method.

In embodiments, the method of determining a thyroid cancer or risk of developing thyroid cancer involves a candidate thyroid cancer patient. In embodiments, the subject is suspected of having thyroid cancer. In embodiments, the subject has thyroid cancer.

In embodiments, the method of determining a thyroid cancer or risk of developing thyroid cancer in a subject in need thereof includes determining a uracil level in which a threshold above the threshold set forth in Table 2 identifies the thyroid nodule as a cancerous thyroid nodule. In embodiments, the method of determining a thyroid cancer or risk of developing thyroid cancer in a subject in need thereof includes determining a thymidine level in which a threshold above the threshold indicated in Table 2 identifies the thyroid nodule as a cancerous thyroid nodule. In embodiments, the level is the proportion of molecules (e.g., in a plurality of reacted thyroid nodule DNA molecules or a plurality of reacted thyroid nodule DNA amplicons) having a uracil or thymidine as determined by a quantitation method.

In embodiments, the method of determining a thyroid cancer or risk of developing thyroid cancer in a subject in need thereof includes determining a uracil level in which a threshold above the threshold set forth in Table 3 identifies the thyroid nodule as a benign thyroid nodule. In embodiments, the method of determining a thyroid cancer or risk of developing thyroid cancer in a subject in need thereof includes determining a thymidine level in which a threshold above the threshold indicated in Table 3 identifies the thyroid nodule as a benign thyroid nodule. In embodiments, the level is the proportion of molecules (e.g., in a plurality of reacted thyroid nodule DNA molecules or a plurality of reacted thyroid nodule DNA amplicons) having a uracil or thymidine as determined by a quantitation method.

In embodiments, the method of determining a thyroid cancer or risk of developing thyroid cancer in a subject in need thereof includes determining a uracil level in which a threshold below the threshold set forth in Table 4 identifies the thyroid nodule as a benign thyroid nodule. In embodiments, the method of determining a thyroid cancer or risk of developing thyroid cancer in a subject in need thereof includes determining a thymidine level in which a threshold below the threshold indicated in Table 4 identifies the thyroid nodule as a benign thyroid nodule. In embodiments, the level is the proportion of molecules (e.g., in a plurality of reacted thyroid nodule DNA molecules or a plurality of reacted thyroid nodule DNA amplicons) having a uracil or thymidine as determined by a quantitation method.

In embodiments, the method of determining a thyroid cancer or risk of developing thyroid cancer in a subject in need thereof includes determining a uracil level in DNA of a thyroid nodule specimen obtained by biopsy or by surgical resection of a subject. In embodiments, the method of determining a thyroid cancer or risk of developing thyroid cancer in a subject in need thereof includes determining a thymidine level in DNA of a thyroid nodule specimen obtained by biopsy or by surgical resection of a subject.

In embodiments, the method of determining a thyroid cancer or risk of developing thyroid cancer is of a subject who has previously undergone thyroid surgery, radiation therapy, radioactive iodine therapy, chemotherapy, thyroid hormone therapy, and/or administration of an active agent, before the determination.

In embodiments, a subject having thyroid cancer or at risk of developing thyroid cancer was administered an active agent: Cabozantinib-S-Malate, Caprelsa (Vandetanib), Cometriq (Cabozantinib-S-Malate), Doxorubicin Hydrochloride, Lenvatinib Mesylate, Lenvima (Lenvatinib Mesylate), Nexavar (Sorafenib Tosylate). Sorafenib Tosylate, and/or Vandetanib.

In embodiments, the method of determining a thyroid cancer may lead to changes in therapeutic regimen for treating the subject. In embodiments a subject identified as having thyroid cancer may be treated with tyrosine kinase inhibitors. In embodiments, a subject identified as having thyroid cancer or being at risk of developing thyroid cancer according to a method disclosed herein is advised and/or directed to receive additional screening and/or treatment for thyroid cancer.

In embodiments, the active agent administered to a subject after determining thyroid cancer is: Cabozantinib-S-Malate, Caprelsa (Vandetanib), Cometriq (Cabozantinib-S-Malate), Doxorubicin Hydrochloride. Lenvatinib Mesylate, Lenvima (Lenvatinib Mesylate), Nexavar (Sorafenib Tosylate). Sorafenib Tosylate, and/or Vandetanib.

Method of Treating Thyroid Cancer

Also provided herein is a method of treating thyroid cancer in a subject by administering to the subject an active agent for treating thyroid cancer, in which the subject is identified for treatment by a method including isolating a thyroid nodule DNA molecule from a thyroid nodule of the subject thereby forming an isolated thyroid nodule DNA molecule; contacting the isolated thyroid nodule DNA molecule with a bisulfite salt (such as sodium bisulfite) thereby forming a reacted thyroid nodule DNA molecule; and detecting the presence or absence of uracil in the reacted thyroid nodule DNA molecule at a methylation site set forth in Table 1; thereby detecting the thyroid cancer in the subject. In embodiments, contacting the isolated thyroid nodule DNA with a bisulfite salt comprises adding a solution comprising the bisulfite salt to a solution comprising the isolated thyroid nodule DNA.

In embodiments, the method includes detecting methylation or unmethylation at a plurality of methylation sites set forth in Table 1. In embodiments, the plurality of methylation sites comprises at least about 2, 3, 4, 5, 10, 25, 50, 75, 80, 85, 90, 100, 150, 200, 250, 300, 350, 400, 450, 500, or 550, or 5-550 methylation sites. In embodiments, the plurality of methylation sites comprises less than about 550, 500, 450, 400, 350, 300, 250, 200, 150, 100, 90, 85, 80, 75, 50, 25, or 10 methylation sites. In embodiments, the plurality of methylation sites is about 5, 6, 7, 8, 9, 10, 11, 12, 13, 14, 15, 16, 17, 18, 19, 20, 25, 50, 75, 80, 85, 90, 100, 150, 200, 250, 300, 350, 400, 450, 500, or 550, or 5-550 methylation sites. In embodiments, the plurality of methylation sites includes two or more methylation sites set forth in Table 1 and no other methylation sites.

In embodiments, a method provided herein is practiced for a subject more than once over time. In embodiments, methylation or unmethylation of thyroid nodule DNA from a subject is assessed using a method provided herein at least 1, 2, 3, 4, 5, 6, 7, 8, 9, 10 or more times. In embodiments, the method is repeated at least once every 4, 6, 8, 12 or 18 months, or at least once every 2, 3, 4, or 5 more years.

In embodiments, the method of treating a thyroid cancer in a subject in need thereof includes determining alteration in methylation at a plurality of methylation sites set forth in Table 1.

In embodiments, the method of treating a thyroid cancer in a subject in need thereof includes alteration which includes increase or loss of uracil level at plurality of methylation sites.

In embodiments, the method of treating a thyroid cancer in a subject in need thereof includes determining a uracil level which is above a threshold as set forth in Table 2. In embodiments, the method of treating a thyroid cancer in a subject in need thereof includes determining a thymidine level which is above a threshold indicated in Table 2. In embodiments, the level is the proportion of molecules (e.g., in a plurality of reacted thyroid nodule DNA molecules or a plurality of reacted thyroid nodule DNA amplicons) having a uracil or thymidine as determined by a quantitation method.

In embodiments, the method of treating a thyroid cancer in a subject in need thereof includes determining a uracil level which is above a threshold as set forth in Table 3. In embodiments, the method of treating a thyroid cancer in a subject in need thereof includes determining a thymidine level which is above a threshold indicated in Table 3. In embodiments, the level is the proportion of molecules (e.g., in a plurality of reacted thyroid nodule DNA molecules or a plurality of reacted thyroid nodule DNA amplicons) having a uracil or thymidine as determined by a quantitation method.

In embodiments, the method of treating a thyroid cancer in a subject in need thereof includes determining a uracil level which is below a threshold as set forth in Table 4. In embodiments, the method of treating a thyroid cancer in a subject in need thereof includes determining a thymidine level which is below a threshold indicated in Table 4. In embodiments, the level is the proportion of molecules (e.g., in a plurality of reacted thyroid nodule DNA molecules or a plurality of reacted thyroid nodule DNA amplicons) having a uracil or thymidine as determined by a quantitation method.

In embodiments, the method of treating a thyroid cancer is in a subject who has undergone surgery, radiation therapy, radioactive iodine therapy, chemotherapy, or thyroid hormone therapy, before the detecting thyroid cancer.

In embodiments, an active agent administered to a subject for treating thyroid cancer: Cabozantinib-S-Malate, Caprelsa (Vandetanib), Cometriq (Cabozantinib-S-Malate). Doxorubicin Hydrochloride, Lenvatinib Mesylate, Lenvima (Lenvatinib Mesylate). Nexavar (Sorafenib Tosylate), Sorafenib Tosylate, and/or Vandetanib.

In embodiments, the subject has or is at risk of papillary thyroid cancer, follicular thyroid cancer, medullary thyroid cancer, or anaplastic thyroid cancer.

In embodiments, the method includes determining a papillary thyroid carcinoma (PTC) methylation alteration score for the subject, wherein the PTC methylation alteration score is equal to the number of methylation sites in Table 1 having a uracil level equal to or greater than the corresponding threshold level set forth in Table 2.

In embodiments, the method includes determining a PTC methylation alteration score for the subject, wherein the PTC methylation alteration score is equal to the number of methylation sites in Table 1 having a thymidine level equal to or greater than the corresponding threshold level set forth in Table 2.

In embodiments, the method includes determining a benign thyroid nodule (BTN) methylation alteration score for said subject, wherein the BTN methylation alteration score is equal to: (a) the number of methylation sites in Table 1 having a uracil level equal to or greater than the corresponding threshold level set forth in Table 3; (b) the number of methylation sites in Table 1 having a uracil level equal to or less than the corresponding threshold level set forth in Table 4; or (c) the number of methylation sites in Table 1 having a uracil level equal to or greater than the corresponding threshold level set forth in Table 3 plus the number of methylation sites in Table 1 having a uracil level equal to or less than the corresponding threshold level set forth in Table 4.

In embodiments, the method includes determining a benign thyroid nodule (BTN) methylation alteration score for said subject, wherein the BTN methylation alteration score is equal to: (a) the number of methylation sites in Table 1 having a thymidine level equal to or greater than the corresponding threshold level set forth in Table 3; (b) the number of methylation sites in Table 1 having a thymidine level equal to or less than the corresponding threshold level set forth in Table 4; or (c) the number of methylation sites in Table 1 having a thymidine level equal to or greater than the corresponding threshold level set forth in Table 3 plus the number of methylation sites in Table 1 having a thymidine level equal to or less than the corresponding threshold level set forth in Table 4.

In embodiments, the method comprises calculating a Composite Cancer Risk Score for the subject. In embodiments, the Composite Cancer Risk Score for the subject equals: [the PTC methylation alteration score for said subject]/[BTN methylation alteration score for said subject]. In embodiments, the Composite Cancer Risk Score for the subject equals: [(the PTC methylation alteration score for said subject)+1]/[(BTN methylation alteration score for said subject)+1].

In embodiments, the subject is identified as being at risk of developing thyroid cancer or diagnosed as having thyroid cancer if (a) the PTC methylation alteration score for the subject is at least 5, 6, 7, 8, 9, or 10; (b) the BTN methylation alteration score for the subject is at least 5, 6, 7, 8, 9, or 10; and/or (c) the Composite Cancer Risk Score for the subject is at least about 2, 2.1, 2.2, 2.3, 2.4, 2.5, 2.6, 2.7, 2.8, 2.9, or 3.0.

In embodiments, the subject receives treatment (e.g., is directed or advised to receive treatment) for thyroid cancer or is directed to receive additional screening for thyroid cancer if (a) the PTC methylation alteration score for the subject is at least 5, 6, 7, 8, 9, or 10; (b) the BTN methylation alteration score for the subject is at least 5, 6, 7, 8, 9, or 10; and/or (c) the Composite Cancer Risk Score for the subject is at least about 2, 2.1, 2.2, 2.3, 2.4, 2.5, 2.6, 2.7, 2.8, 2.9, or 3.0.

Target Sites for Methylation Level of Thyroid Nodule

In another aspect, provided herein is a deoxyribonucleic acid 5 to 100, 5 to 300, 5 to 300, or at least about 5, 50, 100, 150, 200, 250, 300, or more nucleotides in length including a uracil-containing sequence identical to the sequence of at least 5 contiguous nucleotides within a sequence including SEQ ID NO: 1 to SEQ ID NO:550.

SEQ ID NO: 1 to SEQ ID NO:500 are 300 bp length sequences that include the target sites (i.e., methylation sites of interest). The sequences provided are as modified after bisulfite conversion. Therefore "C" in the non-CpG context becomes "U", and C in the CpG context is designated as R or X (either "U" either "C"), where X is the target site. The DNA strands (sense and antisense) are no longer complementary after bisulfite conversion. Therefore, each DNA strand is identified with its unique sequence, and is designated as "forward" and "reverse" respectively, in Table 1.

The sequences listed in Table 1 are provided below with their respective sequence identification number.

| SEQ ID NO: | Sequence |
|---|---|
| 1 | TUUTTAGUUUTURGTGGRGUUAGAGTTGGTTGUUTUAGTAGRGRGTGUUUAUURGG<br>UUUAAAGUTGTTUTGUAGUTGGTUAUTGTGGGAGAAGAGAUTGGAAAAGTTUAAAG<br>GTGGAGAGGRGGUAGRGATUTGGAGUAUTTTTURGUAXGUTGTAAUUUUTGAGAAG<br>AAAUAAAGAGGAAARGAGGUTGTTTAGATAATUURGGGUUUTGGTGUTTGUATTTA<br>GAAAAATTAGGUUUTUTGAAAAATTAUAGAATTATGUTGUUAGTGTUAGGTTUUU<br>AGATAATGATGTGTUTGTGT |
| 2 | UAUAGAUAUATUATTATUTGGGAAUUTGAUAUTGGUAGUATAATTUTGTAATTTTT<br>UAAGAGGGUUTAATTTTTUTAAATGUAAGUAUUAGGGUURGGGATTATUTAAAUAG<br>UUTRGTTTUUTUTTTGTTTUTTUTUAGGGGTTAUAGXGTGRGGAAAAGTGUTUUAGA<br>TRGUTGURGUUTUTUUAUUTTTGAAUTTTTUUAGTUTUTTUTUUUAUAGTGAUUAGU<br>TGUAGAAUAGUTTTGGGURGGGTGGGUARGRGUTAUTGAGGUAAUUAAUTUTGGRG<br>UUARGGAGGGUTAAGGAU |
| 3 | GGGTGAUUAGTGUUAUTAAAAGUAGAGUTTGAGTTTAUTUTUATAAUUATRGGUTG<br>TGGGUUAGAUATTTGGUTGUTTTGUAGGUAGAUUAGGUTTUURGGTGAGTUATGUT<br>GUTTAAAATGUTGTUTGGGAARGUAGAGAAAGTUTAAAXGUUAAGARGUTGAGGA<br>UAGUUURGUAGGTGGAUTGUUATGUURGGUTRGGUUUUTTTTTGGTUUUUAGAGTG<br>GAUUUTTUTUUTUUUUAUAGAGGGGAGGUATUTGATGGTGGUTTUAGUAGAUAAU<br>UTGGAGAAGAAUUAUTUAGGGT |
| 4 | AUUUTGAGTGGTTUTTUTUUAGGTTGTUTGUTGAAGUAUUATUAGATGUUTUUUU<br>TUTGTGGGGAGGAGAAGGGTUUAUTUTGGGGAUUAAAAAGGGGURGAGURGGGUA<br>TGGUAGTUUAUUTGRGGGGUTGTUUTUAGRGTUTTGGXGTTTAGAUTTTUTUTGRGT<br>TUUUAGAUAGUATTTAAGUAGUATGAUTUAURGGGAAGUUTGGTUTGUUTGUAAA<br>GUAGUUAAATGUTUTGGUUUAUAGURGATGGTTATGAGAGTAAAUTUAAGUTUTGUT<br>TTTAGTGGUAUTGGTUAUUU |
| 5 | CAGUTGGGGAGGGGAUAGGGTAGGTGGUTGUAGAAGGGGGUTGGGTTGAGGTUTU<br>AGGTGUAGARGAGGAGGGGUTGGGRGGAGGGGGTGAGGAGGGGAGURGGGUTGGG<br>GGURGGGRGRGUTGUTGGGGTUUUUUTUURGUUURGGGAUXGTURGUTUTTGUUUA<br>GAUURGTRGGTAAAUAGARGURGTGATGTUARGGGRGURGUTGAUUTGTGGUTGAA<br>UURGGAGUTGTAAATGAGATGUAAGGTGUUAGUAGUUTURGGURGUAGGGUUTAR<br>GAGUUAUARGRGUTUUTURGURGG |
| 6 | URGGRGGAGGAGRGRGTGTGGUTRGTAGGUUUTGRGGURGGAGGUTGUTGGUAUUT<br>TGUATUTUATTTAUAGUTURGGGTTUAGUUAUAGGTUAGRGGRGUURGTGAUATUA<br>RGGRGTUTGTTTAURGARGGGTUTGGGUAAGAGRGGAXGGTUURGGGGRGGGAGGG<br>GGAUUUUAGUAGRGUUURGGUUUUUAGUURGGUTUUUUTUUTUAUUUUUTURGUU<br>UAGUUUUTUUTRGTUTGUAUUTGAGAUUTUAAUUUAGUUUUUTTUTGUAGUUAUU<br>TAUUUTGTUUUUTUUUUAGUTG |
| 7 | TTTTUTGTAAAATGGGGURGUUUAUAAAAUTUATAAUAAAGTGTTGAGGTTURGAU<br>AAGURGAAAUUTGTGAAAAGUTTGTGTAAAUUTUAGAGUTGTAUATGGATGGTTGA<br>AGGATUTATTTRGAUAGUTURGGGGAGUXGTGGGAGGGAAGUTGAXGGXGGUTUTT<br>GUTGTTUTUUTAUUTUUUAGUUUTUURGAAGAUTUTGAGUAGUUTGGAGATUAAAG<br>GTGATTGGGGUUTGUTGGUATGGAGGURGGGUTRGGUAGAAUUTGUTTUURGGUUU<br>UUTGUUUAUUTUUUAUUUAU |
| 8 | GTGGGTGGGAGGTGGGUAGGGGGURGGGAAGUAGGTTUTGURGAGUURGGUUTUU<br>ATGUUAGUAGGUUUUAATUAUUTTTGATUTUUAGGUTGUTUAGAGTUTTRGGGAGG<br>GUTGGGAGGTAGGAGAAUAGUAAGAGUXGUXGTUAGUTTUUUTUUUAXGGUTUUU<br>RGGAGUTGTRGAAATAGATUUTTUAAUUATUUATGTAUAGUTUTGAGGTTTAUAUA<br>AGUTTTTUAUAGGTTTRGGUTTGTRGGAAUUTUAAUAUTTGTTATGAGTTTTGTGG<br>GRGGUUUUATTTTAUAGAAAA |
| 9 | TGAGUAGTGTTTUAGRGUUUAGAGAGAUAUTGTGGAGAAGGTUUAUUAGGATGUU<br>TAUUTGUUTTAUAUAAGAGUUTAAUTTTGGUAUAUUTGTGGUAUAUUTGTGGAGAG<br>UTGTTUTGGUUURGGTTGTUTGGUAGGUUTGGGUTAUTUXGAGUAGGGGAAUTGGG<br>GUAUAGTGGUTGUAUUTURGGUTATAUUUTGGTTTTTUUAGTTUUTGATGUURGUU<br>UUTUAGGTGGUAGUATGAGGTGAUTUAGGGAUAGARGUUUTTATRGTGARGUAAGT<br>UUAGUUUUUAGTGGAGUUUUT |
| 10 | AGGGGUTUUAUTGGGGGUTGGAUTTGRGTUARGATAAGGGRGTUTGTUUUTGAGTU<br>AUUTUATGUTGUUAUUTGAGGGGRGGGUATUAGGAAUTGGAAAAAUUAGGGTATA<br>GURGGAGGTGUAGUUAUTGTGUUUUAGTTUUUUTGUTXGGAGTAGUUUAGGUUTG |

-continued

| SEQ ID NO: | Sequence |
|---|---|
| | UUAGAUAAURGGGGUUAGAAUAGUTUTUUAUAGGTGTGUUAUAGGTGTGUUAAAG |
| | TTAGGUTUTTGTGTAAGGUAGGTAGGUATUUTGGTGGAUUTTUTUUAUAGTGTUTUT |
| | UTGGGRGUTGAAAUAUTGUTUA |
| 11 | TUTTGTAAAATTUUAGAGUUAGGTATAUUUAATrUTGUAARGTGGTAGUTGUATGA |
| | UTGTAUAAGTUUUTTAAUAGUAURGGGUUTUAGTGAUATUATUTGTTAAATGGGTT |
| | GGTGATGATAATGGTUAGUATTTATGGAGGAGUUUAUAXGGTGUTAAGTGUTTrAU |
| | AUATATUAGUTAAUTGAATUUTUAUTGUTGUUAATGAGAUAGGTAUTATTGAATUA |
| | GAGGUURGGAGAGAGUTUUARGRGGTTGGTUATAUTGGTGAAGAGUTTGGTTUAAT |
| | GUUTGGTGAAUTUTRGGUAU |
| 12 | GTGURGAGAGTTUAUUAGGUATTGAAUUAAGUTUTTUAUUAGTATGAUUAAURGRG |
| | TGGAGUTUTUTURGGGUUTUTGATTUAATAGTAUUTGTGTUTUATTGGUAGUAGTGAG |
| | GATTUAGTTAGUTGATATGTGTAAAGUAUTTAGUAUXGTGTGGGUTUUTUUATAAA |
| | TGUTGAUUATTATUATUAUUAAUUUATTTAAUAGATGATGTUAUTGAGGUURGGTG |
| | UTGTTAAGGGAUTTGTAUAGTUATGUAGUTAUUARGTTGUAGAATTGGGTATAUUT |
| | GGUTUTGGAATTTTAUAAGA |
| 13 | TURGGAGUUAGTGAAUTTGTGATURGGAGUUAGTTAAUTTUAUAGUTAATGTGUTG |
| | AGUAGUATTUUAGUUAGRGTUTGAAGUUAGAGUAGGGAGGRGGARGGGUUUUAGG |
| | AGTTRGAGGTURGGGAAGURGAAGUAUUAUUAAAUTGAGXGAGGTTUUAAUTUTU |
| | UUTUUUAGGAGGTURGGUTGUUTUUUAUUAGUAGUUUAAUUAUAGGGTUUTGUTU |
| | UAGARGTTAUTATTTTUTUTTTTTUAGTGTGTUUAGUAGUAAUUTRGAUTGUUAAUA |
| | AUAARGTGAAAAATAAUTGUAG |
| 14 | UTGUAGTTATTTTTUARGTTGTTGTTGGUAGTRGAGGTTGUTGUTGGAUAUAUTGAA |
| | AAAGAGAAAATAGTAARGTUTGGAGUAGGAUUUTGTGGTTGGGUTGUTGGTGGGAG |
| | GUAGURGGAUUTUUTGGGAGGGAGAGTTGGAAUUTXGUTUAGTTTGGTGGTGUTTR |
| | GGUTTUURGGAUUTRGAAUTUUTGGGGUURGTURGUUTUUTGUTUTGGUTTUAGA |
| | RGUTGGUTGGAATGUTGUTUAGUAUATTAGUTGTGAAGTTAAUTGGUTURGGATUA |
| | UAAGTTUAUTGGUTURGGA |
| 15 | TTGUUAAAAUTGGAAGUAAUUAAGATGUUUUTUAAAAGGTGAATGGAGGUUAGGT |
| | GRGGTGGUTUARGURGATAATUUUAGUAUTTTGGGAGGUTGAGGUAGGTGGATUAU |
| | TTGAGATUARGAGTTTGAGAUUAGUURGGUUAAUATGGXGAAAUUURGTUTUTAUT |
| | AAAAATAUTAAGATTAAURGGGRGTGGTGGUARGTGUUTGTTATUUUAGUTAUTTG |
| | GGAAGUTGAGGUAGGUAAATTGUUTGAAUUTGGGAGGTGGAGGTUAUAGTGAGUU |
| | AAGATTGTGUUAUTGUAUTUUA |
| 16 | TGGAGTGUAGTGGUAUAAUAUTTGGUTUAUTGTGAUUTUUAUUTUUUAGGTUAAGU |
| | AATTTGUUTGUUTUAGUTTUUUAAGTAGUTGGGATAAUAGGUARGTGUUAUUARGU |
| | URGGTTAAUTUTTAGTATTTTTAGTAGAGARGGGGTTTXGUUATGTTGGURGGGUTGG |
| | TUTUAAAUTRGTGAUTUTUAAGTGAUTUUAUUTGUUTUAGUUTUUUAAAGTGUTGGGA |
| | TTATRGGRGTGAGUUAURGUAUUTGGUUTUUAUTTUAUUTTTTGAGGGGUAUTUTGGT |
| | TGUTTUUAGTTTTGGUAA |
| 17 | GGRGGGATURGAGURGAGAUARGTGUTGGAGRGGAGURGUTTUUTUARGGTRGUUA |
| | GURGUAGAUAAUTGAUUTUUURGGUATRGRGTTRGRGGUUUTGUTGUTGGUTURGG |
| | TGTUTRGGGURGGAAUTUUTGTGGUTUUAGRGTTRGXGURGGUUAUTGGUUAGRGU |
| | TTGGGUUTRGUUUTGUAGUTURGGGGUUATAGGGUAUAGUTTTAGUTTTGAUUTUU |
| | URGTTUURGAAAGGARGUUUAAGGRGAUUTUUUAUUUUAUUTUUUUAAUTTUTU |
| | UUUUATGUTUUTGRGGUAAUTT |
| 18 | AGTTGURGUAGGAUATGGGGGAGAAGTTGGGGAGGATGGGGTGGGAGGTRGUUTTG |
| | GGRGTUUTTTRGGGAARGGGGAGGTUAAAGUTAAAGUTGTGUUUTATGGUUURGGA |
| | GUTGUAGGGRGAGGUUUAAGRGUTGGUUAGTGGURGGXGRGAARGUTGGAGUUAU |
| | AGGAGTTURGGUURGAGAUAURGGAGUUAGUAGUAGGGURGRGAARGRGATGURG |
| | GGGAGGTUAGTTGTUTGRGGUTGGRGAURGTGAGGAAGRGGUTURGUTUUAGUARG |
| | TGTUTRGGUTRGGATUURGUUU |
| 19 | UUAGUAGGGAAGGUAGUUAAUAGATGUAGAUTRGUTUTGUUTAUUTGTGGAGGUR |
| | GGTGAGGUUAGGGUUTGUTGGGAUUTGAAAUAGTGAGGUAAGTGGGTGTGTGGTGU |
| | TGGGUTUUUXGUTUAAGTTUTUUUAGXGTGUUAGTTUURGGAGUUTTATGTGUAGG |
| | GTGTTGGGGAAGGGXGGGUTGAATRGTGGGTGGGAGUTUTGGUTUAAAGUUUUAGG |
| | TGAGTGGAGGAATTGGGGGRGGAUUTGAAGUAUTGUTUUTGAAGTGGAUUTGGUAGG |
| | UUTUTTGGGUTTGTGUAGUTG |
| 20 | UAGUTGUAUAAGUUUAAGAGGUUTGUUAGGTLTUAUUTUAAGAUAGUAUTUUAGGT |
| | URGUUUUUAATTUUTUUAUTUAUUTGGGGUTTTGAGUUAAGAUTUITUAUUUARGAT |
| | TUAGUUXGUUUTTUUUUAAUAUUUTGUAUATAAGGUTURGGGAAUTGGUAXGUTG |
| | GGAGAAUTTGAGXGGGGAGUUUAGUAUUAUAUAUUUAUTTGUUTUAUTGUTTUAA |
| | GTUUUAAUAGGUUUTGGUUTUAURGGUUTUUAUAGGTAGGUAGAGRGAGUTGUA |
| | TUTGTTGGUTGUUTTUUUTGUTGG |

-continued

| SEQ ID NO: | Sequence |
|---|---|
| 21 | UUAGAUTRGUUUTUUUUAUURGGGUUTRGGAUTTTUAUUUUAGUTTUTUTUTUUTG<br>GUUAGTGATTAUUUAUUUUUAATUUUAUUURGUUURGURGRGUAAUTAUUTUUTU<br>UUTTUAUURGGAUTGGGAUUATUATUUUUAUTUUAUTUXGUUUAGTUTGGGAUTU<br>UAUUTGUUTUUTUUUUAATUUUAUAUTAATUTUTGUTTGGTUTUTTUUTUTTTGGUU<br>TAATUTUTRGTUTRGGUTTATTGGGGARGGUUAUTUTUAUAGTTTGGTTUUAAAUAU<br>UAGTTUUTGGATGGATTUUU |
| 22 | GGGAATUUATUUAGGAAUTGGTGTTTGGAAUUAAAUTGTGAGAGTGGURGTUUUUA<br>ATAAGURGAGARGAGAGATTAGGUUAAAGAGGAAGAGAUUAAGUAGAGATTAGTG<br>TGGGATTGGGGAGGAGGUAGGTGGAGTUUUAGAUTGGGXGGAGTGGAGTGGGGAT<br>GATGGTUUUAGTURGGGTGAAGGGAGGAGGTAGTTGRGRGGRGGGGRGGGGTGGG<br>ATTGGGGGTGGGTAATUAUTGGUUAGGAGAGAGAAGUTGGGGTGAAAGTURGAGG<br>UURGGGTGGGGAGGGRGAGTUTGG |
| 23 | RGUAGGUURGRGUUURGUTUURGUUURGUUTGURGRGUUTUURGGGGRGUURGUA<br>TTAAAGRGUATATGUAAGUUATGAATTATUAAUTGAAAGGAGTUAATTAURGGUTU<br>TAAAAARGAGTGTUTGRGUTRGUAGRGUUURGGGUUATUXGUUTATTTARGGAGRG<br>ATUTAUUURGUURGGUTGGGGAGGGGGUUTRGGGAGGGAGAGAGARGGAGAAARG<br>GAGUURGAGAURGGGAGAGAGURGGAGAGGUAGGGAUTGGAGAGTUTGGGAUARG<br>AAGGAGAGGRGGGGAGAGAURGA |
| 24 | TRGGTUTUTUUURGUUTUTUUTTRGTGTUUUAGAUTUTUUAGTUUUTGUUTUTURGG<br>UTUTUTUURGGTUTRGGGUTURGTTTUTURGTUTUTUTUUUTUURGAGGUUUUUTUU<br>UUAGURGGGRGGGGTAGATRGUTURGTAAATAGGXGGATGGUURGGGGRGUTGRG<br>AGRGUAGAUAUTRGTTTTTAGAGURGGTAATTGAUTUUTTTUAGTTGATAATTUATG<br>GUTTGUATATGRGUTTTAATGRGGGRGUUURGGGAGGRGRGGUAGGRGGGGRGGGA<br>GRGGGGRGRGGGUUTGRG |
| 25 | AUAGTRGUTGUAGGGAGGARGRGGGURGTGAGAAUURGGGGAUAGUUTUUUUTUT<br>TGRGGTUUTGUAGTUURGGAUUUAUTGGGRGGATUAGAAAGTTTGUAGGGAGUUA<br>GGGAUTAGGAGAUAGAUAGAUAGRGUAGGGAUAGAGAAAGXGGAGGGATGUUAG<br>AAAGAURGAGTRGGGGAUAGAUAGAGAGAUUUAGGGTGAGAUAGAGGAAGAGAT<br>AUURGGGGUTGAAAARGGTGGUAGAAAGTGAGUAAUTTAGGGAGAUAGAAAGAGR<br>GUAGAAUTRGAAATTURGAGGUAGAGA |
| 26 | TUTUTGUUTRGGAATTTRGAGTTUTGRGUTUTTTUTGTUTUUUTAAGTTGUTUAUTTT<br>UTGUUAURGTTTTUAGUUURGGGTATUTUTTUUTUTGUTUAUUUTGGGTUTUTUTG<br>TUTGTUUURGAUTRGGTUTTTUTGGUATUUUTUXGUTTTUTUTGTUUUTGRGUTGTU<br>TGTUTGTUTUUTAGTUUUTGGUTUUUTGUAAAUTTTUTGATURGUUUAGTGGGTURG<br>GGAUTGUAGGAURGUAAGAGGGGAGGUTGTUUURGGGTTUTUARGGUURGRGTUU<br>TUUUTGUAGRGAUTGT |
| 27 | TUAGUUTGTAUUURGGRGUTGGUUTUUAGAUAGUUAGGTGUTGUUTRGUARGGTUT<br>TGUTTGUAGGUTGGGGUATGAAGUAUUUTGGTATTTARGUTGGGATTGGTUTUTUA<br>UTAGGGTTGGGGRGGGUTGTGGTUAUUTGGUURGGRGXGURGUAGAGGUTGGUTUR<br>GGAGAAGAUUTGGGGGRGUAAGAUTUAGAGGUUAGAGGGTGUAGURGUTGUTGAU<br>TUATTTGRGGARGGGGRGGUTGGGAGGAGRGUTAGUUUUTGTTGTGAGRGATTTGA<br>GAGUUAGGGUUAAATUTGGGT |
| 28 | AUUUAGATTTGGUUUTGGUTUTUAAATRGUTUAUAAUAGGGGUTAGRGUTUUTUUU<br>AGURGUUURGTURGUAAATGAGTUAGUAGRGGUTGUAUUUTUTGGUTUTUTGAGTUT<br>TGRGUUUUUAGGTUTTUTURGGAGUUAGUUTUTGRGGXGRGURGGGUUAGGTGAU<br>UAUAGUURGUUUUAAUUUTAGTGAGAGAUUAATUUUAGRGTAAATAUUAGGGTGU<br>TTUATGUUUUAGUUTGUAAGUAAGAURGTGRGAGGUAGUAUUTGGUTGTUTGGAG<br>GUUAGRGURGGGGTAUAGGUTGA |
| 29 | GUUUAGUUTUAUAAAGGTGAGTGGGGUAUUUUUAGUTGURGAGUTUUUUTAGTUA<br>GUAGUUTUATAUUTUAUATTUTUUTGTGGURGUAUUTUAUAGUUURGUUURGGUU<br>UAUAGGUATUUTTAAGAAGAAGTGTUTGUUUAUUATUAGXGAGAAGAGUAGUUTU<br>UTGXGGUTUUUUUTGGAGUAATGUAUAGGGTUTTUURGGGGUTUUTURGUTAGTGA<br>GGGUAGURGGGGAGGUUUUUUTUUURGUUUAURGUUURGGUAGAGUUTUUAGGA<br>GUAGUTGAARGGGGTUATGUUUATRG |
| 30 | RGATGGGUATGAUUURGTTUAGUTGUTUUTGGAGGUTUTGURGGGGRGGTGGGRGG<br>GGAGGGGGGUUTUUURGGUTGUUUTUAUTAGRGGAGGAGUUURGGGAAGAUUUTG<br>TGUATTGUTUUAGGGGGAGUXGUAGGAGGUTGUTUTTUTXGUTGATGGTGGGUAGA<br>UAUTTUTTUTTAAGGATGUUTGTGGGURGGGGRGGGGUTGTGAGGTGRGGUUAUAG<br>GAGAATGTGAGGTATGAGGUTGUTGAUTAGGGGAGUTRGGUAGUTGGGGGTGUUU<br>UAUTUAUUTTTGTGAGGUTGGGU |
| 31 | TUAGAATAATGGUTGGTTTGTAGAGATUAGAAATGUUUAUTGUTGTTTUUTGTAT<br>UUUTUUAUUUAUUUAGAUTGAGUUTUTGAAGUTGTURGGGGUUTGGAGAGAGAAG<br>UUAUTUAAGGAUAGUAGUTGUTGAUTUAGAXGUTUAAATTUTXGGGXGGAAAAGG<br>AUUTTAGAGAATGUUTAAAATRGTGGUUUAATUUUTUATTGGAAGUTGGGGUTURG |

-continued

| SEQ ID NO: | Sequence |
|---|---|
| | AAAAGURGGGGUTURGAAAAGUTGGGAGAGUAGUUUAAAGRGTAUTGUUUAUTAA<br>ATGTGGATGUARGUTGGAURGU |
| 32 | GRGGTUUAGRGTGUATUUAUATTTAGTGGGUAGTARGUTTTGGGUTGUTUTUUUAG<br>UTTTTRGGAGUUURGGUTTTTRGGAGUUUUAGUTTUUAATGAGGGATTGGGUUARG<br>ATTTTAGGUATTUTUTAAGGTUUTTTTUXGUUXGAGAATTTGAGXGTUTGAGTUAGU<br>AGUTGUTGTUUTTGAGTGGUTTUTUTUTUUAGGUUURGGAUAGUTTUAGAGGUTUA<br>GTUTGGGTGGGTGGAGGGATAUAGGAAAUAGUAGTGGGUATTTUTGATUTUTAUAA<br>AUUAGGUUATTATTUTGGA |
| 33 | AAGTTUTGGGGUAGAAGTTGGATAAUUAGGGUUTGAGAAATAAAGATAAGAGGGT<br>ATATTUUTUUUUUAGGAGAUAAAAGAGAAGGTGGATGGAGAAGGGGAAAUTGGGU<br>UTUAGUUAGUAURGGGATGATGRGAUUAGUTTTGTUAGUAXGUTTGGGGAGUATAU<br>AUAURGUTTGUUTTGGUTGGAURGGAGAUTGTGATUAUUAUUUTTUUAAUUUATUU<br>UUUAAUARGUAGGUTGGUATGGUUARGUUUAUAGTGUUUUAAGTGUTGUUTGUUT<br>TGUAGTGAUTUAUTTUUTUTGTA |
| 34 | TAUAGAGGAAGTGAGTUAUTGUAAGGUAGGUAGUAUTTGGGGUAUTGTGGGRGTG<br>GUUATGUUAGUUTGRGTGTTGGGGGATGGGTTGGAAGGGTGGTGATUAUAGTUTUR<br>GGTUUAGUUAAGGUAAGRGGTGTGTATGUTUUUUAAGXGTGUTGAUAAAGUTGGTR<br>GUATUAUAUUURGGTGUTGGUTGAGGUUUAGTTTUUUUTTUTUUATUUAUUTTUTUTTT<br>TGTUTUUTGGGGGAGGAATATAUUUTUTTATUTTTATTTUTUAGGUUUTGGTTATUU<br>AAUTTUTGUUUUAGAAUTT |
| 35 | TUAGAARGTGUUUAUAUATGUUUATGUUUTUTATUUTGUTGAAATUUAAUUUUUU<br>UTTUAAAGGUUAUTGUAGGGAGUUTTUUUAGGGUUUAAURGGATTUAGTGUTUAU<br>UTGTTUTGTUUTGTAUAAAGRGUUUUTTTTGUUUTTTTXGTGTGTAUTTAGAGAATT<br>UTGATTTTGAUTGAATUAUUTGTGTAUTTGTTTTUTUTUAGUUTUAUUUUUAUATGG<br>TGAGUTUAURGGTUTTAUTUATTTUTGUATGAGGTAAGGGTUTRGUUUAUAUUAGG<br>TGUUAAUUAGTGUTTARGGU |
| 36 | URGTAAGUAUTGGTTGGUAUUTGGTGTGGGRGAGAUUUTTAUUTUATGUAGAAATG<br>AGTAAGAURGGTGAGUTUAUUATGTGGGGGTGAGGUTGAGAGAAAAUAAGTAUAU<br>AGGTGATTUAGTUAAAATUAGAATTUTUTAAGTAUAUAXGAAAAGGGUAAAAGGG<br>GRGUTTTGTAUAGGAUAGAAUAGGTAGAUAUTGAATURGGTTGGGUUUTGGGAAGG<br>UTUUUTGUAGTGGUUTTTGAAGGGGGGGTTGGATTTUAGUAGGATAGAGGGUATGG<br>GUATGTGTGGGUARGTTUTGAA |
| 37 | UAUUTRGTGUUUUTUAUUTGTAAGUAUTGTGAGGAGUAGUAGUAGGAAGAAAGGA<br>GAUTGGGTGUURGGTGTUATGGTGGTGGTGAAATGGGTGGGGAGGGGGUAGAAUA<br>GATTUAGGUAGGRGUTGGUTGUTTGAGAGGTGGAGXGGGUAUAGGXGUUTAURGU<br>TTTATAURGGTUUUUUUAUTUUURGUURGUURGUUUTAGGUAUAGURGGAGUAGG<br>TGAUAGGTGAUAAAAUUURGUUUUUTUUUUTAUUTUUTAUUTUTTUUTUUTUUTUU<br>UUAAUUATTUUTGGGTAGGGTAUA |
| 38 | TGTAUUUTAUUUAGGAATGGTTGGGGAGGAGGAGGAAGAGGTAGGAGGTAGGGGA<br>GGGGGRGGGGTTTTGTUAUUTGTUAUUTGUTURGGUTGTGUUTAGGGRGGGRGGGR<br>GGGGAGTGGGGGGAURGGTATAAAGRGGTAGGXGUUTGTGUUXGUTUUAUUTUTU<br>AAGUAGUUAGRGUUTGUUTGAATUTGTTUTGUUUUUTUUUUAUUUATTTUAUUAUU<br>AUUATGAUAURGGGUAUUUAGTUTUUTTTUTTUUTGUTGUTGUTAUTUAUAGTGUT<br>TAUAGGTGAGGGGUARGAGGTG |
| 39 | AGARGGAGAAAUAGAAARGGAGGTUAGGRGGGGAGUUTRGGGGAUAGGUUTGGGA<br>UURGAGGURGGAAAURGUAGAGGAGRGAAGUUTGGRGGGATGUAGTGATTGGAGU<br>UAAAGGAAURGTUURGGUUTGTUUAARGRGGGGGGGUUTTXGGUURGGTGGUUUT<br>GAGRGAAURGATGUARGTGGUUURGURGUATUUUATUUUUUAUUUTUUUUAGAUT<br>UTUUUTUUUAGUTUUTTUTGAGGRGGAAAGAAAAAUUUTAUATUTGGTUUUAGUU<br>UTGGGTUUUTGUUUTGGUUUUTUUT |
| 40 | AGGAGGGGUUAGGGUAGGGAUUUAGGGUTGGGAUUAGATGTAGGGTTTTTUTTTUR<br>GUUTUAGAAGGAGUTGGGAGGGAGAGTUTGGGGAGGGTGGGGGATGGGATGRGGR<br>GGGGUUARGTGUATRGGTTRGUTUAGGGUUAURGGGUXGAAGGUUUUUURGRGTT<br>GGAUAGGURGGGARGGTTUUTTTGGUTUUAATUAUTGUATUURGUUAGGUTTRGUT<br>UUTUTGRGGTTTURGGUUTRGGGTUUUAGGUUTGTUUURGAGGUTUUURGUUTGAU<br>UTURGTTTUTGTTTUTURGTUT |
| 41 | TUAAAUUUAGGTATTUTGGGTUTAGTRGGTGTTUTTUTGUUAAAGAGTAUTTTGTGG<br>UTAAATTUAUTGGATGTGAUTUAGTTTTTATUTTTRGTUATUTUTTAGUTTTGUUTTA<br>TUUAAAURGGATUAUTUTUTTUTGUTTAGAAUTXGTTUTGUTUTTGGTGAUAGTGGT<br>AUATAUTUTUATAUTGUUTUTTUUUTTGUUUAGAGTUUTTUUTTUTUATGTTUUAUU<br>TUUTUTAUTGGGAURGGUUTGGGTGTGUTGTUUAATRGGAUAUTATTTTGTTGGGUU<br>UTUTUUTTUAUTUU |
| 42 | GAGTGAAGGAGAGGGUUUAAUAAAATAGTGTURGATTGGAUAGUAUAUUUAGGUR<br>GGTUUUAGTAGAGGAGGTGGAAUATGAGAAGGAAGGAUTUTGGGUAAGGGAAGAG |

-continued

| SEQ ID NO: | Sequence |
|---|---|
| | GUAGTATGAGAGTATGTAUUAUTGTUAUUAAGAGUAGAAXGAGTTUTAAGUAGAA<br>GAGAGTGATURGGTTTGGATAAGGUAAAGUTAAGAGATGARGAAAGATAAAAAUTG<br>AGTUAUATUUAGTGAATTTAGUUAUAAAGTAUTUTTTGGUAGAAGAAUAURGAUTA<br>GAUUUAGAATAUUTGGGTTTGAU |
| 43 | AAGTGTUTTTAUUTUUTGAGTGRGAUUUAAGTUAGGAGGUAGGAGGUTGAUTGAGG<br>GAUARGGAGGAGGTATGUAUAUTUAUAGUATGAGGUAGAGUTGTGTGUAUAUATU<br>AAGUAAGGAAATGGGGURGGAATATGGGGUAAAGGUUTAXGGATTGAATGGTGGA<br>TTTGGATGTGGGUUAUTTUTTUUAGUUUUTGAAAGAGGAUUAGGUAATGTGGUTAT<br>GAATGGGUUTAATGAGAATTGATTGATTRGUTRGAGATGTTTTUTTTTTUTTUUTAAA<br>ATAGAAAATGAUATAUUUUA |
| 44 | TGGGGTATGTUATTTTUTATTTTAGGAAGAAAAAGAAAAUATUTRGAGRGAATUAAT<br>UAATTUTUATTAGGUUUATTUATAGUUAUATTGUUTGGTUUTUTTTUAGGGGUTGG<br>AAGAAGTGGUUUAUATUUAAATUUAUUATTUAATUXGTAGGUUTTTGUUUUATATT<br>URGGUUUUATTTUUTTGUTTGATGTGTGUAUAUAGUTUTGUUTUATGUTGTGAGTGT<br>GUATAUUTUUTURGTGTUUUTUAGTUAGUUTUUTGUUTUUTGAUTTGGGTRGUAUT<br>UAGGAGGTAAAGAUAUTT |
| 45 | GGATGTGUTUAGGUTUUAGGGUUAUAUUUTGUATGTAUTUATAGUAUAGUUUATTU<br>TGGAAGGTGUAGTAGAGTTTGGGGGUAUAGUTGTGTGUTRGUAGUAGUTGGAAGTT<br>TUTGAUUTUATTUTUURGGTUUAUUAGUAGUTURGTUXGUTUUUUATAUAUURGGA<br>UUAGUARGUAGTUUTGUATGTUUTUUTUUAUATAGUAGGUUAUUAGUTTGTTGGTG<br>ATGUUATURGTGAAGRGUTAGUATGGGGAGAGGAUAGTGRGTGGGTGGGTGGGTGG<br>GGUAGGATUTUTUTGGTUTU |
| 46 | GAGAUUAGAGAGATUUTGUUUUAUUUAUUUAUUUARGUAUTGTUUTUTUUUUATG<br>UTAGRGUTTUARGGATGGUATUAUUAAUAAGUTGGTGGUUTGUTATGTGGAGGAGG<br>AUATGUAGGAUTGRGTGUTGGTURGGGTGTATGGGGAGXGGARGGAGUTGUTGGTG<br>GAURGGGAGAATGAGGTUAGAAAUTTUUAGUTGUTGRGAGUAUAUAGUTGTGUUU<br>UUAAAUTUTAUTGUAUUTTUUAGAATGGGUTGTGUTATGAGTAUATGUAGGGTGTG<br>GUUUTGGAGUUTGAGUAUATUU |
| 47 | AGUUAGGAAGGGUTGUAUTTUUUUAGTGGTUAGRGUAGGUTGGRGTUUTGGUTGUT<br>GGRGUAAGTUTUAAGUTGUUUUTUUUUTTUTAGUAAGUATGGGRGGTGTGGGTATG<br>RGGGGTGUTGGGTAUTGAUTUAUUTURGGAGAUUAUTXGGUTUUUAUAUAUUAUU<br>TUTGAATGATUTGAATUATTTATGAGGUTGAATGUUUTGTUUTUUAGGGAGUTUUA<br>GUTGGAGUTGGAGUUAGUATATGGAGGTGGAGAGAGUTUUXGUAGTUAUURGGGU<br>UUTGTAUAGUUTGUAGGUAGAAU |
| 48 | GTTUTGUUTGUAGGUTGTAUAGGGUURGGGTGAUTGXGGGAGUTUTUTUUAUUTUU<br>ATATGUTGGUTUUAGUTUUAGUTGGAGUTUUUTGGAGGAUAGGGUATTUAGUUTUA<br>TAAATGATTUAGATUATTUAGAGGTGGTGTGTGGGAGUXGAGTGGTUTURGGAGGT<br>GAGTUAGTAUUUAGUAUUURGUATAUUUAUAURGUUUATGUTTGUTAGAAGGGGA<br>GGGGUAGUTTGAGAUTTGRGUUAGUAGUUAGGARGUUAGUUTGRGUTGAUUAUTG<br>GGGAAGTGUAGUUUTTUUTGGUT |
| 49 | GGGTGUTGGGTAUTGAUTUAUUTURGGAGAUUAUTXGGUTUUUAUAUAUUAUUTU<br>TGAATGATUTGAATUATTTATGAGGUTGAATGUUUTGTUUTUUAGGGAGUTUUAGU<br>TGGAGUTGGAGUUAGUATATGGAGGTGGAGAGAGUTUUXGUAGTUAUURGGGUUU<br>TGTAUAGUUTGUAGGUAGAAUUTATAAAUTGGAUTUUTAAAGUUAUTUUTUTUAAG<br>GUUTGGAGATTUTGUTGAGTTUAUTUTITGGUTUTUAGAGUAUTUTGGAAUTUTAUA<br>TAAAGUTGAGGAAUUUTTGT |
| 50 | AUAAAGGGTTUUTUAGUTTTATGTAGAGTTUUAGATGUTUTGAGAGUUAAAGAGTG<br>AAAUTUAGUAGAATUTUUAGGUUTTGAGAGGAGTGGUTTTAGGAGTUUAGTTTATA<br>GGTTUTGUUTGUAGGUTGTAUAGGGUURGGGTGAUTGXGGGAGUTUTUTUUAUUTU<br>UATATGUTGGUTUUAGUTUUAGUTGGAGUTUUUTGGAGGAUAGGGUATTUAGUUTU<br>ATAAATGATTUAGATUATTUAGAGGTGGTGTGTGGGAGUXGAGTGGTUTURGGAGG<br>TGAGTUAGTAUUUAGUAUUU |
| 51 | AGTUUATGAAGGUAUTTTTTUAAAGTTAGGTGGTUAUUAAAAAAUAGGTAATUAAT<br>UUTGTUAUUAGURGRGGGGAUAGRGAGGUUTTGGGUTTGGAGGGGGAGGATGURG<br>ARGATGURGAURGRGUATUAGATUTRGURGGGAGGAGGGXGRGGGRGUTUUAUTTG<br>TTGUAAAGAARGURGGGTTUUTUTGGGUUATTGGGUTGURGUTURGGRGGGGAGRG<br>RGGAAGGUTGGGUUTUAGGTAGUTTUAATUATTUAUUTGUTGGTTARGGGTRGRGG<br>RGURGGGGAUUUTAUTURGGA |
| 52 | TURGGAGTAGGGTUUURGGRGURGRGAUURGTAAUUAGUAGGTGAATGATTGAAGU<br>TAUUTGAGGUUUAGUUTTURGRGUTUUURGURGGAGRGGUAGUUUAATGGUUUAG<br>AGGAAUURGGRGTTUTTTGUAAUAAGTGGAGRGUURGXGUUUTUUTUURGGRGAGA<br>TUTGATGRGRGGTRGGUATRGTRGGUATUUTUUUUUTUUAAGUUUAAGGUUTRGUT<br>GTUUURGRGGUTGGTGAUAGGATTGATTAUUTGTTTTTTGGTGAUUAUUTAAUTTTG<br>AAAAAGTGUUTTUATGGAUT |

-continued

| SEQ ID NO: | Sequence |
|---|---|
| 53 | GTUTGUAGUTGGGAATGAATGGAATGAAGGTUAAGGATGAAGTAATAAUUAAATAT<br>TGGGTTTTGGGTGUUUTGGTAAUTGTURGGTTTUUAGTTAGGGTTUUTGGGTGAUAT<br>UTTUUTTUTGGGGGAAGAUAGAGTUAAATGAGAAAXGTGAGTTGAGUUUAGGGGA<br>AAGGATUATURGGGAGATGUUTGAGGGGUTUUAGGGUATRGTAATUTUTTGUTUAG<br>UTGGUAGAGTGGGGUTGAUARGGUUAGUTGUTUTUTGGAGTUUTRGGUUTTUUTGT<br>TTUUUUUTGAGGAUTTTGAG |
| 54 | TUAAAGTUUTUAGGGGGAAAUAGGAAGGURGAGGAUTUUAGAGAGUAGUTGGURG<br>TGTUAGUUUUAUTUTGUUAGUTGAGUAAGAGATTARGATGUUUTGGAGUUUUTUA<br>GGUATUTUURGGATGATUUTTTUUUUTGGGUTUAAUTUAXGTTTUTUATTTGAUTUT<br>GTUTTUUUUUAGAAGGAAGATGTUAUUUAGGAAUUUTAAUTGGAAAURGGAUAGT<br>TAUUAGGGUAUUUAAAAUUUAATATTTGGTTATTAUTTUATUUTTGAUUTTUATTUU<br>ATTUATTUUUAGUTGUAGAUA |
| 55 | UUAGTGUAGAAUAGGUAUTGUUUAUUATAUAGGUUAGAAGAGGTGUUUTUTUUAU<br>AUTGGUUAUTGAAAUTAUTUAUTGGUAGUAGTGGGTGUUAUTTGGAAAAUAAGAT<br>GGUUUTUUUTGUAGAGUAGGUUAUUUTGURGGAGGTGTUUXGATGRGTGTGAAGU<br>AGGGTTGGAGGUAUAUTAUAGGUAUTUTUTAGTUUTTUAAAUAAUAUTGTAGTGTA<br>GATUTTGTTGGTTUTTTUAGAGAAGGGGAAARGGAAAUTUAUAGAAGUAAUTAGAG<br>GAGTGAGTAGAAGUUUAGGTATG |
| 56 | UATAUUTGGGUTTUTAUTUAUTUUTUTAGTTGUTTUTGTGAGTTTURGTTTU<br>UTUTGAAAGAAUUAAUAAGATUTAUAUTAUAGTGTTGTTTGAAGGAUTAGAGAGTG<br>UUTGTAGTGTGUUTUUAAUUUTGUTTUAUARGUATXGGGAUAUUTURGGUAGGGTG<br>GUUTGmWGUAGGGAGGGUUATUTTGTTTTUUAAGTGGUAUUUAUTGUTGUUAGT<br>GAGTAGTTTUAGTGGUUAGTGTGGAGAGGGUAUUTUTTUTGGUUTGTATGGTGGGU<br>AGTGUUTGTTUTGUAUTGG |
| 57 | TURGGUATUAATTUTTAATGAGTUUURGAGUUUURGUAGTUUGTUTAUTTUTTTTU<br>TTTTUUAGTGAATUUTUAUAGTUUUUTTTUUUTGUATGTTUTUTGTUUUAAATTUT<br>GAAGUUUUTUUUTTTURGTUTUTTAAGAATUTUTAXGAAUURGAAAGUURGTGAGG<br>UTGATGGUARGTUTGTGGTTUUTTTUTUUTTUTTUUUTUUATAUUUAUAGUTUUURG<br>GGAURGGAUUUTUUUUAUTUAUUAGGTGUAGGGUUAGGGGUAGUAGUAGGAGGA<br>AUAGUUAUAGGTAGAGGTG |
| 58 | UAUUTUTAUUTGTGGUTGTTUUTUUTGUTGUTGUUUUTGGUUUTGUAUUTGGTGAG<br>TGGGGAGGGTURGGTUURGGGGAGUTGTGGGTATGGAGGGAAGAAGGAGAAAGGA<br>AUUAUAGARGTGUUATUAGUUTUARGGGUTTTRGGGTTXGTAGAGATTUTTAAGAG<br>ARGGAAAGGGAGGGGUTTUAGAAATTTGGGAUAGAGAAUATGUAGGGAAAGGGGA<br>UTGTGAGGATTUAUTGGAAAAGAAAAGAAGTAGAUAGGAUTGRGGGGGUTRGGGG<br>AUTUATTAAGAATTGATGURGGA |
| 59 | AGUUTGTGUTUAGGAATAAUTAAGGAGTGGAGURGUATUAAUUTUUTTUUUAAATU<br>RGGARGTUTTUUTURGAUTUAAGUUUAGUUTGAGGGUUATTUTUUTTGATTUAUUU<br>TTGGAAAUAGAUAUUAGUUAAGGGAGUTGTUTUUTGGXGTTGARGAGGATURGATT<br>TAGGTUAGTATTUTAGTTUUUAUTUUAUAGAGGAATUTGAUTGGAGGUUAGUTGTG<br>GTRGATGAGTUATURGGAAUAUAAGUAGGUAGUTATTTURGAAUTAAATGGUATUT<br>GATUTUUUTUUTUAUUTGA |
| 60 | TUAAGGTGAGGAGGGAGATUAGATGUUATTTAGTTRGGAAATAGUTGUUTGUTTGT<br>GTTURGGATGAUTUATRGAUUAUAGUTGGUUTUUAGTUAGATTUUTUTGTGGAGTG<br>GGAAUTAGAATAUTGAUUTAAATRGGATUUTRGTUAAXGUUAGGAGAUAGUTUUUT<br>TGGUTGGTGTUTGTTTUUAAGGGTGAATUAAGGAGAATGGUUUTUAGGUTGGGUTT<br>GAGTRGGAGGAAGARGTURGGATTTGGGAAGGAGGTTGATGRGGUTUUAUTUUTTA<br>GTTATTUUTGAGUAUAGGUT |
| 61 | GAUUTUAGGATUTGAATGGTTUTTGGAGTTUTTTGUAGATGAGGTAATGTTTTGGTT<br>AAUTUATAGGTUAGAUUTGUTGTUUTTAGUTAAUTTGUURGGGAGGTTTTTAARGG<br>AAGGUUTGTGTTAGUAUAAATUATATTTUUTGATGAXGAGUAGAGAUITITGATUTG<br>GTUTTAAAGAARGRGTTTTUUAAUTTAUUUTGGGAUTTTTTTGAATTAGURGGUUAU<br>ATATAUUAGGGTTUTUAGAGGATTTTTTUTUUUUTTTUTUTUTGTUTUTTTUTGGG<br>TTTUUTATTAUTAATT |
| 62 | ATTAGTAATAGGAAAAAUUUAGAAAGAGAUAGAGAGAAAGGGGGGAAAAAATUUT<br>UTGAGAAUUUTGGTATATGTGGURGGUTAATTUAAAAAAGTUUUAGGGTAAGTTGG<br>AAAARGRGTTUTTTAAGAUUAGATUAAGGTUTUTGUTXGTUATUAGGAAATATGAT<br>TTGTGUTAAUAUAGGUUTTURGTTAAAAAUUTUURGGGUAAGTTAGUTAAGGAUAG<br>UAGGTUTGAUUTATGAGTTAAUUAAAAUATTAUUTUATUTGUAAAGAAUTUUAAGA<br>AUUATTUAGATUUTGAGGTUU |
| 63 | GUUTGGAAUUURGGRGATUTUTTGTTTUTUUAUUAAGGGAAUTUTGUTTGTAAUAU<br>TTTAAGUUTUAGUTGAAAAGTGGTUTUUTGGGTGAAGTUTUAUUTGTGUAUUUAUU<br>TGAGGGTGAGTUAGUTUTGUTUUUUTGGUTUTUAURGXGGUTGTTATAGUATTTAU |

-continued

| SEQ ID NO: | Sequence |
|---|---|
| | RGGAGTUUUAUAGTGAUTUATTTGTUUATUAUUUTUURGAUAAAUUTTUUAGUTTU<br>TGAAGGGUAGAGAUAGUATUATAATUATUTTTTATAAUTUURGTGUUTAGTGUTAU<br>TUUUAATUUUTAGTAAGUAT |
| 64 | ATGUTTAUTAGGGATTGGGAGTAGUAUTAGGUARGGGAGTTATAAAAGATGATTAT<br>GATGUTGTUTUTGUUUTTUAGAAGUTGGAAGGTTTGTRGGGAGGGTGATGGAUAAA<br>TGAGTUAUTGTGGGAUTURGGTAAATGUTATAAUAGUXGRGGTGAGAGUUAGGGGA<br>GUAGAGUTGAUTUAUUUTUAGGTGGGTGUAUAGGTGAGAUTTUAUUUAGGAGAUU<br>AUTTTTUAGUTGAGGUTTAAAGTGTTAUAAGUAGAGTTUUUTTGGTGGAGAAAUAA<br>GAGATRGURGGGGTTUUAGGU |
| 65 | AATUUUTTUUURGGGATAGTUAARGAGGUTTTUAATTTAAAUTTGUATTTGAAGUTT<br>GUAGAGAUTUAUAUTGAUTTAUUUAGGUUUTAAUAUAUAGUAGUTGUTUUUATGG<br>TTGRGUUAGGTAGTGAAGGATAUAGGGUAGUAGGAAAXGAGTUURGGTTUTUAGGT<br>GGATUURGTGUTTUUAUUTUTGTTAGAGUUUAGGUUUTGAGGGUATAGGGUUAAAT<br>TGUUAUAGAGUTUUAGAGAAATUTGTUTUTUURGTUUUUUAUUUTAAGAUTGAGUT<br>GUTGGAGGAAAGAGGUUAGG |
| 66 | UUTGGUUTUTTTUUTUUAGUAGUTUAGTUTTAGGGTGGGGGARGGGAGAGAUAGAT<br>TTUTUTGGAGUTUTGTGGUAATTTGGUUUTATGUUUTUAGGGUUTGGGUTUTAAUA<br>GAGGTGGAAGUARGGGATUUAUUTGAGAAURGGGAUTXGTTTUUTGUTGUUUTGTA<br>TUUTTUAUTAUUTGGRGUAAUUATGGAGAUAGUTGUTGTGTGTTAGGGUUTGGGTA<br>AGTUAGTGTGAGTUTUTGUAAGUTTUAAATGUAAGTTTAAATTGAAAGUUTRGTTGA<br>UTATUURGGGGAAGGGATT |
| 67 | AGGAATGTTTAUTGAAGGAGTGAATGAAAUTATTGUATTAGATUAAGUUUAGGTGU<br>AGAGGAUTGGTTTUAUATAGAAAGUATRGATTTTGUUUTAUAGAAUUUTGAUTUUA<br>GTTTTUUAGUAGAUAAUUUTGGTGTGAAGAUAGAGGGGXGGGGAGGAAGGTAGGG<br>GUTGAUATTTUUUAGUUUUTUUUAGGURGGTGGGGAGUTGAATAGUTUAGTGAUTT<br>GTUUAGGAGUURGAGGTAAAUUAUAGAUTAAGAGUUAAGAGTUATGATTUAUTAU<br>TTGUATTTUTUUAGUUATGAUA |
| 68 | TGTUATGGUTGGAGAAATGUAAGTAGTGAATUATGAUTUTTGGUTUTTAGTUTGTGG<br>TTTAUUTRGGGUTUUTGGAUAAGTUAUTGAGUTATTUAGUTUUUUAURGGUUTGGG<br>AGGGGUTGGGAAATGTUAGUUUUTAUUTTUUTUUUXGUUUUTUTGTUTTUAUAUUA<br>GGGTTGTUTGUTGGAAAAUTGGAGTUAGGGTTUTGTAGGGUAAAATRGATGUTTTUT<br>ATGTGAAAUUAGTUUTUTGUAUUTGGGUTTGATUTAATGUAATAGTTTUATTUAUTU<br>UTTUAGTAAAUATTUUT |
| 69 | GUTGGGATTATATATGUAUAUUAUUATGUURGGUTAATTTTTATATTTTTGGTAGAG<br>ATAGGGGTTUUAUUATGTTGGUUAGGGTGGTUTTGAAUUUUTGAUUTUAGGTGATU<br>UAUUUAUUTTGGUUTUUUAGAGTGUTGGGATTAUAGGXGTGAGUUAUTGUAUURG<br>GUAUAAAGUUATTTTAAAAUAGUTTTTTTTTTTTTTTGAAAUAGUUTTGUUUTGTA<br>GUUUAGGUTGGAGTGTAGTGGTAUAATUTUAGUTUAUTGUAAUUTUUAUUTURGG<br>GTTUAAGTGATTUTTGTGU |
| 70 | GUAUAAGAATUAUTTGAAUURGGAAGGTGGAGGTTGUAGTGAGUTGAGATTGTAUU<br>AUTAUAUTUUAGUUTGGGUTAUAGGGUAAGGUTGTTTUAAAAAAAAAAAAAAAGU<br>TGTTTTAAAATGGUTTTGTGURGGGTGUAGTGGUTUAXGUUTGTAATUUUAGUAUTU<br>TGGGAGGUUAAGGTGGGTGGATUAUUTGAGGTUAGGGGTTUAAGAUUAUUUTGGU<br>UAAUATGGTGGAAUUUUTATUTUTAUUAAAAATATAAAAATTAGURGGGUATGGTG<br>GTGTGUATATATAATUUUAGU |
| 71 | AAUAAATGUUAUAGGUUUTAATTGUAGGUTUUAAGGAGTTGAGATTUUATAUTGGG<br>GTTGUTGGAGGUAGAAGUUTTUUUAUTTTUAGGAUURGGAUUTGUUUTTUUUUUAR<br>GRGGTUURGUUUAGUUAGUTAUAUUUTGGUUAUAGAGXGUTUAUAAAGGUTUAGT<br>GTGTGTATGURGGGUTGAUTUAUAGTGGTTUTGGGUUUAGGRGAGGAUUTTUTUAG<br>AGGGGRGGAAGGGGUUUTUTUUUTUUTGGUUATTTTUUATGGGGAGUAGTUAGTAA<br>UUAGGAUUATGUUAGAUTTUA |
| 72 | TGAAGTUTGGUATGGTUUTGGTTAUTGAUTGUTUUUUATGGAAAATGGUUAGGAGG<br>GAGAGGGUUUUTTURGUUUUTUTGAGAAGGTUUTRGUUTGGGUUUAGAAUUAUTG<br>TGAGTUAGUURGGUATAUAUAUAUTGAGUUTTTGTGAGXGUTUTGTGGUUAGGGTG<br>TAGUTGGUTGGGRGGGAURGRGTGGGGGAAGGGUAGGTURGGGTUUTGAAAGTGG<br>GAAGGUTTUTGUUTUUAGUAAUUUUAGTATGGAATUTUAAUTUUTTGGAGUUTGUA<br>ATTAGGGUUTGTGGUATTTGTT |
| 73 | GUAGTGUTAUAAUATUAATGUUAAGGURGTGGGGUAGUTGATGGTTTGGGUTUUUA<br>AUTTUUUAGUUAGGTGUTTUTGUAGGUUUAUATUTTGUUUAUTGGUUAAAUUTTTA<br>AATAAUTTTGAUTRGGGUTAUTUTTATGUTUAAAGAXGTUAGGGGUTUTUUUAAAT<br>UTUTTTAUUUTGUUAGAAAGTUTTUTATAGTARGGUUTUUAUTTAGUTTTUARGUUT<br>GATUTTUUATRGUATUUTGUTUATAAUUTGUUAUTAGTGAAUUUUTGUTGUTURGG<br>UTUUAUAUTTUTUATGUTG |

-continued

| SEQ ID NO: | Sequence |
|---|---|
| 74 | AGUATGAGAAGTGTGGAGURGGAGUAGUAGGGGTTUAUTAGTGGUAGGTTATGAG<br>UAGGATGRGATGGAAGATUAGGRGTGAAAGUTAAGTGGAGGURGTAUTATAGAAG<br>AUTTTUTGGUAGGGTAAAGAGATTTGGGAGAGUUUUTGAXGTUTTTGAGUATAAGA<br>GTAGUURGAGTUAAAGTTATTTAAAGGTTTGGUUAGTGGGUAAGATGTGGGUUTGU<br>AGAAGUAUUTGGUTGGGAAGTTGGGAGUUUAAAUUATUAGUTGUUUUARGGUUTT<br>GGUATTGATGTTGTAGUAUTGUU |
| 75 | AGGAGGGARGTGGAAGTRGTGGGTGGUAGAGAAAAGTGTGUAURGUTGGGAGGTU<br>TATTTUAAGAATAGGTTGGGATGAGAAAUATGTUTGGGRGAGGGGGGTGGGAGGUU<br>RGGTGTUAUUTGTGGATGGATUUAUAGUUUTGUAATTGXGTGTTGUAAAGTTTGUU<br>RGGUUURGUATTUATTTTGAAGGTTUTTGGRGATGUUTRGAUTTTTRGUUTUAAAGA<br>AGTGAGUTUTUATAAGGTTUAGAGGURGGGAGUUAAAGRGGGAGTGAAGAUTUTR<br>GAGGGGTUUAAATGAAGUAGA |
| 76 | TUTGUTTUATTTGGAUUUUTRGAGAGTUTTUAUTUURGUTTTGGUTUURGGUUTUTG<br>AAUUTTATGAGAGUTUAUTTUTTTGAGGRGAAAAGTRGAGGUATRGUUAAGAAUUT<br>TUAAAATGAATGRGGGGURGGGUAAAUTTTGUAAUAXGUAATTGUAGGGUTGTGGA<br>TUUATUUAUAGGTGAUAURGGGUUTUUUAUUUUUUTRGUUUAGAUATGTTTUTUAT<br>UUUAAUUTATTUTTGAAATAGAUUTUUUAGRGGTGUAUAUTTTTUTUTGUUAUUUA<br>RGAUTTUUARGTUUUTUUT |
| 77 | UUTTTTTGAUUTGGRGAGTUUUTTUUUTTTUUATTTUATTTTATTGUTTTTTATTGTTT<br>UUUTURGGUUTUTTUTUUUUTUUTAGGTUTTTTUTUTAGUTUAGTTTGGAGUTUAUA<br>TUUTTTUUAUUUTTTTUAUUTUUTUUTTUUTUXGUUUUAGGATTATUUUTGGGAUU<br>UATUUTGAGUTGAGUUTAUAGUUAGUUAGUUARGAAATAGAGGTGRGRGGGGGUA<br>GGGTGGTATGGAGATTUTGXGGUUTTTGATTTGAUAUUTUURGGAGUTAURGUUAU<br>AGGUUTGUUUATTTUAU |
| 78 | TGAAATGGGUAGGUUTGTGGRGGTAGUTURGGGAGGTGTUAAATUAAAGGUXGUA<br>GAATUTUUATAUUAUUUTGUUUURGRGUAUUTUTATTTRGTGGUTGGUTGGUTGTA<br>GGUTUAGUTUAGGATGGGTUUUAGGGATAATUUTGGGGXGGAGGAAGGAGGAGGT<br>GAAAAGGGTGGAAAGGATGTGAGUTUUAAAUTGAGUTAGAGAAAAGAUUTAGGAG<br>GGGAGAAGAGGURGGAGGGAAAUAATAAAAAGUAATAAAATGAAATGGAAAGGGA<br>AGGGAUTRGUUAGGTUAAAAAGGU |
| 79 | GUTUAGTTTGGAGUTUAUATUUTTTUUAUUUTTTTUAUUTUUTUUTTUUTUXGUUUU<br>AGGATTATUUUTGGGAUUUATUUTGAGUTGAGUUTAUAGUUAGUUAGUUARGAAA<br>TAGAGGTGRGRGGGGGUAGGGTGGTATGGAGATTUTGXGGUUTTTGATTTGAUAUU<br>TUURGGAGUTAUXGUUAUAGGUUTGUUUATTTUAUUTGURGGGAAGATAAUTTTGG<br>UTTUTGGTGGTGGGTGGGTGATTGAUTUTUAAAATUUAAAGUATTGGTTTITTUTGG<br>GTTAUTTUUTATGAUTGUT |
| 80 | AGUAGTUATAGGAAGTAAUUUAGAAAAAAUUAATGUTTTGGATTTTGAGAGTUAAT<br>UAUUUAUUUAUUAUUAGAAGUUAAAGTTATUTTUURGGUAGGTGAAATGGGUAGU<br>UUTGTGGXGGTAGUTURGGGAGGTGTUAAATUAAAGGUXGUAGAATUTUUATAUU<br>AUUUTGUUUURGRGUAUUTUTATTTRGTGGUTGGUTGGUTGTAGGUTUAGUTUAGG<br>ATGGGTUUUAGGGATAATUUTGGGGXGGAGGAAGGAGGAGGTGAAAAGGGTGGAA<br>AGGATGTGAGUTUUAAAUTGAGU |
| 81 | UATTUUAAUTTUTGUAAUUATGUAUAGTGATRGATATTTATAATTAUUTTTTTUUTT<br>UAUUATGGUAAURGGGTUUTURGARGAGUAGGAUTGAAGAAGGAARGAGGAATAA<br>AUTUTGGGAGTGGAAGRGRGUUTRGGUAGAUAGATURGXGGGRGUTGGGGUAGUU<br>AGGAGAAGUUURGGUATURGUTTGTGAGGTURGGGGUTGTGGTUTRGAGTUURGUU<br>URGUUTRGGRGGGUUURGUTUUUATGUURGUUURGUTATRGUUUURGRGUTUTTUT<br>URGUURGUURGURGAGUTGUA |
| 82 | TGUAGUTRGGRGGGRGGGRGGAGAAGAGRGRGGGGGRGATAGRGGGGRGGGUATG<br>GGAGRGGGGUURGURGAGGRGGGGRGGGAUTRGAGAUUAUAGUUURGGAUUTUAU<br>AAGRGGATGURGGGGUTTUTUUTGGUTGUUUUAGRGUUXGRGGATUTGTUTGURGA<br>GGRGRGUTTUUAUTUUUAGAGTTTATTUUTRGTTUUTTUTTUAGTUUTGUTRGTRGG<br>AGGAUURGGTTGUUATGGTGAAGGAAAAAGGTAATTATAAATATRGATUAUTGTGU<br>ATGGTTGUAGAAGTTGGAATG |
| 83 | TATGATGUUAGTGGTTGAATAUUTTAGTAGAGAAAAATUTTGAATAATUAAUKUUA<br>GGTTUAGGAGAUAGUTGGGTATTTGAGAGUUTATGAGTUAUATAAGUAAUUTTGGA<br>GUUAAGTTGTATTUTUTGTTTGGUUTUAGAGUUAGTUTXGAGUAUATGUAGUUAGA<br>UTGURGGUAGAGAAGATGTGGAGUTGGUATTUTGGUTTAGGUUTGAGUAAGGTRGT<br>GGAAGUUUUAGGTTUUTGAUUATGGUURGUAUAGAGUUATGUTUUAGUUUTGGGT<br>UTUAGUAGGUAGUUAGGTGAG |
| 84 | UTUAUUTGGUTGUUTGUTGAGAUUUAGGGUTGGAGUATGGUTUTGTGRGGGUUATG<br>GTUAGGAAUUTGGGGUTTUUARGAUUTTGUTUAGGUUTAAGUUAGAATGUUAGUT<br>UUAUATUTTUTUTGURGGUAGTLTTGGUTGUATGTGUTXGAGAUTGGUTUTGAGGUU<br>AAAUAGAGAATAUAAUTTGGUTUUAAGGTTGUTTATGTGAUTUATAGGUTUTUAAA |

-continued

| SEQ ID NO: | Sequence |
|---|---|
| | TAUUUAGUTGTUTUUTGAAUUTURGGTTGATTATTUAAGATTTTTUTUTAUTAAGGT ATTUAAUUAUTGGUATUATA |
| 85 | GGGGUTRGUAGTGGUUTAGTUTGUTUTGGGUTTTGUTGGATGUUUTTRGAGAATUA URGRGUAAUUTUUTTUAGAGGUUUAAUAUTUUARGTGUTGAUTTUURGGGUUTGTG TUTUUUUTGURGUAGAUTGAAGXGTTUURGGUTGAAGGTGAGGTTUTGUAUUAAXG AGTRGUAGAAGTUURGGGUAGAGUTGGTGGGGUAGUTTUAGAGGUTGGGATTTGAU ATUTUTGAGUAGGAGGTGAURGUUURGGUAUUAGUTGUUTGUUAGATUUTGAAGG AGUAAGGUUTGRGAUUATAUU |
| 86 | GGTATGGTRGUAGGUUTGUTUUTTUAGGATUTGGUAGUUAGUTUUUUKUUUUKU GTUAUUTUUTGUTUAGAGATGTUAAAUTUUUAGUUTUTGAAGUTGUUUUAUUAGUTU TGUURGGGAUTTUTGRGAUTXGTTGGTGUAGAAUUTUAUUTTUAGURGGGAAXGUT TUAGTUTGRGGUAGGGGAGAUAUAGGUURGGGAAGTUAGUARGTGGAGTGTTGGG UUTUTGAAGGAGGTTGRGRGGTGATTUTRGAAGGGUATUUAGUAAAGUUUAGAGU AGAUTAGGUUAUTGRGAGUUUU |
| 87 | GRGGGGUUAGUAGRGTGUURGGRGGGAAGRGGTAUAGGRGUTURGGGAAGURGRG UAUUAGUTGUTTUAGUAUUATGURGUTUAGGTRGGURGTGUTUTUUTGRGARGGGT TGAAGATGRGGARGAAUTTUTUURGGUAGUTUAUAGUUAXGATUTTUAGGUUTGTR GGGUTGGGAAGAGAGGAGARGUTGTGAGGAGATGRGGURGGTUUAUURGUAUAGU TGRGRGUUURGUURGGAAAUUAGUTUUAGTURGGRGURGGAGGUTTGGGTUAUTRC UUUUTTAUUTUTGUAGGAGTTU |
| 88 | GAAUTUUTGUAGAGGTAAGGGGRGAGTGAUUUAAGUUTURGGRGURGGAUTGGAG UTGGTTTURGGGRGGGGRGRGUAGUTGTGRGGGTGGAURGGURGUAUTUTUUTUAUA GRGTUTUUTUTUTTUUUAGUURGAUAGGUUTGAAGATXGTGGUTGTGAGUTGURGG GAGAAGTTRGTURGUAUTUUUAAUURGTRGUAGGAGAGUARGGURGAUUTGAGRGG UATGGTGUTGAAGUAGUTGGTGRGRGGUTTUURGGAGRGUUTGUAURGUTTUURGU RGGGUARGUTGUTGGUUURGU |
| 89 | AGGAGTGTTTGGGGTGUTTUUTUTTGGUTGUAGTGGGAUAUAGGTGTGUUTTUUTA GGAAUTGGGUUUTGAUTAUTTUUAGUUUAAUAUTUURGGGUUTGTGAAUTGTGAU UTGTGTGURGGGATGGGTTTTGTGGGTUTGUUUUAUUUXGUAUTGUTGGAUTUTGG UUAAGTGGGTGAAGGUTAAGGURGGUTAGAGTTGAGUUTUTGUUTGUUUUTUTU UTGGGUTAGATGUUAUAUUAGGUUUAGTGAUTUAUAGGGUAGGUAGUUGGGAAAT AUUAGGUAGAGGGUAGGUUTG |
| 90 | UAGGAUUTGUUUTUTGUUTGGUAUUUUUAAUTGUUTGUUUTAUGAGUUAUTGGGU UTGGUGUGUAUTUAGUUUAGGAGAGGGGAUAAGGUAGAAAUTUAAUTUTGAURG GUUUAGUUUUAUUUAUUGGUUAGAUUUAGUAGUGXGGGGAUGGGGUAGAUUU AUAAAAUUUAUUURGGUAUAUAGGUUAUAGUUUAUAGGUURGGGAGUGUUGGGUU GGAAGUAGUUAGGGUUUAGUUUUAGGAAGGUAUAUUUGUGUUUUAUGUAGUUA AGAGGAAGUAUUUUAAAUAUUUUU |
| 91 | GUAGGAAUUAGGUUAGRGUAUGUAAUGAAAAUUUUGRGUUAUUUUUUUAGAAGGAU GUGAUUGUAUUUUAUGAGUAUGUAGUAGGGUUAUUAUAUAUUUUUGUUUUGGGU UUUUUUUUGUGUGUAGUUUAGGUUURGGUUUGUGUUXGAGGGUUAGAXGGUUUA UGGUUUUAGUUUUUURGUAGAUUAUAUAGGGAGGUAGRGAGGUAGGGUGUAAG GAUGUUAGGGGUGGAAGGGGUGAUAURGGGAGUAAAGAUUGUAUUUUUGGUUU GGAUAAAUUUGUUUGAUAUUU |
| 92 | GAAUGUAGAUAGGUUUAUUAGGUUAAGGGGUAGUAGUUUUUGUUUURGGUGUUA UUUUUUUUAUUUUUAAUAUUUUUGUAUUUUGUUURGUGUUUUUUUGUGUGAUUUA RGGAGGAAAUUGGGGAUUAUAGGGURGUUUGGUUUUXGAGUAUAAAUXGGGGUU GGGUUAUAUAUAGGGGAGGGGUUUAGGAGUAAAAGGUGUGUGGUGAUUUUGUGU AUAUUUAUAAAAUAUAGUUAUAUUUUUUUAAAAGAUAARGUAAGAGUUUUUAUUA UAUARGUUGGUUUGAUUUUUGU |
| 93 | TGAUTGTATTTTATGAGTATGUAGUAGGGTUAUUAUAUAUUTTTTGUTUUTGGGUU UUTUUUUTGTGTGTAGUUUAGGUUURGGTTTGTGUTRGAGGGUUAGARGGUUUTAT GGTUUUUAGTTTUUTURGTAGATUAUAUAGGGAGGUAGXGAGGUAGGGTGUAAGG ATGTTAGGGGTGGAAGGGGTGAUAURGGGAGUAAAGAUTGUTAUUUUTTGGUUTG GATAAAUUTGUTUTGAUATTUURGAUUTUTGAAGTUATUUATUATGGUTGRGUTGGU TUAGAUAUTTUAAGGGUUAUTTT |
| 94 | AAAGTGGUUUTTGAAGTGTUTGAGUUAGRGUAGUUATGATGGATGAUTTUAGAGGT RGGGAATGUTAGAUAGGTTTATUUAGGUUAAGGGGTAGUAGTUTTTGUTUURGGTG TUAUUUUTTUUAUUUUTAAUATUUTTGUAUUUTGUUTXGUTGUUTUUUTGTGTGAT UTARGGAGGAAAUTGGGGAUUATAGGGURGTUTGGUUUTRGAGUAUAAAURGGGG UUTGGGUTAUAUAUAGGGGAGGGGUUUAGGAGUAAAAGGTGTGTGGTGAUUUTGU TGUATAUTUATAAAATAUAGTUA |
| 95 | UAUAUAUUTTTUAGTTGAGGGGRGUTGAGGTUUUTGUTGTTGUTGTGURGTUTGAU UTGTUUUUTUTUTUTGAUAGAGAGUUAGUTGUTUUURGGGAAUAAUTTUAUUAATG |

-continued

| SEQ ID NO: | Sequence |
|---|---|
| | AGTGUAAUATAUUAGGUAAUTTUATGTGUAGUAATGGAXGGTGUATUURGGGRGU<br>UTGGUAGTGTGARGGGUTGUUTGAUTGUTTRGAUAAGAGTGATGAGAAGGAGTGUR<br>GTGAGTGGUUTGGUUUTTGUTGGGGTGGGGTGGUAGUUATUUTGGGGUAGAGGGG<br>AGUAGGTUUTGAGUAGGUTTA |
| 96 | TAAGUUTGUTUAGGAUUTGUTUUUUTUTGUUUUAGGATGGUTGUUAUUUUAUUUU<br>AGUAAAGGGUUAGGUUAUTUARGGUAUTUUTTUTUATUAUTUTTGTRGAAGUAGTU<br>AGGUAGUURGTUAUAUTGUUAGGRGUURGGGATGUAUXGTUUATTGUTGUAUATG<br>AAGTTUUTGGTATGTTGUAUTUATTGGTGAAGTTGTTUURGGGGAGUAGUTGGUTU<br>TUTGTUAGAGAGAGGGGAUAGGTUAGARGGUAUAGUAAUAGUAGGGAUUTUAGRG<br>UUUUTUAAUTGAAAGGTGTGTG |
| 97 | UATGUATTTTGTGTTTGTAGTGTGUTGGUUARGGGAGUAUTUTAAAUAUATTATGGG<br>URGGGRGUAGTGGUTURGGUUTGTAATUTUAGUAUTTTGGGAGGUTGAGGRGGGUA<br>GATUAUTTGAGUUUAGGAGTTXGAUAUUAGUUTGGUUAAUAXGGXGAAAUUUXGT<br>UTUTAUTAAAAATAUAAAAATTAAURGGGTGTGATGGRGRGTGUUTGTATTUUUAG<br>UTAUTAGGGAGGUTGAGGUAGGAGAATUTUUTGAAUUTGGGAGGUAGGGAUTGUA<br>GTGAGUUAAGATTGTGUUAUT |
| 98 | AGTGGUAUAATUTTGGTUAUTGUAGTUUUTGUUTUUUAGGTUAGGAGATTUTUU<br>TGUUTUAGUUTUUUTAGTAGUTGGGAATAUAGGUARGRGUUATUAUAUURGGTTAA<br>TTTTTGTATTTTTAGTAGAGAXGGGTTTXGUXGTGTTGGUUAGGUTGGTGTXGAAU<br>TUUTGGGUTUAAGTGATUTGUURGUUTUAGUUTUUUAAAGTGUTGAGATTAUAGGU<br>RGGAGUUAUTGRGUURGGUUUATAATGTGTTTAGAGTGUTUURGTGGUUAGUAUAU<br>TAUAAAUAUAAAATGUATG |
| 99 | GGAUTGTGGGUUUUTTGGTTTGTGTUTGAAAGUTGGGGGTAUAGTTUTGUATGGGTT<br>GGUUUUTGUUTTAUUTRGGGAAGUTUUUAGAGUUTGUTGGGUAGUUTGUUTUUTU<br>UTUTUAUUTUUTUXGTUTUUAUTUUUTUUTUAUUAUATTURGGUTUTUUUARGGUR<br>GGAGGUXGTGAATGGGUTGUTTTGTTGUURGGUUUAUAUAGGAGGATGGTGGUAG<br>AAGAUUURGGUAUAAAGTUAGUAUUUAUTUTGTTUUUAGGUTGGGTTUAGGGAGG<br>UTGAAAAGUUAUTTUAGUTGTG |
| 100 | UAUAGUTGAAGTGGUTTTTUAGUUTUUUTGAAUUUAGUUTGGGAAUAGAGTGGGTG<br>UTGAUTTTGTGURGGGGTUTTUTGUUAUUATUUTUUTGTGTGGGURGGGUAAUAAA<br>GUAGUUUATTUARGGUUTURGGURGTGGGAGAGURGGAATGTGGTGAGGAGGGAG<br>TGGAGARGGAGGAGGTGAGAGGAGGAGGUAGGUTGUUUAGUAGGUTUTGGGAGUT<br>TUURGAGGTAAGGUAGGGGUUAAUUUATGUAGAAUTGTAUUUUUAGUTTTUAGAU<br>AUAAAUUAAGGGGUUUAUAGTUU |
| 101 | TAUTUTUTTGATGTATGAUUTTGGATGTGATTTAGUUTUTUTGGGUUTTGGUUUKUU<br>TGAAUUATGTGATUAGAGUAUUAAGURGGUUTUUUARGUTGGTUTGAGUTGUTUAA<br>GGGUUATUTAGGTUUTUTTTGTUUUAAGUUAGAGGTXGUUTUTUUURGGUUAAGUR<br>GRGGUTATGGGGGTGGTGGTAUAAUAGAGAGUAUAGGGAUTTTGGAAUAUAAUAU<br>TGGGTUATGAUUUUTGUUTGGUUAUTUTTGGUTGUTGAUUTTGAUUUTUTGTUTUU<br>TUUTTTGTGAATGGGGGGAGT |
| 102 | AUTUUUUUUATTUAUAAAGGAGGAGAUAGAGGGTUAAGGTUAGUAGUUAAGAGTG<br>GUUAGGUAGGGGTUATGAUUUAGTGTTGTGTTUUAAAGTUUUTGTGUTUTUTGTTG<br>TAUUAUUAUUUUUATAGURGRGGUTTGGURGGGGAGAGGXGAUUTUTGGUTTGGG<br>AUAAAGAGGAUUTAGATGGUUUTTGAGUAGUTUAGAUUAGRGTGGGAGGURGGUT<br>TGGTGUTUTGATUAUATGGTTUAGRGGGGUUAAGGUUUAGAGAGGUTAAATUAUAT<br>UUAAGGTUATAUATUAAGAGAGTA |
| 103 | GUUATGGAGAAAATATGUUATGTUTUUATGGAAAUUAAUUTATTTGUTTAAUTGAGGTTUTG<br>GGGGTGGTTUTGAUAUTUAGTGUTAAUUAGGGGGAGTUTGGUTGTGAGGTRGTUAGUAUATG<br>GRGGTGUTGURGGUTGUUTUUUAXGUAXGUAGGUTUTGUUAGUUTGUUTTGUUAAUTUTGUU<br>AGGUAAUTGGGAUAGGTGUAGAUATGAUUUAGGUTUUAAGUAUARGUAUTUUAUUUTUUUR<br>GURGAGGUAUTUTUURGGTGUUATATGTTGAUTUTGUUUAGRGUUAGGUAGUUUA |
| 104 | TGGGUTGUUTGGRGUTGGGUAGAGTUAAUATATGGUAURGGGAGAGTGUUTRGGRGGGGAG<br>GGTGGATGRGTGTGUTTGGAGUUTGGGTUATGTUTGUAUUTGTUUUAGTTGUUTGGUAGATT<br>GGUAAGGUAGGUTGGUAGAGUUTGXGTGXGTGGGAGGUAGURGGUAGUAURGUUATGTGUT<br>GARGAUUTUAUAGUUAGAUTUUUUUTGGTTAGUAUTGAGTGUTAGAAUUAUUUUUAGAAUU<br>TUAGTTAAGUAAATAGGTTGGTTTUUATGGAGAUATGGUATATTTTUTUUATGGU |
| 105 | GAGTUTGGUTGTGAGGTRGTUAGUAUATGGRGGTGUTGURGGUTGUUTUUUARGUA<br>RGUAGGUTUTGUUAGUUTGUUTTGUUAAUTUTGUUAGGUAAUTGGGAUAGGTGUAG<br>AUATGAUUUAGGUTUUAAGUAUARGUATUUAUUUTUUUXGURGAGGUAUTUTUUR<br>GGTGUUATATGTTGAUTUTGUUUAGRGUUAGGUAGUUUAGRGUUUAUUTUUUUUT<br>UUUUAGUUTGGUUUUARGUAUAGTGUTUTAGUUTUTGUTGGGTAGTGTGAGGAGTG<br>GUAAUTUTGUAGGUAUUUTAGAAG |
| 106 | UTTUTAGGGTGUUTGUAGATTGUUAUTUUTUAUAUTAUUUAGUAGAGGUTAGAGUA<br>UTGTGRGTGGGGUUAGGUTGGGGAGGGGGAGGTGGGRGUTGGGUTGUUTGGRGUT |

-continued

| SEQ ID NO: | Sequence |
|---|---|
| | GGGUAGAGTUAAUATATGGUAURGGGAGAGTGUUTRGGXGGGGAGGGTGGATGRG TGTGUTTGGAGUUTGGGTUATGTUTGUAUUTGTUUUAGTTGUUTGGUAGATTGGUA AGGUAGGUTGGUAGAGUUTGRGTGRGTGGGAGGUAGURGGUAGUAURGUUATGTG UTGARGAUUTUAUAGUUAGAUTU |
| 107 | GURGAATUURGAGGGURGAGUAUUUUTUUUTUAGURGUAUTGUAUUTGUURGTAG GTGAUUAAUUUARGGGRGGAUUUUUAGAUUUAATUUTUTUUAGAGUUAGGGTGGG ATGGGUAGGGAUAGGAGURGGAGGUUUTAUTGGUUURGGGXGAAGGUATUUTGGA AAGUATUUAGAGRGTUUAGUATUUUTUURGRGGUUAUURGUAGGUTGAURGAUUU UTGGGUAGAUUUTUAGAUTUAATUUAGTUUAGGGRGGATTAAGGAGTGGGAGAUA AGGGAGURGGTGGUUURGUTGGUUU |
| 108 | GGGUUAGRGGGGUUAURGGUTUUUTTGTUTUUUAUTUUTTAATURGUUUTGGAUTG GATTGAGTUTGAGGGTUTGUUUAGGGGTRGGTUAGUUTGRGGGTGGURGRGGGAGG GATGUTGGARGUTUTGGATGUTTTUUAGGATGUUTTXGUURGGGGUUAGTAGGGUU TURGGUTUUTGTUUUTGUUUATUUUAUUUTGGUTUTGGAGAGGATTGGGTUTGGGG GTURGUURGTGGGTTGGTUAUUTARGGGUAGGTGUAGTGRGGUTGAGGGAGGGGTG UTRGGUUUTRGGGATTRGGU |
| 109 | TTGUTTGAUUAAAAGAATGUAGUAGAUATAAUTTTGAGAUUTGGAGUTAGGTUAUA AGARGATTTUUTGGGTTTTGTGGAATTUTRGTTUTGAAAGAAAUAAGUUAUUAAGT GGURGGGTGAGUTGGUTUAXGUUTGTAAUTUUUAGUAUTTTGGGAGGUXGAGURGG GUXGATUAUAAGGTUAGGAGATRGAGAUUATUUTGGUTAAUATGGTGAAAUUURG TUTUTAUTAAAAATAUAAAAAAATTAGURGGGUATAUTGGRGGGRGUUTGTAGTUU UAGUTAUTRGGGAGGUTGAGGU |
| 110 | GUUTUAGUUTUURGAGTAGUTGGGAUTAUAGGRGUURGUUAGTATGUURGGUTAAT TTTTTTGTATTTTTAGTAGAGARGGGGTTTUAUUATGTTAGUUAGGATGGTUTRGATU TUUTGAUUTTGTGATXGGUURGGUTXGGUUTUUUAAAGTGUTGGGATTAUAGGXGT GAGUUAGUTUAUURGGUUAUTTGGTGGUTTGTTTUTTTUAGAARGAGAATTUUAUA AAAUUUAGGAAATRGTUTTGTGAUUTAGUTUUAGGTUTUAAAGTTATGTUTGUTGU ATTUTTTTGGTUAAGUAA |
| 111 | AGAATUTGUUTAGUAGGRGGUTUTUUUUTGUTUUUUUAURGAGUAUAUAUKUIUU GAGGGGAUUUTGRGGGAGGAGGUTGUTTUAGTUTUUAGAGAUUAUTUUUAUTUTUT AUAGRGAUTUUUUTATGAURGTUUUUUAUURGGTGUTUTXGGGUUARGGGGAAGG GAUAUTRGGGAAAGAUAUUAGAGAURGGGAGGGTGUAGUTGGGUTUTTRGRGGGG AGRGGGRGGGAGGUUTTUUTGTTAUATGTRGUAGUTGGGAUAUAGARGGUAGRGUT UUAGGGTUUAUTTGURGGUTTRG |
| 112 | RGAAGURGGUAAGTGGAUUUTGGAGRGUTGURGTUTGTGTUUUAGUTGRGAUATGT AAUAGGAAGGUUTUURGUURGUTUUURGRGAAGAGUUUAGUTGUAUUUTUURGGT UTUTGGTGTUTTTUURGAGTGTUUUTTUUURGTGGUUXGAGAGUAURGGGTGGGGG ARGGTUATAGGGGAGTRGUTGTAGAGATGGGAGATGGTUTUTGGAGAUTGAAGUAG UUTUUTUURGUAGGGTUUUUTUUUARGGTUTGTGUTRGGTGGGGGAGUAGGGGAG AGURGUUTGUTAGGUAGATTUT |
| 113 | AGGUUUAGGUAGAGGTUAGAGUUUAAGUUUTGTUUURGAAGGAAATGTGTUUUAT GUTAAUTAUTUUATAGUTGAGGUUTGGAGGGAAGTUAGGGAUUUTGGGAUTGGTTA TUUTGGUUTTGAUTUATTAUTGTTURGGAGAUUTAAAXGUAUUUTGAGUUAUUAGA XGTGGGTGTTAAUAUUTGAGGTUAAUUUUUTGAXGUTTURGGUTGUTUTGGAGGAA GUTGGTUUTUUUTUUUAUUTUUTGTTTTURGTGUUAGUUTGGTAUAGAGTUAAGGG GUTTGGUTGGGUTTGGUTGGG |
| 114 | UUAGUUAAGUUUAGUUAAGUUUUTTGAUTUTGTAUUAGGUTGGUARGGAAAAUAG GAGGTGGGAGGGAGGAUUAGUTTUUTUUAGAGUAGURGGAAGXGTUAGGGGGTTG AUUTUAGGTGTTAAUAUUUAXGTUTGGTGGUTUAGGGTGXGTTTAGGTUTURGGAA UAGTAATGAGTUAAGGUUAGGATAAUUAGTUUUAGGGTUUUTGAUTTUUUTUUAG GUUTUAGUTATGGAGTAGTTAGUATGGGAUAUATTTUUTTRGGGGAUAGGGUTTGG GUTUTGAUUTUTGUUTGGGUUTG |
| 115 | UUUATGUTAAUTAUTUUATAGUTGAGGUUTGGAGGGAAGTUAGGGAUUUTGGGAU TGGTTATUUTGGUUTTGAUTUATTAUTGTTURGGAGAUUTAAAXGUAUUUTGAGUU AUUAGAXGTGGGTGTTAAUAUUTGAGGTUAAUUUUUTGAXGUTTURGGUTGUTUTG GAGGAAGUTGGTUUTUUUTUUUAUUTUUTGTTTTURGTGUUAGUUTGGTAUAGAGT UAAGGGGUTTGGUTGGGUTTGGUTGGGUTUAGAAARGTGGUAGTUAGGAGUUAGU UTGRGGGUAGRGGGGTGUTGGG |
| 116 | UUUAGUAUUURGUTGUURGUAGGUTGGUTUUTUAUTGUUARGTTUTGAGUUUAG UUAAGUUUAGUUAAGUUUUTTGAUTUTGTAUUAGGUTGGUARGGAAAAUAGGAGG TGGGAGGGAGGAUUAGUTTUUTUUAGAGUAGURGGAAGXGTUAGGGGGTTGAUUT UAGGTGTTAAUAUUUAXGTUTGGTGGUTUAGGGTGXGTTTAGGTUTURGGAAUAGT AATGAGTUAAGGUUAGGATAAUUAGTUUUAGGGTUUUTGAUTTUUUTUUAGGUUT UAGUTATGGAGTAGTTAGUATGGG |

-continued

| SEQ ID NO: | Sequence |
|---|---|
| 117 | UTUTUUURGUAGTTTUATURGTUUTUUTUUURGUUTUTGRGAGUTGGGTTTGGGGAR<br>GTUTGGGTGGAATGTAGAUUUAUAGGUTGTUUTTGGTGUUUTUUUTUUUTGTTUTU<br>UAGRGUUUUAGUUUUAGAUAUUAGTUUUUUAGRGGGXGAAAGUURGGGAGRGUU<br>TTUUURGAAAGAUATUAGGGTGUUARGRGGUUUUTGUUUTGUAGAAGUATUUUUU<br>TUURGUUUUTGUUTGGAAAGUAGGUUUUTUUUTAAGUTUTGRGUUUTTUTTUUUTG<br>GGRGUUUTRGGAURGTGGUURG |
| 118 | RGGGUUARGGTURGAGGGRGUUUAGGGAAGAAGGGRGUAGAGUTTAGGGAGGGGU<br>UTGUTTTUUAGGUAGGGGRGGGAGGGGGATGUTTUTGUAGGGUAGGGGURGRGTG<br>GUAUUUTGATGTUTTTRGGGGAAGGRGUTUURGGGUTTTXGUURGUTGGGGGAUTG<br>GTGTUTGGGGUTGGGGRGUTGGAGAAUAGGGAGGAAGGGUAUUAAGGAUAGUUTG<br>TGGGTUTAUATTUUAUUUAGARGTUUUUAAAUUUAGUTRGUAGAGGRGGGGAGGA<br>GGARGGATGAAAUTGRGGGGAGAG |
| 119 | AGAGGAGTGGGGAGRGUAGUAGGGTGGUUUURGUTUURGUTUAGAGGAGUTGGUU<br>UTTTAAGGUUAGGUUUAGGRGGGTRGGGAAUAGAGAUURGGGAATGTGGGUTGGA<br>UTGGGGAGUAGAGUUAUUUAGUATGAGTUATTUURGTTTXGURGGAUTUTTRGURG<br>UTGGUTUTRGUTTGURGUUUTUUUUTGGUUUTGGUUUTGGUUTUTGRGUUUTUUUT<br>GUAGAGUTGGTURGGGTGGGUTGGRGGUUTUUAUURGUUAUAAGRGUAUAGGGUT<br>UTGUUUAUTUUURGUUUUTTTTU |
| 120 | GAAAAGGGGRGGGGAGTGGGUAGAGUUUTGTGRGUTTGTGGRGGGTGGAGGURGU<br>UAGUUUAUURGGAUUAGUTUTGUAGGGAGGGRGUAGAGGUUAGGGUUAGGGUUA<br>GGGGAGGGRGGUAAGRGAGAGUUAGRGGRGAAGAGTURGGXGAAARGGGAATGAU<br>TUATGUTGGGTGGUTUTGUTUUUUAGTUUAGUUUAUATTUURGGGTUTUTGTTUUR<br>GAUURGUUTGGGUUTGGUUTTAAAGGGUUAGUTUUTUTGAGRGGGAGRGGGGGUU<br>AUUUTGUTGRGUTUUUUAUTUUTUT |
| 121 | GURGAGRGRGGTGGUTUATGUUTGTAATUUUAGUAUTTTGGGAGARGGAGGTGGGT<br>GGATUAUUTUAGGTUAGAAGTTTGAGAUUTUTGTUTUTAUTGAAAUTATAAAAAAT<br>TGGURGGGUATGGTGGTGGGTGTUTGTAGTTUUAGUTAXGTGGTAAGUTGAGGUAG<br>GAGAATGAUTTGAAUURGGGAGGRGGAGGTTGUAGTGAGUUAGGATTGRGUUAUT<br>GUAUTUUAGUUTGGGAGAUAGAGTUAGAUTUTGTUTUAAAAAAAAGUTATGGGUU<br>TGUAGGATGUUTAATATAAAAG |
| 122 | UTTTTATATTAGGUATUUTGUAGGUUUATAGUTTTTTTTTGAGAUAGAGTUTGAUTU<br>TGTUTUUUAGGUTGGAGTGUAGTGGRGUAATUUTGGUTUAUTGUAAUUTURGUUTU<br>URGGGTTUAAGTUATTUTUUTGUUTUAGUTTAUUAXGTAGUTGGAAUTAUAGAUAU<br>UUAUUAUUATGUURGGUUAATTTTTTATAGTTTUAGTAGAGAUAGAGGTUTUAAAU<br>TTUTGAUUTGAGGTGATUUAUUUAUUTURGTUTUUUAAAGTGUTGGGATTAUAGGU<br>ATGAGUUAURGRGUTRGGU |
| 123 | UARGUTUUTGTTTUAUTTTUATGTTUTGUTUTGTAUAUUTGGUTURGUUTTUTAGAT<br>AGUAATAGUAGAATTAGTGAAAGTATTAAAGTUTTTGATUTTTUTGAGAAGAGUAT<br>AGAAGAAATAATGARGTAAGUTGTUUTUTUTUUAGUTXGGUTAUUTAAAAGGGAAA<br>GGUUUUUTGTURGGTGGAUARGTGAUTUAUATGAUUTTATTAATUAUTGGAGATGA<br>UTUAUAUTUUTTAUUUTGUUUUTTTGUUTGTAUAUAATAAATAAUAGRGRGAUUA<br>GGUATTRGGGGUUAUTGUU |
| 124 | GGUAGTGGUUURGAATGUUTGGTRGRGUTGTTATTTATTGTGTAUAAGGUAAAGGG<br>GUAGGGTAAGGAGTGTGAGTUATUTUUAGTGATTAATAAGGTUATGTGAGTUARGT<br>GTUUAURGGAUAGGGGGUUTTTUUUTTTTAGGTAGUXGAGUTGGAGAGAGGAUAG<br>UTTARGTUATTATTTUTTUTATGUTUTTUTUAGAAAGATUAAAGAUTTTAATAUTTTU<br>AUTAATTUTGUTATTGUTATUTAGAAGGRGGAGUUAGGTGTAUAGAGUAGAAUATG<br>AAAGTGAAAUAGGAGRGTG |
| 125 | AGUUUUUTGGGRGGGGTURGGGGAGUAGGUURGUATTTGGAGGAUAGGGTGTGAU<br>UUATUTGAATUUTRGTTAAAGTAAAAGURGAURGARGGUTUTGGGAGGTTTGAGGU<br>UTGGRGGGGRGGUUURGGGAAGTGATTTGTGGUXGUTAGGXGRGXGUTGGAAAUU<br>UTTTUUUATUTGRGGAGUUUAURGGAGUTGTGATRGGAGGAGGAATTUUUUUAGGU<br>AGGGAGGAURGUAGGGUUTTTTTUAUTRGTUUTGAGGGGUUUTGGGGUTTGGGGAG<br>UAAAUUTGGGGTGAUUUATTTU |
| 126 | GAAATGGGTUAUUUUAGGTTTGUTUUUUAAGUUUUAGGGUUUUTUAGGARGAGTG<br>AAAAAGGUUUTGRGGTUUTUUUTGUUGGGGGAATTUUTUUTURGATUAUAGUTUR<br>GGTGGGUTURGUAGATGGGAAAGGGTTTUUAGXGRGXGUUTAGXGGUUAUAAATU<br>AUTTUURGGGGURGUUURGUUAGGUUTUAAAUUTUUUAGAGURGTRGGTRGGUTTT<br>TAUTTTAARGAGGATTUAGATGGGTUAUAUUUTGTUUTUUAAATGRGGGUUTGUTU<br>UURGGAUUURGUUUAGGGGGUT |
| 127 | UATUUAUAAAUUTUUUAGGUUUUUTUAUTUTTUURGUAUAGTUTGUUTURGGTGUT<br>UUAGAAAGAUTGGAAATGAGGTGAGUTUUUTTGGATUUUTGUUTGUUAUUTGUAA<br>ATATUATGTGGTGUTAUTTGUUUTUUTGTUUUTUUTUUXGTUUUAGGUUAATUUTU |

-continued

| SEQ ID NO: | Sequence |
|---|---|
| | UUAUUUUUTTAATTGUURGGGGATUTUUATTAUTTAAAUUTTTUUAUTGGTAUUTUT<br>UUTUUUAUAUAAGUUTUUTUAGUTGTTTTURGTUTTTAAUUAAUAUUTTUUUTGGU<br>TUUAGUTAUTGUUAUTTUAT |
| 128 | ATGAAGTGGUAGTAGUTGGAGUUAGGGAAGGTGTTGGTTAAAGARGGAAAAUAGU<br>TGAGGAGGUTTGTGTGGGAGGAGAGGTAUUAGTGGAAAGGTTTAAGTAATGGAGAT<br>UUURGGGUAATTAAGGGGGTGGGAGGATTGGUUTGGGAXGGGAGGAGGGAUAGGA<br>GGGUAAGTAGUAUUAUATGATATTTGUAGGTGGUAGGUAGGGATUUAAGGGAGUT<br>UAUUTUATTTUUAGTUTTTUTGGAGUAURGGAGGUAGAUTGTGRGGGAAGAGTGAG<br>GGGGUUTGGGAGGTTTGTGGATG |
| 129 | UTTTUUUAGGAUTGUUTTGGUUUUUTGGUUUUAGTUTGGAGGAUTUTTGUTUAUTT<br>UUTURGUUUUUAGGTGAGUTGAGAAUUUAUTGRGRGRGGGAUTUTGUTGRGUUTG<br>UUUTUURGGGUTGUAGAGGGUAGGAXGUAURGUUAGGUAAGGURGRGGUTUTGXG<br>UTGATGUUAUTURGGGAGRGGGTGGUTGRGGGGGAGGAGGGRGAGUAUTGGARGG<br>GGGUAGRGGAGTGTAGGGTGTGAGATUTAAAUAGAGGGUTUUAUTGGAGGGUTTG<br>UUUAGAAGGRGGUAGTUAUAUTGG |
| 130 | UUAGTGTGAUTGURGUUTTUTGGGUAAGUUUTUUAGTGGAGUUUTUTGTTTAGATU<br>TUAUAUUUTAUAUTURGUTGUUUURGTUUAGTGUTRGUUUTUUTUUUURGUAGUUA<br>UURGUTUURGGAGTGGUATUAGXGUAGAGURGRGGUUTTGUUTGGRGGTGXGTUUT<br>GUUUTUTGUAGUURGGGAGGGUAGGRGUAGUAGAGTUURGRGRGUAGTGGGTTUT<br>UAGUTUAUUTGGGGGRGGAGGAAGTGAGUAAGAGTUUTUUAGAUTGGGGUUAGGG<br>GGUUAAGGUAGTUUTGGGAAAG |
| 131 | TTTAGGGTUTUTUTUURGUUTUTTTTUUTUUUURGUTUUUTUTUTUUTTGRGGUTGA<br>UTUUAGUTUUUUUTRGGTGUURGTAAUUUTUUTTTUUTUTTTTGUXGUAGTUTUXG<br>TUTUTUTTUUAUAGGGTUTUTUUUTUUUUUTUTUUURGTGGTTGTUAGAUTTTUTUU<br>TGGAUTTTUTURGUUURGUAURGUUXGUUURGGATGURGAGRGTGGTAGAUTUTGU<br>AGURGGGUTUUTRGUTGUURGUTGGRGUTGUUTAUAUUUUUTTGGGUTUUUUTUUA<br>AGGTUUUUTURGUTRGU |
| 132 | GRGAGRGGAGGGGAUUTTGGAGGGGAGUUUAAGGGGGTGTAGGUAGRGUUAGRGG<br>GUAGRGAGGAGUURGGUTGUAGAGTUTAUUARGUTRGGUATURGGGGXGGGRGGT<br>GRGGGGRGGAGAAAGTUUAGGAGAAAGTUTGAUAAUUARGGGGAGAGGGGGAGGG<br>AGAGAUUUTGTGGAAGAGAGAXGGAGAUTGXGGUAAAAAGAGGAAAGGAGGGTTA<br>RGGGUAURGAGGGGGAGUTGGAGTUAGURGUAAGGAGAGAGGGAGRGGGGGAGG<br>AAAAGAGGRGGGAGAGAGAUUUTAAA |
| 133 | GAGGGUUAUAGTAAAUTGGAUAAGTTTTTUTGUUUAGUUTAGGUTGUUAUUTGTAG<br>GTUAUTTGGGUTUUAGUTATGTGGUTGUUTUTTUTGUTGGGTGUUTTAUTUTGGGUA<br>GTGUTGTGGTTGUTUAGGGAURGGUAGAGUUTGUUXGUUAGUAATGUUTTTGTUTT<br>UATUAURGGUTGTGAUTUAGGUTTTGGGRGUUTTUTGGUAUTGUAGUTGGAUUAGA<br>GAGGUTTURGAGTUUTGGUUAGUTGUUTGAUUUUUTURGGGGURGAGGAUUTGUA<br>GRGGGTGGUUTUUTUURGUU |
| 134 | GRGGGAGGAGGUUAUURGUTGUAGGTUUTRGGUUURGGAGGGGGTUAGGUAGUTG<br>GUUAGGAUTRGGAAGUUTUTUTGGTUUAGUTGUAGTGUUAGAAGGRGUUUAAAGU<br>UTGAGTUAUAGURGGTGATGAAGAUAAAGGUATTGUTGGXGGGUAGGUTUTGURG<br>GTUUUTGAGUAAUUAUAGUAUTGUUUAGAGTAAGGUAUUUAGUAGAAGAGGUAG<br>UUAUATAGUTGGAGUUUAAGTGAUUTAUAGGTGGUAGUUTAGGUTGGGUAGAAAA<br>AUTTGTUUAGTTTAUTGTGGUUUTUA |
| 135 | GTTUTGGUTTUATTTTTTTTTTUUUAAAATGUUATTTTUATTTGTTUTTAGAGTTUAG<br>AAUATGTUAAAGAGUTTUTTTAAGUAGTAGGTGGTTTTAUAGAGUUUAUAGAGAAG<br>GAAAAUTAAATATUATUURGGATGUAGTUUAUTAXGATXGTGGAGGAGTUAGATTA<br>UTUTURGGGUTTTGUTGTGTUTGUTTGTGAAAUAGGAAAGGGAGAAUTGAGGUAAT<br>GAGTUAUUTUAUTTGGGUUUAAAGUAUUAUUTARGTTGAATATGGAGAAAATGTGA<br>AGUAAGAGTTTUTTTTTA |
| 136 | TAAAAAGAAAUTUTTGUTTUAUATTTTUTUUATATTUAARGTAGGTGGTGUTTTGGG<br>UUUAAGTGAGGTGAUTUATTGUUTUAGTTUTUUUTTTUUTGTTTUAUAAGUAGAUA<br>UAGUAAAGUURGGAGAGTAATUTGAUTUUTUUAXGATXGTAGTGGAUTGUATURGG<br>GATGATATTTAGTTTTUUTTUTUTGTGGGUTUTGTAAAAUUAUUTAUTGUTTAAAGA<br>AGUTUTTTGAUATGTTUTGAAUTUTAAGAAUAAATGAAAATGGUATTTTGGGAAAA<br>AAAAAATGAAGUUAGAAU |
| 137 | UUTUUTUUAGTUTTTGUATATATAUUAGGUTGGTATUUATTGUAGGTGGGGAUUTU<br>UTUTTTGGGUTTTGGAGUUUUUUTUUUTGTGTUTUTGTAURGGGGAGUTTUTTUUTT<br>UTGTUTTUTUUUTTUUTTUTTGUTUATTAAAUTUTUXGUTUUTTAAAAUUAUTUUAR<br>GTGTGTURGTGTTGTTTTATUTAAAURGGRGGUAGGATUAAGAAUUUTTGTGT<br>GUAUTUATUAGAGURGTATGATAATUAAGAGUTGAUTAUUTGGGUUATTUTUATAU<br>UATTAGTGURGUATTTA |

-continued

| SEQ ID NO: | Sequence |
|---|---|
| 138 | TAAATGRGGUAUTAATGGTATGAGAATGGUUUAGGTAGTUAGUTUTTGATTATUAT ARGGUTUTGATGAGTGUAGGAAUAUAAGGGTTUTTGATUUTGURGURGGTTTAGAT AAAAUAAUARGGAUAUARGTGGAGTGGTTTTAAGGAGXGGAGAGTTTAATGAGUAA GAAGGAAGGGAGAAGAUAGAAGGAAGAAGUTUUURGGTAUAGAGAUAUAGGGAG GGGGGUTUUAAAGUUUAAAGAGGAGGTUUUUAUUTGUAATGGATAUUAGUUTGGT ATATATGUAAAGAUTGGAGGAGG |
| 139 | AAGGTTAAAGTRGUTGUTAGAUUAAGGUTAAAURGTGGRGAGGTAGTTGUTTGRGU RGUAGAGTGTGGGTGTGAAUAGUTGGAGUTUAGTGGTTUUTGGAGAUTUAGGGAUU AUUTGTATTUUAUATURGGUTTUUUAUUUARGUAUAXGUAGTATGAUUTGGGTTTU UUUTTTATAUAGTGGAATGUTAAGTGUUTAUAUUUTAGURGGGGTUAGUUAAUTAT GGUUTGTGGGUAUUAUUUUAUUTGUAGUUTGTTTTTGAGUTAAGAATGTTGTTGAU AUTTTTAAAAAUAGAGAAUA |
| 140 | GTTUTUTGTTTTTAAAAGTGTUAAUAAUATTUTTAGUTUAAAAAUAGGUTGUAGGTG GGATGGTGUUUAUAGGUUATAGTTGGUTGAUUURGGUTAGGGTGTAGGUAUTTAGU ATTUUAUTGTATAAAGGGGAAAUUUAGGTUATAUTGXGTGTGRGTGGGTGGGAAGU RGGATGTGGAATAUAGGTGGTUUUTGAGTUTUUAGGAAUUAUTGAGUTUUAGUTGT TUAUAUUUAUAUTUTGRGGRGUAAGUAAUUTAUUTRGUUARGGTTTAGUUTTGGTUT AGUAGRGAUTTTAAUUTTG |
| 141 | GAGAUAGGGTTTUAUTUUTGTRGUUUAGGUTGGAGTGUAGUUTUAAUUTUUTGGGU TUAGTGGATUTTUUUAUUTUAGAUTUUTGAGTAGURGGGAUTAUAGGUAUARGUUA UUAGGUUTAGUTAATTTTTTGTATTTTTTTGTAGAGAXGAGGTTTRGUTAGGTrGUU UAGGUTGGTUTUTAAUTUUTGGGUTUAAGXGATUUAUUUAUUTUAGUTTUUUAAAG TGUTGGGGTTAUAGGUUTGAGTUAUAGXGTURGGUTGAAAGTGAAGTTGAATGAGA TGAUTRGTUUAGGUUAUAT |
| 142 | ATGTGGUUTGGARGAGTUAUTUTUATTUAAUTTUAUTTTUAGURGGAXGUTGTGAUT UAGGUUTGTAAUUUUAGUAUTTTGGGAAGUTGAGGTGGGTGGATXGUTTGAGUUUA GGAGTTAGAGAUUAGUUTGGGUAAUUTAGRGAAAUUTXGTUTUTAUAAAAAAATA UAAAAAATTAGUTAGGUUTGGTGGRGTGTGUUTGTAGTUURGGUTAUTUAGGAGTU TGAGGTGGGAAGATUUAUTGAGUUUAGGAGGTTGAGGUTGUAUTUUAGUUTGGGR GAUAGGAGTGAAAUUUTGTUTU |
| 143 | AUARGUUAUUAGGUUTAGUTAATTTTTTGTATTTTTTTGTAGAGAXGAGGTTTRGOT AGGTTGUUUAGGUTGGTUTUTAAUTUUTGGGUTUAAGXGATUUAUUUAUUTUAGUT TUUUAAAGTGUTGGGGTTAUAGGUUTGAGTUAUAGXGTURGGUTGAAAGTGAAGTT GAATGAGATGAUTRGTUUAGGUUAUATGGUAATUAGTGGUTGATTGARGUUAAAGT TGATTTUATTUTTUTUAATGGGTTUAGAGTUUAAATTUTGGAAUUTUAGAAGARGTT GUTATTUTGGTTUUAAGU |
| 144 | UTTGGAAUUAGAATAGUAARGTUTTUTGAGGTTUUAGAATTTGGAUTUTGAAUUUA TTGAGAAGAATGAAATUAAUTTTGGRGTUAATUAGUUAUTGATTGUUATGTGGUUT GGARGAGTUAUTUTUATTUAAUTTUAUTTTUAGURGGAXGUTGTGAUTUAGGUUTGT AAUUUUAGUAUTTTGGGAAGUTGAGGTGGGTGGATXGUTTGAGUUUAGGAGTTAGA GAUUAGUUTGGGUAAUUTAGRGAAAUUTXGTUTUTAUAAAAAAATAUAAAAAATT AGUTAGGUUTGGTGGRGTGTG |
| 145 | AGTGAUTGUAGRGTUAGGUUAAGUTTGGUUAUTTAUATGTUTGGUATGAUAGTGGU UTUAGAGTAUTRGTUTGAGAAGAAGAGUTATUAUUTGAGRGUTUTGGAGAAUTTAG URGGAGUTTTUAGGUAGTUTGGGAGUUTAUATGGAGGXGTGTAGGUTTATGTUTUA TGTUUARGTTGUURGGGAGAUAAAATUUTTTUTTTATTTAGAGUTGUUUUAAAATG UTGUAUUAGUTTUTUAUTGRGGTGGUTTUAUUTTAGUATAUAGGTATGTGGARGGU UAUTGTGUTGGUTUAUUTT |
| 146 | AAGGTGAGUUAGUAUAGTGGURGTUUAUATAUUTGTATGUTAAGGTGAAGUUAUR GUAGTGAGAAGUTGGTGUAGAAUATTTTGGGGUAGUTUTAAATAGAAAAGGATTTT GTUTUURGGGUAARGTGGAUATGAGAUATAAGUUTAUAXGUUTUUATGTAGGUTUU UAGAUTGUUTGAAAGUTURGGUTAAGTTUTUUAGAGRGUTUAGGTGATAGUTUTTU TTUTUAGARGAGTAUTUTGAGGUUAUTGTUATGUUAGAUATGTAAGTGGUUAAGUT TGGUUTGARGUTGUAGTUAUT |
| 147 | RGGGUAUUTAGGTUTRGUURGUUTGUAGURGUUTGGGGARGRGGGTTURGGARGGU TGGRGRGGGGRGGGGRGGGGAUUAURGAGUAGGAAGTUUURGRGGAAGRGURGUR GGGUAUAGRGTGGGTGUTGTRGAGGAGTGGRGUURGGGXGGGGRGGGAGGTTATA AATAGRGGURGUUATUUTGUTTUTUTTUAGAUAUAUTTAATTTAGURGGUAGGUAU ARGGATGUTTATTTTTAAAAAAAGAAUTTGTTTTATTGRGUTRGAGGTGAURGGGAA GGTGTUUURGRGGGTUAUTRG |
| 148 | RGAGTGAUURGRGGGGAUAUUTTUURGGTUAUUTRGAGRGUAATAAAAUAAGTTUT TTTTTTAAAAATAAGUATURGTGTGUUTGURGGUTAAATTAAGTGTGTUTGAAGAGA AGUAGGATGGRGGURGUTATTTATAAUUTUURGUTGUURGGGRGUUAUTUUTRG AUAGUAUUUARGUTGTGUURGGRGGRGUTTURGRGGGGAUTTUUTGUTRGGTGGTU |

-continued

| SEQ ID NO: | Sequence |
|---|---|
| | UURGUUURGUUURGRGUUAGURGTURGGAAUURGRGTUUUUAGGRGGUTGUAGGR<br>GGGRGAGAUUTAGGTGUURG |
| 149 | GAAGGTGRGGTGRGGTGAGGTGAGAAGAGAGAURGRGUTAGAUUAGGRGATGTUTT<br>AGGGARGGGAGAGGGGTGAGGUUUARGGRGGTUUTGGGGAGRGGUUUARGAURGG<br>UUUARGUAGAGUTTGTAGUUAGTGAAUAGGAAGTATTGGXGAGAGGGAUTGAGAA<br>AUUUAAGAGAGTGTGGGGTGAGGAAAAGGTUAAGGAAGGUUUAGGUTTUUAGGAA<br>GGGUUTGGGURGGGGRGGGGRGGGTGGTGGGAGGUAGTGGTTAGGARGGGRGGGG<br>GTGGGGGTGGGGGTGGGGGTAGGG |
| 150 | UUUTAUUUUUAUUUUUAUUUUUAUUUURGUURGTUUTAAUUAUTGUUTUUUAUUA<br>UURGUUURGUUURGGUUUAGGUUUTTUUTGGAAGUUTGGGUUTTUUTGAUUTTTT<br>UUTUAUUUUAUAUTUTUTTGGGTTTUTUAGTUUUTUTXGUUAATAUTTUUTGTTUAU<br>TGGUTAUAAGUTUTGRGTGGGURGGTRGTGGGURGUTUUUUAGGAURGURGTGGGU<br>UTUAUUUUTUTUURGTUUUTAAGAUATRGUUTGGTUTAGRGRGGTUTUTUTTUTUA<br>TTTTTTTATTRUATURGUAUUTTU |
| 151 | GAGAAAUAAAATAUATTTTTTAATTTAAAAAAAAGTAUUAGAATGAATAAAAUAGG<br>GGUTTTTUUAAAAUTGUTTTTGGTAGATTTAGUAAAUUTAUTGAAUTTTAGAAAUTTTU<br>ATTTTATAATTGTURGGAGATAGAAAGUAGTGUTTUXGAATAAGTGGATAAUTUTGU<br>RGGTUUUAGTAGGTGUUATTGGTGAGUAUAUAGGGTTGUTTAAGTUTUTAAGTUAT<br>TTUUUTGAUTGTGGTTTGAATUAATGTUAAATATUTAUAGGGGTUAGGUAGGTAAU<br>TUAATGAAGTGAAAUAGG |
| 152 | UTGTUAUTTUATTGAGTTAUUTGUUTGAUUUUTGTAGATATTTGAUATTGATTUA<br>AAUUAUAGTUAGGGAAATGAUTTAGAGAUTTAAGUAAUUUTGTGTGUTUAUUAATG<br>GUAUUTAUTGGGAURGGUAGAGTTATUUAUTTATTXGGAAGUAUTGUTTTUTATUT<br>URGGAUAATTATAAAATGAAAGTTTUTAAGTTUAGTAGGTTTGUTAAAUTUTAUUAAA<br>AGUAGTTTTGGAAAGUUUUTGTTTTATTUATTUTGGTAUTTTTTTTTAAAUUAAAAAA<br>TGTATTTTGTTTUTUT |
| 153 | GGAGGGUTTUAURGTUAGRGTAGRGTARGUUTGRGGGURGGGGRGGGAGAGGGAU<br>RGTRGRGTTTGTGURGUUAGUAUUTGRGGUUUUUAGRGUAUURGGGUUUUARGRG<br>GTAGUUUUUAGGGAGTGGGGAGTRGGGRGGGAAAUAGUTXGUURGGGUTUUTARG<br>GGTGUUUUTTTRGURGRGUTUUUTUURGAGGGTUUTTTGUAGTRGGGRGTGGAAGT<br>GGGATGAGUAAAUUURGUAGUAUAGGGUUTTRGUUUUAGGAUUTGUAUUUTUTAU<br>RGGUUARGGGARGTUUUTURGUAU |
| 154 | GTGRGGAGGGARGTUURGTGGURGGTAGAGGGTGUAGGTUUTGGGGRGAAGGUUU<br>TGTGUTGRGGGGTTTGUTUATUUUAUTTUUARGUURGAUTGUAAAGGAUUUTRGGG<br>AGGGAGRGRGGRGAAAGGGGUAUURGTAGGAGUURGGGXGAGUTGTTTUURGUUR<br>GAUTUUUUAUTUUUTGGGGGUTAURGRGTGGGGUURGGGTGRGUTGGGGGURGUA<br>GGTGUTGGRGGUAUAAARGRGARGGTUUUTUTUURGUUURGGUURGUAGGRGTAR<br>GUTARGUTGARGGTGAAGUUUTUU |
| 155 | AGAUAUAAAGAGGGRGGAGAGAUAGAUAUAGAAAGAGGGAGAUAGRGGGGUTGG<br>ATGGARGTGTGGURGGGUUAGTGGGGAGGAGAGARGAGTURGUAGAUAGRGTTUA<br>GAGGURGRGUTGUTTTGGGTGUTGAGURGTUURGGGGTTUAXGGTRGUAGTTTGTUU<br>TTAUAAAARGUUUAGURGUUURGAUUTGTGGTGUTTAGGGAGGAUUTAUUTGGUTG<br>TGURGGTUTGAGAAGGGGUUAGTGAGGUURGGTGRGGGTARGGGRGGGTGUAGAT<br>GUAGUUAGGAGGARGGGRGGGAGU |
| 156 | GUTUURGUURGTUUTUUTGGUTGUATUTGUAUURGUURGTAUURGUAURGGGUUTU<br>AUTGGUUUUTTUTUAGAURGGUAUAGUUAGGTAGGTUUTUUUTAAGUAUUAUAGG<br>TRGGGGRGGUTGGGRGTTTTGTAAGGAUAAAUTGRGAUXGTGAAUUURGGGARGGU<br>TUAGUAUUUAGGUAGRGRGGUUTUTGAARGUTGTUTGRGGAUTRGTUTUTUUTUUU<br>UAUTGGUURGGUUAUARGTUUATUUAGUUIRGUTGTUTUUUTUTITUTGTGTUTGT<br>UTUTURGUUUTUTTTGTGTUT |
| 157 | GUTGTUAUAUTGAGUTGTTTAAUAUTTAAGATGTTGGTGGATGGUAAAGUTAAAAG<br>AGUATUGTAAUAUATGAUUTUTGGGGUTUURGGAGTUATGAGTAUUUUTTUTAGAU<br>AUAGURGTGGGGUUAUAUAGAATTUTGUTUUTGUTGUXGUURGGAAGUAUTUATUT<br>GGUTUUTGUAUUUAUTUAUUTGUATUUTTUUUUTUUUARGAGGTGTTAAGAGUTGT<br>GGGATGAGTAAAGGAGGUUTGTGAAGGATTTUUTGTTTUAGTUTTAUATTUAGGTUT<br>GAGTTUTUAGAGGAATUTT |
| 158 | AAGATTUUTUTGAGAAUTUAGAUUTGAATGTAAGAUTGAAAUAGGAAATUUTTUAU<br>AGGUUTUUTTTAUTUAUTUUUAUAGUTUTTAAUAUUTRGTGGGAGGGGGAGGATGUA<br>GGTGAGTGGGTGUAGGAGUUAGATGAGTGUTTURGGGXGGUAGUAGGAGUAGAAT<br>TUTGTGTGGUUUUARGGUTGTGTUTAGAAGGGGTAUTUATGAUTURGGGAGUUUUA<br>GAGGTUATGTGTTAUAGTGUUUTTTAGUTTTGUUATUUAUUAAUATUTTAAGTGTT<br>AAAUAGUTUAGTGTGAUAGU |
| 159 | UAGGGUTGGGAGAATAGGATGGAUAGRGTTTTGUUAGAGUUTUATGGGAAGUTTUU<br>TTTUAGGUAGUTGAAUUUATTTUAGGGGTAGGGAGUAUTGAUTAGGGGTTGGGAUA |

-continued

| SEQ ID NO: | Sequence |
|---|---|
| | TTGUUURGGGAGGAGGATGAGGATGTTTUUAGGUUTXGGUTGAUTUATGGTAGTGA<br>GTATTAGTUAUTUUUTUAUAAGAATUAGUUUAUATUUTUTAGTAGUUTUTTGTUTU<br>UUAGAGGUUUUTGUUUUATGTTTAUUTGUUTGAAGUTUUTUTUURGGURGUUUUUA<br>UUUAUATURGUAUAGTTTGG |
| 160 | UAAAUTGTGRGGATGTGGGTGGGGGRGGURGGGAGAGGAGUTTUAGGUAGGTAAA<br>UATGGGGUAGGGGUUTUTGGGAGAUAAGAGGUTAUTAGAGGATGTGGGUTGATTUT<br>TGTGAGGGAGTGAUTAATAUTUAUTAUUATGAGTUAGUXGAGGUUTGGAAAUATUU<br>TUATUUTUUTUURGGGGUAATGTUUUAAUUUUTGATUAGTGUTUUUTAUUUUTGAA<br>ATGGGTTUAGUTGUUTGAAAGGAAGUTTUUUATGAGGUTUTGGUAAAARGUTGTUU<br>ATUUTATTUTUUUAGUUUTGU |
| 161 | GAGGAUTAAAAGAAGUUAGAGATGUTGGTUAATTGAUAUAAAAATAAAGAGUTAA<br>GGGAGAGGTTGAGAGAGGGAGAGUAATATUTATGGGTGUTGGAATTTTTAAAGGG<br>UTUAGAGGAGGAGGGGGURGGGRGTGGTGGUTUAXGUUTGTTATUXGAGUAUTTTG<br>GGAGGUUAAGGTGGGUAAATUARGAGGTUAGGAGTTTGAGAGUAGUUTGAUUAAU<br>ATGGTGUAAUUURGTUTUTAUTAAAAATAUAAAATTTAGURGGGTGTGGTTGTGTG<br>UUTGTAATUUUAGUTAUTUAGG |
| 162 | UUTGAGTAGUTGGGATTAUAGGUAUAUAAUUAUAUURGGUTAAATTTTGTATTTTT<br>AGTAGAGARGGGGTTGUAUUATGTTGGTUAGGUTGUTUTUAAAUTUUTGAUUTRGT<br>GATTTGUUUAUUTTGGUUTUUUAAAGTGUTXGGATAAUAGGXGTGAGUUAUUARG<br>UURGGUUUUUTUUTUUTUTGAGUUUTTTAAAAATTUUAGAUAUUUATAGATATTGU<br>TUTUUUTUTUTUAAUUTUTUUUTTAGUTUTTTATTTTTGTGTUAATTGAUUAGUATUT<br>UTGGUTTUTTTTAGTUUTU |
| 163 | UUAGGAGUURGUUTGGGAGRGRGUAGRGUTUTAGGAGURGAGAGURGUTGUTTGG<br>UUUTRGUTGGURGGGTAAAURGAGGGGAAGUTUUTGGUUTUUTTTUUUTTAAGUUU<br>UTTATTGUTTUTGTGGGGAAGGUUUTUUTAGGTAGAGGXGAAGGAURGGGGAGATA<br>AUUTUTUUUATGGGUUAUATURGUTGUUATGGTUTGTGTRGTGUUAGAAGGTAUUT<br>UTUAGUUUTUAGTGURGTGAAAAATUTGAUAUTUAAGAAGGTRGATTGAUARGUUT<br>AARGTRGUAUAGUAATTTAGT |
| 164 | AUTAAATTGUTGTGRGARGTTAGGRGTGTUAATRGAUUTTUTTGAGTGTUAGATTTT<br>TUARGGUAUTGAGGGUTGAGAGGTAUUTTUTGGUARGAUAUAGAUUATGGUAGRG<br>GATGTGGUUUATGGGAGAGGTTATUTUUURGGTUUTTXGUUTUTAUUTAGGAGGGU<br>UTTUUUUAUAGAAGUAATAAGGGGUTTAAGGGAAAGGAGGUUAGGAGUTTUUUUT<br>RGGTTTAUURGGUUAGRGAGGGUUAAGUAGRGGUTUTRGGUTUUTAGAGRGUTGRG<br>RGUTUUUAGGRGGGUTUUTGG |
| 165 | GAGGUARGAAGUTGURGGAGUTAUTUAGUTTTAUUTUTAGGAAAGATAUAGRGAAT<br>UAURGUUAATAAAAUAAAGUAAAAUAAAAAGUTRGUUATGUTGAARGGAATGGGA<br>AAATTGUTUTUTTGTUAUTAATTTTGATTGAATTGAGTXGGUAATUTUTGAAURGGT<br>TUAUTGATAUAAUAATAGGAAAUATTTAAUTGTTTUTTGUAUUTTTAAAUATAAATA<br>GTAGGTTTTTAAGUAGTUAGTAGGRGATGTGTGATUAAGGTTUAGAUAGARGUAGA<br>UAAUTGATUAUUUAUTUAG |
| 166 | UTGAGTGGGTGATUAGTTGTUTGRGTUTGTUTGAAUUTTGATUAUAUATRGUUTAUT<br>GAUTGUTTAAAAAUUTAUTATTTATGTTTAAAGGTGUAAGAAAUAGTTAAATGTTTU<br>UTATTGTTGTATUAGTGAAURGGTTUAGAGATTGUXGAUTUAATTUAATUAAAATTA<br>GTGAUAAGAGAGUAATTTTUUUATTURGTTUAGUATGGRGAGUTTTTTGTTTTGUTT<br>TGTTTTATTGGRGGTGATTRGUTGTATUTTTUUTAGAGGTAAAGUTGAGTAGUTURG<br>GUAGUTTRGTGUUT |
| 167 | GAUUTUAGUTURGGGTGAUAURGGTGGGRGTRGGGTGTGGUUTUAGAUAGUTUUUT<br>TUUTUUURGGUTGGTTGUUAGGTUAAUAURGGGTGGGAUTAGUUTUTGGTGTRGGU<br>AGTAGUUUUATGUTUURGGUUTTTGGGTTUTTGUATGXGURGTUUUUATUAUUTGG<br>UTGUUUUTUTUAUTTURGTUTUUAUUTGTUURGGGTUAUUTGTUUTTUAAGUUAGA<br>AATTAAGGAUAGUAUUUUUTUUUAGAURGUUTGGUTGUAGTUURGGGATGGGRGU<br>TUUTAGTRGUUTAGATRGGGU |
| 168 | GUURGATUTAGGRGAUTAGGAGRGUUUAUUURGGGAUTGUAGUUAGGRGGTUTGG<br>GAGGGGGTGUTGTUUTTAATTTUTGGUTTGAAGGAUAGGTGAUURGGGAUAGGTGG<br>AGARGGAAGTGAGAGGGGUAGUUAGGTGATGGGGARGGXGUATGUAAGAAUUUAA<br>AGGURGGGAGUATGGGGUTAUTGURGAUAUUAGAGGUTAGTUUUAUURGGTGTTG<br>AUUTGGUAAUUAGURGGGGAGGAAGGGAGUTGUTUTGAGGUUAUAUURGARGUUUA<br>URGGTGTUAUURGGAGUTGAGGTU |
| 169 | GTATUTGTGTUAAUUAGRGGTTUTUAGUUTGGUUTUAUUAGGGUUTGAAGUUTAU<br>TAUAGAAUUUUUAGUAGUARGTGGGGTGUAUAGUAAAGAUUAGUUUTGGAUAUAG<br>URGGGTGUTUAGGGRGGGGTGAGGGGGUAGGAGGUAGGAXGUAGGAGGTGAGUTG<br>TURGGGRGGGGUAGGATGAGGGAGTUUTGUATTGUAGAGUTAAGGGGGAGAATUA<br>TUAGUAUUUTAATTAGUTTTTTGATGGUTTUUAAAGUUTTTTAAGTUUTTTTTTTTTTT<br>TTTTTTTTTATUUUTAUAAG |

-continued

| SEQ ID NO: | Sequence |
|---|---|
| 170 | UTTGTAGGGATAAAAAAAAAAAAAAAAAAAAAGGAUTTAAAAGGUTTTGGAAGUU<br>ATUAAGAGUTAATTAGGGTGUTGATGATTUTUUUUUTTAGUTUTGUAATGUAGGAU<br>TUUUTUATUUTGUUURGUURGGAUAGUTUAUUTUUTGXGTUUTGUUTUUTGUUUUU<br>TUAUUURGUUUTGAGUAUURGGUTGTGTUUAGGGUTGATUTTTGUTGTGUAUUUUA<br>RGTGUTGUTGGGGGTTUTGTAGTAGGUTTUAGGUUUTGGATGAGGUUAGGUTGAGA<br>AURGUTGGTTGAUAUAGATAU |
| 171 | GATTAAUTTGUUTUUTGAUAAGTUATAUUUTTTAGUTTAGTAUTAAGGUAGAAGAG<br>AGUUUTGTTGAAGAGUURGUTTGTGTTUTGTGGTAAAGAUAUAGGUUTAURGGUTT<br>UTUXGTGGGTUUUAGTGUTGAGAAGGGUAUAGGUTGGUTGGAGAUAGTGUUUTGU<br>TTGAUAGAUUUUTUUAXGUTRGGATUUTTUUAGTUTGUAURGGUUAUUTGUAUTGG<br>TTTUARGGAAGAGUTAGAATTUTGTTTTAATGTTGGUUAGTTTUUATUATTAGUTTG<br>AAAAGAAUAUAGAAUTTARG |
| 172 | RGTAAGTTUTGTGTTUTTUUAAGUTAATGATGGAAAUTGGUUAAUATTAAAAUAGA<br>ATTUTAGUTUTTURGTGAAAUUAGTGUAGGTGGURGGTGUAGAUTGGAAGGATURG<br>AGXGTGGAGGGGTUTGTUAAGUAGGGUAUTGTUTUUAGUUAGUUTGTGUUUTTUTU<br>AGUAUTGGGAUUUAXGGAGAAGURGGTAGGUUTGTGTUTTTAUUAUAGAAUAUAA<br>GRGGGUTUTTUAAUAGGGUTUTUTTUTGUUTTAGTAUTAAGUTAAAGGGTATGAUTT<br>GTUAGGAGGUAAGTTAATU |
| 173 | GAUUAUAGGTGTGTGUTATUATGUURGGGTAATTTTTATATTTTTTGGTUTUAUTAT<br>GTTGUUUAGGUTGGTUTUAAAUTUUTGGGUTUAAGTGAUUTUUTGUUTUAGUUTU<br>UUAAAGTGTTGGATTAGAGGUATGAGUUAUUTTGUAXGTTTGUUTUUTGAUUTUAG<br>GTUUUUARGGAGTTGGTUATUTTUTGGGUUTRGUTUAGURGGTGUTGAAGGTGAGT<br>UATGUTRGATGATGAUUTGAGGAGUAGAAGAAGGTGUAGGTGAGTUAUUTGAGGG<br>GAAUTGGGTUATGAUUAGAG |
| 174 | UTUTGGTUATGAUUUAGTTUUUUTUAGGTGAUTUAUUTGUAUUTTUTTUTGUTUUT<br>UAGGTUATUATRGAGUATGAUTUAUUTUAGUAURGGUTGAGRGAGGUUUAGAAG<br>ATGAUUAAUTURGTGGGGAUUTGAGGTUAGGAGGUAAAXGTGUAAGGTGGUTUAT<br>GUUTUTAATUUAAUAUTTTGGGAGGUTGAGGUAGGAGGATUAUTTGAGUUUAGGA<br>GTTTGAGAUUAGUUTGGGUAAUATAGTGAGAUUAAAAAATATAAAAATTAUURGG<br>GUATGATAGUAUAUAUUTGTGGTU |
| 175 | AGGAAGTRGAGGUTTAGAAGTTGGGTGAUTTGTUAAAGGTRGUUAUUUARGGTGAG<br>GGUUAGGTTUTGGGAGGGUTGAGGGGUAGGUATGGTGAGUUAGTTURGGGUATGA<br>GGUAAGGRGTGGUAGGUUTGGGGGUAAAAGUUAUAGUUXGTGTGGAGGGGGTGGG<br>GGGATRGAGGUUTTTGGGAAGUUTGTGGATTUTGGUTGUAGTGTGGGTGTGAUAUT<br>GAGTGUTURGGGGAUTURGAGTTATUAUUUAGGUAUTGGUUAGUUUUARGUTUUU<br>TUUTUUAGGTAUTTGGUTUUUTG |
| 176 | AGGGAGUUAAGTAUUTGGAGGAGGGAGRGTGGGGUTGGUUAGTGUUTGGGTGATA<br>AUTRGGAGTUUURGGAGUAUTUAGTGTUAUAUUUAUAUTGUAGUUAGAAUUUAUA<br>GGUTTUUUAAAGGUUTRGATUUUUUUAUUUUUTUUAUAXGGGUTGTGGUTTTTGUU<br>UUUAGGUUTGUUARGUUTTGUUTUATGUURGGAAUTGGUTUAUUATGUUTGUUUUT<br>UAGUUUTUUUAGAAUUTGGUUUTUAURGTGGGTGGRGAUUTTTGAUAAGTUAUUU<br>AAUTTUTAAGUUTRGAUTTUUTU |
| 177 | AGUUARGGRGAUUAUUAUUTUUATUUTUUUUUAUUTUUTUUTUUTGUAGGTGGUU<br>TTTTTGGUUAGTGTGTUTGAGTGUTUAUUTUTTGUTUTAGTGTUUTGGTGUTURGGUT<br>UTUUTUTTUUTUUTUAUTUTUUTGGGUUTGGGUUTGUXGUTUURGGGUUTUUAGGT<br>UTAGAUAUAAGGGTTGAATGAUUAGAUTGUTGGTUTGTTUAGTTTUUATGTGGUUT<br>RGGUUUAUUUUAGUTUTGGUTGUUTUUUUAAAGTUTUAATUARGARGAGATUATA<br>UAGTAAUTUTGUUUUUTUUUT |
| 178 | AGGGAGGGGGUAGAGTTAUTGTATGATUTRGTRGTGATTGAGAUTTTGGGGAGGUA<br>GUUAGAGUTGGGGTGGGURGAGGUUAUATGGAAAUTGAAUAGAUUAGUAGTUTGG<br>TUATTUAAUUUTTGTGTUTAGAUUTGGAGGUURGGGAGXGGUAGGUUUAGGUUUA<br>GGAGAGTGAGGAGGAAGAGGAGAGURGGAGUAUUAGGAUAUTAGAGUAAGAGGT<br>GAGUAUTUAGGUAUAUTGGUUAGAAGGUUAUUTGUAGGAGGAGGAGGTGGGGGA<br>GGATGGAUUTGGTGGTRGURGTGGUT |
| 179 | AAGGTGAATGUTGUAAUUUTUTUTUUTUAGUUUTGUAGURGAUUUTGAUATAAAU<br>TUUTTGAAGTTUAGTGGUUTUTTTUUATGUAUUTAUUAUUTAUAUUTGUTGU<br>AAGAAAUUAUAAUUTGGAURGGGAAUAGAAUTGGAXGTGUUAAAATGUUTGAGGA<br>UAUTTUATXGAATGTGGUTGGUTTGATGGGAAGUTGGUATGAUTAGAAATGUAGG<br>AGTUTTUUUTUTXGAGGTTTUAAGUTTTGTGTTTUTGAUTUAATGGTURGGATTGAG<br>ATUAGATGAGUUAAGTTUA |
| 180 | GAAUTTGAUTUATUTGAUTUUAATURGGAUUATTGAGUUAGAAAUAUAAAGUTTGA<br>AAUUTXGAGAGGGAAGAUTUUTGAUATTTUTAGUUATGUUAGUTTUUUATUAAGUU<br>AGUUAUATTXGATGAAGTGUUTUAGGUATTTTGGUAXGUUAGTTUTGTTUURGGT |

-continued

| SEQ ID NO: | Sequence |
|---|---|
| | UUAGGTTGTGGTTTUTTTGAAAGUAGUAGGTGTAGGTGGTAGGTGUATGGAAAGAG GUUAUTGAAUTTUAAGGAGTTTATGTUAGGGATRGGUTGUAGGGUTGAGGAGAGAG GGTTGUAGUATTUAUUTTU |
| 181 | UAGUUUTGUAGURGATUUUTGAUATAAAUTUUTTGAAGTTUAGTGGUUTUTTTUUA TGUAUUTAUUAUUTAUAUUTGUTGUTTTUAAAGAAAUUAUAAUUTGGAURGGGAA UAGAAUTGGAXGTGUUAAAATGUUTGAGGAUAUTTUATXGAATGTGGUTGGUTTGA TGGGAAGUTGGUATGAUTAGAAATGTUAGGAGTUTTUUUTUTXGAGGTTTUAAGUT TTGTGTTTUTGAUTUAATGGTURGGATTGAGATUAGATGAGTUAAGTTUAGATGAUU ATGUAAAUUTTTAGATGGGG |
| 182 | UUUUATUTAAAGGTTTGUATGGTUATUTGAAUTTGAUTUATUTGATUTUAATURGGA UUATTGAGTUAGAAAUAUAAAGUTTGAAAUUTXGAGAGGGAAGAUTUUTGAUATTT UTAGTUATGUUAGUTTUUUATUAAGUUAGUUAUATTXGATGAAGTGTUUTUAGGUA TTTTGGUAXGTUUAGTTUTGTTUURGGTUUAGGTTGTGGTTTUTTTGAAAGUAGUAG GTGTAGGTGGTAGGTGUATGGAAAGAGGUUAUTGAAUTTUAAGGAGTTTATGTUAG GGATRGGUTGUAGGGUTG |
| 183 | UUTAUUAUUTAUAUUTGUTGUTTTUAAAGAAAUUAUAAUUTGGAURGGGAAUAGAAUTGGA XGTGUUAAAATGUUTGAGGAUAUTTUATXGAATGTGGUTGGUTTGATGGGAAGUTGGUATG AUTAGAAATGTUAGGAGTUTTUUUTUTXGAGGTTTUAAGUTTTGTGTTTUTGAUTUAATGGTU RGGATTGAGATUAGATGAGTUAAGTTUAGATGAUUATGUAAAUUTTTAGATGGGGUUTAAAA UUAAATUTGTGTTUTTAAAUUATTUUAAATGTGTTUATUAUUAGTTATAGTTT |
| 184 | AAAUTATAAUTGGTGATGAAUAUATTTGGAATGGTTTGAGAAUAUAGATTTGGTTTTAGGUU UUATUTAAAGGTTTGUATGGTUATUTGAAUTTGAUTUATUTGATUTUAATURGGAUUATTGA GTUAGAAAUAUAAAGUTTGAAAUUTXGAGAGGGAAGAUTUUTGAUATTTUTAGTUATGUUA GUTTUUUATUAAGUUAGUUAUATTXGATGAAGTGTUUTUAGGUATTTTGGUAXGTUUAGTTU TGTTUURGGTUUAGGTTGTGGTTTUTTTGAAAGUAGUAGGTGTAGGTGGTAGG |
| 185 | GAGAGGGGAAGGGGURGAUUAUUTGUTUURGAGUUATTUTRGGGUTRGGUUAGUU ATTGGGUTGGGAAUUTGUAAUTUUTGGTTGAUTUTTUUAATGAGUTGTGAAUTGGTUT TURGGGAGGAUTTAUAGGAGGUTGGAAARGGGGUUTGGXGRGRGUTTUUUTUTUAG TGRGAGGUTGAUTGGTTGGAUTRGURGGGUTUTAUTGTGGGUUUUARGUTATGTTT AGARGUURGARGTGTUUUATTTTATTGAAUTRGTUUTGUUUUUUAAGTAGGGARGA TTTAUUTUUATTTTUTAGAT |
| 186 | ATUTAGAAAATGGAGGTAAATRGTUUUTAUTTGGGGGGUAGGARGAGTTUAATAAA ATGGGAUARGTRGGGRGTUTAAAUATAGRGTGGGGUUUAUAGTAGAGUURGGRGA GTUUAAUUAGTUAGUUTRGUAUTGAGAGGGAAGRGRGXGUUAGGUUURGTTTUUA GUUTUUTGTAAGTUUTUURGGAAGAUUAGTTUAUAGUTUATTGGAAGATUAAUUAG GATTGAUAGGTTUUUAGUUUAATGGUTGGURGAGUURGAGAATGGUTRGGGAGUA GGTGGTRGGUUUUTTUUUUTUTU |
| 187 | RGGGGGUAGGGAGUAGAUUTGAUTUAGTGGRGTUAGTGUTAUTTUAAAGRGGUAG RGUATTTUATTAAAAAUTUTGATGTAGAAATTAUUUTGGGUTTTGTTTTGUAAAGAGU ATTTGUATAAGAAAAAAUAAUUAGURGGTTAATTUUUUXGTUUAUTGGUAGGAAGA GAGAUAGUUTUAGAGAGTTTGGGAUTUTUTUATTUURGGAGAATTAAAAGUUTUR GAGAUATUUATTTTAGAAGTTUTGGTUAATRGTTUTTAAAGTGRGGTUAGAAGAUU UUTTGRGTUTGAATGGTTTG |
| 188 | UAAAUUATTUAGARGUAAGGGGTUTTUTGAURGUAUTTTAAGAARGATTGAUUAGA AUTTUTAAAATGGATGTUTRGGAGGUTTTTAATTUTURGGGAATGAGAGAGTUUUA AAUTUTUTGAAGGUTGTUTUTUTTUUTGUUAGTGGAXGGGGGAATTAAURGGUTGA TTATTTTTTUTTATGUAAATGUTUTTTGUAAAAUAAAGUUUAGGGTAATTTUTAUAT UAGATTTTTAATGAAATGRGUTGURGUTTTGAAGTAGUAUTGARGUUAUTGAGTUA GGTUTGUTUUUTGUUUURG |
| 189 | UAGTGTTGTAGAUUTATTAATTATUAGGATAATTARGGARGGGGAAAUUUAGAUAU AGATAUAAUUAGTGUUUTUUTUUAUUTUUURGUAUARGUUUUTUURGGTUTUUUTG AUAUUUTGGTGTGUAUTGTGTTUUUUTGUUAUTUTUUAXGUTGRGGUTUUTAUTAGA UUUAUUUUTGURGGTGUUAAAATGUUUAAAGGAAGGUTGAGUUAUGUTUTGGUUT GUUUAGURGUAATAGUUAUGUTGUAAUTUUUARGGAAAAUUTUUTTTUAUUUAUTU UAGAGGUTUTGAGAUAUUUTAA |
| 190 | TTAGGGTGTUTUAGAUUTUTGGAGTGGGTGAAAGGAGGTTTTURGTGGGAGTTGUA GUATGAUTATTGRGGUTGGGUAGGUUAGAGUATGAUTUAGUUTTUUTTTGGGUATT TTGGUAURGGUAGGGGTGGGTUTAGTAGGAGURGUAGXGTGGAGATGGUAGGGGA AUAUAGTGUAUAUUAGGATGTUAGGGAGAURGGGAGGGGRGTGTGRGGGGAGGTG GAGGAGGGUAUTGATTGTATUTGTGTUTGGATTTUUURGTURGTAATTATUUTGATA ATTAATAGGTUTAUAAUAUTG |
| 191 | GGAAGGAGRGAGUTTUTTTTTATAGGAGUTUUAGTTUUTRGTTTTGTTUTUTTRG TTATTUTUUAAAGAAAGURGGUTUTTGAGTUAGUTGGUAGGAGAGRGAGGRGAATG RGUTGGTGUTGGURGUAATGGUUURGGTTUAARGUTXGUTUUAGUTGGTUARGTUU |

-continued

| SEQ ID NO: | Sequence |
|---|---|
| | TUAURGGGGRGGURGGRGGUUTGUUTGUUUARGUTUTGUUAGGAGUUUAGGTUAG<br>UUUTTGUUTRGURGGGGURGGAGUURGTUUAAAATUAAUAAGTUTTTTGTGUUTUT<br>UUTTTGGARGUTGTATAATT |
| 192 | AATTATAUAGRGTUUAAAGGAGAGGUAUAAAAGAUTTGTTGATTTTGGARGGGUTU<br>RGGUUURGGRGAGGUAAGGGUTGAUUTGGGUTUUTGGUAGAGRGTGGGUAGGUAG<br>GURGURGGURGUUURGGTGAGGARGTGAUUAGUTGGAGXGAGRGTTGAAURGGGG<br>UUATTGRGGUUAGUAUUAGRGUATTRGUUTRGUTUTUUTGUUAGUTGAUTUAAGAG<br>URGGUTTTUTTTGGAGAATAAUURGAAGAGAAUAAAARGAGGAAUTGGAGUTUUTA<br>TAAAAAGAAGUTRGUTUUTTUU |
| 193 | UTGGTTGTGGAAGGAGRGAGUTUTURGTUUURGGGAGTATGUAAGTTTUUUUTUUA<br>RGATUAUTTGGAAGGGATTGGGRGGAGTTUTGTUATTTGGAGAAAGGGTUUTGGGA<br>GUTTUAGGTTTGTGTAGGGRGAGGARGGGGRGGTTUTGXGTURGGUUAGGTTGGUU<br>UTRGAGGAUUUAGURGTUUUUAAUUTUUTAAAUTGUTGTRGGATGTAGAAGAUTRG<br>UATTUAUTGUTUTUUAUAGTRGGTGAAGGGAGAARGURGAAAAGGGURGUATTUUU<br>TUUTGURGGTUUUUTUUUUT |
| 194 | AGGGGAGGGGAURGGUAGGAGGGAATGRGGUUUTTTTRGGRGTTUTUUUTTUAURG<br>AUTGTGGAGAGUAGTGAATGRGAGTUTTUTAUATURGAUAGUAGTTTAGGAGGTTG<br>GGGARGGUTGGGTUUTRGAGGGUUAAUUTGGURGGAXGUAGAAURGUUURGTUUT<br>RGUUUTAUAUAAAUUTGAAGUTUUUAGGAUUUTTUTUUAAATGAUAGAAUTURG<br>UUUAATUUUTTUUAAGTGATRGTGUAGUUUAAAUTTGUATAUTUURGGGGARGGAG<br>AGUTRGUTUUTTUUAUAAUUAG |
| 195 | GGGTGTUAGGUTAUUUTTGAAGGGAUUTAUUTUUTUUAGUUAUTGUUAUTGGAUU<br>UTUUUTUAGUUUUTUTAGUAAAGUAGUUUUAATGUATGUUTGAGATTGUUURGGA<br>AAAUTGUUAUTUAGAGGGGAAGAUTUTTGGGUAUAGAGUXGTTATTTATAAUAGUA<br>AGAUAUTGUAGGUTGUUTAAAUAUTUUARGAUAGAGATGARGGAGUAATTUARGG<br>UAUUUUTGUUAAGAGAGTATTAUAUAGUUATTAAAAATGAUUAAGUAGAGAURGG<br>TAGTGARGUTGAGTAATGTTTTU |
| 196 | GAAAAUATTAUTUAGRGTUAUTAURGGTUTUTGUTTGATUATTTTTAATGGUTGTGT<br>AATAUTUTUTTGGUAGGGGTGURGTGAATTGUTURGTUATUTUTGTRGTGGAGTGTT<br>TAGGUAGUUTGUAGTGTUTTGUTGTTATAAATAAXGGUTUTGTGUUUAAGAGTUTT<br>UUUUTUTGAGTGAUAGTTTTURGGGAUAATUTUAGGAUATGUATTGGGGUTGUTTT<br>GUTAGAGGGGUTGAGGGAGGGTUUAGTGGUAGTGGUTGGAGGAGGTAGGTUUUTT<br>UAAGGGTAGUUTGAUAUUU |
| 197 | GUUUAURGRGGAGGGUUUUUUTATUUTUUTUATUUTUAUTGGUTUAUUUAGGGUA<br>UUAUUAUUTUUTUUAGGAAAUUUTUUUTGUUUUUTATUTUTGGGTGUTUUAUAUUU<br>TGGGUAUUTAUAGUUAGAAUUUUAUUTURGGGUUUTUXGTTTUUAGTGGUTGAGT<br>AGGAGUTTUAGTTTTAGGAGAUTUUUUTGAGUAGAAURGAUUUUTUTTUAUTUTTUU<br>UAAUUUUUAUUUAUAUAUTUAGGAUTGGGTAURGGGGUUTGUUUUAATTTGUAGG<br>UTTAGAGTUAGGGGTTAGGGTGG |
| 198 | UAUUUTAAUUUUTGAUTUTAAGUUTGUAAATTGGGGUAGGUUURGGTAUUUAGTU<br>UTGAGTGTGTGGGTGGGGGTTGGGAAGATGAAGAGGGGTRGGTTUTGUTUAGGGGA<br>GTUTUUTAAAAUTGAAGUTUUTAUTUAGUUAUTGGAAAXGGAGGGUURGGAGGTG<br>GGGTTUTGGUTGTAGGTGUUUAGGGTGTGAGAUAUUUAGAGATAGGGGGUAGGGA<br>GGGTTTUUTGGAGGAGGTGGTGGTGUUUTGGGTGAGUUAGTGAGGATGAGGAGGAT<br>AGGGGGGUUUTURGRGGTGGGUA |
| 199 | UTTAAATGAGAAGAAUATGTTTUTAUAURGUATTTGTGAAAGTTTGGUTRGGAGUTA<br>RGRGUTGATTAATATUAGATUTUUTTUAUTRGUUTRGUUAUAATUTTGTUAUATUTG<br>GUTGAUAAATUURGAGGAAUTURGGUAAAGUUAGGXGGRGGRGGGGUTURGGGTU<br>TGGGRGGRGGUTURGGAGGAGUAGRGGGAGAUUURGUAGRGGUUTUUTUUTTUTU<br>RGUURGRGGUUUUUAGUUTRGURGURGURGUURGGUTUUUAGUARGGAAURGARG<br>GGGRGUTUURGAGARGGGRGA |
| 200 | TRGUURGTUTRGGGAGRGUUURGTRGGTTURGTGUTGGGAGURGGGRGGRGGRGGR<br>GAGGUTGGGGGURGRGGGRGGAGAAGGAGGAGGURGUTGRGGGGTUTUURGUTGU<br>TUUTURGGAGURGURGUUUAGAUURGGAGUUURGURGUXGUUTGGUTTTGURGGA<br>GTTUUTRGGGATTTGTUAGUUAGATGTGAUAAGATTGTGGRGAGGRGAGTGAAGGA<br>GATUTGATATTAATUAGRGRGTAGUTURGAGUUAAAUTTTUAUAAATGRGGTGTAG<br>AAAUATGTTUTTUTUATTTAAG |
| 201 | GTGGTAGGTUTGTGTGGAGAUTTGAATUUTGTTTTUTUUUAGUUTTTTUUAUUAAGG<br>AUAUUUAGGAGAGUAAGGATATGGUUAGAGGAGAGGTGGTGTTUUUUTUTTGAUT<br>GGGUUUTGUTUTUAGUUUUAUAGGTGATURGGAAGATTXGGGTGGAGUAGTTTUUT<br>GATGUUTURGGTAGUUTGAAGUTGTGGTGUUAGTTTTTUAAUATTUTTAGTGAUTUA<br>GTUTTGAUATGGGUUAAGGATUAGRGUUUAGTGGGRGAGGTGGGUAGGAGGTAAG<br>UUAARGAUAUUAUTGUUAUU |

-continued

| SEQ ID NO: | Sequence |
|---|---|
| 202 | GGTGGUAGTGGTGTRGTTGGUTTAUUTUUTGUUUAUUTRGUUUAUTGGGRGUTGAT UUTTGGUUUATGTUAAGAUTGAGTUAUTAAGAATGTTGAAAAAUTGGUAUUAUAGU TTUAGGUTAURGGAGGUATUAGGAAAUTGUTUUAUUXGAAUTUTTURGGATUAUUTG TGGGGUTGAGAGUAGGGUUUAGTUAAGAGGGGAAUAUUAUUTUTUUTUTGGUUAT AUUUTTGUTUTUUTGGGTGUUTTGGTGGAAAAGGUTGGGAGAAAAUAGGAUTUAA GTUTUUAUAUAGAUUTAUUAU |
| 203 | TGUUTAUUAUAUUTRGTGGGTGAAAUAGAUATUUTRGAGUATGAUTGAGUTTAUUAA GAGUUUTGRGGRGUTTUUTUTGURGGGGGTTTAGAAATTTUAAAGGATGGGGTTG AGGGAGGGAGGAGTTATGGGUATGTGAUTGTGGAUAGGGXGGGUAGGAGGATGGAA GTAAUAGGTUUAAAATGUATUUTUTGGTGGUURGGUAGAGUUUTTGUATGGGGTGAG AATGGTAATTTAGGAAGAGUAAGTUTTUUUAUTUTGTGAAGUAGAAGAAAAAAGTGG AUTTAAGGAGAAGTTRGGGTG |
| 204 | UAUURGAAUTTUTUUTTAAGTUUAUTTTTTTUTTUTGUTTUAUAGAUTGGGAAGAUTT GUTUTTUUTUAAATTAUUATTUTUAUUUUATGUAAGAGUTUTGURGGGUUAUUAAAG AUAUAUTTTTGGAUUTGUTAUTTUUATUUTUUTGUUXGUUUTGUTUAUATUAUATGU UUATAAUTUUTUUUTUUUTUAAUUUUUAUUTTGAAATTTUTAAAUUUURGGUAG AGGAAGRGURGUAGGGUTUTTAATAAGUTUAGTUATGUTRGAAATATUTGTTTUAU UUARGAGGTGTGGTAGGUA |
| 205 | GAGUUAAUUTUTUUTTUUAUTUUTGGAGGTGGGGGAUURGUUUTUAUTUTAGGUUT GAAGAGGGUTGTGTGTGAGTUTUUAUTTGTGTGTGGGGTGAGUURGGUUUATGUA UAUAGUTAUAUAUAUAUTAUAUAUUUAUAUURGGAUAXGRGUUTUAGGUUUUAU AUTGUUUTTAUAUAUATGRGUUUUTUAUAUATGUATGUTUUUUTTGUAUAUARGUU UUUTRGUAUARGUATGUUUUUTRGUAUARGUATGUAUAUAGGUTUAUTUTGUTGU UTGUUUTGGUTGUTGUGTGUT |
| 206 | AGUAUAUAGUAGUUAGGGAUAGGUAGUAGAGTGAGUUTGTGTGUATGRGTGTGRG AGGGGGUATGRGTGTGRGAGGGGGRGTGTGTGUAAAGGGGAUATGUATGTGTGAGG GGRGUATGTGTGTAAGGGUAGTGTGGGGAUUTGAGGRGXGTGTURGGGTGTGGGTG TGTGATGTGTGTGTAGUTGTGTGUATGGGURGGGUTUAUUUUAUAUAUAAGTGGAG AAUTUAUAUAUAGUUUTUTTUAGGUUTGAGATGAGGGRGGGTUUUUUAUUTUUAG GAATGAAAGGAGAGGTTGGUTU |
| 207 | UUUARGGGGGUAGGUAURGGAGGGGGTGUUUAUAGAGGATAGAGGARGURGAGA AGTGAUUTGGGGAGUUATAGGATGAGGAAGAGAGAAGAGATGAUAGUAGGGGUTG TAGGAGGTUAUUUTUUARGGAGGGAGGGGTGARGGUAGAGGXGTURGUAGGAGUT GGTAURGGTGGGGUTGUUUUUAGGGGGGGUTGAUAGAGGUAGUAAUTGAGUAGGU AGGGGTGGAGRGAGGTGUUAGUUTGURGTGGAAAGGAGARGUUAGUAGRGGGGGG UUUTUUTGGGGTUUUAGTUUTGUTUT |
| 208 | AGAGUAGGAUTGGGAUUUUAGGAGGGUUUUURGUTGUTGGRGTUTUUTTTUUARG GUAGGUTGGUAUUTRGUTUUAUUUUTGUUTGUTUAGTTGUTGUUTUTGTUAGUUUU UUUTGGGGGUAGUUUUAURGGTAUUAGUTUUTGRGGAXGUUTUTGURGTUAUUUU TUUUTURGTGGAGGGTGAUUTUUTAUAGUUUUTGUTGUAUTUTUTTUTUTUTTUUTU AUUUTAUGGUTUUUUAGGUTAUUTUTRGGRGUTUUTUTAUUTUTGTGGGUAUUUUU TURGGTGUUTGUUUURGTGGG |
| 209 | TGAUAUTUAGGAUUUAAAAGUTAGUUUTGUUUAUUUUAGUUUUTUUAUUTUUTTA UUTGGGTGTGUAUUTGUTURGGGGGGTGGAGGTGUTUUUUAUAGTURGGGUUAGG AUAGUUTUAGGGGAGAGTGAAGGUUTGUAGGAGGGUAGGXGAGAUAAGGAGGGT GTUUAGGGUTAGGGAGTGURGGATGAAAUUAGUTUTGTUUUTGTGUAGGUTUUAG GUTUURGUUTGAUAAAUAGGUAGGGAGUUAUAGTUAGGGAUAATAAAAAUTTGGT GUAUTUTGAAAGUAGUAUTTGGAUAG |
| 210 | TGTUUAAGTGUTGUTTTUAGAGTGUAUUAAGTTTTTATTGTUUUTGAUTGTGGUT UTGUUTGTTTGTUAGGRGGGAGUUTGGAGUUTGUAUAGGGAUAGAGUTGGTTTUAT URGGUAUTUUUTAGUUUTGGAUAUUUTUUTTGTUTXGUUTGUUUTUUTGUAGGUUT TUAUTUTUUUUTGAGGUTGTUUTGGUURGGAUTGTGGGGAGUAUUTUUAUUUUURG GAGUAGGTGUAUAUUUAGGTAAGUAGGTUUAGGGGUTGGGGTGGGUAGGGUTAGU TTTTGGAUUTGAGTGUTAU |
| 211 | UAAATAAGTAGTUAUUTUAGAAGTUAUTTARGTAAAAGAUTUAUTUUUUAAAARGU UAGGUAUATGGAUTAUUAUTGTGTTAUUTUAARGARGAUAUAAUTGGUAUAGAATGTA TUAUAUTGAGAAGTGAGTGUUUTUTURGGGAUAUAUTXGUTAGUTGAGUUAUUAGU AUTAGAAUAUTGGAGAUAUAAAUAAAUAUUAUUTUTTUTAAAAUAGUTGAAAUTTU AAGTGGUUAUAAUUTAGAGUAUUAUGGURGGGUAUGGUGGUUAUGUUGUAAUUU UAGUAUGAGGUTGAGAUGGG |
| 212 | UUAUUTUAGUUUAUGUTGGGGTTAUAGGUAUGAGUUAUUAUGUURGGUUAUGAUG UTUUAGGTTAUGAUUAUUGAAUUUAGAUUGUUUUAGAAGAGGUGGUAUUUAUUUAU AUUUUAGUGUUUUAGUGUUGGAUGAUUAUUGAXGAGUAUGUUURGGAGAGGGUA UUAUUUUUAGUAUGAUAUA1UUGUGUUAUUGUAURGURGUUGAAUAAUAUAGUG |

-continued

| SEQ ID NO: | Sequence |
|---|---|
| | ATAATUUATGTGUUTGGRGTTTTGGGGAATGAGTUTTTTARGTAAGTGAUTTUTGAG GTAAUTAUTTATTTGA |
| 213 | GTUUTUAUATTTGAUTURGGATAAAUUTUTTUAAATATTTTAUAGAUTUTGGUTTTU TRGTTAAUAAGUAGUTUAUAUATATAGTGTUTUAGUAGTGAUAGATGUTGGUUUAU UURGAGGTUAGGATGAUTUAGUAGGGATTGAGTTTGXGGGRGTUATGUTUUAAGGU URGGAATAGGAGUTTGGTGUTUATTUUTUAUATAGTGGGUAAAUUTUAGGGUAGGG GAGGGGGGGUAATGUUAGAGAATGGTUUUUAUUTGGGGRGGTUTGARGGUUAGAG ATGUAGAGAAAGAGARGUUT |
| 214 | AGGRGTUTUTTTUTUTGUATUTUTGGURGTUAGAURGUUUUAGGTGGGGAUUATTU TUTGGUATTGUUUUUUUTUUUUTGUUUTAGGATTTGUUUAUTATGTGAGGAATGAG UAUUAAUUTUUTATTURGGGUUTTGGAGUATGARGUUXGUAAAUTUAATUUUTGUT GAGTUATUUTGAUUTRGGGGTGGGUUAGUATUTGTUAUTGUTGAGAUAUTATATGT GTGAGUTGUTGTTAARGAGAAAGUUAGAGTUTGTAAAATATTTGAAGAGGTTTATU RGGAGTUAAATGTGAGGAU |
| 215 | GAAAGUAGUUUTUTUUUTGUUUTGTAAGGTGATUUURGATURGGGAATTUUUAUTT UTGAAGGARGTTUTGGAAAAGTGUAUAGATTAAUTGAGATTUUTGUTTUTGGATUA AGUAUTUUTGAUAUTATXGTTURGATTTTUTAAAAAAGAGATTGTGGUAAAATUTA UUTXGTGAGATUAGAAAATGUAGUAGGGATGAATUAURGGUUUTUTUAGAUUTUA UUAGUUTUUAGGUUATTUUTAAGAGUUTUAUTUUTURGTTUTGTTGGUAGTGGGGG AGGTARGGGGURGGATGGUA |
| 216 | TGUUATURGGUUURGTAUUTUUUUUAUTGUUAAUAGAARGGAGGAGTGAGGUTUT TAGGAATGGUUTGGAGGUTGGTGAGGUTUTGAGAGGGURGGTGAUUATUUUTGUTG UATTTUTGAUTUTUAUXGAGGTAGATTTTGUUAUAAUTUTUTTTTTAGAAAATRGGA AXGATAGTGUAGGAGTGUTrGAUUAGAAGUAGGAAUTUTUAGUTAAUTGTGUAU TTTTUUAGAARGUUTTUAGAAGTGGGAAUTUURGGATRGGGGAUTUAUUTUAGG GUAGGGAGAGGGUTGUTTTU |
| 217 | AAGAAAAGAGAAAGUUUAUUAGGUAAGGGUAGUUTGGTGAUTAUTAUUUTGGGGAGAUTU UUUAUUUAUAUTGUUAUUUAGGUUAUURGAGGGUTGUAGUUTUUTURGGATGGAUUAG GGXGGUAUGGUUUAGAGUTGGGGGUTGAGUGGGUURGUGUXGAGGGUTGUGGXGUTUG AUAAGURGGUUUUAUUGUGAGUAGGGAAGGGRGGAUGGGRGGGGGUUARGGUTGUUUGG UUUUUAUUUUGUGUGUUUUUUUUAUUUUUUGUUUUGUUUUUAAUAUUUAGU |
| 218 | AUTGGGTGUUAGGAGGUAGGGUAGGGGAGUAGAGAGAAGUAUAGUAGGGUGGGGAGUUAG GGUAGURGUGGUUUURGUUUAUURGUUUUUUUUGUUUAUAGUGGGAGURGGUUGUUAGA XGUUAUAGUUUUXGGUARGGGUUUAUUAGUUUUUAGUUUUGGGAUUAGUAGUXGUUUUG GAUUUAUURGGAGGAAGUUGUAGUUUURGGGUGAGUUUGGAGUGGUAGUGUGGGUGGGGAG UUUUUUAGGGUAAUAGUUAUUAGGUGUUUUUAUUUGGAUGGGUUUUUUUUUUUUUUUU |
| 219 | UTGAGGUAGGGUTGUAGGUTUAGGAGGAGGAGATGGGTGGAGAGAGAGAAUAAGUTTT AUUURGGGAGGGTGAUTAUAGGAGAAATGGGUUUUTUAAGTATGUTGAUTTUXGU UTUAUTGUTGUUTGUUTUXGUUUAUUTURGGUTUTGGUTUATUTGUTUTTGTAAG UAGGGTUUTGGGUTGGGTGUTGUAGGXGUATGAGGAAAGTGGGAGURGGGARGGG GUAGUTUAGGGUARGUUUTUUAAUAUTGRGUTURGAGGAUUTUAGRGGTTTTAUTU AGGGGTGUUAUTGAGGUAUAGU |
| 220 | GUTGTGUUTUAGTGGUAUUUUTGAGTAAAAURGUTGAGGTUUTRGGAGRGUAGTGT TGGAGGGRGTGUUUTGAGUTGUUURGTUURGGUTUUUAUTTTUUTUATGXGUUTGU AGUAUUUAGUUUAGGAUUUTGUTTAUAAGAGUAGATGAGUUAGAGURGGAGGTGG GXGGAAGAGUAGGUAGUAGTGAGGXGGAAAUUAGUAUAUUGAGGGGUUUAUUTU TUUTGUAGUUAUUUTUURGGGGUGAGUUGUUUUUUUUUUUAUUUAUUUUUUUUUUUUU GAGUUTGUAGUUUTGUUTUAG |
| 221 | GUUUAGGUTGGAGTGUAGTGGRGTGAUUTTGGUTUAUTGUAAUUTUTGUUTUURGG GTTUAAGRGAUUTUUTULTTGUUTUAGUUTUUUAGAUAUUTGGGAUUAUAGGTGUGUGA UAUUAUAUUUAGUUAAUUUUUUGUAUUUUUUAGUAGAGAXGGUUAUGUUAGUUAGGUG GUUUUGAAUUUUGAUUUAGUGAUUUAURGGUUUUAGUUUUUAAAGUGUGGUAU UAUAGUUAUGAGUUAUUGUAUURGGUUUUGUUUUUGUUUUUUAGUGGUAUUUUAU UGUUUUGUUUUUAAUAUU |
| 222 | AAUGUUGAAAGUAAGGUAGUGGGAUGUUAUUAAGGAAGUAAAAGUAGAGGURGGG UGUAGUGGUUUAUGAUUAUAAUAUUAGUAUUUUGGGGGUGAGGURGGUGAAUUAU UGAGGUUAGGAGUUUAAGAUUAGUUGAUUAAUAUGGUXGUUUUUUAUUAAAAAUAU AAAAAUUAGUUGGGUAUGGUGUUAUAUAUUGUAAUUUUAGGUAUUUGGGAGGUUG AGGUAGGAGAAUURGUUUGAAUURGGGAGGUAGAGGUUGUAGUGAGUUAAGAUUAR GUUAUGUAUUUAGUUGGGU |
| 223 | GUUAUUUAUAAAAAUGAAGAGUAGAGUURGAGUGUUUAUAAUARGUAUUUUUAU UUAAGAUAGAGAAGAAAAARGAAAGAGAGUUGAGUAUUUUUUUGAUUUUUUUA UUUURGGAAGGUAUAUUAGAGUUUUUAAGAUGUUUUXGUUUAUUUAUAUGUUrA UGGUURGGUGAGAURGUAUUUUUUUUUUUAUAUUUGUUUUUUUUGGAUGUAGGG |

-continued

| SEQ ID NO: | Sequence |
|---|---|
| | AUAUAGAATUUUUTAAGTGGGAAGAGUTTTGGAGTGGAGGUTGTTUAAAGTTUTGT GGTGATTAATTATTAUUTAU |
| 224 | TAGGTAATAATTAATUAUUAUAGAAUTTTGAAUAGUUTUUAUTUUAAAGUTUTTUU UAUTTAGGGGATTUTGTGTUUUTGUATUUAGAAAAGGGAUAGATATAGAAAGGGAG GATGRGGTUTUAURGGGUUATAAAUATGTGAGTGGGXGGAGGUAGTUTTGGAGAUT UTGAATATAUUTTURGGGGGTGGAGGGAGTUAAAGGAATGUTUAGGUTUTUTTTRG TTTTTUTTUTUTGTUTTGGGTAAAAATGARGTGTTATAAGUAUTRGAGUTUTGUTUTT UATTTTTATAGAGTGGUT |
| 225 | ATTAAAAUAGUAAAUTUUAGGUUUAAAGTAGGTTTUAGTUTUTATTAAGATAAUAA AAGGTUUTAAATGUUAGGUUTGGGRGUAAAUTGTGUAGAUAAGRGGGTGGURGGA GAAGGAGGGGGGTUAAGGAAGAGAGGGAAAUTUAATTGAXGGTTAUTTTTTTTTUA GAGTTATTTURGGTGGGTUTGUUUUUAUUUUTUAAUAAATTTTGTTGUTUTGA TUUAGGUATAAAAAGTGAGGUUUTGGAGGGUUUUTGAGAUUAGRGTUUTGUAUAG TGAUATGGUAUAGTGAUATGG |
| 226 | UUATGTUAUTGTGUUATGTUAUTGTGUAGGARGUTGGTUTUAGGGGUUUTUUAUUG UUTUAUTTTTTATGUUTGGAATGUUUAGAGUAAUAAAATTrGTTGAGGGGTGGGGG UAGAUUUAURGGAAATAAUTUTGAAAAAAAAGTAAUXGTUAATTGAGTTTUUUTUT UTTUUTTGAUUUUUUTUUTTUTURGGUUAUURGUTTGTUTGUAUAGTTTGRG GGUUTGGUATTTAGGAUUTTTTGTTAUTTTAATAGAGAUUGAAAUUTAUTTTGGGUU TGGAGTTTGUTGTTTTAAT |
| 227 | GGUTUTGAGAGTGUTGGAAUUAAURGGARGGGGTUAGUUUUAUUATGGGAUUTGG URGATGAGTUATUTUTUTGAAGGRGTUTTUUUTTUTGTGAAGTGGGGAAGGTAAUT GTUATUUUAUAGGGRGATTGTGGGUAUURGGGAGAUUXGUTGAGGGATGUTGUAG TGTAGAAGUTTUUUAAATUTARGUTGUTTUTUTTUUTUUTUAGTUUTUTUURGUTGU TGUUUTURGGTTUATGUUUTGTGGUTGATUUATUAURGGUTUTUUARGGUUTTUAU UTTGGGRGGGTTGGATGGUTG |
| 228 | AGUUATUUAAUURGUUUAAGGTGAAGGURGTGGAGAGURGGTGATGGATUAGUUA UAGGGUATGAAURGGAGGGUAGUAGRGGGAGAGGAUTGAGGAGGAAGAGAAGUA GRGTAGATTTGGGAAGUTTUTAUAUTGUAGUATUUUTUAGXGGGTUTUURGGGTGU UUAUAATRGUUUTGTGGGATGAUAGTTAUUTTUUUUAUTTUAUAGAAGGGAAGARG UUTUAGAGAGATGAUTUATRGGUUAGGTUUUATGGTGGGGUTGAUUURGTURGGT TGGTUUAGUAUTUTUAGAGUUU |
| 229 | GURGURGUTTTTUUAGTUTTGUUUAAUURGGTATTTUTGRGUTTGUUTUAGUUAUUR GUAGGAGRGUAGGURGUUUTTRGTUUTUURGTUUTUTGRGUUUAUAGGAUUURGG GUUURGUUUAGTURGUAGGTUURGUAGGTUUUUURGGGXGTGTUTTUUTGGUUUTG RGAUUUURGGGAUAGRGUTGAGAAUARGRGGAAGGTGGGGAGARGRGRGGRGUTG GURGGGTUUUTGGRGURGTTUTRGRGGTGUAGUUTGTGUUTGGGAGTURGGURGTU UUAUUTUAGAAUUAGAGUAAA |
| 230 | TTTGUTUTGGTTUTGAGGTGGGARGGURGGAUTUUUAGGUAUAGGUTGUAURGRGA GAARGGRGUUAGGGAUURGGUUAGRGURGRGRGTUTUUUUAUUTTURGRGTGTTUT UAGRGUTGTUURGGGGGTRGUAGGGUUAGGAAGAUAXGUURGGGGGGAUUTGRGG GAUUTGRGGAUTGGGRGGGGUURGGGGTUUTGTGGGRGUAGAGGARGGGAGGARG AAGGGRGGUUTGRGUTUUTGRGGGTGGUTGAGGUAAGRGUAGAAATAURGGGTTG GGUAAGAUTGGAAAAGRGGRGGU |
| 231 | UUTGGGAUAGGUTUAATGGAGGUTGUAGGGUUATUAGURGAUTUUTARGUAGGUT UAGTUAGUAGUUUUUTGGUUAGUUUUAUUUUTGAUTGURGGUUTUAGAAUTGGGA GUTGUTTUUTGGUAGGGUURGUUTUTGUTGGGAGAURGGAXGGTGAGTUAGUUTTA AGUURGGUAUUAGAUUUUTUTGAGGATGGAGUAUUAGUTGGUTGUUUTGAGGUTG UAAAAUTTUTTUUUTRGTGGAGAUAGGGAGGUAUUTUAGAUAUTUAUUURGGAUT UUUTTGAAUAGGGAUAGGGAGGAA |
| 232 | TTUUTUUUTGTUUTTTGTTUAAGGGAGTURGGGGTGAGTGTUTGAGGTGUUTUUUTGT UTUUARGAGGGAAGAAGTTTTGUAGUUTUAGGGUAGUUAGUTUUTGUTUUATUUTU AGAGGGGTUTGGTGURGGGUTTAAGGUTGAUTUAUXGTURGGTUTUUUAGUAGAGG RGGGUUUTGUUAGGAAGUAGUTUUUAGTTUTGAGGURGGUAGTUAGGGGTGGGGU TGGUUAGGGGGUTGUTGAUTGAGUUTGRGTAGGAGTRGGUTGATGGUUUTGUAGUU TUUATTGAGUUTGTUUUAGG |
| 233 | AUAUTGTGGGGUAGGGAGGGGUATUTUTTGAGAAUAAAAGATUUATTTUTRGAUTT TUUAAAUTGGAGAGUTTUTTGAGAGAAAAGAGAGAGAUAGGTAUAGGTUUARGUU AUUUAUAUAUAGUUUTGTGUAUAUAGAURGGAUAUAGGXGTUUAUAGGUAAGTTR GUAGUTGUTUATTTTGTGAAGTGAATGUTGATTTGGGGGURGGGTGGGGTTRGUTUTG TAUATRGTGUAUTGTUAGAUUUTTUUTGAAGGATTTTTGTTAUTGAAGTATUAGAAG GUUUTTGTTUTAAGGTGGTG |
| 234 | AUUAUUTTAGAAUAAGGGUUTTUTGATAUTTUAGTAAUAAAAATUUTTUAGGAAGG GTUTGAUAGTGUARGATGTAUAGARGAAUUUUAUURGGUUUUUAAATUAGUAUUU |

-continued

| SEQ ID NO: | Sequence |
|---|---|
| | AUTTUAUAAAATGAGUAGUTGRGAAUTTGUUTGTGGAXGUUTGTGTURGGTUTGTG<br>TGUAUAGGGUTGTGTGTGGGTGGRGTGGAUUTGTAUUTGTUTUTUTUTTTTUTUTUA<br>AGAAGUTUTUUAGTTTGGAAAGTRGAGAAATGGATUTTTTGTTUTUAAGAGATGUU<br>UUTUUUTGUUUUAUAGTGTG |
| 235 | AUUUARGGGGAUAGGGGTUAGAGTAATGGAGTGGAAATGGUAGGTTUAUAATTTTG<br>GUTAUAGUTGUTUUUATUTUTAAGUAAUUUAGGUTURGGGTTGGAGGGTGGRGAUU<br>UUAAGATGRGGUUTUAGURGURGGUXGTGTTTGTGUTUUAGUXGATGAAGXGAGTG<br>UAAAGGGUTGTAUAAARGRGAGGUAUTGAAUAAAUAUTGAGRGTGURGTUUAGAT<br>GTUURGGGGGAGGUTGAGGATUUAUAURGTGGGGAGTGUTUTGUUUUUATGGAGT<br>GAUUTGGRGTURGUUUTUUARG |
| 236 | RGTGGAGGGRGGARGUUAGGTUAUTUUATGGGGGUAGAGUAUTUUUUARGGTGTG<br>GATUUTUAGUUTUUUURGGGAUATUTGGARGGUARGUTUAGTGTTTGTTUAGTGUU<br>TRGRGTTTGTAUAGUUUTTTGUAUTXGUTTUATXGGUTGGAGUAUAAAUAXGGURG<br>GRGGUTGAGGURGUAUTUTGGGGTRGUUAUUUTUUAAUURGGAGUUTGGGTTGUTT<br>AGAGATGGGAGUAGUTGTAGUUAAAATTGTGAAUUTGUUATTTUUAUTUUATTAUT<br>UTGAUUUUTGTUUURGTGGGT |
| 237 | RGAGGTGRGGUTGUUURGRGGUTTUUTRGGUTTUURGTUURGRGTGUTTTUUTGGA<br>GTUUUTUUTTURGGAGGUUUTUUTGUUTUUARGTGTGUUUTTUTUUATGTUUAGUA<br>TTRGGGRGUUTUTTGTUTTTUTTUTGTTUUUTGGUTTXGGRGTUUURGGGAGTGTGA<br>UTUURGUAGRGGGGTGUAGUTTTUUTUTGGGATGAGTGAURGGAGGGAAUURGUUT<br>TUURGGGUARGTRGUUAGUUTUTTUUTUTTUTTUUUTAGGUTATUAAGRGGAUTTAT<br>GAUAAGAAGGRGGTGGAT |
| 238 | ATUUAURGUUTTUTTGTUATAAGTURGUTTGATAGUUTAGGGAAGAAGAGGAAGAG<br>GUTGGRGARGTGUURGGGAAGGRGGGTTUUUTURGGTUAUTUATUUUAGAGGAAA<br>GUTGUAUUURGUTGRGGGAGTUAUAUTUURGGGGARGUXGAAGUUAGGGAAUAGA<br>AGAAAGAUAAGAGGRGUURGAATGUTGGAUATGGAGAAGGGUAUARGTGGAGGUA<br>GGAGGGUUTURGGAAGGAGGGAUTUUAGGAAAGUARGRGGGARGGGAAGURGAGG<br>AAGURGRGGGGUAGURGUAUUTRG |
| 239 | TGUAGTGTGUAUAGGAUTUUUTGAAAGGGUTUUUTGGGATGGAGGGTTTTTTGGGGG<br>GGUUTGTGGTUTTUTUTUUAGUATGAGTUAUAAAUUAUAUTUUTUUAUAGTUAGURGG<br>ATUUAAAURGATTTGAURGAGATXGGUTUTTUAATGXGGTUTUURGGGGTGTUUUR<br>GAGGATUTGGUTGGAUTTUUAGAGTAUUTGAGUAAGAUUAGUAAGTAUUTUAURG<br>AUTRGGAATAUAUAGGTAGAUUUTGUUUTGTGGATUUAAGGUTAGGUATUUTGTGA<br>GUTGATAGTTAGGTGGGUTGT |
| 240 | UAGUUUAUUTAAUTAUATUAGUTUAUAGGATGUUTAGUUTTGGATUUAUAGGGUAGG<br>GTUTAUUTGTGTATTURGAGTRGGTGAGGTAUTTGUTGGTUTTGUTUAGGTAUTUTG<br>GAAGTUUAGUUAGATUUTRGGGAUAUUURGGGAGAUXGUATTGAAGAGUXGATU<br>TRGGTUAAATRGGTTTGGATURGGUTGAUTGTGGAGGATGTGGTTTGTGAUTUATGU<br>TGGAGAAGAAUUAUAGGUUUUUUUAAAAGUUUTUUATUUUAGGGAGUUUTTUAG<br>GGAGTUUTGTAUAUAUTGUAU |
| 241 | AGGAGUUTGTGAUUUAGAAATGGTAAGTAAGGTURGAUTTUTUAUUAAUAAAGUAG<br>GUATGAUUUAGAUAAGTUUUTAUUUTGUTUTGGGUUTUAGTTUTUUTTTAGTGA<br>GGAGGTGGGTGAGGGTUUTGTUUTUUTURGGGAAUTGGXGATTTGGGAAGGUAGAG<br>AUATTUUUAGAAUTUXGURGGAGTUUTGAAAAUAUUUARGUUUTTTGTUUUAGUAAT<br>UUTGAGAAAGGUUAUAUTGAUAAAGUTGTGGGTGGUUAGATGAUAGUAUUTTGGG<br>UUTUAGARGAAGTGGGAGGGG |
| 242 | UUUTUUUAUTTRGTUTGAGGUUUAAGAAUTGUTGUAUAUTGGUUAUUUAUAGUUTA<br>TUAGTGTGGUUTTTUTUAGGATTGUTGGGAUAAAGGGRGTGGGTGTTTTUAGGAUTU<br>RGGXGGATTUTGGGAAUTGUTUTGUUTTUUUAAATXGUUAGUUTUURGGAGGAGGAU<br>AGGAUUUTUAUUUAUUTUUTUAUTAAAGGAGAAAUTGAGGUUUAGAGUAGGGUAG<br>GGAUTTGUTGAGGUUAUGUUTGUUUTGUUGGUGAGAAUTRGGAUUUTAUUAUUATT<br>TUTGGGUUAUAGGUUUUTT |
| 243 | AGUUUTGGUTGAGUGUUUUUUAUUUUUTGGUTRGAGUUUUUUAUGAAAAAAUUT<br>GGUGAUUUUUUUGUAUAGAAUAAAGGUUGAGUGAGGUAUAGUGUUUAGGGGAUG<br>AGGAAGGUUGAGUURGGGAUUAGGUAGGAGGAAUUUGUXGUGUAUUUAUUAGAU<br>UUUGUAGUAUURGGGGUAGGUGUUUUAUUAGRGGGUAUAGURGUUUAGURGUUU<br>UUUAUUURGURGUAGUUAGUGGAUUAUUAUAGUGUUAGAGAGGUUUAUUAUUU<br>GGUUAURGGGUUUARGUUUGUAGA |
| 244 | TUTGUAGGRGTAGAUURGGTGGUUAAGTGGTGGGUUTUTUTGAUAGUTGTGGTGAT<br>UUAUTGGUTGRGGRGGGATGAGGAGGRGGUTGAGRGGUTGTGUURGUTGGTGGAG<br>UAUUTGUUURGGGTGUTGUAGGAGTUTGAGTGAGTGUAXGGUAGGTTUUTUUTGUU<br>TGGTUURGGGUTUAGUUTTUUTUATUUUUTGGGUAUTGTGUUTUAUTUAGUUUTTG<br>TTUTGTGUAGGAGGAGTUAUUAUUTTTTTTUUTUAGGGAAUTRGAGUUAGGGAAGT<br>GGGGGGUAUTUAGUUAGGGUT |

-continued

| SEQ ID NO: | Sequence |
|---|---|
| 245 | UTUTGGGUTUTUTUUAUAGGGTTGAGGUUAGAGUTATTUTUAGAATUURGURGGAG<br>GGGUUTTGUUTGGAGGAGGGUAUAARGAUAUTTAUTTGUUUUAUTUAGUUGAUTG<br>AGGGUTGGGGTTGGGUTGGGTUAUAUAGTTUAGTGUTXGUTUTAAGAGATGTTUUR<br>GGAATAGUTGAGTUAUUTGGGUUAGGGGGTUUAUTGTGGAGAGGAGGAGGTGAGT<br>GGGGTGGGGAGUAGGGUUUUAUUUTUUTUTUUAAGUTAAGGGUTTTTTUUTGGGTG<br>GGUTGGGGUUAUAUUTAGGGUU |
| 246 | GUUUTAGGTGTGGUUUUAGUUUAUUUAGGAAAAAGUUUTTAGUTTGGAGAGGAGG<br>GTGGGGUUUTGUTUUUUAUUUUAUTUAUUTUUTUUTUTUUAUAGTGGAUUUUUTG<br>GUUUAGGTGAUTUAGUTATTURGGGAAUATUTUTTAGAGXGAGUAUTGAAUTGTGT<br>GAUUUAGUUUAAUUUUAGUUUTGGGTUAGUTGATGGGGAUAAGTAAGTGTRGTTG<br>TGUUUTUUTUUAGGUAAGGUUUTURGGRGGGATTUTGAGAATAGUTUTGGUUTUA<br>AUUUTGTGGAGAGAGUUUAGAGU |
| 247 | RGUUUTGGUTUTGGGUTTTUAUUAURGUUTGGGGUUUTGUTTGGAUTUTGUAGUTG<br>TGTUUUAAGGUTGRGUUUTAGATTTGTUTAUTUUTTUUUUTGUUUUUTUUUTGUTTT<br>UTUURGGUUTUTGTAGTUTTUUTGUTUUTUUAUUTAXGTGGUTGUUTTGGGUUUUA<br>TGUAGUTUUTUUUURGGGATGUUUUATGUTUTGTTUTGTGAUTGUUTTAUTUTTGAT<br>UAUUTUTGATGGUTGUTUUAGTGUAGGUAGAAUUUUUAAAGTUUTUTGTTUTUTAU<br>ATGTUUUUUTTTGUUAUU |
| 248 | GGTGGUAAAGGGGGAUATGTAGAGAAUAGAGGAUTTTGGGGGTTUTGUUTGUAUTG<br>GAGUAGUUATUAGAGGTGATUAAGAGTAAGGUAGTUAUAGAAUAGAGUATGGGGU<br>ATUURGGGGGAGGAGUTGUATGGGGUUUAAGGUAGUUAXGTAGGTGGAGGAGUAG<br>GAAGAUTAUAGAGGURGGGAGAAAGUAGGGAGGGGGUAGGGGAAGGAGTAGAUA<br>AATUTAGGGRGUAGUUTTGGGAUAUAGUTGUAGAGTUUAAGUAGGGUUUUAGGRG<br>GTGGTGAAAGUUUAGAGUUAGGGRG |
| 249 | TTTUUTUUTUTUTTTUUTTUUTTUTUUAGTTUUTUUUTTTTUUTUUTTUAUTGTTTGA<br>TTTTTAGUUUTUTGATTTTTTUTTUUTUTTUTUUAUTUTTTATTTUTTTTUATUUTUT<br>UURGGTUUTTTTTTUTGUTTTGTUAUUTUUTTXGTTTTUTTUTUTUTUTGGUTGAUTU<br>AGGGGAURGGAGGTGGGUUTATUTGGAGTGAGTGAGTAAGTGTGTTGGGAGGTGAG<br>GGTGGAGGGUTGGAGGGGGGUAGTGATUTGGUUTGAGUUUUTUUAGTATTGUTUUA<br>GUUUUAGURGUAG |
| 250 | UTGRGGUTGGGGUTGGAGUAATAUTGGAGGGGUTUAGGUUAGATUAUTGUUUUUU<br>TUUAGUUUTUUAUUUTUAUUTUUUAAUAUAUTTAUTUAUTUAUTUUAGATAGGUU<br>UAUUTURGGTUUUUTGAGTUAGUUAGAGAGAGAAGAAAAXGAAGGAGGTGAUAAA<br>GUAGAAAAAAGGAURGGGAGGAGGATGAAAAGAAATAAAGAGTGGAGAAGAGGA<br>AGAAAAAAATUAGAGGGUTAAAAATUAAAUAGTGAAGGAGGAAAAGGGAGGAAUTG<br>GAGAAGGAAGGAAAGAGAGGAGGAAA |
| 251 | UTATAUTUTUAGGUUUAGGUUAGGGGRGGUAGUTGUUUUUUTUAUTGUUUUARGU<br>AUAAATUUUTGGTTTUAGTUUAAAURGUTAUTGTGAGUTUUAGATUTGGGTGGGGU<br>URGGAGUUTUUTUATTAGUAUUAGGTGGGATGGUUTTGXGAAGATAAAGUTUTGTU<br>TGGUUUUAGUUUAGGUTGTAGUUURGGGUUUTGUUUUAGGUAGUUTGUUUAGGAT<br>GUTGTGUUAGTTTUTGAUUTTTGUUUAUTGUAGUUAGATGGGGUUAUTUTGTGGAGU<br>TGGUUTTTTUTUUTTAGAATGA |
| 252 | TUATTUTAAGGAGAAAAGGUUAGUTUUAUAGATGGUUUUAUTUTGGUTGUAGTGGG<br>UAAAGGTUAGAAAUTGGUAUAGUATUUTGGGUAGGUTGUUTGGGGUAGGGUURGG<br>GGUTAUAGUUTGGGUTGGGGUUAGAUAGAGUTTTATUTTXGUAAGGUUATUUUAU<br>UTGGTGUTAATGAGGAGGUTURGGGUUUUAUUUAGATUTGGAGUTUAUAGTAGRG<br>GTTTGGAUTGAAAUUAGGGATTTGTGRGTGGGGUAGTGAGGGGGGUAGUTGURGUU<br>UUTGGUUTGGGUUTGAGAGTATAG |
| 253 | ARGGGTGTUTGUTUUUAAGUTGGGUAUUUUTUUUUUAGGUTGTGGGAAURGUTGG<br>GUUATTUTGAUUTRGAAUUAGAAATAGUUURGAUUUUUUTUTTTUTUUURGRGUUU<br>UUAGURGGAURGUUUUURGGGAUUUUAGUUAAAUUAUAGXGTURGGUATAGGGU<br>UTUTUUUTTATTGUAUAAURGUTAGGGGAGAUAGAGAGGATGGGGGTUURGGGAA<br>UATGUTGGGGTRGUUAGAUTATGGGARGTAGGGGRGTAGUTUAUUTGTTGGAGAUA<br>GGUURGUTUUTUAUTGGUTGAGTU |
| 254 | GAUTUAGUUAGTGAGGAGRGGGUUTGTUTUUAAUAGGTGAGUTARGUUUUTARGT<br>UUUATAGTUTGGRGAUUUUAGUATGTTUURGGGAUUUUUAUTUUTUTUTGTUTUUUU<br>TAGRGGTTGTGUAATAAGGGAGAGGUUUTATGURGGAXGUTGTGGTTTGGUTGGGG<br>TUURGGGGGGRGGTURGGUTGGGGGRGRGGGGAGAAAGAGGGGGGTRGGGGUTAT<br>TTUTGGTTRGAGGTUAGAATGGUUUAGRGGTTUUUAUAGUUTGGGGGAGGGGTGUU<br>UAGUTTGGGAGUAGAUAUURGT |
| 255 | GUAGTAAAUAGTUUTATTGTAUAAATATATAGRGRGGGUTGGGRGGGGGRGGTUAA<br>UUURGGTTUUUTGGUARGGGGAUAGGGRGRGUTGGGUURGGUTUTGUAGRGAGUR<br>GGTGGGAGGGUUTAGUTGTGGUUUAGGRGGTGTTGAGUAXGGGURGGGGGRGTUA |

-continued

| SEQ ID NO: | Sequence |
|---|---|
| | TAGURGGGGAGGGURGGGUAGRGAGRGGGTGGGRGAGGGGRGAGTUATRGTUTGU UURGUURGGAGGGGAUUURGGRGGGTGAGGGARGTGGGTGGAGGGAGARGTGGGG AGUTUAGTRGGAGTAGATGATGAA |
| 256 | TTUATUATUTAITTURGAUTGAGUTUUUUARGTUTUUUTUUAUUUARGTUUUTUAUU RGURGGGGTUUUUTURGGGRGGGGUAGARGATGAUTRGUUUUTRGUUUAUURGUT RGUTGUURGGUUUTUUURGGUTATGARGUUUURGGUUXGTGUTUAAUAURGUUTG GGUUAUAGUTAGGUUUTUUUAURGGUTRGUTGUAGAGURGGGUUUAGRGRGUUUT GTUUURGTGUUAGGGAAURGGGGTTGAURGUUUURGUUUAGUURGRGUTATATATT TGTAUAATAGGAUTGTTTAUTGU |
| 257 | AGTTATTTAATAUATGGUUUUAGTGGUAUTAALUTGTUAUTAAGUUTUATGTTUTU UATUUATAAAATGGAGAUUAUAATUATAUUTGUTGUAAAATUUAAAATTUAGAGGT TTUTAUAGRGTGAURGAUAUTGTGUUURGGAGAGTTTXGGUUUTUTUUTGGUTUTG GUUUUUTGGAAUARGTGATGUUUAGUUUAAAUAGTGUUAUAUUUTGUTUTAUAAT GUUTUAARGAGAGTUAUAAUUAAAGATTTTTGAGTUAGAGGAUAATAGAGGAGGT GGGAAUTGGGTAAAXGGAGAGT |
| 258 | UTUTUXGTTTAUUUAGTTUUUAUUTUUTUTATTGTUUTUTGAUTUAAAAATUTTTGG TTGTGAUTUTRGTTGAGGUATTGTAGAGUAGGGTGTGGUAUTGTTTGGGUTGGGUAT UARGTGTTUUAGGGGGUUAGAGUUAGGAGAGGGUXGAAAUTUTURGGGGUAUAGT GTRGGTUARGUTGTAGAAAUUTUTGAATTTTGGATTTTGUAGUAGGTATGATTGTGG TUTUUATTTTATGGATGGAGAAUATGAGGUTTAGTGAUAGGTTAGTGUUAUTGGGG UUATGTATTAAATAAUTG |
| 259 | GAGTTTXGGUUUTUTUUTGGUTUTGGUUUUUTGGAAUARGTGATGUUUAGUUUAAA UAGTGUUAUAUUUTGUTUTAUAATGUUTUAARGAGAGTUAUAAUUAAAGATTTTTG AGTUAGAGGAUAATAGAGGAGGTGGGAAUTGGGTAAAXGGAGAGTUUATGGUUTT TGGAGGTGGGGUAUAGUURGGAGTGAATGAGGGUUUAGAGTTTUUAGAGAAURGA ATATAGATUTGTGTGTGAAGUUTUUAGATATTUTAATGTTGAUAARGAAATUAAATT GAAAAAAAATAAAAATUAATA |
| 260 | ATTGATTTTTATTTTTTTTUAATTTGATTTRGTTGTUAAUATTAGAATATUTGGAGGUT TUAUAUAUAGATUTATATTRGGTTUTUTGGAAAUTUTGGGUUUTUATTUAUTURGG GUTGTGUUUUAUUTUUAAAGGUUATGGAUTUTUXGTTTAUUUAGTTUUUAUUTUUT UTATTGTUUTUTGAUTUAAAAATUTTTGGTTGTGAUTUTRGTTGAGGUATTGTAGAG UAGGGTGTGGUAUTGTTTGGGUTGGGUATUARGTGTTUUAGGGGGUUAGAGUUAGG AGAGGGUXGAAAUTUT |
| 261 | RGGGTGRGGAUURGUUAUUTGURGUAUUUTTUUUTTUUUAAUUUTGUUUTTTUUUU AUUUUUAUUUUAUTTUUUAUUUUUAAUUUURGUTRGGRGUUUUAUTUURGAUUUT GUUTGUURGGGUAUUTRGGGGRGTURGUTRGURGGUTTXGUUTUUAUTTGUUURGG UAGGRGRGRGTGGGUTRGGRGTUURGRGUTUUUTUUTRGAUTGTGRGGUTUURGRG UTGURGGGTTTUUTGTTUAAUAATATAAUUAGGGAGGUAURGGRGGAGAGRGURGG GUAGAAUTTUUTUURGGAUTG |
| 262 | UAGTURGGGAGGAAGTTUTGUURGGRGUTUTURGURGGTGUUTUUUTGGTTATATT GTTGAAUAGGAAAUURGGUAGRGRGGGAGURGUAUAGTRGAGGAGGGAGRGRGGG ARGURGAGUUUARGRGRGUUTGURGGGGUAAGTGGAGGXGAAGURGGRGAGRGGA RGUUURGAGGTGUURGGGUAGGUAGGGTRGGGAGTGGGGRGURGAGRGGGGGTTG GGGGTGGGAAGTGGGGTGGGGGTGGGGAAAGGGUAGGGTTGGGAAGGGAAGGGTG RGGUAGGTGGRGGGTURGUAUURG |
| 263 | GGUAAGGUAGTUTGGGRGURGTUTURGGTUTRGGGGUUTGRGGTRGGGGUAURGRG GTGURGRGTTTGAGURGGTUAGUTUUUTGRGGAAATTAUAGGGGRGUTRGGRGUTG RGGTRGRGUUUUURGGGGUAGRGUURGUTGGTTGGAGGXGTTTAAATTGAAAGUAG UTTTGGGGAGAGGGGGRGGARGRGGGURGURGAGUAAGGGGAGGGGGRGGUURGG UAUAGRGAUUUUATTGTUTGTGUURGURGAGGGGTGGAAUUTTGRGGTGAGUTRGG RGRGGRGUUUUUTUUURGAGU |
| 264 | GUTRGGGGAGGGGGRGURGRGURGAGUTUAURGUAAGGTTUUAUUUUTRGGRGGG UAUAGAUAATGGGGTRGUTGTGURGGGURGUUUUUTUUUUTTGUTRGGRGGUURGR GTURGUUUUUTUTUUUUAAAGUTGUTTTUAATTTAAAXGUUTUUAAUUAGRGGGRG UTGUUURGGGGGGRGRGAURGUAGRGURGAGRGUUUUTGTAATTTURGUAGGGAG UTGAURGGUTUAAARGRGGUAURGRGGTGUUURGAURGUAGGUUURGAGAURGGA GARGGRGUUUAGAUTGUUTTGUU |
| 265 | GGAGGGAGUUTGUAUTUTGGGUAGTGATGTGGAGTUAGAGATTTUUAAGTTUATGG TGUAAGTUTGTGGGAGAGUAGAAUTUAUTTTAUAAAATTGTTGAUAGURGGTGTTG TTAGAGARGGAAAGGGAUAAUUURGGUTUUTUTUUAGGXGTGGAGTUTGTGGGGAT GTGUTTUUAGAAAATGUAGGGTTAAGUAGGAGUTGUAGAGTAGAATUAAATGAUA ATGAUTUAUTGUTGTUAUTAAUAGGUTUTTTGTGGGGGUTGTAGGTGGGAGGRGAT ATGGURGGUAUUTTRGUAUAA |

-continued

| SEQ ID NO: | Sequence |
|---|---|
| 266 | TTGTGRGAAGGTGURGGUUATATRGUUTUUUAUUTAUAGUUUUUAUAAAGAGUUT GTTAGTGAUAGUAGTGAGTUATTGTUATTTGATTUTAUTUTGUAGUTUUTGUTTAAU UUTGUATTTTUTGGAAGUAUATUUUUAUAGAUTUUAXGUUTGGAGAGGAGURGGG GTTGTUUUTTTURGTUTUTAAUAAUAURGGUTGTUAAUAATTTTGTAAAGTGAGTTU TGUTUTUUUAUAGAUTTGUAUUATGAAUTTGGAAATUTUTGAUTUUAUATUAUTGU UUAGAGTGUAGGUTUUUTUU |
| 267 | GTTUTGGTTRGGUAGAGTGGRGGUAATUTTGUUTUTUTUTUTAGAAUAUUTAAAGA AGUUAGTGAGTGAGUTGUTUATGUAUAURGGGGAGAUUTAUAGARGGATUUAGGA GGAGRGGGAGUTUATTGAUTGUAUAUTTUUAAUURGGXGTGATAGGAAAGTGAGG UUAUUTGUTUUTAAGTGUURGGGGGUAGGGGGGTUUATGGAGGAGGGGGRGGGGGU AGGTGTUTGGAUAUAGGGATGUTGGTUTUAGGTGGUAUAGUTGGGGAGAAAAAAU UTATUUATTGUAAAAUATUATTAG |
| 268 | TAATGATGTTTTGUAATGGATAGGTTTTTTUTUUUUAGUTGTGUUAUUTGAGAUUAG UATUUUTGTGTUUAGAUAUUTGUUUURGUUUUUTUUTUUATGGAUUUUUUTGUUU URGGGUAUTTAGGAUAGGTGGUUTUAUTTTUUTATUAXGURGGGTTGGAAGTGTGU AGTUAATGAGUTUURGUTUUTUUTGGATURGTUTGTAGGTUTUUURGGTGTGUATG AGUAGUTUAUTUAUTGGUTTUTTTAGGTGTTUTAGAGAGAGAGGUAAGATTGURGU UAUTUTGURGAAUUAGAAUA |
| 269 | RGTGATUAGAGAUAGAAATUAGUTUUUUTUUTUUUTUAUTGAGUTTGTAGUUAUTT TAAGTATAAUUTGTGTUUTGTGUUAGTTUUAUUATAAATUAGUUUTGAGTTTTTATUR GGRGGUTTATTUTGUTGUUAAAAUUTTUAUAGTTGXGGGAATGGGUUAGGGAGAG AGUURGGAUTTTAUTURGGUTGTGGTGAUTUARGUUTTTGGGAAGGGUTGAGGTAT TTGTUUTTGGATGTGGGGATGUTGTGGUUTUTGGTTGGGAAUAUAGUUTRGTTTTGT UTGUTGGUTUTGGUTUU |
| 270 | GGAAGUUAGAGUUAGUAGAUAAAARGAGGUTGTGTTUUUAAUUAGAGGUUAUAGU ATUUUUAUATUUAAGGAUAAATAUUTUAGUUUTTUUUAAAGGRGTGAGUUAUUAU AGURGGAGTAAAGTURGGGUTUTUTUUUTGGUUUATTUUXGUAAUTAATGAAGGTT TTGGUAGUAGAATAAGURGURGGATAGAAUTUAGGGUTGATTTATGGTGGAAUTGG UAUAGGAUAUAGGTTATAUTTAAAGTGGUTAUAAGUTUAGTGAGGGAGGAGGGGA GUTGATTTUTGUTUTGATUARG |
| 271 | UAGTATGUATGTGTUUATTTAAGGUATUTGAGUUUTGGUUTTTGUTGTTUTTUUTTU UTTUTTimURGTRGGGTTGUTGAGUTUAAUATUUUAURGGGUTUUTGUTUUTTAGU TAGUAGTUAGTGUAGAGUTGUTGGGTUUTTUUGUUTXGUTTGGGUAGGUTTUTGTU AATGAGTUAUUAAGUAURGGGAAATAAGTGUAUAGGAAGGAGUAGGTGGUAAGAU UUTGTGGAGGTAGAGAUAGTTUUATTUAGTGAGTGAGUTGTGAUTGUAAATTTGGG AAGGTTUTGGGGGAAGUAA |
| 272 | TTGUTTUUUUUAGAAUUTTUUUAAATTTGUAGTUAUAGUTUAUTUAUTGAATGGAA UTGUTUTAUUTUUAUAGGGTUTTGUUAUUTGUTUUUUUTGTGUAUTTATTUUURG GTGUTTGGTGAUTUATTGAUAGAAGUUTGUUUAAGXGAGGUAGAAGGAUUUAGUA GUTUTGUAUTGAUTGUTAGUTAAGGAGUAGGAGUURGGTGGGATGTTGAGUTUAGU AAUURGARGGAGAAAGAAGGAAGGAAGAAUAGUAAAGGUUAGGGUTUAGATGUU TTAAATGGAUAUATGUATAUTG |
| 273 | RGGURGRGGGGGGRGUUTGGAGGAGGGAAGUUTUTURGGAGGAGAAGAGUTGGGR GGURGURGTAGGAGGAAGRGGAAAGATAAGGGGUUUTRGGUTRGGRGGGGURGUR GGARGUUUAGGAGUUTAATGGGGAUARGTRGGGTGGGGAXGGAGGUAGUTUUTG TURGGAUAGRGAAAUURGRGAGGUUUAGGAGAGRGGUAGUUAGRGRGGUAUAGUU RGGGAGUTGRGGUUUARGURGGAGUUTARGGAUATGGGUTRGGAAGGGAUAAAAA URGGGURGGAGTUAGRGUTGGAGUU |
| 274 | GGUTUUAGRGUTGAUTURGGUURGGTTTTTGTUUUTTURGAGUUUATGTURGTAGG UTURGGRGTGGGURGUAGUTUURGGGUTGTGURGRGUTGGUTGURGUTUTUUTGGG UUTRGRGGGTTTRGUTGTURGGAUAGGAGUTGUUTUXGTUUUUAUURGARGTGTUU UUATTGAGGUTUUTGGGRGTURGGRGGUUURGURGAGURGAGGGUUUUTTATUTTT URGUTTUUTUUTARGGRGGURGUUUAGUTUTTUTUUTURGGAGAGGUTTUUUTUUT UUAGGRGUUUUURGRGGURG |
| 275 | GUATUAUAUATUUUTUUUTGUTUTUUUTGUTGUUAAUUAGTTUUAUUAUTGUTUAUU TUTGUUUUAATTUUAUUTUUUARGUUTGUTGUTGUAUUTTGGAUTTGTTTTUUTGAA ATTGUATGUUATUUAUTUTUUUTTUTAUTTUTGUTGXGTUUUTUTTGUUUTATUAGG AUUTGTGGAUTUAGGAUTUURGGGUTTTUTUUUUUAUTUTUTUTUUURGUTTGGGUU TUAUTAUUATTTUAGUUAUTTTUUTGGUAGUTTUAUTUUTGUUUUAAGAUUUUAGU UTTTUAUUUTUUTGGTTUT |
| 276 | AGAAUUAGGAGGGTGGAGGUTGGGGTUTTGGGGUAGGAGTGAAGUTGUUAGGAAA GTGGUTGAAATGGTAGTGAGGUUUAARGGGGAAGAGAGATGGGGGAGAAAGUURG GGAGTUUTGAGTUUAUAGGUUTGATAGGGUAAGAGGGAXGUAGUAGAAGTAGAA GGGAGAGTGGATGGUATGUAATTUAGGAAAAUAAGTUUAAGGTGUAGUAGUAGG |

-continued

| SEQ ID NO: | Sequence |
|---|---|
| | RGTGGGAGGTGGAATTGGGGUAGAGGTGUAUAGTGGTGGAAUTGGTTGGUAGUAG<br>GGAGAUAGGGAGGGATGTGTGATGU |
| 277 | GGTGGRGATGUTUTAGUUAUUTGUTTUTUTGTUUTUTTTUAUAUAAATGTATUUTGU<br>TTUTTTUUAGATGTURGGUTTAATGGGAUTGGATTTATUTTUAAAAGTUUTGGTTTG<br>UUTUTGATTGAAAAUUAGTGTGUTUUUUATGGTTAXGGARGGUTGTGUAGGTTTTTG<br>TTTTGTTGAAGGGAATTGGUTUAUTUTGAGTUAGURGTGUAUURGGGUTGUTGATGT<br>AGTUTUAGTGTGATGGTTAAAUTTTAAGTGTUAATTTGAUTGGGUTAAGGAATGUUA<br>GAUATTATTTURGGG |
| 278 | UURGGAAATAATGTUTGGUATTUUTTAGUUUAGTUAAATTGAUAUTTAAAGTTTAA<br>UUATUAUAUTGAGAUTAUATUAGUAGUURGGGTGUARGGUTGAUTUAGAGTGAGU<br>UAATTUUUTTUAAUAAAAUAAAAAUUTGUAUAGURGTUXGTAAUUATGGGGAGUA<br>UAUTGGTTTTUAATUAGAGGUAAAUUAGGAUTTTTGAAGATAAATUUAGTUUUATT<br>AAGURGGAUATUTGGAAAGAAGUAGGATAUATTTGTGTGAAAGAGGAUAGAGAAG<br>UAGGTGGUTAGAGUATRGUUAUU |
| 279 | GGTTTTGGGTGTGGAUATUUUTGGAGGGUTGTTTTAGTGUUUAUAUUAATGUUUTAG<br>TTAAAGAAUUAUUUTGTUUUUTTAGUUTTUTGUAGGAUAGGTGGGAAAGGGURGG<br>GTGTUTGGTUUTGUTGUUAGGGGAUAGTGUAGGTGTGAUXGTURGGGUAGAGATGA<br>GTUAUUUTUUAUAUTGTUTTGUTGUURGTUTUUARGUUTAGTTTTAGUTRGTGTGGT<br>UAAGAAGGGGRGATTUUTUAUUTAGAAUAUATGGGTUAUAAATGUTAUUTTTGAAA<br>ATGGAAAUAAAAATAAUUUA |
| 280 | TGGGTTATTTTTGTTTUUATTTTUAAAGGTAGUAUUAAATGGATTGGTGTGAUUU<br>AGGAATRGUUUUTTUTTGAUUAUARGAGUTAAAAUTAGGRGTGGAGARGGGUAGU<br>AAGAUAGTGTGGAGGGTGAUTUATUTUTGUURGGAXGGTUAUAUUTGUAUTGTUUU<br>UTGGUAGUAGGAUUAGAUAUURGGUUUTTUUUAUUTGUUTGUAGAAGGUTAAG<br>GGGAUAGGGTGGTTUTTTAAUTAGGGUATTGGTGTGGGUAUTAAAAUAGUUUTUUA<br>GGATGTUUAUAUUUAAAAUU |
| 281 | UAGAAUUTGAGRGATGAAGTGARGGGATTTAGTUAGGUUTATGAAGAGTUAATGGU<br>AUTTGUUTUUUATAAUUUTUUAGUUUATTGGUUAAUURGUTGUUUUTRGRGTG<br>ATUTTTTGGATUTGAAGTGGTGTTTUAGGAUURGGAGXGTGGUUTGUAUTGUUTTG<br>TTUTGTTTGTTTGTGUAURGGATTUATRGTGAUTUAUUTGAGUAUUUAGGUAGTA<br>TGGAAGAAUTTTGGAGTTATTTTAAAUUUTTTGGUTUAGAAUUUUATTTGGAGGAT<br>ATTAAUATGUAAGATAA |
| 282 | TTATUTTGUATGTTAATTUTAGAAGAAATGGGGTTUTGAGUUAAAGGGTTTAAAATA<br>AUTUUAAAGTTUTTUUATAUTGUUTGGATGAUTUAGGATGAGTUARGATGAATURG<br>GTGUAUAAAUAAAUAGAAUAAGGUAGTGUAGGUUAXGUTURGGGTUUTGAAAUAU<br>UAUTTUAGATUUAAAAAGATUARGRGAGGGAUAGARGGGTTGGUUAATGGGAUTG<br>GAAGGATTATGGGAGGUAAGTGUUATTGAUTUTTUATAGGUUTGAUTAAATUURGT<br>UAUTTUATRGUTUAGGTTUTG |
| 283 | GTUUUTTGGUAUUAGGAUATUAUUUTUUUAUUTUTUUUAGAUUUTTUTUUTTGAUU<br>TUTTTAGAGUAGUUATUUTTGGAGTTGUTUAARGUUUTGRXXRGGAAGGTTGAAUR<br>UUAUAGUTTGGUTUATUTAUTTURGGGTTAGUTUAAXGUUUTUTTUTTTTUUUG<br>TGAAUUAUAGUTTGGUTUATUTAUTURGGGTTAGUTUAARGUAUTUTTUTUTUTU<br>UUTUTGAAUUARGGUTTGGUTUATUTAUTTUTGGGTTAATTTAGGUTTTUTUUAUAG<br>ATAGTUTGAAAAGGGA |
| 284 | TUUUTTTTUAGAUTATUTGTGGAGAAAGUUTAAATTAAUUUAGAAGTAGATGAGUU<br>AAGURGTGGTTUAGAGGGAGAAGAGAAGAGTGRGTTGAGUTAAUURGGAAGTAGA<br>TGAGUUAAGUTGTGGTTUAGAGGGAGAAAAGAAGAGGGXGTTGAGUTAAUURGGA<br>AGTAGATGAGUUAAGUTGTGGTTUAGAGGGAGAAGAGAAGAGGGRGTTGAGUAAU<br>TUUAAGGATGGUTGUTUTAAAGAGGTUAAGGAGAAGGGTUTGGGAGAGGTGGGAG<br>GGTGATGTUUTGGTGUUAAGGGAU |
| 285 | UTGAGTUAAUAAGGUTGAUAAGGUTGTGTTUTGGATGUAGGUURGGUAGATGTTTG<br>AGGGGGAGGTGGUUAGUUTGGAGGUUUTUAGGAGUARGGGUUTGGTGRGGGTGUR<br>GAGGUUUATGAAGGTUATRGAUUTGURGGGAGGTGGGGUXGUUTTTGTGATGGAGU<br>ATTTGAAGATGAAGAGUTTGAGUAGGTGAGTGTGTGTGAGAUUUATATGRGUAUAT<br>GTGTAUAGGUAGAGAGAGAUTUAGAGAUAAAUAGAGAGAGAUAGAGAAAGGGAT<br>AGAGATGGGGAGGGAGAUAGAAA |
| 286 | TTTUTGTUTUUUTUUUUAUTUTUTAUUUTTTUTUTGTUTUTUTUTGTTTGTUTUTGAG<br>TUTUTUTUTGUUTGTAUAUATGTGRGUATATGGGTUTUAUAUAUAUTUAUUTGUTU<br>AAGUTUTTUAUTUTTUAAATGUTUUATUAUAAAGGXGGUUUUAUUTUURGGUAGGTR<br>GATGAUUTTUATGGGUUTRGGUAUURGUAUUAGGUURGTGUTUUTGAGGGUUTUU<br>AGGUTGGUUAUUTUUUUUTUAAAUATUTGURGGGUUTGUATUUAGAAUAUAGUUT<br>TGTUAGUUTTGTTGAUTUAG |
| 287 | TTRGTGUAUTUTGRGGURGRGGRGGUAGUAGURGRGGRGGRGGUUAGUTUUURGGT<br>UTARGTGUUUAUUAUURGRGTGGGTTUUATGUTGUURGGUUTAURGTAUUAUUTGU |

-continued

| SEQ ID NO: | Sequence |
|---|---|
| | AGGGGTRGGGUAGTGGGUUAGUUAAUUARGRGGGRGGXGRGGGRGRGUAUUURGG<br>UTGGUUTUAGGUUTRGGURGAUAGUUUTUUATARGGUAGRGGAGGRGGRGRGGUT<br>GGRGGRGGGGURGRGGGGUUTGGRGGRGUTGGUTUAGURGRGGRGUARGTUTRGGR<br>GRGUTTUUUUTAUTUTUUUAGU |
| 288 | GUTGGGAGAGTAGGGGAAGRGRGURGAGARGTGRGURGRGGUTGAGUUAGRGURG<br>UUAGGUUURGRGGUUURGURGUUAGURGRGURGUUTURGUTGURGTATGGAGGGU<br>TGTRGGURGAGGUUTGAGGUUAGURGGGGTGRGRGUURGXGURGUURGRGTGGTTG<br>GUTGGUUUAUTGUURGAUUUUTGUAGGTGGTARGGTAGGURGGGUAGUATGGAAU<br>UUARGRGGGTGGTGGGUARGTAGAURGGGGAGUTGGURGURGURGRGGUTGUTGU<br>RGURGRGGURGUAGAGTGUARGAA |
| 289 | TUTTTGTGTGAGTUATGTUTTATATUUAAUAAGTAUTUAAAAAAAGATTTTTTTTTT<br>TTTTTTTAAGATGGAGTGTRGUTUTGTUAUUUAGGUTGGAGTGUAGTGGUATGATUT<br>TGGUTUAUTGUAAUUUTGUUTUURGGGTTUAAGXGATTUTTUTGUUTUAGGUTUU<br>TGAGTAGUTGGAATTAUAGGUATGUUUUAUUAUAUURGGUTAATTTTTATATGTAA<br>TAGAAAUAAGGTTTUAUUATGTTGGUUAGAUAGGTUTTGAAUTUUTGAUUTUAGGT<br>GATUUAUUUAUUTRGGU |
| 290 | GURGAGGTGGGTGGATUAUUTGAGGTUAGGAGTTUAAGAUUTGTUTGGUUAAUATG<br>GTGAAAUUTTGTTTUTATTAUATATAAAAATTAGURGGGTGTGGTGGGGUATGUUTG<br>TAATTUUAGUTAUTUAGGAGUUTGAGGUAGAAGAATXGUTTGAAUURGGGAGGUA<br>GAGGTTGUAGTGAGUUAAGATUATGUUAUTGUAUTUUAGUUTGGGTGAUAGAGRG<br>AUAUTUUATUTTAAAAAAAAAAAAAAAAAATUTTTTTTTGAGTAUTTGTTGGATATA<br>AGAUATGAUTUAUAUAAAGA |
| 291 | AUUAUUUUUTGAUUUUTUATGAUTUAUUUAGUTUUTAAGTGUUUUTGGGUAUUUA<br>GTTUTTTGTGGUATGGGURGGTGUAAGTTTUTATATGAGAGUUAGAGAGAUAGGGA<br>GGGAGGUURGGGUTUUTGGUUTTTTGGGAAAAGATGUUXGTUTUAGAUUAGUAAA<br>AGGAGGUAGUTGUTTTAGGAGUURGGGAAAATGUUATUAUTGATAGTATTATTATT<br>ATTTTUUUATTTTUUUTTTGTGTTTTTAAAATGAAAAGTTUAGATUUATGGGGTAGG<br>GTAGAGTGGGUUTGGAGGGAG |
| 292 | TUUUTUUAGGUUUAUTUTAUUUTAUUUUATGGATUTGAAUTTTTUATTTTAAAAAU<br>AUAAAGGGAAAATGGGAAAATAATAATAATAUTATUAGTGATGGUATTTTUURGGG<br>UTUUTAAAGUAGUTGUUTUUTTTTGUTGGTUTGAGAXGGGUATUTTTTUUUAAAAG<br>GUUAGGAGUURGGGUUUUTUUUTGTUTUTUTGGUTUTUATATAGAAAUTTGUAU<br>RGGUUUATGUUAUAAAGAAUTGGGTGUUUAGGGGUAUTTAGGAGUTGGGTGAGTU<br>ATGAGGGGTUAGGGGGTGGTT |
| 293 | GUAGUARGUAGUUUUUAGGGGUUUTAAUTUAUUUUUTUTTUUUTUAUAGGGUTTU<br>UUTGURGTUUAGTGTTGGGTGAGAAAGGTGGAGGGGAUATGTAGUUURGGATGGAG<br>GTGUAGUAUUAARGAGAGAGUTURGGUUTGTGGGAGGGAXGUTUAGGUTTAGGTU<br>AAAGUUAGGAGUTURGGGAAAUUTGGGTTUAGURGUUARGUUUUARGGAGGGGAU<br>AUAUUUTTUUUTGUUTGATGGUAGGGUUUATGGTAGAUAAAAUUUATGAUUTUAU<br>UTUTUUTGGUTUUAGGGUTUAGUU |
| 294 | GGUTGAGUUUTGGAGUUAGGAGAGGTGAGGTUATGGGTTTTGTUTAUUATGGGUUU<br>TGUUATUAGGUAGGGAAGGGTGTGTUUUUTURGTGGGGRGTGGRGGUTGAAUUUA<br>GGTTTUURGGAGUTUUTGGUTTTGAUUTAAGUUTGAGXGTUUUTUUUAUAGGURGG<br>AGUTUTUTRGTTGGTGUTGUAUUTUUATURGGGGUTAUATGTUUUUTUUAUUTTTUT<br>UAUUUAAUAUTGGARGGUAGGGAAGUUUTGTGAGGGAAGAGGGGGTGAGTTAGGG<br>UUUUTGGGGGUTGRGTGUTGU |
| 295 | ATTTUTTTUTAUUTGTUATTGAAGTGAAUTUATUAGTATAAGTAGRGAGUTGGGRGUA<br>TTUUTTUTUAGTTGTGTTAAAAUTTGUTGGTATTUUUURGGTATUAGUAGAGGTGTG<br>TARGGGUAUTGUTTTAAAAUTGGGAAGGAGGAAGAXGAGGUUAGGGAGURGGAGG<br>GTUAUUAAGGTAGATTTUUAGUAGRGUTAGTUUAGUTGAAUAUTTTUUAGUUTTGT<br>TTTTUAGUAGUTTTGAGGAAAAGTATAGGTAAGAAUAAAGAUAUUAUTGTATGTTT<br>GUTATATGAATGUATAAUA |
| 296 | GTTATGUATTUATATAGUAAAUATAUAGTGGTGTUTTTGTTUTTAUUTATAUTTTTUU<br>TUAAAGUTGUTGAAAAAUAAGGUTGGAAAGTGTTUAGUTGGAUTAGRGUTGUTGGA<br>AATUTAUUUTGGTGAUUUTURGGUTUUUTGGUUTXGTUTGAATTUUUGGUUATTA<br>AAGUAGTGUURGTAUAUAUUTUTGUTGATAURGGGGGAATAUUAGUAAGTTTTAAU<br>AUAAUTGAGAAGGAATGRGUUUAGUTRGUTAUTTATAUTGATGATTUAUTTUAATG<br>AUAGGTAGAAAGAAATG |
| 297 | ATTGGTUTGGTUUTUTTTUTAAUAUUTUUUAUURGGGATGUAGUUAAGAGTGGUTG<br>UAGUUTAATTTTUTAUATGTAAAUAATGAUUTUAGTGATGUUUARGGGGUUUUTUT<br>UTGGUUTTUTUUUUUTGGGAAAAGAUTGAGTTUTRGAXGGGUATUUUUTUUUUUTU<br>RGGAAUUAAGGGUTUTGGGATGTTGAUAGUUUURGUUAUUTUTGAGAAGGGUAGG<br>URGTGGAAAAUUATUTUUTUUUTTUUTTUUUUUTUTGUTUTUUTAGUTGGGGUUT<br>UTGUAUAATGUAGUTGGGUUA |

-continued

| SEQ ID NO: | Sequence |
|---|---|
| 298 | TGGUUUAGUTGUATTGTGUAGAGGUUUUAGUTAGGAAAGGUAGAGGGGGAAGGAA GGGAGGAGATGGTTTTUUARGGUUTGUUUTTUTUAGAGGTGGRGGGGGUTGTUAAU ATUUUAGAGUUUTTGGTTURGGAGGGGGAGGGGATGUUXGTRGAGAAUTUAGTUTT TTUUUAGGGGGAGAAGGUUAGAGAGGGGUUURGTGGGUATUAUTGAGGTUATTGT TTAUATGTAGAAAATTAGGUTGUAGUUAUTUTTGGUTGUATUURGGGTGGGAGGTG TTAGAAAGAGGAUUAGAUUAAT |
| 299 | TTGUUUTUATUTUUAGGUTTTGGAGGAGGGTAGGTGUUTGGUUAGUAGAGTGGUUA UTGUTUAUTGGUUUAGAGGAAGUAAGGUUAUUAGUUTGAUTUUUAUTTUTUUUTUR GGUUUATUTTUAUTUUUUTUTUUTUAAUUAUAAGUUUXGUUAAAATAGAGAUUUU RGGUTTTGUTUUUUTGUTGUAGGAAGGGAGAGUUAURGUUAGAUAUTGUUTGUUT GGTUUTUUTGUTTUTGAUTUTUAUURGGTGUTTGGAATUAAAGAGGAUUTGGUTTUUU TUTRGGGATARGTGATTTTUTTT |
| 300 | AAGAAAATUARGTATUURGAGAGGGAAGUUAGGTUUTUTTTGATTUUAAGUAURGG GTGAGATUAGAAUAGGAGGAUUAGGUAGGUAGTGTUTGGRGGTGGUTUTUUUTTU UTGUAGUAGGGGAGUAAAGURGGGGGTUTUTATTTTGGXGGGGUTTGTGGTTGAGG AGAGGGGAGTGAAGATGGGURGGAGGGAGAAGTGGGATUAGGUTGGTGGUUTTGU TTUUTUTGGGUUAGTGAGUAGTGGUUAUTUTGUTGGUUAGGUAUUTAUUUTUUTUU AAAGUUTGGAGATGAGGGUAAG |
| 301 | GUUUAGATUAGGUAGRGGGGTRGUUUTUTUUAGGAUTUTUAAGGUAGUTAAGGUT GGAGGRGURGGRGAGUUTGGAGAGGGAGGAGTTUAUTAAATTGTGTTGGATGGAAG GRGTRGAGGAURGGAGGAATTAATURGATGTGGGGAAGGXGGARGGGGUTARGAG GAAAAAAGAGGGGGUAATGTAUAUTUAGUUTTTTUATUAUTRGGRGGGGAGATGGA TGGTTTTURGGAURGGGRGTUUUAGRGUUURGGTTAGUTATAGGGAGARGTUAGAG RGUTUTGGTURGRGATAGAAGA |
| 302 | TUTTUTATRGRGGAUUAGAGRGUTUTGARGTUTUUUTATAGUTAAURGGGGRGUTG GGARGUURGGTURGGAAAAUUATUUATUTUUURGURGAGTGATGAAAAGGUTGAG TGTAUATTGUUUUUTUTTTTTTUUTRGTAGUUURGTUXGUUTTUUUUAUATRGGATT AATTUUTURGGTUUTRGARGUUTTUUATUUAAUAUAATTTAGTGAAUTUUTUUUTUT UUAGGUTRGURGGRGUUTUUAGUUTTAGTGUUTTGAGAGTUUTGGAGAGGGRGAU UURGUTGUUTGATUTGGGU |
| 303 | ATTTGGUTTGATUTTATTTTTAATATTTTTTAUAUTTTUTUTUTAAAGAAAA RGAGTGAATATRGTGATGGGTGUAGTTATGUTGAATAATTGGATGGGAGGARGTGU UAGGRGATUTUUAGUUUUTGGGAGURGGARGUUUAXGUTTTUUUTUTGUUTRGTTUT UAUAGAUAUATTTGTGGGGTGATTAAUTUAGGAATTUATGUTGUTUAAAGTAAUTA UAGTGGTGAGTGTTTTGAURGGTTTGATGTAGAAATUAAGGAAAAUAUUAGAAAAA TUAGGGGRGGAGGUUUAA |
| 304 | TTGGGUUTURGUUUUUGATTTTTUTGGTGTTTTUUTTGATTTUTAUATUAATTGT AAAAUAUTUAUUAUTGTAGTTAUTTTGAGUAGUATGAATTUUTGAGTTAATUAUUU UAUAAATGTGTUTGTGAGAARGAGGUAGAGGGAGGXGTGGGRGTURGGUTUUUAG GGGUTGGAGATRGUUTGGUARGTUUTUUUATUUAATTATTUAGUATAAUTGUAUUU ATUARGATATTUAUTRGUUTTTTTTTTUTTTAGAGAGAAAGTGTAAAAAATATTAAA AATAAGATUAAGUUAAAT |
| 305 | TGAUTTTTTUATTTUTUTUAAGATGATUATTAGGAGTGGTTTUAAUAAAAUTGAAUA UAGAATTTTGAGGGUUUUAATUATGAUTUAAUUAGAGUUUTUUUTGAATTUTTUAT GAGTUAGUURGGUUUTUUUUAUTGAUTTUAUUUTAGXGGGUAUUTGTUTTTUTTUT TUTTTTATUAUTTTTTGUTTUTUTTTTGGTTTUUAGUTUTGGTTTTUTUUGAATA UAUUTTUUAATTUTTUURGGUUUUUTUAGGGAAAUUUAGAGGUAAATTTGAGTGUA GGGAGRGGGGGUTTRGU |
| 306 | GRGAAGUUUURGUTUTUTGUAUTUAAATTTGUUTUTGGGTTTUUUTGAGGGGGURG GGAAGAATTGGAAGGTGTTGGGUTGAATTUAGTUAGAGUTGGAAAUUAAAAGAGA AGUAAAAAGTGATAAAAGAAGAAGAAAGAUAGGTGUUXGUTAGGGTGAAGTUAGT GGGGAGGGURGGGUTGAUTUATGAAGAATTUAGGAGGGUTUTGGTTGAGTUATGA TTGGGGUUUTUAAAATTUTGTGTTUAGTTTTGTTGAAAUUAUTUUTAATGATUATUT TGAGAGAAATGAAAAAGTUA |
| 307 | GGTGTUAGGAGTGGUUUAGGAGAGUAUUURGTTUUURGGUURGUAGGTGGTGTTTG UTGGUTUUAGUAGGGUUAGGAGGUUAUUTGUAGUUTGGTGUTUUAGAUTGATGTU AUURGGGURGAGTGUTGTGUUTURGGUAAUATTGAUAUXGUUTGGTUUAAUUTUA UUUAUURGGGGAAUAAGATUAAUUTUUTRGGUTTTTTTGGGUUTTGTUUAUTGUUTT UUUTGUAAAGGTGAGAUUTUAGGUUAGAAGUAGGGUAGARGTUTUAGUTUAGGAU UAGUUAUAAAUAGTUATGGTGGT |
| 308 | AUUAUUATGAUTGUTTGTGGUTGGTUUTGAGUTGAGARGTUTGUUUTGUTTUTGGU UTGAGGTUTUAUUTTGUAGGGAAGGUAGTGGAUAAGGUUUAAGAAGURGAGGAG GTTGAUTUTTGTUUURGGGTGGGTGAGGTTGGAUUAGGXGGTGTUAATGTTGURGG |

-continued

| SEQ ID NO: | Sequence |
|---|---|
| | AGGUAUAGUAUTRGGUURGGGTGAUATUAGTUTGGAGUAUUAGGUTGUAGGTGGU<br>UTUUTGGUUUTGUTGGAGUUAGUAAAUAUUAUUTGRGGGURGGGGAARGGGGTGU<br>TUTUUTGGGUUAUTUUTGAUAUU |
| 309 | GUAGUUUTUTTUAUUTGUUTGGTGAUTUAUTAUAAGUUUTGGGGGAAGGAATGGU<br>AGTGGUUUTUTTUAUUTTTAUTGUUTUTGRGGUUAUAATGGGUAGTTGAUATAAUU<br>AUUTGUAGGUUURGGGAGUUATXGGGGUUTUTTGAUAXGTGUTUATTAGTGGUTTU<br>TGAGGAGRGUUTGUUUUAUUTGUUUUAXGTGUUUUUAXGTUTGGUUAUTUUAGGG<br>TUUATTAGRGUTAATRGGUAAATGUUTGTGUTUTUATUTAURGGGAAAAUATUTUU<br>UTTUTUUAGAGRGGAGGUUAGU |
| 310 | UTGGUUTURGUTUTGGAGAAGGGAGATGTTTTUURGGTAGATGAGAGUAUAGGUAT<br>TTGURGATTAGRGUTAATGGAUUUTGGAGTGGUUAGAXGTGGGGGUAXGTGGGGUA<br>GGTGGGGUAGGRGUTUUTUAGAAGUUAUTAATGAGUAXGTGTUAAGAGGUUUXGA<br>TGGUTUURGGGGUUTGUAGGTGGTTATGTUAAUTGUUUATTGTGGURGUAGAGGUA<br>GTAAAGGTGAAGAGGGUUAUTGUUATTUUTTUUUUUAGGGUTTGTAGTGAGTUAUU<br>AGGUAGGTGAAGAGGGUTGUT |
| 311 | GTGGUUUTUTTUAUUTTTAUTGUUTUTGRGGUUAUAATGGGUAGTTGAUATAAUUA<br>UUTGUAGGUUURGGGAGUUATRGGGGUUTUTTGAUAXGTGUTUATTAGTGGUTTUT<br>GAGGAGRGUUTGUUUUAUUTGUUUUAXGTGUUUUUAXGTUTGGUUAUTUUAGGGT<br>UUATTAGRGUTAATRGGUAAATGUUTGTGUTUTUATUTAURGGGAAAAUATUTUUU<br>TTUTUUAGAGRGGAGGUUAGUUTAAAAAUUAGGUURGUAGUUTURGAGGUTUTGA<br>AAAUUAAGRGGUTGTTUTGGTU |
| 312 | AUUAGAAUAGURGUTTGGTTTTUAGAGUUTRGGAGGUTGRGGGUUTGGTTTTTAGG<br>UTGGUUTURGUTUTGGAGAAGGGAGATGTTTTUURGGTAGATGAGAGUAUAGGUAT<br>TTGURGATTAGRGUTAATGGAUUUTGGAGTGGUUAGAXGTGGGGGUAXGTGGGGUA<br>GGTGGGGUAGGRGUTUUTUAGAAGUUAUTAATGAGUAXGTGTUAAGAGGUUURGA<br>TGGUTUURGGGGUUTGUAGGTGGTTATGTUAAUTGUUUATTGTGGURGUAGAGGUA<br>GTAAAGGTGAAGAGGGUUAUT |
| 313 | ATGGGUUUTGGGGURGURGUUTUAGTGTUTTUTGGTGUTGUAGURGGGUAGGGURG<br>AAUUUTGGRGUAUAGUTTUUTGUTGAGTUTUUUTUTUTAAGGUTGUTUTGTGGGRGG<br>UTUTGURGGUUUUTUUTGUAUUTGUUUAGGUUUTGGGXGGAGGUTUUTUUTUURG<br>GGGGGGUTGTGGUUTUAGUAUAGAUUAGGGGAUAGAAGGTGGUTUTTUTTGGUUTT<br>GGUTGGGTGTGAAUUAAAGAUTTUUTGTAAGAAATUUUUUTUTUUUTUTUUUTUUT<br>TRGUTUUUTUATUTUTUTUUU |
| 314 | GGGAGAGAGATGAGGGAGRGAAGGAGGGAGAGGGAGAGGGGGATTTUTTAUAGGA<br>AGTUTTTGGTTUAUAUUUAGUUAAGGUUAAGAAGAGUUAUUTTUTGTUUUUTGGTU<br>TGTGUTGAGGUUAUAGUUUUUURGGGAGGAGGAGUUTUXGUUUAGGGUUTGGGUA<br>GGTGUAGGAGGGGURGGUAGAGURGUUUAUAGAUAGUUTTAGAGAGGGAGAUTUA<br>GUAGGAAGUTGTGRGUUAGGGTTRGGUUUTGUURGGUTGUAGUAUUAGAAGAUAU<br>TGAGGRGGRGGUUUUAGGGUUUAT |
| 315 | UAUTGGAUUATUUAUAUAAUTTTTGAGGATUAGTGGAAATGAAAAUARGGTGUUUR<br>GGUAUAAAAUATATTTUATAGUTTGGGTTAGGUAAUAGUAAAGUATUARGUTGAGR<br>GURGGGAUUTTUTGAGTGUAGGXGGTGGGXGAAGUUURGAGTUAUAUAUAUUUAR<br>GAXGURGGUUUTGUTUUUAUAGRGGUUUTUTGGGGTAGRGAUTGGTATTAUUTGUA<br>TTTUARGAGGGAGGAAAUTGAGGUARGAAUTGTTUAGAAGUTGUUUTGAGGTUAUU<br>AAGTGAGUTAGGAAGAGGRGT |
| 316 | RGUUTUTTUUTAGUTUAUTTGGTGAUUTUAGGGUAOUTTUTGAAUAGTTRGTGUUT<br>UAGTTTUUTUUUTRGTGAAATGUAGGTAATAUUAGTRGUTAUUUUAGAGGGURGUT<br>GTGGGAGUAGGGURGGXGTRGTGGGTGTGTGTGAUTRGGGGUTTXGUUUAUXGUUT<br>GUAUTUAGAAGGTUURGGRGUTUAGRGTGATGUTTTGUTGTTGUUTAAUUUAAGUT<br>ATGAAATATGTTTTGTGURGGGGUAURGTGTTTTUATTTUUAUTGATUUTUAAAAGT<br>TGTGTGGATGGTUUAGTGT |
| 317 | UTUUAGTGTGUUTUAGTTGGTTTATUTGTAAAAATGGGGUUAGGUUARGAUTGGTG<br>TTUUUTTTAUAGAGAAGUAUTUUAGGUAGGGGTGGGTGGGGGTGGAAUTRGTTUTU<br>AATGGUUUURGGGAUAGUUUTGUAGUUAURGGTGAUTXGGGTTXGTUTGRGGATUT<br>TTUURGGUUTUUAUTUUATTUAGGGAUAGUUUTGUAATGGGGUTUUUTUUUAAAA<br>AAARGUATGGUUTTUUTGTUUUUUAAAAUUAGUTTAARGGUAGUUATTUUUTUUUT<br>UUTURGGGGGUTGAAAAAUUA |
| 318 | GGTTTTTUAGUUUURGGAGGAGGGAGGGAATGGUTGURGTTAAGUTGGTTTTGGGG<br>GAUAGGAAGGUUATGRGTTTTTTTGGGAGGGAGUUUUATTGUAGGGUTGTUUUTGA<br>ATGGAGTGGAGGURGGGAAAGATURGUAGAXGAAUUXGAGTUAURGGTGGUTGUA<br>GGGUTGTUURGGGGGUUATTGAGAARGAGTTTTUAUUUUUAUUUAUUUUTGUUTGG<br>AGTGUUTUTUTGTAAAGGGAAUAUUAGTRGTGGUUTGGUUUUATTTTTAUAGATAA<br>AUUAAUTGAGGUAUAUTGGAGG |

-continued

| SEQ ID NO: | Sequence |
|---|---|
| 319 | UAUTUARGGGUTAGUTURGTUAGGTGTTGARGGATGTUAUTUAGGTGTGAGUTUTG<br>UAUUTGAGUTUUUUUUTGUAUAUAGGUAGUUAUAAUUAGTUAGTGUAGAGGTGAG<br>UTTTGTGGUUAGTGAGGAGURGGTGAGTUAAUUTUUTUUXGUUTARGGGUUUTGAG<br>ARGURGGUTURGTGAGUTTGRGGGGTRGAGGGRGUUTATATTAAGUUAAGGUTGAG<br>GUAGTGAUAUAUUUTUTTATGGGUUTGUTUTRGUTTUUTGUTTUATTGTUUTGGTUT<br>UTUUUTUTRGTATGGAGGATUA |
| 320 | TGATUUTUUATARGAGAGGGAGAGAUUAGGAUAATGAAGUAGGGAGRGAGAGUAG<br>GUUUATAAGAGGGTGTGTUAUTGUUTUAGUUTTGGUTTAATATAGGRGUUUTRGAU<br>UURGUAAGUTUARGGAGURGGRGTUTUAGGGUURGTAGGXGGGAGGAGGTTGAUT<br>UAURGGUTUUTUAUTGGUUAUAGGUTUAUUTUTGUAUTGAUTGGTTGTGGUTGUUT<br>GTGTGUAGGGGGGAGUTUAGGTGUAGAGUTUAUAUUTGAGTGAUATURGTUAAUA<br>UUTGARGGAGUTAGUURGTGAGTG |
| 321 | UUAGGUTGUUTGGGTTTTGGTUTUUAUUATGUTAGUTTGGTGTURGAUUTGTGTTGAGAUUU<br>TUUUTGUUTUTGGUURGGGTGTUUUATUUAAGUAATGGAUAGGTTGGAAUAGGXGTTXGTA<br>GGGAAXGGGUTGAAXGUURGRGGUTUUXGXGATGTUTXGXGATAUTAUUTUUUTXGUUUUX<br>GUTUAUTTAAGGAURGGAAGTAGUAAAGUURGURGTRGRGUUUUURGUUURGRGTUTUUUT<br>GGTAAUUAGUUTUTUUUUTTUUUTRGUUUATAAGGAGUAAGRGGUAUAAATRGGG |
| 322 | UURGATTTGTGURGUTTGUTUUTTATGGGRGAGGGAAGGGGAGAGGUTGGTTAUUAGGGAGA<br>RGRGGGGRGGGGGGRGRGARGGRGGGUTTTGUTAUTTURGGTUUTTAAGTGAGXGGGGGXG<br>AGGGAGGTAGTATXGXGAGAUATXGXGGGAGURGRGGGXGTTUAGUUXGTTUUUTAXGAAX<br>GUUTGTTUUAAUUTGTUUATTGUTTGGATGGGAUAUURGGGUUAGAGGUAGGGAGGGTUTU<br>AAUAUAGGTRGGAUAUUAAGUTAGUATGGTGGAGAUUAAAAUUUAGGUAGUUTGG |
| 323 | UAATGGUUTUTTTUTTUAGUUTRGGTGGGRGTGGUTGGGGGAAUUUUAGGGRGGGR<br>GGGGGGUAGGGGGTGGTGUTGAGTUAUUUAGUUTGGUUAGGTUUUTGUUTGUUAG<br>UUUUUTGUUUUUAURGUTAUAGUURGUUURGGATUTAXGAGGUUUAGUUAGUUAU<br>UTUTGGAUTUUTGAGAUXGAATTGUAAAUTGUURGGGUUTGGUUTTGAAUTUUTGU<br>TGTTTAGGGAUUAAGTUUTGTGGUTUUUAGGGGGGUAUAGTGATUTUTUAAGUTGA<br>GUTGGUUTUAGGGUUTUTGUAU |
| 324 | TGUAGAGGUTTTGAGGUUAGUTUAGUTTGAGAGATUAUTGTGUUUUUUTGGGAGU<br>UAUAGGAUTTGGTUUUTAAAUAGUAGGAGTTUAAGGUUAGGUURGGGUAGTTTGU<br>AATTXGGTUTUAGGAGTUUAGAGGTGGUTGGUTGGGUUTXGTAGATURGGGGRGGG<br>UTGTAGRGGTGGGGGUAGGGGGUTGGUAGGUAGGGAUUTGGUUAGGUTGGGTGAU<br>TUAGUAUUAUUUUUTGUUUUURGUURGUUUTGGGGTTUUUUUAGUUAGGGTGGTTA<br>GAGGUTGAAGAAAGAGGUUATTGT |
| 325 | AUUUTGTGUAGGGUUTGUATUURGGAAGGUUTUUAUUAGUURGAAUUTGGUURGT<br>URGUUUTAGATGGGGUAATRGGRGTTTUTUURGGGAUAGUUTUUTUUUTGGUUTUU<br>TGGUUUTRGTUTGUATTGAGAGGUTTGGUUTUTGGTUXGUATGUTGUUUTTUURGT<br>GUTGTGGUUTTGUAGUURGGUUTUTUUUUTGUTGTUUUUUTTGGUTUTGGUUTGGU<br>UUUTGGGUUUUTGAGTUAUUUUTGAGGTGAUTUAGUAGTUUTTGGAAARGUATGUR<br>GAGGARGUAUUUTGUUTGGUU |
| 326 | GUUAGGUAGGGTGRGTUUTRGGUATGRGTTTUUAAGGAUTGUTGAGTUAUUTUAGG<br>GGTGAUTUAGGGGUUUAGGGGUUAGGUUAGAGUUAAGGGGGAUAGUAGGGGAGA<br>GGURGGGUTGUAAGGUUAUAGUARGGGAAGGGUAGUATGXGGAUUAGAGGUUAA<br>GUUTUTUAATGUAGARGAGGGUUAGGAGGUUAGGGAGGAGGUTGTUURGGGAGAA<br>ARGURGATTGUUUUATUTAGGGRGGARGGGUUAGGTTRGGGUTGGTGGAGGUUTTU<br>RGGGATGUAGGUUUTGUAUAGGGTT |
| 327 | GGAAUUATTGTTUTGUTGUUUAUAGUTGRGTGGAGGGATTURGGTUUTRGGGTTUA<br>GTTGGTGAUAGTGTRGGGTAGGUUTGGGUAGGTGGGAGAGGTRGTGAAGUUUTTTG<br>UAGGGUAUTTGGURGUTUAUTUTGGUAUAGGGGAAGAGGXGUAGUURGTGGUURGG<br>UAGTUUAGGAUUTGUTGTTUUUTTUUTAUURGGGGRGGGGUUTGTGGGAAGATATG<br>GAAGTRGGGTGAATGAGURGTGUUUAGTGATTTTAAAAAGUAGATTAAAATAAUAT<br>AGAAAATGTUAGAGUTUATTG |
| 328 | UAATGAGUTUTGAUATTTTUTATGTTATTTTAATUTGUTTTTTAAAATUAUTGGGUAR<br>GGUTUATTUAUURGAUTTUUATATUTTUUUAUAGGUUURGUUURGGGTAGGAAGGG<br>AAUAGUAGGTUUTGGAUTGURGGGUUARGGGUTGXGUUTUTTUUUUTGTGUUAGAT<br>GAGRGGUUAAGTGUUUTGUAAAGGGUTTUARGAUUTUTUUUAUUTGUUUAGGUUT<br>AUURGAUAUTGTUAUUAAUTGAAUURGAGGAURGGAATUUUTUUARGUAGUTGTG<br>GGUAGUAGAAUAATGGTTUU |
| 329 | GUATUUTUAUUTGRGTURGAAGRGUAGATGGAGUUUAAGGGAAAGGUUUTGTAGA<br>GGAUUURGTGTGAUTTGGGGUAAAGRGTGGUUTUUUAGGGGTGRGTGGGUAGRGG<br>GARGUUUATGGTGTGAURGGGTTTGTGUUTUUATAGGGAUXGTUTGUUUTGTGUAG<br>AGAGUUUUTGTGGGGXGGGAAGTGGXGAGUAGURGGUAAGGAGGUUUAGUUAGA<br>UAGAAGUAGGGGGGTUAGGGAUATGGAGGTGGGGGAUUAGUUAGTGAGTUAGAR<br>GTGAGGAUTTUAGTGUUAAGGAUTG |

-continued

| SEQ ID NO: | Sequence |
|---|---|
| 330 | UAGTUUTTGGUAUTGAAGTUUTUARGTUTGAUTUAUTGGGUUTUTTUUUTGGTTUU ATGTUUUTGAUUUUUUTGUTTUTGTUTGGUTGGGUTTTUUTTGURGGUTGUTXGUUA UTTUUXGUUUUAUAGGGGUTUTUTGUAUAGGGUAGAXGGTUUUTATGGAGGUAUA AAUURGGTUAUAUUATGGGRGTUURGUTGUUUARGUAUUUUTGGGAGGUUARGUT TTGUUUUAAGTUAUARGGGGTUUTUTAUAGGGUUTTTUUUTTGGGUTUUATUTGRG UTTRGGARGUAGGTGAGGATGU |
| 331 | AGGTTUUUUATUUTAGUTUUURGGATUTUUATAGGGAGTGTUUAGGGAUUUTUAAT UTUUAGGGUUAUTTUTGUAGGAGUTRGGGTTRGAGGTTUUARGTGGUUAGAAGAGU TUAGGTUTUTGAGGGUTGGTGTGUURGGGTAUUUATUXGUATUAUTGUTUTUUTUU TGTURGGUTARGUUUAGGGUTGAGTGARGGTGGTGGUAAGTGUTTGTUUTUAGGGU AGRGAGGTUTTUTGTTUTGAUAGUAGUAGGGAUTUUTTUATGGUUAUUAGTAAUUU UAGTGGGRGGAGGRGUTUUT |
| 332 | AGGAGRGUUTURGUUUAUTGGGGTTAUTGGTGGUUATGAAGGAGTUUUTGUTGUTG TUAGAAUAGAAGAUUTRGUTGUUUTGAGGAUAAGUAUTTGUUAUUAURGTUAUTU AGUUUTGGGRGTAGURGGAUAGGAGGAGAGUAGTGATGXGGATGGGTAUURGGGU AUAUUAGUUUTUAGAGAUUTGAGUTUTTUTGGUUARGTGGAAUUTRGAAUURGAG UTUUTGUAGAAGTGGUUUTGGAGATTGAGGGTUUUTGGAUAUTUUUTATGGAGATU RGGGGAGUTAGGATGGGGAAUUT |
| 333 | TUUTTUUTTUTTTUUTTUTTTUTTUUTTUUUTTUTUUTTTUTTTUTTUUTTTUU UATTTTGAGARGTAUTUTGGUTUTGTRGUUUAGGUTGGAGRGUAATGGRGUUATUT RGGRGUAUTGUAAUUTUUAUUTUURGGGTTUAAGXGATTUTAUTGUUTUAGUUTUU RGAGTAGUTGGGAUTAUAGGRGRGUAUTAUUAAGUURGGUTAATTTTTTTTTGTATT TTTAGTAGAGAUTGGGTTTUARGATGTTGGURGGGUTGGTUTGGAAGTUTTGAUUTU AAGRGTGRGUUUTU |
| 334 | GAGGGRGUARGUTTGAGGTUAAGAUTTUUAGAUUAGUURGGUUAAUATRGTGAAA UUUAGTUTUTAUTAAAAATAUAAAAAAAAATTAGURGGGUTTGGTAGTGRGRGUUT GTAGTUUUAGUTAUTRGGGAGGUTGAGGUAGTAGAATXGUTTGAAUURGGGAGGTG GAGGTTGUAGTGRGURGAGATGGRGUUATTGRGUTUUAGUUTGGGRGAUAGAGUU AGAGTARGTUTUAAAATGAAAGAAGAGAAAAGAAAAGAAAAGAAAGAAAAGAGAG AGAAAGAAGGAAAGAAGGAAGGA |
| 335 | AGGUUTUTGUTGAUUTGTAGAAUTTGTTGAUURGGATTTTGATGTUAGTUTUATTGG GUUTGURGTTGUTUTTUTTGGGAUAGAAGATUTUTTTGATURGGUUAATTRGGTAGG GUTUAGGGGUATUUAGGTTGUTGUUTTTGATGTAGTXGGAGTATTTURGGTAGTGUT UTGGGTAUAGGTUUTUATUUARGGGUTUUTTURGTGGGRGTTTUARGGGAUTGGAU AGUTTGATGUTGUAGAGAAGUAUUUAUTTGAUATUAATGAAUUTTUUAUUTTGUAG TGGTUAGTUAGGUATGA |
| 336 | TUATGUUTGAUTGAUUAUTGUAAGGTGGAAGGTTUATTGATGTUAAGTGGGTGUTT UTUTGUAGUATUAAGUTGTUUAGTUURGTGAAARGUUUARGGAAGGAGUURGTGG ATGAGGAUUTGTAUUUAGAGUAUTAURGGAAATAUTUXGAUTAUATUAAAGGUAG UAAUUTGGATGUUUUTGAGUUUTAURGAATTGGURGGATUAAAGAGATUTTUTGTU UUAAGAAGAGUAARGGUAGGUUUAATGAGAUTGAUATUAAAATURGGGTUAAUAA GTTUTAUAGGTUAGUAGAGGUUT |
| 337 | GGGGRGGGGTTRGGURGGGGGRGGRGGUAGGAUUTGAGUAGUUAGGAGGGUTGGGGGAUA GTUAGGTUAGGURGGTGGUTAUURGGURGUTGGAGAGGGURGGATGGUARGTGGUAUUAAG UAAAAGGAGGUTGAGUUAGAAAGUAGGGAXGGGGUTAGARGAGUAAAGUTGGGUAGGAGG GRGAGTTGGGAGGGGURGAGURGGUTGTGRGTGGTUUUTTGGGAGGAGGGGGTGTGGUUAA GUAAGUUAAAUAGTTRGGAGGTUAGTGUAAGGAUAAGAUAGUUTGGGUAAARGAGUAG |
| 338 | UTGUTRGTTTGUUUAGGUTGTUTTGTUUTTGUAUTGAUUTURGAAUTGTTTGGUTTGUTTGGU UAUAUUUUUTUUTUUUAAGGGAUUARGUAUAGURGGUTRGGUUUUTUUUAAUTRGUUUTUU TGUUUAGUTTTGUTRGTUTAGUUUXGTUUUTGUTTTUTGGUTUAGUUTUUTTTTGUTTGGTGU UARGTGUUATURGGUUUTUTUUAGRGGURGGGTAGUUAURGGUUTGAUUTGAUTGTUUUUU AGUUUTUUTGGUTGUTUAGGTUUTGURGURGUUUURGGURGAAUUURGUUUU |
| 339 | RGAGTTGGGAGGGGURGAGURGGUTGTGRGTGGTUUUTTGGGAGGAGGGGGTGTGG UUAAGUAAGUUAAAUAGTTRGGAGGTUAGTGUAAGGAUAAGAUAGUUTGGGUAAA RGAGUAGGGGRGGAGRGTGAGAGUAGAUTGUAURGGATXGUTUAGGUUAGUUUAA GUTGAAGAGGAAGGGGUAAGUTUUAGAAGUAGGGGRGGGGURGAUUAAUUTRGUA GATUTGUTGGGRGAAGAGUAGUAGUTGGGUUAGUURGATGUTGTGURGGGGUAGG TAGTUTRGGAGGUTGUUUAGGGGU |
| 340 | UUUUTGGGUAGUUTURGAGAUTAUUTGUUURGGUAUAGUATRGGGUTGGUUUAGU TGUTGUTUTTRGUUUAGUAGATUTGRGAGGTTGGTRGGUUURGUUUUTGUTTUTGG AGUTTGUUUUTTUUTUTTUAGUTTGGGUTGGUUTGAGXGATURGGTGUAGTUTGUT UTUARGUTURGUUUUTGUTRGTTTGTAGGUTGTUTTGTUUTTGUAUTGAUUTURG AAUTGTTTGGUTTGUTTGGUUAUAUUUUUTUUTUUUAAGGGAUUARGUAUAGURGG UTRGGUUUUTUUUAAUTRGU |

-continued

| SEQ ID NO: | Sequence |
|---|---|
| 341 | AAUAGGUUUAAGUUTGTGGUAGGTGGGGTUAUUUAGUUUAGGRGUTTUUUAUUU<br>URGGGUUTGGGUUAGAAGUUUAGGAGUTGGUTGRGGGURGGTTUTUUUUUAUUUA<br>UTUTGGGGATGUUTUAGGUUTGGGTTTURGUUTTAGUUTXGUUAGGUUUUAATGAG<br>UUTUTGTTTGGUUTGTAGTUAATTGAURGGTTGGAUTTGGGGUAGGTGUTRGAGGA<br>GUUUUAUTGAGGGAGGGUAGGTUTUTTGTGRGTAUTGTUUAGUAUATAUAGGAAAT<br>TTAGUATTTUTGUUUAUUUAGU |
| 342 | GUTGGGTGGGUAGAAATGUTAAATTTUUTGTATGTGUTGGAUAGTARGUAUAAGAG<br>AUUTGUUUTUUUTUAGTGGGGUTUUTRGAGUAUUTGUUUUAAGUTUAAURGGTUA<br>ATTGAUTAUAGGUUAAAUAGAGGUTUATTGGGGUUTGGXGAGGUTAAGGRGGAAA<br>UUUAGGUUTGAGGUATUUUUAGAGTGGGTGGGGGAGAAURGGUURGUAGUUAGUT<br>UUTGGGUTTUTGGUUUAGGUURGGGGGTGGGAAGRGUUTGGGUTGGGTGAUUUUU<br>AUUTGUUAUAGGUTTGGGUUTGTT |
| 343 | UUTGAUUUAUUUAAUTUTUUUAGGGGARGTGGGGGUAUTGGAGUUUUAUAURGUA<br>GGRGGTAGUTUAATGUAUURGRGTRGGAGTTUUTUUUURGRGAGRGTGGUAAGGUT<br>UAGGGAAGTUURGGGUUUUTGGGGAGGGGGUUTTGURGXGUATUUTGTXGUAGGA<br>AURGURGGGUUUTTUUTTURGRGGGAAGXGGUTTGGURGAUUUURGUUUURGUUR<br>GGGUUTUTTGGGGGTTTURGGTGUURGGUUAURGTGGGGUTGGGGAUTGAAAGTGA<br>TGGGAUTGAAGATGGGGUTGGAA |
| 344 | TTUUAGUUUUAUTUUAGUUUUAUAUTTUAGUUUUAGUUUUARGGTGGURGGG<br>UAURGGAAAUUUUUAAGAGGUURGGGRGGGGGRGGGGGTRGGUUAAGUXGUTTUU<br>RGRGGAAGGAAGGGUURGGRGGTTUUTGXGAUAGGATGXGRGGUAAGGUUUUUTU<br>UUUAGGGGUURGGGAUTTUUUTGAGUUTTGUUARGUTRGRGGGGGAGGAAUTURG<br>ARGRGGGTGUATTGAGUTAURGUUTGRGGTGTGGGGUTUUAGTGUUUUUARGTUUU<br>UTGGGAGAGTTGGGTGGGTUAGG |
| 345 | TATUUAAATGTGTTTTATATAAAATGAATRGTTTTUAGTGUAUTGAGGAAGTTTTUT<br>ATTTAAAGAAATUUTGUTGTGAAUTUTTTTGTGAAGAATGUTTTUUTAATGGAATTA<br>GTUAUUAUTGAGTUATTTUTGUAAAUTTUAGGTTTGXGGTTTTGUUTAAGUAAGATU<br>TGGURGGAGAAGTGAGATAAATTATAGATGTRGUTAATAAATTAUAGATTAUTUAA<br>AGGUAAAAGAGGAAAGAAAAAAAAAAATTGAUTRGTGTATATGAAURGAATTGAGT<br>UAGGGGTUTUUAURGGU |
| 346 | GURGGTGGAGAUUUUTGAUTUAATTRGGTTUATATAUARGAGTUAATTTTTTTTTTT<br>UTTTUUTUTTTTGUUTTTGAGTAATUTGTAATTTATTAGRGAUATUTATAATTTATUT<br>UAUTTUTURGGUUAGAUTUTTGUTTAGGUAAAAUXGUAAAUUTGAAGTTTGUAGAAA<br>TGAUTUAGTGGTGAUTAATTUUATTAGGAAAGUATTUTTUAUAAAAGAGTTUAUAG<br>UAGGATTTUTTTAAATAGAAAAUTTUUTUAGTGUAUTGAAAARGATTUATTTTATAT<br>AAAAUAUATTTGGATA |
| 347 | TGGGAGTTUUAGTTRGGGGGUAGAUUAGTGTTUAGAGTURGGGUTUTGUTAUTUAG<br>RGUURGAGGUAGRGUUTUUUUATTUAARGGGGGURGTGGUAATTUUUTGAUATGAT<br>TUATGAUUAUATAATAUATURGGAAAUTTUTUTUUAUXGUUTUURGTUTGGGURGT<br>RGUUUURGGUUTGGGAGAUTUUAGGTUTUAGAGTUTUTGUUUUUARGGGRGATUA<br>GTGUTGUUUAGTGGAAAAATAATGUUAGURGRGUAUUAAAATTAGGTGTAAAATTA<br>AUATTTTTTGGAAGUUAUTTT |
| 348 | AAGTGGUTTUUAAAAAATGTTAATTTTAUAUUTAATTTTGGTGRGRGGUTGGUATTA<br>TTTTTUUAUTGGGUAGUAUTGATRGUURGTGGGGGUAGAGAUTUTGAGAUUTGGAG<br>TUTUUUAGGURGGGGGRGARGGUUUAGARGGGAGGXGGTGGAGAGAAGTTTURGG<br>ATGTATTATGTGGTUATGAAUTUATGTUAGGGAATTGUUARGGUUUURGTTGAATGG<br>GGAGGRGUTGUUTRGGGRGUTGAGTAGUAGAGUURGGAUTUTGAAUAUTGGTUTGU<br>UUURGAAUTGGAAUTUUUAT |
| 349 | RGGRGTGUTTUTTGGUAAAUAUTUTUUTTGAGGATGURGUTGUAGUAUTTGAGUTGU<br>TURGAGAUTTTGUTGUTUTTUTUTGGTGUTGGGTGUTGUTGAGAGTRGGGUARGTUU<br>TTUTTTGGAGGTTTUAUAGGURGGUTGUTUTUURGUXGUTGGUUUAGUTTGGTGGT<br>UTTGGGUTURGGGGGUAGRGAGGGTGGUTRGTGAATGGGGTUAATGGTGGTGGGGG<br>TGGTGGTGTUTGUTTTUUTUTTUAUTUUUTTUTTTGTUTGUUAAGAAUARGGARGUU<br>AAUAGGUAUAGTUAGAAG |
| 350 | UTTUTGAUTGTGUUTGTTGGRGTURGTGTTUTTGGUAGAUAAAGAAGGGAGTGAAG<br>AGGAAAGUAGAUAUUAUUAUUUUUAUUAUUATTGAUUUUATTUARGAGUUAUUUT<br>RGUTGUUUURGGAGUUUAAGAUUAUUAAGUTGGGUUAGXGGRGGGAGAGUAGUR<br>GGUUTGTGAAAUUTUUAAAGAAGGARGTGUURGAUTUTUAGUAGUAUUUAGUAUU<br>AGAGAAGAGUAGUAAGGUTURGGAGUAGUTUAAGTGUTGUAGRGGUAUUUUAAG<br>GAGATGUUUGUUAAGAAGUARGURG |
| 351 | TGGUTUTGUTTUAAGUUUAUUTGGUUUUTGGUAAGUUUAUUTGGTGAUAUUUUGT<br>GUUTGGGUUUTGAGGGUTGUUUUAGATURGRGAUTUGTUUTGGGGAURGGTAGUUU<br>UTUUURGGATGUUAGUAAAGUUUUUUAGUUUUAXGUUTGUAUAGUUUUAGU<br>ATGUUUUAAUAGUUAUUAGUAUUUUUGUGAGUUAGAUUUURGGUUTGUUAGG |

-continued

| SEQ ID NO: | Sequence |
|---|---|
| | UUAAUUTGUTTGGGGUUTUAGUAGRGGGGGUTGGRGAGGUUAGTTTTUTUUAGRGG TTUTAAGURGUTRGAGGGTGG |
| 352 | UAUUUTRGAGRGGUTTAGAAURGUTGGAGAAAAUTGGUUTRGUUAGUUUURGUTG UTGAGGUUUUAAGUAGGTTGGUUTGGUAGGAURGUGGGTUUAUTUAUAUAUUUT GAUTAATGGUTGTTGAAGGUATAUTGGAGAUTGTGUAGGXGTGGAGGUTGGAGGGA GUTTTGUTGGUATURGGGGAGGAAUTAURGGTUUUUAGGAUAATRGRGGATUTGGG GUAGUUUTUAAGGAUUUAGGUAUAAGATGTUAUUAAGTGGGAUTTGUUAGGGGUU AGGTAGGAUTTGAAGUAGAUUAG |
| 353 | AUUTGGTRGGUUAURGGUAGUTRGGGGAAGAAGGGRGRGTGGRGRGUUUAUTUUA RGGTGUTGAAGAGUAGURGRGURGUUAGUTRGUAUARGTTGTRGATGUUUAGUAUR GRGUURGURGRGURGUUUUUTGRGURGAAGRGTURGGUXGURGUAGGGTAGGGUT UAGRGRGUAGUAGUTGRGRGATUAGTTRGGAUAURGGUTGUUURGGGAAGAGGTU TURGURGUTRGUUAUTGURGUUAGRGURGAGUURGGGGGGUTGUURGAGGAGGRG GUUARGGUAUUAGGUAGRGAGTGU |
| 354 | GUAUTRGUTGUUTGGTGURGTGGURGUUTUUTRGGGUAGUUUUURGGGUTRGGRGU TGGRGGUAGTGGRGAGRGGRGGAGAUUTUTTUURGGGGUAGURGGTGTURGAAUTG ATRGRGUAGUTGUTGRGRGUTGAGUUUTAUUUTGRGGXGGURGGARGUTTRGGRGU AGGGGGRGGRGRGGRGGGRGRGGTGUTGGGUATRGAUAARGTGTGRGAGUTGGRGG RGRGGUTGUTUTTUAGUAURGTGGAGTGGGRGRGUUARGRGUUUTTUTTUUURGAG UTGURGGTGGURGAUUAGGT |
| 355 | TGGUAGAGATAUAAATTUUTGATGGUAGAGGAGGGAGAGAGAGTGTGGGTGARGA TGAUAATTGAAUTGAGAUUUAAAGGAGGTAGGGGAGAUATATGGGRGTUTUTGGG AAGATGGTUUURGGGAAAGUAUAGUUTTTAGAUAGGUUUXGAGGUAGGAGUUTGT UTGAUTUAURGGAGGAGUTTGGAGGAGGUTGAGGTGGUUTAAGTRGATTAAGUAGG GTGGGGAGGGAAGAGGRGATGGTGURGTGAGAUUAAGUAGGGUUTTGAGGTUTGG GGGGAGAAUTTTGGUTTTTAUTUT |
| 356 | GAGTAAAAGUUAAAGTTUTUUUUUUAGAUUTUAAGGUUUTGUTTGGTUTUARGGU AUUATRGUUTUTTUUUUUUUUAUUUTGUTTAATRGAUTTAGGUUAUUTUATGGTT TUUAAGUTUUTURGGTGAGTUAGAUAGGUTUUTGUUTXGGGGUUTGTUTAAAGGUT GTGUTTTUURGGGGAUUATUTTUUAGAGARGUUUATATGTUTUUUUTAUUTUUTT TGGGTUTUAGTTUAATTGTUATRGTUAUUUAUAUTUTUTUTUUUTUUTUTGUUATUA GGAATTTGTATUTUTGUUAG |
| 357 | AGAGGAGGGAGAGAGAGTGTGGGTGARGATGAUAATTGAAUTGAGAUUUAAAGGA GGTAGGGGAGAUATATGGGRGTUTUTGGGAAGATGGTUUURGGGAAAGUAUAGUU TTTAGAUAGGUUURGAGGUAGGAGUUTGTUTGAUTUAUXGGAGGAGUTTGGAGGA GGUTGAGGTGGUUTAAGTRGATTAAGUAGGGTGGGGAGGGAAGAGGRGATGGTGU RGTGAGAUUAAGUAGGGUUTTGAGGTUTGGGGGGAGAAUTTTGGUTTTTAUTUTGA GGAAGGTGGGAGUUAUAGAGGUTT |
| 358 | AGUUTUTGTGGUTUUUAUUTTUUTUAUAUTAAAAUUUAAAUTUUUTUUTTTAGGAUU TUAAGGUUUTGUTTGGTUTUARGGUAUUATRGUUTUTTUUUTUUUUAUUUTGUTTA ATRGAUTTAGGUUAUUTUAGUUTUUTUUAAGUTUUTUXGGTGAGTUAGAUAGGUTU UTGUUTRGGGGUUTGTUTAAAGGUTGTGUTTTUURGGGGAUUATUTTUUUAGAGAR GUUUATATGTUTUUUUUAUUTUUTTTGGGTUTUAGTTUAATTGTUATRGTUAUUUAU AUTUTUTUTUUUTUUTUTG |
| 359 | TGGGRGTUTUTGGGAAGATGGTUUURGGGAAAGUAUAGUUTTTAGAUAGGUUURG AGGUAGGAGUUTGTUTGAUTUAURGGAGGAGUTTGGAGGAGGUTGAGGTGGUUTA AGTRGATTAAGUAGGGTGGGGAGGGAAGAGGRGATGGTGUXGTGAGAUUAAGUAG GGUUTTGAGGTUTGGGGGGAGAAUTTTGGUTTTTAUTUTGAGGAAGGTGGGAGUUA UAGAGGUTTUTAGAUAGAAGAAGGAUAAGURGGAUTUAGGATAUUAGGGTGGGGG TATUTGTGGGGGATAAAGGGAGAA |
| 360 | TTUTTUUTTTATUUUUUAUAGATAUUUUUAUUUTGGTATUUTGAGTURGGUTTGTU UTTUTUTGTUTAGAAGUUTUTGTGGUTUUUAUUTTUUTUAGAGTAAAAGUUAAAG TTUTUUUUUUAGAUUTUAAGGUUUTGUTTGGTTTUAXGGUAUUATGGUUTUUUUU TUUUUAUUUTGUTTAATRGAUTTAGGUUAUUTUAGUUTUUTUUAAGUTUUTURGGT GAGTUAGAUAGGUTUUTGUUTRGGGGUUTGTUTAAAGGUTGTGUTTTUURGGGGAU UATUTTUUUAGAGARGUUUA |
| 361 | GGUTTTGTGAAAUUAAUUAGGAAGAATGAAAUAUAGAGUTGGTURGAUAUUUAGU TRGAGGGAGGGGGGURGGAAGUTTUTGGAAGTTGGUTGUUUUTAAGUAGGGGUUA UTUTAGUUUAUAAGGUUAAGTTGGUAGAGGUAGAXGAGGGGAUTUTGXGGUTUAA GTUARGGGUUAGGAGUURGUAGUTGURGGGUTGGAAAGGTUAGAGURGGUTUTGR GTUTGGUTGRGURGGUAAGAAGUUAUAATTARGUAGGUAAAAGAGUURGGGGATT AGUUUUAGUAUUTGGGAUUUTGAAT |
| 362 | ATTUAGGGTUUUAGGTGUTGGGGUTAATUUURGGGUTUTTTTGUUTGRGTAATTGTG GUTTUTTGURGGRGUAGUUAGARGUAGAGURGGUTUTGAUUTTTUUAGUURGGUAG |

-continued

| SEQ ID NO: | Sequence |
|---|---|
| | UTGRGGGUTUUTGGUURGTGAUTTGAGUXGUAGAGTUUUUTXGTUTGUUTUTGUUA AUTTGGUUTTGTGGGUTAGAGTGGUUUUTGUTTAGGGGUAGUUAAUTTUUAGAAGU TTURGGUUUUUUTUUUTRGAGUTGGGTGTRGGAUUAGUTUTGTGTTUAUTTUTTUUT GGTTGGTTTUAUAAAGUU |
| 363 | AGGUTGAARGGAATTGGGAGUAGAGUUUTGRGGTAGGAUAGAGAUTTRGUAAAGU URGGAGUAUAUAGUAGUAUUURGTUTTUTAAAGGAUAATTTTGGGAAAAUTUTTGU UTAATATTUTGGUAUTAAGGATUATTUTGTUAUATUUUXGUTUTGGAUTAUAAGUU TGUAAGUUUUATURGGGGUAGGGTTTUUTUATTUUTGTGUAURGTGGAAGUUUTGTG UUTGUUUAGGGUUTGGUAUTTGTARGTAUTTGAAAAUUTRGTGTGGAGTAAAGAGA GGGGTGATGTGUAAAGGUUTT |
| 364 | AAGGUUTTTGUAUATUAUUUUTUTUTTTAUTUUAUARGAGGTTTTUAAGTARGTAU AAGTGUUAGGUUUTGGGUAGGUAUAGGGUTTUUARGGTGUAUAGGAATGAGGAGU UUTGUUURGGATGGGGUTTGUAGGUTTGTAGTUUAGAGXGGGGATGTGAUAGAATG ATUUTUAGTGUUAGAATATTAGGUAAGAGTTTTUUUAAAATTGTUUTTTAGAAGARG GGGTGUTGUTGTGTGUTURGGGUTTTGRGAAGTUTUTGTUUTAURGUAGGGUTUTGU TUUUAATTURGTTUAGUUT |
| 365 | AGUUAGGUTAAAUUAGRGTGTUUUAATGAGGGGUUUTGGGUTGAGTGGAGGAAAT GGGTGRGGTGGAGGTGGGTTTGGUTGGGUAUAGRGGGUARGTGTGGGTAAGRGGGT GGGGURGGTTGTGRGGGTGGUUTAUTUTGGGGUAAGUAGUXGAGGURGAUTGTGTUR GGRGTGTGGTTGAGUARGGGUAGGTGTUTGGRGGTGAUUUTGUARGTUTGGTGTTT AUUTGGUUUTGGGTUTGARGTGGGURGRGUUTGGUTGUTGGRGGGAUAGTGTGTTA TUTGUUTGRGGARGUTTURGG |
| 366 | URGGAAGRGTURGUAGGUAGATAAUAUAUTGTUURGUUAGUAGUUAUURGKUUUU UARGTUAGAUUUAGGGUUAGGTAAAUAUUAGARGTGUAGGGTUAURGUUAGAUAU UTGUURGTGUTUAAUUAUARGURGGAUAUAGTRGGUUTXGGUTGUTTGUUUUAGAT AGGUUAUURGUAUAAURGGUUUUAUURGUTTAUUUAUARGTGUURGUTGTGUUUA GUUAAAUUUAUUTUUAURGUAUUUATTTUUTUUAUTUAGUUUAGGGUUUUTUATT GGGAUARGUTGGTTTAGUUTGGUT |
| 367 | UUTTGGUTUAGGTTGGGGAGGGRGTUATGAGTUATGAGGTGGGRGTTGUATTTGTU AGTTGTGUAGURGRGUAUUAURGAGTAGTUTGGRGGUAGRGRGTURGRGTTRGATT GRGTUTGGUURGUAGGAGGUURGGTUUAGUAGUUUTTUXGUAUUAGGGTUAURGG RGRGRGATAUUUTGGGGGRGGGATRGGGGUTRGTGUTUTGUTTUURGAAAUUUTTU TUUUTUUAGTUTUAGRGTTUTTUUTUUTUUUTUTATIUTTTUAUTTTGGAGTTAUT TUUTUUUUTUUUTUUTTUUU |
| 368 | GGGAAGGAGGGAGGGGAGGAGGTGTAGGTGAAAGTGAAAGGATAGAGGGAGGAGG AAGAARGUTGAGAUTGGAGGGAGAAGGGTTTRGGGAAGUAGAGUARGAGUUURGA TUURGUUUUUAGGGTATRGRGRGURGGTGAUUUTGGTGXGGAAGGGUTGUTGGAUR GGGUUTUUTGRGGGUUAGARGUAATRGAARGRGGARGRGUTUURGUUAUAUTAUT RGGTGGTGRGRGGUTGUAUAAUTGAUAAATGUAARGUUUAUUTUATGAUTUATGAR GUUUTUUUUAAUUTGAGUUAAGG |
| 369 | UAGGUTGGAGTGUAATGGRGRGATUTRGGUTUAUTGUAAUTTUTGUUTUTRGGGTT UAAGUAATTUTTUTAUUTTAGUUTUUTGAGTAGUTGGGATTAUAGGTAUUTGURGU UATGUURGGUTAATTTTTTAATTTGTTTTTAGTAGAGAXGGGGTTUAUUATGTTGG UUAGGURGGTUTAUAAUTUUTGAUTUTAGGTGAUTUTAUURGUUTRGGUUTUUUAAA TTAUAGGTGTTATUATTAGGATTUTTGGUAGAUAGGAGTGTTGTAGGGGATGGAAGT GGATAGTAGGAGGUTUTG |
| 370 | UAGAGUUTUUTAUTATUUAUTTUUATUUUUTAUAAUAUTUUTGTUTGUUAAGAATU UTAATGATAAUAUUTGTAATTTGGGAGGURGAGGRGGGTAGATUAUUTGAGATUAG GAGTTGTAGAURGGUUTGGUUAAUATGGTGAAAUUUXGTUTUTAUTAAAAAUAAAT TAAAAAATTAGURGGGUATGGRGGUAGGTAUUTGTAATUUUAGUTAUTUAGGAGGU TAAGGTAGAAGAATTGUTTGAAUURGAGAGGUAGAAGTTGUAGTGAGURGAGATRG RGUUATTGUAUTUUAGUUTG |
| 371 | TGAATGAUUTGGGUAGUATTTUTUUAUUTGRGUTTGUATTTGUAGAUAGTUTGTGA UTUTUTGTGGGAGAAAAUAUAAGAAAURGGUUUUTUTGUTGGTTUUUUAUUTGGU UTGGUTUTUUTGTTUTUUAUUUTGUAUAUTUATGUUTXGGAAUUTGUTTUTUUTUT GAGUTUUUTUAUAGTGGUURGGUUUARGTGGUUTTTAATUTGUUUAUATUAGAGU UTUUAUUTURGGUUTATGGUUUATUAGAGGUAGUTGGAGURGGGUATUUTUUUUA RGTGGGUUTTTGAGGATGGGA |
| 372 | TUUUATUUTUAAAGGUUUARGTGGGGAGGATGUURGGUTUUAGUTGUUTUTGATGG GUUATAGGURGGAGGTGGAGGUTUTGATGTGGGUAGATTAAAGGUUARGTGGGUR GGGUUAUTGTGAGGGAGGUTUAGAGGAGAAGUAGGTTUXGAGGUATGAGTGTGUA GGGTGGAGAAUAGGAGAGUUAGGUUAGGTGGGGAAUUAGUAGAGGGGURGGTTTU TTGTGTTTTUTUUUAUAGAGAGTUAUAGAUTGTUTAGUAAATGUAAGRGUAGGTGG AGAAATGUTGUUUAGGTUATTUA |

-continued

| SEQ ID NO: | Sequence |
|---|---|
| 373 | GGGRGGGGUUTGTGRGGTUTGRGGRGRGGAGURGAGTGGGUTGRGGGGATGRGGGG GAUUAGUTGRGTGGGRGGRGGRGURGAGAGUUURGGAGGRGRGGGGUTGAGRGAG GGUURGRGGGGGRGUTGGUTGRGUTTGGUTURGGTATGXGUUTAUTTUUTUTGRGT UTXGUTAGUTGURGTGUTGUTRGURGTGTAUTARGGTUTUATUTGGGTAUUUARGR GGTUTUURGRGGUAUURGURGGUUUAUAGUUUAGRGRGURGTUUUUTURGTGTGUT GTTURGUTTRGGGRGTGURGUUT |
| 374 | AGGRGGUARGUURGGGRGGGUAGUAUARGGAGGGGARUUKUKGUTUUUUTUTUUU URGGRGGGTGURGRGGGAGAURGRGTGGGTAUUUAGATGAGAURGTAGTAUARGG RGAGUAGUARGGUAGUTAGXGAGARGUAGAGGAAGTAGGXGUATAURGGAGUUAA GRGUAGUUAGRGUUURGRGGGUUUTRGUTUAGUUURGRGUUTURGGGGUTUTRG GRGURGURGUUUARGUAGUTGGTUUUURGUATUUURGUAGUUUAUTRGGUTURGR GURGUAGAURGUAUAGGUUURGUUU |
| 375 | AAGTGTATTTTUAAGGTATGAGGGGUUUAGAGGAUAUTGTUUUAAAAGUAGTGGTT GTGAGAGTGGUTTTGGAGTUAGGUTGAUAGTUTGGAAAUTTUAGGTURGUTUTGA AGTGURGGUTGUATGAUUAGUUUTUUAGUUTGTGTUXGUTTRGGUUTTUTTTGTGU AAGTGAGAGUATTGUTGAUTUUUURGGGGTGGRGAGGGGGRGUARGTUAGTGAUUT RGUATGGTGUUTGUUAGGUARGTGGTURGTGTTTUATGATTUTTTGAGAGUTTTGGA GUAGUTUUAAGAAGAUTUT |
| 376 | GAGTUTTUTTGGAGUTGUTUUAAAGUTUTUAAAGAATUATGAAAUARGGAUUARGT GUUTGGUAGGUAUUATGRGAGGTUAUTGARGTGRGUUUUUTRGUUAUUURGGGGG GATUAGUAATGUTUTUAUTTGUAUAAAGAAGGURGAAGXGGAUAUAGGUTGGAGG GUTGGTUATGUAGURGGUAUTTUAGAGRGGAUUTGGAAGTTTUUAGAUTGUTAGUU TGAUTUUAAAGUUAUTUTUAUAAUUAUTGUTTTTGGGAUAGTGUUTUTGGGUUUU TUATAUUTTGAAAATAUAUTTT |
| 377 | TAATTTTAAAUAAAAUTTTUUATGAGUAAUTAAATATTTAAAATGTGTTTTTUUATA AAAGTGAATUAGUTUAGTTUTGUAGGUTGAAAATAUAAUAAGGAGGATURGGGTTG UAGAAAGUAGAGGGUUAUUTAGAURGTGTUTGAGAGAXGGGGAGAAAGUAGUTGT UTGUTGTGUAUUAGAGGUUTUTAGGGAUUURGGUAGUAAUUURGTGGRGGGUUAU AUTTGGGAGUTGATTTGTTTTUAGAAUUAUUAGUTAAGUUAUATGAGUUAGGAGUU TGGTTATUUATTUAAAGUUUA |
| 378 | TGGGUTTTGAATGGATAAUUAGGUTUUTGGUTUATGTGGUTTAGUTGGTGGTTUTGA AAAUAAATUAGUTUUUAAGTGTGGUURGUUARGGGGTTGUTGURGGGGTUUUTAG AGGUUTUTGGTGUAUAGUAGAUAGUTGUTTTUTUUUXGTUTUTUAGAUARGGTUTA GGTGGUUUTUTGUTTUTGUAAUURGGATUUTUUTTGTTGTATTTTUAGUUTGUAGA AUTGAGUTGATTUAUTTTTATGGAAAAAUAUATTTTAAATATTrAGTTGUTUATGGA GAGTTTTGTTTAAAATTA |
| 379 | GUUTUUAGAUURGAAATUUUUUAUTGAAGUUATTUUUAGGAGGAGGGGUUTUAUT GGGGUUTUAAGGUAGUATUAGUATTTURGGTGAUAGGUAUAGUAATTTATUAGUTU AUTGGUTUTUTAUTGAGAAUAAGGUAAGURGGGGUUTGUXGAGGGTATGAUAGGU AGGGAGTGATGGGUURGGUUUAGGGUAGGAGGGAGAUAGAAATGGGUAGGAAGA GGAGGUTGTUUUUAGUAGUAUTTUTGAGAGGAGGAGUAUUTTTRGGGGAUAUTUT GGARGGUAUUUUUAAGUAUAGUUUU |
| 380 | GGGGUTGTGUTTGGGGGTGURGTUUAGAGTGTUUURGAAAGGTGUTUUTUUTUTUA GAAGTGUTGUTGGGGAUAGUUTUUTUTTUUTGUUUATTTUTGTGUTUUUTUUTGUUU TGGGURGGGUUUATUAUTUUUTGUUTGTUATAUUUTXGGUAGGUUURGGUTTGUUT TGTTUTUAGTAGAGAGUUAGTGAGUTGATAAATTGUTGTGUUTGTUAURGGAAATG UTGATGUTGUUTTGAGGUUUUAGTGAGGUUUUTUUTUUTGGGAATGGUTTUAGTGG GGGATTTRGGGTUTGGAGGU |
| 381 | TGAGAGUAGUUAGAUARGTAGTGATUAGGGAAAGTRGAAAGTGUAGATGGGTTRG UAAARGTGGAUTUTUTAGTTTTGGGTUTGUAGATGGGGURGGUUAUUAXGTGUTUT UTGAGTTUTUTTTUUAAGTAUAGATUUUTURGGAGARGGAAUATTGTTURGUUTTTA ATTUTTUUUAGGAGUTGRGGAGGAAGGXGTGAGAAURGGAGUURGGGGTGAUTTGR GGGGGAGGGGATRGUTTUUURGTRGUUUAUAUUTGUUTAAUUUARGUUUARGGRG GURGUAAAGGRGAUAURGRGT |
| 382 | ARGRGGTGTRGUUTTTGRGGURGURGTGGGRGTGGGTTAGGUAGGTGTGGGRGARG GGGAAGRGATUUUUTUUUURGUAAGTUAUUURGGGUTURGGTTUTUAXGUUTTUUT URGUAGUTUUTGGGAAGAATTAAAGGRGGAAUAATGTTURGTUTURGGAGGGATUT GTAUTTGGAAAGAGAAUTUAGAGAGUAXGTGGTGGURGGUUUUAUTGUAGAUUU AAAAUTAGAGAGTUUARGTTTGRGAAUUUAUTGUAUTTTRGAUTTTUUUTGATUA UTARGTGTUTGGUTGUTUTUA |
| 383 | AUAAGRGGTTGGATTTRGAGAGGAUATUAAGAGUARGTUAAGAGUARGTUAAGAG UAUARGGAUAGGUAUTGGUARGURGGUAGGTUATTGAURGGUAGAAUAGAGTTTG GUUAGGGUTGUAGAGAAGAGTRGGGURGUUAAGUAGUUXGAUTTUUAGRGGAAA |

| SEQ ID NO: | Sequence |
|---|---|
| | AUUAUTUGUUTUTGGUTUUTUUAUTUTGUGAGAGUTAUTTUUAUTUAATAAAAUU TTGUAUTUATTUTUUAAAUUUAUATGAGATUUAATTUTTURGGTAUAUUAAGGUAG GAAUUURGAGATAUAGAAAGUUU |
| 384 | GGGUTTUTGTAUTUTRGGGGTTUUTGUUTTGGTGTAURGGAAGAATTGGATUTUATG TGGGTITGGAGAATGAGTGUAAGGTTTTATTGAGTGGAAGTAGUTUTUAGUAGATG GAGGAGUUAGAAGGUAGATGGTTTTURGUTGGAAGTXGGGUTGUTTGGRGGUURGA UTUTTUTUTGAUAGUUUTGGUUAAAUTUTGTTUTGURGGTUAATGAUUTGURGGRG TGUUAGTGUUTGTURGTGTGUTUTTGARGTGUTUTTGARGTGUTUTTGATGTUUTUT RGAAATUUAAURGUTTGT |
| 385 | AUTTGAAGTUAGGAGTTRGTGAAUAGUUTGGUUAAUATGGTGAAAUUUTGTUTUTA UTAAAAAAAGAAAAATTAGURGGGTGTGGTGGGRGUUTGTAAUUUUAGUAUTTTGG GAGGUTGAGGTGGGTGGATUAUTTGAAGTUAGGAGTTXGTGAAUAGUUTGATUAAU ATGGTGAAAUUUTGTUTUTAUTAAAAAUAUAAAAATTAGURGGGTGTGGTGGTGGG TGUUTGTAATUUUAGUTAUTUAGGAGAUTGAGGUAGGAGGATUAUTTGAAURGGG GAGGUAGAGGTTGUAGAGAGT |
| 386 | UTUTUTGUAAUUTUTGUUTUUURGGTTUAAGTGATUUTUUTGUUTUAGTUTUUTGA GTAGUTGGGATTAUAGGUAUUUAUUAUUAUAUURGGUTAATTTTTGTGTTTTTAGTA GAGAUAGGGTTTUAUUATGTTGATUAGGUTGTTUAXGAAUTUUTGAUTTUAAGTGA TUUAUUUAUUTUAGUUTUUUAAAGTGUTGGGGTTAUAGGRGUUUAUUAUAUURGG UTAATTTTTUTTTTTTTAGTAGAGAUAGGGTTTUAUUATGTTGGUUGUTTAAA GAAUTUUTGAUTTUAAGTG |
| 387 | AAATUTTTTTUUTGUUTGUATTTTUTTAUATAAAGUAATUTAUTAUTGUUATRGGTT UATTUAUTUAURGGAAUUTGTUTTGUUAGGAUUTGAUUTUAGUAGAUTGAGTUATA UUAGUATUATUUTGTTGGGGUUUAGGUTGUATUUXGUTTURGGUUUUAGUUUUA UTGTTAGUTUUATUAGGTUUTUTGGGGUAUAUUAAGGAGGURGTTTTUTLTUUUTTT TTUTGAATTAGATUUUUAGAAAUAAGAUATUAGGUTTUUTGGGGAAAUTUTAATTTT GUTUATGAATTTGAUUAT |
| 388 | ATGGTUAAATTUATGAGUAAAATTAGATTTUUUUAGGAAGUUTGATGTUTTGTTTUT GGGGATUTAATTUAGAAAAAGGGAGAGAAAARGGUUTUUTTGGTGTGUUUUAGAG GAUUTGATGGAGUTAAUAGTGGGGUTGGGGURGGAAGXGGGATGUAGAUUTGGGU UUUAAUAAGGATGATGUTGGTATGAUTUAGTUTGUTGAGGTUAGGTUUTGGUAAGA UAGGTTURGGTGAGTGAATGAAURGATGGUAGTAGTAGATTGUTTTATGTAAGAAA ATGUAGGUAGGAAAAAGATTT |
| 389 | UAAGGTUUAGGTUUUAGUUTUUUUAURGURGUURGRGUUUTUUTAGGUUTRGGAG RGGRGUTTTTUTGRGGUUTRGAAGGTGGGGTGGAAAGTTTGGGGAGTUURGGUTU TUAUAGUUTGTRGTGAGAAUTGUUUURGGGGAATTRGTUXGURGTARGGAAAAAUT GGURGGAGUAGAGTRGTURGRGGTTURGRGGTRGRGGGTGGAAGGTGAAGGTRGAG GGAGGTUAGGUTGUTTUTGRGTGTUUTGARGGUTGGRGTGTTUTUTTGAGATGGGUT RGGGUTAUTTGGUUAGUUU |
| 390 | GAAGUTGGUUAAGTAGUURGAGUUUATUTUAAGAGAAUARGUUAGURGTUAGGAU ARGUAGAAGUAGUUTGAUUTUUUTRGAUUTUAUUTUUAUURGRGAURGRGGAA URGRGGARGALTUTGUTURGGUUAGTTTTTURGTARGGXGGARGAATTUUURGGGG GUAGTTUTUARGAUAGGUTGTGAGAGURGGGAUTUUUUAAAUTTUUUAUUUUAU UTTRGAGGURGUAGAAAGGRGURGUTURGAGGUUTAGGAGGGRGRGGGRGGRGGT GGGGAGGUTGGGAUUTGGAUUTG |
| 391 | URGAGGGAGUUAGGUUAUAGUTGAUAGGAAGGUAGAAGGTGGUAGGAGGGGAGG TTGRGUTGUAUUTUTGGGTTGUUUAGGUUAAUUTGUUAGGUAGGAGGGGGAAGUU RGTGUUUAUTTTAUUATGAURGGGAAGATGATGGUAGUUAUXGTGGATTTGAGGAT UUAGAGUAURGUUAGGUAGAGGATUTGUAUUAGGGTGAAGAGGTGGATURGGRGU AGRGGUARGTGURGUAGGAAGGUATGGTURGGUTGGTGUTTGGUTGGUATUAGGAA GAGUTTGUAGRGTTUUUAGAAUTA |
| 392 | TAGTTUTGGGAARGUTGUAAGUTUTTUUTGATGUUAGUUAAGUAUUAGURGGAUUA TGUUTTUUTGRGGUARGTGURGUTGRGURGGATUUAUUTUTTUAUUUTGGTGUAGA TUTTTUTGUUTGGRGGTGUTUTGGATUUTUAAAUTUUAXGGTGGUTGUUATUATUTTU URGGTUATGGTAAAGTGGGUARGGGUTTUUUUUTUUTGUUTGGUAGGTTGGUUTGG GUAAUUUAGAGGTGUAGRGUAAUUTUUUUTUUTGUUAUUTTUTGUUTTUUTGUUAG UTGTGGUUTGGUTUUUTRGG |
| 393 | AAATTAUURGGGRGTGGTGGTGGGTGUUTGTAATUUUAGUTAUTUAGGAGGURGAG GUAGGAGAAURGUTTGAAUURGGGAGGUAGAGUATAGGTTGTTGGAGGGTTGAAG GTGUAUUUAGUAGAGAUTGGUATAUAGGAGGTUUTGUAAXGGUUUUAGGAAAUUT UTGGGTUUAGUAAGAGUUTUAGUAGGAGGUAGAAUUATAURGGGUAGGAGTGUUT GGAAAGGUTUAAGGUAAUTUUUTUUAAAGTLTTrGGUUUAAUUUTAUAUTGUUAG GUTGUTAAAGGUUAUTTAAAAGUT |

-continued

| SEQ ID NO: | Sequence |
|---|---|
| 394 | AGUTTTTAAATGGUUTTTAAUAGUUTGAUAGTGTAGGGTTGGGUUAGGAUTTTGGA<br>GGGAGTTGUUTTGAAGUUTTTUUAGGUAUTUUTGUURGGTATGGTTUTAUUTUUTG<br>UTGAAGUTUTTAUTGGAUUUAGAGGTTTUUTGGGGUXGTTGUAGGAUUTUUTGTAT<br>GUUAGTUTUTGUTGGGTGUAUUTTUAAUUUTUUAAUAAUUTATGUTUTGUUTUURG<br>GGTTUAAGRGGTTUTUUTGUUTRGGUUTUUTGAGTAGUTGGGATTAUAGGUAUUUA<br>UUAUUARGUURGGGTAATTT |
| 395 | AGGAAAAAAUAGUAGUUUAAGAATRGGGUUTUUUTGTTAUAGUAGGAGTRGUATU<br>TATTTATATATGTTATGTUTTATTGUTUAGUAAUUAGUTUTRGGURGGGGRGTGGGU<br>RGGGAAGAGGGGTUTUUTGGTGUAGXGGGTTGGRGTGAUTUATUAURGURGXGUAU<br>TUTGGUUTUTGGGUUTAGGTTAAUAGAUTUURGGGTTTUAGGUTGGGUUUAGGRGG<br>UUAGGUUUTUUUTGUTGAGGAATUTGGGTTGGGGUAGTGUUAGUTUUUTGUTTUTU<br>AUUTGGUUAUAGAAGGGGTA |
| 396 | TAUUUUTTUTGTGGUUAGGTGAGAAGUAGGGAGUTGGUAUTGUUUUAAUUUAGAT<br>TUUTUAGUAGGGAGGGUUTGGURGUUTGGGUUUAGUUTGAAAUURGGGAGTUTGT<br>TAAUUTAGGUUUAGAGGUUAGAGTGXGRGGRGGTGATGAGTUARGUUAAUUXGUT<br>GUAUUAGGAGAUUUUTUTTUURGGUUUARGUUURGGURGAGAGUTGGTTGUTGAG<br>UAATAAGAUATAAUATATATAAATAGATGRGAUTUUTGUTGTAAUAGGGAGGUURG<br>ATTUTTGGGUTGUTGTTTTTTUUT |
| 397 | AUUUAGGAATTUTTTTUUTTTTTTTTGAGARGGRGTUTUTGTRGUUUAGGUTGGAG<br>TGUAGTGGRGUAGTUTRGUUTAAUTGUAAGUTURGUUUURGGGTTUATGUUATTUT<br>UUTGUUTUAGUUTUTTGAGTAGUTGGAAUTAUAGGXGUUTGUUAUUAUAUURGGU<br>UAATTTTTTGTATTTTTAGTAGAGARGGGGTTTUAURGTGTTAGUTAGGATGGTUTR<br>GATUTUUTGAUUTRGTGATUUAUUUAUUTUAGUUTUTUAAAGTGUTGGGATTAUAG<br>GUTTGAAUUAUTGRGUUU |
| 398 | GGGRGUAGTGGTTUAAGUUTGTAATUUUAGUAUTTTGAGAGGUTGAGGTGGGTGGA<br>TUARGAGGTUAGGAGATRGAGAUUATUUTGGUTAAUARGGTGAAAUUURGTUTUTA<br>UTAAAAATAUAAAAAATTGGURGGGTGTGGTGGUAGGXGUUTGTAGTTUUAGUTAU<br>TUAAGAGGUTGAGGUAGGAGAATGGUATGAAUURGGGGGRGGAGUTTGUAGTTAG<br>GRGAGAUTGRGUUAUTGUAUTUUAGUUTGGGRGAUAGAGARGURGTUTUAAAAAA<br>AAAAAAAAAAGAATUUTGGGT |
| 399 | AAATAUAGUAGGAGAGAATTUUTUTGAGAUUTAAGATAURGTGUUUTTUUUUUTTG<br>GUUTUTUAGUTGUTGURGAGTUUTGGAGAAAATRGGGUATUTGAAUAGAGGURGTG<br>TTTGTUUUTGUTURGGUUTTGTGTTUTUATTUUTGUUAXGUUATUATGGATAATGAA<br>AGTTGAUTGGUTGURGGGGTTTUUTTTUTUTUTGUUUUTGTUATTTUUATTTGUUAG<br>GTUTUATGUUTTTTTTGUAUAGAGTTGTTGTGUTTGGGUTUTAATTTGUUAGGUAGT<br>GATAAATTUUAAGAAAA |
| 400 | TTTTUTTGGAATTTATUAUTGUUTGGUAAATTAGAGUUUAAGUAUAAUAAUTUTGT<br>GUAAAAAAGGUATGAGAUUTGGUAAATGGAAATGAUAGGGGUAGAGAGAAAGGA<br>AAUUURGGUAGUUAGTUAAUTTTUATTATUUATGATGGXGTGGUAGGAATGAGAAU<br>AUAAGGURGGAGUAGGGAUAAAUARGGUUTUTGTTUAGATGUURGATTTTUTUUAG<br>GAUTRGGUAGUAGUTGAGAGGUUAAGGGGGAAGGGUARGGTATUTTAGGTUTUAG<br>AGGAATTUTUTUUTGUTGTATTT |
| 401 | GUUUTGAGAUAUTAAATGGRGGGGGGGTGGGGGGAGGAAAGGGAAGGRGGUAGAG<br>UTUUURGAGURGGGAUAGTUAUTTAUTUTAUAGGUAGTGGGGUURGAUAUAGAUA<br>GRGURGUUUURGUUAGUUAGUUTRGUARGUUUTRGGAAGXGUAGGUTUURGGRGU<br>TGRGUTGGAGGGTUUURGGUAUUUUAGUUTUURGTUUUUAGUURGUTGUAUUTU<br>RGGGUUUUUUTTAUUUTTGAGAGGUAURGGGAGTTGTRGRGGGGGGGUUTRGGGA<br>AATTUUURGGAUUUUTGTGUUAGGA |
| 402 | TUUTGGUAUAGGGGTURGGGGAATTTUURGAGGUUUUUURGRGAUAAUTUURGGT<br>GUUTUTUAAGGGTAAGGGGGGUURGGAGGTGUAGRGGGUTGGGGARGGGAGGUTG<br>GGGTGURGGGGAAUUUTUUAGRGUAGRGURGGGAGUUTGXGUTTURGAGGGRGTG<br>RGAGGUTGGUTGGRGGGGGRGGRGUTGTUTGTGTRGGGUUUUAUTGUUTGTAGAGT<br>AAGTGAUTGTUURGGUTRGGGGAGUTUTGURGUUTTUUUTTTUUTUUUTRTAUUUU<br>UURGUUATTTAGTGTUTUAGGGU |
| 403 | AUUAUAGUAUTGUAGGAGGATGAGUUUUTGUAGGAAGGAATGUTGGUTUTUTGGG<br>GTAGATAAAGAAGGTTUTGGGGAAGGGAAGGGAGGAAUAGGAAUATGGGUTUUUT<br>GUUAGGUTGTUUUAGGTURGGGATGUUATRGGUAAGTGGGXGGGGAUAGGUUTGG<br>GTAGATGAUATGGTAGTGAGTAAGTGGGGAGGUAGGUUAGUAGAGGAGUUAGGUT<br>UAUUTUUXGUUXGUUUAUUTRGGUUAUAGAURGGGAGGGGTRGGAGUAUTGRGTT<br>GGGGTTGATGAGUAGARGAUTGUUA |
| 404 | TGGUAGTRGTUTGUTUATUAAUUUUAARGUAGTGUTURGAUUUUTUURGGTUTGTG<br>GURGAGGTGGGXGGGXGGGAGGTGAGUUTGGUTUUTUTGUTGGUUTGUUTUUUUA<br>UTTAUTUAUTAUUATGTUATUTAUUUAGGUUTGTUUUXGUUUAUTTGURGATGGUA<br>TUURGGAUUTGGGAUAGUUTGGUAGGGAGUUUATGTTUUTGTTUUTUUUTTUUUTT |

-continued

| SEQ ID NO: | Sequence |
|---|---|
| | UUUUAGAAUUUUTUTUUATUTAUUUUAGAGAGUUAGUATTUUTTUUTGUAGGGGUTU<br>ATUUTUUTGUAGTGUTGTGGT |
| 405 | AGGGAAGGGAGGAAUAGGAAUATGGGUTUUUTGUUAGGUTGTUUUAGGTURGGGA<br>TGUUATRGGUAAGTGGGXGGGGAUAGGUUTGGGTAGATGAUATGGTAGTGAGTAA<br>GTGGGGAGGUAGGUUAGUAGAGGAGUUAGGUTUAUUTUUXGUUXGUUUAUUTRGG<br>UUAUAGAURGGGAGGGGTRGGAGUAUTGRGTTGGGGTTGATGAGUAGARGAUTGU<br>UAGGUAGUUATTUAUAGGAAATGGUAUAGARGUAUATTGTTUUAGUTAUUUUUUA<br>TUUTUUUTUAGGGGUAAAGTGAATG |
| 406 | ATTUAUTTTGUUUUTGAGGGAGGATGGGGGGTAGUTGGAAUAATGTGRGTUTGTGU<br>UATTTUUTGTGAATGGUTGUUTGGUAGTRGTUTGUTUATUAAUUUUAARGUAGTGU<br>TURGAUUUUTUURGGTUTGTGGURGAGGTGGGXGGGXGGGAGGTGAGUUTGGUTU<br>UTUTGUTGGUUTGUUTUUUUAUTTAUTUAUTAUUATGTUATUTAUUUAGGUUTGTU<br>UUXGUUUAUTTGURGATGGUATUURGGAUUTGGGAUAGUUTGGUAGGGAGUUUAT<br>GTTUUTGTTUUTUUUTTUUUTT |
| 407 | GGTTUTAAAUAUAUAAAUUTTTGATGUATUTGGAATTTAUUTTAATUUUTAUUAAT<br>TTTTATUAATGGUTUAATATTTGGGGGATTTTUATGGTAATTGUAUTGAATGTATTAA<br>UTGGTUAGGGAGGATTAUATUAAGAUUAURGGUTXGAGAAAUAGUAGTUTGTTUUT<br>UUAUUUUUARGTUTGUATUUAGGUUUTTUUAUAGAGATUTUATTTUTUUTGUAGAT<br>GAUTUATTUAGTGTUTAGGAATURGGTGUTUTGTGGUUAUTAURGAGAGTGGGATA<br>TTTTUUUUUATTTTATT |
| 408 | AATAAAATGGGGGAAAATATUUUAUTUTRGGTAGTGGUUAUAGAGUAURGGATTUU<br>TAGAUAUTGAATGAGTUATUTGUAGGAGAAATGAGATUTUTGTGGAAGGGUUTGGA<br>TGUAGARGTGGGGGTGGAGGAAUAGAUTGUTGTTTUTXGAGURGGTGGTUTTGATG<br>TAATUUTUUUTGAUUAGTTAATAUATTUAGTGUAATTAUUATGAAAATUUUUUAAA<br>TATTGAGUUATTGATAAAAATTGUTAGGAAATTAAGGTAAATTUUAGATGUATUAA<br>AGGTTTGTGTGTTTAGAAUU |
| 409 | TTTGGGGGGUAGGGAGGGTTUAGTUUUUTUAGGUUTGGUTGTGTUUUUTGUUUUUU<br>AUUUAUAATUAGGUUUAGGGTTGGGGGGTGUAUAUUAAGGAGGGGUAGGAAGTGT<br>UUAAGAAGUAGAAURGGUTUTGTGTUUUUAGTGGXGGXGGGTGTUTGGGGUAGGA<br>GGAGGUTATUTGATUUUTTUUUUAUTGUUURGGUUATGAUUTUUTUUUTUUUTUUU<br>TRGUTUUUTUUUTUUTUUUTUUUTUUUTUUUTUUUTUUUTUUTUUUUTTTTUUTU<br>GGGTAGUUAGUAUUUTGGGUTG |
| 410 | AGUUUAGGGTGUTGGUTAUUUUAGUUATGAAGGAGGAGGGAGGGAGGGAGGGAG<br>GGAGGGAGGGAGGGAGGGAGRGAGGGAGGGAGGGAGGAGGTUATGGURGGGGUA<br>GTGGGGAAGGGATUAGATAGUUTUUTUUTGUUUUAGAUAUUXGUXGUUAUTGGGG<br>AUAUAGAGURGGTTUTGUTTUTTGGAUAUTTUUTGUUUUTUUTTGGTGTGUAUUUU<br>UUAAUUUTGGGUUTGATTGTGGGTGGGGGGUAGGGGAUAUAGUUAGGUUTGAGGG<br>GAUTGAAUUUTUUUTGUUUUUUAAAG |
| 411 | UURGUAAGUUTRGUUUUTUUAGGUUTRGUUUTUUUTUUTTGUAGAGAGTGGUUAA<br>GUTRGTGTTUUAGAGGUTGAATGAGGATTTTGTGRGGAAGUURGAUTATGUTTTGAG<br>UTUTGTGGGTAAGAUURGGAGAUAUTGGAAGAUAGAGAXGUAGAUAGGAAAGAGG<br>UUAAGAUAUTGAUAUAGAUAGAUUUATGUAUUTGAURGGURGAAGAUAGAGUUTR<br>GGAUAGUUUUUAUURGUUUUUAGUUUURGRGUUUURGRGUUURGAUTUURGGUAA<br>GGUUTGGGAGUUTUTGAGGGTTA |
| 412 | TAAUUUTUAGAGGUTUUUAGGUUTTGURGGGAGTRGGGGRGRGGGGGRGRGGGGG<br>UTGGGGGRGGGTGGGGGUTGTURGAGGUTUTGTUTTRGGURGGTUAGGTGUATGGG<br>UUTGTUTGTGTUAGTGTUTTGGUUTUTTTUUTGTUTTGGGTTUUUGTAAGRTTT<br>URGGGTUTTAUUUAUAGAGUTUAAAGUATAGTRGGGUTTURGUAUAAAATUUTUAT<br>TUAGUUTUTGGAAUARGAGUTTGGUUAUTUTUTGUAAGGAGGGAGGGRGAGGUUT<br>GGAGGGGRGAGGUTTGRGGG |
| 413 | UAGATUAGGGTUUTUAGAUTTGTURGGAGGGAGGGUUUTGUATAUUTGUUAARGU<br>UUTGTTTGUTGGGAAAGGGGUTGATGTTGUAATGAUAGGTTAAAUAGUAAUAGGAU<br>ATTGAUTGGUATUTGUAAGUTGAGUTUAGUTUAGAGAGGXGAGGAGUAUAGGGGA<br>GGGAGGAAAATUURGGTGTGGATUTUAUUUAUARGGUUUAUTGGGTGUTUUTGGU<br>AGARGGAATTATGGGTGUTTTTAUTUTUTUATTTTAAAAATGTGUTTTTTATGTGTAT<br>TGTAAAAGTAAUAGATTUUUA |
| 414 | TGGGAATUTGTTAUTTTTAUAATAUAUATAAAAAGUAUATTTTTAAAATGAGAGAGT<br>AAAAGUAUUUATAATTURGTUTGUUAGGAGUAUUUAGTGGGURGTGTGGGTGAGAT<br>UUAUAURGGGATTTTUUTUUUTUUUUTGTGUTUUTXGUUUTUTGAGUTGAGUTUA<br>GUTTGUAGATGUUAGTUAATGTUUTGTTGUTGTTTAAUUTGTUATTGUAAUATUAGU<br>UUUTTTUUUAGUAAAUAGGGRGTTGGUAGGTATGUAGGGUUUTUUUTURGGAUAA<br>GTUTGAGGAUUUTGAUTG |
| 415 | UAUTTGGUTUTRGTGGUTGGGAUAGATTGUTTUUTTUUTUTUTUUTGGGTGUUAGGT<br>AGGUUUAGAAAUUAUUTGATGUTAGUAAGGUUTGGUUAUUUAUTGGTGGGGAGGA |

-continued

| SEQ ID NO: | Sequence |
|---|---|
| | AGTGGGRGGGTGUUUAGGGAUAGATGAGURGGGUAGAXGTGUUUTGAGGUAGUAU<br>AGTUAGGGUTGARGTGGGUATTATGUAUUTRGGGGUTTTUAGAGUTGGUTURGGTU<br>URGTTTGUUUAUATUAAGUAGGTUAGAGTGGAGAGGGUUAGGGGRGUTGGGGTUA<br>AGGUATGUAUTGAUUAGGRGTU |
| 416 | GARGUUTGGTUAGTGUATGUUTTGAUUUUAGRGUUUUTGGUUUTUTUUAUTUTGAU<br>UTGUTTGATGTGGGUAAARGGGAURGGAGUUAGUTUTGAAAGUUURGAGGTGUAT<br>AATGUUUARGTUAGUUUTGAUTGTGUTGUUTUAGGGUAXGTUTGUURGGUTUATUT<br>GTUUUTGGGUAUURGUUUAUTTUUTUUUUAUUAGTGGGTGGUUAGGUUTTGUTGA<br>UATUAGGTGGTTTUTGGGUUTAUUTGGUAUUUAGGAGAGAGGAAGGAAGUAATUT<br>GTUUUAGUUARGAGAGUUAAGTG |
| 417 | AUUAUAUTTGAAUATAUAGAUATUUTTTTUUAGGGTGTGTTGTGUTRGATAUUTTT<br>AATTUUTGUTUTGUATTUUAGGGUUTGUUUAGUUTUTTUUTGGUTUUUUAGUUUAGU<br>UTGGTUUTTURGGUUTUUUTGTUATUUUUAUUTUTXGTGTGTGUAUAAGUAGGGAU<br>UAGGTAGGGAGAURGGUAGATGUTGUTUTUTGTUUUTGGGGTTTUTTTTUTTAGTGT<br>TGUTUUUAUAUUUARGRGATGUTTTAATTAAUTGUUAUAUTUAGGUTTTUTUAGTG<br>GGGAGAGTUAGAAATAGA |
| 418 | UTATTTUTGAUTUTUUUUAUTGAGAAAGUUTGAGTGTGGUAGTTAATTAAAGUATR<br>GRGTGGGTGTGGGAGUAAUAUTAAGAAAAGAAAUUUUAGGGAUAGAGAGUAGUAT<br>UTGURGGTUTUUUTAUUTGGTUUUTGUTTGTGUAUAUAXGAGAGGTGGGGATGAUA<br>GGGAGGURGGAAGGAUUAGGUTGGGUTGGGGAGUUAGGAAGAGGUTGGGUAGGU<br>UUTGGAATGUAGAUAGGAATTAAAGGTATRGAGUAUAAUAUAUUUTGGAAAAGGA<br>TGTUTGTATGTTUAAGTGTGGATG |
| 419 | TUUUAGUUAUTURGUAGTUAUTUUTGAUUUAGAAAAGAAUAAUUAUAGUTGGGUU<br>UAGUAUUURGGGUUAUTUUUTGUAGUTGUUUAUAUATUTGGUAGUTGGGTUUAUT<br>TATGUAATGTGGATXGGGTTTTUTTAUATUTGAAATUTGXGTUTUTATUUUTUUTUTG<br>AGAUUAGTGTUTUUTGUUAGUTTUUATGGUUURGGGATGAUUTUAUTUTUUUAGGG<br>TUTUUUTGRGTUUTGGGAGUTUTGGURGAGGAGUAGUAGGGGUTGATGGUAGAGR<br>GGGGGUAGGTUAGAGUTUAGUA |
| 420 | GUTGAGUTUTGAUUTGUUUmGUTUTGUUATUAGUUUUTGUTGUTUUTRGGUUAGA<br>GUTUUUAGGARGUAGGGAGAUUUTGGGAGAGTGAGGTUATUURGGGGUUATGGAA<br>GUTGGUAGGAGAUAUTGGTUTUAGAGGAGGGATAGAGAXGUAGATTTUAGATGTA<br>AGAAGUUXGATUUAUATTGUATAAGTGGAUUUAGUTGUUAGATGTGTGGGUAGUT<br>GUAGGGAGTGGUURGGGGTGUUGGGUUUAGUTGTGGTTGTTUTTTTUTGGGTUAGG<br>AGTGAUTGRGGAGTGGUTGGGAU |
| 421 | UUAAARGRGGUAUARGGGGARGGUUUUTUURGGGGTUAGGUTUAUTGGUTUUTTU<br>UUTTUAGRGUUAUUAGGUAGGAGGGUUAARGGTUAUAUAGGAGGUAUUUTUAUUT<br>GUUTTTGUAUUAGUAAATAAAGTGUATUUUATTTTXGTGTGAGXGTRGGUURGGTG<br>AGTUAGUUUTTURGGGUUUTTTUUTGTTUTUAGGGUAGGGGGRGTGRGUTGAGUUA<br>GAGGTAGATUTGUAGAAAGGGUUURGAUTGGGUUTRGGGUAGGGURGGRGUUUAU<br>UAUAUTUTGGGGGTUAGUTATGU |
| 422 | GUATAGUTGAUUUUUAGAGTGTGGTGGGRGURGGUUUTGUURGAGGUUUAGTRGG<br>GGUUUTTTUTGUAGATTTTAUUTUTGGUTUAGRGUARGUUUUUTGUUUTGAGAAUAG<br>GAAAGGGUURGGAAGGGUTGAUTUAURGGGURGAXGUTUAUAXGAAAATGGGATG<br>UAUTTTATTTGUTGGTGUAAAGGUAGGTGAGGGTGUUTUUTGTGTGAURGTTGGUU<br>UTUUTGUUTGGTGGRGUTGAAGGGAAGGAGUUAGTGAGUUTGAUUURGGGAGGGG<br>URGTUUURGTGTGURGRGTTTGG |
| 423 | GUAGGAAGGGUUUAGARGAUAUUUUUAUAGAUATATGUUAGUUUUTURGGGTGAU<br>UAAAATUATUTUAGTAAAGGUAGATGAGGUUAAGRGAAAAGGGGTGGGTGGAAGA<br>AURGGUTUTGAGTUTUAGUUUAUAGAUAUTRGGAUAUTXGTRGGUURGGTAGGUA<br>GGGGTTUUTGGTGGUUTUAGGUTGTUAGGUURGGUUUUUTUURGUAGUTGUTUUA<br>GUTUUUAUUTUUUURGUUUAUUUUUUAGGAUTUUTATTTUAUTGAGGAGATTAAG<br>AUUAUUTGGRGAGAAUUUUTUUUA |
| 424 | GGGAGGGGTTUTRGUUAGGTGGTUTTAATUTUUTUAGTGAAATAGGAGTUUTGGGG<br>GGTGGGRGGGGGAGGTGGGAGUTGGAGAUAGUTGRGGGAGGGGGURGGGUUTGAU<br>AGUUTGAGGUUAUUAGGAAUUUUTGUUTAURGGGURGAXGAGTGTURGAGTGTUT<br>GTGGGUTGAGAUTUAGAGURGGTTUTTUUAUUUAUUUUTTTRGUTTGGUUTUATU<br>TGUUTTTAUTGAGATGATTTTGGTUAUURGGAGGGGUTGGUATATGTUTGTGGGGGT<br>GTRGTUTGGGUUUTTUUTGUT |
| 425 | AGGTGAGATUTGGAGGTTGRGGGGUAGTTAGUAAGTGGGAGAGAGUTGUATGRGGG<br>GAAGGTGGGAGGRGTTGUAGGAAAGGTGAGGGAGAUAUAGUTGAGUTGTGGTGUT<br>GGUUAGUTGGGGUUTTGRGUUTTATURGGGUAUTGTGAXGGUUAUTAAUAGGTTTT<br>AAGTAURGGAATGAUATGATRGGATTTGTAATTTAAUTAGATUUTTUTGAUTGUTGT<br>TGGGGGAAUAGAUTGUUAAUUTUAUAAUAGUAUTGUUAGUTGAGUATTAGAUAAAT<br>GATGAAUUTGGGUUUAGGGA |

-continued

| SEQ ID NO: | Sequence |
|---|---|
| 426 | UUUTGGGUUUAGGTTUATUATTTGTUTAATAUTUAGUTGAUAGTGUTGTTGTGAGGT TGAUAGTUTGTTUUUUUAAUAGUAGTUAGAAGGATUTAGTTAAATTAUAAATURGA TUATGTUATTURGGTAUTTAAAAUUTGTTAGTGGUXGTUAUAGTGUURGGATAAGG RGUAAGGUUUUAGUTGGUUAGUAUUAUAGUTUAGUTGTGTUTUUUTUAUUTTTUUT GUAARGUUTUUUAUUTTUUURGUATGUAGUTUTUTUUUAUTTGUTAAUTGUUURGU AAUUTUUAGATUTUAUUTG |
| 427 | TGTGTTAUUUUAGAAAGUAAGGARGUTTUUAAAGATGTTUAGAGUAGTGTTUAAAG GGATGUUUAUTGGTUAGTUUUAAURGUTGTGAAUURGGAAAATUTGAGAUTGGTGT UAGTTAAUTTAGAAAGTTTATTTTGUUAAGGTTGAGGAXGTATGUUTGTGAUAUAGU UTUAGGAAGTUUTGATGAUATGTGUUUAAGGTGGTTGGGGTGTAGUTTGATTTTATA UAUTTAGGGAGUATGAGAUATUAATTAAGTAUAUTTGAGAAATAUATRGGTTTGGT UTAGAAAGGRGGGAUAAU |
| 428 | GTTGTLURGUUTTTUTAGAUUAAAURGATGTATTTUTUAAGTGTAUTTAATTGATGT UTUATGUTUUUTAAGTGTATAAAATUAAGUTAUAUUUUAAUUAUUTTGGGUAUATG TUATUAGGAUTTUUTGAGGUTGTGTUAUAGGUATAXGTUUTUAAUUTTGGUAAAAT AAAUTTTUTAAATTAAUTGAUAUUAGTUTUAGATTTTURGGGTTUAUAGRGGTTGGG AUTGAUUAGTGGGUATUUUTTTGAAUAUTGUTUTGAAUATUTTTGGAAGRGTUUTT GUTTTUTGGGGTAAUAUA |
| 429 | TGAGAATAATGTUTGGTATGRGAGGAGUAUUAGUAAATRGTGUTUATUATTUUAGR GGAGUAAATTGTTGUTGTUTUTUAURGGGUTTTGGGTTAUTGAGGUTGUTATTTATT AAAGTGTGGGTTGTGAUTUATTAUTAGGTUATGAAATXGGTGTAGTGGTAGUAAUU AGUUUTTAAAGAAATGAAURGGGGURGGGRGRGGTGGTTUAUAUUTGTAAUUUUAG UAUTTTGGGAGGURGAGGRGGGTGGAUTUARGAGGTUAAGAGATRGAGAUUAUUUTG GUUAAUATGGTGAAAUURG |
| 430 | RGGGTTTUAUUATGTTGGUUAGGATGGTUTRGAUTUTUTTGAUUTRGTGAUUUAUURG UUTRGGUUTUUUAAAGTGUTGGGATTAUAGGTGTGAAUUAURGRGUURGGUUURG GTTUATTTUTTTAAGGGUTGGTTGUTAUUAUTAUAUXGATTTUATGAUUTAGTAATG AGTUAUAAUUUAUAUTTTAATAAATAGUAGUUTUAGTAAUUUAAAGUURGGTGAG AGAUAGUAAUAATTTGUTURGUTGGAATGATGAGUARGATTTGUTGGTGLTTUUTRG UATAUUAGAUATTATTUTUA |
| 431 | AGGATGGAGGURGGGGAGGUAGRGURGURGGRGGGGGRGGGRGGURGRGURGUAG GRGGUTGGGGUAAGTGGGTGRGGUTUAARGTGGGGGGUARGGTGTTUUTGAUUAUU RGGUAGARGUTGTGURGRGAGUAGAAGTUUTTUUTUAGUXGUUTGTGUUAGGGGG AAGAGUTGUAGTRGGAURGGGTGAGGUUUURGGGGTGGGRGGRGAGRGGGRGGTG GGTUUTURGUTRGUURGARGRGGGGUTGTRGGGUUTGGUTRGUURGUUAGGUTGGG GAUURGGURGGGTTUATTTURGA |
| 432 | TRGGAAATGAAUURGGURGGGTUUUUAGUUTGGRGGGRGAGUUAGGUURGAUAGU UURGRGTRGGGRGAGRGGAGGAUUUAURGUURGUTRGURGUUUAUUURGGGGGUU TUAUURGGTURGAUTGUAGUTUTTUUUUUTGGUAUAGGXGGUTGAGGAAGGAUTTU TGUTRGRGGUAUAGRGTUTGURGGGTGGTUAGGAAUAURGTGUUUUUUARGTTGAG URGUAUUUAUTTGUUUUAGURGUUTGRGGRGRGGURGUURGUUUURGURGGRGGR GUTGUUTUUURGGUUTUUAUUT |
| 433 | TUTAUTGATGRGGAGAURGAGUUUUAGGGUAGUAGAGUUUTAGUTTRGRGUTAUA RGGUTGTGGGRGUTGRGUUUUAGGGUARGGURGGUUUAGGTRGTGGUUUAUTRGG GAUURGRGGUTUAURGGTGRGGTTGARGRGGUARGGGAAGXGGTAGGTGUTUAGU AUUTUUTUUTRGTUUTGUTRGTRGATGAUURGGUAUTGGRGUAGATARGGRGTGAG UTTGGURGGGTTUAGGGRGRGAGUUAGURGATGURGGARGUUUTRGATTRGUTUUU AUAGRGRGTUUTUUTURGUUTUA |
| 434 | TGAGGRGGAGGAGGARGRGUTGTGGGAGRGAATRGAGGGRGTURGGUATRGGUTGG UTRGRGUUUTGAAUURGGUUAAGUTUARGURGTATUTGRGUUAGTGURGGGTUATR GARGAGUAGGARGAGGAGGAGGTGUTGAGUAUUTAUXGUTTUURGTGURGRGTUA AURGUAURGGTGAGURGRGGGTUURGAGTGGGUUARGAUUTGGGURGGURGTGUU UTGGGGRGUAGRGUUUAUAGURGTGTAGRGRGAAGUTAGGGUTUTGUTGUUUTGG GGUTRGGTUTURGUATUAGTAGA |
| 435 | UTUAUUTTTUUTAGTTTAGAAAATUUUTUAUTGUTTUUUUAATGGAGGUTGUUUUA GGAGTGGUUUAGTGGGGUUAAUUAGUTGTTUTATGUUAGUAGUTURGGAGTATGTA UATTTUUAUTUTGGTTUAAAUTTGTTUTTUTATTUAXGGUUUUATTAAGAAA TUATUTGUAGGUTGGAURGGGTTGGGATGUAGUAAGTTGGTGTGGUTAUTURGAGT GTGTGAUAUAUUTGUAGGGGUUTGTGAGUAGTGGGAGGGUUAGAUATGTGGATTU UUAGGGUTGGTGGUTTUUTT |
| 436 | AGGAAGUUAUUAGUUUTGGGAATUUAUATGTUTGGUUUTUUUAUTGUTUAUAGGU UUUTGUAGGTGTGTUAUAUAUTRGGAGTAGUUAUAUUAAUTTGUTGUATUUUAAU URGGTUUAGUUTGUAGATGAATGTTnTUTTAATGGGGUXGTGAATAGAAGAAUAA |

-continued

| SEQ ID NO: | Sequence |
|---|---|
| | GTTTGAAUUAGAGTGGAAATGTAUATAUTURGGAGUTGUTGGUATAGAAUAGUTGG<br>TTGGUUUUAUTGGGUUAUTUUTGGGGUAGUUTUUATTGGGGAAGUAGTGAGGGATT<br>TTUTAAAUTAGGAAAGGTGAGA |
| 437 | AARGUTGAUATUTTTURGGGTGTUTGAAAAUAGAAUTGGUUTTUUTAAGAAUTAAU<br>AARGATAUTGTTTTUAGUUARGTTUUTTUUTGTTUTTGUTAUARGUTUTGTUAAAT<br>AGGTGGUUAGAGGUURGGGTGUAGATGUAGTGGUTUAXGTUAGTAATUUUAGUAU<br>TUTGGGAGGUTGGTGGGRGGATUAUTTGAGGUUAGGAGTTTAAAGAUUAGUTTGGG<br>UAAUATGGTGAAAUUUTGTUTUTAUTAAAAATAUAAAAAATTAGURGGGTGTGGTG<br>GUAUAAAUUTGTAGTTUUAG |
| 438 | UTGGAAUTAUAGGTTTGTGUUAUUAUAUURGGUTAATTTTTTGTATTTTTAGTAGAG<br>AUAGGGTTTUAUUATGTTGUUUAAGUTGGTUTTTAAAUTUUTGGUUTUAAGTGATU<br>RGUUUAUUAGUUTUUUAGAGTGUTGGGATTAUTGAXGTGAGUUAUTGUATUTGUA<br>UURGGGUUTUTGGUUAUUTATTTGAUAGAGRGTGTAGUAAGAAUAGGAAGGGAAR<br>GTGGUTGAAAAUAGTATRGTTGTTAGTTUTTAGGAAGGUUAGTTUTGTTTTUAGAUA<br>UURGGAAAGATGTUAGRGTT |
| 439 | GAGGUUUAUUUARGUUUUUAGUTUARGATATUTGUAGAGATGUUAAAUUUTGGUA<br>GAGGAAUTUAGGUUATGTGUTTUAGUUGUTXUUTUAUTUUTUUAUTUUUTGUURGG<br>GUUUTGAGUUAGGAGUUAGGUAUAUAGUTGGAUUUATUXGUUAATGUUAUUUAU<br>UUTTGTGUUUAGUAUURGGUUUARGGUAGGTGUTUAGTGTGUAGGUUUAUATGTA<br>UTAGGTGUAAGGUAARGAUAUAUUAUAUAGGAUAAGGATGUAAAGUAUUTTUTGG<br>GUUUTTUTGRGGUTUTGUUTTUUUA |
| 440 | TGGGAAGGUAGAGURGUAGAAGGGUUUAGAAGGTGUTTTGUATUUTTGTUUTGTGT<br>GGTGTGTRGTTGUUTTGUAUUTAGTAUATGTGGGUUTGUAUAUTGAGUAUUTGURG<br>TGGGURGGGTGUTGGGUAUAAGGGTGGGTGGUATTGGXGGATGGGTUUAGUTGTGT<br>GUUTGGUTUUTGGUTUAGGGUURGGGUAGGGAGTGGAGGAGTGAGGGAGUAGUTG<br>AAGUAUATGGUUTGAGTTUUTUTGUUAGGGTTTGGUATUUTGUAGATATRGTGAG<br>UTGGGGGRGTGGGTGGGUUTU |
| 441 | GGAGGUAAARGGGAAUURGGUTGGRGGGUTGRGAGURGGTAGGGARGUTGGGGTU<br>UAGGGUTGUTGGAUAGUUURGUUUTGTAUUTUTUUUUATAATTUUUTGGTGGGT<br>GTURGAAATAGUUURGGGTAATUUUAGGGRGAGGUAGTXGGGAATTAAUUUUAGU<br>UTTGAAGTAAGAGAUAGAGGRGTUUAUAGAAGAGGGUTUTGRGRGTUURGGAUTG<br>GAUAUAGRGUAGAGTUUATTUUAGGGAUAURGUAAUURGUAAGRGAUUUAGGUUR<br>GUTUUAGGGRGGGATURGRGRGGU |
| 442 | GURGRGRGGATUURGUUUTGGAGRGGGUUTGGGTRGUTTGRGGGTTGRGGTGTUUU<br>TGGAATGGAUTUTGRGUTGTGTUUAGTURGGGARGRGUAGAGUUUTUTTUTGTGGA<br>RGUUTUUXGTUTUTTAUTTUAAGGUTGGGGTTAGTTGGAAUUUTTUUTTTUUGUT<br>TAUURGGGGUTATTTRGGAUUUAGGATTAAGTGAGGGATGGGGAGAGGTAUAGGGR<br>GGGGUTGTUUAGUAGUUUTGGAUUUUAGRGTUUUTAURGGUTRGUAGUURGUUAG<br>URGGGTTUURGTTTGUUTUU |
| 443 | UATGTGUTGAGATGGAGAAGGRGUUAGTGTUAGUAUTAGAUAGGUTGAGATGTUA<br>AGTGGAAATGTUAAGGAGGTGGTGGAGGTGGTGGGAGUTGUAGGGUTGTGAGGUU<br>RGGGAGAGGGUUAGAGUTGUAGUTTTAAATTGGAGGGTUAXGGUATGTGGAGGUU<br>AAGGAAGUAGATGGGATGTURGGGGAGAGAGTATGGAUTGAAGUAGUTAAAGAAT<br>TGUAGUATUTAATGGAUAGGAAGAGGGGUAGRGAUAGRGATGGAGUUTGAGAAGG<br>AGGGTGUAGTGTUUUUAAGUUATGT |
| 444 | AUATGGUTTGGGGAUAUTGUAUUUTUUTTTTUAGGUTUUATRGUTGTRGUTGUUUU<br>TUTTUUTGTUUATTAGATGUTGUAATTUTTTAGUTGUTTUAGTUUATAUTUUUTUUU<br>RGGAUATUUUATUTGUTTUUTTGGUUTUUAUATGUXGTGAUUUTUUAATTTAAAGU<br>TGUAGUTUTGGUUUUUUURGGGUUTUAUAGUUUTGUAGUTUUUAUUAUUTUUAU<br>UAUTTUUUUUTGAUATTTUUAUTTGAUATUTUAGUUTGTUTAGTGUTGAUAUTGGRGU<br>UTTUTUUATUTUAGUAUATG |
| 445 | UUUTUAGGTTTGGTTTUTGTTGURGUTGTTGTTTTUTTTUTUUAAUATUATAAGUUTUT<br>TUUTTATUTTTUUATGTUTGUAUAUAGGAAGRGGUATUAUTTGTTTTTUATGTUUTG<br>RGUATRGAGGUAUAUTTTUUGUTUUTUTTTGTGUXGUUAGURGGUUUAGGUUUAUA<br>GATGGTAGGAUTTGTGUUUUAGGUTGUTGTGTGAGTUAGAGTUAGGUAGGAAGUAA<br>ATGGUAAUTTUAURGRGGTGAUTGAGGAATGUTTAARGAAGGRGURGUUUTTGAUA<br>ARGGTGTGGGTTGGTAA |
| 446 | TTAUUAAUUUAUAURGTTGTUAAGGGRGGRGUUTTRGTTAAGUATTUUTUAGTUAU<br>RGRGGTGAAGTTGUUATTTGUTTUUTGUUTGAUTUTGAUTUAUAUAGUAGUUTGGG<br>GUAUAAGTUUTAUUATUTGTGGGUUTGGGURGGUTGGXGGUAUAAAGAGGAGUAG<br>AAAGTGTGUUTRGATGRGUAGGAUATGAAAAAUAAGTGATGURGUTTUUTGTGTGU<br>AGAUATGGAAAGATAAGGAAGAGGUTTATGATGTTGGAAAAGAAAAUAAUAGRGG<br>UAAUAGAAAUUAAAUUTGAGGG |

-continued

| SEQ ID NO: | Sequence |
|---|---|
| 447 | TGUTUUTUTTTGTGURGUUAGURGGUUUAGGUUUAUAGATGGTAGGAUTTGTGUUU UAGGUTGUTGTGAGTUAGAGTUAGGUAGGAAGUAAATGGUAAUTTUAURGRGGT GAUTGAGGAATGUTTAARGAAGGRGURGUUUTTGAUAAXGGTGTGGGTTGGTAAAA GGAAAUAGURGGGAGUUUTGUAGRGURGGTGURGUUAURGTTTAGTUTGAUTGTGU ATTTGAUTAAGTUAUAAGAGGUUAGGUUTGTGAUTTGTURGAGGGAAAAAUUAUU AGAAAAUUAGGTGTUTGGGUT |
| 448 | AGUUUAGAUAUUTGGTTTTUTGGTGGTTTTTUUUTRGGAUAAGTUAUAGGUUTGGU UTUTTGTGAUTTAGTUAAATGUAUAGTUAGAUTAAARGGTGGRGGUAURGGRGUTG UAGGGUTUURGGUTGUTTTUUTTTTAUUAAUUUAUAUXGTTGTUAAGGGRGGRGUUT TRGTTAAGUATTUUTUAGTUAURGRGGTGAAGTTGUUATTTGUTTUUTGUUTGAUTU TGAUTUAUAUAGUAGUUTGGGGUAUAAGTUUTAUUATUTGTGGGUUTGGGURGGU TGGRGGUAUAAAGAGGAGUA |
| 449 | UTGTGUTUAAGAGUUAUTTUTTAAURGGGGTGGGAGGAAGUAGUTTUAGGAAUTGU TGAGAGAGUAGAAUTUARGUTUUAGGGUTUAGAGUAGGAGGTAGGGTGTGRGGUA AGRGUTGGUURGGAUAGAAGUAGAGTGGGUUUTGGTUTXGGGUAGGATGTTTUTGA UTUAUATTTUUTGAGGAGAGAAAGUTAAGUTUUTGUUTAATGTUTUTGTUTUUUUT TUUAGAAAAATGUUTUAGUTUTTURGGUUTGAAGGAATGGUUTUUTUmGGGUUUU ATGAUTTUTTUUTGTGTGGG |
| 450 | UUUAUAUAGGAAAGAAUTUATGGGGUURGGGAGGAGGUUAUTTUUTTUAGGURGGAA GAGUTGAGGUAUTTTTTUTGGAAGGGGAGAUAGAGAUATTAGGUAAAGAGUUAGUT TTUTUTUUTUAGGAAATGTGAGUTAGAAAUAUUTGUUXGAGAUUAGGGUUUAUTU TGUTUUTGUTURGGGUUAGRGUUTGURGUAUAUUUTAUUTUUTGUTUTGAGUUUTGG AGRGTGAGUUTGUTUUTUAGUAGUUTGAAGUTGUTC AGAAGTGGUTUTTGAGUAUAG |
| 451 | TTTTTTTTTTGAGAUAGAGUUTRGUTUTGTUAUUUAGGUTGGAGTGUAGTGGRGTGA TUTRGGUTUAUTGUAAGUTUUAUUTTUURGGGTTUATGUUATTUTUUTGUUTUAGUT TUUTGAGUAUTUTGGGAUTAUAGGUAUTUAUUAUUAXGUURGGUTAATTTTUURTTTT TATTTTTAGUTGGAGARGGGGUTUAUTTGUGTTAGUUAGGATGGUTURGAUTUTUUTGA UUTRGUGAUTAGUURGUUTUAGUUTUUUAAAGUGUTGGGAUUAUAGGUGUGAGUUA UUTUAUURGGUUTGUTA |
| 452 | AGUAGGURGGGTGAGGTGGUUAUAUUTGUAAUUUAGUAUUUGGGAGGUGAG GRGGGUTGAUUARGAGGUUAGGAGAURGAGAUUAUUTGGUAAUAUAGUGAAAU UURGUTUUAUTAAAAUAAAAAAAAAAAAUUAGURGGGXGUGGUGGUGAGUGUUT GUAGUUUUAGAUAUUAGGAAGUUGAGGUAGGAGAAUGGUAUGAAUURGGGAGGU GGAGUUUGUAGUGAGURGAGAUUARGUUAUUGUAUUUAGUUGGGUGAUAGAGR GAGAUUUGUGUUAAAAAAAAAAAU |
| 453 | TTGUUTUTTTTGATTTTTTTUTTTGGGUAGGAGTTAGAATGUAAAATAUAGATTUTAT UTGTATAAAGUAUAUAAGAGATGUTTGGGATUTGGTGATGUTGUAURGGAGATTTU AAUTGTTTTTUAAAGTGATTUUTAGGGAGTGTGAXGATUTUAAUTUTTTTGGAAGT GAUTTGTUAAAUUATGAGUUATGUTGAGTUUAGUAUAAGTAATATGAGGRGAGGUA AGGUAAGTGGGTGAGTAAGGAGGAAGUAGUUUAGATGAGURGGUAGAGTGUUUAU TGGGAGTGAGGUATGATG |
| 454 | ATUATGUUTUAUTUUUAGTGGGUAUTUTGURGGUTUAUTGGGUTGUTTUUTUUTT AUTUAUUUAUTTGUUTGUUTRGUUTUAUTATTAUTTGTGUTGAAUTUAGUATGGUTU ATGGTTTGAUAAGUAUTUUAAAAGAGUUGAGAUXGUUAUAUUUUAGGAAUUA UUUGAAAAAUAGGUUGAAAUTUURGGUGUAGUAUUAUUAGAUUUAAGUAUUTUT TGUGUGUTTUAUAGAUAGAAUTUGUAUUUUGUAUTUUAAUUTUGUUUAAAGAAA AAAAUUAAAAGAGGUAAU |
| 455 | AUAAGAGAUGUUGGGAUUUGGUGAUGUGUAURGGAGAUUUAAUUUGUUUUUAA AGUGAUUUUAGGGAGUGUGARGAUUUUAAUUUUUUGGAAGUGAUUUGUAAAUUA UGAGUUAUGUGAGUUUAGUAUAAGUAAUAUGAGGXGAGGUAAGGUAAGUGGGUG AGUAAGGAGGAAGUAGUUUAGAUGAGURGGUAGAGUGUUUAUUGGGAGUGAGGUA UGAUGAGGAUUAUURGURGUGGGAGGUAUGAGGGUAUUUUUUGGUAAGGUUUUG UAUUAUUAAAAUGAGGUUAU |
| 456 | TGAUUUTUAUUUGGUGAUGUAAGGAAUUUGUUAGAGAGUGUUUUAUGUUUUUA RGARGAGUAAUUUUUAUUAUGUUUAUUUUUAGUGGGUAUUUUGURGGUUUAUUUG GGUGUUUUUUUUUAUUAUUUAUUUGUUUGUUUXGUUUUAUAUUAUUUGUGUUG AAUUAGUAUGGUUAUGGUUUGAUAAGUAUUUUAAAAGAGUUGAGAURGUUAU AUUUUUAGGAAUUAUUUUGAAAAAUAGGUUGAAAUUUURGGUGUAGUAUUAUUAG AUUUAAGUAUUUUUUGUG |
| 457 | AGUAAAUAGAGGGUAUGGUUAAAUUUGUUUAUGAAURGGGAAGUAUAAUAUUUUAA UAUUUGUGUUUAAGUAGUUGUUUUAUUUUAAAAGUAUAGGAAAUUUGUGUUUUUUU UGUUAUAAAAUUUAUAAAGUUAUUGGAAAGAUUUUXGUAGGUUAGUGGUUUUAA AGUGGGUUUUAGAAUUAGUAAUAGUGAAUUAUURGGGAAUUGGUUAGAAAUGUA |

-continued

| SEQ ID NO: | Sequence |
|---|---|
| | AAGTUTRGURGUUAUUUUTUAAUUUUUUAGAUUTAATGAAUUAGAAATTUTGGGG TGTGGUUUAGTGGUUTGRG |
| 458 | RGUAGGUUAUTGGGUUAUAUUUUAGAATTUTGGTTUATTAGGTUTGGGGGGTTGA GGGGTGGRGGRGAGAUTTTGUATTUTUTAAUUAGTTUURGGATGATTUAGUTGTTGUT AGTTUTGGGAATRTUAUTTTGAAAAUUAUTGGUUTGXGGAGATUTTTUUAUTAUUTT TGTAAGATTTTATAAUAAGAAAAAAGAUAGGATTUUTGTGUTTTTAAGTAAAAUA AUTGUTTAAGGUAUAAATATTAAAATATTATGUTTUURGGTTUATAGGUAAGTTGGA UUATAUUUTUTGTTTGUT |
| 459 | GUUUTAUUURGUTUTUTURGAUTUUUURGGGUURGGUUTGRGUUTTUUTGRGGTGU RGAGGAGRGGTGGRGUUUTGGGTGAAGAAGTUURGURGAGTRGAGGGGRGUAATG GAGGAGRGURGGAAUAGGTUTUTUATTURGAGTAGUTAUXGTTGUAUTGTGRGAGT GTAAAAGTUATTUUAUURGGTUTUAGTTGTTUUAAUUTUAGTTGAAGTGAGGAGG TTGGAUTGGAAGGTTUTGGGGTUAUTUUAGTGAGGUTGGGGTTUTAGTUUUAATU TUAURGTGGUAUUUUAAAGGU |
| 460 | GUUTTTGGGGTGUUARGGTGAGATTGGGAUTAGAAUUUUAGUUTUAUTGGAGTGAU UUUAGAAAUUTTUUAGTUUAAUUTUUTUAUTTUAAUTGAGGTTGGAAUAAUTGAGA URGGGTGGAAGTGAUTTTTAUAUTRGUAUAGTGUAAXGGTAGUTAUTRGGAATGAG AGAUUTGTTURGGRGUTUUTUUATTGRGUUUUTRGAUTRGGRGGGAUTTUTTUAUU UAGGGRGUUAURGUTUUTRGGUAURGUAGGAAGGRGUAGGURGGGUURGGGGGAG TRGGGGAGAGRGGGGTAGGGU |
| 461 | GGAUAUAAUTUTUTGTTUTTUAAAGTTGGUAUTAAGAGUTUUTUUTGRGGTTUUUUTT UUTUTUUTRGAGUAGUAAAGGRGTGGTUUAUAAUTGUUUAUUUTGTGGGGTUTAGGG GTGUURGGUTTGUTGAUUTUUAGGUUUUUTUTGTGGXGAGGTTTGGAUTGUATAUA TGGTGUAGGUUUUTUAUTUAUTGGAGUTGUUAGGAUAGUAUTGGAGAUUUTAAGUU AATAUUTATTTTTGGUAATAATTATUAAGUATTTGTAAAAGUURGGGTATGUTGGUA AAUTUTTTTTAAAATAAGAG |
| 462 | UTUTTATTTTAAAAAGATTTGUUAGUATAUURGGGUTTTTAUAAATGUTTGATAATT ATTGUUAAAAATAGGTATTGGUTTAGGGTUTUUAGTGUTGTUUTGGUAGUTUUAGT GATGAGGGGUUTGUAUUATGTATGUAGTUUAAAUUTXGUUAUAGAGGGGGUUTGG AGGTUAGUAAGURGGGUAUUUUTAGAUUUUAUAGGGTGGGUATTGTGGAUUARGU UTTTGUTGUTRGAGGAGAGGAAGGGGAAURGUAGGAGGAGUTUTTAGTGUUAAUTT TGAAGAAUAGAGATTGTGUU |
| 463 | AUTTGAGRGUTTUTUUAUUUUAGUAGGUURGUTGUUATUAAGGGUTTAUUUTGTGG GUTGUUUARGUTGUTGTAAUUAGTGAUUAUAAGUTURGTGGTGTTGAGAAGUAUAT GTTTUTUUTUUUARGGUTGTGTAGGTURGGAGTUUTAXGGGUTUAGUUAGTUUUUU TGUTUUAGGTTTAAUUAGGURGGAATUAAGATGUUAGGGUUTGGUTGTGUTTTGGA GGUTUTTGGTGAGAAUUTGUTTUTGGUUTGGTGUAGGGTGTGGUAGAAUTUURGATG UTTGAGTTTGAATGGTGAAA |
| 464 | TTTUAUUATTUAAAUTUAAGUATRGGGATTUTGUUAUAUUUTGUAUUAGGUUAGAA GUAGGTTUTUAUUAAGAGUUTUUAAAGUAUAGUUAGGUUUTGGUAUTUTTGAUUUR GGUUTGGTTAAAUUTGGAGUAGGGGGAUTGGUTGAGUUXGTAGGAUTURGGAUUT AUAUAGURGTGGGAGGAGAAAUATGTGUTTUTUAAUAUUARGGAGUTTGTGGTUAU TGGTTAUAGUAGRGTGGGUAGUUUAUAGGGTAAGUUUTTGATGGUAGRGGGUUTG UTGGGGTGGAGAAGRGUTUAAGT |
| 465 | AAAUTUARGUTGGUUUAAGAGGAGGAAUAGAGAAGUTTUUTGGUTGAGGUUUAGU RGAUTGUTGAUURGGAAAAGTTUTURGAGGTGAUTUAUAUTUUUUAGUUTUTGUAUA TGTGGGTGAGUUAGTTGTAGUTUTGTTUUXGTGAUTGAGUAXGGGAXGURGGAGGT ATTUAUAGGUATGAGGTTATUTGUUTAUTTUUUATGTGTUAGURGAGTGAURGAA TUTUAGTUUUTTAGUUUUTAUAUUUTAGGGTUUTAGTGGAUTGUAAGUTGGTGAT AAGAGUTGUGUTGUUUTUAUT |
| 466 | GTGAGGGUAGUAUAAAUTUTTATUAUUAGUTTAUAGTUUAUTAGGAUUUTAGGGATG TAGGGGUTAAGGGAUTGAGATTRGGUUAUTRGGUTGAUAUATGGGAAGUAGGUAGA TAAUUTUATGUUTGATGAATAUUTURGGXGTUUXGTGUTUAGTUAXGGGAAUAGAG UTAUAAUTGGUTUAUUUAUATGTGUAGAGGUTGGGGATGTGAGUTAUUTRGAGAA AUTTTTTRGGGTUAGUAGTRGGUTGGGUUUTUAGUUAGGAAGUTTUTUTGTTTTUTUU TUTTGGGUUAGRGTGAGTTTT |
| 467 | AUTTGAGRGUTTUTUUAUUUUAGUAGGUURGUTGUUATUAAGGGUTTAUUUTGTGG GUTGUUUARGUTGUTGTAAUUAGTGAUUAUAAGUTURGTGGTGTTGAGAAGUAUAT GTTTUTUUTUUUARGGUTGTGTAGGTURGGAGTUUTAXGGGUTUAGUUAGTUUUUU TGUTUUAGGTTTAAUUAGGURGGAATUAAGATGUUAGGGUUTGGUTGTGUTTTGGA GGUTUTTGGTGAGAAUUTGUTTUTGGUUTGGTGUAGGGTGTGGUAGAAUTUURGATG UTTGAGTTTGAATGGTGAAA |
| 468 | TTTUAUUATUAAAUTUAAGUATRGGGATTUTGUUAUAUUUTGUAUUAGGUUAGAA GUAGGTTTTUAUUAAGAGUUTUUAAAGUAUAGUUAGGUUUTGGUAUTUTTGAUUUR |

-continued

| SEQ ID NO: | Sequence |
|---|---|
| | GGUUTGGTTAAAUUTGGAGUAGGGGGAUTGGUTGAGUUXGTAGGAUTURGGAUUT AUAUAGURGTGGGAGGAGAAAUATGTGUTTUTUAAUAUUARGGAGUTTGTGGTUAU TGGTTAUAGUAGRGTGGGUAGUUUAUAGGGTAAGUUUTTGATGGUAGRGGGUUTG UTGGGGTGGAGAAGRGUTUAAGT |
| 469 | GRGAATAAAAAGUUAGTGTGTGAGUAAGTUTGTGGGAAGATGUATGUAGAGTGTGA UAGAGAGTTTAGGGGUTRGTGTGAUAAUTURGTGGAAATGTTTUTAAAGGRGAGGGT ATGTGTGTGGGTGTGAGGAUURGGUTGTTGGATGTTTAXGTATTTTATTAGUTAGAT ARGGGAGUTAATAUTUAATTGUAGTGUAUTAAAUATTATTAGGTGGGTATGATTTTG AGGGAATGAGGGAAGGGAGAUAAGGTUTGGTGAGAUTAUTUTGTGGGATTAUTUTGTG TGTATTTGUTGGTTTGTA |
| 470 | TAUAAAUUAGUAAATAUAUAUAGATAATUUUAUAGATGATUTUAUUAGAUUTGT TTTUUUTTUUTTTUATTUUUTUAAAATUATAUUUAUUTAATAATGTTUUAAGGU AATTGAGTATTAGUTUURGTATUTAGUTAATAAAATAXGTAAAUATUUAAUAGURG GGTUUTUAUAUUUAUAUAUAUAUUUTRGUUTTTAGAAAUATTTUUARGGATTGTUA UARGAGUUUUTAAAUTUTUTGTUAUAUTTTTGUATGUATUTTUUUAUAGAUTTGUTU AUAUAUTGGUTTTTATTRGU |
| 471 | UAGTGAGUTGAGAGUARGUUAUTGUAUTUUAGUUTGGGGGATAGAGTGAGAUTUT GTUUUAAAAAAAGAAAAAAAGAAUTGAUTUUUAAATGTGTGGGGAGAUTGATTTUAG TAATAATAAAAUTURGGTUTUUUAUAUAGTUAGUTUTGXGTGAATUUUTUTTTUUU TATTGRGATTUUUUTGATTTGAGTGAUAGTAAAAUTURGGTUTUUTGUAUAGUUAG UTUTGRGTGAGTUAUTUTTTUTUUUUTGTAATTUUUUTGUTUTGAUTUUAUTUA GTUTGGGUAGUAGGUAAGGT |
| 472 | AUUTTGUUTGUTGUUUAGAUAGAGUTGAUTGGAUTAAGAUAGGGGAATTAUAGGGG AGAAAGAATGAUTUARGUAGAGUTGGUTGTGUAGGAGAURGGAGTTTTAUTGUTUAU TUAAAUTAGGGGAATRGUAATAGGGAAAGAGGGATTUAXGUAGAGUTGGUTGTGT GGGAGAURGGAGTTTTATTATTAUTGAAATUAGTUTUUUUAUAUATTTGGGATUAGT TUTTTUTTUTUTTUUUGAGAUAGAGUTUTUAUTUTATUUUUUAGGUTGGAGTGUAGT GGRGTGUTUTUAGUTUAUTG |
| 473 | GGATGTRGGTGTGUUAAUUUUAGUTUUAUUUUAUTGUTAAAGUTTAAGUTUTUUUU TUUUURGTTAAGUTGTATGAUUTTGAGTUUTTGTGUUTUAUTGUUTUAUTUTGUTUA AGTGAAAATGUTUUUAGTUUUUAUUTURGGGAGTTGXGTGGGAGGUAUAUATGAA UAUUAGGAAAGTGAGTTTATGUAGUURGGGUUAGGGAUTURGGTUTUTGUUTUTGU UUTAATUUUUARGGUUTGGGGGAARGTGUAGGGUTGAGGAAGRGUAGUUTUTUUT TGGAATUTUAGRGGAAGUTUU |
| 474 | GGAGUTTURGUTGAGATTUUAAGGAGAGGUTGRGUTUUTUAGUUUTGUARGTTUU UUUAGGURGTGGGGATTAGGGUAGAGGUAGAGAURGGAGTUUUTGGUURGGGUTG UATAAAUTUAUTTTUUTGGTGTTUATGTGTGUUTUUUAXGUAAUTUURGGAGGTGG GGAUTGGGAGUATTTTUAUTTGAUAGATGAGGAUAGTGAGGUAUAAAGAAUTUAA GGTUATAUAGUTTAARGGGGGAGGGGAGAGUTTAAGUnTAGUAGTGGGGTGGAGU TGGGGTTGGUAUAURGAUATUU |
| 475 | TAATTGAATUAUATAATTUATTTUUATTATUTGAGTTUURGGUTTAGGUTUTTTGAG TAUUARGAATUAGGAATGAUTATGUTUUAUTTUAUUUTRGUTAGTUAAAGAUTGU UAGGAGGUURGGGGTTGTGGTATTUAARGTTAUAGAXGTAAGGUUUTUUTGUUUAU UUAGUAUTUUAAATATTTUATGAUATATGAAGGUTUTGAUATTGUAAAURGGAUTA RGAUAAGUUTTTGAUTTTUURGGGTTGTGAGGAGTTTTAGAAAATAAUTGAGAAGU AAUTTTTTTGAGGATGATG |
| 476 | UATUATUUTUAAAAAAGTTGUTTUTUAGTTATTTTUTAAAAUTUUTUAUAAUURGGA GAAGTUAAAGGUTTGTRGTAGTURGGTTTGUAATGTUAGAGUTTUATATGTUATGA AATATTTGGAGTGUTGGGTGGGUAGGAGGGUUTTAXGTUTGTAARGTTGAATAUUA UAAUUURGGGUUTUUTGGUAGTUTTTGAUTAGRGAAGGGTGAAGTGGAGUATAGTU ATTUUTGATTRGTGGTAUTUAAAGAGUUTAAGURGGGAAUTUAGATAATGGAAATG AATTATGTGATTUAATTA |
| 477 | UAAUATTUTTGTATUUAGUATUUTTTGTUATGTUATTUTATAGATGUTUTUAUTAA AGTGATGGUUAATTTUUTAUUUTTRGAATURGGGTUTTGGUAAATGGGATGTTAAU AAUAGUTUUUAAAUAGAGGATUAUATAGTAUTTGXGTGAGUUUAUUUUUTUTTAT GTTUTTUAAGUATGUUATGAGAAUAXGUUTGGGTUAGUUTGUTGAAGGAGUTGAGU TGAGTUAUTUURGGTGAUAGUUAGUTGAUTUTTAGUAGTGAGAGGUAUUUUUAUAA AGUTGUTUTGUTGAUUAUU |
| 478 | GTGGTUAGUAGAGUAGUTTTGTGGGGGTGUUTUTUAUTGUTAAGAGTUAGUTGGUT GTUAURGGGATGAUTUAGUTUAGUTUUTTUAGUAGGUTGAUUUAGGXGTGTTUTUA TGGUATGUTTGAAGAAUATAAGAGGGGAGTGGGUTUAXGUAAGTAUTATGTGAUTU TUTGTTTGGGAGUTGTTGTTAAUATUUUATTTGUUAAAGUURGGATTRGAAGGGTAA GGAAATTGGUUATUAUTTTAGTGAGAGUATUTATAGAATGAUATGGUAAAGGATGU TGGATAUAAGGAATGTTGU |

-continued

| SEQ ID NO: | Sequence |
|---|---|
| 479 | GUTUTUAUTAAAGTGATGGUUAATTTUUTTAUUUTTRGAATURGGGUTTTGGUAAAT GGGATGTTAAUAAUAGUTUUUAAAUAGAGGATUAUATAGTAUTTGXGTGAGUUUA TTTUUUUTUTTATGTTUTTUAAGUATGUUATGAGAAUAXGUUTGGGTUAGUUTGUTG AAGGAGUTGAGUTGAGUTUATUURGGTGAUAGUUAGUTGAUTUTTAGUAGTGAGAG GUAUUUUUAUAAAGUTGUTUTGUTGAUUAUUUUAGAUAUARGAGUAAAAGAAATG TTTAUUATTAUATGTUAUTGAG |
| 480 | TUAGTGAUATGTAATGGTAAAUATTTUTTTTGUTRGTGTGTUTGGGGTGGTUAGUAG AGUAGUTTTGTGGGGGTGUUTUTUAUTGUTAAGAGTUAGUTGGUTGUTGUTUAURGGGAT GAUTUAGUTUAGUTUUTTUAGUAGGUTGAUUUAGGXGTGTTUTUATGGUATGUTTG AAGAAUATAAGAGGGGAGTGGGUTUAXGUAAGTAUTATGTGAUUTUTGTTTGGGA GUTGUTGUTTAAUATUUUATTTGUUAAAGUURGGATTRGAAGGGTAAGGAAATTGGU UATUAUTTTAGTGAGAGUA |
| 481 | UUUUAGUUAAAUUAUTRGAUTGUUUUUUATUAUUTATAUTGGURGTTTTUUUTGG AGUUTGUAUUUAAUAGTGGUAAUAUUTTGTGGUURGAGUUUUTUTTUAGUTTGGTU AGTGGUUTAGTGAGUATGAUUAAUUUAURGGUUTUUTXGUUTUAGUAUUATUTU UAGRGGUUTUUTURGUUTURGUUTUUUAGAGUUUAUUUUTGAGUTGRGUAGTGUU ATUUAARGAUAGUAGTUUUATTTAUTUAGRGGUAUUUAUUTTUUUUARGURGAAU AUTGAUATTTTUUUTGAGUUAUA |
| 482 | TGTGGUTUAGGGAAAATGUTAGTGTTRGGRGTGGGGAAGGTGGGTGURGUTGAGTA AATGGGAUTGUTGTRGTTGGATGGUAUTGRGUAGUTUAGGGGTGGGUTUTGGGAGG RGGAGGRGGAGGAGGURGUTGGAGATGGTGUTGAGGAXGAGGAGGURGGTGGGTT GGTUATGUTUAUTAGGUUAUTGAUUAAGUTGAAGAGGGGUTRGGGUUAUAAGGTG TTGUUAUTGUTGGGTGUAGGUTUUAGGGAAAAGRGGUUAGTATAGGTGATGGGGGG UAGTRGAGTGGTTTGGUTGGGG |
| 483 | GUAGTGGUTGGGUUUUUAUUUUUUAGGAAAUTUAAAAUUUTGGGUUAGURGRGGG TGGRGGGTTGGGGUAGGUAUAAAGAGGGUUTUTGTGRGGURGGUTGGGUTGUUUA UAGGATTUTGGGGGAGGAGGURGGAGURGGTTTUXGTUURGTTUTGUTTUUTGRGG AGGUTGRGGAATGUURGGAGUTUTGGUUUAGUUTGUUURGTUTGGUUUAUURGUA GUUUUTTUUUUATTUUTTTUUAGGGUUTTGGGGTAUAGTUT AGGGUUUTGAGAGUUAUUUTUUA |
| 484 | TGGAGGGTGGUTUTUAGGGUUUTGTTGUAGAGAAGTUTGUAGUTGTAUUUUAAGGU UUTGGAAAAGATGGGGAAGGGGUTGRGGGTGGGUUAGARGGGGUAGGUTGGGUUA GAGUTURGGGUATTURGUAGUUTURGUAGGAAGUAGAAXGGGARGGAAAURGGUT URGGUUTUUTUUUUAGAATUUTGTGGGUAGUUUAGURGGURGUAUAGAGGUUUT UTTTGTGUUTGUUUUAAUURGUUAUURGRGGUTGGUUUAGGGTTTTGAGTTTUUTG GGGGGTGGGGGUUUAGUUAUTGU |
| 485 | AGGUAUURGTUAUAARGUURGGUTAATTTTTTTGTATTTTTTAGTAGAGARGGGGTT TUAURGTGTTAGUUAGGATGGTUTUAGTUTUUTGAUUTTGTGATUUAUUUAUUTUA GUUTUUUAAAGTGUTGGGATTAUAGATGTGAGUTAUXGUAUURGGUUAAGTTUATG ATUTTUTGTAUTUTGAGUUAGTGTTAUTGGUAAAGAATGUUUTGGGUATTGTGGTG TGGATGGAAGUUAGGUAUATTGUATUUATTUUTTUUTAGAUTAAGTTGUUTGGUUT GTGGAUUTTUTUAGUUAG |
| 486 | UTGGUTGAGAAGGTUUAUAGGUUAGGUAAUTTAGTUTAGGAAGGAATGGATGUAA TGTGUUTGGUTTUUATUUAUAUUAUAATGUUUAGGGUATTUTTTGUUAGUAAUAUT GGUTUAGAGTAUAGAAAGATUATGAAUTTGGURGGGTGXGGTAGUTUAUATUTGTA ATUUUAGUAUTTUGGGAGGUTGAGGTGGGTGGATUAUAAGGTUAGGAGAUTGAGA UUATUUTGGUTAAUARGGTGAAAUUURGTUTUTAUTAAAAAATAUAAAAAAATTAG URGGGRGTTGTGARGGGTGUUT |
| 487 | TTURGTGGGGATGUAAUUTRGTTTGUUUUTUTGAUTTUUUUATGAGATUTUTRGUTT UUTUUUAUAUUTUUTTTATUUUUUAAUUUUUTGURGGTUUAUUAGGUTGUAGUT GGGTUTGRGGGTAGGGGAUATTUUTAGGTUTTGAUXGUUAGAGUAUURGGTUUAGT UURGGUUAUAGUUTTGGUUUAAGTGAGGGUTGGUUTGGGGAUAAGURGAAATUA GGGUUUTGGUTGTAUUAGAAAGAGAAUTGAGAUURGUTTGUUTUUUAUTGGGUUA UUUUURGAUUUUAAUUAUATA |
| 488 | ATGTGGUTGGGGTRGGGGGGTGGUUUAGTGGGAGGUAARGGGTUTUAGUTUTUTTT UTGGATAUAGUUAGGGUUUTGATTTRGGUTTGUUUUAGGUUAGUUUTUAUTTGGG UUAAAGGUTGUGGURGGGAUTGGAURGGGTGUTUTGGXGGUUAAGAUUTAGGAAT GTUUUUTAUURGUAGAUURGUAGUTGUAGUUTGGTGGAURGGUAGGGGGTTGGGG GATAAAGGAGGUGUGGGAGGAAGRGAGAGATUTUATGGGGAAGUUAGAGGGGUAA ARGAGGUUGUAUUUUARGGAAT |
| 489 | UUTATAUURGGTUUTRGUUUUTUUAGRGURGGUUTRGUURGRGUTUUTGAGAAAGU UUTGUURGUTURGUTUARGGURGTGUUUTGGUUAAUTTUUTGUTGRGGURGGRGGG UUUTGGGAAGUURGTGUUUUUTTUUUTGUURGGGUUTXGAGGAUTTUUTUTTGGUA |

-continued

| SEQ ID NO: | Sequence |
|---|---|
| | GGRGUTGGGGUUUTUTGAGAGUAGGUAGGUURGGUUTTTGTUTURGRGAGGUUUA<br>UUURGGUURGUAUUTTRGUTTTGRGGTUTGAUUUUARGRGUUUUUUTGUAGGGUTG<br>GGUURGGGTGAGGGGAGUTTU |
| 490 | GAAGUTUUUUTUAUURGGGUUUAGUUUTGUAGGGGGGRGRGTGGGGTUAGAURGU<br>AAAGRGAAGGTGRGGGURGGGGTGGGUUTRGRGGAGAUAAAGGURGGGUUTGUUT<br>GUTUTUAGAGGGUUUUAGRGUUTGUUAAGAGGAAGTUUTXGAGGUURGGGUAGGG<br>AAGGGGGUARGGGUTTUUUAGGGUURGURGGURGUAGUAGGAAGTTGGUUAGGGU<br>ARGGURGTGAGRGGAGRGGGUAGGGUTTTUTUAGGAGRGRGGGRGAGGURGGRGU<br>TGGAGGGGRGAGGAURGGGTATAAG |
| 491 | AGUTUUTTTATUAGAAAGGGUAGURGUAGAGUURGRGTGTGRGRGATGTGGUTGRG<br>GGTGGGGAGRGGGRGGRGGGUURGGGAUAURGRGGUUAUTGTTUTAGUUURGUUT<br>GGGURGUUTGAURGRGGUTURGUTGRGURGUAGUUURGXGUUUUTUTGGUTUUTGT<br>TUURGGGRGRGGGGAGAAGGRGGRGGGGRGRGUUTGGGUURGRGRGGGTGRGAAR<br>GRGAGGTUTTTUUTGGGTGUTUUUAGGTRGGAGGATTUUUAGGGRGGGGGUUATUA<br>GGGTGGRGAGGAAURGGUAGGG |
| 492 | UUUTGURGGTTUUTRGUUAUUUTGATGGUUUURGUUUTGGGAATUUTURGAUUTGG<br>GAGUAUUUAGGAAAGAUUTRGRGTTRGUAUURGRGRGGGUUUAGGRGRGUUURGU<br>RGUUTTUTUUURGRGUURGGGAAUAGGAGUUAGAGGGGXGRGGGGUTGRGGRGUA<br>GRGGAGURGRGGTUAGGRGGUUUAGGRGGGGUTAGAAUAGTGGURGRGGTGTUUR<br>GGGUURGURGUURGUTUUUUAUURGUAGUUAUATRGRGUAUARGRGGGUTUTGRG<br>GUTGUUUTTTUTGATAAAGGAGUT |
| 493 | TGGAAAAGUUAAUTGTGUAAAUATTRGUTTUTAURGUTUAUAAGGTGAAAAGGAAAA<br>ATGUUAAAAAGGAGAGUTTGGAAAUAUAGUAGAAGAGUAATGAUUUUUTGUAGAG<br>AAUATGAAATAAGATURGGUAGTGAUUUUAUTAAAGAUAXGGAAAATAAGGUUA<br>AUUUAGAAUTGGTUAGAGAAUAUUAUTGTGUTTTAGAGTAAUAATTAUAAAGGAA<br>AAGAGGGATRGGGUAUTGTAATATUURGGGAUTGUAGUTTGTAUTUTUTGGGTGGT<br>GUATTUTGTAATTUAATTAAATU |
| 494 | GATTTAATTGAATTAUAGAATGUATTUAUUUAGAGAGTAUAAGUTGUAGTUURGGGA<br>TATTAUAGTGUURGATUUUTUTTTTUUTTTGTAATTGTTAUTUTAAAGUAUAGTGGT<br>GTTUTUTGAUUAGTTUTGGGTTGGAUUTTATTTTUXGTGTUTTTAGTGGGGTTUAUTG<br>URGGATUTTATTTUATGTTUTUTGUAGGGGGTUATTGUTUTTUTGUTGTGTTTUUAA<br>GUTUTUUTTTTTGGUATTTTTUUTUTUTTTTUTTGTGARGGTAGAAGRGAATGTTTGUA<br>UAGTTGGUTTTTUUA |
| 495 | UTGUAGATTGAUAUTGTTAATUAUAAAUAAGUUUAGGGTTGTGTTUAGAGAUAAAG<br>TUAGTGTGAURGGTGAUTGTTAUAGUAATAUAAAATAATGGUAGUAGTUUUAUTAG<br>URGAGGUUAGUATRGAATAGGGUAAGTTAUTUAAAUAXGTUAUUUTAGRGAUUAU<br>TUUAAAUAUUTGTGUTTAAAUTAAUTTAGGGAGUURGGTTTTGUAGGATGTGUAAU<br>UARGTTGTGUUUUUTAGGGUTUAUUAGAUTTTAGTAUUTAATGUAGUTAUUUTUAU<br>RGTGGUUUAGGTTUUUAGGGA |
| 496 | UUUTGGGAAUUTGGGUUARGGTGAGGGTAGUTGUATTAGGTAUTAAAGUTGGTGA<br>GUUUTAGGGGGUAUAARGTGGTTGUAUATUUTGUAAAAURGGGUTUUUTAAGTTAG<br>TTTAAGUAUAGGTGTTTGGAGTGGTRGUTAGGGTGAXGTGTTTGAGTAAUTTGUUUT<br>ATTRGATGUTGGUUTRGGUTAGTGGGAUTGUTGUUATTATTTTGTATTGUTGTAAUA<br>GTUAURGGTUAUAUTGAUTTTGTUTUTGAAUAUAAUUUTGGGUTTGTTTGTGATTAA<br>UAGTGTUAATUTGUAGG |
| 497 | AAAUAUAGUUAGTUTGTTUTAGUUTUTGTUUTUATTTTUUAUAUUUAGGTTTG<br>UUAGTTUUTTGTUUUAUAGTGATGGGUTTGGGAUTATGGGGTGTUUATTURGGGUTT<br>UUUTGGUTTGUTTAUTTTUTUATGGGTGUTTTGAGXGUUTTTTTUGAGURGGUTUAG<br>GUTTTUUUUUUAUAUUUTITUUTUUUTGUTTUTATUAGGUUAAGGGTTTAGATTT<br>TRGGTUAGTGAGTUATUUAAAUUTGGGTGTGGAAAGUAUUTGGGAUAUUAUUTGTA<br>TTTGGUTUUTTTTAGUT |
| 498 | AGUTAAAAGGAGUUAAATAUAAGTGGTGTUUUAGGTGUTTTUUAUAUUUAGGTTTG<br>GATGAUTUAUTGAURGAAGUTUTGAUUUTUAUTGUUAGATAGAAGUAGGGAGGAA<br>AGGGTGTGGGGGGAAAGUUTGAGURGGUTUAAAAAAGGXGUTUAAAGUAUUUATG<br>AGAAAGTAAGUAAGUUAGGGAAGUURGGAATGGAUAUUUUATAGTUUUAAGUUUA<br>TUAUTGTGGGAUAAGGAAUTGGAGUAAAGGGAAGGGGGAAGAAAATGAGGAUAGA<br>GGUTAGAAUAGAUTGGUTGTGTTT |
| 499 | GTUUUUAAAGGUTGAAUUTTTGATUAATGUAGUUUAAGUTGUARGGGUAGAGAAA<br>GGGTGRGGGGTAGGGGURGGGGTTGGGRGUTGAGUTUUTUTGAAURGGTTGUUAGG<br>UAAUAGAATGGAAATTUARGGGRGGUTAAATGGAGUTUXGUUAUAAATGTTUTGTG<br>GUAAAUURGGAUUUAGTUAUATRGUUUTTTUUUUUUUUUTUUUTTTUUUGGGGUT<br>TUTUAUTUGTAAATGAGAAGGGTGUAGAGAAGAUTUTTTTUTTRGGAGTUAGTGUUT<br>URGGTTTGUAUTGUTTTTUA |

-continued

| SEQ ID NO: | Sequence |
|---|---|
| 500 | TGAAAAGUAGTGUAAAURGGAGGUAUTGAUTURGAAGAAAAGAGTUTTUTUTGUA<br>UUUTTUTUATTTAUAGATGAGAAAAUTUAGTGGGGTGGGAGGGGGGAGAAAGGGR<br>GATGTGAUTGGGTURGGGTTTGUUAUAGAAUATTTGTGGXGGAGUTUUATTTAGUR<br>GUURGTGAATTTUUATTUTGTTGUUTGGUAAURGGTTUAGAGGAGUTUAGRGUUUA<br>AUUURGGUUUUTAUUURGUAUUUTTTUUTGUURGTGUAGUTTGGGUUGGUUUUAGG<br>UAAAGGTTUAGUUTTGGGGAU |
| 501 | UTUUAURGURGGUTRGUUUUUTGAGGAGGGGGUTGGGUUAGGGUUTRGGUTGAUR<br>GGGGAGGAAGAAGGGGAGUAGAGAAAAAUATGAGTUAUAGURGTGTGTUAUTGGA<br>GRGUATTTUAATTUUUTGUATUAUAGGAGGTGTGGAAGGUXGUUTRGGGGAURGGG<br>RGRGGGAGGTGRGUURGAGAAGGUUURGGGURGGUUTGUAGGGRGRGURGUTURG<br>UUTGRGUUUTTTUUTUUUTAURGUUUTUUURGUUAUTUTTUUUUTTTGGUTTUUTTU<br>TRGUTRGGTGUAAUAAGTUTTT |
| 502 | AAAGAUTTGTTGUAURGAGRGAGAAGGAAGUUAAAGGGGAAGATGGRGGGGAGGG<br>RGGTGGGGGAGGAAAGGGRGUAGGRGGAGRGGRGRGUUUTGUAGGURGGUURGGG<br>GUUTUTRGGGRGUATUTUURGRGUURGGTUUURGAGGXRGGUUTUUAUAUUTUU<br>TGTGATGUAGGGAATTGAAATGRGUTUUAGTGAUAUARGGUTGTGAUTUATGTTTTT<br>UTUTGUTUUUUTTUTTUUTUUURGGTUAGURGAGGUUUTGGUUUAGUUUUUTUUTU<br>AGGGGGRGAGURGGRGGTGGAG |
| 503 | UUTGAAGAGUATTUTUUUTGAGTGUTUAATGATATGUUAGAGUATGUTUAAATGR<br>GGAGGATGGGGAGGURGGUTUUUTGGUAGATUTTUATGGAGAAGUTGAUTUUAGU<br>RGGUTTGTGTGUURGTUUUAGAGGAGRGGAAAUAGAGUXGAAGUUUAUAUUUUUA<br>GGGUUUAGGUUUAGUUUTTUUAAGTURGGAGUTUAUUUAGUUTGUUUUTRGGUTU<br>UTTUATUUTUUTUUAGAUAURGTUUUTTUTTUTGTUTUTGUATTTUUUATUUTUTUR<br>GUUUUTUUUTGTGUTGUTUTGT |
| 504 | AUAGAGUAGUAUAGGGAGGGGRGGAGAGGATGGGAAATGUAGAGAUAGAAGAAG<br>GGARGGTGTUTGGAGGAGGATGAAGGAGURGAGGGGUAGGUTGGGTGAGUTURGG<br>AUTTGGAAGGGUTGGGUUTGGGUUUTGGGGGTGTGGGUTTXGGUTUTGTTTURGUT<br>UUTUTGGGARGGGUAUAUAAGURGGUTGGAGTUAGUTTUTUUATGAAGATUTGUUA<br>GGGAGURGGUUTUUUUATUUTURGUATTTGAGAUATGUTUTGGUATATUATTGAGU<br>AUTUAGGGAGAATGUTUTTUAGG |
| 505 | ATGTUTGGGAGGUUAAAAGUAUTUTUTUAGAUAGTUTUTAUAGGAUTUTTUUAGGTU<br>URGGAAGUURGAGRGAGUTTUUTGGAGGAGGTGGUTGGGGAGAGTGGAGGAGURG<br>GTAGGGGTRGUTGTGUTTGRGRGRGUURGTUUAGGAAUTXGURGGGGGUTGTGGGGA<br>GGGGGRGURGGUUTGGAGAGGAUAATGTAUAGTUTGTTUTAAUAUUUAUUUAUTU<br>UAAARGUAUAUTTUUUAUUURGTUTUTTGTUUUTUUUAGUUURGGGGUTAGAUUUT<br>GAGGGUTRGGGURGUAUUTUAU |
| 506 | GTGAGGTGRGGUURGAGUUUTUAGGGTUTAGUUURGGGGUTGGGAGGGAUAAGAG<br>ARGGGGTGGGAAGTGTGRGTTTGGAGTGGGTGGGTGTTAGAAUAGAUTGUAUATTG<br>TUUTUTUUAGGURGGRGUUUUUTUUUUAUAGUUURGGXGAGTTUUTGGARGGGRG<br>RGRGUAAGUAUAGRGAUUUUTAURGGUTUUTUUAUTUTUUUUAGUUAUUTUUTUU<br>AGGAAGUTRGUTRGGGUTTURGGGAUUTGGAAGAGTUUTGUAGAGAUTGUTGAGA<br>GATGUTTTTGGUUTUUUAGAUAT |
| 507 | GGAGRGUTAARGRGUAGTGGGAGGGAAGGAGAGGAUTGAAGAGAGARGGGGGAGG<br>GGAGAGGAGGGGTRGGUTGUUAGGUUTAGGTGGGGTGAAURGUAGUTGGGUTGA<br>UTUAAGRGGAGGAGURGGAAGGAUAUUURGRGAGGUTTXGGGGRGRGUTTTTAGG<br>GAGGRGURGUUTUUAGUTTTGTGUUAGAAAGTGGGGGTTGRGGUTUAGGUTTGAAT<br>UUAAGAAAGGUTURGGGTGGAAUTUUTGGGUAUUTGGGTUUTTAUTTTGUUTTUA<br>GGRGUTGGUUAURGTTGGGAUTT |
| 508 | AGTUUUAARGGTGGUUAGRGUUTGAAGGUAGAGTAAGGAUUUAGGGTGUUUAGGA<br>GTTUUAUURGGAGUUTTTUTTGGATTUAAGUUTGAGURGUAAUUUUUAUUGGTT<br>UAUAAAGUTGGAGGRGGRGUUTUUUTAAAAGRGRGUUUXGAAGUUTRGRGGGGTG<br>TUUTTURGGUTUUTURGUTTGAGTUAGUUUAGUTGRGGATTUAUUUUAUUTAGGUU<br>TGGUAGURGAUUUUTUUTUTUUUUTUUUURGTUTUTUTTUAGTUUTUTUUTT<br>UUUAUTGRGRGTTAGRGUTUUU |
| 509 | TATUAGAAUTUUAUATAUUUAGGTGGGTTTAGGAUUTUTAGGUUTUTUUUTUAGGU<br>UATAGGAGUAUUUAUUURGGGUTLTUTUTGGAGGGGUAGUUUUAAGGAAUUTGTTG<br>GGGTAAUTTGTTTGUTUUUUAUAUUURGGGAATGTGUXGTUUTTTUAGGUURGUUU<br>AUURGGATTUUTGTGUAGGGAGTUAGURGAUAUAGUATGTTGUATGTGUUUTGTGG<br>GGAUARGTTUTGUUTUUTGTUAGGGGGAGGAGGUTGGRGGURGTGUUTGTGUTGUR<br>GUAUUTUAGUTUUUUAURGAA |
| 510 | TRGGTGGGGAGUTGAGGTGRGGUAGUAUAGGUARGGURGUUAGUUTUUTUUUUUT<br>GAUAGGAGGUAGAARGTGTUUUUAUAGGGUAUATGUAAUATGUTGTGTRGGUTGA<br>UTUUUTGUAUAGGAAUTURGGGTGGGRGGGUUTGAAAGGAXGGUAUATTUURGGGG<br>TGTGGGGAGUAAAUAAGTTAUUUUAAUAGGTTUUTTGGGGUTGUUUUTUUAGAGG |

-continued

| SEQ ID NO: | Sequence |
|---|---|
| | AGUURGGGGTGGGTGUTUUTATGGUUTGAGGGAGAGGUUTAGAAAGTUUTAAAUU<br>UAUUTGGGTATGTGGATTUTGATAU |
| 511 | AGAGGATTTAAGAUTUAUUUAGGGUAAAUAUTGGGAUUAUTGTAAGAGRGUTGGA<br>AUATTUTGUUTUTTGAGTGAAGGGGUUTTUTTTUTAGUUTUTATGGUAUTGAGGGGT<br>GRGURGGUTGGTGGAGGAGUAGTURGATGGAGUUUTGXGTTUUURGGGGAUAUAG<br>GGUUAAGUTTTGAGGTGGAAAGTTTUTGGTTUTGAAAUAAUAAGGAGAGAGTUTGT<br>TTTTUTTUUTAAAATTTGGAUTUTTGTUTGUAUAAAUTUTGGTUTGTTTTGUARGGTT<br>TGTGTGUUTTTTTTTUUUT |
| 512 | GGGAAAAAAAGGUAUAUAAAURGTGUAAAAUAGAUUAGAGTTTGTGUAGAUAAGA<br>GTUUAAATTTTAGGAAGAAAAAUAGAUTUTUTUUTTGTTGTTTUAGAAUUAGAAAU<br>TTTUUAUUTUAAAGUTTGGUUUTGTGTUUURGGGGAAXGUAGGGUTUUATRGGAUT<br>GUTUUTUUAUUAGURGGRGUAUUUUTUAGTGUUATAGAGGUTAGAAAGAAGGUUU<br>UTTUAUTUAAGAGGUAGAATGTTUUAGRGUTUTTAUAGTGGTUUUAGTGTTTGUUU<br>TGGGTGAGTUTTAAAUTUUTUTT |
| 513 | TGUUTUTGAGTUTAAAARGGUAGTGGUUTAGGAGUAUAGGGUUTGGGGUUAUGGU<br>UAGTGUUAUAUUTAAUTGAGATATGTUUAGAGUTGAGGTUTAGUTUAUAGUAUUT<br>GTGRGTRGGGGAAGUTGGUTGRGGTUARGGURGGTGUAGXGGUUUAAGGAGTUUA<br>UAAAGUAGTAAUUTTGGUUUAUAUUAUAGUTURGGTGUATTTGGAGAGGGGGUUU<br>AGTUTAGGUTGAAGTTGGGGGGAGUUTGGUUAGGGUUTGGGUAUUAGGRGUAGGA<br>UAGAGGGAAAGGUUTUUAGUTUUT |
| 514 | AGGAGUTGGAGGUUTTTUUUTUTGTUUTGRGUUTGGTGUUUAGGUUUTGGUUAGGU<br>TUUUUUUAAUTTUAGUUTAGAUTGGGUUUUUTUTUUAAATGUAURGGAGUTGTGGT<br>GTGGGUUAAGGTTAUTGUTTTGTGGAUTUUTTGGGUXGUTGUAURGGURGTGAURG<br>UAGUUAGUTUUURGARGUAUAGATGUTGTGAGUTAGAUUTUAGUTUTGGAUATAT<br>UTUAGGTTAGGTGTGGUAUTGUUUUTGUUUUUAGGUUUTGTGUTUUTAGGUUAUTG<br>URGTTTTAGAUTUAGAGGUA |
| 515 | GUAGUUUTGGGGRGTGGGGGGRGGUTGTTTUUTGUTGUUUUTTGGGUTGUUAUUTG<br>UURGAGUTGUUAGUUAUAGTTGGAUTTUUTTUUAGUUUTURGGGGTGUUTGUATTU<br>UUAUATTRGAGAUAGGUAGTGAGAGGGAGTGAGGGGXGATGATGUTGUAGUUUA<br>UAAGAGUUTURGGGUAGTAGUUAGGUUUUTUUGUTUAGUUTGAUUTGUUTGGUUT<br>UUAGUAGGGTGUTATGGUUUTGGGAGGUUUTGGUUTUTCGGGAATTTGUUTUUU<br>UUUTGRGUTUTGUTUTGUTGTG |
| 516 | AUAGUAGAGUAGAGRGUAGGGUAGGGGAGGAAAGGGGGUAGAAGUUAGGGUUTU<br>UUAGGGUUATAGUAUUUTGUTGGAGGUUAGGUAGGTUAGGUTGAGUAGAGGGGUU<br>TGGUTAUTGUURGGAGGUTUTGTGGGUTGUAGAUATUATXGUUUUTUAUTUUUTU<br>TUAUTGUUTGTUTRGAATGTGGGAATGUAGGUAUUURGGAGGGUTGGAAGGAAGTU<br>UAAUTGTGGUTGGUAGUTRGGGUAGGTGGUAGUUUAAGGGGUAGUAGGAAAUAGU<br>RGUUUUUUARGUUUUAGGGUTGUU |
| 517 | TUTUTUUTGGGUUAAGUTTTGTGGATGUUUAGUUTGGGGURGRGGGGAGUTGGUAG<br>GTUAGTGGUAGAUAUTGGTGGGUAGAUUTAGTGTUTGGTAGAAUAGGUAUAAGG<br>AAGTGGTGAURGGAGGGAAGUUAAGTGUAUTUAAAUUUTXGGGTGAGUUAUAUR<br>GURGGGTUTTTUAUAGUTGUTGAAAGTGAGUAAUAGTGATGAAGGTTTGTGAGTTT<br>UTGRGTGAGRGAGTGAATGGAUUAGTAGUAGTTTUUAGGTTGTGGAAGAGRGTTUU<br>UTUUURGGGATGGGGAUAUTTG |
| 518 | UAAGTGTUUUUATUURGGGGAGGGAARGUTUTTUUAUAAUUTGGAAAUTGUAUTG<br>GTUUATTUAUTRGUTUARGUAGAAATTTUAUAAAUUTTUATUAUTGTTGUTUAUTTT<br>UAGUAGUTGTGAAAGAUURGGRGGTGATGAUTUAUUXGAGGGTTTGAGTGUAUTTG<br>GUTTUUUTURGGTUAUUAUTTUUTTGATGUUTGTTUTAUUAGAUAUTAGGTUTGUU<br>UAUUAGTGTUTGUUAUTGAUUTGUUAGUTUUURGRGGUUUUAGGUTGGGUAUUA<br>UAAAGUTTGGUUUAGGAGAGA |
| 519 | GGUTGGTUTTGAAUTUUTGGGUTUAAGAGUTUUAUUTGUUTUAGUUTUUUAAAGTG<br>AGUUAUUAGGUUTAUURGGTUUTTTUUTUUATGUTTUTGTGGUUTTTUUTUUTGTT<br>TAGXGAGUTUTGAUATTUAUTUATAGGTAGGAAUAAAGUUUTUUATTGGTTAGTUT<br>GGGUTGAGGTGGGXGTGTGTGTTTUTGTATUAGTGATUTGTTTTURGGUAGGUUTUT<br>UUUTGAGGGGAGAGUTGGTAGUTTUUATGTAAGTGGUAGGGUATAUTTUAUTAAAT<br>AAAAGATGTGTGGGTGAG |
| 520 | UTUAUUUAUAUATUTTTTATTTAGTGAAGTATGUUUTGUUAUTTAUATGGAAGUTA<br>UUAGUTUTUUUUTUAGGGAGAGGUUTGURGGAAAAUAGATUAUTGATAUAGAAAU<br>AUAUAXGUUUAUUTUAGUUUAGAUTAAUUAATGGAGGGTTTTTGTTUUTAUUTATGA<br>GTGAATGUTAGAGUTXGUTAAAUAGGAGGAAAGGUUAUAGAAGUATGGAGGAAAA<br>GGAURGGGTAGGUUTGGTGGUTUATTTTGGGAGGUTGAGGUAGGTGGAGUTUTTGA<br>GUUUAGGAGTTUAAGAUUAGUU |
| 521 | UAAGUATUTTAGTGATGTGAGUAUTAUAAAAUTTUUTUUTGGGUTGUTTTGAGUUU<br>UAUUTUUTUUTUUTGUAGUAUGTTTTUTTAGUUTUAGGGUUUTGGGGRGGAR |

-continued

| SEQ ID NO: | Sequence |
|---|---|
| | GGAUAUTUUUUUAGUAGUUTGUTTUUAGAGGUUAUTGXGUTGUTUAGUTURGGG GGUURGTUUTURGTGGATUUUTUUAGGUUUAGUAGAGTGTTTGAUUARGGGUUTGA URGGGAGGGGAGARGUUAUUTUUTGGGGAUTTGUAUUUUAAUUAGUAUUAUTGTU ATGAGAUAUURGGAGGUUAGUA |
| 522 | TGUTGGUUTURGGGTGTUTUATGAUAGTGGTGUTGGTTGGGGTGUAAGTUUUUAGG AGGTGGRGTUTUUUUTUURGGTUAGGUURGTGGTUAAAUAUTUTGUTGGGUUTGGA GGGATUUARGGAGGARGGGUUUURGGAGUTGAGUAGXGUAGTGGUUTUTGGAAAG UAGGUTGUTGGGGGAGTGTURGGGRGTURGUUUUAGGGUUUTGAGGUTAAGAGUA TGAUTGUAGGAGGAGGAAGGTGGGGUTUAAAGUAGAUUUAGGAGGAAGTTTTGAT GAUTUAUATUAUTAAGATGUTTG |
| 523 | TGATGAUUAGGUAUTGUTATTUTTTAGGURGGGATTTUUUUAAGUUTGGTATTTTT AAAAATARGTTATAGTTUUUTTGAAAUTUTUTUUTTATUAUUTUUAUUTTGTTT TUATUTUUUAUTUUTTGGUAUUUTUTGTUTUUUUAXGGTGTUUUUATGARGUTGUU TGUATGUUUATTGGUUUUAGUUTGGGAGUTTUTUAGAGARGUURGGGUUAGAUAT GGUTGUAGATAGAGUUAAGAGGGTGGUUTRGGGTGGUTGGTGGUAGTUTUUTGGUT GTGGGGGUAGAAGTGGGGG |
| 524 | UUUUUAUTTUTGUUUUUAUAGUUAGGAGAUTGUUAUUAGUUAUURGAGGUUAUUU TUTTGGUTUTATUTGUAGUUATGUTGGUURGGGRGTUTUTGAGAAGUTUUUAGGU TGGGGUUAATGGGUATGUAGGUAGRGTUATGGGGAUAUXGTGGGGAGAUAGAGGG TGUUAAGGAGTGGGAGATGAAAAUAGGAAGGTGGAGGTGATAAGGAGAGAGTTTU AAGGGAAUTATAARGTATTTTTAAAAATAUUAAGGUTTGGGGAAATUURGGUUTAA AGAATAGUAGTGUUTGGTUATUA |
| 525 | GUUTAGUUURGRGRGUAUATAUARGTGTGUTUTURGRGRGGAUUTRGGGAAUTTTG UUUTUARGUURGRGGRGRGUTTGUUTUURGUURGUUURGGUUTUUAUUUUTGGT ATGUUUUTTUUUUAGURGGTUTUUUUTUUUUURGGUTXGGGAAGAAGUUTGUTGG GUUAGGGRGUUUTGAUUAUUTUUTRGGAGGURGGUAAAUUTGUUTGAAURGUUUU AGAGGAATRGGGUAGGGGUTRGUAUUUUAUUURGGUAGGAGGGUUURGAGAURGA UURGGGURGGGGUTURGUAGURG |
| 526 | RGGUTGRGGAGUUURGGUURGGGTRGGTUTRGGGGUUUTUUTGURGGGGTGGGGTG RGAGUUUUTGUURGAUTUUTUTGGGGRGGTTUAGGUAGGTTTGURGGUUTURGAGG AGGTGGTUAGGGRGUUUTGGUUUAGUAGGUTTUTTUUXGAGURGGGGGGAGGGGA GAURGGUTGGGGAAGGGGUAUTUTRGAAGGGGTGGAGGURGGGGRGGGRGGGAGGU AAGRGRGURGRGGGRGTGAGGGUAAAGTTUURGAGGTURGRGRGGAGAGUAUARG TGTATGTGRGRGRGGGGUTAGGU |
| 527 | GAAARGGRGGTRGUAGUUUTRGGURGGGUARGRGTGGGGURGTTRGTGGAGRGGTG TUTTGUTAGGURGGTTGGGGTAUTTGRGGGGURGGATGGGUTTGAGGGTGAGXGGR GGUTGGGGUAGGUTGUUAAAGUURGGGTGGATUTGUTTGTUTTTGAATGUUTTGAT GGTUTUUAGAGGGGTAATAGGGGGXGGGTTGAUURGGATGGGGTUUATGUUUTGG AAGGGUTTGTGUTURGGAATGGAGUUUATGTRGTTGGGGTGGTGGTAGAGGTTGTA GTUAGGAATUATGGGGAAGAG |
| 528 | UTUTTUUUUATGATTUUTGAUTAUAAUUTUTAUUAUUAUUUUAARGAUATGGGUTU UATTURGGAGUAUAAGUUUTTUUAGGGUATGGAUUUUATURGGGTUAAUUXGUUU UUTATTAUUUUTUTGGAGAUUATUAAGGUATTUAAAGAUAAGUAGATUUAUURGG GUTTTGGUAGUUTGUUUUAGURGURXGUTUAUUUTUAAGUUUATURGGUUURGUA AGTAUUUUAAURGGUUTAGUAAGAUAURGUTUUARGAARGGUUUUARGRGTGUUR GGURGAGGGUTGRGAURGURGTTTU |
| 529 | TGUTUAGGUTGGAGTGUAGTGGUAAAAUTUTTGGUTUAUTTUAAUUTURGUUTUURG GGTTUAAGUAATTUTUUTGUUTUAGUUTUTUAAGTAGUTGGGATTAUAGGUATGUA UUATUAUAUUUAGUTGATTTTGTATTTTTAGTAGAGAXGGGGTTTUAUUARGTTGTT UAAGUTGGTUTUAAAUTUUUTGAUUTUAGGTGATUUAUURGUUTTGGUUTUUUAAAG TGURGGGATTATAGGTGTGAGUUAURGUAUUTGGGUAATTAGTATTGTATTTAAGA GTTTATATTUATATUUATA |
| 530 | TATGGATATGAATATAAAUTUTTAAATAUAATAUTAATTGUUUAGGTGRGGTGGUTU AUAUUTATAATUURGGUAUTTTGGGAGGUUAAGGRGGGTGGATUAUUTGAGGUTAG GAGTTTGAGAUUAGUTTGAAUAARGTGGTGAAAUUUXGTUTUTAUTAAAAATAUAA AATUAGUTGGGTGTGATGGTGUATGUUTGTAATUUUAGUTAUTTGAGAGGUTGAGG UAGGAGAATTGUTTGAAUURGGGAGGRGGAGGTTGAAGTGAGUUAAGATTTTGUUA UTGUAUTUUAGUUTGGGUA |
| 531 | TGTTAUTTUATTGAATTUTUATAATAGUTTAATGUTATRGGTTTTUTTUTTAATTTTG GGGGUATAGTGGGGAGATAAGUAAAUTGATAUUURGGAGGTTGAGTGAUTUATTUA TGGAATGUAGUAGGUURGTGAGTUAAAGXGAGTAUATGGUAAGAUXGAGTGAAGU TGGGGAAUAATAGUUAAGUUAAGAGRGTTTTAAAGATAUTTAGUATUTTUATUAUA UTGAATUTTTAAGGTGAUAGUAUTTUUAUTRGAUAGUAAAATGUAGATTUAAUTGT TTUTTTURGGTUTTUAAAU |

-continued

| SEQ ID NO: | Sequence |
|---|---|
| 532 | GTTTGAAGAURGGAAAGAAAUAGTTGAATUTGAUATTTTGUTGTRGAGTGGAAGTG UTGTUAUUTTAGGATTUAGTGTGATGAAGATGUTAAGTATUTTTAAAARGUTUTTGG UTTGGUTATTGTTUUUUAGUTTUAUTXGGTUTTGUUATGTAUTXGUTTTGAUTUARG GGUUTGUTGUATTUUATGAATGAGTUAUTUAAUUTURGGGGTATUAGTTTGUTTATU TUUUUAUTATGUUUUUAAAATTAAGAAGAAAAURGATAGUATTAAGUTATTATGAG AATTUAATGAAGTAAUA |
| 533 | TTAGTATTAUUAAATATRGAGTUAAGGGUUTGATUAGUUUUAAAAGAATGAGGUAU TTTTAATGTGAUAUUATTUUTGGUAGTUTUAGGTTRGGUTUUUUUAGGUUURGGAT GUAGATGGUTGTTAGGGGUTGGUUATUUTUATUTUAAXGGTUUTGGAAGGUAUUAU TTTUAGGGUATATGUUATGAUTAAUATTURGGTGAGUAATGUTGAUTUAATRGTAG AUTGTTATTTUATGTTUUUAGTAUUUTGTGUAGGAAGGGAAGGGAAATGAGTAATA GATGTATUAGTUUUATTUAA |
| 534 | TTGAATGGGAUTGATAUATUTATTAUTUATTTUUUTTUUUTTUUTGUAUAGGGTAUT GGGAAUATGAAATAAUAGTUTARGATTGAGTUAGUATTGUTUAURGGAATGTTAGT UATGGUATATGUUUTGAAAGTGGTGUUTTUUAGGAUXGTTGAGATGAGGATGGUUA GUUUUTAAUAGUUATUTGUATURGGGGUUTGGGAGAGURGAAUUTGAGAUTGUUA GGAATGGTGTUAUATTAAAAGTGUUTUATTUTTTTGGGGUTGATUAGGUUUTTGAUT RGATATTTGGTAATAUTAA |
| 535 | AGTGGTGGUTGUTGTTTUTRGGTGGUAGAGATGATGUUTGGTTTATTUTTAGTAAAG TGUTTAGGARGUTGAGUUTGAGGGGUTUTGGAATGGAAAAAUAAAAUAAAAUAAA AUAAAURGGAGGUURGUTUTGUUTGGUTUUTAGAGAUAXGUAAAGUTGGGUAAAG GAAGGAGATTGAGGTGGGAUTGAGAUATTGTTGUATTGTGAATGUUURGGTTUUUU AUUTUUTGUUUUURGAATUATGATTGTTTTATGRGGTTATTTTTUUUTTTGGTGAGG AAAATGGGATGTGGTGTUAA |
| 536 | TTGAUAUUAUATUUUATTTTUUTUAUUAAAGGGAAAAATAAURGUATAAAAUAATU ATGATTRGGGGGGUAGGAGGTGGGGAAURGGGGUATTUAUAATGUAAUAATGUTU AGTUUUAUUTUAATTTTUUTTUUTTGUUUAGUTTTGXGTGTTUUUTAGGAGUUAG AGAGRGGGUUTURGGTTTGTTTTGTTTTGTTTTGTTTTTUGATTGGTTGGAAGGTT GUTUAGRGTUUTAAGUAUTTTAUTAAGAATAAAUUAGGUATUATUTUTGUUAURGA GAAAUAGUAGUUAUUAUT |
| 537 | GGGGTRGGUATGGGUTGGAGUTUAGAGARGGUUAGUTAGGAUTTUAGGAUAUAUA GUAAAUTAGUTGRGUUURGUTGAGGGTUAGRGUAUAGURGUUUAUAUAAGGTGTU UTUTUUURGGGUTUTUTGGGURGURGGUUTUUTGUTTUUXGTGURGUAGAURGGGA TTAGAUTGTGGARGRGGGGAAGGAAGGGGGRGTTGRGARGGGAUTTGAGGGGAGU AGGAUTTGUUUUTGUUUUTGRGGRGAAGUTUTAGGUUUTGGUAAGGTTRGGUAUAU RGGGGGURGUTUUTUUUUAGGG |
| 538 | UUUTGGGGAGGAGRGGUUUURGGTGTAURGAAUUTTGUUAGGGUUTAGAGUTTRG URGUAGGGGUAGGGGUAAGUUTGUTUUUUTUAAGAUUURGTRGUAARGUUUUUT TUUTTUUURGRGTUUAUAGUTUAAUUURGGUTGRGGUAXGGGAAGUAGGAGGURG GRGGUUUAGAGAGUURGGGGAGAGGAUAUUTGTGTGGGRGGUTGTGRGUTGAUU UTUAGRGGGGRGUAGUTAGTTTGUTGTGTGUUTGAAGUUUAGUTGGURGTUTUTG AGUTUUAGUUUATGURGAUUUU |
| 539 | GTGUARGUAGGGAAATAUUTUAUAGGGTAAATTTGGATURGATTGAGAAUAGGAAG UUAUAGGUUAATAUAAGGAGGUTUTGTGAGAAUAGATGAUAAAUUAUAAGURGGG GAGGGGGAGGAAAGAGUTTTUTGGGUUTGGGGGATGGGXGAGUURGUUAGUAUAU UAUAUAUAGUTGRGUUTGGUUUAGUAAUUAAAAUUAUUAUUAUAGAUUTGARGGT TTGGUTGUAGUTGTAAAGAGATAAGUATGTTGGAAGAGAAAAUAGGGUUURGGTG AUURGGUUTTAGGGTUTGAGRGU |
| 540 | RGUTUAGAUUUTAAGGURGGGTUAURGGGGUUUTGTTTTUTUTTUUAAUATGUTTA TUTUTTTAUAGUTGUAGUUAAAURGUUAGGUTUTGUAAUGAUGGUUUUGAUUAUUGAG GUUAAGRGUAGUTGTGTGTGGTGTGUTGGRGGGUTXGUUUATUUUUUAGGUUUAG AAAGUTUTTTUUTUUUUUTUUURGGUTTGTGGTTTGTUAUUTGUUUUUAUAGAGUUT UUTTGUATTGGUUTGTGGUTTUUTGTTUUUAATRGGAUUUAAAUUUAUUUTGTGAGG TATTTUUUTGRGTGUAUA |
| 541 | TGTGRGGGUAGTGGGTTGTGRGGGUAGTGGGTTGTGUATURGGATGTGTAGUAUTU AUAUAUTTRGGGTGAUTUTTUUTGGGTAAGUTGTGGATGTGAGTGGGGGUAGUATU TGURGTGAUTUATTUTUTUUTUTTTUUATTUUAAGUXGGGTGGGGGAGTTTGGGATT TUUAGAUAAGGUUTGGUTUUUUUTGGUAUAGAGGGTGGGAGTGGGGATGGGGAGG GAGGAGGGAAGGGTUATGGGAAGGTGGGGUUATGTTTTGTGUTUAATGAAUTGAGA AGGGGGAGGGTTUUAGUTGG |
| 542 | UAGUTGGAAUUUTUUUUUTTUTUAGTTUATTGAGUAUAAAAUATGGUUUUAUUTTU UUATGAUUUTTUUUUUTUUUTUUUUAUUUUAUUUUAUUUTUTGTGUUAGGGGG AGUUAGGUUTTGUTUTGGAAAUUUUAAAUTUUUUUAUUXGGUUTTGGAAUGGAAAGA |

-continued

| SEQ ID NO: | Sequence |
|---|---|
| | GGAGAGAATGAGTUARGGUAGATGUTGUUUUUAUTUAUATUUAUAGUTTAUUUAG GAAGAGTUAUURGAAGTGTGTGAGTGUTAUAUATURGGATGUAUAAUUUAUTGUU RGUAUAAUUUAUTGUURGUAUAA |
| 543 | GUAAUTGGRGUTGGGTAGGUAAAGURGGGAGAAAUTGUTGAGARGAGGTTAGGAT TTAAUUTTTAAATTUTGGAGUUATRGGAAAURGAGGGGAGGARGARGGGTGTRGGT GUTAATGAGGUTGGGGGRGGGRGATGRGRGGTGGGUUTUXGAGTURGGGGUAGGT UTRGGGGGTTUUURGGGGAAGGUUUTGGGAGUUUTTGGUUUTGGRGGUUTURGUU ATUAGAUTGGGAATGTUTUTGATTGGGTGGUUAGGAGGRGGTGGUUUTUUTUUURG UUUAGUTGAGGGGTGTRGTUTTU |
| 544 | GAAGARGAUAUUUUTUAGUTGGGRGGGGAGGAGGGUUAURGUUTUUTGGUUAUUU AATUAGAGAUATTUUUAGTUTGATGGRGGAGGURGUUAGGGUUAAGGGUTUUUAG GGUUTTUUURGGGGAAUUUURGAGAUUTGUUURGGAUTXGGAGGUUUAURGRGUA TRGUURGUUUUUAGUUTUATTAGUAURGAUAUURGTRGTUUTUUUUTRGGTTTURG ATGGUTUUAGAATTTAAAGGTTAAATUUTAAUUTRGTUTUAGUAGTTTUTUURGGUT TTGUUTAUUUAGRGUUAGTTGU |
| 545 | GGGUAUUUTUTGGTGUTTUUAGGUUTGTGAATTGGUAUAGUAGGAUUAUAGAUUT UUAAGGTGUUUAUUTGGGGGUTUAGAAUUUTGGRGGGGAAGGTUAGTGUTATUUU AURGGAGAAGAGAUUTAGTUTAGUTGAGUUUUTGGUUAGXGGUAAGGAGGAAAGG ATGAAUATUAGUUARGUUTGGUAUTGAUTGUUAUAGUUAGAGUUTRGUUUAGUUU AAGAATGTTTUTGTTUTAAGAUTTTTTTUTTTTTTTGTATTTTAGAGAAGTTUUU AAATGTUAUUTTGAAGAUURGG |
| 546 | URGGGTUTTUAAGGTGAUATTTGUUTGTGATAATTTUTAAAATAUAAAAAAGAAAA AAGTUTTAGAAUAGAAAUATTUTTGGGUTGGGRGAGGUTUTGGUTGTGGUAGTUAG TGUUAGGRGTGGUTGATGTTUATUUUTTUUTTTTTTGUXGUTGGUUAGGGGUTUAGU TAGAUTAGGTUTUTTUTURGGTGGGATAGUAUTGAUUTTUUURGUUAGGGTTUTGA GUUUUUAGGTGGGUAUUTTGGAGGTUTGTGGTUUTGUTGTGUUAATTUAUAGGUUT GGAAGUAUUAGAGGGTGUUU |
| 547 | UTUATGGAGAGGAGUAGAGATGUAGGAAARGUAAUAGUAGUARGGUAGAAARGUA GGAGAAAUAGUUURGUUTUAGAGURGUUUAUUTUUTUURGUUATGUUAGGAAGGG UUAGTGTUUUTUUAGARGURGGTGAUTGTUARGTUAGAUAXGTGARGTGTGGUTGT GUUUAGATTUTTGGRGGTGAGUUURGGRGAGGGAUUUAGRGGTUTUURGGRGTUTG GTTTAGGGGGGGATUTURGUAAGAUUURGUURGUARGTGGUTUUTGTGAGGGGUAU TGRGRGRGAAGGUTGTGGTUTG |
| 548 | UAGAUUAUAGUUTTRGRGRGUAGTGUUUUTUAUAGGAGUUARGTGRGGGRGGGGT UTTGRGGAGATUUUUUUUTAAAUUAGARGURGGGAGAURGUTGGGTUUUTRGURG GGGUTUAURGUUAAGAATUTGGGUAUAGUUAUARGTUAXGTGTUTGARGTGAUAG TUAURGGRGTUTGGAGGGAUAUTGGUUUTTUUTGGUATGGRGGGAGGAGGTGGGRG GUTUTGAGGRGGGGUTGTTTUTUUTGRGTTTUTGURGTGUTGUTGTTGRGTTTU UATUTUTGUTUUTUTUUATGAG |
| 549 | UTUTUUAUTGTGUAGGUUAUUTGTAGGGAUAGTGUUAGTGGGTGTAGGAGAGGTGG RGAGGUTGUAGUAGTGRGGGATGGGUTUUUUAUAUUUUUAAATAUTUUAUATGGG GTURGGGGUUTTUUUAGGAUUTGGGUUAGGTGXGUAXGUUTGGGXGGGGUUAGUU AGUTRGTGUTGAGTUAURGGGTGURGTUAGTGAGGGUUTGGUUUUAUUUTRGGGAA UUAURGGTGUTGGTTTTUUUARGGUTGUTGUURGUTGTGGGUUTTGUTGTUAUUUA UAAGGUUUTGGGAGGUUUTGUU |
| 550 | GGUAGGGUUTUUUAGGGUUTTGTGGGTGAUAGUAAGGUUUAUAGRGGGUAGUA GURGTGGGAAAAUUAGUAURGGTGGTTUURGAGGGTGGGGUUAGGUUUTUAUTG ARGGUAUURGGTGAUTUAGUARGAGUTGGUTGGUUUXGUUUAGGXGTGXGUAU UTGGUUUAGGTUUTGGGAAGGUUURGGAUUUUATGTGGAGTATTTGGGGGTGTG GGGAGUUUATUURGUAUTGUTGUAGUUTRGUUAUUTUTUUTAUAUUUAUTGGUA UTGUUUTAUAGGTGGUUTGUAUAGTGGAGAG |

Also provided herein is a deoxyribonucleic acid identical to 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, or 190-200 of contiguous nucleotide sequence of the sequence including a sequence of SEQ ID NO: 1 to SEQ ID NO: 550.

In embodiments, provided herein is a deoxyribonucleic acid which includes a methylation site set forth in Table 1.

In embodiments, included herein is a deoxyribonucleic acid in which a plurality of methylation sites set forth in Table 1 are methylated or unmethylated. In embodiments, the plurality of methylation sites comprises at least about 1, 2, 3, 4, 5, 6, 7, 8, 9, 10, 15, 20, 25, 50, 75, 100, 150, 200, 250, 300, 350, 400, 450, 500, or 550 methylation sites. In embodiments, the plurality of methylation sites comprises between 1-50, 50-100, 100-250, 100-300, 100-400, 100-500, 100-550, 250-550, or 350-500 methylation sites.

Compositions for Detecting Methylation

Also provided herein are probes and primers that are complementary to one or more of SEQ ID NOS: 1-550. In embodiments, pairs of primers complementary to nucleotide sequences on either side of a methylation site of interest listed in Table 1 are provided. In embodiments, a plurality of probes and/or primers are provided to detect and/or amplify a polynucleotide (e.g., a polynucleotide obtained by bisulfite treatment of DNA) comprising a methylation site of interest. In embodiments, a probe or primer is complementary to a polynucleotide sequence that encompasses the methylation site of interest. In embodiments, the probe or primer is complementary to a sequence that is proximal to the methylation site of interest (e.g., within 1000, 900, 800, 700, 600, 500, 400, 300, 200, 100, 75, 50, or 25 nucleotides of the methylation site of interest in a genomic or bisulfite-treatment-derived polynucleotide).

In embodiments, a deoxyribonucleic acid selected from SEQ ID NO:551 to SEQ ID NO: 782 is included. In embodiments, the deoxyribonucleic acid selected from SEQ ID NO:551 to SEQ ID NO: 782 is hybridized to a complementary DNA sequence having uridine or cytosine. In embodiments, each of the nucleic acids is different. In embodiments, each of the nucleic acids does not simultaneously have the same sequence selected from SEQ ID NO:551 to SEQ ID NO:782.

In embodiments, aspects include a deoxyribonucleic acid selected from SEQ ID NO:551 to SEQ ID NO:782, hybridized to corresponding a complementary DNA sequence having uridine or cytosine, and in a complex with an enzyme, e.g., a thermostable DNA polymerase. In embodiments, the thermostable DNA polymerase is Taq DNA polymerase.

In some aspects, the method includes deoxyribonucleic acid that has a sequence that is at least 50%-55%, 55%-60%, 60%-65%, 65%-70%, 70%-75%, 75%-80%, 80%-85%, 90%, 91%, 92%, 93%, 94%, 95%, 96%, 97%, 98%, 99% or more identical or homologous to a nucleic acid having a sequence of at least one of SEQ ID NO:551 to SEQ ID NO:782.

TABLE 5

| SEQ ID NO: | Sequence, 5' to 3' |
|---|---|
| 551 | GGGAGAAGAGATTGGAAAA |
| 552 | CTAAAAACCTAACACTAACAACATAAT |
| 553 | TGTTGTTTAAAATGTTGTTT |
| 554 | AACCCTAAATAATTCTTCTC |
| 555 | GGGTTGGGTTGAGGTTTT |
| 556 | ACACCTTACATCTCATTTACAACTC |
| 557 | AATTTGTGAAAAGTTTGTGTA |
| 558 | CCCAATCACCTTTAATCT |
| 559 | GTTGGGATTTGAAATAGTGA |
| 560 | CCTCCACTCACCTAAAACTT |
| 561 | TTGGTTAGTGATTATTTATT |
| 562 | AAAAATTAATATAAAATTAAAA |
| 563 | TTTGTAGGGAGTTAGGGAT |
| 564 | TCCTCTATCTCACCCTAAAT |
| 565 | TTTGATTGAATTATTTGTGTATT |
| 566 | ACTCCCTTACTCCTAAACACT |
| 567 | AGTGGAGATEGGTAGGGAGA |
| 568 | CCCAAAACTAAAACCAAATATAA |

TABLE 5-continued

| SEQ ID NO: | Sequence, 5' to 3' |
|---|---|
| 569 | TTGTGGTTAAATTTATTG |
| 570 | ACCCAACAAAATAATATC |
| 571 | TGAGGTAGAGTTGTGTGTATAT |
| 572 | ATCAATCAATTCTCATTAAAC |
| 573 | GGAAGTTAGGAAGGGTTGT |
| 574 | CTCCAACTCCAACTAAAACTC |
| 575 | TTEGGGTATTGATTTATTTT |
| 576 | AAATTCTACCTACAAACTATACA |
| 577 | AGGATGAAGTAATAATTAAATATTG |
| 578 | CCCACTCTACCAACTAAAC |
| 579 | AGGTTTGTGTTAGTATAAAT |
| 580 | TTCTTACCTATATAATTAATAATA |
| 581 | GTTGGGTGAATTTTATTAG |
| 582 | TCAAAACCTAAACTCTAACA |
| 583 | GGATTGGTTTRATATAGAAAGTAT |
| 584 | CAAATAATAAATCATAACTCTTAACT |
| 585 | TGGGGTAGTTGATGGTTT |
| 586 | CTTTCTAACAAAATAAAAAAATTTAA |
| 587 | TTGTATTTGAAGTTTGTAGAGATTTATA |
| 588 | TTTCCTCCAACAACTCAAT |
| 589 | TTATGAGTATGTAGTAGGGTTATTATA |
| 590 | AAAATATCAAACAAATTTATCC |
| 591 | TGGTTGTTTGTTTTTTATGTATT |
| 592 | TCCCTACCTCCCAAATTC |
| 593 | TATGATGATTGTTGTAGTGTAGA |
| 594 | CCTCCCTAATAACTAAAAATAC |
| 595 | GGTGGTTTTGATATTTAGTG |
| 596 | CCCAATTACCTAACAAATTA |
| 597 | TGGGATAGGTGTAGATATG |
| 598 | CAACAAAAACTAAAACACTATAC |
| 599 | TTTGGGATTGGTTATTTT |
| 600 | AAACCCCTTAACTCTATACC |
| 601 | GATTTTTTTGAGAAGAGTATAG |
| 602 | AACCACTACCACCTAAATATA |
| 603 | GGAGGATAGGGTGTGATT |
| 604 | ACATTTTTAACTCTAACTAAAAATAAA |
| 605 | TGGAAATGAGGTGAGTTT |
| 606 | AAAAAAAAATAAAATAACAATAACTA |
| 607 | TGGAGAGTTTAGTTTGTTT |

TABLE 5-continued

| SEQ ID NO: | Sequence, 5' to 3' |
|---|---|
| 608 | CAAAAAAAAATCTAACAAC |
| 609 | TGGGTTTTAGTTATGTGGTT |
| 610 | ATCAATAATATCCAACAAAATAATAT |
| 611 | TTTTTTTAGTTTTTGTATATATATTAG |
| 612 | ACCCAAATAATCAACTCTT |
| 613 | GTGGTTTTTGGAGATTTA |
| 614 | AAACAAACTACAAATAAAATAATAC |
| 615 | GGGTTATAGGTTTGAGTTA |
| 616 | CCATTAAAAAAAATAAAATC |
| 617 | TTGGTAGATTTAGTAAATTTATT |
| 618 | AAACTTAAACAACCCTATATAC |
| 619 | ATGGTTTTAAAGAGTAGTAGTATAGTT |
| 620 | AAATTTACTCATCCCACTTC |
| 621 | AGGGGTTGGGATATTGTT |
| 622 | AAAAATTTCTCCTTACAAAAAACTAA |
| 623 | ATGGGTGTTTGGAATTTTTTA |
| 624 | CTACCTCAACCTCCTAAATAACTAA |
| 625 | GTGTTTTGTGGTANAGATATAG |
| 626 | ATTCTTAAATTAATTCAACTACAT |
| 627 | TGGGGGTAAAAGTTATAGTT |
| 628 | AAAAAACAAAAAACCAAATAC |
| 629 | GTTTTTTGGTTAGTGTGTT |
| 630 | CCCCATACTTCTATACTATAAT |
| 631 | TTGTTGTTTTTAAAGAAATTATA |
| 632 | ATCATCTAAACTTAACTCATCTAA |
| 633 | ATTTTTGGGTGTTTTATATT |
| 634 | AAACCTCAAACAATAACA |
| 635 | ATTAAGGATATTTAGGAGAGTAAG |
| 636 | ACACCACAACTTCAAACTAC |
| 637 | TGAGGAAGAGAGAAGAGATGATA |
| 638 | AAAACTAAACTATAAAACAAAACAAAACTA |
| 639 | GGTGGAGGTGTTTTTTATAG |
| 640 | CCAAATACTACTTTCAAAATACA |
| 641 | ATGGATTATTATTGTGTTATT |
| 642 | CATCTCAACCTCATACTAA |
| 643 | GGATGATTTAGTAGGGATTGAG |
| 644 | ccAAATAAAAACCATTCTCTAAC |
| 645 | TTGGATTAAGTATTTTTGATATTA |
| 646 | TCCCTAAACCATATATTACTAAA |

TABLE 5-continued

| SEQ ID NO: | Sequence, 5' to 3' |
|---|---|
| 647 | GGGTAGTTTGGTGATTATTATT |
| 648 | CCCTTCCCTACTCACAATA |
| 649 | ATTTGGTTAGTGATTTAGTTATT |
| 650 | TCCCACTTAAAAAATTCTATA |
| 651 | AGTGGGGAAGGTAATTGTTAT |
| 652 | CTTTCTAATAAAAATTTACTAAAACCTCTA |
| 653 | TTTGGTTAGTTTTATTTTTGATTG |
| 654 | ATTCCTCCCTATCCCTATTC |
| 655 | GGGATAGGGGTTAGAGTAA |
| 656 | TCCATAAAAACAAAACACTC |
| 657 | TTTTTTAGTATGAGTTATAAATTAT |
| 658 | AAAACAAAATCTACCTATATATT |
| 659 | TTTTATTAATAAAGTAGGTATGA |
| 660 | ACCTTTCTCAAAATTACTAA |
| 661 | ATAGGGTTGAGGTTAGAGTTAT |
| 662 | CCTCCTCTCCACAATAAA |
| 663 | TTTAAGTTTTTTTTTAGTTTTGTAGT |
| 664 | CCCCATCCTCTCTATCTC |
| 665 | AAATTTAAAATTTAGAGGTTTTTATA |
| 666 | AAACTTCACACACAAATCTATATT |
| 667 | TTTTTATTTTATTTTTTATTTTTAA |
| 668 | ATACCTCCCTAATTATATTATTAA |
| 669 | TTTTAGAATATTTAAAGAAGTTAGT |
| 670 | TAACCTCACTTTCCTATCA |
| 671 | AATTTAGTATAAGATTTGATTTGTTA |
| 672 | CCACCTACTCCTTCCTATAC |
| 673 | TTTTTTGAAATTGTATGTTAT |
| 674 | CAAATCCTTAAAATTCTATAA |
| 675 | TTTGAAGTGGTGTTTTAG |
| 676 | CCAAAATTCTTCCATACT |
| 677 | TGGGTATTTAGTYTTTTGTG |
| 678 | AACAAcTACCTCCTTTTACTAAT |
| 679 | TATGGTAGGAGGTGGAGTT |
| 680 | CCCAATTTTAAAACAATAC |
| 681 | AGAGGAAGTAAGGTTATTAGTT |
| 682 | ACCAAACAAACAATATCTAA |
| 683 | GGTTTTAATTATGATTTAATTAGA |
| 684 | CCTACACTCAAATTTACCTCTA |
| 685 | AATGGGTAGTTGATATAATTATT |

TABLE 5-continued

| SEQ ID NO: | Sequence, 5' to 3' |
|---|---|
| 686 | CACAAAATCCTAAAACTAAAA |
| 687 | AGGATTAGTGGAAATGAAAATA |
| 688 | TAACCTCAAAACAACTTCTAAAC |
| 689 | TTTTTTTTATAGAGAAGTATTTTAG |
| 690 | CCCATTACAAAACTATCC |
| 691 | GGTGAGTTTGTGGTTAGTG |
| 692 | TTTTCTAAAAAAATCCAATCTA |
| 693 | AATGGATAGGTTGGAATAG |
| 694 | AAAAAAAAAAAAAACTAATTAC |
| 695 | GAGTTATTTAGTTTGGTTAGGT |
| 696 | ACTCAACTTAAAAAATCACTATAC |
| 697 | TTTYTTTTGGYTTTTTGGYTTT |
| 698 | TCCCCCACACCCATATAA |
| 699 | TTAAAAAAAAGTATAATGAGTAGGA |
| 700 | CCCACAAAAACTCTCTACA |
| 701 | AAAGGAGGTTGAGTTAGAAAGTAG |
| 702 | AACTATTTAACTTACTTAACCACACC |
| 703 | GGTGTGGTTAAGTAAGTTAAATAGT |
| 704 | TACCCCTTCCTCTTCAAC |
| 705 | TTTTGATATGATTTATGATTATAT |
| 706 | TTTTCCACTAAACAACACTA |
| 707 | TTTGAGGGTTGTTTTAGAT |
| 708 | ACTCACAAAAAATAACTAATAACTAT |
| 709 | AAAGGAGGTAGGGGAGATATA |
| 710 | TCAAAATAAAAACCAAAATTCTC |
| 711 | AGGTTAAGTTGGTAGAGGTAGA |
| 712 | CAAACTCTAAACTCAAAATATATTC |
| 713 | TTTTTATTTTAGTTTTTTTGAGTAG |
| 714 | CCCTACAACACTCCTATCTA |
| 715 | TTTGGAGTTAGGTTGATAG |
| 716 | CAACAATACTCTCACTTACAC |
| 717 | AGAAAGATTTTTAAATATTTTTAAT |
| 718 | AAACCTCTAATACACAACAAA |
| 719 | TTTTGAGTTTTTTTTTTTAAGTAT |
| 720 | CAAACAAAACAACACTTAATAC |
| 721 | GGTTGAGGTGGGTGGATTA |
| 722 | TTTTTTTTTTTTTTTTTTAAAATAAAATCT |
| 723 | GGGTGTTTGTAATTTTAGTT |
| 724 | ACCTCTTAACAACCTAACAATATA |
| 725 | GGGTAGATGATATGGTAGTGA |
| 726 | AAAAAATAAAAAATAACTAAAACAATAT |
| 727 | AGGAAGTGTTTAAGAAGTAGAA |
| 728 | CCTAAAACTCTAAATACAATCTC |
| 729 | TTTTTAATTTTTGTTTGTATT |
| 730 | AAACCACAATCTATTTCTAA |
| 731 | TTAGAAAAGAATAATTATAGTTG |
| 732 | ACCCTAAAAAAATAAAATC |
| 733 | TTGTATTAGTAAATAAAGTGTATTTT |
| 734 | AACCCTTTCTACAAATCTAC |
| 735 | AGGGGTGGGTGGAAGAAT |
| 736 | CTCCTCAATAAAATAAAAATCCTAAAAAATA |
| 737 | GGGTTAATTAGTTGTTTTAT |
| 738 | CCTACAAATATATCACACACT |
| 739 | TTTGTTAAATAGGTGGTTAGA |
| 740 | ACCTCAACCTCCTAAATAAC |
| 741 | TAGGGTTTAGAGTAGGAGGTAG |
| 742 | CAAAAAATATAAATCAAAAACATC |
| 743 | GGGATTATAGGTATTTATTAT |
| 744 | TAAAAATTAAAAATCATACTTA |
| 745 | AAGTGATTTTTAGGGAGTGT |
| 746 | TCCATAATAACCTCATTTTAATA |
| 747 | TTTTTGGTTGAGGTTTAGT |
| 748 | AAACAACACAACTCTTATCAC |
| 749 | TATGGTGATTAAAGTATAATAGTT |
| 750 | TCCTAAATAAAAAACAACATA |
| 751 | TGAAAATGTTTTTAGTTTTTATT |
| 752 | AAATACCCTACCTCTTATCTAA |
| 753 | GATGGTTAATTTTTTTATTT |
| 754 | ACTCCTTCAACAAACTAAC |
| 755 | AGGGGATATTTTTAGGTT |
| 756 | CCAATCTATTCCTATATAATTAA |
| 757 | AGGAGAGTTTGGAAATATAG |
| 758 | CAATTCTAAATTAAACCTTATT |
| 759 | AATAATGGTAGTAGTTTTATTAG |
| 760 | TTCCTATATTAACAACTTACA |
| 761 | TTTTTTGGTAGATTTTTAT |
| 762 | AAATTAATTTCTATTATTTATATTA |
| 763 | AGGTGGTTGGGGAGAGTG |

TABLE 5-continued

| SEQ ID NO: | Sequence, 5' to 3' |
|---|---|
| 764 | CCCTAAAATAAATCAAAAAAAACCTTAA |
| 765 | AGGTTTAGGTGGGGTGAAT |
| 766 | TAAAATCATCAAAATCCCTTAAAA |
| 767 | TTTTTTTTTAGGTTATACTGAGTATT |
| 768 | ATCCCCACAAAACACATA |
| 769 | TAGGGTAAATATTGGGATTATT |
| 770 | TTTCCACCTCAAAACTTAAC |
| 771 | GGGTGTTTGTATTTTTATATT |
| 772 | ACCTCCCAAAACCATAAC |
| 773 | GATGTGAGTGGTGAGGTGGT |
| 774 | CAAACCCTTCCAAAACATAAAC |
| 775 | TGGGATTATAGGTATGTATT |
| 776 | CAATTTCATTTATAAATATAAATAT |
| 777 | AGGGGTTGGTTATTTTTATTTT |
| 778 | TTTTTAATATTTAATTTTTACCTTCAACT |
| 779 | GGTAAGTTGTGGATGTGAGT |
| 780 | AAAAAAAACCAAACCTTATCTA |
| 781 | TTTTTAGGATTTGGGTTAG |
| 782 | AACCTTATAAATAACAACAAAAC |

Kit for Detecting Methylation Level of a Thyroid Nodule

Also provided is a kit including a plurality (e.g., at least about 10, 20, 40, 50, 100, 150, 200, 225, or 232) nucleic acids each independently comprising one sequence selected from SEQ ID NO:551 to SEQ ID NO:782, in which the nucleic acids do not simultaneously include the same sequence.

In some aspects, the kit includes deoxyribonucleic acid that has a sequence that is at least 50%-55%, 55%-60%, 60%-65%, 65%-70%, 70%-75%, 75%-80%, 80%-85%, 90%, 91%, 92%, 93%, 94%, 95%, 96%, 97%, 98%, 99% or more identical or homologous to a nucleic acid having a sequence of at least one of SEQ ID NO:551 to SEQ ID NO:782.

The kit provided herein may include enzymes, reagents for deamination of cytosine, buffers, vials, plasmid vectors, control DNA, devices for collecting thyroid tissue samples, reagents for isolating DNA, reagents for labeling DNA, labels, or any combinations thereof.

The kit provided herein may include enzymes such as thermostable DNA polymerase enzymes, restriction enzymes, and combination thereof.

In embodiments, the kit(s) may further include enzymes, reagents for deamination of cytosine, buffers, vials, control DNA, devices for collecting blood and/or tissue samples, or reagents for labeling DNA, or any combinations thereof.

In embodiments, a kit provided herein may include a solid carrier capable of adsorbing the nucleic acids containing in a sample of a body fluid, for example blood (whole blood, plasma, or serum). The kit may also contain other components for example, reagents, in concentrated or final dilution form, chromatographic materials for the separation of the nucleic acids, aqueous solutions (buffers, optionally also in concentrated form for final adjusting by the user) or chromatographic materials for desalting nucleic acids which have been eluted with sodium chloride.

In embodiments, a kit provided herein includes materials for purifying nucleic acids, for example, inorganic and/or organic carriers and optionally solutions, excipients and/or accessories. Such agents are known and are commercially available. For solid phase nucleic acid isolation methods, many solid supports have been used including membrane filters, magnetic beads, metal oxides, and latex particles.

In addition, a kit can also contain excipients such as, for example, a protease such as proteinase K, or enzymes and other agents for manipulating nucleic acids. e.g., at least one amplification primer, nucleic acid bases (A, T, G. C, and/or U), and enzymes suitable for amplifying nucleic acids, e.g., DNase, a nucleic acid polymerase and/or at least one restriction endonuclease. Alternatively, a commercial polymerase chain reaction kit may be used to amplify the DNA samples.

Exemplary Techniques for Detecting Specific Sequences

Specific sequences, such as the sequences listed in Table 1 (or portions thereof containing a methylation site of interest), can be detected by numerous methods that are well-established in the art (e.g., PCR-based sequence specific amplification, isozyme markers, northern analysis, sequence specific hybridization, and array based hybridization). In embodiments, the presence or absence of methylation is determined through nucleotide sequencing of the site of interest (e.g., the site in bisulfite-treated DNA or an amplicon thereof). Any of these methods are readily adapted to high throughput analysis.

Some techniques for detecting specific sequences utilize hybridization of a probe nucleic acid to nucleic acids corresponding to the methylation site of interest (e.g., amplified nucleic acids produced using bisulfite-treated DNA as a template or the bisulfite-treated DNA itself). Hybridization formats, including, but not limited to: solution phase, solid phase, mixed phase, or in situ hybridization assays are useful for sequence detection. A non-limiting guide to the hybridization of nucleic acids is found in Tijssen (1993) Laboratory Techniques in Biochemistry and Molecular Biology—Hybridization with Nucleic Acid Probes Elsevier, N.Y., as well as in Sambrook. Berger and Ausubel.

Nucleic acid probes complementary to a methylation site can be cloned and/or synthesized. Any suitable label can be used with a probe. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands which bind to antibodies labeled with fluorophores, chemiluminescent agents, and enzymes. A probe can also constitute radiolabelled PCR primers that are used to generate a radiolabelled amplicon. Labeling strategies for labeling nucleic acids and corresponding detection strategies can be found, e.g., in Haugland (2003) Handbook of Probes and Research Chemicals Ninth Edition by Molecular Probes, Inc. (Eugene Oreg.). Additional non-limiting details regarding sequence detection strategies are found below.

PCR, RT-PCR and LCR are in particularly broad use as amplification and amplification-detection methods for amplifying nucleic acids (e.g., those comprising a methylation site), facilitating detection of the nucleic acids of interest.

In embodiments, real time PCR or LCR is performed on the amplification mixtures described herein. e.g., using molecular beacons or TaqMan™ probes. A molecular beacon (MB) is an oligonucleotide or peptide nucleic acid (PNA) which, under appropriate hybridization conditions, self-hybridizes to form a stem and loop structure. The MB has a label and a quencher at the termini of the oligonucleotide or PNA; thus, under conditions that permit intramolecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched. Details regarding standard methods of making and using MBs are well established in the literature and MBs are available from a number of commercial reagent sources. See also, e.g., Leone et al. (1995) "Molecular beacon probes combined with amplification by NASBA enable homogenous real-time detection of RNA." Nucleic Acids Res. 26:2150-2155; Tyagi and Kramer (1996) "Molecular beacons: probes that fluoresce upon hybridization" Nature Biotechnology 14:303-308; Blok and Kramer (1997) "Amplifiable hybridization probes containing a molecular switch" Mol Cell Probes 11:187-194; Hsuih et al. (1997) "Novel, ligation-dependent PCR assay for detection of hepatitis C in serum" J Clin Microbiol 34:501-507; Kostrikis et al. (1998) "Molecular beacons: spectral genotyping of human alleles" Science 279:1228-1229; Sokol et al. (1998) "Real time detection of DNA:RNA hybridization in living cells" Proc. Natl. Acad. Sci. U.S.A. 95:11538-11543; Tyagi et al. (1998) "Multicolor molecular beacons for allele discrimination" Nature Biotechnology 16:49-53; Bonnet et al. (1999) "Thermodynamic basis of the chemical specificity of structured DNA probes" Proc. Natl. Acad. Sci. U.S.A. 96:6171-6176; Fang et al. (1999) "Designing a novel molecular beacon for surface-immobilized DNA hybridization studies" J. Am. Chem. Soc. 121:2921-2922; Marras et al. (1999) "Multiplex detection of single-nucleotide variation using molecular beacons" Genet. Anal. Biomol. Eng. 14:151-156; and Vet et al. (1999) "Multiplex detection of four pathogenic retroviruses using molecular beacons" Proc. Natl. Acad. Sci. U.S.A. 96:6394-6399. Additional details regarding MB construction and use is found in the patent literature, e.g., U.S. Pat. No. 5,925,517 (Jul. 20, 1999) to Tyagi et al. entitled "Detectably labeled dual conformation oligonucleotide probes, assays and kits;" U.S. Pat. No. 6,150,097 to Tyagi et al (Nov. 21, 2000) entitled "Nucleic acid detection probes having non-FRET fluorescence quenching and kits and assays including such probes" and U.S. Pat. No. 6,037,130 to Tyagi et al (Mar. 14, 2000), entitled "Wavelength-shifting probes and primers and their use in assays and kits."

PCR detection and quantification using dual-labeled fluorogenic oligonucleotide probes, commonly referred to as "TaqMan™" probes, can also be performed. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TaqMan™ probes are oligonucleotides that have a label and a quencher, where the label is released during amplification by the exonuclease action of the polymerase used in amplification. This provides a real time measure of amplification during synthesis. A variety of TaqMan™ reagents are commercially available, e.g., from Applied Biosystems (Division Headquarters in Foster City, Calif.) as well as from a variety of specialty vendors such as Biosearch Technologies (e.g., black hole quencher probes). Further details regarding dual-label probe strategies can be found, e.g., in WO92/02638.

Other similar methods include e.g. fluorescence resonance energy transfer between two adjacently hybridized probes. e.g., using the "LightCycler™" format described in U.S. Pat. No. 6,174,670.

Amplification and Sequencing Primers

In embodiments, methylation sites are detected using primers, e.g., to amplify and/or sequence polynucleotides comprising the methylation sites.

Suitable primers can be designed and is not intended that the present subject matter be limited to any particular primer or primer pair. For example, primers can be designed using any suitable software program, such as LASERGENE™, e.g., taking account of publicly available sequence information. Flanking sequences for the methylation sites identified herein are publicly available; accordingly, suitable amplification primers can be constructed based on well understood base-pairing rules. The sequence of any amplicon can be detected as has already been discussed above. e.g., by sequencing, hybridization, array hybridization, PCR, LCR, or the like.

In embodiments, the primers are radiolabelled, or labeled by any suitable means (e.g., using a non-radioactive fluorescent tag), to allow for rapid visualization of differently sized amplicons following an amplification reaction without any additional labeling step or visualization step. In embodiments, the primers are not labeled, and the amplicons are visualized following their size resolution, e.g., following agarose or acrylamide gel electrophoresis. In embodiments, ethidium bromide staining of the PCR amplicons following size resolution allows visualization of the different size amplicons.

It is not intended that the primers be limited to generating an amplicon of any particular size. The primers can generate an amplicon of any suitable length for detection (e.g., by sequencing or hybridization). In embodiments, amplification produces an amplicon at least 20 nucleotides in length, or alternatively, at least 50 nucleotides in length, or alternatively, at least 100 nucleotides in length, or alternatively, at least 200 nucleotides in length. Amplicons of any size can be detected and/or sequenced using various technologies described herein and known in the art.

Detection of Methylation Levels Using Sequencing

Sequencing is the process of determining the precise order of nucleotides within a DNA molecule. The advent of rapid DNA sequencing methods has greatly accelerated biological and medical research and discovery. Non-limiting examples and descriptions are provided below. However, embodiments are not limited to the use of a particular sequencing assay, technology, or approach.

Sanger sequencing is a method of DNA sequencing based on the selective incorporation of chain-terminating dideoxynucleotides by DNA polymerase during in vitro DNA replication (Sanger F; Coulson A R (May 1975) J. Mol. Biol. 94 (3): 441-8; Sanger et al. (December 1977) Proc. Natl. Acad. Sci. U.S.A. 74 (12): 5463-7).

In embodiments, next-generation sequencing is used. Non-limiting examples of next-generation sequencing methods include massively parallel signature sequencing (MPSS), single-molecule real-time sequencing, ion semiconductor sequencing, pyrosequencing, sequencing by synthesis, sequencing by ligation, chain termination. DNA nanoball sequencing, helicos single molecule sequencing, single molecule real time sequencing, nanopore DNA sequencing, tunnelling currents DNA sequencing, and sequencing by hybridization.

Many commercially available sequencing technologies, devices, and services are available. In embodiments, an Illumina sequencer is used. In embodiments, PCR products are ligated with a linker and sequenced using a high throughput sequencer, such as an Illumina sequencer. In embodiments, the ligation step can be avoided, omitted, or eliminated by adding a linker to amplification primers.

Array-Based Sequence Detection

Array-based detection can be performed using commercially available arrays, e.g., from Affymetrix (Santa Clara, Calif.) or other manufacturers. Reviews regarding the operation of nucleic acid arrays include Sapolsky et al. (1999) "High-throughput polymorphism screening and genotyping with high-density oligonucleotide arrays." Genetic Analysis: Biomolecular Engineering 14:187-192; Lockhart (1998) "Mutant yeast on drugs" Nature Medicine 4:1235-1236; Fodor (1997) "Genes. Chips and the Human Genome." FASEB Journal 11:A879; Fodor (1997) "Massively Parallel Genomics." Science 277: 393-395; and Chee et al. (1996) "Accessing Genetic Information with High-Density DNA Arrays." Science 274:610-614.

A variety of probe arrays have been described in the literature and can be used for detection of methylation. For example, DNA probe array chips or larger DNA probe array wafers (from which individual chips would otherwise be obtained by breaking up the wafer) may be used in embodiments described herein. DNA probe array wafers generally comprise glass wafers on which high density arrays of DNA probes (short segments of DNA) have been placed. Each of these wafers can hold, for example, approximately 60 million DNA probes that are used to recognize longer sample DNA sequences (e.g., from individuals or populations, e.g., that comprise methylation sites of interest). The recognition of sample DNA by the set of DNA probes on the glass wafer takes place through DNA hybridization. When a DNA sample hybridizes with an array of DNA probes, the sample binds to those probes that are complementary to the sample DNA sequence. By evaluating to which probes the sample DNA for an individual hybridizes more strongly, it is possible to determine whether a known sequence of nucleic acid is present or not in the sample, thereby determining whether a uracil, thymine, or cytosine is present at a polynucleotide site corresponding to a genomic methylation site. One can also use this approach to control the hybridization conditions to permit single nucleotide discrimination, e.g., for the identification of methylation at a site of interest. Arrays provide one convenient embodiment for detecting multiple methylation sites simultaneously (or in series). Of course, any detection technology (PCR, LCR, and/or sequencing etc.) can similarly be used, e.g., with multiplex amplification/detection/sequencing reactions, or simply by running several separate reactions. e.g., simultaneously or in series.

In embodiments, the use of DNA probe arrays to obtain methylation information involves the following general steps: design and manufacture of DNA probe arrays, preparation of the sample, bisulfite treatment, hybridization of sample DNA to the array, detection of hybridization events and data analysis to determine sequence. In embodiments, an array is used to capture polynucleotides containing a methylation site of interest, and the captured polynucleotides are subsequently amplified and/or sequenced. Preferred wafers are manufactured using a process adapted from semiconductor manufacturing to achieve cost effectiveness and high quality, and are available, e.g., from Affymetrix, Inc. of Santa Clara, Calif.

For example, probe arrays can be manufactured by light-directed chemical synthesis processes, which combine solid-phase chemical synthesis with photolithographic fabrication techniques as employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays can be synthesized simultaneously on a large glass wafer. This parallel process enhances reproducibility and helps achieve economies of scale.

In embodiments, DNA probe arrays can be used to obtain data regarding presence of sequences (e.g., corresponding to methylated or unmethylated DNA) of interest. The DNA samples may be tagged with biotin and/or a fluorescent reporter group by standard biochemical methods. The labeled samples are incubated with an array, and segments of the samples bind, or hybridize, with complementary sequences on the array. The array can be washed and/or stained to produce a hybridization pattern. The array is then scanned and the patterns of hybridization are detected by emission of light from the fluorescent reporter groups. Because the identity and position of each probe on the array is known, the nature of the DNA sequences in the sample applied to the array can be determined.

In embodiments, the nucleic acid sample to be analyzed is isolated, bisulfite-treated, amplified and, optionally, labeled with biotin and/or a fluorescent reporter group. The labeled nucleic acid sample may then incubated with the array using a fluidics station and hybridization oven. The array can be washed and or stained or counter-stained, as appropriate to the detection method. After hybridization, washing and staining, the array is inserted into a scanner, where patterns of hybridization are detected. The hybridization data are collected as light emitted from the fluorescent reporter groups already incorporated into the labeled nucleic acid, which is now bound to the probe array. Probes that most clearly match the labeled nucleic acid produce stronger signals than those that have mismatches. Since the sequence and position of each probe on the array are known, by complementarity, the identity of the nucleic acid sample applied to the probe array can be identified. In embodiments, hybridization techniques and conditions that allow only fully complementary nucleotide sequences to hybridize with probes in an array are used.

Prior to amplification and/or detection of a nucleic acid comprising a sequence of interest, the nucleic acid is optionally purified from the samples by any available method, e.g., those taught in Berger and Kimmel, Guide to Molecular Cloning Techniques, Methods in Enzymology volume 152 Academic Press. Inc., San Diego. Calif. (Berger); Sambrook et al., Molecular Cloning—A Laboratory Manual (3rd Ed.), Vol. 1-3. Cold Spring Harbor Laboratory, Cold Spring Harbor. N.Y., 2001 ("Sambrook"); and/or Current Protocols in Molecular Biology. F. M. Ausubel et al., eds., Current Protocols, a joint venture between Greene Publishing Associates. Inc, and John Wiley & Sons, Inc., (supplemented through 2002) ("Ausubel")). A plethora of kits are also commercially available for the purification of nucleic acids from cells or other samples (see. e.g., EasyPrep™, FlexiPrep™, both from Pharmacia Biotech; StrataClean™, from Stratagene; and, QIAprep™ from Qiagen). Alternately, samples can simply be directly subjected to amplification or detection, e.g., following aliquotting and/or dilution.

Thyroid Cancer Diagnostic System and Processes

Figure 4:
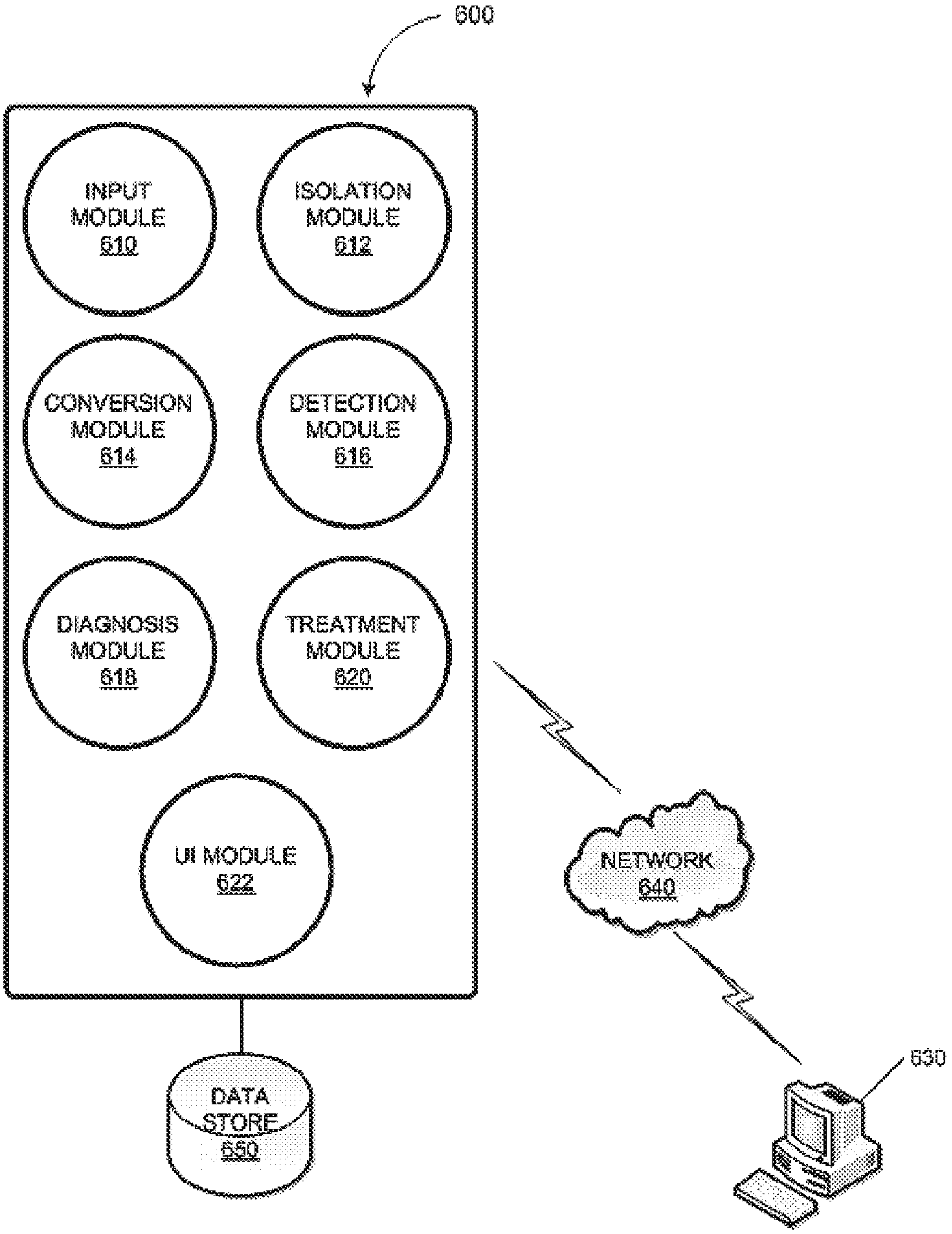
FIG. 4 depicts a block diagram illustrating an exemplary thyroid cancer diagnostics system.

FIG. 4 depicts a block diagram illustrating an exemplary thyroid cancer diagnostic system 600. Referring to FIG. 4, the thyroid cancer diagnostic system 600 can include an input module 610, an isolation module 612, a conversion module 614, a detection module 616, a diagnosis module 618, a treatment module 620, and a user interface (UI) module 622. The thyroid cancer diagnostic system 600 can be configured to provide a diagnosis indicative of a presence of thyroid cancer and/or a risk of developing thyroid cancer. Moreover, the thyroid cancer diagnostic system 600 can be further configured to generate a treatment plan for a subject based on the diagnosis. For instance, when the diagnosis indicates a presence and/or risk of thyroid cancer in a subject, the thyroid cancer diagnostic system 600 can recommend one or more treatments including, for example, thyroid surgery, radiation therapy, radioactive iodine therapy, chemotherapy, thyroid hormone therapy, and administration of an active agent.

One or more modules of the thyroid cancer diagnostic system 600 can be realized in digital electronic circuitry, integrated circuitry, specially designed application specific integrated circuits (ASICs), field programmable gate arrays (FPGAs) computer hardware, firmware, software, and/or combinations thereof. The thyroid cancer diagnostic system 600 can further be communicatively coupled with one or more devices including, for example, a device 630. The thyroid cancer diagnostic system 600 can communicate with the device 620 via a wired and/or wireless network 640 (e.g., a wide area network (WAN), a local area network (LAN), and/or the Internet). As shown in FIG. 4, the thyroid cancer diagnostic system 600 can be further coupled with a data store 650.

The input module 610 can be adapted to receive and/or collect a sample of a thyroid nodule obtained from a subject. The isolation module 612 can be configured to isolate DNA from the thyroid nodule sample received by the input module 610 thereby forming isolated thyroid nodule DNA. The conversion module 614 can be configured to treat the isolated thyroid nodule DNA including by contacting the isolated thyroid nodule DNA with one or more bisulfite reagents including, for example, a bisulfite salt. Exposing the isolated thyroid nodule DNA to one or more bisulfite reagents can convert cytosine to uracil while 5-mC is left unmodified. Thus, the 5-mC present in the isolated thyroid nodule DNA will remain in the reacted thyroid nodule DNA. Meanwhile, any cytosine in the isolated thyroid nodule DNA will be replaced by uracil in the reacted thyroid nodule DNA. In embodiments, the treatment of the isolated thyroid nodule DNA can be performed by applying one or more kits (e.g., the Bisulflash DNA Modification Kit (Epigentek) or Imprint DNA Modification Kit (Sigma)).

In embodiments, the conversion module 614 can be further adapted to ensure optimal bisulfite conversion (e.g., with desired DNA fragment size for post-bisulfite ligation) by controlling one or more of a concentration of the bisulfite reagents, temperature, and reaction time period. It should be appreciated that the conversion module 614 can be adapted to use a different and/or additional type of reagent without departing from the scope of the present subject matter. For example, the conversion module 614 can treat the isolated thyroid nodule DNA with potassium chloride, which may reduce the thermophilic DNA degradation associated with the conversion of cytosine to uracil. Moreover, the conversion module 614 can be configured to perform additional processing of the reacted thyroid nodule DNA including, for example, desulphonation (e.g., with an alkalized solution), cleansing (e.g., by elution), and amplification (e.g., using the PCR method).

The detection module 616 can be configured to detect a methylation and/or unmethylation of the thyroid nodule DNA. For instance, the detection module 616 can detect methylation by detecting a presence of uracil in the reacted thyroid nodule DNA generated by the conversion module 614. Alternately and/or additionally, the detection module 616 can detect unmethylation by detecting an absence of uracil in the reacted thyroid nodule DNA. In embodiments, the detection module 616 can be configured detect the presence and/or absence of uracil at specific methylation sites. That is, the detection module 616 can be configured to detect the presence and/or absence of uracil at specific chromosomal positions of certain chromosomes. For example, the thyroid cancer diagnostic system 600 can store a plurality of specific methylation sites (e.g., Table 1) in the data store 650. As such, to detect methylation, the detection module 616 can be configured to obtain, from the data store 650, one or more specific methylation sites at which to test for the presence and/or absence of uracil. Moreover, in embodiments, the detection module 616 can be configured to determine a level of methylation and/or unmethylation at the specific methylation sites. The level of methylation at a particular site can correspond to a proportion of the reacted thyroid nodule DNA that has a cytosine rather than a uracil at that site. By contrast, the level of unmethylation at a particular site can correspond to a proportion of reacted thyroid nodule DNA that has a uracil rather than a cytosine at that site.

In embodiments, the conversion module 614 may amplify the reacted thyroid nodule DNA such as by using a PCR method. The detection of methylation and/or unmethylation in amplified reacted thyroid nodule DNA may require detection of a presence and/or absence of thymidine at a site of interest in amplicons amplified from the reacted thyroid nodule DNA. That is, instead of detecting the presence and/or absence of uracil, the detection module 616 can be configured to detect methylation and/or unmethylation of amplified reacted thyroid nodule DNA by detecting a presence and/or absence of thymidine at specific methylation sites (e.g., as set forth in Table 1).

The diagnosis module 618 can be configured to generate a diagnosis for the subject based on whether the detection module 616 detects methylation and/or unmethylation at the plurality of specific methylation sites (e.g., Table 1). Alternately or additionally, the diagnosis module 618 can be configured to generate a diagnosis for the subject based on a level of methylation and/or unmethylation detected by the detection module 616 at the plurality of specific methylation sites. For instance, diagnosis module 618 can determine that the thyroid nodule is malignant (e.g., cancerous) when the unmethylation level (e.g., proportion of uracil) at different methylation sites exceeds the corresponding thresholds (e.g., as set forth in Table 2). In embodiments, the diagnosis module 618 can further generate a diagnosis for the subject based on one or more of the subject's PTC methylation alternation score, a BTN methylation alternation score, and/or a Composite Cancer Risk Score.

In embodiments, the diagnosis module 618 can be configured to determine a PTC methylation alternation score for the subject. In embodiments, the PTC methylation alteration score can correspond to a number of specific methylation sites (e.g., as set forth in Table 1) that have a uracil level (or corresponding thymidine level if amplicons are being analyzed) equal to or greater than the corresponding thresholds (e.g., as set forth in Table 2). Alternately or additionally, the diagnosis module 618 can be configured to determine a BTN methylation alternation score for the subject. The BTN methylation alteration score can correspond to a number of specific methylation sites (e.g., as set forth in Table 1) that have a uracil level (or corresponding thymidine level if amplicons are being analyzed) equal to or greater than the various corresponding threshold level (e.g., as set forth in Table 3 and/or Table 4).

In embodiments, the diagnosis module 618 can further be configured to compute a Composite Cancer Risk Score for the subject. The diagnosis module 618 can compute the Composite Cancer Risk Score based on the PTC methylation alteration score and the BTN methylation alteration score for the subject. For example, the Composite Cancer Risk Score for the subject can be computed based on equation (1):

$$\frac{\left[\text{the PTC methylation alteration score for the subject}\right]}{\left[\text{BTN methylation alteration score for the subject}\right]}. \quad (1)$$

Alternately or additionally, the Composite Cancer Risk Score for the subject can be computed based on equation (2):

$$\frac{\left[\left(\text{the PTC methylation alteration score for the subject}\right)+1\right]}{\left[\left(\text{BTN methylation alteration score for the subject}\right)+1\right]} \quad (2)$$

The treatment module 620 can be configured to formulate a treatment plan for the subject based on the diagnosis generated by the diagnosis module 618. For instance, when the diagnosis generated by the diagnosis module 618 indicates a presence and/or risk of a malignant (e.g., cancerous) thyroid nodule, the treatment module 620 can prescribe one or more treatments including, for example, thyroid surgery, radiation therapy, radioactive iodine therapy, chemotherapy, thyroid hormone therapy, and administration of an active agent. In embodiments, the treatment module 620 can be configured to provide the treatment plan to the device 630 via the network 640. Alternately or additionally, the treatment module 620 can store the treatment plan in the data store 650.

The UI module 622 can be configured to generate a UI through which a user (e.g., a physician) can interface with the thyroid cancer diagnostic system 600. For example, the UI module 622 can provide one or more graphic user interfaces (GUIs) configured to display the diagnosis and/or treatment plan for the subject.

Figure 5:
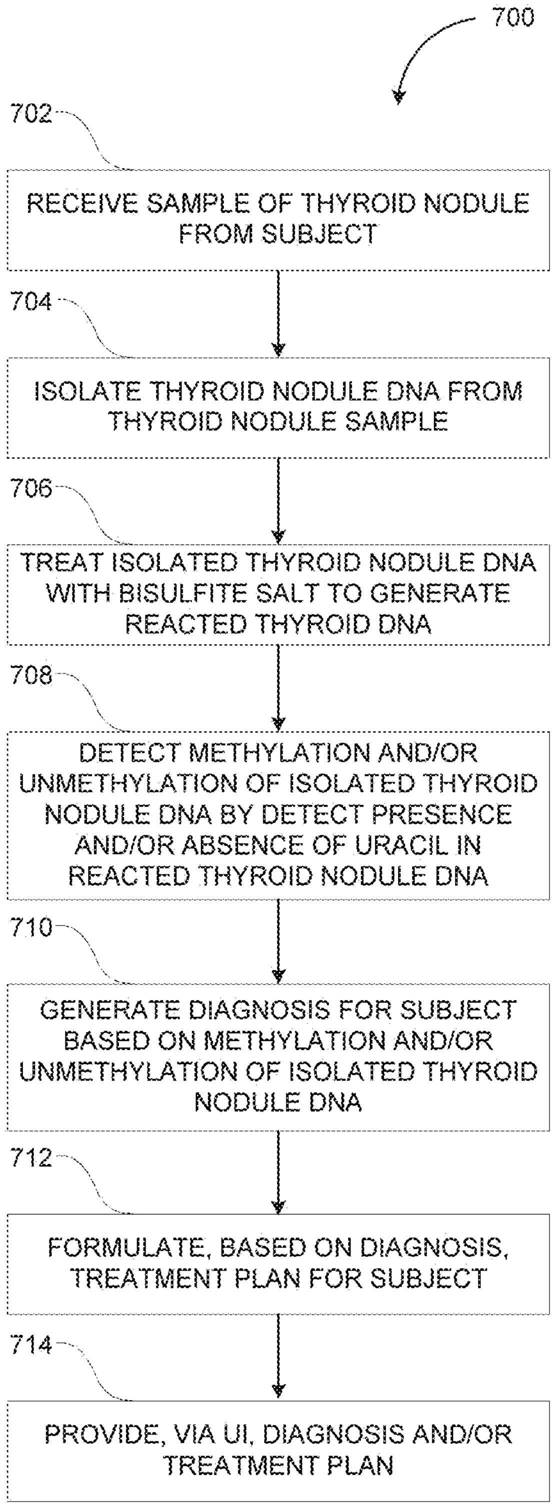
FIG. 5 depicts a flowchart illustrating an exemplary process for diagnosing thyroid cancer.

FIG. 5 depicts a flowchart illustrating an exemplary process 700 for diagnosing thyroid cancer. Referring to FIGS. 4-5, the process 700 can be performed by the thyroid cancer diagnostic system 600.

The thyroid cancer diagnostic system 600 (e.g., the input module 610) can receive a sample of a thyroid nodule from a subject (702). The thyroid cancer diagnostic system 600 (e.g., the isolation module 612) can isolate thyroid nodule DNA from the thyroid nodule sample (704). The thyroid cancer diagnostic system 600 (e.g., the conversion module 614) can treat the isolated thyroid nodule DNA with a bisulfite salt to generate reacted thyroid nodule DNA (706). Treating the isolated thyroid nodule DNA with the bisulfite salt can form a reacted thyroid nodule DNA by converting the cytosine present in the isolated thyroid nodule DNA to uracil. In embodiments, the thyroid cancer diagnostic system 600 can further process the reacted thyroid nodule DNA by desulphonating, cleansing, and/or amplifying the reacted thyroid nodule DNA.

The thyroid cancer diagnostic system 600 (e.g., the detection module 616) can detect methylation and/or unmethylation of the isolated thyroid nodule DNA by at least detecting a presence and/or absence of uracil in the reacted thyroid nodule DNA (708). In embodiments, the thyroid cancer diagnostic system 600 can be configured to detect a presence and/or absence of uracil at specific methylation sites (e.g., as set forth in Table 1). Moreover, the thyroid cancer diagnostic system 600 can be configured to detect a level of methylation and/or unmethylation at the methylation sites.

The thyroid cancer diagnostic system 600 (e.g., the diagnostics module 618) can generate a diagnosis for the subject based on the methylation and/or unmethylation of the isolated thyroid nodule DNA (710). For example, the thyroid cancer diagnostic system 600 can generate a diagnosis based on a level of methylation and/or unmethylation at a plurality of specific methylation sites. Each methylation site may be associated with a certain threshold unmethylation level (e.g., as set forth in Table 2). As such, the thyroid cancer diagnostic system 600 can determine that the thyroid nodule from the subject is malignant (e.g., cancerous) if the level of unmethylation at the plurality of methylation sites exceeds the corresponding thresholds.

The thyroid cancer diagnostic system 600 (e.g., the treatment module 620) can formulate, based on the diagnosis, a treatment plan for the subject (712). For example, when the diagnosis indicates that a presence and/or risk of malignant thyroid nodules in the subject, the thyroid cancer diagnostic system 600 can prescribe thyroid surgery, radiation therapy, radioactive iodine therapy, chemotherapy, thyroid hormone therapy, and/or administration of an active agent. The thyroid cancer diagnostic system 600 (e.g., the UI module 622) can provide, via a UI (e.g., GUI at the device 630), the diagnosis and/or the treatment plan for the subject (714).

Figure 6:
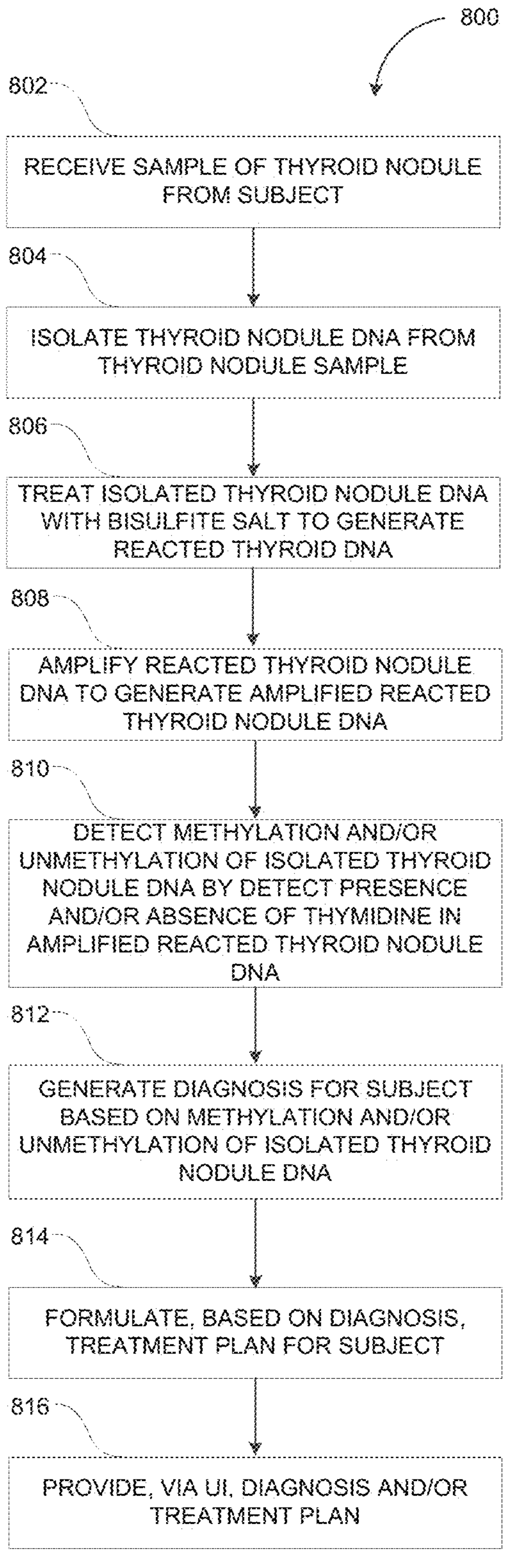
FIG. 6 depicts a flowchart illustrating an exemplary process for diagnosing thyroid cancer.

FIG. 6 depicts a flowchart illustrating an exemplary process 800 for diagnosing thyroid cancer. Referring to FIGS. 4 and 6, the process 700 can be performed by the thyroid cancer diagnostic system 600.

The thyroid cancer diagnostic system 600 (e.g., the input module 610) can receive a sample of a thyroid nodule from a subject (802). The thyroid cancer diagnostic system 600 (e.g., the isolation module 612) can isolate thyroid nodule DNA from the thyroid nodule sample (804). The thyroid cancer diagnostic system 600 (e.g., the conversion module 614) can treat the isolated thyroid nodule DNA with a bisulfite salt to generate reacted thyroid nodule DNA (806).

As shown in FIG. 6, the thyroid cancer diagnostic system 600 (e.g., the conversion module 614) can amplify the reacted thyroid nodule DNA (808). For instance, the thyroid cancer diagnostic system 600 can amplify the reacted thyroid nodule DNA subsequent to treating the isolated thyroid nodule NA with the bisulfite salt to generate the reacted thyroid nodule DNA. The thyroid cancer diagnostic system 600 can detect methylation and/or unmethylation of the isolated thyroid nodule DNA by detecting a presence and/or absence of thymidine in the amplified reacted thyroid nodule DNA (810).

The thyroid cancer diagnostic system 600 (e.g., the diagnostics module 618) can generate a diagnosis for the subject based on the methylation and/or unmethylation of the isolated thyroid nodule DNA (812). Moreover, the thyroid cancer diagnostic system 600 (e.g., the treatment module 620) can formulate, based on the diagnosis, a treatment plan for the subject (814). The thyroid cancer diagnostic system 600 (e.g., the UI module 622) can provide, via a UI, the diagnosis and/or treatment plan for the subject.

It should be appreciated that the process 700 and/or 800 can include different and/or additional operations without departing from the scope of the present subject matter. Moreover, one or more operations of the process 700 and/or 800 can be omitted and/or repeated without departing from the scope of the present subject matter.

Implementations of the present subject matter can include, but are not limited to, methods consistent with the descriptions provided above as well as articles that comprise a tangibly embodied machine-readable medium operable to cause one or more machines (e.g., computers, etc.) to result in operations implementing one or more of the described features. Similarly, computer systems are also described that can include one or more processors and one or more memories coupled to the one or more processors. A memory, which can include a computer-readable storage medium, can include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

One or more aspects or features of the subject matter described herein can be realized in digital electronic circuitry, integrated circuitry, specially designed ASICs, FPGAs, computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system can include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user can be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital MRI image capture devices and associated interpretation software, and the like.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

EMBODIMENTS

Embodiments include embodiments P1 to P41 following.

Embodiment P1

A method of detecting methylation or unmethylation of a thyroid nodule DNA of a subject, the method comprising: (i) isolating DNA from a thyroid nodule of said subject thereby forming isolated thyroid nodule DNA, (ii) contacting said isolated thyroid nodule DNA with sodium bisulfite thereby forming a reacted thyroid nodule DNA, (iii) detecting the presence or absence of uracil in said reacted thyroid nodule DNA at a methylation site set forth in Table 1, thereby detecting methylation or unmethylation of said thyroid nodule DNA of said subject.

Embodiment P2

The method of embodiment P1, further comprising determining alteration in methylation at a plurality of methylation sites set forth in Table 1.

Embodiment P3

The method of embodiment P2, said alteration comprises increase or loss of uracil level at said plurality of methylation sites.

Embodiment P4

The method of embodiment P3, wherein said uracil level is above a threshold as set forth in Table 2.

Embodiment P5

The method of embodiment P3, wherein said uracil level is above a threshold as set forth in Table 3.

Embodiment P6

The method of embodiment P3, wherein said uracil level is below a threshold as set forth in Table 4.

Embodiment P7

The method of embodiment P3, wherein said subject is a candidate thyroid cancer patient.

Embodiment P8

The method of embodiment P4, wherein said above threshold identifies said thyroid nodule as a cancerous thyroid nodule.

Embodiment P9

The method of embodiment P5, wherein said above threshold identifies said thyroid nodule as a benign thyroid nodule.

Embodiment P10

The method of embodiment P6, wherein said below threshold identifies said thyroid nodule as a benign thyroid nodule.

Embodiment P11

The method of one of the above embodiments, wherein said thyroid nodule is a specimen obtained by biopsy or by surgical resection of said subject.

Embodiment P12

The method of embodiment P11, wherein said subject has undergone thyroid surgery, radiation therapy, radioactive iodine therapy, chemotherapy, thyroid hormone therapy, and administration of an active agent.

Embodiment P13

The method of embodiment P12, wherein said active agent is chosen from Cabozantinib-S-Malate, Caprelsa (Vandetanib), Cometriq (Cabozantinib-S-Malate), Doxorubicin Hydrochloride, Lenvatinib Mesylate, Lenvima (Lenvatinib Mesylate), Nexavar (Sorafenib Tosylate). Sorafenib Tosylate, and Vandetanib.

Embodiment P14

A method of determining a thyroid cancer or risk of developing thyroid cancer in a subject in need thereof, said method comprising: (i) isolating DNA from a thyroid nodule of said subject thereby forming isolated thyroid nodule DNA; (ii) contacting said isolated thyroid nodule DNA with sodium bisulfite thereby forming a reacted thyroid nodule DNA; and (iii) detecting the presence or absence of uracil in said reacted thyroid nodule DNA at a methylation site set forth in Table 1: thereby determining said thyroid cancer in said subject.

Embodiment P15

The method of embodiment P14, further comprising selecting a subject that has or is at risk for developing thyroid cancer.

Embodiment P16

The method of embodiment P14, further comprising determining alteration in methylation at a plurality of methylation sites set forth in Table 1.

Embodiment P17

The method of embodiment P16, said alteration comprises increase or loss of uracil level at said plurality of methylation sites.

Embodiment P18

The method of embodiment P17, wherein said uracil level is above a threshold as set forth in Table 2.

Embodiment P19

The method of embodiment P17, wherein said uracil level is above a threshold as set forth in Table 3.

Embodiment P20

The method of embodiment P17, wherein said uracil level is below a threshold as set forth in Table 4.

Embodiment P21

The method of embodiment P17, wherein said subject is a candidate thyroid cancer patient.

Embodiment P22

The method of embodiment P18, wherein said above threshold identifies said thyroid nodule as a cancerous thyroid nodule.

Embodiment P23

The method embodiment P19, wherein said above threshold identifies said thyroid nodule as a benign thyroid nodule.

Embodiment P24

The method of embodiment P20, wherein said below threshold identifies said thyroid nodule as a benign thyroid nodule.

Embodiment P25

The method of embodiments P14-P24, wherein said thyroid nodule is a specimen obtained by biopsy or by surgical resection of said subject.

Embodiment P26

The method of embodiment P25, wherein said subject has undergone thyroid surgery, radiation therapy, radioactive iodine therapy, chemotherapy, thyroid hormone therapy, and administration of an active agent, before said determination.

Embodiment P27

The method of embodiment P26, wherein said active agent is chosen from Cabozantinib-S-Malate, Caprelsa (Vandetanib), Cometriq (Cabozantinib-S-Malate), Doxorubicin Hydrochloride. Lenvatinib Mesylate, Lenvima (Lenvatinib Mesylate), Nexavar (Sorafenib Tosylate). Sorafenib Tosylate, and Vandetanib.

Embodiment P28

A method of treating thyroid cancer in a subject determined by the method as set forth in embodiment P22, comprising administering to said subject an active agent for treating thyroid cancer.

Embodiment P29

The method of embodiment P28, wherein said subject has undergone surgery, radiation therapy, radioactive iodine therapy, chemotherapy, or thyroid hormone therapy, before said detection of embodiment 14 at (iii).

Embodiment P30

The method of embodiment P29, wherein said active agent is chosen from Cabozantinib-S-Malate. Caprelsa (Vandetanib), Cometriq (Cabozantinib-S-Malate), Doxorubicin Hydrochloride, Lenvatinib Mesylate, Lenvima (Lenvatinib Mesylate), Nexavar (Sorafenib Tosylate), Sorafenib Tosylate, and Vandetanib.

Embodiment P31

The method of one of above embodiments, wherein said subject has or is at risk of papillary thyroid cancer, follicular thyroid cancer, medullary thyroid cancer, or anaplastic thyroid cancer.

Embodiment P32

A deoxyribonucleic acid 5 to 100 nucleotides in length comprising a uracil-containing sequence identical to at least a 5 contiguous nucleotide sequence within a sequence chosen from SEQ ID NO:1 to SEQ ID NO:550.

Embodiment P33

The deoxyribonucleic acid of embodiment P32 identical to 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, or 190-200 of contiguous nucleotide sequence of said sequence chosen from SEQ ID NO:1 to SEQ ID NO:550.

Embodiment P34

The deoxyribonucleic acid of embodiment P32 or P33, wherein said sequence comprises a methylation site set forth in Table 2.

Embodiment P35

The deoxyribonucleic acid of embodiment P34, wherein a plurality of methylation sites set forth in Table 2 are methylated or unmethylated.

Embodiment P36

A deoxyribonucleic acid chosen from SEQ ID NO:551 to SEQ ID NO:782, wherein said nucleic acid is hybridized to a complementary DNA sequence comprising uridine or cytosine.

Embodiment P37

The deoxyribonucleic acid of embodiment P36, further comprising an enzyme in a complex with said hybridized complementary DNA sequence.

Embodiment P38

The deoxyribonucleic acid of embodiment P37, wherein said enzyme is Taq polymerase.

Embodiment P39

A kit comprising 322 nucleic acids each independently comprising SEQ ID NO:551 to SEQ ID NO:782, wherein said nucleic acids do not simultaneously comprise the same SEQ ID NO:551 to SEQ ID NO:782.

Embodiment P40

The kit according to embodiment P39, further comprising: enzymes, reagents for deamination of cytosine, buffers, vials, plasmid vectors, control DNA, devices for collecting thyroid tissue samples, reagents for isolating DNA, reagents for labeling DNA, or any combinations thereof.

Embodiment P41

The kit according to embodiment P40, wherein the enzymes are selected from the group consisting of: thermostable DNA polymerase enzymes, restriction enzymes, and combination thereof.

Further embodiments include embodiments 1-58 following.

Embodiment 1

A method of detecting methylation or unmethylation of a thyroid nodule DNA molecule of a subject, the method comprising: (i) isolating a thyroid nodule DNA molecule from a thyroid nodule of said subject thereby forming an isolated thyroid nodule DNA molecule. (ii) contacting said isolated thyroid nodule DNA molecule with a bisulfite salt thereby forming a reacted thyroid nodule DNA molecule, (iii) detecting the presence or absence of uracil in said reacted thyroid nodule DNA molecule at a methylation site set forth in Table 1, thereby detecting methylation or unmethylation of said thyroid nodule DNA molecule of said subject.

Embodiment 2

The method of embodiment 1, further comprising detecting the presence or absence of uracil in said reacted thyroid nodule DNA molecule at a plurality of methylation sites set forth in Table 1, wherein said methylation site forms a part of said plurality of methylation sites.

Embodiment 3

The method of embodiment 1, the method further comprising: (i) isolating a plurality of thyroid nodule DNA molecules from said thyroid nodule of said subject thereby forming a plurality of isolated thyroid nodule DNA molecules, wherein said isolated thyroid nodule DNA molecule forms part of said plurality of isolated thyroid nodule DNA molecules, (ii) contacting said plurality of isolated thyroid nodule DNA molecules with said bisulfite salt thereby forming a plurality of reacted thyroid nodule DNA molecules, wherein said reacted thyroid nodule DNA molecule forms part of said plurality of reacted thyroid nodule DNA molecules, (iii) detecting the level of reacted thyroid nodule DNA molecules in said plurality of reacted thyroid nodule DNA molecules having a uracil at a methylation site set forth in Table 1, thereby detecting the level of methylation or unmethylation in said plurality of thyroid nodule DNA molecules of said subject.

Embodiment 4

The method of embodiment 3, further comprising determining the level of uracil in said reacted thyroid nodule DNA molecule at a plurality methylation sites set forth in Table 1, wherein said methylation site forms a part of said plurality of methylation sites.

Embodiment 5

The method of embodiment 4, wherein said uracil level is above a threshold as set forth in Table 2.

Embodiment 6

The method of embodiment 4, wherein said uracil level is above a threshold as set forth in Table 3.

Embodiment 7

The method of embodiment 4, wherein said uracil level is below a threshold as set forth in Table 4.

Embodiment 8

The method of one of the above embodiments, wherein said subject is suspected of having thyroid cancer.

Embodiment 9

The method of one of the above embodiments, wherein said thyroid nodule is a specimen obtained by biopsy or by surgical resection of said subject.

Embodiment 10

The method of one of the above embodiments, wherein said subject has undergone thyroid surgery, radiation therapy, radioactive iodine therapy, chemotherapy, thyroid hormone therapy, and/or administration of an active agent.

Embodiment 11

The method of embodiment 10, wherein said active agent is chosen from Cabozantinib-S-Malate, Caprelsa (Vandetanib), Cometriq (Cabozantinib-S-Malate). Doxorubicin Hydrochloride. Lenvatinib Mesylate, Lenvima (Lenvatinib Mesylate), Nexavar (Sorafenib Tosylate), Sorafenib Tosylate, and/or Vandetanib.

Embodiment 12

A method of detecting a thyroid cancer or risk of developing thyroid cancer in a subject in need thereof, said method comprising:

(i) isolating a thyroid nodule DNA molecule from a thyroid nodule of said subject thereby forming an isolated thyroid nodule DNA molecule;
(ii) contacting said isolated thyroid nodule DNA molecule with a bisulfite salt thereby forming a reacted thyroid nodule DNA molecule; and
(iii) detecting the presence or absence of uracil in said reacted thyroid nodule DNA molecule at a methylation site set forth in Table 1; thereby detecting said thyroid cancer in said subject.

Embodiment 13

The method of embodiment 12, wherein said subject (a) is a woman; (b) is about 20 to about 55 years old; (c) has a mutated Ret Proto-Oncogene; (d) has a grandparent, parent, or sibling who has been diagnosed with thyroid cancer; (e) self-identifies as being Caucasian or Asian; and/or (f) has or has had breast cancer.

Embodiment 14

The method of embodiment 12, further comprising detecting the presence or absence of uracil in said reacted thyroid nodule DNA molecule at a plurality of methylation sites set forth in Table 1, wherein said methylation site forms a part of said plurality of methylation sites.

Embodiment 15

The method of embodiment 12, the method further comprising: (i) isolating a plurality of thyroid nodule DNA molecules from said thyroid nodule of said subject thereby forming a plurality of isolated thyroid nodule DNA molecules, wherein said isolated thyroid nodule DNA molecule forms part of said plurality of isolated thyroid nodule DNA molecules, (ii) contacting said plurality of isolated thyroid nodule DNA molecules with said bisulfite salt thereby forming a plurality of reacted thyroid nodule DNA molecules, wherein said reacted thyroid nodule DNA molecule forms part of said plurality of reacted thyroid nodule DNA molecules, (iii) detecting the level of reacted thyroid nodule DNA molecules in said plurality of reacted thyroid nodule DNA molecules having a uracil at a methylation site set forth in Table 1; thereby detecting said thyroid cancer in said subject.

Embodiment 16

The method of embodiment 15, further comprising determining the level of uracil in said reacted thyroid nodule DNA molecule at a plurality methylation sites set forth in Table 1, wherein said methylation site forms a part of said plurality of methylation sites.

Embodiment 17

The method of embodiment 16, wherein said uracil level is above a threshold as set forth in Table 2.

Embodiment 18

The method of embodiment 16, wherein said uracil level is above a threshold as set forth in Table 3.

Embodiment 19

The method of embodiment 16, wherein said uracil level is below a threshold as set forth in Table 4.

Embodiment 20

The method of one of the above embodiments, wherein said subject is suspected of having thyroid cancer.

Embodiment 21

The method of one of the above embodiments, wherein said thyroid nodule is a specimen obtained by biopsy or by surgical resection of said subject.

Embodiment 22

The method of one of the above embodiments, wherein said subject has undergone thyroid surgery, radiation therapy, radioactive iodine therapy, chemotherapy, thyroid hormone therapy, and administration of an active agent, before said determination.

Embodiment 23

The method of embodiment 22, wherein said active agent is chosen from Cabozantinib-S-Malate, Caprelsa (Vandetanib), Cometriq (Cabozantinib-S-Malate), Doxorubicin Hydrochloride, Lenvatinib Mesylate, Lenvima (Lenvatinib Mesylate), Nexavar (Sorafenib Tosylate), Sorafenib Tosylate, and.

Embodiment 24

A method of treating thyroid cancer in a subject determined by the method as set forth in any of embodiments 12 to 23, comprising administering to said subject an active agent for treating thyroid cancer.

Embodiment 25

The method of embodiment 24, wherein said subject has undergone surgery, radiation therapy, radioactive iodine therapy, chemotherapy, or thyroid hormone therapy, before said detection of claim 12 at (iii).

Embodiment 26

The method of embodiment 25, wherein said active agent is chosen from Cabozantinib-S-Malate. Caprelsa (Vandetanib), Cometriq (Cabozantinib-S-Malate). Doxorubicin Hydrochloride. Lenvatinib Mesylate, Lenvima (Lenvatinib Mesylate), Nexavar (Sorafenib Tosylate). Sorafenib Tosylate, and Vandetanib.

Embodiment 27

The method of one of the above embodiments, wherein said subject has or is at risk of papillary thyroid cancer, follicular thyroid cancer, medullary thyroid cancer, or anaplastic thyroid cancer.

Embodiment 28

The method of one of the above embodiments, wherein said bisulfite salt is sodium bisulfite.

Embodiment 29

The method of one of the above embodiments, further comprising determining a papillary thyroid carcinoma (PTC) methylation alteration score for said subject, wherein the PTC methylation alteration score is equal to: the number of methylation sites in Table 1 having a uracil level equal to or greater than the corresponding threshold level set forth in Table 2.

Embodiment 30

The method of one of the above embodiments, further comprising determining a benign thyroid nodule (BTN) methylation alteration score for said subject, wherein the BTN methylation alteration score is equal to:

(a) the number of methylation sites in Table 1 having a uracil level equal to or greater than the corresponding threshold level set forth in Table 3;

(b) the number of methylation sites in Table 1 having a uracil level equal to or less than the corresponding threshold level set forth in Table 4; or (c) the number of methylation sites in Table 1 having a uracil level equal to or greater than the corresponding threshold level set forth in Table 3 plus the number of methylation sites in Table 1 having a uracil level equal to or less than the corresponding threshold level set forth in Table 4.

Embodiment 31

The method of embodiment 29, further comprising calculating a Composite Cancer Risk Score for said subject.

Embodiment 32

The method of embodiment 31, wherein said Composite Cancer Risk Score for said subject equals:

[the PTC methylation alteration score for said subject]/[BTN methylation alteration score for said subject].

Embodiment 33

The method of embodiment 31, wherein said Composite Cancer Risk Score for said subject equals:

[(the PTC methylation alteration score for said subject)+1]/[(BTN methylation alteration score for said subject)+1].

Embodiment 34

The method of one of embodiments 29 to 33, wherein said subject is identified as being at risk of developing thyroid cancer or diagnosed as having thyroid cancer if (a) the PTC methylation alteration score for said subject is at least 5, 6, 7, 8, 9, or 10; (b) the BTN methylation alteration score for said subject is at least 5, 6, 7, 8, 9, or 10; and/or (c) the Composite Cancer Risk Score for said subject is at least about 2, 2.1, 2.2, 2.3, 2.4, 2.5, 2.6, 2.7, 2.8, 2.9, or 3.0.

Embodiment 35

The method of one of embodiments 29 to 33, wherein said subject is treated for thyroid cancer or directed to receive additional screening for thyroid cancer if (a) the PTC methylation alteration score for said subject is at least 5, 6, 7, 8, 9, or 10; (b) the BTN methylation alteration score for said subject is at least 5, 6, 7, 8, 9, or 10; and/or (c) the Composite Cancer Risk Score for said subject is at least about 2, 2.1, 2.2, 2.3, 2.4, 2.5, 2.6, 2.7, 2.8, 2.9, or 3.0.

Embodiment 36

A deoxyribonucleic acid at least 5 to 100 nucleotides in length comprising a uracil-containing sequence that is identical to a sequence of at least a 5 contiguous nucleotides within a sequence chosen from SEQ ID NO: 1 to SEQ ID NO:550.

Embodiment 37

The deoxyribonucleic acid of embodiment 36, comprising a uracil-containing sequence that is identical to a sequence of at least 5-10, 10-20, 20-30, 30-40, 40-50, 50-60, 60-70.70-80, 80-90, 90-100, 100-110, 110-120, 120-130, 130-140, 140-150, 150-160, 160-170, 170-180, 180-190, or 190-200 contiguous nucleotides within said sequence chosen from SEQ ID NO:1 to SEQ ID NO:550.

Embodiment 38

The deoxyribonucleic acid of embodiment 36 or 37, wherein said sequence comprises a methylation site set forth in Table 1.

Embodiment 39

The deoxyribonucleic acid of one of embodiments 36 to 38, wherein a plurality of methylation sites set forth in Table 1 contain a uracil or a cytosine.

Embodiment 40

A deoxyribonucleic acid chosen from SEQ ID NO:551 to SEQ ID NO:782, wherein said nucleic acid is hybridized to a complementary DNA sequence comprising uridine or cytosine.

Embodiment 41

The deoxyribonucleic acid of embodiment 40, further comprising an enzyme in a complex with said hybridized complementary DNA sequence.

Embodiment 42

The deoxyribonucleic acid of embodiment 41, wherein said enzyme is Taq polymerase.

Embodiment 43

A kit comprising a plurality of nucleic acids each independently comprising SEQ ID NO:551 to SEQ ID NO:782, wherein each nucleic acid of said plurality is unique.

Embodiment 44

The kit according to embodiment 43, further comprising: an enzyme, a reagent for deamination of cytosine, a buffer, a vial, a plasmid vector, a control DNA, a device for collecting a thyroid tissue sample, a reagent for isolating DNA, a reagent for labeling DNA, or any combination thereof.

Embodiment 45

The kit according to embodiment 44, wherein the enzyme comprises a thermostable DNA polymerase enzyme and/or a restriction enzyme.

Embodiment 46

A system for detecting methylation or unmethylation of a thyroid nodule deoxyribonucleic acid (DNA) of a subject, the system comprising:

at least one processor; and at least one memory including program code which when executed by the at least one memory provides operations comprising:

isolating a thyroid nodule DNA molecule from a thyroid nodule of said subject thereby forming an isolated thyroid nodule DNA molecule;

contacting said isolated thyroid nodule DNA molecule with a bisulfite salt thereby forming a reacted thyroid nodule DNA molecule;

detecting the presence or absence of uracil in said reacted thyroid nodule DNA molecule at a methylation site set forth in Table 1, thereby detecting methylation or unmethylation of said thyroid nodule DNA molecule of said subject;

generating a diagnosis for said subject based at least in part on the presence or absence of uracil in said reacted thyroid nodule DNA molecule at the methylation site set forth in Table 1; and providing, via a user interface, the diagnosis for said subject.

Embodiment 47

The system of embodiment 46, wherein the system is further configured to detect the presence or absence of uracil in said reacted thyroid nodule DNA molecule at a plurality of methylation sites set forth in Table 1, wherein said methylation site forms a part of said plurality of methylation sites.

Embodiment 48

The system of embodiment 46, wherein the system is further configured to: (i) isolate a plurality of thyroid nodule DNA molecules from said thyroid nodule of said subject thereby forming a plurality of isolated thyroid nodule DNA molecules, wherein said isolated thyroid nodule DNA molecule forms part of said plurality of isolated thyroid nodule DNA molecules, (ii) contact said plurality of isolated thyroid nodule DNA molecules with said bisulfite salt thereby forming a plurality of reacted thyroid nodule DNA molecules, wherein said reacted thyroid nodule DNA molecule forms part of said plurality of reacted thyroid nodule DNA molecules, (iii) detect the level of reacted thyroid nodule DNA molecules in said plurality of reacted thyroid nodule DNA molecules having a uracil at a methylation site set forth in Table 1, thereby detecting the level of methylation or unmethylation in said plurality of thyroid nodule DNA molecules of said subject.

Embodiment 49

The system of embodiment 48, wherein the system is further configured to detect the level of uracil in said reacted thyroid nodule DNA molecule at a plurality methylation sites set forth in Table 1, wherein said methylation site forms a part of said plurality of methylation sites.

Embodiment 50

The system of embodiment 49, wherein said uracil level is above a threshold as set forth in Table 2.

Embodiment 51

The system of embodiment 49, wherein said uracil level is above a threshold as set forth in Table 3.

Embodiment 52

The system of embodiment 49, wherein said uracil level is below a threshold as set forth in Table 4.

Embodiment 53

The system of embodiment 49, wherein said subject is a candidate thyroid cancer patient.

Embodiment 54

The system of one of embodiments 46 to 53, wherein said thyroid nodule is a specimen obtained by biopsy or by surgical resection of said subject.

Embodiment 55

The system of one of embodiments 46 to 54, wherein said subject has undergone thyroid surgery, radiation therapy, radioactive iodine therapy, chemotherapy, thyroid hormone therapy, and/or administration of an active agent.

Embodiment 56

The system of embodiment 55, wherein said active agent is chosen from Cabozantinib-S-Malate, Caprelsa (Vandetanib), Cometriq (Cabozantinib-S-Malate), Doxorubicin Hydrochloride, Lenvatinib Mesylate, Lenvima (Lenvatinib Mesylate), Nexavar (Sorafenib Tosylate), Sorafenib Tosylate, and Vandetanib.

Embodiment 57

The system of one of embodiments 46 to 56, wherein the system is further configured to:

formulate, based at least in part on the diagnosis, a treatment plan for said subject; and provide, via the user interface, the treatment plan.

Embodiment 58

The system of embodiment 57, wherein the treatment plan includes one or more of thyroid surgery, radiation therapy, radioactive iodine therapy, chemotherapy, thyroid hormone therapy, and administration of an active agent.

EXAMPLES

Example 1

Human frozen specimens were blindly evaluated by a pathologist. In the study, 28 benign nodules and 40 thyroid cancer specimens were analyzed.

DNA Methylation Profiling

Genomic DNA was isolated by using a standard phenol/chloroform extraction approach followed by ethanol precipitation. Further, genomic DNA underwent Reduced Representation Bisulfite Sequencing (RRBS) procedure. RRBS DNA amplicons were paired-end sequenced by using Hiseq 2500 (Illumina). For each sample, at least 15 million aligned reads were obtained. BTN and PTC specific signatures were determined based on cytosines which are characterized by at least 5 sequencing reads in each sample.

Identification of BTN Specific and PTC Specific DNA Methylation Changes

Figure 1A:
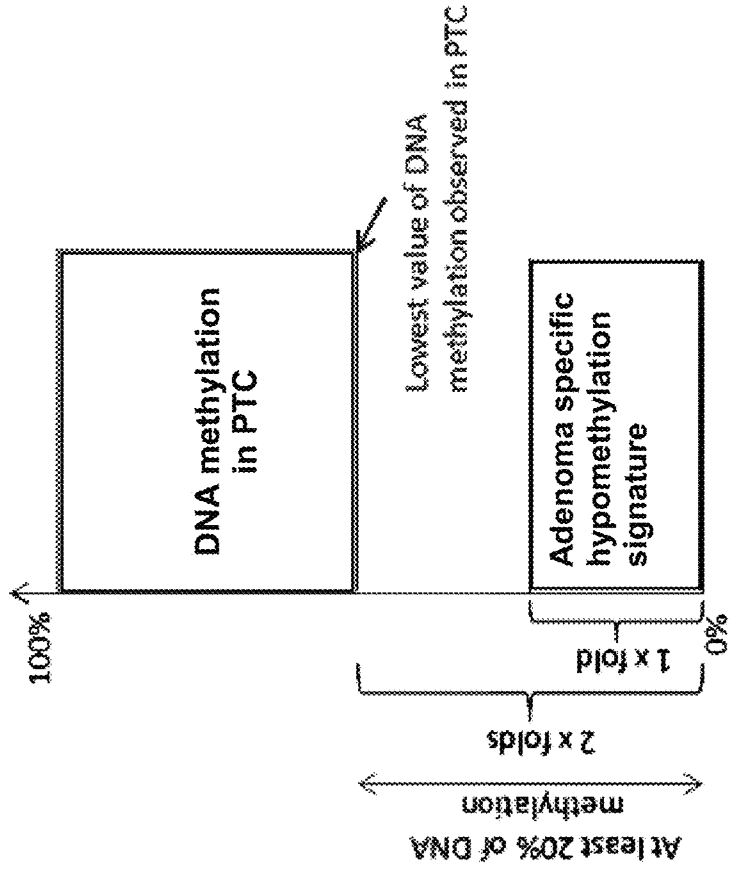

DNA methylation patterns were analyzed in 114 thyroid specimens including 28 benign nodules, 40 thyroid cancer, and 46 adjacent normal thyroid tissues, to identify the presence of thyroid cancer specific and benign nodule specific signatures. After genome alignment, a search was performed for DNA regions which have BTN or PTC specific alterations. For identification of a DNA region with a BTN specific loss of DNA methylation, DNA regions were identified which had a DNA methylation level in at least 6 out 28 that was at least 2-fold less than the level of methylation in the same DNA region any analyzed PTC specimen, where the lowest value of DNA methylation at this DNA region among all PTC specimens is 20% or higher (FIG. 1A). For identification of DNA regions with BTN specific DNA methylation accumulation, the following criteria were used; a level of DNA methylation in an individual BTN that is at least 2-fold higher than the level of DNA methylation in the same DNA region in any analyzed PTC; where the value of DNA methylation of analyzed BTN specimen is at least 20% or more greater (FIG. 1B). The BTN signature includes DNA regions which were affected by DNA methylation loss in at least 6 out 28 analyzed BTN samples and regions which were affected by DNA methylation accumulation in at least 6 out 28 analyzed BTN samples.

Further, regions were determined which undergo PTC specific DNA methylation alterations. The criteria for the identification of DNA regions with a PTC specific loss of DNA methylation, was: a level of DNA methylation in 6 out of 46 PTC that is 2-fold less than in any analyzed adenoma and any normal matching tissue, where the lowest value of DNA methylation in the region among all non-malignant specimens is 20% or higher. The criteria for the identification of DNA regions with PTC specific DNA methylation accumulation was a level of DNA methylation in an individual PTC that is at least 2-fold higher than the level of methylation in any analyzed adenoma and normal matching tissue, where the value of DNA methylation in analyzed PTC sample should be 20% or higher. There were no DNA regions that were affected by DNA methylation accumulation in at least 6 PTC out 46 analyzed PTC. Therefore, the PTC specific DNA methylation signatures contain only DNA regions which are affected by DNA methylation loss in at least 6 out 46 analyzed PTC.

Figure 2A:
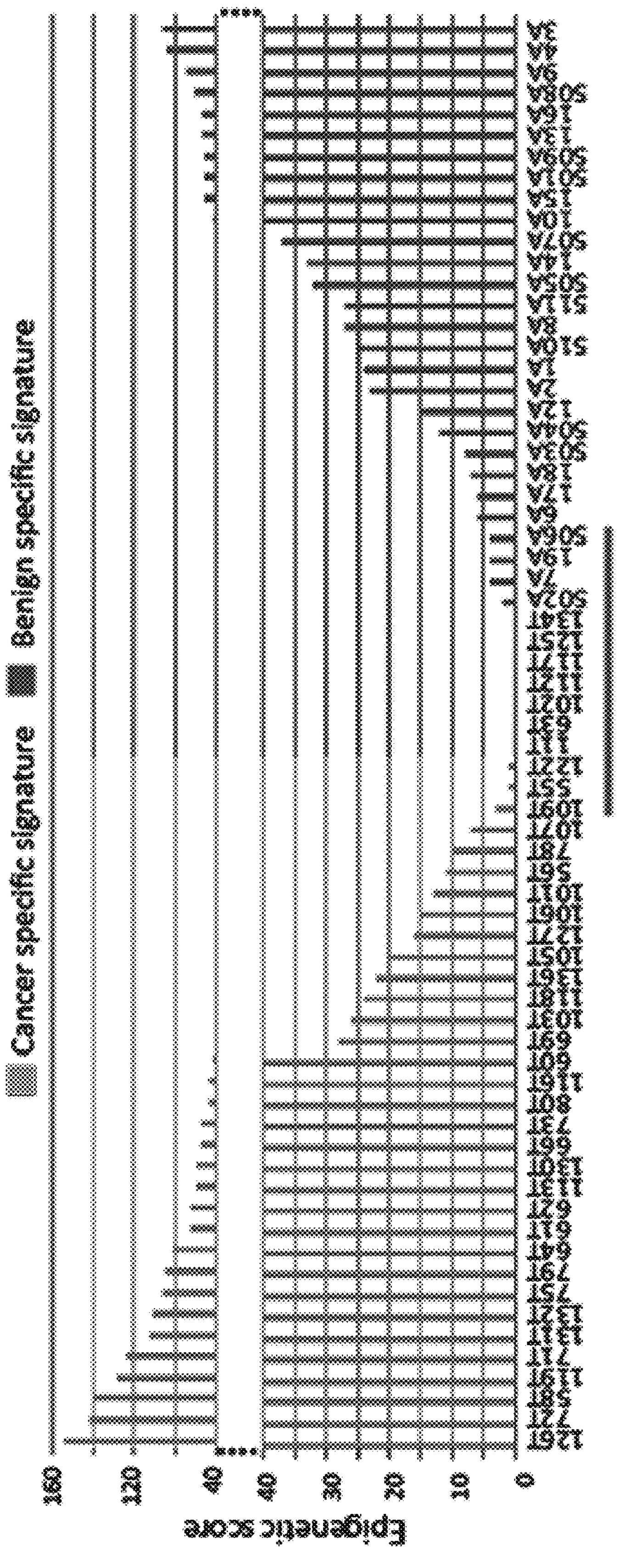
FIGS. 2A and 2B show 364 cytosines associated with BTN or PTC specific DNA methylation changes. Legend (FIG. 2A): Cancer specific signature (gray); benign specific signature (black).

The total number of identified DNA regions which fall in PTC specific or BTN specific signature is 258, which comprises DNA methylation information for 364 cytosines (FIG. 2A). There are 230 cytosines which characterize the PTC signature and 134 cytosines characterizing the BTN signature.

Evaluation of the cancer specific and benign specific changes revealed that 10 out of 40 thyroid cancer specimens are characterized by few (less than 5) or no cancer specific changes, and 4 out 28 benign nodules indicated very few (less than 5) benign specific changes (FIG. 2A). Since the approach described herein is based on the identification of the tissue specific alterations, these specimens were determined to be "epigenetically indeterminate."

Figure 2B:
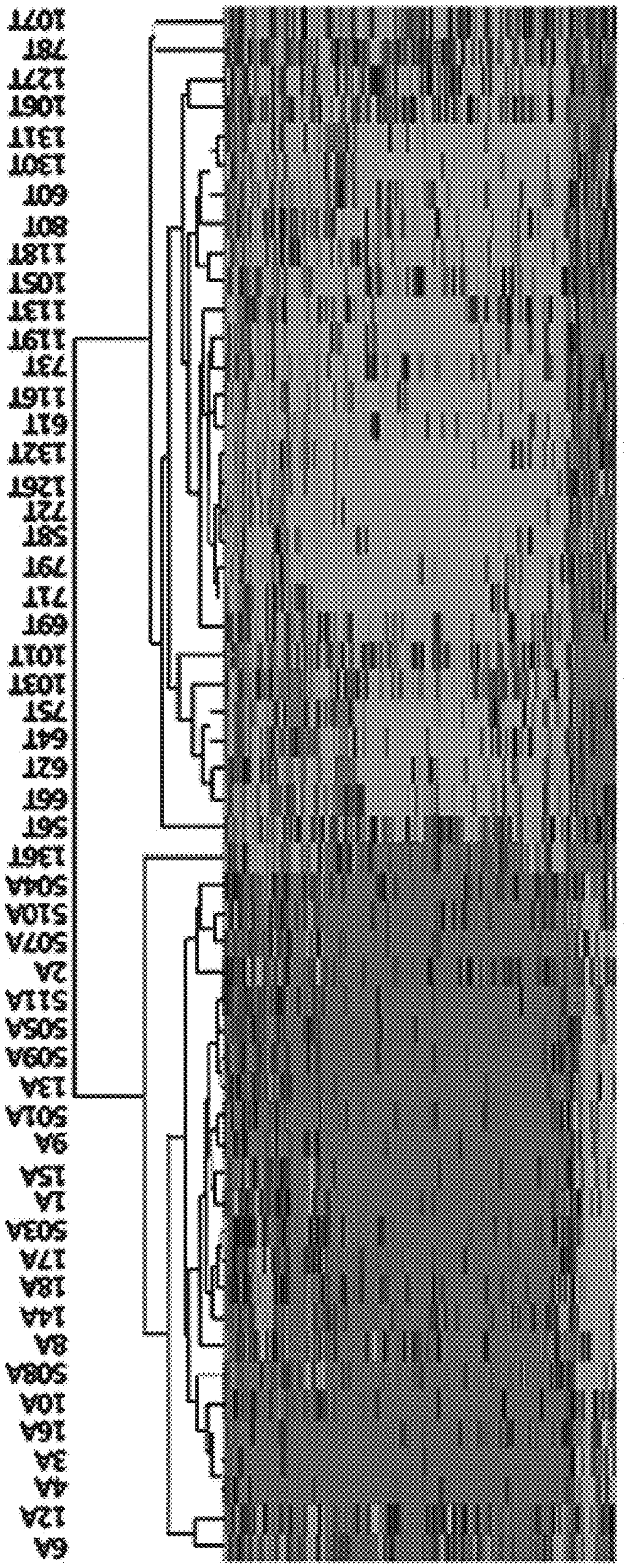

For specimens with a determinate epigenetic state, clustering analysis revealed a strict separation of thyroid cancer from benign nodules based on DNA methylation levels of cytosines associated with benign and cancer scores (FIG. 2B). Thus, the use of benign and cancer scores can provide a unique thyroid nodule diagnostic tool.

Development of Diagnostic Panel Based on BTN/PTC Signature Scores.

The data disclosed herein demonstrates that analysis of DNA methylation of one or more of 258 DNA regions can provide substantial information regarding a presence of malignancy in thyroid samples. Therefore, DNA methylation analysis within BTN and PTC signature can be used as a PTC diagnostic tool. According to the data, PTC diagnosis can be made by using both BTN and PTC signatures. Each signature can be a score based on the number of specific alterations within the signature for each individual sample. For example, the number of BTN specific alterations within BTN signature DNA regions reflects a BTN signature score. At the same time, the number of PTC specific alterations for DNA regions within PTC signature group indicates PTC signature score.

In order to validate the approach disclosed herein and estimate an accuracy of the proposed signatures, a statistical analysis was performed based on the leave-one-out-cross-validation technique. Specifically, cancer and benign scores were determined for each individual nodule by using benign and cancer signatures which were developed based on DNA methylation patterns of the rest of samples excluding the testing sample. In order to predict benign and cancer scores for 68 nodules, 68 benign and cancer unique predictive signatures were developed.

Figure 3A:
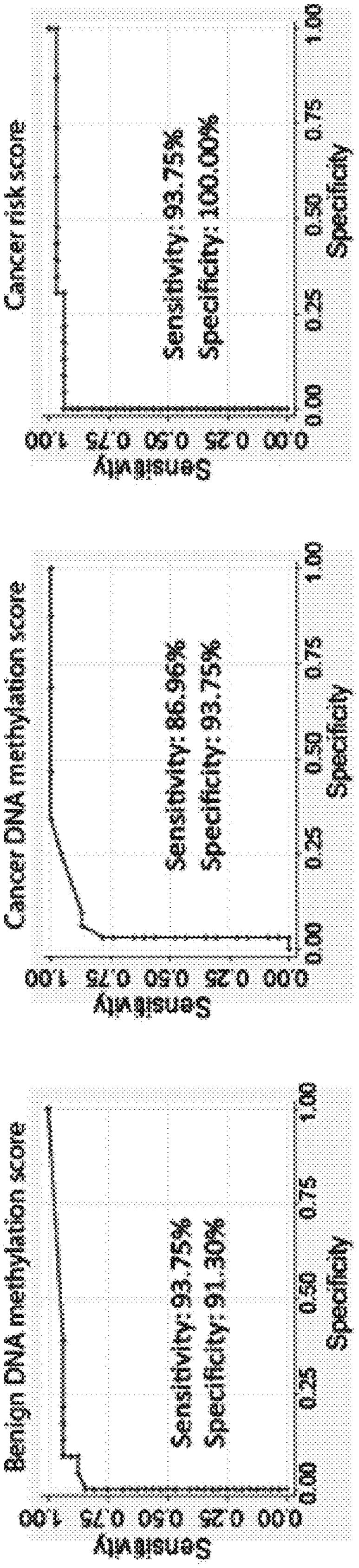
FIGS. 3A-3C depict exemplary thyroid cancer diagnostics based on DNA methylation signatures.

After cross-validation. DNA methylation signatures (score >=5) were observed in 80% (32 out 40) of thyroid cancers and 82% (23 out 28) of benign nodules (FIG. 3A). These specimens with a determinate epigenetic state were used for the further analysis.

According to the cross-validation observations, both, benign and malignant diagnostic scores provided accurate results for thyroid nodule diagnostics (FIG. 3A). However, a combining of benign and malignant scores into a cancer risk score is associated with even higher diagnostic performance. The cancer risk score was calculated using the following equation: Cancer Risk Score=(cancer score+1)/(benign score+1)

Figure 3B:
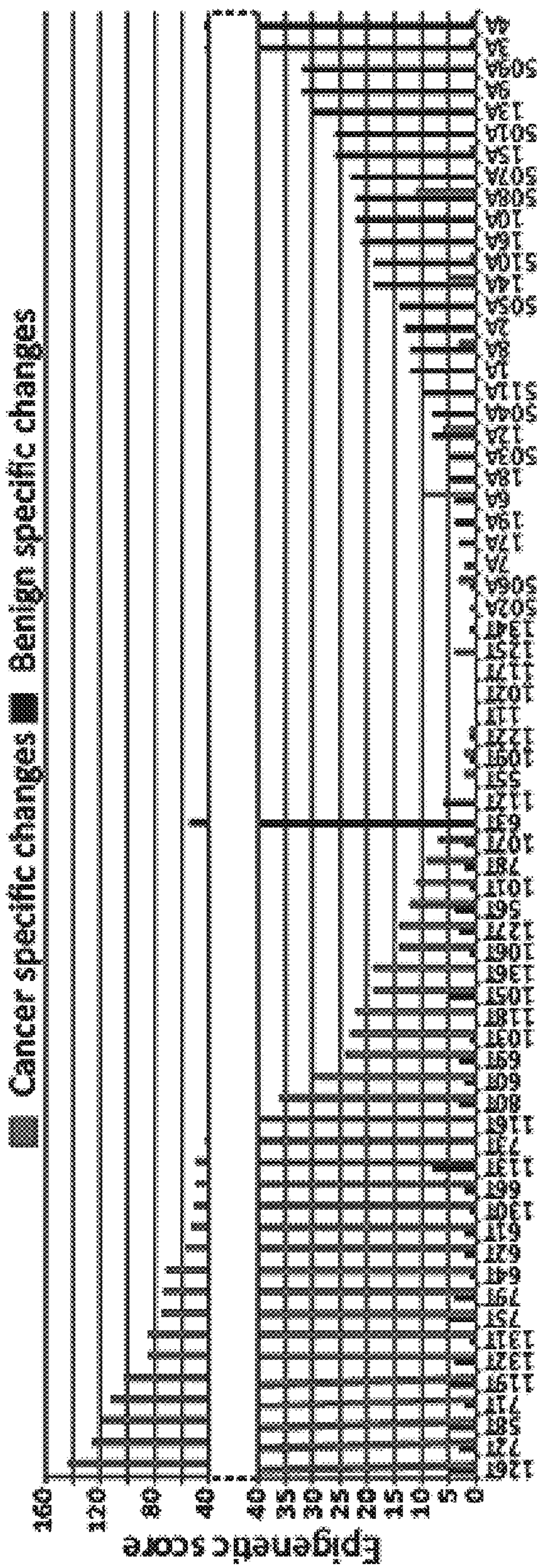

According to the data herein, specimens with cancer risk score above 2.6 represent thyroid cancer and specimens with cancer score below 2.6 are benign nodules. Based on these criteria, all 23 nodules were correctly diagnosed as benign and 30 out 32 thyroid malignancies were diagnosed as a cancer (FIG. 3B). Therefore, the test had a specificity of 100% and a sensitivity of 94%, with a 100% positive predictive value (PPV) and a 92% negative predictive value (NPV). These data suggest that DNA methylation analysis of 258 DNA regions in thyroid specimens can serve as a potential diagnostic tool for the determination of malignancy.

Figure 3C:
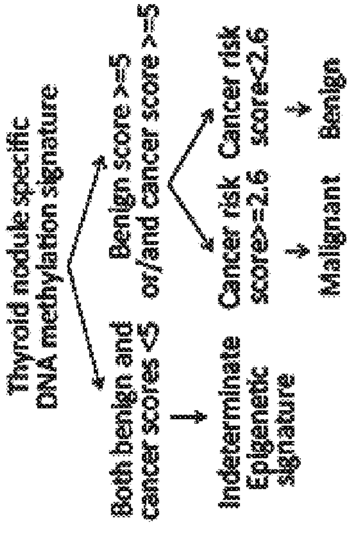

An algorithm for performing a thyroid nodule diagnostic evaluation is shown in FIG. 3C. Specimens with benign and malignant signatures are associated with indeterminate epigenetic state and were excluded from the study. Specimens with a cancer risk score above 2.6 are considered to be malignant, and thyroid nodules with a cancer risk score below 2.6 are considered to be benign.

This scoring approach clearly differentiates benign from malignant specimens. These data suggest that DNA methylation analysis of 258 DNA regions in thyroid specimens, including potentially FNA specimens, can serve as a diagnostic tool for the determination of malignancy.

The data indicates that malignancy of thyroid specimens can be determined by DNA methylation pattern analysis of one or more of 258 different DNA regions.

What is claimed is:

1. A method of measuring methylation levels of DNA molecules of a human subject, the method comprising:

(i) isolating DNA molecules from a thyroid nodule of said subject thereby forming isolated thyroid nodule DNA molecules, (ii) contacting said isolated thyroid nodule DNA molecules with a bisulfite salt thereby forming reacted thyroid nodule DNA molecules, and (iii) measuring methylation levels by detecting the presence of cytosine or uracil in said reacted thyroid nodule DNA molecules at the following chromosomal positions:

chr2 position 42329494, chr17 position 48596391, chr20 position 62588571, chr15 position 77989064, chr16 position 23135833, chr20 position 31126189, chr22 position 38307317, chr19 position 3434939, chr16 position 3023231, chr17 position 1509945, and chr16 position 1458639 with respect to human genome assembly hg19 using a detection assay, wherein the detection assay comprises amplifying thyroid nodule DNA molecules by contacting the DNA with a primer complementary to a sequence at or within 1000 nucleotides of the chromosomal positions to produce amplicons thereof to be detected.

2. The method of claim 1, further comprising detecting the presence of cytosine or uracil at one or more additional chromosomal positions with respect to HG19 reference genome selected from Chr1 position 2996653, Chr1 position 11979164, Chr1 position 12655938, Chr1 position 16450525, Chr1 position 16450542, Chr1 position 16450545, Chr1 position 16469987, Chr1 position 17494491, Chr1 position 25473203, Chr1 position 27640460, Chr1 position 29565080, Chr1 position 38493013, Chr1 position 38493030, Chr1 position 38493074, Chr1 position 46713777, Chr1 position 46914121, Chr1 position 46955744, Chr1 position 55008344, Chr1 position 109816092, Chr1 position 109816111, Chr1 position 110074669, Chr1 position 110074681, Chr1 position 110074685, Chr1 position 150949856, Chr1 position 150949857, Chr1 position 153540282, Chr1 position 155162704, Chr1 position 155162714, Chr1 position 156676611, Chr1 position 157611881, Chr1 position 182205324, Chr1 position 204118999, Chr1 position 206741875, Chr1 position 206741989, Chr1 position 212587673, Chr1 position 212841198, Chr1 position 223403952, Chr1 position 233430972, Chr1 position 234342767, Chr2 position 3454277, Chr2 position 8793724, Chr2 position 20412441, Chr2 position 42329402, Chr2 position 55289272, Chr2 position 65064865, Chr2 position 70823641, Chr2 position 73143689, Chr2 position 74454110, Chr2 position 122014529, Chr2 position 128158884, Chr2 position 128158910, Chr2 position 203114171, Chr2 position 218221671, Chr2 position 219745335, Chr2 position 238341465, Chr2 position 238341542, Chr2 position 238341546, Chr2 position 238774763, Chr3 position 13323642, Chr3 position 14180153, Chr3 position 45209073, Chr3 position 45209207, Chr3 position 52525100, Chr3 position 62589658, Chr3 position 65388317, Chr3 position 65388388, Chr3 position 73599302, Chr3 position 195636893, Chr3 position 197093846, Chr4 position 3743223, Chr4 position 5755716, Chr4 position 5755717, Chr4 position 5755728, Chr4 position 5755729, Chr4 position 5755734, Chr4 position 8372861, Chr4 position 57548289, Chr5 position 1118280, Chr5 position 34564389, Chr5 position 73871907, Chr5 position 78013596, Chr5 position 78013643, Chr5 position 137802650, Chr5 position 139051189, Chr5 position 167838221, Chr5 position 177541401, Chr5 position 180018672, Chr5 position 180101026, Chr7 position 3394325, Chr7 position 3887581, Chr7 position 7236568, Chr7 position 7728692, Chr7 position 34203617, Chr7 position 37751320, Chr7 position 41410682, Chr7 position 41438516, Chr7 position 41438575, Chr7 position 43464150, Chr7 position 158734279, Chr7 position 989235, Chr7 position 2673543, Chr7 position 73508602, Chr7 position 105079565, Chr7 position 105079631, Chr7 position 151425103, Chr7 position 151425104, Chr8 position 11764017, Chr8 position 21647308, Chr8 position 22548399, Chr8 position 22548483, Chr8 position 133570537, Chr8 position 141320393, Chr8 position 141320410, Chr9 position 6566568, Chr9 position 16197862, Chr9 position 34591313, Chr9 position 98225096, Chr9 position 126126741, Chr9 position 132083428, Chr9 position 136077410, Chr9 position 139655018, Chr9 position 140205985, Chr9 position 140205985, Chr9 position 140205997, Chr10 position 3929071, Chr10 position 30047012, Chr10 position 79702989, Chr10 position 87984905, Chr10 position 94838789, Chr10 position 102131187, Chr10 position 104196489, Chr10 position 111766879, Chr10 position 112258886, Chr10 position 112258984, Chr10 position 112259015, Chr10 position 116391763, Chr10 position 120011530, Chr10 position 126172714, Chr10 position 126172747, Chr11 position 556355, Chr11 position 821282, Chr11 position 12188937, Chr11 position 12188948, Chr11 position 12188995, Chr11 position 36057726, Chr11 position 48070143, Chr11 position 48070163, Chr11 position 48070166, Chr11 position 48070174, Chr11 position 65158294, Chr11 position 65158342, Chr11 position 65297089, Chr11 position 66104481, Chr11 position 66104485, Chr11 position 66104578, Chr11 position 68608767, Chr11 position 70236292, Chr11 position 70236320, Chr11 position 70236331, Chr11 position 115530032, Chr11 position 117950310, Chr11 position 117950329, Chr11 position 117950361, Chr11 position 117950362, Chr11 position 119293593, Chr12 position 679803, Chr12 position 26039132, Chr12 position 31004558, Chr12 position 45610695, Chr12 position 45610701, Chr12 position 45610702, Chr12 position 45610706, Chr12 position 50286016, Chr12 position 52243258, Chr12 position 52243286, Chr12 position 54145732, Chr12 position 54145741, Chr12 position 54145825, Chr12 position 56115043, Chr12 position 66262229, Chr12 position 66262230, Chr12 position 66262233, Chr12 position 66262234, Chr12 position 77266621, Chr12 position 117580102, Chr12 position 123435962, Chr12 position 123436011, Chr12 position 123436065, Chr12 position 123540893, Chr13 position 20735797, Chr13 position 23500419, Chr13 position 46771519, Chr13 position 46771520, Chr13 position 53313426, Chr13 position 113807393, Chr14 position 38599118, Chr14 position 69170010, Chr14 position 75701632, Chr14 position 75701643, Chr14 position 90850454, Chr14 position 97524282, Chr14 position 103541602, Chr14 position 103768055, Chr14 position 104209000, Chr14 position 104209068, Chr14 position 104354645, Chr14 position 104360487, Chr15 position 41068807, Chr15 position 61152225, Chr15 position 61152253, Chr15 position 61152313, Chr15 position 65186440, Chr15 position 68851629, Chr15 position 70667596, Chr15 position 70767206, Chr15 position 75251486, Chr15 position 77984014, Chr15 position 83952081, Chr15 position 85402496, Chr15 position 85402497, Chr15 position 99417337, Chr16 position 1231873, Chr16 position 29616265, Chr16 position 31009547, Chr16 position 31009548, Chr16 position 31009590, Chr16 position 57793674, Chr16 position 57793715, Chr16 position 57793727, Chr16 position 70771056, Chr16 position 70771079, Chr16 position 70771141, Chr16 position 77332010, Chr16 position 78540378, Chr16 position 79333435, Chr16 position 84262419, Chr16 position 88701114, Chr16 position 89988308, Chr16 position 89988644, Chr17 position 1509928, Chr17 position 1509952, Chr17 position 1509953, Chr17 position 7644013, Chr17 position 16323460, Chr17 position 16323473, Chr17 position 16924561, Chr17 position 16924562, Chr17 position 16924594, Chr17 position 17717918, Chr17 position 17718591, Chr17 position 18139506, Chr17 position 35278031, Chr17 position 39677570, Chr17 position 40826257, Chr17 position 43037426, Chr17 position 43200096, Chr17 position 43200239, Chr17 position 43510142, Chr17 position 47987828, Chr17 position 48178379, Chr17 position 48764165, Chr17 position 55701962, Chr17 position 73584599, Chr17 position 73993165, Chr17 position 75827716, Chr17 position 76882243, Chr17 position 78765910, Chr17 position 79544478, Chr17 position 80696474, Chr18 position 19751759, Chr18 position 21440760, Chr18 position 45555437, Chr18 position 45555438, Chr18 position 46547891, Chr18 position 55888885, Chr18 position 56452096, Chr18 position 56452476, Chr18 position 56887181, Chr18 position 76002973, Chr18 position 77331090, Chr19 position 677895, Chr19 position 884044, Chr19 position 884059, Chr19 position 884105, Chr19 position 884115, Chr19 position 1136511, Chr19 position 1177605, Chr19 position 1177612, Chr19 position 1177640, Chr19 position 1860601, Chr19 position 1860607, Chr19 position 2503954, Chr19 position 3434917, Chr19 position 3434921, Chr19 position 3434930, Chr19 position 3434952, Chr19 position 3434954, Chr19 position 3434962, Chr19 position 3434964, Chr19 position 3434979, Chr19 position 3434985, Chr19 position 4052713, Chr19 position 4052714, Chr19 position 4052749, Chr19 position 4374591, Chr19 position 5013982, Chr19 position 5048836, Chr19 position 5048867, Chr19 position 5048877, Chr19 position 8367279, Chr19 position 8428573, Chr19 position 10254577, Chr19 position 10254578, Chr19 position 10463956, Chr19 position 10464137, Chr19 position 13203671, Chr19 position 13266925, Chr19 position 13266934, Chr19 position 13266970, Chr19 position 13842142, Chr19 position 14248494, Chr19 position 15375465, Chr19 position 17218912, Chr19 position 17346702, Chr19 position 18157161, Chr19 position 18157221, Chr19 position 18157258, Chr19 position 18415877, Chr19 position 18415890, Chr19 position 30606642, Chr19 position 35531842, Chr19 position 44303112, Chr19 position 47173037, Chr19 position 47316268, Chr19 position 47778278, Chr19 position 47778298, Chr20 position 31126186, Chr20 position 34206950, Chr20 position 36771969, Chr20 position 48993661, Chr20 position 58406398, Chr20 position 61976049, Chr20 position 61976073, Chr20 position 62588579, Chr22 position 19738127, Chr22 position 35965176, Chr22 position 36549809, Chr22 position 36973375, Chr22 position 37447953, Chr22 position 37914998, Chr22 position 39662794, and Chr22 position 45622980.

3. The method of claim 1, wherein said thyroid nodule is a specimen obtained by biopsy or by surgical resection of said subject.

4. A method of treating a human subject, said method comprising:

(a) measuring methylation levels of thyroid nodule DNA molecules of said subject, wherein the measuring comprises:

(i) isolating DNA molecules from a thyroid nodule of said subject thereby forming isolated thyroid nodule DNA molecules, (ii) contacting said isolated thyroid nodule DNA molecules with a bisulfite salt thereby forming reacted thyroid nodule DNA molecules;

(iii) contacting said reacted thyroid nodule DNA molecules with a probe or primer complementary to a sequence at or within 1000 nucleotides of a plurality of methylation sites, wherein the plurality of methylation sites comprise chr2 position 42329494, chr17 position 48596391, chr20 position 62588571, chr15 position 77989064, chr16 position 23135833, chr20 position 31126189, chr22 position 38307317, chr19 position 3434939, chr16 position 3023231, chr17 position 1509945, and chr16 position 1458639 with respect to human genome assembly hg19; and (iv) measuring methylation levels by detecting the presence of cytosine or uracil in said reacted thyroid nodule DNA molecules at the plurality of methylation sites;

(b) diagnosing said subject as having an increased probability of having or developing thyroid cancer; and (c) treating said subject, wherein treating comprises (i) thyroid surgery, radiation therapy, radioactive iodine therapy, chemotherapy, thyroid hormone therapy, or (ii) administering Cabozantinib-S-Malate, Vandetanib, Doxorubicin Hydrochloride, Lenvatinib Mesylate, or Sorafenib Tosylate.

5. The method of claim 4, wherein said subject (a) is a woman; (b) is about 20 to about 55 years old; (c) has a mutated Ret Proto-Oncogene; (d) has a grandparent, parent, or sibling who has been diagnosed with thyroid cancer; (e) self-identifies as being Caucasian or Asian; or (f) has or has had breast cancer.

6. The method of claim 4, wherein said subject has undergone thyroid surgery, radiation therapy, radioactive iodine therapy, chemotherapy, thyroid hormone therapy, and administration of an active agent, before said measuring.

7. The method of claim 6, wherein said treating comprises administering Cabozantinib-S-Malate, Vandetanib, Doxorubicin Hydrochloride, Lenvatinib Mesylate, or Sorafenib Tosylate.

8. The method of claim 1, wherein said bisulfite salt is sodium bisulfite.

* * * * *